US009181588B2

(12) United States Patent
Perou et al.

(10) Patent No.: US 9,181,588 B2
(45) Date of Patent: Nov. 10, 2015

(54) METHODS OF TREATING BREAST CANCER WITH TAXANE THERAPY

(71) Applicants: Charles M. Perou, Carrboro, NC (US); Philip S. Bernard, Salt Lake City, UT (US); Torsten O. Nielsen, North Vancouver (CA); Matthew J. Ellis, St. Louis, MO (US); Joel S. Parker, Chapel Hill, NC (US); Miguel Martin, Madrid (ES); Eva Carrasco, Madrid (ES); Rosalia Caballero, Madrid (ES)

(72) Inventors: Charles M. Perou, Carrboro, NC (US); Philip S. Bernard, Salt Lake City, UT (US); Torsten O. Nielsen, North Vancouver (CA); Matthew J. Ellis, St. Louis, MO (US); Joel S. Parker, Chapel Hill, NC (US); Miguel Martin, Madrid (ES); Eva Carrasco, Madrid (ES); Rosalia Caballero, Madrid (ES)

(73) Assignees: The University of Utah Research Foundation, Salt Lake City, UT (US); British Columbia Cancer Agency Branch, Vancouver, British Columbia (CA); Washington University, St. Louis, MO (US); The University of North Carolina at Chapel Hill, Chapel Hill, NC (US); Bioclassifier, LLC, St. Louis, MO (US)

( * ) Notice: Subject to any disclaimer, the term of this patent is extended or adjusted under 35 U.S.C. 154(b) by 68 days.

(21) Appl. No.: 13/690,891

(22) Filed: Nov. 30, 2012

(65) Prior Publication Data

US 2013/0345161 A1 Dec. 26, 2013

Related U.S. Application Data

(60) Provisional application No. 61/565,133, filed on Nov. 30, 2011, provisional application No. 61/635,048, filed on Apr. 18, 2012.

(51) Int. Cl.
*C12Q 1/68* (2006.01)
*G01N 33/53* (2006.01)

(52) U.S. Cl.
CPC ........ *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2009/0239223 A1 | 9/2009 | Gehrmann et al. |
| 2009/0299640 A1 | 12/2009 | Ellis et al. |
| 2010/0015607 A1 | 1/2010 | Geiss et al. |
| 2010/0279957 A1 | 11/2010 | Potti et al. |
| 2011/0129822 A1 | 6/2011 | Shen et al. |
| 2011/0145176 A1 | 6/2011 | Perou et al. |
| 2011/0150979 A1 | 6/2011 | Ray et al. |
| 2011/0230360 A1 | 9/2011 | Stephan et al. |
| 2011/0286960 A1 | 11/2011 | Vainas et al. |
| 2013/0004482 A1 | 1/2013 | Perou et al. |
| 2013/0337444 A1 | 12/2013 | Ferree et al. |
| 2014/0037620 A1 | 2/2014 | Ferree et al. |

FOREIGN PATENT DOCUMENTS

WO WO-2009-158143 A1 * 12/2009

OTHER PUBLICATIONS

Albain et al. "Prognostic and Predictive Value of the 21-Gene Recurrence Score Assay in Postmenopausal Women with Node-Positive, Oestrogen-Receptor-Positive Breast Cancer on Chemotherapy: A Retrospective Analysis of a Randomised Trial." *Lancet Oncol.* 11.1(2010):55-65.

Ayers et al. "Gene Expression Profiles Predict Complete Pathologic Response to Neoadjuvant Paclitaxel and Fluorouracil, Doxorubicin, and Cyclophosphamide Chemotherapy in Breast Cancer." *J. Clin. Oncol.* 22.12(2004):2284-2293.

Cheang et al. "PAM5 HER2-Enriched Subtype Enriches for Tumor Response to Neoadjuvant Anthracyclines/Taxane and Trastuzumab/Taxane Containing Regimens in HER2-Positive Breast Cancer." *Cancer Res.* 71.24S(2011):110s. (Abstract #S5-2).

Harris et al. Genome-Wide Profiling of Archived Material from CALGB 9840 and 9342 for Paclitaxel (P) and Trastuzumab (T) Response Biomarkers Using Gene Expression and Copy Number Analysis. *Cancer Res.* 69.24S(2009). (Poster #4032).

Hatzis et al. "A Genomic Predictor of Response and Survival Following Taxane-Anthracycline Chemotherapy for Invasive Breast Cancer." *JAMA.* 305.18(2011):1873-1881.

Hess et al. "Pharmacogenomic Predictor of Sensitivity to Preoperative Chemotherapy With Paclitaxel and Fluorouracil, Doxorubicin, and Cyclophosphamide in Breast Cancer." *J. Clin. Oncol.* 24.26(2006):4236-4244.

Isakoff. "Triple Negative Breast Cancer: Role of Specific Chemotherapy Agents." *Cancer J.* 16.1(2010):53-61.

Lee et al. "Prospective Comparison of Clinical and Genomic Multivariate Predictors of Response to Neoadjuvant Chemotherapy in Breast Cancer." *Clin. Cancer Res.* 16.2(2010):711-718.

Liedtke et al. "Genomic Grade Index Is Associated With Response to Chemotherapy in Patients With Breast Cancer." *J. Clin. Oncol.* 27.19(2009):3185-3191.

(Continued)

*Primary Examiner* — James Martinell
(74) *Attorney, Agent, or Firm* — Cooley LLP; Ivor R. Elrifi; Matthew Pavao

(57) ABSTRACT

The application describes methods for screening subjects with breast cancer to determine if the breast cancer will be responsive to a breast cancer therapy including a taxane or a taxane derivative. The application also describes methods for treating subjects with breast cancer by screening them for the likelihood of the effectiveness of treating the cancer with a therapy including a taxane or a taxane derivative and administering the therapy in subjects when it is found that a taxane or a taxane derivative is likely to be effective.

20 Claims, 5 Drawing Sheets
(4 of 5 Drawing Sheet(s) Filed in Color)

(56) References Cited

OTHER PUBLICATIONS

Martín et al. "PAM50 Proliferation Index Predicts Response to Weekly Adjuvant Paclitaxel in Node-Positive Operable Breast Cancer." *Breast Cancer Res*. 71.24S(2011):177s. (Poster #P1-06-04).
Nielsen et al. "A Comparison of PAM50 Intrinsic Subtyping with Immunohistochemistry and Clinical Prognostic Factors in Tamoxifen-Treated Estrogen Receptor-Positive Breast Cancer." *Clin. Cancer Res*. 16.21(2010):5222-5232.
Parker et al. "Supervised Risk Predictor of Breast Cancer Based on Intrinsic Subtypes." *J. Clin. Oncol*. 27.8(2009):1160-1167.
Wu et al. "Response and Prognosis of Taxanes and Anthracyclines Neoadjuvant Chemotherapy in Patients with Triple-Negative Breast Cancer." *J. Cancer Res. Clin. Oncol*. 137.10(2011):1505-1510.

* cited by examiner

SEQUENCE LISTING

<160> NUMBER OF SEQ ID NOS: 152

<210> SEQ ID NO 1
<211> LENGTH: 19
<212> TYPE: DNA
<213> ORGANISM: Artificial sequence
<220> FEATURE:
<223> OTHER INFORMATION: Chemically synthesized primer

<400> SEQUENCE: 1
aaagattcct gggacctga 19

<210> SEQ ID NO 2
<211> LENGTH: 21
<212> TYPE: DNA
<213> ORGANISM: Artificial sequence
<220> FEATURE:
<223> OTHER INFORMATION: Chemically synthesized primer

<400> SEQUENCE: 2
acagccactt tcagaagcaa g 21

<210> SEQ ID NO 3
<211> LENGTH: 22
<212> TYPE: DNA
<213> ORGANISM: Artificial sequence
<220> FEATURE:
<223> OTHER INFORMATION: Chemically synthesized primer

<400> SEQUENCE: 3
ctggaagagt tgaataaaga gc 22

<210> SEQ ID NO 4
<211> LENGTH: 18
<212> TYPE: DNA
<213> ORGANISM: Artificial sequence
<220> FEATURE:
<223> OTHER INFORMATION: Chemically synthesized primer

<400> SEQUENCE: 4
tacctgaacc ggcacctg 18

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 5
gcacaaagcc attctaagtc 20

<210> SEQ ID NO 6
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 6
gctggctgag cagaaag 17

<210> SEQ ID NO 7
<211> LENGTH: 19
<212> TYPE: DNA
<213> ORGANISM: Artificial Sequence -continued
<220> FEATURE:
<223> OTHER INFORMATION: Chemically synthesized primer

<400> SEQUENCE: 7
ctttcgcctg agcctattt 19

<210> SEQ ID NO 8
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 8
ggccaaaatc gacaggac 18

<210> SEQ ID NO 9
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 9
ctgtctgagt gccgtggat 19

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 10
gtaaatcacc ttctgagcct 20

<210> SEQ ID NO 11
<211> LENGTH: 18
<212> TYPE: DNA
<213> ORGANISM: Artificial sequence
<220> FEATURE:
<223> OTHER INFORMATION: Chemically synthesized primer

<400> SEQUENCE: 11
ggaggcggaa gaaaccag 18

<210> SEQ ID NO 12
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 12
gacaaggaga atcaaaagat cagc 24

<210> SEQ ID NO 13
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 13
gtggcagcag atcacaa 17

<210> SEQ ID NO 14
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 14
cctcacgaat tgctgaactt 20

<210> SEQ ID NO 15
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 15
catgaaatag tgcatagttt gcc 23

<210> SEQ ID NO 16
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 16
acacagaatc tatacccacc agagt 25

<210> SEQ ID NO 17
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 17
gctggctctc acactgatag 20

<210> SEQ ID NO 18
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 18
gcagggagag gagtttgt 18

<210> SEQ ID NO 19
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 19
cccatccatg tgaggaagta taa 23

<210> SEQ ID NO 20
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 20
cttcttggac cttggcg 17

<210> SEQ ID NO 21
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 21
gctactacgc agacacg 17

<210> SEQ ID NO 22
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 22
gatgttcgag tcacagagg 19

<210> SEQ ID NO 23
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 23
ttcggctgga aggaacc 17

<210> SEQ ID NO 24
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 24
cgtggcagat gtgaacga 18

<210> SEQ ID NO 25
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 25
ggagatccgt caactccaaa 20

<210> SEQ ID NO 26
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 26
tgggtcgtgt caggaaac 18

<210> SEQ ID NO 27

<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 27
cgcagtcatc cagagatgtg 20

<210> SEQ ID NO 28
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 28
actcagtaca agaaagaacc g 21

<210> SEQ ID NO 29
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 29
gttggaccag tcaacatctc tg 22

<210> SEQ ID NO 30
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 30
tgtggctcat taggcaac 18

<210> SEQ ID NO 31
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 31
gactccaagc gcgaaaac 18

<210> SEQ ID NO 32
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 32
ccacaaaata ttcatggttc ttg 23

<210> SEQ ID NO 33
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 33
ccagtagcat tgtccgag 18

<210> SEQ ID NO 34
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 34
gtctctggta atgcacact 19

<210> SEQ ID NO 35
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 35
gtggaatgcc tgctgacc 18

<210> SEQ ID NO 36
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 36
aggggtgccc tctgagat 18

<210> SEQ ID NO 37
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 37
cgagatcgcc aagatgtt 18

<210> SEQ ID NO 38
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 38
aggcgaacac acaacgtc 18

<210> SEQ ID NO 39
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 39
agcctcgaac aattgaaga 19

<210> SEQ ID NO 40
<211> LENGTH: 27
<212> TYPE: DNA

<213> ORGANISM: Artificial Sequence
<220> FEATURE:
<223> OTHER INFORMATION: Chemically synthesized primer

<400> SEQUENCE: 40
atcgactgtg taaacaacta gagaaga 27

<210> SEQ ID NO 41
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 41
tttaagaggg caatggaagg 20

<210> SEQ ID NO 42
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 42
tgccgcagaa ctcacttg 18

<210> SEQ ID NO 43
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 43
cctcagatga tgcctatcca 20

<210> SEQ ID NO 44
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 44
cagcaagcga tggcatagt 19

<210> SEQ ID NO 45
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 45
aatgccaccg aagcctc 17

<210> SEQ ID NO 46
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 46
tcgaactgaa ggctatttac gag 23

<210> SEQ ID NO 47
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 47
gtcgaagccg caattagg 18

<210> SEQ ID NO 48
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 48
caaacgtgtg ttctggagg 19

<210> SEQ ID NO 49
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 49
tgccctgtat gatgtcagga 20

<210> SEQ ID NO 50
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 50
gtgaggggtg tcagctcagt 20

<210> SEQ ID NO 51
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 51
tggggcagtt ctgtattact tc 22

<210> SEQ ID NO 52
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 52
cgatggtttt gtacaagatt tctc 24

<210> SEQ ID NO 53
<211> LENGTH: 17
<212> TYPE: DNA
<213> ORGANISM: Artificial Sequence
<220> FEATURE:

<223> OTHER INFORMATION: Chemically synthesized primer

<400> SEQUENCE: 53
gcaaatcctt gggcaga 17

<210> SEQ ID NO 54
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 54
gccgtacagt tccacaaagg 20

<210> SEQ ID NO 55
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 55
gacgcttcct atcactctat tc 22

<210> SEQ ID NO 56
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 56
ttcctccatc aagagttcaa ca 22

<210> SEQ ID NO 57
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 57
gggcacatcc agatgttt 18

<210> SEQ ID NO 58
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 58
gggtctgcac agactgcat 19

<210> SEQ ID NO 59
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 59
tccttgtaat ggggagacca 20

<210> SEQ ID NO 60
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 60
acttgggata tgtgaataag acc 23

<210> SEQ ID NO 61
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 61
ggggaaagac aaagtttcca 20

<210> SEQ ID NO 62
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 62
actgtctggg tccatggcta 20

<210> SEQ ID NO 63
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 63
ggatttcgtg gtgggttc 18

<210> SEQ ID NO 64
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 64
ccacagtctg tgataaacgg 20

<210> SEQ ID NO 65
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 65
ccatcaacat tctctttatg aacg 24

<210> SEQ ID NO 66
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 66
atcaactccc aaacggtcac 20

<210> SEQ ID NO 67
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 67
gcccttacac atcggagaac 20

<210> SEQ ID NO 68
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 68
gacttcaggg tgctggac 18

<210> SEQ ID NO 69
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 69
tgtgaagcca gcaatatgta tc 22

<210> SEQ ID NO 70
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 70
tattgggagg caggaggttt a 21

<210> SEQ ID NO 71
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 71
ctgagttcat gttgctgacc 20

<210> SEQ ID NO 72
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 72
gacagctact attcccgtt 19

<210> SEQ ID NO 73
<211> LENGTH: 21

<212> TYPE: DNA
<213> ORGANISM: Artificial Sequence
<220> FEATURE:
<223> OTHER INFORMATION: Chemically synthesized primer

<400> SEQUENCE: 73
tatgtgagta agctcggaga c 21

<210> SEQ ID NO 74
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 74
agtgggcatc ccgtaga 17

<210> SEQ ID NO 75
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 75
agtggacatg cgagtggag 19

<210> SEQ ID NO 76
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 76
caccgctgga aactgaac 18

<210> SEQ ID NO 77
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 77
cgtgcacatc catgacctt 19

<210> SEQ ID NO 78
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 78
gaggagatga ccttgcc 17

<210> SEQ ID NO 79
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 79
gccatagcca ctgccact 18

<210> SEQ ID NO 80
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 80
cttcgactgg actctgt 17

<210> SEQ ID NO 81
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 81
cagacatgtt ggtattgcac att 23

<210> SEQ ID NO 82
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 82
aggcgatcct gggaaattat 20

<210> SEQ ID NO 83
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 83
cccatttgtc tgtcttcac 19

<210> SEQ ID NO 84
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 84
ctgatggttg aggctgtt 18

<210> SEQ ID NO 85
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 85
cgcactccag cacctagac 19

<210> SEQ ID NO 86
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 86
tcacagggtc aaacttccag t 21

<210> SEQ ID NO 87
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 87
gatggtagag ttccagtgat t 21

<210> SEQ ID NO 88
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 88
tctggtcacg cagggcaa 18

<210> SEQ ID NO 89
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 89
acacagatga tggagatgtc 20

<210> SEQ ID NO 90
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 90
agtagctaca tctccaggtt ctctg 25

<210> SEQ ID NO 91
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 91
cggattttat caacgatgca g 21

<210> SEQ ID NO 92
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 92
catttgccgt ccttcatcg 19

<210> SEQ ID NO 93
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 93
gcaggtcaaa actctcaaag 20

<210> SEQ ID NO 94
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 94
agcgggcttc tgtaatctga 20

<210> SEQ ID NO 95
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 95
gcctcagatt tcaactcgt 19

<210> SEQ ID NO 96
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 96
ctgctgagaa tcaaagtggg a 21

<210> SEQ ID NO 97
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 97
ggaacaaact gctctgcca 19

<210> SEQ ID NO 98
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 98
acagctcttt agcatttgtg ga 22

<210> SEQ ID NO 99
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 99
gggactatca atgttgggtt ctc 23

<210> SEQ ID NO 100
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 100
cacacagttc actgctccac a 21

<210> SEQ ID NO 101
<211> LENGTH: 2199
<212> TYPE: DNA
<213> ORGANISM: Homo sapiens

<400> SEQUENCE: 101
cagcggcgct gcggcggctc gcgggagacg ctgcgcgcgg ggctagcggg cggcggagcg 60
gacggcgacg gggcgctctc gggctgccgg cggggccgag cgccgcgcgt cccgagcatg 120
gcaggctccc tgcctccctg cgtggtggac tgtggcaccg ggtataccaa gcttggctac 180
gcaggcaaca ctgagcccca gttcattatt ccttcatgta ttgccatcag agagtcagca 240
aaggtagttg accaagctca aaggagagtg ttgaggggag ttgatgacct tgactttttc 300
ataggagatg aagccatcga taaacctaca tatgctacaa agtggccgat acgacatgga 360
atcattgaag actgggatct tatggaaagg ttcatggagc aagtggtttt taaatatctt 420
cgagctgaac ctgaggacca ttattttta atgacagaac ctccactcaa tacaccagaa 480
aacagagagt atcttgcaga aattatgttt gaatcattta acgtaccagg actctacatt 540
gcagttcagg cagtgctggc cttggcggca tcttggacat ctcgacaagt gggtgaacgt 600
acgttaacgg ggatagtcat tgacagcgga gatggagtca cccatgttat cccagtggca 660
gaaggttatg taattggaag ctgcatcaaa cacatcccga ttgcaggtag agatattacg 720
tatttcattc aacagctgct aagggagagg gaggtgggaa tccctcctga gcagtcactg 780
gagaccgcaa aagccattaa ggagaaatac tgttacattt gccccgatat agtcaaggaa 840
tttgccaagt atgatgtgga tccccggaag tggatcaaac agtacacggg tatcaatgcg 900
atcaaccaga agaagtttgt tatagacgtt ggttacgaaa gattcctggg acctgaaata 960
ttctttcacc cggagtttgc caacccagac tttatggagt ccatctcaga tgttgttgat 1020
gaagtaatac agaactgccc catcgatgtg cggcgcccgc tgtataagaa tgtcgtactc 1080
tcaggaggct ccaccatgtt cagggatttc ggacgccgac tgcagaggga tttgaagaga 1140
gtggtggatg ctaggctgag gctcagcgag gagctcagcg gcgggaggat caagccgaag 1200
cctgtggagg tccaggtggt cacgcatcac atgcagcgct acgccgtgtg gttcggaggc 1260
tccatgctgg cctcgactcc cgagttcttt caggtctgcc acaccaagaa ggactatgaa 1320
gagtacgggc ccagcatctg ccgccacaac cccgtctttg gagtcatgtc ctagtgtctg 1380
cctgaacgcg tcgttcgatg gtgtcacgtt ggggaacaag tgtccttcag aacccagaga 1440
aggccgccgt tctgtaaata gcgacgtcgg tgttgctgcc cagcagcgtg cttgcattgc 1500
cggtgcatga ggcgcggcgc gggcccttca gtaaaagcca tttatccgtg tgccgaccgc 1560
tgtctgccag cctcctcctt ctcccgccct cctcaccctc gctctccctc ctcctcctcc 1620

```
tccgagctgc tagctgacaa atacaattct gaaggaatcc aaatgtgact ttgaaaattg   1680
ttagagaaaa caacattaga aaatggcgca aaatcgttag gtcccaggag agaatgtggg   1740
ggcgcaaacc cttttcctcc cagcctattt ttgtaaataa aatgtttaaa cttgaaatac   1800
aaatcgatgt ttatatttcc tatcattttg tattttatgg tatttggtac aactggctga   1860
tactaagcac gaatagatat tgatgttatg gagtgctgta atccaaagtt tttaattgtg   1920
aggcatgttc tgatatgttt ataggcaaac aaataaaaca gcaaactttt ttgccacatg   1980
tttgctagaa aatgattata ctttattgga gtgacatgaa gtttgaacac taaacagtaa   2040
tgtatgagaa ttactacaga tacatgtatc ttttagtttt ttttgtttga actttctgga   2100
gctgttttat agaagatgat ggtttgttgt cggtgagtgt tggatgaaat acttccttgc   2160
accattgtaa taaaagctgt tagaatattt gtaaatatc                          2199

<210> SEQ ID NO 102
<211> LENGTH: 1989
<212> TYPE: DNA
<213> ORGANISM: Homo sapiens

<400> SEQUENCE: 102

cagcggcgct gcggcggctc gcgggagacg ctgcgcgcgg ggctagcggg cggcggagcg     60
gacggcgacg gggcgctctc gggctgccgg cggggccgag cgccgcgcgt cccgagcatg    120
gcaggctccc tgcctccctg cgtggtggac tgtggcaccg ggtataccaa gcttggctac    180
gcaggcaaca ctgagcccca gttcattatt ccttcatgta ttgccatcag agagtcagca    240
aaggtagttg accaagctca aaggagagtg ttgaggggag ttgatgacct tgactttttc    300
ataggagatg aagccatcga taaacctaca tatgctacaa agtggccgat acgacatgga    360
atcattgaag actgggatct tatggaaagg ttcatggagc aagtggtttt taaatatctt    420
cgagctgaac ctgaggacca ttattttta atgacagaac ctccactcaa tacaccagaa    480
aacagagagt atcttgcaga aattatgttt gaatcattta acgtaccagg actctacatt    540
gcagttcagg cagtgctggc cttggcggca tcttggacat ctcgacaagt gggtgaacgt    600
acgttaacgg ggatagtcat tgacagcgga gatggagtca cccatgttat cccagtggca    660
gaaggttatg taattggaag ctgcatcaaa cacatcccga ttgcaggtag agatattacg    720
tatttcattc aacagctgct aagggagagg gaggtgggaa tccctcctga gcagtcactg    780
gagaccgcaa aagccattaa ggagaaatac tgttacattt gccccgatat agtcaaggaa    840
tttgccaagt atgatgtgga tccccggaag tggatcaaac agtacacggg tatcaatgcg    900
atcaaccaga agaagtttgt tatagacgtt ggttacgaaa gattcctggg acctgaaata    960
ttctttcacc cggagtttgc caacccagac tttatggagt ccatctcaga tgttgttgat   1020
gaagtaatac agaactgccc catcgatgtg cggcgcccgc tgtataagcc cgagttcttt   1080
caggtctgcc acaccaagaa ggactatgaa gagtacgggc ccagcatctg ccgccacaac   1140
cccgtctttg gagtcatgtc ctagtgtctg cctgaacgcg tcgttcgatg gtgtcacgtt   1200
ggggaacaag tgtccttcag aacccagaga aggccgccgt tctgtaaata gcgacgtcgg   1260
tgttgctgcc cagcagcgtg cttgcattgc cggtgcatga ggcgcggcgc gggcccttca   1320
gtaaaagcca tttatccgtg tgccgaccgc tgtctgccag cctcctcctt ctcccgccct   1380
cctcaccctc gctctccctc ctcctcctcc tccgagctgc tagctgacaa atacaattct   1440
gaaggaatcc aaatgtgact ttgaaaattg ttagagaaaa caacattaga aaatggcgca   1500
aaatcgttag gtcccaggag agaatgtggg ggcgcaaacc cttttcctcc cagcctattt   1560
```

ttgtaaataa aatgtttaaa cttgaaatac aaatcgatgt ttatatttcc tatcattttg 1620
tattttatgg tatttggtac aactggctga tactaagcac gaatagatat tgatgttatg 1680
gagtgctgta atccaaagtt tttaattgtg aggcatgttc tgatatgttt ataggcaaac 1740
aaataaaaca gcaaactttt ttgccacatg tttgctagaa aatgattata ctttattgga 1800
gtgacatgaa gtttgaacac taaacagtaa tgtatgagaa ttactacaga tacatgtatc 1860
ttttagtttt ttttgtttga actttctgga gctgttttat agaagatgat ggtttgttgt 1920
cggtgagtgt tggatgaaat acttccttgc accattgtaa taaaagctgt tagaatattt 1980
gtaaatatc 1989

<210> SEQ ID NO 103
<211> LENGTH: 4786
<212> TYPE: DNA
<213> ORGANISM: Homo sapiens

<400> SEQUENCE: 103
ctcggcgctg aaattcaaat ttgaacggct gcagaggccg agtccgtcac tggaagccga 60
gaggagagga cagctggttg tgggagagtt cccccgcctc agactcctgg tttttttccag 120 gagacacact gagctgagac tcacttttct cttcctgaat ttgaaccacc gtttccatcg 180
tctcgtagtc cgacgcctgg ggcgatggat ccgtttacgg agaaactgct ggagcgaacc 240
cgtgccaggc gagagaatct tcagagaaaa atggctgaga ggcccacagc agctccaagg 300
tctatgactc atgctaagcg agctagacag ccactttcag aagcaagtaa ccagcagccc 360
ctctctggtg gtgaagagaa atcttgtaca aaaccatcgc catcaaaaaa acgctgttct 420
gacaacactg aagtagaagt ttctaacttg gaaaataaac aaccagttga gtcgacatct 480
gcaaaatctt gttctccaag tcctgtgtct cctcaggtgc agccacaagc agcagatacc 540
atcagtgatt ctgttgctgt cccggcatca ctgctgggca tgaggagagg gctgaactca 600
agattggaag caactgcagc ctcctcagtt aaaacacgta tgcaaaaact tgcagagcaa 660
cggcgccgtt gggataatga tgatatgaca gatgacattc ctgaaagctc actcttctca 720
ccaatgccat cagaggaaaa ggctgcttcc cctcccagac ctctgctttc aaatgcctcg 780
gcaactccag ttggcagaag gggccgtctg gccaatcttg ctgcaactat ttgctcctgg 840
gaagatgatg taaatcactc atttgcaaaa caaaacagtg tacaagaaca gcctggtacc 900
gcttgtttat ccaaattttc ctctgcaagt ggagcatctg ctaggatcaa tagcagcagt 960
gttaagcagg aagctacatt ctgttcccaa agggatggcg atgcctcttt gaataaagcc 1020
ctatcctcaa gtgctgatga tgcgtctttg gttaatgcct caatttccag ctctgtgaaa 1080
gctacttctc cagtgaaatc tactacatct atcactgatg ctaaaagttg tgagggacaa 1140
aatcctgagc tacttccaaa aactcctatt agtcctctga aaacgggggt atcgaaacca 1200
attgtgaagt caactttatc ccagacagtt ccatccaagg gagaattaag tagagaaatt 1260
tgtctgcaat ctcaatctaa agacaaatct acgacaccag gaggaacagg aattaagcct 1320
ttcctggaac gctttggaga gcgttgtcaa gaacatagca aagaaagtcc agctcgtagc 1380
acaccccaca gaaccccat tattactcca aatacaaagg ccatccaaga aagattattc 1440
aagcaagaca catcttcatc tactacccat ttagcacaac agctcaagca ggaacgtcaa 1500
aaagaactag catgtcttcg tggccgattt gacaagggca atatatggag tgcagaaaaa 1560
ggcggaaact caaaaagcaa acaactagaa accaaacagg aaactcactg tcagagcact 1620

-continued

```
cccctcaaaa aacaccaagg tgtttcaaaa actcagtcac ttccagtaac agaaaaggtg   1680
accgaaaacc agataccagc caaaaattct agtacagaac ctaaaggttt cactgaatgc   1740
gaaatgacga aatctagccc tttgaaaata acattgtttt tagaagagga caaatcctta   1800
aaagtaacat cagacccaaa ggttgagcag aaaattgaag tgatacgtga aattgagatg   1860
agtgtggatg atgatgatat caatagttcg aaagtaatta atgacctctt cagtgatgtc   1920
ctagaggaag gtgaactaga tatggagaag agccaagagg agatggatca agcattagca   1980
gaaagcagcg aagaacagga agatgcactg aatatctcct caatgtcttt acttgcacca   2040
ttggcacaaa cagttggtgt ggtaagtcca gagagtttag tgtccacacc tagactggaa   2100
ttgaaagaca ccagcagaag tgatgaaagt ccaaaaccag gaaaattcca aagaactcgt   2160
gtccctcgag ctgaatctgg tgatagcctt ggttctgaag atcgtgatct tctttacagc   2220
attgatgcat atagatctca aagattcaaa gaaacagaac gtccatcaat aaagcaggtg   2280
attgttcgga aggaagatgt tacttcaaaa ctggatgaaa aaaataatgc ctttccttgt   2340
caagttaata tcaaacagaa aatgcaggaa ctcaataacg aaataaatat gcaacagaca   2400
gtgatctatc aagctagcca ggctcttaac tgctgtgttg atgaagaaca tggaaaaggg   2460
tccctagaag aagctgaagc agaaagactt cttctaattg caactgggaa gagaacactt   2520
ttgattgatg aattgaataa attgaagaac gaaggacctc agaggaagaa taaggctagt   2580
ccccaaagtg aatttatgcc atccaaagga tcagttactt tgtcagaaat ccgcttgcct   2640
ctaaaagcag attttgtctg cagtacggtt cagaaaccag atgcagcaaa ttactattac   2700
ttaattatac taaaagcagg agctgaaaat atggtagcca caccattagc aagtacttca   2760
aactctctta acggtgatgc tctgacattc actactacat ttactctgca agatgtatcc   2820
aatgactttg aaataaatat tgaagtttac agcttggtgc aaaagaaaga tccctcaggc   2880
cttgataaga agaaaaaaac atccaagtcc aaggctatta ctccaaagcg actcctcaca   2940
tctataacca caaaaagcaa cattcattct tcagtcatgg ccagtccagg aggtcttagt   3000
gctgtgcgaa ccagcaactt cgcccttgtt ggatcttaca cattatcatt gtcttcagta   3060
ggaaatacta agtttgttct ggacaaggtc cccttttttat cttctttgga aggtcatatt   3120
tatttaaaaa taaaatgtca agtgaattcc agtgttgaag aaagaggttt tctaaccata   3180
tttgaagatg ttagtggttt tggtgcctgg catcgaagat ggtgtgttct ttctggaaac   3240
tgtatatctt attggactta tccagatgat gagaaacgca agaatcccat aggaaggata   3300
aatctggcta attgtaccag tcgtcagata gaaccagcca acagagaatt ttgtgcaaga   3360
cgcaacactt ttgaattaat tactgtccga ccacaaagag aagatgaccg agagactctt   3420
gtcagccaat gcagggacac actctgtgtt accaagaact ggctgtctgc agatactaaa   3480
gaagagcggg atctctggat gcaaaaactc aatcaagttc ttgttgatat tcgcctctgg   3540
caacctgatg cttgctacaa acctattgga aagccttaaa ccgggaaatt tccatgctat   3600
ctagaggttt ttgatgtcat cttaagaaac acacttaaga gcatcagatt tactgattgc   3660
attttatgct ttaagtacga aagggtttgt gccaatattc actacgtatt atgcagtatt   3720
tatatctttt gtatgtaaaa ctttaactga tttctgtcat tcatcaatga gtagaagtaa   3780
atacattata gttgattttg ctaaatctta atttaaaagc ctcattttcc tagaaatcta   3840
attattcagt tattcatgac aatatttttt taaaagtaag aaattctgag ttgtcttctt   3900
ggagctgtag gtcttgaagc agcaacgtct ttcaggggtt ggagacagaa acccattctc   3960
caatctcagt agttttttcg aaaggctgtg atcatttatt gatcgtgata tgacttgtta   4020
```

ctagggtact gaaaaaaatg tctaaggcct ttacagaaac atttttagta atgaggatga 4080
gaactttttc aaatagcaaa tatatattgg cttaaagcat gaggctgtct tcagaaaagt 4140
gatgtggaca taggaggcaa tgtgtgagac ttgggggttc aatattttat atagaagagt 4200
taataagcac atggtttaca tttactcagc tactatatat gcagtgtggt gcacattttc 4260
acagaattct ggcttcatta agatcattat ttttgctgcg tagcttacag acttagcata 4320
ttagtttttt ctactcctac aagtgtaaat tgaaaaatct ttatattaaa aaagtaaact 4380
gttatgaagc tgctatgtac taataatact ttgcttgcca aagtgtttgg gttttgttgt 4440
tgtttgtttg tttgtttgtt tttggttcat gaacaacagt gtctagaaac ccattttgaa 4500
agtggaaaat tattaagtca cctatcacct ttaaacgcct ttttttaaaa ttataaaata 4560
ttgtaaagca gggtctcaac ttttaaatac actttgaact tcttctctga attattaaag 4620
ttctttatga cctcatttat aaacactaaa ttctgtcacc tcctgtcatt ttattttta 4680 ttcattcaaa tgtatttttt cttgtgcata ttataaaaat atattttatg agctcttact 4740
caaataaata cctgtaaatg tctaaaggaa aaaaaaaaaa aaaaaa 4786

<210> SEQ ID NO 104
<211> LENGTH: 3885
<212> TYPE: DNA
<213> ORGANISM: Homo sapiens

<400> SEQUENCE: 104
aggccggggc ggggctggga agtagtcggg cggggttgtg agacgccgcg ctcagcttcc 60
atcgctgggc ggtcaacaag tgcgggcctg gctcagcgcg ggggggcgcg gagaccgcga 120
ggcgaccggg agcggctggg ttcccggctg cgcgcccttc ggccaggccg ggagccgcgc 180
cagtcggagc ccccggccca gcgtggtccg cctccctctc ggcgtccacc tgcccggagt 240
actgccagcg ggcatgaccg acccaccagg ggcgccgccg ccggcgctcg caggccgcgg 300
atgaagaaga aaacccggcg ccgctcgacc cggagcgagg agttgacccg gagcgaggag 360
ttgaccctga gtgaggaagc gacctggagt gaagaggcga cccagagtga ggaggcgacc 420
cagggcgaag agatgaatcg gagccaggag gtgacccggg acgaggagtc gacccggagc 480
gaggaggtga ccagggagga aatggcggca gctgggctca ccgtgactgt cacccacagc 540
aatgagaagc acgaccttca tgttacctcc cagcagggca gcagtgaacc agttgtccaa 600
gacctggccc aggttgttga agaggtcata ggggttccac agtcttttca gaaactcata 660
tttaagggaa aatctctgaa ggaaatggaa acaccgttgt cagcacttgg aatacaagat 720
ggttgccggg tcatgttaat tgggaaaaag aacagtccac aggaagaggt tgaactaaag 780
aagttgaaac atttggagaa gtctgtggag aagatagctg accagctgga agagttgaat 840
aaagagctta ctggaatcca gcagggtttt ctgcccaagg atttgcaagc tgaagctctc 900
tgcaaacttg ataggagagt aaaagccaca atagagcagt ttatgaagat cttggaggag 960
attgacacac tgatcctgcc agaaaatttc aaagacagta gattgaaaag gaaaggcttg 1020
gtaaaaaagg ttcaggcatt cctagccgag tgtgacacag tggagcagaa catctgccag 1080
gagactgagc ggctgcagtc tacaaacttt gccctggccg agtgaggtgt agcagaaaaa 1140
ggctgtgctg ccctgaagaa tggcgccacc agctctgccg tctctggagc ggaatttacc 1200
tgatttcttc agggctgctg gggcaactgg gccatttgcc aattttccta ctctcacact 1260
ggttctcaat gaaaaatagt gtctttgtga ttttgagtaa agctcctatc tgttttctcc 1320

-continued

```
ttctgtctct gtggttgtac tgtccagcaa tccacctttt ctggagaggg ccacctctgc   1380
ccaaatttc ccagctgttt ggacctctgg gtgctttctt tgggctggtg agagctctaa   1440
tttgccttgg gccagtttca ggtttatagg ccccctcagt cttcagatac atgagggctt   1500
ctttgctctt gtgatcgtgt agtcccatag ctgtaaaacc agaatcacca ggaggttgca   1560
cctagtcagg aatattggga atggcctaga acaaggtgtt tggcacataa gtagaccact   1620
tatccctcat tgtgacctaa ttccagagca tctggctggg ttgttgggtt ctagactttg   1680
tcctcacctc ccagtgaccc tgactagcca caggccatga gataccaggg ggccgttcct   1740
tggatggagc ctgtggttga tgcaaggctt ccttgtcccc aagcaagtct tcagaaggtt   1800
agaacccagt gttgactgag tctgtgcttg aaaccaggcc agagccatgg attaggaagg   1860
gcaaagagaa ggcaccagaa tgagtaaagc aggcaggtgg tgaagccaac cataaacttc   1920
tcaggagtga catgtgcttc cttcaaaggc atttttgtta accatatcct tctgagttct   1980
atgtttcctt cacagctgtt ctatccattt tgtggactgt cccccacccc caccccatca   2040
ttgtttttaa aaaattaagg cctggcgcag cagctcatgc ctataatccc agcactttgg   2100
gaggctgagg cgggcggatc acttgaggcc aggagtttga gaccagccca ggcaacatag   2160
caaaacccca ttctgcttta aaaaaaaaaa aaaaaaaaat tagcttggcg tagtggcatg   2220
tgcctataat cccagctact ggggaggctg aggcacaaga atcatttgaa cctgggaggt   2280
agaggttgct gtgagccgag attacgcccc tgcactccag cctgggtcac agagtgagac   2340
tccatctcag aaaaaaaaaa aattgagtca ggtgcagtag ctccttcctg tagtcccagc   2400
tacttgggag gctgaggcta gaggatcact tgagcccagg agtttgagtc tagtctgggc   2460
aacatagcaa gaccccatct ctaaaattta agtaagtaaa agtagataaa taaaaagaaa   2520
aaaaaactgt ttatgtgctc atcataaagt agaagagtgg tttgcttttt tttttttttt   2580
tggattaatg aggaaatcat tctgtggctc tagtcataat ttatgcttaa taacattgat   2640
agtagccctt tgcgctataa ctctacctaa agactcacat catttggcag agagagagtc   2700
gttgaagtcc caggaattca ggactgggca ggttaagacc tcagacaagg tagtagaggt   2760
agacttgtgg acaaggctcg ggtcccagcc caccgcaccc caactttaat cagagtggtt   2820
cactattgat ctatttttgt gtgatagctg tgtggcgtgg gccacaacat ttaatgagaa   2880
gttactgtgc accaaactgc cgaacaccat tctaaactat tcatatatat tagtcattta   2940
attcttacat aacttgagag gtagacagat atccttattt tagagatgag gaaaccaaga   3000
gaacttaggt cattagcgca aggttgtaga gtaagcggca aagccaagac acaaagctgg   3060
gtggtttggt ttcagagcca gtgcttttcc cctctactgt actgcctctc aaccaacaca   3120
gggttgcaca ggcccattct ctgatttttt tcctcttgtc ctctgcctct ccctctagct   3180
cccacttcct ctctgctcta gttcattttc tttagagcag cccgagtgat catgaagtgc   3240
aaatcttgcc atgtcagtcc cctgcttaga accctccaat ggctcacttt ctctttaggc   3300
aaaagtcttt accccatgcc ttctcccatc tcatctcaac cccctcattt gttggctgtc   3360
tgctgtcagc cactcttctt tcaggtcctc agatgcactg caccctctcc tgcctggggg   3420
tctttgctcc tgctactacc tctgcttgaa cagctcctca ccttccttcc tccaacccta   3480
cccttgtata ggtgactttt gttcatcctt cagaattcaa ctcacatgtc tcttgcatgg   3540
agaaccctca cctactgtgt tgagaccctg tccagccccc aggtgggatc ctctctcgac   3600
ttcccataca tttctttcac agcatttaca tagtccatga tagtttactt gtgggattat   3660
ttggttaatc tttgccttta acaccagggt tccttgggtg aaggagcttc tttatcttgg   3720
```

taacagcatt atttcaagca taacttgtaa tatagttata ttacatatat aacatatata 3780
tatataacat aacatatata acatatataa caagcataac ttgttatata gtcttgtata 3840
tagtaagacc tcaataaata tttggagaac aaaaaaaaaa aaaaa 3885

<210> SEQ ID NO 105
<211> LENGTH: 6492
<212> TYPE: DNA
<213> ORGANISM: Homo sapiens

<400> SEQUENCE: 105
tttctgtgaa gcagaagtct gggaatcgat ctggaaatcc tcctaatttt tactccctct 60
ccccgcgact cctgattcat tgggaagttt caaatcagct ataactggag agtgctgaag 120
attgatggga tcgttgcctt atgcatttgt tttggtttta caaaaaggaa acttgacaga 180
ggatcatgct gtacttaaaa aatacaacat cacagaggaa gtagactgat attaacaata 240
cttactaata ataacgtgcc tcatgaaata aagatccgaa aggaattgga ataaaaattt 300
cctgcatctc atgccaaggg ggaaacacca gaatcaagtg ttccgcgtga ttgaagacac 360
cccctcgtcc aagaatgcaa agcacatcca ataaaatagc tggattataa ctcctcttct 420
ttctctgggg gccgtggggt gggagctggg gcgagaggtg ccgttggccc ccgttgcttt 480
tcctctggga aggatggcgc acgctgggag aacagggtac gataaccggg agatagtgat 540
gaagtacatc cattataagc tgtcgcagag gggctacgag tgggatgcgg gagatgtggg 600
cgccgcgccc ccgggggccg cccccgcacc gggcatcttc tcctcccagc ccgggcacac 660
gccccatcca gccgcatccc gggacccggt cgccaggacc tcgccgctgc agaccccggc 720
tgcccccggc gccgccgcgg ggcctgcgct cagcccggtg ccacctgtgg tccacctgac 780
cctccgccag gccggcgacg acttctcccg ccgctaccgc cgcgacttcg ccgagatgtc 840
cagccagctg cacctgacgc ccttcaccgc gcgggggacgc tttgccacgg tggtggagga 900
gctcttcagg gacggggtga actgggggag gattgtggcc ttctttgagt tcggtggggt 960
catgtgtgtg gagagcgtca accgggagat gtcgcccctg gtggacaaca tcgccctgtg 1020
gatgactgag tacctgaacc ggcacctgca cacctggatc caggataacg gaggctggga 1080
tgcctttgtg gaactgtacg gccccagcat gcggcctctg tttgatttct cctggctgtc 1140
tctgaagact ctgctcagtt tggccctggt gggagcttgc atcaccctgg gtgcctatct 1200
gggccacaag tgaagtcaac atgcctgccc caaacaaata tgcaaaaggt tcactaaagc 1260
agtagaaata atatgcattg tcagtgatgt accatgaaac aaagctgcag gctgtttaag 1320
aaaaaataac acacatataa acatcacaca cacagacaga cacacacaca cacaacaatt 1380
aacagtcttc aggcaaaacg tcgaatcagc tatttactgc caaagggaaa tatcatttat 1440
tttttacatt attaagaaaa aaagatttat ttatttaaga cagtcccatc aaaactcctg 1500
tctttggaaa tccgaccact aattgccaag caccgcttcg tgtggctcca cctggatgtt 1560
ctgtgcctgt aaacatagat tcgctttcca tgttgttggc cggatcacca tctgaagagc 1620
agacggatgg aaaaaggacc tgatcattgg ggaagctggc tttctggctg ctggaggctg 1680
gggagaaggt gttcattcac ttgcatttct ttgccctggg ggctgtgata ttaacagagg 1740
gagggttcct gtgggggggaa gtccatgcct ccctggcctg aagaagagac tctttgcata 1800
tgactcacat gatgcatacc tggtgggagg aaaagagttg ggaacttcag atggacctag 1860
tacccactga gatttccacg ccgaaggaca gcgatgggaa aaatgccctt aaatcatagg 1920

-continued

```
aaagtatttt tttaagctac caattgtgcc gagaaaagca ttttagcaat ttatacaata   1980
tcatccagta ccttaagccc tgattgtgta tattcatata ttttggatac gcacccccca   2040
actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340
gtagaggggt gtggctgggc ctgtcaccct ggggccctcc aggtaggccc gttttcacgt   2400
ggagcatggg agccacgacc cttcttaaga catgtatcac tgtagaggga aggaacagag   2460
gccctgggcc cttcctatca gaaggacatg gtgaaggctg ggaacgtgag gagaggcaat   2520
ggccacggcc cattttggct gtagcacatg gcacgttggc tgtgtggcct tggcccacct   2580
gtgagtttaa agcaaggctt taaatgactt tggagagggt cacaaatcct aaaagaagca   2640
ttgaagtgag gtgtcatgga ttaattgacc cctgtctatg gaattacatg taaaacatta   2700
tcttgtcact gtagtttggt tttatttgaa aacctgacaa aaaaaaagtt ccaggtgtgg   2760
aatatggggg ttatctgtac atcctggggc attaaaaaaa aaatcaatgg tggggaacta   2820
taaagaagta acaaaagaag tgacatcttc agcaaataaa ctaggaaatt tttttttctt   2880
ccagtttaga atcagccttg aaacattgat ggaataactc tgtggcatta ttgcattata   2940
taccatttat ctgtattaac tttggaatgt actctgttca atgtttaatg ctgtggttga   3000
tatttcgaaa gctgctttaa aaaaatacat gcatctcagc gttttttttgt ttttaattgt   3060
atttagttat ggcctataca ctatttgtga gcaaaggtga tcgttttctg tttgagattt   3120
ttatctcttg attcttcaaa agcattctga gaaggtgaga taagccctga gtctcagcta   3180
cctaagaaaa acctggatgt cactggccac tgaggagctt tgtttcaacc aagtcatgtg   3240
catttccacg tcaacagaat tgtttattgt gacagttata tctgttgtcc ctttgacctt   3300
gtttcttgaa ggtttcctcg tccctgggca attccgcatt taattcatgg tattcaggat   3360
tacatgcatg tttggttaaa cccatgagat tcattcagtt aaaaatccag atggcaaatg   3420
accagcagat tcaaatctat ggtggtttga cctttagaga gttgctttac gtggcctgtt   3480
tcaacacaga cccacccaga gccctcctgc cctccttccg cgggggcttt ctcatggctg   3540
tccttcaggg tcttcctgaa atgcagtggt gcttacgctc caccaagaaa gcaggaaacc   3600
tgtggtatga agccagacct ccccggcggg cctcagggaa cagaatgatc agacctttga   3660
atgattctaa tttttaagca aaatattatt ttatgaaagg tttacattgt caaagtgatg   3720
aatatggaat atccaatcct gtgctgctat cctgccaaaa tcattttaat ggagtcagtt   3780
tgcagtatgc tccacgtggt aagatcctcc aagctgcttt agaagtaaca atgaagaacg   3840
tggacgtttt taatataaag cctgttttgt cttttgttgt tgttcaaacg ggattcacag   3900
agtatttgaa aaatgtatat atattaagag gtcacggggg ctaattgctg gctggctgcc   3960
ttttgctgtg ggggttttgtt acctggtttt aataacagta aatgtgccca gcctcttggc   4020
cccagaactg tacagtattg tggctgcact tgctctaaga gtagttgatg ttgcattttc   4080
cttattgtta aaaacatgtt agaagcaatg aatgtatata aaagcctcaa ctagtcattt   4140
ttttctcctc ttcttttttt tcattatatc taattatttt gcagttgggc aacagagaac   4200
catccctatt ttgtattgaa gagggattca catctgcatc ttaactgctc tttatgaatg   4260
aaaaaacagt cctctgtatg tactcctctt tacactggcc agggtcagag ttaaatagag   4320
```

```
tatatgcact ttccaaattg gggacaaggg ctctaaaaaa agccccaaaa ggagaagaac   4380
atctgagaac ctcctcggcc ctcccagtcc ctcgctgcac aaatactccg caagagaggc   4440
cagaatgaca gctgacaggg tctatggcca tcgggtcgtc tccgaagatt tggcaggggc   4500
agaaaactct ggcaggctta agatttggaa taaagtcaca gaattaagga agcacctcaa   4560
tttagttcaa acaagacgcc aacattctct ccacagctca cttacctctc tgtgttcaga   4620
tgtggccttc catttatatg tgatctttgt tttattagta aatgcttatc atctaaagat   4680
gtagctctgg cccagtggga aaaattagga agtgattata aatcgagagg agttataata   4740
atcaagatta aatgtaaata atcagggcaa tcccaacaca tgtctagctt tcacctccag   4800
gatctattga gtgaacagaa ttgcaaatag tctctatttg taattgaact tatcctaaaa   4860
caaatagttt ataaatgtga acttaaactc taattaattc caactgtact tttaaggcag   4920
tggctgtttt tagactttct tatcacttat agttagtaat gtacacctac tctatcagag   4980
aaaaacagga aaggctcgaa atacaagcca ttctaaggaa attagggagt cagttgaaat   5040
tctattctga tcttattctg tggtgtcttt tgcagcccag acaaatgtgg ttacacactt   5100
tttaagaaat acaattctac attgtcaagc ttatgaaggt tccaatcaga tctttattgt   5160
tattcaattt ggatctttca gggatttttt ttttaaatta ttatgggaca aaggacattt   5220
gttggagggg tgggagggag gaagaatttt taaatgtaaa acattcccaa gtttggatca   5280
gggagttgga agttttcaga ataaccagaa ctaagggtat gaaggacctg tattggggtc   5340
gatgtgatgc ctctgcgaag aaccttgtgt gacaaatgag aaacattttg aagtttgtgg   5400
tacgaccttt agattccaga gacatcagca tggctcaaag tgcagctccg tttggcagtg   5460
caatggtata aatttcaagc tggatatgtc taatgggtat ttaaacaata aatgtgcagt   5520
tttaactaac aggatattta atgacaacct tctggttggt agggacatct gtttctaaat   5580
gtttattatg tacaatacag aaaaaaattt tataaaatta agcaatgtga aactgaattg   5640
gagagtgata atacaagtcc tttagtctta cccagtgaat cattctgttc catgtctttg   5700
gacaaccatg accttggaca atcatgaaat atgcatctca ctggatgcaa agaaaatcag   5760
atggagcatg aatggtactg taccggttca tctggactgc cccagaaaaa taacttcaag   5820
caaacatcct atcaacaaca aggttgttct gcataccaag ctgagcacag aagatgggaa   5880
cactggtgga ggatggaaag gctcgctcaa tcaagaaaat tctgagacta ttaataaata   5940
agactgtagt gtagatactg agtaaatcca tgcacctaaa ccttttggaa aatctgccgt   6000
gggccctcca gatagctcat ttcattaagt ttttccctcc aaggtagaat ttgcaagagt   6060
gacagtggat tgcatttctt ttggggaagc tttcttttgg tggttttgtt tattatacct   6120
tcttaagttt tcaaccaagg tttgcttttg ttttgagtta ctggggttat ttttgtttta   6180
aataaaaata agtgtacaat aagtgttttt gtattgaaag cttttgttat caagattttc   6240
atacttttac cttccatggc tctttttaag attgatactt ttaagaggtg gctgatattc   6300
tgcaacactg tacacataaa aaatacggta aggatacttt acatggttaa ggtaaagtaa   6360
gtctccagtt ggccaccatt agctataatg gcactttgtt tgtgttgttg gaaaaagtca   6420
cattgccatt aaactttcct tgtctgtcta gttaatattg tgaagaaaaa taaagtacag   6480
tgtgagatac tg                                                        6492
```

<210> SEQ ID NO 106
<211> LENGTH: 2724
<212> TYPE: DNA

-continued

<213> ORGANISM: Homo sapiens

<400> SEQUENCE: 106
cccagaaggc cgcggggggt ggaccgccta agagggcgtg cgctcccgac atgccccgcg 60
gcgcgccatt aaccgccaga tttgaatcgc gggacccgtt ggcagaggtg gcggcggcgg 120
catgggtgcc ccgacgttgc cccctgcctg gcagcccttt ctcaaggacc accgcatctc 180
tacattcaag aactggccct tcttggaggg ctgcgcctgc accccggagc ggatggccga 240
ggctggcttc atccactgcc ccactgagaa cgagccagac ttggcccagt gtttcttctg 300
cttcaaggag ctggaaggct gggagccaga tgacgacccc attgggccgg gcacggtggc 360
ttacgcctgt aataccagca ctttgggagg ccgaggcggg cggatcacga gagaggaaca 420
taaaaagcat tcgtccggtt gcgctttcct ttctgtcaag aagcagtttg aagaattaac 480
ccttggtgaa tttttgaaac tggacagaga aagagccaag aacaaaattg caaaggaaac 540
caacaataag aagaaagaat ttgaggaaac tgcggagaaa gtgcgccgtg ccatcgagca 600
gctggctgcc atggattgag gcctctggcc ggagctgcct ggtcccagag tggctgcacc 660
acttccaggg tttattccct ggtgccacca gccttcctgt gggcccctta gcaatgtctt 720
aggaaaggag atcaacattt tcaaattaga tgtttcaact gtgctcttgt tttgtcttga 780
aagtggcacc agaggtgctt ctgcctgtgc agcgggtgct gctggtaaca gtggctgctt 840
ctctctctct ctctcttttt tgggggctca tttttgctgt tttgattccc gggcttacca 900
ggtgagaagt gagggaggaa gaaggcagtg tccctttgc tagagctgac agctttgttc 960
gcgtgggcag agccttccac agtgaatgtg tctggacctc atgttgttga ggctgtcaca 1020
gtcctgagtg tggacttggc aggtgcctgt tgaatctgag ctgcaggttc cttatctgtc 1080
acacctgtgc ctcctcagag gacagttttt ttgttgttgt gtttttttgt ttttttttt 1140
ttggtagatg catgacttgt gtgtgatgag agaatggaga cagagtccct ggctcctcta 1200
ctgtttaaca acatggcttt cttattttgt ttgaattgtt aattcacaga atagcacaaa 1260
ctacaattaa aactaagcac aaagccattc taagtcattg gggaaacggg gtgaacttca 1320
ggtggatgag gagacagaat agagtgatag gaagcgtctg gcagatactc cttttgccac 1380
tgctgtgtga ttagacaggc ccagtgagcc gcggggcaca tgctggccgc tcctccctca 1440
gaaaaaggca gtggcctaaa tccttttaa atgacttggc tcgatgctgt gggggactgg 1500
ctgggctgct gcaggccgtg tgtctgtcag cccaaccttc acatctgtca cgttctccac 1560
acgggggaga gacgcagtcc gcccaggtcc ccgctttctt tggaggcagc agctcccgca 1620
gggctgaagt ctggcgtaag atgatggatt tgattcgccc tcctccctgt catagagctg 1680
cagggtggat tgttacagct tcgctggaaa cctctggagg tcatctcggc tgttcctgag 1740
aaataaaaag cctgtcattt caaacactgc tgtggaccct actgggtttt taaaatattg 1800
tcagtttttc atcgtcgtcc ctagcctgcc aacagccatc tgcccagaca gccgcagtga 1860
ggatgagcgt cctggcagag acgcagttgt ctctgggcgc ttgccagagc cacgaacccc 1920
agacctgttt gtatcatccg ggctccttcc gggcagaaac aactgaaaat gcacttcaga 1980
cccacttatt tctgccacat ctgagtcggc ctgagataga cttttccctc taaactggga 2040
gaatatcaca gtggttttg ttagcagaaa atgcactcca gcctctgtac tcatctaagc 2100
tgcttatttt tgatatttgt gtcagtctgt aaatggatac ttcactttaa taactgttgc 2160
ttagtaattg gctttgtaga gaagctggaa aaaaatggtt ttgtcttcaa ctcctttgca 2220
tgccaggcgg tgatgtggat ctcggcttct gtgagcctgt gctgtgggca gggctgagct 2280

-continued

```
ggagccgccc ctctcagccc gcctgccacg gcctttcctt aaaggccatc cttaaaacca   2340
gaccctcatg gctaccagca cctgaaagct tcctcgacat ctgttaataa agccgtaggc   2400
ccttgtctaa gtgcaaccgc ctagactttc tttcagatac atgtccacat gtccattttt   2460
caggttctct aagttggagt ggagtctggg aagggttgtg aatgaggctt ctgggctatg   2520
ggtgaggttc caatggcagg ttagagcccc tcgggccaac tgccatcctg gaaagtagag   2580
acagcagtgc ccgctgccca gaagagacca gcaagccaaa ctggagcccc cattgcaggc   2640
tgtcgccatg tggaaagagt aactcacaat tgccaataaa gtctcatgtg gttttatcta   2700
aaaaaaaaaa aaaaaaaaaa aaaa                                          2724
```

```
<210> SEQ ID NO 107
<211> LENGTH: 4934
<212> TYPE: DNA
<213> ORGANISM: Homo sapiens

<400> SEQUENCE: 107
```

```
aatgagggta tttataaact acttaaatta taaaaagaat gagacatcag acttacagtt     60
ttggatacta atttttttca cttaacgttc attatgtgat aggagttttc catcctatta    120
taccgctgtg cgatctgatc ttgggcacgt taaccaacct cttgttgcct cgattttctc    180
acctgtaaaa gtgggggtaa tcataatgct tacttagtag gatagccctg aagaataagt    240
gacttagcga acataaatag cttacaatag ggttttcagc atgggaagga ttcagtaaat    300
gttagctgtc atcatcacca cctacaaagg aagcaatact gtgctgaaag tttttccatc    360
attaatgtaa tttctatagt acgattccca agaagatatt aaaattatgg aaataaaggt    420
attggtatat tcctaattat ttcctaaaag attgtattga taaatatgct catccttccc    480
ttaacgggat gcattccaga aaaacaagtc aaatgttaga caaagtatca gaagggaaat    540
tctgtagcca gagagctaaa aattacaata gggtctctaa ttatacttca actttttttag   600
gaataattct cagtgtgttt tcccacattt catatgtaat tttttttttt tttttttttt    660
gagacagagc ctcgccctgt caccaggctg gagtacagtg gcgcgatctc ggctcactgc    720
aacttccacc tgctgggttc aagcaattct tctgacctca ggtgatccac ccgcctcggc    780
ctcccaaagt gctgggatta taacaggcgt ggcatgagtc accgcgcccg gccgatcttt    840
actttttat tctttgtacc ccctgcctat ccagttagca tgtgattaaa gtcaaagatt    900
tgccactttg ggccacatct attaattttc atctttgtta taattgtatt tagtttttga    960
tctacactgc ttattactcc cagtcatttt ttatagaact gaaaatctgg taaaatactc   1020
aaaattgcac tgacttctat gtagaggcga cactccatca gaaccgtggg ctgacaggga   1080
atcccactgt gcaggagctg cgcgcatttt catttctgat tctctttggc gtatccagga   1140
ctctgatgac atgatcatat atttatcagt agtaacaggt tgggccattt gtttttttgtg  1200
gtaaatcata tatttaagat tttagaaata agttgatagc catgtatttt ggaatttgaa   1260
aaagacattg cattactcag cttcaaatta agctttaatc aaatagtgaa actttccatt   1320
aatggacagt gtatacctttt ttgtgtattt aaaaaaaaaa acactgaata tagtgccttt  1380
gtgacagggg agcttggttc ctgacaatgt cctcttgagc cttttttttt tttttgagat   1440
ggagtctcac tgtgtcaccc aggctggagt gcagtggcgc catcttggct cactgcaacc   1500
tccgcccccct gggttcaagt gattctcatt cctcagcttc ctaagtagct gggattacag  1560
gcacgcacca ccatgaccag ctaattttta tacttttagt agagacaggg ttttgccatg   1620
```

-continued

```
ttggctaggt tggtctcgaa ctcctgacct caagtaatcc acccaccatg gcctccccaa   1680
agtgctggga ttacaggcgt gagccatttc acccggcctc tcttccgtct ttgagctgtg   1740
aggaaatagc tacattacat gagctgctag atctgcctta tggtcagaaa tgaaggttga   1800
actctcagga acagtgacat atatacacac tgatatttcc aaagtacaat gccccaaatt   1860
gatccacaaa ggaattaagg tcatttgcaa caaaatcaca gaatagtaac aaataaatag   1920
aagataaata tggccaggga tgctgcaaac tgatatactg ccaagtttat cagttgggaa   1980
tcccaacagt gaaaagcata aaaatgaaag gaattttaag gagacttttt atagaagagt   2040
gggaaggatt ggaggagcca acaagtgatg gtgaggcaca cagggaagag cttcagtggg   2100
caccatcccc tctctggttt gaaggggtag ggaggggacc agagctggga ggagggggct   2160
ggaatactgc tggaggagcc actcccttcc agacctgctg tggccatcac agaatgcagc   2220
cactgccaga gcagcagccc gaggaaccag gcagggggag cacaagtacc ctagcctctc   2280
tctttctgtt tcttgcctgc cgatctcctc cactggctaa acccagctgg atgctaagag   2340
tacagtcagc ctgcctgctg aggagggacc accagggacc accatcagca agggatccaa   2400
tgtctttctg cctctgcaga atgaaggttg gggcgcgggg ggcgctctac ttcttaggga   2460
tattgtggga ataaaaggaa ataggcaaaa aatgtttttg aaaaacaaag cacatactgc   2520
gcacccgtgg gccactactg cttttgaccc ctggctctgt ttcatgaagt aatgtcgtgt   2580
cattctcttt ttaggtgcta caggatttct ttaggtttgt tttctgtcca ccatatttca   2640
actcatgtgt gctgtttgtt gtgctaaaac aaatatttgc tgatgcctga gtgaatagtt   2700
gaatatttta tataagtcaa atttatacgt aatgattttt cttgtaactt agccgtttct   2760
cttttacaaa ctcagaaaac ctcagacttt gaaaaggcct tgaagttcct cacctgaaat   2820
ctgagaactt ggagcgcctt aaaaaatcta aaggaaaaca aaacagtgaa agaacatgat   2880
atagtcagtg tagagaataa aattatttat gtaattaata ttgaggatgc agataacaca   2940
ttgtgaaatc ttgcttgtaa aaaatctcga tctgctgaag aaagatgttc tctctagaga   3000
tctttgaaag cataattatt gagcttttaa aatgttagaa acaaaagtta gacccacaca   3060
tattctggcg tgtggaagat ttgcattcct tcccctgccc gccccgcccc cacacttgtg   3120
agttgtgcct gtgtacgcag ttcctgtagc actcggctgg gcagaaatca tctttcagca   3180
ctaagggaac atagttatga tctggacctt ctgggagtgg tcagtgccca agaacaggta   3240
tgggactcca gaaagttctg ctctcaaccc tattttgaaa tagagttaca cattgttcta   3300
caattatttg agttaataag cagctctttt caaacgtgat tatgcccttc caagtttaaa   3360
tacactagac tttagtgaaa gtaattgacc tcatctcatt tctctcctgt tatattaaga   3420
tcactttcag taaaaggtag aagcttttga agtggtgagg aggaggtaga ggagggacat   3480
agagcagata ggggctggaa agtggggtga ggaagagagt ggcttctctt tggcagagta   3540
ccaaggaaaa gccctatctg tacagaacct ttgtgcctgg gaacttgatg gctgcaacct   3600
gagcctcaac ctagtttgct tgcggagcca gaagagaagc taaaaacctt cagttaacca   3660
agccagacac caagaaagtt aaaccgaaag agaacccccc accccccgca aaaaaaagaa   3720
gtaaagtggg ttaaagtgat atcatgttag cacagaaaga gaacataagg gtcatctaag   3780
ttcatctgcc ccctcttcta tttcaaggtg cagaaactaa ggcacaaggg accccgtgtc   3840
ctgctcttga tcacatagct agtgggtgcc aagccaggtc tagaactctg ttctctgggg   3900
tcacaggctg gctcttcatc cctctagaga gatagctcat ctgtgtgcac ctgagcccgt   3960
tgtgtttcgg agtcaaagca aataaaggct caaactccaa gactgttttg cagaccggct   4020
```

```
gcagtagata tggggggagg agaaacctgc tttaaattgc ttcaagcaag ttgtttctgc   4080
aaaggtgttg actttttttct ttcaactttc tagtgagtca ctgcagcctg agctgttatt   4140
tgtcattatg caataattca ggaactaact caagattctt ctttttaaat tatttgttta   4200
tttagagaca gagtcttgct ctgttgccca ggctggagtg cagtggtgtg atctcggctc   4260
actgcagcct ctgcctcctg ggttcaagca attctcatgt ctcagcctcc cgaatagctg   4320
gtattgcagg ctcgtgccac caccccctgc taatttttgt aattttagtg gagacacggt   4380
ttcgccatgt tggccgggct cgtcttgagc tcctggcctc aggtgatccg cccgcctcgg   4440
cctcccaaag tgctgggatt gcagccgtga gcctccacac ccggcctatt tatttatttt   4500
taaattggct gctcttagaa aggcatacca tgtttctgga tgggaaggct tattaattca   4560
ccctaattta atgtataaat ttgatgcaat catagtcaca gtcccagtgg aatttttttaa  4620
cttggtaaga tgttctaaaa ttaatgagag aacttgaatt accaggtatt gaaacactgt   4680
aaagccacaa tcatgtaaac agtatgttat aaccatggga atagaggtct gtgatacagc   4740
agaaaaaagt gaaaaaaaga ataactgtat tcataaaaat ttaaatgtgg agtcactggg   4800
ggaaaggatt aaatattcga taatgtagaa acaactcaac tatttggaga aatgtaaatt   4860
tagagcctta tctcatgcca tataccaaaa tactatttag atttgattaa aaaataaaaa   4920
aaaaaaaaaa aaaa                                                     4934
```

<210> SEQ ID NO 108
<211> LENGTH: 2177
<212> TYPE: DNA
<213> ORGANISM: Homo sapiens

<400> SEQUENCE: 108

```
cgaacgcctt cgcgcgatcg ccctggaaac gcattctctg cgaccggcag ccgccaatgg     60
gaagggagtg agtgccacga acaggccaat aaggagggag cagtgcgggg tttaaatctg    120
aggctaggct ggctcttctc ggcgtgctgc ggcggaacgg ctgttggttt ctgctgggtg    180
taggtccttg gctggtcggg cctccggtgt tctgcttctc cccgctgagc tgctgcctgg    240
tgaagaggaa gccatggcgc tccgagtcac caggaactcg aaaattaatg ctgaaaataa    300
ggcgaagatc aacatggcag gcgcaaagcg cgttcctacg gcccctgctg caacctccaa    360
gcccggactg aggccaagaa cagctcttgg ggacattggt aacaaagtca gtgaacaact    420
gcaggccaaa atgcctatga agaaggaagc aaaaccttca gctactggaa aagtcattga    480
taaaaaacta ccaaaacctc ttgaaaaggt acctatgctg gtgccagtgc cagtgtctga    540
gccagtgcca gagccagaac ctgagccaga acctgagcct gttaaagaag aaaaactttc    600
gcctgagcct attttggttg atactgcctc tccaagccca atggaaacat ctggatgtgc    660
ccctgcagaa gaagacctgt gtcaggcttt ctctgatgta attcttgcag taaatgatgt    720
ggatgcagaa gatggagctg atccaaacct ttgtagtgaa tatgtgaaag atatttatgc    780
ttatctgaga caacttgagg aagagcaagc agtcagacca aaatacctac tgggtcggga    840
agtcactgga aacatgagag ccatcctaat tgactggcta gtacaggttc aaatgaaatt    900
caggttgttg caggagacca tgtacatgac tgtctccatt attgatcggt tcatgcagaa    960
taattgtgtg cccaagaaga tgctgcagct ggttggtgtc actgccatgt ttattgcaag   1020
caaatatgaa gaaatgtacc ctccagaaat tggtgacttt gcttttgtga ctgacaacac   1080
ttatactaag caccaaatca gacagatgga aatgaagatt ctaagagctt taaactttgg   1140
```

tctgggtcgg cctctacctt tgcacttcct tcggagagca tctaagattg gagaggttga 1200
tgtcgagcaa catactttgg ccaaatacct gatggaacta actatgttgg actatgacat 1260
ggtgcacttt cctccttctc aaattgcagc aggagctttt tgcttagcac tgaaaattct 1320
ggataatggt gaatggacac caactctaca acattacctg tcatatactg aagaatctct 1380
tcttccagtt atgcagcacc tggctaagaa tgtagtcatg gtaaatcaag gacttacaaa 1440
gcacatgact gtcaagaaca agtatgccac atcgaagcat gctaagatca gcactctacc 1500
acagctgaat tctgcactag ttcaagattt agccaaggct gtggcaaagg tgtaacttgt 1560
aaacttgagt tggagtacta tatttacaaa taaaattggc accatgtgcc atctgtacat 1620
attactgttg catttacttt taataaagct tgtggcccct tttacttttt tatagcttaa 1680
ctaatttgaa tgtggttact tcctactgta gggtagcgga aaagttgtct taaaaggtat 1740
ggtggggata tttttaaaaa ctccttttgg tttacctggg gatccaattg atgtatatgt 1800
ttatatactg ggttcttgtt ttatatacct ggcttttact ttattaatat gagttactga 1860
aggtgatgga ggtatttgaa aattttactt ccataggaca tactgcatgt aagccaagtc 1920
atggagaatc tgctgcatag ctctatttta aagtaaaagt ctaccaccga atccctagtc 1980
cccctgtttt ctgtttcttc ttgtgattgc tgccataatt ctaagttatt tacttttacc 2040
actatttaag ttatcaactt tagctagtat cttcaaactt tcactttgaa aaatgagaat 2100
tttatattct aagccagttt tcattttggt tttgtgtttt ggttaataaa acaatactca 2160
aatacaaaaa aaaaaaa 2177

<210> SEQ ID NO 109

<400> SEQUENCE: 109

000

<210> SEQ ID NO 110
<211> LENGTH: 2011
<212> TYPE: DNA
<213> ORGANISM: Homo sapiens

<400> SEQUENCE: 110
gcggccgcca gcgcggtgta gggggcaggc gcggatcccg ccaccgccgc gcgctcggcc 60
cgccgactcc cggcgccgcc gccgccactg ccgtcgccgc cgccgcctgc cgggactgga 120
gcgcgccgtc cgccgcggac aagaccctgg cctcaggccg gagcagcccc atcatgccga 180
gggagcgcag ggagcgggat gcgaaggagc gggacaccat gaaggaggac ggcggcgcgg 240
agttctcggc tcgctccagg aagaggaagg caaacgtgac cgttttttttg caggatccag 300 atgaagaaat ggccaaaatc gacaggacgg cgagggacca gtgtgggagc cagccttggg 360
acaataatgc agtctgtgca gacccctgct ccctgatccc cacacctgac aaagaagatg 420
atgaccgggt ttacccaaac tcaacgtgca agcctcggat tattgcacca tccagaggct 480
ccccgctgcc tgtactgagc tgggcaaata gagaggaagt ctggaaaatc atgttaaaca 540
aggaaaagac atacttaagg gatcagcact ttcttgagca acaccctctt ctgcagccaa 600
aaatgcgagc aattcttctg gattggttaa tggaggtgtg tgaagtctat aaacttcaca 660
gggagacctt ttacttggca caagatttct ttgaccggta tatggcgaca caagaaaatg 720
ttgtaaaaac tcttttacag cttattggga tttcatcttt atttattgca gccaaacttg 780
aggaaatcta tcctccaaag ttgcaccagt ttgcgtatgt gacagatgga gcttgttcag 840

```
gagatgaaat tctcaccatg gaattaatga ttatgaaggc ccttaagtgg cgtttaagtc    900
ccctgactat tgtgtcctgg ctgaatgtat acatgcaggt tgcatatcta aatgacttac    960
atgaagtgct actgccgcag tatccccagc aaatctttat acagattgca gagctgttgg   1020
atctctgtgt cctggatgtt gactgccttg aatttcctta tggtatactt gctgcttcgg   1080
ccttgtatca tttctcgtca tctgaattga tgcaaaaggt ttcagggtat cagtggtgcg   1140
acatagagaa ctgtgtcaag tggatggttc catttgccat ggttataagg gagacgggga   1200
gctcaaaact gaagcacttc aggggcgtcg ctgatgaaga tgcacacaac atacagaccc   1260
acagagacag cttggatttg ctggacaaag cccgagcaaa gaaagccatg ttgtctgaac   1320
aaaatagggc ttctcctctc cccagtgggc tcctcacccc gccacagagc ggtaagaagc   1380
agagcagcgg gccggaaatg gcgtgaccac cccatccttc tccaccaaag acagttgcgc   1440
gcctgctcca cgttctcttc tgtctgttgc agcggaggcg tgcgtttgct tttacagata   1500
tctgaatgga agagtgtttc ttccacaaca gaagtatttc tgtggatggc atcaaacagg   1560
gcaaagtgtt ttttattgaa tgcttatagg tttttttaa ataagtgggt caagtacacc   1620
agccacctcc agacaccagt gcgtgctccc gatgctgcta tggaaggtgc tacttgacct   1680
aagggactcc cacaacaaca aaagcttgaa gctgtggagg gccacggtgg cgtggctctc   1740
ctcgcaggtg ttctgggctc cgttgtacca agtggagcag gtggttgcgg gcaagcgttg   1800
tgcagagccc atagccagct gggcaggggg ctgccctctc cacattatca gttgacagtg   1860
tacaatgcct ttgatgaact gttttgtaag tgctgctata tctatccatt ttttaataaa   1920
gataatactg tttttgaaaa aaaaaaaaaa aaaaaaaaaa aaaaaaaaaa aaaaaaaaaa   1980
aaaaaaaaaa aaaaaaaaaa aaaaaaaaaa a                                  2011
```

<210> SEQ ID NO 111
<211> LENGTH: 1737
<212> TYPE: DNA
<213> ORGANISM: Homo sapiens

<400> SEQUENCE: 111

```
gagggcacgg gctccgtagg caccaactgc aaggacccct ccccctgcgg gcgctcccat     60
ggcacagttc gcgttcgaga gtgacctgca ctcgctgctt cagctggatg cacccatccc    120
caatgcaccc cctgcgcgct ggcagcgcaa agccaaggaa gccgcaggcc cggccccctc    180
acccatgcgg gccgccaacc gatcccacag cgccggcagg actccgggcc gaactcctgg    240
caaatccagt tccaaggttc agaccactcc tagcaaacct ggcggtgacc gctatatccc    300
ccatcgcagt gctgcccaga tggaggtggc cagcttcctc ctgagcaagg agaaccagcc    360
tgaaaacagc cagacgccca ccaagaagga acatcagaaa gcctgggctt tgaacctgaa    420
cggttttgat gtagaggaag ccaagatcct tcggctcagt ggaaaaacca caaaaatgcg    480
ccagagggtt atcacgaaca gactgaaagt actctacagc caaaaggcca ctcctggctc    540
cagccggaag acctgccgtt tacattcctt ccctgccaag accgtatcct ggatgcgcct    600
gaaatcgaat gactattaac tgaacctgtg ggactggcag tccggggaat gtccgggccg    660
ggccacggcc acgaggtgtt ccgtgtggag tgcaagctgg gacacaccgt gccgcttgtg    720
cacagggcca cgcggggaaa taatcccggg gcgcgcaaag cggcactggc gagagccgca    780
cgggccggtg ctgggggtgg tacaacaggc caaaacaaca cacaaggcca acaagacata    840
cgcgcgctga caccacggtg caaagcgctc agacgagtag taaccggcac tgtggttgct    900
gcctccccac ctctcccgct ctcagcgtaa gataaaagaa agaagagcaa aaagcaaaga    960
```

```
aagaagacga gacgagacac acaggaacga acagtaaagc aagctaaagc aaacgcaaga   1020
ccagacaaca gaaatagaaa gaaccaacag agaggagaca gaacaggacg ccagcaacat   1080
agcaacaaac gaacagaaga gagcactaaa caaaagcagc agcaagacga gacaggagag   1140
aaggaggaag gagggccgag cgagcaggga gcgcgagcag cgaggcgaag cagcagacaa   1200
gggcaggcga agggcaacga gaggaggcac cacacaaaaa ggagagggga caggagaagc   1260
agcgagagaa gcggaggagc aacaagagga agaaaaggag agggagagga gggagagagc   1320
ggaaggagga agaaacagca cgaggcgacg aaggggggag acgcgggggc aggaaaagac   1380
acaggaaggc agcgcggagg aggagaaggg gaagcaggaa ggagacggaa ggagaagagg   1440
gagaggacag cgcaagagag cgcgcgcggc gacagcgagg gacggagcga gagagaggaa   1500
acggaaagcg agagggaaga ggagaggcaa cgcagcgaac caaccgaaaa cagcagaaag   1560
agaggagaag gacgcgcaaa gaggcaagcg caagacgaca ggaaacgaag cgagagacga   1620
gaagccggtg acgagcagga gaaagggaag gcaggagaca ggacaggcgg aagagagaca   1680
cgcgagacgc aaagagtgag cagaacgaag cgaagagcaa cgcacgagag aaacgac      1737
```

<210> SEQ ID NO 112
<211> LENGTH: 3053
<212> TYPE: DNA
<213> ORGANISM: Homo sapiens

<400> SEQUENCE: 112

```
gagcgcggct ggagtttgct gctgccgctg tgcagtttgt tcaggggctt gtggtggtga     60
gtccgagagg ctgcgtgtga gagacgtgag aaggatcctg cactgaggag gtggaaagaa    120
gaggattgct cgaggaggcc tggggtctgt gaggcagcgg agctgggtga aggctgcggg    180
ttccggcgag gcctgagctg tgctgtcgtc atgcctcaaa cccgatccca ggcacaggct    240
acaatcagtt ttccaaaaag gaagctgtct cgggcattga acaaagctaa aaactccagt    300
gatgccaaac tagaaccaac aaatgtccaa accgtaacct gttctcctcg tgtaaaagcc    360
ctgcctctca gccccaggaa acgtctgggc gatgacaacc tatgcaacac tccccattta    420
cctccttgtt ctccaccaaa gcaaggcaag aaagagaatg gtccccctca ctcacataca    480
cttaagggac gaagattggt atttgacaat cagctgacaa ttaagtctcc tagcaaaaga    540
gaactagcca aagttcacca aaacaaaata ctttcttcag ttagaaaaag tcaagagatc    600
acaacaaatt ctgagcagag atgtccactg aagaaagaat ctgcatgtgt gagactattc    660
aagcaagaag gcacttgcta ccagcaagca aagctggtcc tgaacacagc tgtcccagat    720
cggctgcctg ccagggaaag ggagatggat gtcatcagga atttcttgag ggaacacatc    780
tgtgggaaaa aagctggaag cctttacctt tctggtgctc ctggaactgg aaaaactgcc    840
tgcttaagcc ggattctgca agacctcaag aaggaactga aaggctttaa aactatcatg    900
ctgaattgca tgtccttgag gactgcccag gctgtattcc cagctattgc tcaggagatt    960
tgtcaggaag aggtatccag gccagctggg aaggacatga tgaggaaatt ggaaaaacat   1020
atgactgcag agaagggccc catgattgtg ttggtattgg acgagatgga tcaactggac   1080
agcaaaggcc aggatgtatt gtacacgcta tttgaatggc catggctaag caattctcac   1140
ttggtgctga ttggtattgc taataccctg gatctcacag atagaattct acctaggctt   1200
caagctagag aaaaatgtaa gccacagctg ttgaacttcc caccttatac cagaaatcag   1260
atagtcacta ttttgcaaga tcgacttaat caggtatcta gagatcaggt tctggacaat   1320
```

-continued gctgcagttc aattctgtgc ccgcaaagtc tctgctgttt caggagatgt tcgcaaagca 1380
ctggatgttt gcaggagagc tattgaaatt gtagagtcag atgtcaaaag ccagactatt 1440
ctcaaaccac tgtctgaatg taaatcacct tctgagcctc tgattcccaa gagggttggt 1500
cttattcaca tatcccaagt catctcagaa gttgatggta acaggatgac cttgagccaa 1560
gaaggagcac aagattcctt ccctcttcag cagaagatct tggtttgctc tttgatgctc 1620
ttgatcaggc agttgaaaat caaagaggtc actctgggga agttatatga agcctacagt 1680
aaagtctgtc gcaaacagca ggtggcggct gtggaccagt cagagtgttt gtcactttca 1740
gggctcttgg aagccagggg cattttagga ttaaagagaa acaaggaaac ccgtttgaca 1800
aaggtgtttt tcaagattga agagaaagaa atagaacatg ctctgaaaga taaagcttta 1860
attggaaata tcttagctac tggattgcct taaattcttc tcttacaccc cacccgaaag 1920
tattcagctg gcatttagag agctacagtc ttcattttag tgctttacac attcgggcct 1980
gaaaacaaat atgacctttt ttacttgaag ccaatgaatt ttaatctata gattctttaa 2040
tattagcaca gaataatatc tttgggtctt actattttta cccataaaag tgaccaggta 2100 gaccctttt aattacattc actacttcta ccacttgtgt atctctagcc aatgtgcttg 2160
caagtgtaca gatctgtgta gaggaatgtg tgtatattta cctcttcgtt tgctcaaaca 2220
tgagtgggta ttttttgtt tgtttttttt gttgttgttg tttttgaggc gcgtctcacc 2280
ctgttgccca ggctggagtg caatggcgcg ttctctgctc actacagcac ccgcttccca 2340
ggttgaagtg attctcttgc ctcagcctcc cgagtagctg ggattacagg tgcccaccac 2400
cgcgcccagc taattttta atttttagta gagacagggt tttaccatgt tggccaggct 2460
ggtcttgaac tcctgaccct caagtgatct gcccaccttg gcctccctaa gtgctgggat 2520
tataggcgtg agccaccatg ctcagccatt aaggtatttt gttaagaact ttaagtttag 2580
ggtaagaaga atgaaaatga tccagaaaaa tgcaagcaag tccacatgga gatttggagg 2640
acactggtta aagaatttat ttctttgtat agtatactat gttcatggtg cagatactac 2700
aacattgtgg cattttagac tcgttgagtt tcttgggcac tcccaagggc gttggggtca 2760
taaggagact ataactctac agattgtgaa tatatttatt ttcaagttgc attctttgtc 2820
tttttaagca atcagatttc aagagagctc aagctttcag aagtcaatgt gaaaattcct 2880
tcctaggctg tcccacagtc tttgctgccc ttagatgaag ccacttgttt caagatgact 2940
actttggggt tgggttttca tctaaacaca tttttccagt cttattagat aaattagtcc 3000
atatggttgg ttaatcaaga gccttctggg tttggtttgg tggcattaaa tgg 3053

<210> SEQ ID NO 113
<211> LENGTH: 1843
<212> TYPE: DNA
<213> ORGANISM: Homo sapiens

<400> SEQUENCE: 113
gcggaatggg gcgggacttc cagtaggagg cggcaagttt gaaaagtgat gacggttgac 60
gtttgctgat ttttgacttt gcttgtagct gctccccgaa ctcgccgtct tcctgtcggc 120
ggccggcact gtagattaac aggaaacttc caagatggaa actttgtctt tccccagata 180
taatgtagct gagattgtga ttcatattcg caataagatc ttaacaggag ctgatggtaa 240
aaacctcacc aagaatgatc tttatccaaa tccaaagcct gaagtcttgc acatgatcta 300
catgagagcc ttacaaatag tatatggaat tcgactggaa catttttaca tgatgccagt 360
gaactctgaa gtcatgtatc cacatttaat ggaaggcttc ttaccattca gcaatttagt 420
tactcatctg gactcatttt tgcctatctg ccgggtgaat gactttgaga ctgctgatat 480
tctatgtcca aaagcaaaac ggacaagtcg gtttttaagt ggcattatca actttattca 540
cttcagagaa gcatgccgtg aaacgtatat ggaatttctt tggcaatata aatcctctgc 600
ggacaaaatg caacagttaa acgccgcaca ccaggaggca ttaatgaaac tggagagact 660
tgattctgtt ccagttgaag agcaagaaga gttcaagcag ctttcagatg gaattcagga 720
gctacaacaa tcactaaatc aggattttca tcaaaaaacg atagtgctgc aagagggaaa 780
ttcccaaaag aagtcaaata tttcagagaa aaccaagcgt ttgaatgaac taaaattgtc 840
ggtggtttct ttgaaagaaa tacaagagag tttgaaaaca aaaattgtgg attctccaga 900
gaagttaaag aattataaag aaaaaatgaa agatacggtc cagaagctta aaaatgccag 960
acaagaagtg gtggagaaat atgaaatcta tggagactca gttgactgcc tgccttcatg 1020
tcagttggaa gtgcagttat atcaaaagaa aatacaggac ctttcagata atagggaaaa 1080
attagccagt atcttaaagg agagcctgaa cttggaggac caaattgaga gtgatgagtc 1140
agaactgaag aaattgaaga ctgaagaaaa ttcgttcaaa agactgatga ttgtgaagaa 1200
ggaaaaactt gccacagcac aattcaaaat aaataagaag catgaagatg ttaagcaata 1260
caaacgcaca gtaattgagg attgcaataa agttcaagaa aaaagaggtg ctgtctatga 1320
acgagtaacc acaattaatc aagaaatcca aaaaattaaa cttggaattc aacaactaaa 1380
agatgctgct gaaagggaga aactgaagtc ccaggaaata tttctaaact tgaaaactgc 1440
tttggagaaa taccacgacg gtattgaaaa ggcagcagag gactcctatg ctaagataga 1500
tgagaagaca gctgaactga agaggaagat gttcaaaatg tcaacctgat taacaaaatt 1560
acatgtcttt ttgtaaatgg cttgccatct tttaattttc tatttagaaa gaaaagttga 1620
agcgaatgga agtatcagaa gtaccaaata atgttggctt catcagtttt tatacactct 1680
cataagtagt taataagatg aatttaatgt aggcttttat taatttataa ttaaaataac 1740
ttgtgcagct attcatgtct ctactctgcc ccttgttgta aatagtttga gtaaaacaaa 1800
actagttacc tttgaaatat atatattttt ttctgttact atc 1843

<210> SEQ ID NO 114
<211> LENGTH: 3686
<212> TYPE: DNA
<213> ORGANISM: Homo sapiens

<400> SEQUENCE: 114
ggctagcgcg ggaggtggag aaagaggctt gggcggcccc gctgtagccg cgtgtgggag 60
gacgcacggg cctgcttcaa agctttggga taacagcgcc tccgggggat aatgaatgcg 120
gagcctccgt tttcagtcga cttcagatgt gtctccactt ttttccgctg tagccgcaag 180
gcaaggaaac atttctcttc ccgtactgag gaggctgagg agtgcactgg gtgttctttt 240
ctcctctaac ccagaactgc gagacagagg ctgagtccct gtaaagaaca gctccagaaa 300
agccaggaga gcgcaggagg gcatccggga ggccaggagg ggttcgctgg ggcctcaacc 360
gcacccacat cggtcccacc tgcgaggggg cgggacctcg tggcgctgga ccaatcagca 420
cccacctgcg ctcacctggc ctcctcccgc tggctcccgg gggctgcggt gctcaaaggg 480
gcaagagctg agcggaacac cggcccgccg tcgcggcagc tgcttcaccc ctctctctgc 540
agccatgggg ctccctcgtg gacctctcgc gtctctcctc cttctccagg tttgctggct 600
gcagtgcgcg gcctccgagc cgtgccgggc ggtcttcagg gaggctgaag tgaccttgga 660

-continued

```
ggcgggaggc gcggagcagg agcccggcca ggcgctgggg aaagtattca tgggctgccc    720
tgggcaagag ccagctctgt ttagcactga taatgatgac ttcactgtgc ggaatggcga    780
gacagtccag gaaagaaggt cactgaagga aaggaatcca ttgaagatct tcccatccaa    840
acgtatctta cgaagacaca agagagattg ggtggttgct ccaatatctg tccctgaaaa    900
tggcaagggt cccttccccc agagactgaa tcagctcaag tctaataaag atagagacac    960
caagattttc tacagcatca cggggccggg ggcagacagc ccccctgagg gtgtcttcgc   1020
tgtagagaag gagacaggct ggttgttgtt gaataagcca ctggaccggg aggagattgc   1080
caagtatgag ctctttggcc acgctgtgtc agagaatggt gcctcagtgg aggaccccat   1140
gaacatctcc atcatagtga ccgaccagaa tgaccacaag cccaagttta cccaggacac   1200
cttccgaggg agtgtcttag agggagtcct accaggtact tctgtgatgc agatgacagc   1260
cacagatgag gatgatgcca tctacaccta caatggggtg gttgcttact ccatccatag   1320
ccaagaacca aaggacccac acgacctcat gttcacaatt caccggagca caggcaccat   1380
cagcgtcatc tccagtggcc tggaccggga aaaagtccct gagtacacac tgaccatcca   1440
ggccacagac atggatgggg acggctccac caccacggca gtggcagtag tggagatcct   1500
tgatgccaat gacaatgctc ccatgtttga cccccagaag tacgaggccc atgtgcctga   1560
gaatgcagtg ggccatgagg tgcagaggct gacggtcact gatctggacg cccccaactc   1620
accagcgtgg cgtgccacct accttatcat gggcggtgac gacggggacc attttaccat   1680
caccacccac cctgagagca accagggcat cctgacaacc aggaagggtt tggattttga   1740
ggccaaaaac cagcacaccc tgtacgttga agtgaccaac gaggcccctt ttgtgctgaa   1800
gctcccaacc tccacagcca ccatagtggt ccacgtggag gatgtgaatg aggcacctgt   1860
gtttgtccca ccctccaaag tcgttgaggt ccaggagggc atccccactg gggagcctgt   1920
gtgtgtctac actgcagaag accctgacaa ggagaatcaa aagatcagct accgcatcct   1980
gagagaccca gcagggtggc tagccatgga cccagacagt gggcaggtca cagctgtggg   2040
caccctcgac cgtgaggatg agcagtttgt gaggaacaac atctatgaag tcatggtctt   2100
ggccatggac aatggaagcc ctcccaccac tggcacggga acccttctgc taacactgat   2160
tgatgtcaac gaccatggcc cagtccctga gccccgtcag atcaccatct gcaaccaaag   2220
ccctgtgcgc caggtgctga acatcacgga caaggacctg tctccccaca cctcccctttt   2280
ccaggcccag ctcacagatg actcagacat ctactggacg gcagaggtca acgaggaagg   2340
tgacacagtg gtcttgtccc tgaagaagtt cctgaagcag gatacatatg acgtgcacct   2400
ttctctgtct gaccatggca acaaagagca gctgacggtg atcagggcca ctgtgtgcga   2460
ctgccatggc catgtcgaaa cctgccctgg accctggaaa ggaggtttca tcctccctgt   2520
gctgggggct gtcctggctc tgctgttcct cctgctggtg ctgcttttgt tggtgagaaa   2580
gaagcggaag atcaaggagc ccctcctact cccagaagat gacacccgtg acaacgtctt   2640
ctactatggc gaagaggggg gtggcgaaga ggaccaggac tatgacatca cccagctcca   2700
ccgaggtctg gaggccaggc cggaggtggt tctccgcaat gacgtggcac caaccatcat   2760
cccgacaccc atgtaccgtc ctaggccagc caacccagat gaaatcggca actttataat   2820
tgagaacctg aaggcggcta acacagaccc cacagccccg ccctacgaca ccctcttggt   2880
gttcgactat gagggcagcg gctccgacgc cgcgtccctg agctccctca cctcctccgc   2940
ctccgaccaa gaccaagatt acgattatct gaacgagtgg ggcagccgct tcaagaagct   3000
ggcagacatg tacggtggcg gggaggacga ctaggcggcc tgcctgcagg gctggggacc   3060
```

aaacgtcagg ccacagagca tctccaaggg gtctcagttc cccttcagc tgaggacttc 3120 ggagcttgtc aggaagtggc cgtagcaact tggcggagac aggctatgag tctgacgtta 3180
gagtggttgc ttccttagcc tttcaggatg gaggaatgtg ggcagtttga cttcagcact 3240
gaaaacctct ccacctgggc cagggttgcc tcagaggcca agtttccaga agcctcttac 3300
ctgccgtaaa atgctcaacc ctgtgtcctg ggcctgggcc tgctgtgact gacctacagt 3360
ggactttctc tctggaatgg aaccttctta ggcctcctgg tgcaacttaa ttttttttt 3420 taatgctatc ttcaaaacgt tagagaaagt tcttcaaaag tgcagcccag agctgctggg 3480
cccactggcc gtcctgcatt tctggtttcc agaccccaat gcctcccatt cggatggatc 3540
tctgcgtttt tatactgagt gtgcctaggt tgccccttat tttttatttt ccctgttgcg 3600
ttgctataga tgaagggtga ggacaatcgt gtatatgtac tagaactttt ttattaaaga 3660
aacttttccc aaaaaaaaaa aaaaaa 3686

<210> SEQ ID NO 115
<211> LENGTH: 10316
<212> TYPE: DNA
<213> ORGANISM: Homo sapiens

<400> SEQUENCE: 115
gagaccagaa gcgggcgaat tgggcaccgg tggcggctgc gggcagtttg aattagactc 60
tgggctccag cccgccgaag ccgcgccaga actgtactct ccgagaggtc gttttcccgt 120
ccccgagagc aagtttattt acaaatgttg gagtaataaa gaaggcagaa caaaatgagc 180
tgggctttgg aagaatggaa agaagggctg cctacaagag ctcttcagaa aattcaagag 240
cttgaaggac agcttgacaa actgaagaag gaaaagcagc aaaggcagtt tcagcttgac 300
agtctcgagg ctgcgctgca gaagcaaaaa cagaaggttg aaaatgaaaa aaccgagggt 360
acaaacctga aaagggagaa tcaaagattg atggaaatat gtgaaagtct ggagaaaact 420
aagcagaaga tttctcatga acttcaagtc aaggagtcac aagtgaattt ccaggaagga 480
caactgaatt caggcaaaaa acaaatagaa aaactggaac aggaacttaa aaggtgtaaa 540
tctgagcttg aaagaagcca acaagctgcg cagtctgcag atgtctctct gaatccatgc 600
aatacaccac aaaaaatttt tacaactcca ctaacaccaa gtcaatatta tagtggttcc 660
aagtatgaag atctaaaaga aaaatataat aaagaggttg aagaacgaaa aagattagag 720
gcagaggtta aagccttgca ggctaaaaaa gcaagccaga ctcttccaca agccaccatg 780
aatcaccgcg acattgcccg gcatcaggct tcatcatctg tgttctcatg gcagcaagag 840
aagaccccaa gtcatctttc atctaattct caaagaactc caattaggag agatttctct 900
gcatcttact tttctgggga acaagaggtg actccaagtc gatcaacttt gcaaataggg 960
aaaagagatg ctaatagcag tttctttgac aattctagca gtcctcatct tttggatcaa 1020
ttaaaagcgc agaatcaaga gctaagaaac aagattaatg agttggaact acgcctgcaa 1080
ggacatgaaa aagaaatgaa aggccaagtg aataagtttc aagaactcca actccaactg 1140
gagaaagcaa aagtggaatt aattgaaaaa gagaaagttt tgaacaaatg tagggatgaa 1200
ctagtgagaa caacagcaca atacgaccag gcgtcaacca agtatactgc attggaacaa 1260
aaactgaaaa aattgacgga agatttgagt tgtcagcgac aaaatgcaga aagtgccaga 1320
tgttctctgg aacagaaaat taaggaaaaa gaaaaggagt ttcaagagga gctctcccgt 1380
caacagcgtt ctttccaaac actggaccag gagtgcatcc agatgaaggc cagactcacc 1440

-continued

```
caggagttac agcaagccaa gaatatgcac aacgtcctgc aggctgaact ggataaactc   1500
acatcagtaa agcaacagct agaaaacaat ttggaagagt ttaagcaaaa gttgtgcaga   1560
gctgaacagg cgttccaggc gagtcagatc aaggagaatg agctgaggag aagcatggag   1620
gaaatgaaga aggaaaacaa cctccttaag agtcactctg agcaaaaggc cagagaagtc   1680
tgccacctgg aggcagaact caagaacatc aaacagtgtt taaatcagag ccagaatttt   1740
gcagaagaaa tgaaagcgaa gaatacctct caggaaacca tgttaagaga tcttcaagaa   1800
aaaataaatc agcaagaaaa ctccttgact ttagaaaaac tgaagcttgc tgtggctgat   1860
ctggaaaagc agcgagattg ttctcaagac cttttgaaga aaagagaaca tcacattgaa   1920
caacttaatg ataagttaag caagacagag aaagagtcca aagccttgct gagtgcttta   1980
gagttaaaaa agaaagaata tgaagaattg aaagaagaga aaactctgtt ttcttgttgg   2040
aaaagtgaaa acgaaaaact tttaactcag atggaatcag aaaaggaaaa cttgcagagt   2100
aaaattaatc acttggaaac ttgtctgaag acacagcaaa taaaaagtca tgaatacaac   2160
gagagagtaa gaacgctgga gatggacaga gaaaacctaa gtgtcgagat cagaaacctt   2220
cacaacgtgt tagacagtaa gtcagtggag gtagagaccc agaaactagc ttatatggag   2280
ctacagcaga aagctgagtt ctcagatcag aaacatcaga aggaaataga aaatatgtgt   2340
ttgaagactt ctcagcttac tgggcaagtt gaagatctag aacacaagct tcagttactg   2400
tcaaatgaaa taatggacaa agaccggtgt taccaagact tgcatgccga atatgagagc   2460
ctcagggatc tgctaaaatc caaagatgct tctctggtga caaatgaaga tcatcagaga   2520
agtcttttgg cttttgatca gcagcctgcc atgcatcatt cctttgcaaa tataattgga   2580
gaacaaggaa gcatgccttc agagaggagt gaatgtcgtt tagaagcaga ccaaagtccg   2640
aaaaattctg ccatcctaca aaatagagtt gattcacttg aattttcatt agagtctcaa   2700
aaacagatga actcagacct gcaaaagcag tgtgaagagt tggtgcaaat caaaggagaa   2760
atagaagaaa atctcatgaa agcagaacag atgcatcaaa gttttgtggc tgaaacaagt   2820
cagcgcatta gtaagttaca ggaagacact tctgctcacc agaatgttgt tgctgaaacc   2880
ttaagtgccc ttgagaacaa ggaaaaagag ctgcaacttt taaatgataa ggtagaaact   2940
gagcaggcag agattcaaga attaaaaaag agcaaccatc tacttgaaga ctctctaaag   3000
gagctacaac ttttatccga aaccctaagc ttggagaaga aagaaatgag ttccatcatt   3060
tctctaaata aaagggaaat tgaagagctg acccaagaga atgggactct taaggaaatt   3120
aatgcatcct taaatcaaga gaagatgaac ttaatccaga aaagtgagag ttttgcaaac   3180
tatatagatg aaagggagaa aagcatttca gagttatctg atcagtacaa gcaagaaaaa   3240
cttattttac tacaaagatg tgaagaaacc ggaaatgcat atgaggatct tagtcaaaaa   3300
tacaaagcag cacaggaaaa gaattctaaa ttagaatgct tgctaaatga atgcactagt   3360
ctttgtgaaa ataggaaaaa tgagttggaa cagctaaagg aagcatttgc aaaggaacac   3420
caagaattct taacaaaatt agcatttgct gaagaaagaa atcagaatct gatgctagag   3480
ttggagacag tgcagcaagc tctgagatct gagatgacag ataaccaaaa caattctaag   3540
agcgaggctg gtggtttaaa gcaagaaatc atgactttaa aggaagaaca aaacaaaatg   3600
caaaaggaag ttaatgactt attacaagag aatgaacagc tgatgaaggt aatgaagact   3660
aaacatgaat gtcaaaatct agaatcagaa ccaattagga actctgtgaa agaaagagag   3720
agtgagagaa atcaatgtaa ttttaaacct cagatggatc ttgaagttaa agaaatttct   3780
ctagatagtt ataatgcgca gttggtgcaa ttagaagcta tgctaagaaa taaggaatta   3840
```

-continued

```
aaacttcagg aaagtgagaa ggagaaggag tgcctgcagc atgaattaca gacaattaga   3900
ggagatcttg aaaccagcaa tttgcaagac atgcagtcac aagaaattag tggccttaaa   3960
gactgtgaaa tagatgcgga agaaaagtat atttcagggc ctcatgagtt gtcaacaagt   4020
caaaacgaca atgcacacct tcagtgctct ctgcaaacaa caatgaacaa gctgaatgag   4080
ctagagaaaa tatgtgaaat actgcaggct gaaaagtatg aactcgtaac tgagctgaat   4140
gattcaaggt cagaatgtat cacagcaact aggaaaatgg cagaagaggt agggaaacta   4200
ctaaatgaag ttaaaatatt aaatgatgac agtggtcttc tccatggtga gttagtggaa   4260
gacataccag gaggtgaatt tggtgaacaa ccaaatgaac agcaccctgt gtctttggct   4320
ccattggacg agagtaattc ctacgagcac ttgacattgt cagacaaaga agttcaaatg   4380
cactttgccg aattgcaaga gaaattctta tctttacaaa gtgaacacaa aattttacat   4440
gatcagcact gtcagatgag ctctaaaatg tcagagctgc agacctatgt tgactcatta   4500
aaggccgaaa atttggtctt gtcaacgaat ctgagaaact ttcaaggtga cttggtgaag   4560
gagatgcagc tgggcttgga ggaggggctc gttccatccc tgtcatcctc ttgtgtgcct   4620
gacagctcta gtcttagcag tttgggagac tcctcctttt acagagctct tttagaacag   4680
acaggagata tgtctctttt gagtaattta gaaggggctg tttcagcaaa ccagtgcagt   4740
gtagatgaag tattttgcag cagtctgcag gaggagaatc tgaccaggaa agaaacccct   4800
tcggccccag cgaagggtgt tgaagagctt gagtccctct gtgaggtgta ccggcagtcc   4860
ctcgagaagc tagaagagaa aatggaaagt caagggatta tgaaaaataa ggaaattcaa   4920
gagctcgagc agttattaag ttctgaaagg caagagcttg actgccttag gaagcagtat   4980
ttgtcagaaa atgaacagtg gcaacagaag ctgacaagcg tgactctgga gatggagtcc   5040
aagttggcgg cagaaaagaa acagacggaa caactgtcac ttgagctgga agtagcacga   5100
ctccagctac aaggtctgga cttaagttct cggtctttgc ttggcatcga cacagaagat   5160
gctattcaag gccgaaatga gagctgtgac atatcaaaag aacatacttc agaaactaca   5220
gaaagaacac caaagcatga tgttcatcag atttgtgata aagatgctca gcaggacctc   5280
aatctagaca ttgagaaaat aactgagact ggtgcagtga aacccacagg agagtgctct   5340
ggggaacagt ccccagatac caattatgag cctccagggg aagataaaac ccagggctct   5400
tcagaatgca tttctgaatt gtcattttct ggtcctaatg ctttggtacc tatggatttc   5460
ctggggaatc aggaagatat ccataatctt caactgcggg taaaagagac atcaaatgag   5520
aatttgagat tacttcatgt gatagaggac cgtgacagaa aagttgaaag tttgctaaat   5580
gaaatgaaag aattagactc aaaactccat ttacaggagg tacaactaat gaccaaaatt   5640
gaagcatgca tagaattgga aaaaatagtt ggggaactta agaaagaaaa ctcagattta   5700
agtgaaaaat tggaatattt ttcttgtgat caccaggagt tactccagag agtagaaact   5760
tctgaaggcc tcaattctga tttagaaatg catgcagata aatcatcacg tgaagatatt   5820
ggagataatg tggccaaggt gaatgacagc tggaaggaga gatttcttga tgtggaaaat   5880
gagctgagta ggatcagatc ggagaaagct agcattgagc atgaagccct ctacctggag   5940
gctgacttag aggtagttca aacagagaag ctatgtttag aaaaagacaa tgaaaataag   6000
cagaaggtta ttgtctgcct tgaagaagaa ctctcagtgg tcacaagtga gagaaaccag   6060
cttcgtggag aattagatac tatgtcaaaa aaaaccacgg cactggatca gttgtctgaa   6120
aaaatgaagg agaaaacaca agagcttgag tctcatcaaa gtgagtgtct ccattgcatt   6180
```

-continued caggtggcag aggcagaggt gaaggaaaag acggaactcc ttcagacttt gtcctctgat 6240
gtgagtgagc tgttaaaaga caaaactcat ctccaggaaa agctgcagag tttggaaaag 6300
gactcacagg cactgtcttt gacaaaatgt gagctggaaa accaaattgc acaactgaat 6360
aaagagaaag aattgcttgt caaggaatct gaaagcctgc aggccagact gagtgaatca 6420
gattatgaaa agctgaatgt ctccaaggcc ttggaggccg cactggtgga gaaaggtgag 6480
ttcgcattga ggctgagctc aacacaggag gaagtgcatc agctgagaag aggcatcgag 6540
aaactgagag ttcgcattga ggccgatgaa aagaagcagc tgcacatcgc agagaaactg 6600
aaagaacgcg agcgggagaa tgattcactt aaggataaag ttgagaacct tgaaagggaa 6660
ttgcagatgt cagaagaaaa ccaggagcta gtgattcttg atgccgagaa ttccaaagca 6720
gaagtagaga ctctaaaaac acaaatagaa gagatggcca gaagcctgaa agtttttgaa 6780
ttagaccttg tcacgttaag gtctgaaaaa gaaaatctga caaaacaaat acaagaaaaa 6840
caaggtcagt tgtcagaact agacaagtta ctctcttcat ttaaaagtct gttagaagaa 6900
aaggagcaag cagagataca gatcaaagaa gaatctaaaa ctgcagtgga gatgcttcag 6960
aatcagttaa aggagctaaa tgaggcagta gcagccttgt gtggtgacca agaaattatg 7020
aaggccacag aacagagtct agacccacca atagaggaag agcatcagct gagaaatagc 7080
attgaaaagc tgagagcccg cctagaagct gatgaaaaga agcagctctg tgtcttacaa 7140
caactgaagg aaagtgagca tcatgcagat ttacttaagg gtagagtgga gaaccttgaa 7200
agagagctag agatagccag gacaaaccaa gagcatgcag ctcttgaggc agagaattcc 7260
aaaggagagg tagagaccct aaaagcaaaa atagaaggga tgacccaaag tctgagaggt 7320
ctggaattag atgttgttac tataaggtca gaaaaagaaa atctgacaaa tgaattacaa 7380
aaagagcaag agcgaatatc tgaattagaa ataataaatt catcatttga aaatattttg 7440
caagaaaaag agcaagagaa agtacagatg aaagaaaaat caagcactgc catggagatg 7500
cttcaaacac aattaaaaga gctcaatgag agagtggcag ccctgcataa tgaccaagaa 7560
gcctgtaagg ccaaagagca gaatcttagt agtcaagtag agtgtcttga acttgagaag 7620
gctcagttgc tacaaggcct tgatgaggcc aaaaataatt atattgtttt gcaatcttca 7680
gtgaatggcc tcattcaaga agtagaagat ggcaagcaga aactggagaa gaaggatgaa 7740
gaaatcagta gactgaaaaa tcaaattcaa gaccaagagc agcttgtctc taaactgtcc 7800
caggtggaag gagagcacca actttggaag gagcaaaact tagaactgag aaatctgaca 7860
gtggaattgg agcagaagat ccaagtgcta caatccaaaa atgcctcttt gcaggacaca 7920
ttagaagtgc tgcagagttc ttacaagaat ctagagaatg agcttgaatt gacaaaaatg 7980
gacaaaatgt cctttgttga aaaagtaaac aaaatgactg caaaggaaac tgagctgcag 8040
agggaaatgc atgagatggc acagaaaaca gcagagctgc aagaagaact cagtggagag 8100
aaaaataggc tagctggaga gttgcagtta ctgttggaag aaataaagag cagcaaagat 8160
caattgaagg agctcacact agaaaatagt gaattgaaga agagcctaga ttgcatgcac 8220
aaagaccagg tggaaaagga agggaaagtg agagaggaaa tagctgaata tcagctacgg 8280
cttcatgaag ctgaaaagaa acaccaggct ttgcttttgg acacaaacaa acagtatgaa 8340
gtagaaatcc agacataccg agagaaattg acttctaaag aagaatgtct cagttcacag 8400
aagctggaga tagacctttt aaagtctagt aaagaagagc tcaataattc attgaaagct 8460
actactcaga ttttggaaga attgaagaaa accaagatgg acaatctaaa atatgtaaat 8520
cagttgaaga aggaaaatga acgtgcccag gggaaaatga agttgttgat caaatcctgt 8580
aaacagctgg aagaggaaaa ggagatactg cagaaagaac tctctcaact tcaagctgca 8640
caggagaagc agaaaacagg tactgttatg gataccaagg tcgatgaatt aacaactgag 8700
atcaaagaac tgaaagaaac tcttgaagaa aaaaccaagg aggcagatga atacttggat 8760
aagtactgtt ccttgcttat aagccatgaa aagttagaga aagctaaaga gatgttagag 8820
acacaagtgg cccatctgtg ttcacagcaa tctaaacaag attcccgagg gtctcctttg 8880
ctaggtccag ttgttccagg accatctcca atcccttctg ttactgaaaa gaggttatca 8940
tctggccaaa ataaagcttc aggcaagagg caaagatcca gtggaatatg ggagaatggt 9000
agaggaccaa cacctgctac cccagagagc ttttctaaaa aaagcaagaa agcagtcatg 9060
agtggtattc accctgcaga agacacggaa ggtactgagt ttgagccaga gggacttcca 9120
gaagttgtaa agaaagggtt tgctgacatc ccgacaggaa agactagccc atatatcctg 9180
cgaagaacaa ccatggcaac tcggaccagc cccgcctgg ctgcacagaa gttagcgcta 9240
tccccactga gtctcggcaa agaaaatctt gcagagtcct ccaaaccaac agctggtggc 9300
agcagatcac aaaaggtcaa agttgctcag cggagcccag tagattcagg caccatcctc 9360
cgagaaccca ccacgaaatc cgtcccagtc aataatcttc ctgagagaag tccgactgac 9420
agccccagag agggcctgag ggtcaagcga ggccgacttg tccccagccc caaagctgga 9480
ctggagtcca acggcagtga gaactgtaag gtccagtgaa ggcactttgt gtgtcagtac 9540
ccctgggagg tgccagtcat tgaatagata aggctgtgcc tacaggactt ctctttagtc 9600
agggcatgct ttattagtga ggagaaaaca attccttaga agtcttaaat atattgtact 9660
ctttagatct cccatgtgta ggtattgaaa aagtttggaa gcactgatca cctgttagca 9720
ttgccattcc tctactgcaa tgtaaatagt ataaagctat gtatataaag ctttttggta 9780
atatgttaca attaaaatga caagcactat atcacaatct ctgtttgtat gtgggtttta 9840
cactaaaaaa atgcaaaaca cattttattc ttctaattaa cagctcctag gaaaatgtag 9900
acttttgctt tatgatattc tatctgtagt atgaggcatg gaatagtttt gtatcgggaa 9960
tttctcagag ctgagtaaaa tgaaggaaaa gcatgttatg tgtttttaag gaaaatgtgc 10020
acacatatac atgtaggagt gtttatcttt ctcttacaat ctgttttaga catctttgct 10080
tatgaaacct gtacatatgt gtgtgtgggt atgtgtttat ttccagtgag ggctgcaggc 10140
ttcctagagg tgtgctatac catgcgtctg tcgttgtgct tttttctgtt tttagaccaa 10200
ttttttacag ttctttggta agcattgtcg tatctggtga tggattaaca tatagccttt 10260
gttttctaat aaaatagtcg ccttcgtttt ctgtaaaaaa aaaaaaaaaa aaaaaa 10316

<210> SEQ ID NO 116
<211> LENGTH: 2639
<212> TYPE: DNA
<213> ORGANISM: Homo sapiens

<400> SEQUENCE: 116
ggcacgaggg gccgacgcga gcgccgcgct tcgcttcagc tgctagctgg cccaagggag 60
gcgaccgcgg agggtggcga ggggcggcca ggacccgcag ccccggggcc gggccggtcc 120
ggaccgccag ggagggcagg tcagtgggca gatcgcgtcc gcgggattca atctctgccc 180
gctctgataa cagtcctttt ccctggcgct cacttcgtgc ctggcacccg gctgggcgcc 240
tcaagaccgt tgtctcttcg atcgcttctt tggacttggc gaccatttca gagatgtctt 300
ccagaagtac caaagattta attaaaagta agtggggatc gaagcctagt aactccaaat 360

```
ccgaaactac attagaaaaa ttaaagggag aaattgcaca cttaaagaca tcagtggatg    420
aaatcacaag tgggaaagga aagctgactg ataaagagag acacagactt ttggagaaaa    480
ttcgagtcct tgaggctgag aaggagaaga atgcttatca actcacagag aaggacaaag    540
aaatacagcg actgagagac caactgaagg ccagatatag tactaccgca ttgcttgaac    600
agctggaaga gacaacgaga gaaggagaaa ggagggagca ggtgttgaaa gccttatctg    660
aagagaaaga cgtattgaaa caacagttgt ctgctgcaac ctcacgaatt gctgaacttg    720
aaagcaaaac caatacactc cgtttatcac agactgtggc tccaaactgc ttcaactcat    780
caataaataa tattcatgaa atggaaatac agctgaaaga tgctctggag aaaaatcagc    840
agtggctcgt gtatgatcag cagcgggaag tctatgtaaa aggactttta gcaaagatct    900
ttgagttgga aaagaaaacg gaaacagctg ctcattcact cccacagcag acaaaaaagc    960
ctgaatcaga aggttatctt caagaagaga agcagaaatg ttacaacgat ctcttggcaa   1020
gtgcaaaaaa agatcttgag gttgaacgac aaaccataac tcagctgagt tttgaactga   1080
gtgaatttcg aagaaaatat gaagaaaccc aaaaagaagt tcacaattta aatcagctgt   1140
tgtattcaca aagaagggca gatgtgcaac atctggaaga tgataggcat aaaacagaga   1200
agatacaaaa actcagggaa gagaatgata ttgctagggg aaaacttgaa gaagagaaga   1260
agagatccga agagctctta tctcaggtcc agtttcttta cacatctctg ctaaagcagc   1320
aagaagaaca aacaagggta gctctgttgg aacaacagat gcaggcatgt actttagact   1380
ttgaaaatga aaaactcgac cgtcaacatg tgcagcatca attgcatgta attcttaagg   1440
agctccgaaa agcaagaaat caaataacac agttggaatc cttgaaacag cttcatgagt   1500
ttgccatcac agagccatta gtcactttcc aaggagagac tgaaaacaga gaaaaagttg   1560
ccgcctcacc aaaaagtccc actgctgcac tcaatgaaag cctggtggaa tgtcccaagt   1620
gcaatataca gtatccagcc actgagcatc gcgatctgct tgtccatgtg gaatactgtt   1680
caaagtagca aaataagtat ttgttttgat attaaaagat tcaatactgt attttctgtt   1740
agcttgtggg cattttgaat tatatatttc acattttgca taaaactgcc tatctacctt   1800
tgacactcca gcatgctagt gaatcatgta tcttttaggc tgctgtgcat ttctcttggc   1860
agtgatacct ccctgacatg gttcatcatc aggctgcaat gacagaatgt ggtgagcagc   1920
gtctactgag actactaaca ttttgcactg tcaaaatact tggtgaggaa aagatagctc   1980
aggttattgc taatgggtta atgcaccagc aagcaaaata ttttatgttt tgggggtttg   2040
aaaaatcaaa gataattaac caaggatctt aactgtgttc gcattttttta tccaagcact   2100
tagaaaacct acaatcctaa ttttgatgtc cattgttaag aggtggtgat agatactatt   2160
ttttttttca tattgtatag cggttattag aaaagttggg gattttcttg atctttattg   2220
ctgcttacca ttgaaactta acccagctgt gttccccaac tctgttctgc gcacgaaaca   2280
gtatctgttt gaggcataat cttaagtggc cacacacaat gttttctctt atgttatctg   2340
gcagtaactg taacttgaat tacattagca cattctgctt agctaaaatt gttaaaataa   2400
actttaataa acccatgtag ccctctcatt tgattgacag tattttagtt atttttggca   2460
ttcttaaagc tgggcaatgt aatgatcaga tctttgtttg tctgaacagg tatttttata   2520
catgcttttt gtaaaccaaa aactttttaaa tttcttcagg ttttctaaca tgcttaccac   2580
tgggctactg taaatgagaa aagaataaaa ttatttaatg ttttaaaaaa aaaaaaaaa    2639
```

<210> SEQ ID NO 117
<211> LENGTH: 2632

<212> TYPE: DNA
<213> ORGANISM: Homo sapiens

<400> SEQUENCE: 117

```
ggcggctgag cctgagcggg gatgtagagg cggcggcagc agaggcggca ctggcggcaa      60

gagcagacgc ccgagccgag cgagaagagc ggcagagcct tatcccctga agccgggccc     120

cgcgtcccag ccctgcccag cccgcgccca gccatgcgcg ccgcctgctg agtccgggcg     180

ccgcacgctg agccctccgc ccgcgagccg cgctcagctc gggggtgatt agttgctttt     240

tgttgttttt taatttgggc cgcggggagg gggaggaggg gcaggtgctg caggctcccc     300

cccctccccg cctcgggcca gccgcggcgg cgcgactcgg gctccggacc cgggcactgc     360

tggcggctgg agcggagcgc accgcggcgg tggtgcccag agcggagcgc agctccctgc     420

cccgcccctc cccctcggcc tcgcggcgac ggcggcggtg gcggcttgga cgactcggag     480

agccgagtga agacatttcc acctggacac ctgaccatgt gcctgccctg agcagcgagg     540

cccaccaggc atctctgttg tgggcagcag ggccaggtcc tggtctgtgg accctcggca     600

gttggcaggc tccctctgca gtggggtctg ggcctcggcc ccaccatgtc gagcctcggc     660

ggtggctccc aggatgccgg cggcagtagc agcagcagca ccaatggcag cggtggcagt     720

ggcagcagtg gcccaaaggc aggagcagca gacaagagtg cagtggtggc tgccgccgca     780

ccagcctcag tggcagatga cacaccaccc cccgagcgtc ggaacaagag cggtatcatc     840

agtgagcccc tcaacaagag cctgcgccgc tcccgcccgc tctcccacta ctcttctttt     900

ggcagcagtg gtggtagtgg cggtggcagc atgatgggcg gagagtctgc tgacaaggcc     960

actgcggctg cagccgctgc ctccctgttg gccaatgggc atgacctggc ggcggccatg    1020

gcggtggaca aaagcaaccc tacctcaaag cacaaaagtg gtgctgtggc cagcctgctg    1080

agcaaggcag agcgggccac ggagctggca gccgagggac agctgacgct gcagcagttt    1140

gcgcagtcca cagagatgct gaagcgcgtg gtgcaggagc atctcccgct gatgagcgag    1200

gcgggtgctg gcctgcctga catggaggct gtggcaggtg ccgaagccct caatggccag    1260

tccgacttcc cctacctggg cgctttcccc atcaacccag gcctcttcat tatgaccccg    1320

gcaggtgtgt tcctggccga gagcgcgctg cacatggcgg gcctggctga gtaccccatg    1380

cagggagagc tggcctctgc catcagctcc ggcaagaaga agcggaaacg ctgcggcatg    1440

tgcgcgccct gccggcggcg catcaactgc gagcagtgca gcagttgtag gaatcgaaag    1500

actggccatc agatttgcaa attcagaaaa tgtgaggaac tcaaaaagaa gccttccgct    1560

gctctggaga aggtgatgct tccgacggga gccgccttcc ggtggtttca gtgacggcgg    1620

cggaacccaa agctgccctc tccgtgcaat gtcactgctc gtgtggtctc cagcaaggga    1680

ttcgggcgaa gacaaacgga tgcacccgtc tttagaacca aaaatattct ctcacagatt    1740

tcattcctgt ttttatatat atattttttg ttgtcgtttt aacatctcca cgtccctagc    1800

ataaaaagaa aaagaaaaaa atttaaactg ctttttcgga agaacaacaa caaaaaagag    1860

gtaaagacga atctataaag taccgagact tcctgggcaa agaatggaca atcagtttcc    1920

ttcctgtgtc gatgtcgatg ttgtctgtgc aggagatgca gtttttgtgt agagaatgta    1980

aattttctgt aacctttgga aatctagtta ctaataagca ctactgtaat ttagcacagt    2040

ttaactccac cctcatttaa acttcctttg attctttccg accatgaaat agtgcatagt    2100

ttgcctggag aatccactca cgttcataaa gagaatgttg atggcgccgt gtagaagccg    2160

ctctgtatcc atccacgcgt gcagagctgc cagcagggag ctcacagaag ggagagggagc    2220
```

accaggccag ctgagctgca cccacagtcc cgagactggg atcccccacc ccaacagtga 2280
ttttggaaaa aaaaatgaaa gttctgttcg tttatccatt gcgatctggg gagccccatc 2340
tcgatatttc caatcctggc tacttttctt agagaaaata agtccttttt ttctggcctt 2400
gctaatggca acagaagaaa gggcttcttt gcgtggtccc ctgctggtgg gggtgggtcc 2460
ccaggggccc ccctgcggcc tgggcccccc tgcccacggc cagcttcctg ctgatgaaca 2520
tgctgtttgt attgttttag gaaaccaggc tgttttgtga ataaaacgaa tgcatgtttg 2580
tgtcacgaaa aaaaaaaaaa aaaaaaaaaa aaaaaaaaaa aaaaaaaaaa aa 2632

<210> SEQ ID NO 118
<211> LENGTH: 5616
<212> TYPE: DNA
<213> ORGANISM: Homo sapiens

<400> SEQUENCE: 118
ccccggcgca gcgcggccgc agcagcctcc gcccccgca cggtgtgagc gcccgacgcg 60
gccgaggcgg ccggagtccc gagctagccc cggcggccgc cgccgcccag accggacgac 120
aggccacctc gtcggcgtcc gcccgagtcc ccgcctcgcc gccaacgcca caaccaccgc 180
gcacggcccc ctgactccgt ccagtattga tcgggagagc cggagcgagc tcttcgggga 240
gcagcgatgc gaccctccgg gacggccggg gcagcgctcc tggcgctgct ggctgcgctc 300
tgcccggcga gtcgggctct ggaggaaaag aaagtttgcc aaggcacgag taacaagctc 360
acgcagttgg gcacttttga agatcatttt ctcagcctcc agaggatgtt caataactgt 420
gaggtggtcc ttgggaattt ggaaattacc tatgtgcaga ggaattatga tctttccttc 480
ttaaagacca tccaggaggt ggctggttat gtcctcattg ccctcaacac agtggagcga 540
attcctttgg aaaacctgca gatcatcaga ggaaatatgt actacgaaaa ttcctatgcc 600
ttagcagtct tatctaacta tgatgcaaat aaaaccggac tgaaggagct gcccatgaga 660
aatttacagg aaatcctgca tggcgccgtg cggttcagca acaaccctgc cctgtgcaac 720
gtggagagca tccagtggcg ggacatagtc agcagtgact ttctcagcaa catgtcgatg 780
gacttccaga accacctggg cagctgccaa aagtgtgatc caagctgtcc caatgggagc 840
tgctggggtg caggagagga gaactgccag aaactgacca aaatcatctg tgcccagcag 900
tgctccgggc gctgccgtgg caagtccccc agtgactgct gccacaacca gtgtgctgca 960
ggctgcacag gcccccggga gagcgactgc ctggtctgcc gcaaattccg agacgaagcc 1020
acgtgcaagg acacctgccc cccactcatg ctctacaacc ccaccacgta ccagatggat 1080
gtgaaccccg agggcaaata cagctttggt gccacctgcg tgaagaagtg tccccgtaat 1140
tatgtggtga cagatcacgg ctcgtgcgtc cgagcctgtg gggccgacag ctatgagatg 1200
gaggaagacg gcgtccgcaa gtgtaagaag tgcgaagggc cttgccgcaa agtgtgtaac 1260
ggaataggta ttggtgaatt taaagactca ctctccataa atgctacgaa tattaaacac 1320
ttcaaaaact gcacctccat cagtggcgat ctccacatcc tgccggtggc atttaggggt 1380
gactccttca cacatactcc tcctctggat ccacaggaac tggatattct gaaaaccgta 1440
aaggaaatca cagggttttt gctgattcag gcttggcctg aaaacaggac ggacctccat 1500
gcctttgaga acctagaaat catacgcggc aggaccaagc aacatggtca gttttctctt 1560
gcagtcgtca gcctgaacat aacatccttg ggattacgct ccctcaagga gataagtgat 1620
ggagatgtga taatttcagg aaacaaaaat ttgtgctatg caaatacaat aaactggaaa 1680
aaactgtttg ggacctccgg tcagaaaacc aaaattataa gcaacagagg tgaaaacagc 1740

-continued

```
tgcaaggcca caggccaggt ctgccatgcc ttgtgctccc ccgagggctg ctggggcccg   1800
gagcccaggg actgcgtctc ttgccggaat gtcagccgag gcagggaatg cgtggacaag   1860
tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag gtcttgaagg ctgtccaacg   2160
aatgggccta agatcccgtc catcgccact gggatggtgg gggccctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga acgtactggt gaaaacaccg cagcatgtca agatcacaga ttttgggctg   2820
gccaaactgc tgggtgcgga agagaaagaa taccatgcag aaggaggcaa agtgcctatc   2880
aagtggatgg cattggaatc aattttacac agaatctata cccaccagag tgatgtctgg   2940
agctacgggg tgaccgtttg ggagttgatg acctttggat ccaagccata tgacggaatc   3000
cctgccagcg agatctcctc catcctggag aaaggagaac gcctccctca gccacccata   3060
tgtaccatcg atgtctacat gatcatggtc aagtgctgga tgatagacgc agatagtcgc   3120
ccaaagttcc gtgagttgat catcgaattc tccaaaatgg cccgagaccc ccagcgctac   3180
cttgtcattc aggggggatga aagaatgcat ttgccaagtc ctacagactc caacttctac   3240
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttctttccc   3780
aaggaagcca agccaaatgg catctttaag ggctccacag ctgaaaatgc agaataccta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt tgcaacgttt acaccgacta   4020
gccaggaagt acttccacct cgggcacatt ttgggaagtt gcattccttt gtcttcaaac   4080
```

tgtgaagcat ttacagaaac gcatccagca agaatattgt ccctttgagc agaaatttat 4140
ctttcaaaga ggtatatttg aaaaaaaaaa aaagtatatg tgaggatttt tattgattgg 4200
ggatcttgga gtttttcatt gtcgctattg atttttactt caatgggctc ttccaacaag 4260
gaagaagctt gctggtagca cttgctaccc tgagttcatc caggcccaac tgtgagcaag 4320
gagcacaagc cacaagtctt ccagaggatg cttgattcca gtggttctgc ttcaaggctt 4380
ccactgcaaa acactaaaga tccaagaagg ccttcatggc cccagcaggc cggatcggta 4440
ctgtatcaag tcatggcagg tacagtagga taagccactc tgtcccttcc tgggcaaaga 4500
agaaacggag gggatggaat tcttccttag acttactttt gtaaaaatgt ccccacggta 4560
cttactcccc actgatggac cagtggtttc cagtcatgag cgttagactg acttgtttgt 4620
cttccattcc attgttttga aactcagtat gctgcccctg tcttgctgtc atgaaatcag 4680
caagagagga tgacacatca aataataact cggattccag cccacattgg attcatcagc 4740
atttggacca atagcccaca gctgagaatg tggaatacct aaggatagca ccgcttttgt 4800
tctcgcaaaa acgtatctcc taatttgagg ctcagatgaa atgcatcagg tcctttgggg 4860
catagatcag aagactacaa aaatgaagct gctctgaaat ctcctttagc catcacccca 4920
accccccaaa attagtttgt gttacttatg gaagatagtt ttctcctttt acttcacttc 4980
aaaagctttt tactcaaaga gtatatgttc cctccaggtc agctgccccc aaaccccctc 5040
cttacgcttt gtcacacaaa aagtgtctct gccttgagtc atctattcaa gcacttacag 5100
ctctggccac aacagggcat tttacaggtg cgaatgacag tagcattatg agtagtgtgg 5160
aattcaggta gtaaatatga aactagggtt tgaaattgat aatgctttca caacatttgc 5220
agatgtttta gaaggaaaaa agttccttcc taaaataatt tctctacaat tggaagattg 5280
gaagattcag ctagttagga gcccaccttt tttcctaatc tgtgtgtgcc ctgtaacctg 5340
actggttaac agcagtcctt tgtaaacagt gttttaaact ctcctagtca atatccaccc 5400
catccaattt atcaaggaag aaatggttca gaaaatattt tcagcctaca gttatgttca 5460
gtcacacaca catacaaaat gttccttttg cttttaaagt aatttttgac tcccagatca 5520
gtcagagccc ctacagcatt gttaagaaag tatttgattt ttgtctcaat gaaaataaaa 5580
ctatattcat ttccactcta aaaaaaaaaa aaaaaa 5616

<210> SEQ ID NO 119
<211> LENGTH: 4816
<212> TYPE: DNA
<213> ORGANISM: Homo sapiens

<400> SEQUENCE: 119
gttcccggat ttttgtgggc gcctgccccg cccctcgtcc ccctgctgtg tccatatatc 60
gaggcgatag ggttaaggga aggcggacgc ctgatgggtt aatgagcaaa ctgaagtgtt 120
ttccatgatc ttttttgagt cgcaattgaa gtaccacctc ccgagggtga ttgcttcccc 180
atgcggggta gaacctttgc tgtcctgttc accactctac ctccagcaca gaatttggct 240
tatgcctact caatgtgaag atgatgagga tgaaaacctt tgtgatgatc cacttccact 300
taatgaatgg tggcaaagca aagctatatt caagaccaca tgcaaagcta ctccctgagc 360
aaagagtcac agataaaacg ggggcaccag tagaatggcc aggacaaacg cagtgcagca 420
cagagactca gaccctggca gccatgcctg cgcaggcagt gatgagagtg acatgtactg 480
ttgtggacat gcacaaaagt gagtgtgcac cggcacagac atgaagctgc ggctccctgc 540
cagtcccgag acccacctgg acatgctccg ccacctctac cagggctgcc aggtggtgca 600

-continued

```
gggaaacctg gaactcacct acctgcccac caatgccagc ctgtccttcc tgcaggatat    660
ccaggaggtg cagggctacg tgctcatcgc tcacaaccaa gtgaggcagg tcccactgca    720
gaggctgcgg attgtgcgag gcacccagct ctttgaggac aactatgccc tggccgtgct    780
agacaatgga gacccgctga acaataccac ccctgtcaca ggggcctccc caggaggcct    840
gcgggagctg cagcttcgaa gcctcacaga gatcttgaaa ggaggggtct tgatccagcg    900
gaacccccag ctctgctacc aggacacgat tttgtggaag gacatcttcc acaagaacaa    960
ccagctggct ctcacactga tagacaccaa ccgctctcgg gcctgccacc cctgttctcc   1020
gatgtgtaag ggctcccgct gctggggaga gagttctgag gattgtcaga gcctgacgcg   1080
cactgtctgt gccggtggct gtgcccgctg caaggggcca ctgcccactg actgctgcca   1140
tgagcagtgt gctgccggct gcacgggccc caagcactct gactgcctgg cctgcctcca   1200
cttcaaccac agtggcatct gtgagctgca ctgcccagcc ctggtcacct acaacacaga   1260
cacgtttgag tccatgccca atcccgaggg ccggtataca ttcggcgcca gctgtgtgac   1320
tgcctgtccc tacaactacc tttctacgga cgtgggatcc tgcaccctcg tctgccccct   1380
gcacaaccaa gaggtgacag cagaggatgg aacacagcgg tgtgagaagt gcagcaagcc   1440
ctgtgcccga gtgtgctatg gtctgggcat ggagcacttg cgagaggtga gggcagttac   1500
cagtgccaat atccaggagt ttgctggctg caagaagatc tttgggagcc tggcatttct   1560
gccggagagc tttgatgggg acccagcctc caacactgcc ccgctccagc cagagcagct   1620
ccaagtgttt gagactctgg aagagatcac aggttaccta tacatctcag catggccgga   1680
cagcctgcct gacctcagcg tcttccagaa cctgcaagta atccggggac gaattctgca   1740
caatggcgcc tactcgctga ccctgcaagg gctgggcatc agctggctgg ggctgcgctc   1800
actgagggaa ctgggcagtg gactggccct catccaccat aacacccacc tctgcttcgt   1860
gcacacggtg ccctgggacc agctctttcg gaacccgcac caagctctgc tccacactgc   1920
caaccggcca gaggacgagt gtgtgggcga gggcctggcc tgccaccagc tgtgcgcccg   1980
agggcactgc tggggtccag ggcccaccca gtgtgtcaac tgcagccagt tccttcgggg   2040
ccaggagtgc gtggaggaat gccgagtact gcaggggctc cccagggagt atgtgaatgc   2100
caggcactgt ttgccgtgcc accctgagtg tcagccccag aatggctcag tgacctgttt   2160
tggaccggag gctgaccagt gtgtggcctg tgcccactat aaggaccctc ccttctgcgt   2220
ggcccgctgc cccagcggtg tgaaacctga cctctcctac atgcccatct ggaagtttcc   2280
agatgaggag ggcgcatgcc agccttgccc catcaactgc acccactcct gtgtggacct   2340
ggatgacaag ggctgccccg ccgagcagag agccagccct ctgacgtcca tcatctctgc   2400
ggtggttggc attctgctgg tcgtggtctt gggggtggtc tttgggatcc tcatcaagcg   2460
acggcagcag aagatccgga agtacacgat gcggagactg ctgcaggaaa cggagctggt   2520
ggagccgctg acacctagcg gagcgatgcc caaccaggcg cagatgcgga tcctgaaaga   2580
gacggagctg aggaaggtga aggtgcttgg atctggcgct tttggcacag tctacaaggg   2640
catctggatc cctgatgggg agaatgtgaa aattccagtg gccatcaaag tgttgaggga   2700
aaacacatcc cccaaagcca acaaagaaat cttagacgaa gcatacgtga tggctggtgt   2760
gggctcccca tatgtctccc gccttctggg catctgcctg acatccacgg tgcagctggt   2820
gacacagctt atgccctatg gctgcctctt agaccatgtc cgggaaaacc gcggacgcct   2880
gggctcccag gacctgctga actggtgtat gcagattgcc aaggggatga gctacctgga   2940
```

-continued ggatgtgcgg ctcgtacaca gggacttggc cgctcggaac gtgctggtca agagtcccaa 3000
ccatgtcaaa attacagact tcgggctggc tcggctgctg gacattgacg agacagagta 3060
ccatgcagat gggggcaagg tgcccatcaa gtggatggcg ctggagtcca ttctccgccg 3120
gcggttcacc caccagagtg atgtgtggag ttatggtgtg actgtgtggg agctgatgac 3180
ttttggggcc aaaccttacg atgggatccc agcccgggag atccctgacc tgctggaaaa 3240
gggggagcgg ctgccccagc ccccccatctg caccattgat gtctacatga tcatggtcaa 3300
atgttggatg attgactctg aatgtcggcc aagattccgg gagttggtgt ctgaattctc 3360
ccgcatggcc agggaccccc agcgctttgt ggtcatccag aatgaggact tgggcccagc 3420
cagtcccttg gacagcacct tctaccgctc actgctggag gacgatgaca tgggggacct 3480
ggtggatgct gaggagtatc tggtacccca gcagggcttc ttctgtccag accctgcccc 3540
gggcgctggg ggcatggtcc accacaggca ccgcagctca tctaccagga gtggcggtgg 3600
ggacctgaca ctagggctgg agccctctga agaggaggcc cccaggtctc cactggcacc 3660
ctccgaaggg gctggctccg atgtatttga tggtgacctg ggaatggggg cagccaaggg 3720
gctgcaaagc ctccccacac atgaccccag ccctctacag cggtacagtg aggaccccac 3780
agtacccctg ccctctgaga ctgatggcta cgttgccccc ctgacctgca gcccccagcc 3840
tgaatatgtg aaccagccag atgttcggcc ccagcccccct tcgccccgag agggccctct 3900
gcctgctgcc cgacctgctg gtgccactct ggaaaggccc aagactctct ccccagggaa 3960
gaatggggtc gtcaaagacg tttttgcctt tgggggtgcc gtggagaacc ccgagtactt 4020
gacaccccag ggaggagctg cccctcagcc ccaccctcct cctgccttca gcccagcctt 4080
cgacaacctc tattactggg accaggaccc accagagcgg ggggctccac ccagcacctt 4140
caaagggaca cctacggcag agaacccaga gtacctgggt ctggacgtgc cagtgtgaac 4200
cagaaggcca agtccgcaga agccctgatg tgtcctcagg gagcagggaa ggcctgactt 4260
ctgctggcat caagaggtgg gagggccctc cgaccacttc caggggaacc tgccatgcca 4320
ggaacctgtc ctaaggaacc ttccttcctg cttgagttcc cagatggctg gaaggggtcc 4380
agcctcgttg gaagaggaac agcactgggg agtctttgtg gattctgagg ccctgcccaa 4440
tgagactcta gggtccagtg gatgccacag cccagcttgg ccctttcctt ccagatcctg 4500
ggtactgaaa gccttaggga agctggcctg agaggggaag cggccctaag ggagtgtcta 4560
agaacaaaag cgacccattc agagactgtc cctgaaacct agtactgccc cccatgagga 4620
aggaacagca atggtgtcag tatccaggct ttgtacagag tgcttttctg tttagttttt 4680
actttttttg ttttgttttt ttaaagatga aataaagacc caggggggaga atgggtgttg 4740 tatggggagg caagtgtggg gggtccttct ccacacccac tttgtccatt tgcaaatata 4800
ttttggaaaa cagcta 4816

<210> SEQ ID NO 120
<211> LENGTH: 6466
<212> TYPE: DNA
<213> ORGANISM: Homo sapiens

<400> SEQUENCE: 120
atggtcataa cagcctcctg tctaccgact cagaacggat tttaccaaaa ctgaaaatgc 60
aggctccatg ctcagaagct ctttaacagg ctcgaaaggt ccatgctcct ttctcctgcc 120
cattctatag cataagaaga cagtctctga gtgataatct tctcttcaag aagaagaaaa 180
ctaggaagga gtaagcacaa agatctcttc acattctccg ggactgcggt accaaatatc 240

```
agcacagcac ttcttgaaaa aggatgtaga ttttaatctg aactttgaac catcactgag    300
gtggcccgcc ggtttctgag ccttctgccc tgcggggaca cggtctgcac cctgcccgcg    360
gccacggacc atgaccatga ccctccacac caaagcatct gggatggccc tactgcatca    420
gatccaaggg aacgagctgg agcccctgaa ccgtccgcag ctcaagatcc ccctggagcg    480
gcccctgggc gaggtgtacc tggacagcag caagcccgcc gtgtacaact accccgaggg    540
cgccgcctac gagttcaacg ccgcggccgc cgccaacgcg caggtctacg gtcagaccgg    600
cctcccctac ggccccgggt ctgaggctgc ggcgttcggc tccaacggcc tggggggttt    660
ccccccactc aacagcgtgt ctccgagccc gctgatgcta ctgcacccgc cgccgcagct    720
gtcgcctttc ctgcagcccc acggccagca ggtgccctac tacctggaga acgagcccag    780
cggctacacg gtgcgcgagg ccggcccgcc ggcattctac aggccaaatt cagataatcg    840
acgccagggt ggcagagaaa gattggccag taccaatgac aagggaagta tggctatgga    900
atctgccaag gagactcgct actgtgcagt gtgcaatgac tatgcttcag gctaccatta    960
tggagtctgg tcctgtgagg gctgcaaggc cttcttcaag agaagtattc aaggacataa   1020
cgactatatg tgtccagcca ccaaccagtg caccattgat aaaaacagga ggaagagctg   1080
ccaggcctgc cggctccgca aatgctacga agtgggaatg atgaaaggtg ggatacgaaa   1140
agaccgaaga ggagggagaa tgttgaaaca caagcgccag agagatgatg gggagggcag   1200
gggtgaagtg gggtctgctg gagacatgag agctgccaac ctttggccaa gcccgctcat   1260
gatcaaacgc tctaagaaga acagcctggc cttgtccctg acggccgacc agatggtcag   1320
tgccttgttg gatgctgagc cccccatact ctattccgag tatgatccta ccagaccctt   1380
cagtgaagct tcgatgatgg gcttactgac caacctggca gacagggagc tggttcacat   1440
gatcaactgg gcgaagaggg tgccaggctt tgtggatttg accctccatg atcaggtcca   1500
ccttctagaa tgtgcctggc tagagatcct gatgattggt ctcgtctggc gctccatgga   1560
gcacccaggg aagctactgt ttgctcctaa cttgctcttg gacaggaacc agggaaaatg   1620
tgtagagggc atggtggaga tcttcgacat gctgctggct acatcatctc ggttccgcat   1680
gatgaatctg cagggagagg agtttgtgtg cctcaaatct attattttgc ttaattctgg   1740
agtgtacaca tttctgtcca gcaccctgaa gtctctggaa gagaaggacc atatccaccg   1800
agtcctggac aagatcacag acactttgat ccacctgatg gccaaggcag gcctgaccct   1860
gcagcagcag caccagcggc tggcccagct cctcctcatc ctctcccaca tcaggcacat   1920
gagtaacaaa ggcatggagc atctgtacag catgaagtgc aagaacgtgg tgcccctcta   1980
tgacctgctg ctggagatgc tggacgccca ccgcctacat gcgcccacta gccgtggagg   2040
ggcatccgtg gaggagacgg accaaagcca cttggccact gcgggctcta cttcatcgca   2100
ttccttgcaa aagtattaca tcacgggggga ggcagagggt ttccctgcca cggtctgaga   2160
gctccctggc tcccacacgg ttcagataat ccctgctgca ttttaccctc atcatgcacc   2220
actttagcca aattctgtct cctgcataca ctccggcatg catccaacac caatggcttt   2280
ctagatgagt ggccattcat ttgcttgctc agttcttagt ggcacatctt ctgtcttctg   2340
ttgggaacag ccaaagggat tccaaggcta aatctttgta acagctctct ttcccccttg   2400
ctatgttact aagcgtgagg attcccgtag ctcttcacag ctgaactcag tctatgggtt   2460
ggggctcaga taactctgtg catttaagct acttgtagag acccaggcct ggagagtaga   2520
cattttgcct ctgataagca ctttttaaat ggctctaaga ataagccaca gcaaagaatt   2580
```

-continued

```
taaagtggct cctttaattg gtgacttgga gaaagctagg tcaagggttt attatagcac   2640
cctcttgtat tcctatggca atgcatcctt ttatgaaagt ggtacacctt aaagctttta   2700
tatgactgta gcagagtatc tggtgattgt caattcattc cccctatagg aatacaaggg   2760
gcacacaggg aaggcagatc ccctagttgg caagactatt ttaacttgat acactgcaga   2820
ttcagatgtg ctgaaagctc tgcctctggc tttccggtca tgggttccag ttaattcatg   2880
cctcccatgg acctatggag agcagcaagt tgatcttagt taagtctccc tatatgaggg   2940
ataagttcct gatttttgtt tttatttttg tgttacaaaa gaaagccctc cctccctgaa   3000
cttgcagtaa ggtcagcttc aggacctgtt ccagtgggca ctgtacttgg atcttcccgg   3060
cgtgtgtgtg ccttacacag gggtgaactg ttcactgtgg tgatgcatga tgagggtaaa   3120
tggtagttga aaggagcagg ggccctggtg ttgcatttag ccctggggca tggagctgaa   3180
cagtacttgt gcaggattgt tgtggctact agagaacaag agggaaagta gggcagaaac   3240
tggatacagt tctgaggcac agccagactt gctcagggtg gccctgccac aggctgcagc   3300
tacctaggaa cattccttgc agaccccgca ttgccctttg ggggtgccct gggatccctg   3360
gggtagtcca gctcttcttc atttcccagc gtggccctgg ttggaagaag cagctgtcac   3420
agctgctgta gacagctgtg ttcctacaat tggcccagca ccctggggca cgggagaagg   3480
gtggggaccg ttgctgtcac tactcaggct gactggggcc tggtcagatt acgtatgccc   3540
ttggtggttt agagataatc caaaatcagg gtttggtttg gggaagaaaa tcctccccct   3600
tcctcccccg ccccgttccc taccgcctcc actcctgcca gctcatttcc ttcaatttcc   3660
tttgacctat aggctaaaaa agaaaggctc attccagcca cagggcagcc ttccctgggc   3720
ctttgcttct ctagcacaat tatgggttac ttccttttc ttaacaaaaa agaatgtttg    3780
atttcctctg ggtgacctta ttgtctgtaa ttgaaaccct attgagaggt gatgtctgtg   3840
ttagccaatg acccaggtga gctgctcggg cttctcttgg tatgtcttgt ttggaaaagt   3900
ggatttcatt catttctgat tgtccagtta agtgatcacc aaaggactga gaatctggga   3960
gggcaaaaaa aaaaaaaaag tttttatgtg cacttaaatt tggggacaat tttatgtatc   4020
tgtgttaagg atatgtttaa gaacataatt cttttgttgc tgtttgttta agaagcacct   4080
tagtttgttt aagaagcacc ttatatagta taatatatat ttttttgaaa ttacattgct   4140
tgtttatcag acaattgaat gtagtaattc tgttctggat ttaatttgac tgggttaaca   4200
tgcaaaaacc aaggaaaaat atttagtttt tttttttttt tttgtatact tttcaagcta   4260
ccttgtcatg tatacagtca tttatgccta aagcctggtg attattcatt taaatgaaga   4320
tcacatttca tatcaacttt tgtatccaca gtagacaaaa tagcactaat ccagatgcct   4380
attgttggat actgaatgac agacaatctt atgtagcaaa gattatgcct gaaaaggaaa   4440
attattcagg gcagctaatt ttgcttttac caaaatatca gtagtaatat ttttggacag   4500
tagctaatgg gtcagtgggt tctttttaat gtttatactt agattttctt ttaaaaaaat   4560
taaaataaaa caaaaaaaaa tttctaggac tagacgatgt aataccagct aaagccaaac   4620
aattatacag tggaaggttt tacattattc atccaatgtg tttctattca tgttaagata   4680
ctactacatt tgaagtgggc agagaacatc agatgattga aatgttcgcc caggggtctc   4740
cagcaacttt ggaaatctct ttgtattttt acttgaagtg ccactaatgg acagcagata   4800
ttttctggct gatgttggta ttgggtgtag gaacatgatt taaaaaaaaa ctcttgcctc   4860
tgctttcccc cactctgagg caagttaaaa tgtaaaagat gtgatttatc tgggggggctc   4920
aggtatggtg gggaagtgga ttcaggaatc tggggaatgg caaatatatt aagaagagta   4980
```

ttgaaagtat ttggaggaaa atggttaatt ctgggtgtgc accagggttc agtagagtcc 5040
acttctgccc tggagaccac aaatcaacta gctccattta cagccatttc taaaatggca 5100
gcttcagttc tagagaagaa agaacaacat cagcagtaaa gtccatggaa tagctagtgg 5160
tctgtgtttc ttttcgccat tgcctagctt gccgtaatga ttctataatg ccatcatgca 5220
gcaattatga gaggctaggt catccaaaga gaagacccta tcaatgtagg ttgcaaaatc 5280
taacccctaa ggaagtgcag tctttgattt gatttcccta gtaaccttgc agatatgttt 5340
aaccaagcca tagcccatgc cttttgaggg ctgaacaaat aagggactta ctgataattt 5400
acttttgatc acattaaggt gttctcacct tgaaatctta tacactgaaa tggccattga 5460
tttaggccac tggcttagag tactccttcc cctgcatgac actgattaca aatactttcc 5520
tattcatact ttccaattat gagatggact gtgggtactg ggagtgatca ctaacaccat 5580
agtaatgtct aatattcaca ggcagatctg cttggggaag ctagttatgt gaaaggcaaa 5640
tagagtcata cagtagctca aaaggcaacc ataattctct ttggtgcagg tcttgggagc 5700
gtgatctaga ttacactgca ccattcccaa gttaatcccc tgaaaactta ctctcaactg 5760
gagcaaatga actttggtcc caaatatcca tcttttcagt agcgttaatt atgctctgtt 5820
tccaactgca tttcctttcc aattgaatta aagtgtggcc tcgtttttag tcatttaaaa 5880
ttgttttcta agtaattgct gcctctatta tggcacttca attttgcact gtcttttgag 5940
attcaagaaa aatttctatt cttttttttg catccaattg tgcctgaact tttaaaatat 6000
gtaaatgctg ccatgttcca aacccatcgt cagtgtgtgt gtttagagct gtgcacccta 6060
gaaacaacat attgtcccat gagcaggtgc ctgagacaca gaccccttttg cattcacaga 6120 gaggtcattg gttatagaga cttgaattaa taagtgacat tatgccagtt tctgttctct 6180
cacaggtgat aaacaatgct ttttgtgcac tacatactct tcagtgtaga gctcttgttt 6240
tatgggaaaa ggctcaaatg ccaaattgtg tttgatggat taatatgccc ttttgccgat 6300
gcatactatt actgatgtga ctcggttttg tcgcagcttt gctttgttta atgaaacaca 6360
cttgtaaacc tcttttgcac tttgaaaaag aatccagcgg gatgctcgag cacctgtaaa 6420
caattttctc aacctatttg atgttcaaat aaagaattaa actaaa 6466

<210> SEQ ID NO 121
<211> LENGTH: 3478
<212> TYPE: DNA
<213> ORGANISM: Homo sapiens

<400> SEQUENCE: 121
aaattgaaag gtcagccttt cgcgcgctgt gtaggcaagt tacccgtgtt ctgcgttgcc 60
ggccgtgggt gctctggcca cagtgagtta ggggcgtcgg agcgggtttc tccaaccgca 120
atcggctccg ctcaagggga ggaggagagt cccttctcgg aaggcctaag gaaacgtgtc 180
gtctggaatg ggcttggggg ccacgcctgc acatctccgc gagacagagg gataaagtga 240
agatggtgct gttattgtta cctcgagtgc cacatgcgac ctctgagata tgtacacagt 300
cattcttact atcgcactca gccattctta ctacgctaaa gaagaaataa ttattcgagg 360
atatttgcct ggcccagaag aaacttatgt aaatttcatg aactattata tccgttttcc 420
tcggagtgag agaaaactct ttttagatat catctgagag aactagtgaa tcccagtcac 480
tgagtggagt tgagagtcta agaacctctg aaatttgaga actgctggac cagagccttt 540
agagctctga taaggtgtca acagggtagt taatttggca ccatggggat acagggattg 600

-continued

```
ctacaattta tcaaagaagc ttcagaaccc atccatgtga ggaagtataa agggcaggta    660
gtagctgtgg atacatattg ctggcttcac aaaggagcta ttgcttgtgc tgaaaaacta    720
gccaaaggtg aacctactga taggtatgta ggattttgta tgaaatttgt aaatatgtta    780
ctatctcatg ggatcaagcc tattctcgta tttgatggat gtactttacc ttctaaaaag    840
gaagtagaga gatctagaag agaaagacga caagccaatc ttcttaaggg aaagcaactt    900
cttcgtgagg ggaaagtctc ggaagctcga gagtgtttca cccggtctat caatatcaca    960
catgccatgg cccacaaagt aattaaagct gcccggtctc agggggtaga ttgcctcgtg   1020
gctccctatg aagctgatgc gcagttggcc tatcttaaca aagcgggaat tgtgcaagcc   1080
ataattacag aggactcgga tctcctagct tttggctgta aaaaggtaat tttaaagatg   1140
gaccagtttg gaaatggact tgaaattgat caagctcggc taggaatgtg cagacagctt   1200
ggggatgtat tcacggaaga gaagtttcgt tacatgtgta ttctttcagg ttgtgactac   1260
ctgtcatcac tgcgtgggat tggattagca aaggcatgca aagtcctaag actagccaat   1320
aatccagata tagtaaaggt tatcaagaaa attggacatt atctcaagat gaatatcacg   1380
gtaccagagg attacatcaa cgggtttatt cgggccaaca ataccttcct ctatcagcta   1440
gtttttgatc ccatcaaaag gaaacttatt cctctgaacg cctatgaaga tgatgttgat   1500
cctgaaacac taagctacgc tgggcaatat gttgatgatt ccatagctct tcaaatagca   1560
cttggaaata aagatataaa tacttttgaa cagatcgatg actacaatcc agacactgct   1620
atgcctgccc attcaagaag tcatagttgg gatgacaaaa catgtcaaaa gtcagctaat   1680
gttagcagca tttggcatag gaattactct cccagaccag agtcgggtac tgtttcagat   1740
gccccacaat tgaaggaaaa tccaagtact gtgggagtgg aacgagtgat tagtactaaa   1800
gggttaaatc tcccaaggaa atcatccatt gtgaaaagac caagaagtgc agagctgtca   1860
gaagatgacc tgttgagtca gtattctctt tcatttacga agaagaccaa gaaaaatagc   1920
tctgaaggca ataaatcatt gagcttttct gaagtgtttg tgcctgacct ggtaaatgga   1980
cctactaaca aaaagagtgt aagcactcca cctaggacga gaaataaatt tgcaacattt   2040
ttacaaagga aaaatgaaga aagtggtgca gttgtggttc cagggaccag aagcaggttt   2100
ttttgcagtt cagattctac tgactgtgta tcaaacaaag tgagcatcca gcctctggat   2160
gaaactgctg tcacagataa agagaacaat ctgcatgaat cagagtatgg agaccaagaa   2220
ggcaagagac tggttgacac agatgtagca cgtaattcaa gtgatgacat tccgaataat   2280
catattccag gtgatcatat tccagacaag gcaacagtgt ttacagatga agagtcctac   2340
tcttttgaga gcagcaaatt tacaaggacc atttcaccac ccactttggg aacactaaga   2400
agttgtttta gttggtctgg aggtcttgga gatttttcaa gaacgccgag cccctctcca   2460
agcacagcat tgcagcagtt ccgaagaaag agcgattccc ccacctcttt gcctgagaat   2520
aatatgtctg atgtgtcgca gttaaagagc gaggagtcca gtgacgatga gtctcatccc   2580
ttacgagaag aggcatgttc ttcacagtcc caggaaagtg gagaattctc actgcagagt   2640
tcaaatgcat caaagctttc tcagtgctct agtaaggact ctgattcaga ggaatctgat   2700
tgcaatatta agttacttga cagtcaaagt gaccagacct ccaagctacg tttatctcat   2760
ttctcaaaaa aagacacacc tctaaggaac aaggttcctg ggctatataa gtccagttct   2820
gcagactctc tttctacaac caagatcaaa cctctaggac ctgccagagc cagtgggctg   2880
agcaagaagc cggcaagcat ccagaagaga aagcatcata atgccgagaa caagccgggg   2940
ttacagatca aactcaatga gctctggaaa aactttggat ttaaaaaaga ttctgaaaag   3000
```

```
cttcctcctt gtaagaaacc cctgtcccca gtcagagata acatccaact aactccagaa   3060

gcggaagagg atatatttaa caaacctgaa tgtggccgtg ttcaaagagc aatattccag   3120

taaatgcaga ctgctgcaaa gcttttgcct gcaagagaat ctgatcaatt tgaagtccct   3180

gtttgggaat gaggcactta tcagcatgaa gaattttttc tcattctgtg ccattttaaa   3240

aatagaatac attttgtata ttaactttat aattgggttg tggttttttt gctcagcttt   3300

ttatattttt ataagaagct aaatagaaga ataattgtat ctctgacagg tttttggagg   3360

ttttagtgtt aattgggaaa atcctctgga gtttataaaa gtctactcta aatatttctg   3420

taatgttgtc aagtagaaag atagtaaatg gagaaactac aaaaaaaaaa aaaaaaa      3478
```

<210> SEQ ID NO 122
<211> LENGTH: 5192
<212> TYPE: DNA
<213> ORGANISM: Homo sapiens

<400> SEQUENCE: 122

```
ccatgacctg ccttgagaag gggcagggga agccagatgg actggaagtg gagtggcagt     60

gaccaaggag gaggaggtgt gataggcttc ccacgcaggg tagatccaga gacaccagtg    120

ccacccatag gcccctagga ctgcagtggt cacccgattc ctttgtccca gctgagactc    180

agttctgagt gttctatttt ggggaacaga ggcgtccttg gtagcatttg gaagaggata    240

gccagctggg gtgtgtgtac atcacagcct gacagtaaca gcatccgaac cagaggtgac    300

tggctaaggg cagacccagg gcaacaggtt aaccgttcta gggccgggca cagggaggag    360

aacattccaa cactctgtgt gcccagtgcc gacgcacgtt ctctctttta tcctcaaaac    420

agtcctatga ggatataagc cagagagaga cagagacaag gaattacaag ttggtgagag    480

tcaggatttg aacttggctc tggcagatgg aaaattaggg tctgtattct ttacaaaacc    540

gtgtgtgcct cagatggagt tggtgcataa caagcagagg tatccagggt cgcggtcctg    600

cttgccacgg aaggggccgc cttgtcagtt gtgaccaccc agccctggaa atgtcagtaa    660

tgctgtaagg agtggggatc ggatcagatg ccatccagat gctgaagttt gaccttgtgt    720

catttttcac tttctttttt ggctcttctg caatcaattc atttatttag caaaaaagaa    780

attatgtgtg ccgagagcat gcagaagata tgtctccgtt ctctgcttcc ctccaaaaaa    840

gaatcccaaa actgctttct gtgaacgtgt gccagggtcc cagcaggact cagggagagc    900

aggaagccca gcccagaccc cttgcacaac ctaccgtggg gaggccttag gctctggcta    960

ctacagagct ggttccagtc tgcactgcca cagcctggcc agggacttgg acacatctgc   1020

tggccacttc ctgtctcagt ttccttatct gcaaaataag ggaaaagccc ccacaaaggt   1080

gcacgtgtag caggagctct ttccctcccc tattttagga aggcagttgg tgggaagtcc   1140

agcttgggtc cctgagagct gtgagaagga gatgcggctg ctgctggccc tgttgggggt   1200

cctgctgagt gtgcctgggc ctccagtctt gtccctggag gcctctgagg aagtggagct   1260

tggtatggct tctgaggtgg gagagggtgg caggggtggg aagagtgggc accaggaggg   1320

ggctgctggg ctgagcaaag ctggaaagga tccttgccca ggccctgaga aggtggcggc   1380

agggcagggc tcaaccactg agactcagtc agtgcctggc ttccagcaag cattcatcta   1440

tcactgtgtc tgcgagagag gactggcctt gcagggcgca gggccctaag ctgggctgca   1500

gagctggtgg tgagctcctt gcctgggtgt gtgtgcgtgt gtgtgtgtgt tctgtgcact   1560

gggtgtgtga cctaggaggt ccaggcagca tgtgtggtat aagcattatg agggtgatat   1620
```

-continued gccccggtgc agcatgaccc tgtatgtggc accaacagca tgtgccttgt gtgtgtgtgt 1680
gtccgtatgt gtgtgtgtgt atgcgtgtgt gtgtgtgtgt gtgtgtgtct tggccactgt 1740
catgtgcact aaatgctgtg tgtgtgacat gccccaagag tgtggcattt gccctgggtg 1800
tggcatccgc agcatgtggc tgtgtgggtg tcaaggagtg gtggctcctt cagcatgcgt 1860
tgcgaagtgc ttgtgccctg catgtgcggt gtgttctctg tacacaggag gctgcctcag 1920
atggggctgc ggggtctgct gacctctgcc ctctgcccac agagccctgc ctggctccca 1980
gcctggagca gcaagagcag gagctgacag tagcccttgg gcagcctgtg cggctgtgct 2040
gtgggcgggc tgagcgtggt ggccactggt acaaggaggg cagtcgcctg gcacctgctg 2100
gccgtgtacg gggctggagg ggccgcctag agattgccag cttcctacct gaggatgctg 2160
gccgctacct ctgcctggca cgaggctcca tgatcgtcct gcagaatctc accttgatta 2220
caggtgactc cttgacctcc agcaacgatg atgaggaccc caagtcccat agggacctct 2280
cgaataggca cagttacccc cagcaaggtc agtaggtctc caaggacttg tgtccccgct 2340
gctgctcatc tgatcactga gaagaggagg cctgtgtggg aacacacggt cattctaggg 2400
gccttcccct gccctccagc accctactgg acacaccccc agcgcatgga gaagaaactg 2460
catgcagtac ctgcggggaa caccgtcaag ttccgctgtc cagctgcagg caaccccacg 2520
cccaccatcc gctggcttaa ggatggacag gcctttcatg ggagaaccg cattggaggc 2580
attcggctgc gccatcagca ctggagtctc gtgatggaga gcgtggtgcc ctcggaccgc 2640
ggcacataca cctgcctggt agagaacgct gtgggcagca tccgttataa ctacctgcta 2700
gatgtgctgg agcggtcccc gcaccggccc atcctgcagg ccgggctccc ggccaacacc 2760
acagccgtgg tgggcagcga cgtggagctg ctgtgcaagg tgtacagcga tgcccagccc 2820
cacatccagt ggctgaagca catcgtcatc aacggcagca gcttcggagc cgacggtttc 2880
ccctatgtgc aagtcctaaa gactgcagac atcaatagct cagaggtgga ggtcctgtac 2940
ctgcggaacg tgtcagccga ggacgcaggc gagtacacct gcctcgcagg caattccatc 3000
ggcctctcct accagtctgc ctggctcacg gtgctgccag gtgagcacct gaagggccag 3060
gagatgctgc gagatgcccc tctgggccag cagtgggggc tgtggcctgt tgggtggtca 3120
gtctctgttg gcctgtgggg tctggcctgg ggggcagtgt gtggatttgt gggtttgagc 3180
tgtatgacag cccctctgtg cctctccaca cgtggccgtc catgtgaccg tctgctgagg 3240
tgtgggtgcc tgggactggg cataactaca gcttcctccg tgtgtgtccc cacatatgtt 3300
gggagctggg agggactgag ttagggtgca cggggcggcc agtctcacca ctgaccagtt 3360
tgtctgtctg tgtgtgtcca tgtgcgaggg cagaggagga ccccacatgg accgcagcag 3420
cgcccgaggc caggtatacg gacatcatcc tgtacgcgtc gggctccctg gccttggctg 3480
tgctcctgct gctggccagg ctgtatcgag ggcaggcgct ccacggccgg cacccccgcc 3540
cgcccgccac tgtgcagaag ctctcccgct tccctctggc ccgacagttc tccctggagt 3600
caggctcttc cggcaagtca agctcatccc tggtacgagg cgtgcgtctc tcctccagcg 3660
gccccgcctt gctcgccggc ctcgtgagtc tagatctacc tctcgaccca ctatgggagt 3720
tcccccggga caggctggtg cttgggaagc ccctaggcga gggctgcttt ggccaggtag 3780
tacgtgcaga ggcctttggc atggaccctg cccggcctga ccaagccagc actgtggccg 3840
tcaagatgct caaagacaac gcctctgaca aggacctggc cgacctggtc tcggagatgg 3900
aggtgatgaa gctgatcggc cgacacaaga acatcatcaa cctgcttggt gtctgcaccc 3960
aggaagggcc cctgtacgtg atcgtggagt gcgccgccaa gggaaacctg cgggagttcc 4020

-continued

```
tgcgggcccg gcgcccccca ggccccgacc tcagccccga cggtcctcgg agcagtgagg   4080
ggccgctctc cttcccagtc ctggtctcct gcgcctacca ggtggcccga ggcatgcagt   4140
atctggagtc ccggaagtgt atccaccggg acctggctgc ccgcaatgtg ctggtgactg   4200
aggacaatgt gatgaagatt gctgactttg ggctggcccg cggcgtccac cacattgact   4260
actataagaa aaccagcaac ggccgcctgc ctgtgaagtg gatggcgccc gaggccttgt   4320
ttgaccgggt gtacacacac cagagtgacg tgtggtcttt tgggatcctg ctatgggaga   4380
tcttcaccct cgggggctcc ccgtatcctg gcatcccggt ggaggagctg ttctcgctgc   4440
tgcgggaggg acatcggatg gaccgacccc cacactgccc cccagagctg tacgggctga   4500
tgcgtgagtg ctggcacgca gcgccctccc agaggcctac cttcaagcag ctggtggagg   4560
cgctggacaa ggtcctgctg gccgtctctg aggagtacct cgacctccgc ctgaccttcg   4620
gaccctattc cccctctggt ggggacgcca gcagcacctg ctcctccagc gattctgtct   4680
tcagccacga ccccctgcca ttgggatcca gctccttccc cttcgggtct ggggtgcaga   4740
catgagcaag gctcaaggct gtgcaggcac ataggctggt ggccttgggc cttggggctc   4800
agccacagcc tgacacagtg ctcgaccttg atagcatggg gcccctggcc cagagttgct   4860
gtgccgtgtc caagggccgt gcccttgccc ttggagctgc cgtgcctgtg tcctgatggc   4920
ccaaatgtca gggttctgct cggcttcttg gaccttggcg cttagtcccc atcccgggtt   4980
tggctgagcc tggctggaga gctgctatgc taaacctcct gcctcccaat accagcagga   5040
ggttctgggc ctctgaaccc cctttcccca cacctccccc tgctgctgct gccccagcgt   5100
cttgacggga gcattggccc ctgagcccag agaagctgga agcctgccga aaacaggagc   5160
aaatggcgtt ttataaatta tttttttgaa at                                 5192
```

<210> SEQ ID NO 123
<211> LENGTH: 3124
<212> TYPE: DNA
<213> ORGANISM: Homo sapiens

<400> SEQUENCE: 123

```
taagatccac atcagctcaa ctgcacttgc ctcgcagagg cagcccgctc acttcccgcg     60
gaggcgctcc ccggcgccgc gctccgcggc agccgcctgc ccccggcgct gcccccgccc    120
gccgcgccgc cgccgccgcc gcgcacgccg cgcccccgcag ctctgggctt cctcttcgcc   180
cgggtggcgt tgggcccgcg cgggcgctcg ggtgactgca gctgctcagc tcccctcccc    240
cgccccgcgc cgcgcggccg cccgtcgctt cgcacagggc tggatggttg tattgggcag    300
ggtggctcca ggatgttagg aactgtgaag atggaagggc atgaaaccag cgactggaac    360
agctactacg cagacacgca ggaggcctac tcctccgtcc cggtcagcaa catgaactca    420
ggcctgggct ccatgaactc catgaacacc tacatgacca tgaacaccat gactacgagc    480
ggcaacatga ccccggcgtc cttcaacatg tcctatgcca acccgggcct aggggccggc    540
ctgagtcccg gcgcagtagc cggcatgccg gggggctcgg cgggcgccat gaacagcatg    600
actgcggccg gcgtgacggc catgggtacg gcgctgagcc cgagcggcat gggcgccatg    660
ggtgcgcagc aggcggcctc catgaatggc ctgggcccct acgcggccgc catgaacccg    720
tgcatgagcc ccatggcgta cgcgccgtcc aacctgggcc gcagccgcgc gggcggcggc    780
ggcgacgcca agacgttcaa gcgcagctac ccgcacgcca agccgcccta ctcgtacatc    840
tcgctcatca ccatggccat ccagcaggcg cccagcaaga tgctcacgct gagcgagatc    900
```

-continued

```
taccagtgga tcatggacct cttcccctat taccggcaga accagcagcg ctggcagaac    960
tccatccgcc actcgctgtc cttcaatgac tgcttcgtca aggtggcacg ctccccggac   1020
aagccgggca agggctccta ctggacgctg cacccggact ccggcaacat gttcgagaac   1080
ggctgctact tgcgccgcca gaagcgcttc aagtgcgaga agcagccggg ggccggcggc   1140
gggggcggga gcggaagcgg gggcagcggc gccaagggcg gccctgagag ccgcaaggac   1200
ccctctggcg cctctaaccc cagcgccgac tcgcccctcc atcggggtgt gcacgggaag   1260
accggccagc tagagggcgc gccggccccc gggcccgccg ccagccccca gactctggac   1320
cacagtgggg cgacggcgac agggggcgcc tcggagttga agactccagc ctcctcaact   1380
gcgccccccca taagctccgg gcccggggcg ctggcctctg tgcccgcctc tcacccggca   1440
cacggcttgg caccccacga gtcccagctg cacctgaaag gggaccccca ctactccttc   1500
aaccacccgt tctccatcaa caacctcatg tcctcctcgg agcagcagca taagctggac   1560
ttcaaggcat acgaacaggc actgcaatac tcgccttacg gctctacgtt gcccgccagc   1620
ctgcctctag gcagcgcctc ggtgaccacc aggagcccca tcgagccctc agccctggag   1680
ccggcgtact accaaggtgt gtattccaga cccgtcctaa acacttccta gctcccggga   1740
ctgggggggtt tgtctggcat agccatgctg gtagcaagag agaaaaaatc aacagcaaac   1800
aaaaccacac aaaccaaacc gtcaacagca taataaaatc ccaacaacta tttttatttc   1860
atttttcatg cacaaccttt cccccagtgc aaaagactgt tactttatta ttgtattcaa   1920
aattcattgt gtatattact acaaagacaa ccccaaacca attttttttcc tgcgaagttt   1980
aatgatccac aagtgtatat atgaaattct cctccttcct tgcccccctc tctttcttcc   2040
ctctttcccc tccagacatt ctagtttgtg gagggttatt taaaaaaaca aaaaaggaag   2100
atggtcaagt ttgtaaaata tttgtttgtg ctttttcccc ctccttacct gaccccctac   2160
gagtttacag gtctgtggca atactcttaa ccataagaat tgaaatggtg aagaaacaag   2220
tatacactag aggctcttaa aagtattgaa agacaatact gctgttatat agcaagacat   2280
aaacagatta taaacatcag agccatttgc ttctcagttt acatttctga tacatgcaga   2340
tagcagatgt ctttaaatga aatacatgta tattgtgtat ggacttaatt atgcacatgc   2400
tcagatgtgt agacatcctc cgtatattta cataacatat agaggtaata gataggtgat   2460
atacatgata cattctcaag agttgcttga ccgaaagtta caaggacccc aacccctttg   2520
tcctctctac ccacagatgg ccctgggaat caattcctca ggaattgccc tcaagaactc   2580
tgcttcttgc tttgcagagt gccatggtca tgtcattctg aggtcacata acacataaaa   2640
ttagtttcta tgagtgtata ccatttaaag aattttttttt tcagtaaaag ggaatattac   2700
aatgttggag gagagataag ttatagggag ctggatttca aaacgtggtc caagattcaa   2760
aaatcctatt gatagtggcc attttaatca ttgccatcgt gtgcttgttt catccagtgt   2820
tatgcacttt ccacagttgg acatggtgtt agtatagcca gacgggtttc attattattt   2880
ctctttgctt tctcaatgtt aatttattgc atggtttatt ctttttcttt acagctgaaa   2940
ttgctttaaa tgatggttaa aattacaaat taaattgtta atttttatca atgtgattgt   3000
aattaaaaat attttgattt aaataacaaa aataatacca gattttaagc cgtggaaaat   3060
gttcttgatc atttgcagtt aaggacttta aataaatcaa atgttaacaa aaaaaaaaaa   3120
aaaa                                                                 3124
```

<210> SEQ ID NO 124
<211> LENGTH: 3452

<212> TYPE: DNA
<213> ORGANISM: Homo sapiens

<400> SEQUENCE: 124
atgcaggcgc gctactccgt gtccagcccc aactccctgg gagtggtgcc ctacctcggc 60
ggcgagcaga gctactaccg cgcggcggcc gcggcggccg ggggcggcta caccgccatg 120
ccggccccca tgagcgtgta ctcgcaccct gcgcacgccg agcagtaccc gggcggcatg 180
gcccgcgcct acgggcccta cacgccgcag ccgcagccca aggacatggt gaagccgccc 240
tatagctaca tcgcgctcat caccatggcc atccagaacg ccccggacaa gaagatcacc 300
ctgaacggca tctaccagtt catcatggac cgcttcccct tctaccggga caacaagcag 360
ggctggcaga acagcatccg ccacaacctc tcgctcaacg agtgcttcgt caaggtgccg 420
cgcgacgaca agaagccggg caagggcagc tactggacgc tggacccgga ctcctacaac 480
atgttcgaga acggcagctt cctgcggcgg cggcggcgct tcaagaagaa ggacgcggtg 540
aaggacaagg aggagaagga caggctgcac ctcaaggagc cgcccccgcc cggccgccag 600
cccccgcccg cgccgccgga gcaggccgac ggcaacgcgc ccggtccgca gccgccgccc 660
gtgcgcatcc aggacatcaa gaccgagaac ggtacgtgcc cctcgccgcc ccagcccctg 720
tccccggccg ccgccctggg cagcggcagc gccgccgcgg tgcccaagat cgagagcccc 780
gacagcagca gcagcagcct gtccagcggg agcagccccc cgggcagcct gccgtcggcg 840
cggccgctca gcctggacgg tgcggattcc gcgccgccgc cgcccgcgcc ctccgccccg 900
ccgccgcacc atagccaggg cttcagcgtg gacaacatca tgacgtcgct gcgggggtcg 960
ccgcagagcg cggccgcgga gctcagctcc ggccttctgg cctcggcggc cgcgtcctcg 1020
cgcgcgggga tcgcaccccc gctggcgctc ggcgcctact cgcccggcca gagctccctc 1080
tacagctccc cctgcagcca gacctccagc gcgggcagct cgggcggcgg cggcggcggc 1140
gcgggggccg cgggggggcgc gggcggcgcc gggacctacc actgcaacct gcaagccatg 1200
agcctgtacg cggccggcga gcgcgggggc cacttgcagg gcgcgcccgg gggcgcgggc 1260
ggctcggccg tggacgaccc cctgcccgac tactctctgc ctccggtcac cagcagcagc 1320
tcgtcgtccc tgagtcacgg cggcggcggc ggcggcggcg ggggaggcca ggaggccggc 1380
caccaccctg cggcccacca aggccgcctc acctcgtggt acctgaacca ggcgggcgga 1440
gacctgggcc acttggcgag cgcggcggcg gcggcggcgg ccgcaggcta cccgggccag 1500
cagcagaact tccactcggt gcgggagatg ttcgagtcac agaggatcgg cttgaacaac 1560
tctccagtga acgggaatag tagctgtcaa atggccttcc cttccagcca gtctctgtac 1620
cgcacgtccg gagctttcgt ctacgactgt agcaagtttt gacacaccct caaagccgaa 1680
ctaaatcgaa ccccaaagca ggaaaagcta aaggaaccca tcaaggcaaa atcgaaacta 1740
aaaaaaaaaa atccaattaa aaaaaacccc tgagaatatt caccacacca gcgaacagaa 1800
tatccctcca aaaattcagc tcaccagcac cagcacgaag aaaactctat tttcttaacc 1860
gattaattca gagccacctc cactttgcct tgtctaaata aacaaacccg taaactgttt 1920
tatacagaga cagcaaaatc ttggtttatt aaaggacagt gttactccag ataacacgta 1980
agtttcttct tgcttttcag agacctgctt tcccctcctc ccgtctcccc tctcttgcct 2040
tcttccttgc ctctcacctg taagatatta ttttatccta tgttgaaggg agggggaaag 2100
tccccgttta tgaaagtcgc tttcttttta ttcatggact tgttttaaaa tgtaaattgc 2160
aacatagtaa tttattttta atttgtagtt ggatgtcgtg gaccaaacgc cagaaagtgt 2220
tcccaaaacc tgacgttaaa ttgcctgaaa ctttaaattg tgcttttttt ctcattataa 2280
aaagggaaac tgtattaatc ttattctatc ctcttttctt tctttttgtt gaacatattc 2340
attgtttgtt tattaataaa ttaccattca gtttgaatga gacctatatg tctggatact 2400
ttaatagagc tttaattatt acgaaaaaag atttcagaga taaaacacta gaagttacct 2460
attctccacc taaatctctg aaaaatggag aaaccctctg actagtccat gtcaaatttt 2520
actaaaagtc tttttgttta gatttatttt cctgcagcat cttctgcaaa atgtactata 2580
tagtcagctt gctttgaggc tagtaaaaag atatttttct aaacagattg gagttggcat 2640
ataaacaaat acgttttctc actaatgaca gtccatgatt cggaaatttt aagcccatga 2700
atcagccgcg gtcttaccac ggtgatgcct gtgtgccgag agatgggact gtgcggccag 2760
atatgcacag ataaatattt ggcttgtgta ttccatataa aattgcagtg catattatac 2820
atccctgtga gccagatgct gaatagatat tttcctatta tttcagtcct ttataaaagg 2880
aaaaataaac cagtttttaa atgtatgtat ataattctcc cccatttaca atccttcatg 2940
tattacatag aaggattgct tttttaaaaa tatactgcgg gttggaaagg gatatttaat 3000
ctttgagaaa ctattttaga aaatatgttt gtagaacaat tatttttgaa aaagatttaa 3060
agcaataaca agaaggaagg cgagaggagc agaacatttt ggtctagggt ggtttctttt 3120
taaaccattt tttcttgtta atttacagtt aaacctaggg gacaatccgg attggccctc 3180
ccccttttgt aaataaccca ggaaatgtaa taaattcatt atcttagggt gatctgccct 3240
gccaatcaga ctttggggag atggcgattt gattacagac gttcgggggg gtggggggct 3300
tgcagtttgt tttggagata atacagtttc ctgctatctg ccgctcctat ctagaggcaa 3360
cacttaagca gtaattgctg ttgcttgttg tcaaaatttg atcattgtta aaggattgct 3420
gcaaataaat acactttaat ttcagtcaaa aa 3452

<210> SEQ ID NO 125
<211> LENGTH: 1749
<212> TYPE: DNA
<213> ORGANISM: Homo sapiens

<400> SEQUENCE: 125
gtggcctcga ggtggtggca gggccgcccc ctgcagtccg gagacgaacg cacggaccgg 60
gcctccggag gcaggttcgg ctggaaggaa ccgctctcgc ttcgtcctac acttgcgcaa 120
atgtctccga gcttactcac atagcatatt ggtatatcaa aatgaaatgc aaggaaccaa 180
aaataacata attgaaggca gtaaaagtga aattaaatag gaagatcatc agtcaaggaa 240
gacccactgg agaggacaga aaatgaagca gtgttttatc atgtgtattt cagcaggtct 300
tcttgaaatt taactaaaaa tatgactgct ctctcttcag agaactgctc ttttcagtac 360
cagttacgtc aaacaaacca gcccctagac gttaactatc tgctattctt gatcatactt 420
gggaaaatat tattaaatat ccttacacta ggaatgagaa gaaaaaacac ctgtcaaaat 480
tttatggaat atttttgcat ttcactagca ttcgttgatc ttttactttt ggtaaacatt 540
tccattatat tgtatttcag ggattttgta cttttaagca ttaggttcac taaataccac 600
atctgcctat ttactcaaat tatttccttt acttatggct ttttgcatta tccagttttc 660
ctgacagctt gtatagatta ttgcctgaat ttctctaaaa caaccaagct ttcatttaag 720
tgtcaaaaat tattttattt ctttacagta attttaattt ggatttcagt ccttgcttat 780
gttttgggag acccagccat ctaccaaagc ctgaaggcac agaatgctta ttctcgtcac 840
tgtcctttct atgtcagcat tcagagttac tggctgtcat ttttcatggt gatgatttta 900
tttgtagctt tcataacctg ttgggaagaa gttactactt tggtacaggc tatcaggata 960
acttcctata tgaatgaaac tatcttatat tttccttttt catcccactc cagttatact 1020
gtgagatcta aaaaaatatt cttatccaag ctcattgtct gttttctcag tacctggtta 1080
ccatttgtac tacttcaggt aatcattgtt ttacttaaag ttcagattcc agcatatatt 1140
gagatgaata ttccctggtt atactttgtc aatagttttc tcattgctac agtgtattgg 1200
tttaattgtc acaagcttaa tttaaaagac attggattac ctttggatcc atttgtcaac 1260
tggaagtgct gcttcattcc acttacaatt cctaatcttg agcaaattga aaagcctata 1320
tcaataatga tttgttaata ttattaatta aaagttacag ctgtcataag atcataattt 1380
tatgaacaga aagaactcag gacatattaa aaaataaact gaactaaaac aacttttgcc 1440
ccctgactga tagcatttca gaatgtgtct tttgaagggc tataccagtt attaaatagt 1500
gttttatttt aaaaacaaaa taattccaag aagtttttat agttattcag ggacactata 1560
ttacaaatat tactttgtta ttaacacaaa aagtgataag agttaacatt tggctatact 1620
gatgtttgtg ttactcaaaa aaactactgg atgcaaactg ttatgtaaat ctgagatttc 1680
actgacaact ttaagatatc aacctaaaca tttttattaa atgttcaaat gtaagcaaga 1740
aaaaaaaaa 1749

<210> SEQ ID NO 126
<211> LENGTH: 2285
<212> TYPE: DNA
<213> ORGANISM: Homo sapiens

<400> SEQUENCE: 126
acccgccccc atctgcccaa gataatttta gtttccttgg gcctggaatc tggacacaca 60
gggctccccc ccgcctctga cttctctgtc cgaagtcggg acaccctcct accacctgta 120
gagaagcggg agtggatctg aaataaaatc caggaatctg gggGttccta gacggagcca 180
gacttcggaa cgggtgtcct gctactcctg ctggggctcc tccaggacaa gggcacacaa 240
ctggttccgt taagcccctc tctcgctcag acgccatgga gctggatctg tctccacctc 300
atcttagcag ctctccggaa gacctttgcc cagcccctgg gacccctcct gggactcccc 360
ggccccctga taccccctctg cctgaggagg taaagaggtc ccagcctctc ctcatcccaa 420
ccaccggcag gaaacttcga gaggaggaga ggcgtgccac ctccctcccc tctatcccca 480
accccttccc tgagctctgc agtcctccct cacagagccc aattctcggg ggcccctcca 540
gtgcaagggg gctgctcccc cgcgatgcca gccgccccca tgtagtaaag gtgtacagtg 600
aggatggggc ctgcaggtct gtggaggtgg cagcaggtgc cacagctcgc cacgtgtgtg 660
aaatgctggt gcagcgagct cacgccttga gcgacgagac ctgggggctg gtggagtgcc 720
acccccacct agcactggag cggggtttgg aggaccacga gtccgtggtg gaagtgcagg 780
ctgcctggcc cgtgggcgga gatagccgct tcgtcttccg gaaaaacttc gccaagtacg 840
aactgttcaa gagctcccca cactccctgt tcccagaaaa aatggtctcc agctgtctcg 900
atgcacacac tggtatatcc catgaagacc tcatccagaa cttcctgaat gctggcagct 960
ttcctgagat ccagggcttt ctgcagctgc ggggttcagg acggaagctt tggaaacgct 1020
ttttctgctt cttgcgccga tctggcctct attactccac caagggcacc tctaaggatc 1080
cgaggcacct gcagtacgtg gcagatgtga acgagtccaa cgtgtacgtg gtgacgcagg 1140
gccgcaagct ctacgggatg cccactgact tcggtttctg tgtcaagccc aacaagcttc 1200
gaaatggcca caaggggctt cggatcttct gcagtgaaga tgagcagagc cgcacctgct 1260
ggctggctgc cttccgcctc ttcaagtacg gggtgcagct gtacaagaat taccagcagg 1320
cacagtctcg ccatctgcat ccatcttgtt tgggctcccc acccttgaga agtgcctcag 1380
ataataccct ggtggccatg gacttctctg gccatgctgg gcgtgtcatt gagaaccccc 1440
gggaggctct gagtgtggcc ctggaggagg cccaggcctg gaggaagaag acaaaccacc 1500
gcctcagcct gcccatgcca gcctccggca cgagcctcag tgcagccatc caccgcaccc 1560
aactctggtt ccacgggcgc atttcccgtg aggagagcca gcggcttatt ggacagcagg 1620
gcttggtaga cggcctgttc ctggtccggg agagtcagcg gaaccccccag ggctttgtcc 1680 tctctttgtg ccacctgcag aaagtgaagc attatctcat cctgccgagc gaggaggagg 1740
gccgcctgta cttcagcatg gatgatggcc agacccgctt cactgacctg ctgcagctcg 1800
tggagttcca ccagctgaac cgcggcatcc tgccgtgctt gctgcgccat tgctgcacgc 1860
gggtggccct ctgaccaggc cgtggactgg ctcatgcctc agcccgcctt caggctgccc 1920
gccgcccctc cacccatcca gtggactctg gggcgcggcc acaggggacg ggatgaggag 1980
cgggagggtt ccgccactcc agttttctcc tctgcttctt tgcctccctc agatagaaaa 2040
cagcccccac tccagtccac tcctgacccc tctcctcaag ggaaggcctt gggtggcccc 2100
ctctccttct cctagctctg gaggtgctgc tctagggcag ggaattatgg gagaagtggg 2160
ggcagcccag gcggtttcac gccccacact ttgtacagac cgagaggcca gttgatctgc 2220
tctgttttat actagtgaca ataaagatta ttttttgata caaaaaaaaa aaaaaaaaaa 2280
aaaaa 2285

<210> SEQ ID NO 127
<211> LENGTH: 935
<212> TYPE: DNA
<213> ORGANISM: Homo sapiens

<400> SEQUENCE: 127
agtcagaggt cgcgcaggcg ctggtacccc gttggtccgc gcgttgctgc gttgtgaggg 60
gtgtcagctc agtgcatccc aggcagctct tagtgtggag cagtgaactg tgtgtggttc 120
cttctacttg gggatcatgc agagagcttc acgtctgaag agagagctgc acatgttagc 180
cacagagcca cccccaggca tcacatgttg gcaagataaa gaccaaatgg atgacctgcg 240
agctcaaata ttaggtggag ccaacacacc ttatgagaaa ggtgttttta agctagaagt 300
tatcattcct gagaggtacc catttgaacc tcctcagatc cgatttctca ctccaattta 360
tcatccaaac attgattctg ctggaaggat ttgtctggat gttctcaaat tgccaccaaa 420
aggtgcttgg agaccatccc tcaacatcgc aactgtgttg acctctattc agctgctcat 480
gtcagaaccc aaccctgatg acccgctcat ggctgacata tcctcagaat ttaaatataa 540
taagccagcc ttcctcaaga atgccagaca gtggacagag aagcatgcaa gacagaaaca 600
aaaggctgat gaggaagaga tgcttgataa tctaccagag gctggtgact ccagagtaca 660
caactcaaca cagaaaagga aggccagtca gctagtaggc atagaaaaga aatttcatcc 720
tgatgtttag gggacttgtc ctggttcatc ttagttaatg tgttctttgc caaggtgatc 780
taagttgcct accttgaatt ttttttaaa tatatttgat gacataattt ttgtgtagtt 840
tatttatctt gtacatatgt attttgaaat cttttaaacc tgaaaaataa atagtcattt 900
aatgttgaaa aaaaaaaaaa aaaaaaaaaa aaaaa 935

<210> SEQ ID NO 128
<211> LENGTH: 2896
<212> TYPE: DNA
<213> ORGANISM: Homo sapiens

<400> SEQUENCE: 128
acgcttgcgc gcgggattta aactgcggcg gtttacgcgg cgttaagact tcgtagggtt 60
agcgaaattg aggtttcttg gtattgcgcg tttctcttcc ttgctgactc tccgaatggc 120
catggactcg tcgcttcagg cccgcctgtt tcccggtctc gctatcaaga tccaacgcag 180
taatggttta attcacagtg ccaatgtaag gactgtgaac ttggagaaat cctgtgtttc 240
agtggaatgg gcagaaggag gtgccacaaa gggcaaagag attgattttg atgatgtggc 300
tgcaataaac ccagaactct tacagcttct tcccttacat ccgaaggaca atctgccctt 360
gcaggaaaat gtaacaatcc agaaacaaaa acggagatcc gtcaactcca aaattcctgc 420
tccaaaagaa agtcttcgaa gccgctccac tcgcatgtcc actgtctcag agcttcgcat 480
cacggctcag gagaatgaca tggaggtgga gctgcctgca gctgcaaact cccgcaagca 540
gttttcagtt cctcctgccc ccactaggcc ttcctgccct gcagtggctg aaataccatt 600
gaggatggtc agcgaggaga tggaagagca agtccattcc atccgaggca gctcttctgc 660
aaaccctgtg aactcagttc ggaggaaatc atgtcttgtg aaggaagtgg aaaaaatgaa 720
gaacaagcga gaagagaaga aggcccagaa ctctgaaatg agaatgaaga gagctcagga 780
gtatgacagt agttttccaa actgggaatt tgcccgaatg attaaagaat ttcgggctac 840
tttggaatgt catccactta ctatgactga tcctatcgaa gagcacagaa tatgtgtctg 900
tgttaggaaa cgcccactga ataagcaaga attggccaag aaagaaattg atgtgatttc 960
cattcctagc aagtgtctcc tcttggtaca tgaacccaag ttgaaagtgg acttaacaaa 1020
gtatctggag aaccaagcat tctgctttga ctttgcattt gatgaaacag cttcgaatga 1080
agttgtctac aggttcacag caaggccact ggtacagaca atctttgaag gtggaaaagc 1140
aacttgtttt gcatatggcc agacaggaag tggcaagaca catactatgg gcggagacct 1200
ctctgggaaa gcccagaatg catccaaagg gatctatgcc atggcctccc gggacgtctt 1260
cctcctgaag aatcaaccct gctaccggaa gttgggcctg gaagtctatg tgacattctt 1320
cgagatctac aatgggaagc tgtttgacct gctcaacaag aaggccaagc tgcgcgtgct 1380
ggaggacggc aagcaacagg tgcaagtggt ggggctgcag gagcatctgg ttaactctgc 1440
tgatgatgtc atcaagatga tcgacatggg cagcgcctgc agaacctctg ggcagacatt 1500
tgccaactcc aattcctccc gctcccacgc gtgcttccaa attattcttc gagctaaagg 1560
gagaatgcat ggcaagttct ctttggtaga tctggcaggg aatgagcgag gcgcggacac 1620
ttccagtgct gaccggcaga cccgcatgga gggcgcagaa atcaacaaga gtctcttagc 1680
cctgaaggag tgcatcaggg ccctgggaca gaacaaggct cacaccccgt tccgtgagag 1740
caagctgaca caggtgctga gggactcctt cattggggag aactctagga cttgcatgat 1800
tgccacgatc tcaccaggca taagctcctg tgaatatact ttaaacaccc tgagatatgc 1860
agacagggtc aaggagctga gcccccacag tgggcccagt ggagagcagt tgattcaaat 1920
ggaaacagaa gagatggaag cctgctctaa cggggcgctg attccaggca atttatccaa 1980
ggaagaggag gaactgtctt cccagatgtc cagctttaac gaagccatga ctcagatcag 2040
ggagctggag gagaaggcta tggaagagct caaggagatc atacagcaag gaccagactg 2100
gcttgagctc tctgagatga ccgagcagcc agactatgac ctggagacct ttgtgaacaa 2160

-continued

```
agcggaatct gctctggccc agcaagccaa gcatttctca gccctgcgag atgtcatcaa   2220

ggccttgcgc ctggccatgc agctggaaga gcaggctagc agacaaataa gcagcaagaa   2280

acggccccag tgacgactgc aaataaaaat ctgtttggtt tgacacccag cctcttccct   2340

ggccctcccc agagaacttt gggtacctgg tgggtctagg cagggtctga gctgggacag   2400

gttctggtaa atgccaagta tgggggcatc tgggcccagg gcagctgggg agggggtcag   2460

agtgacatgg gacactcctt ttctgttcct cagttgtcgc cctcacgaga ggaaggagct   2520

cttagttacc cttttgtgtt gcccttcttt ccatcaaggg gaatgttctc agcatagagc   2580

tttctccgca gcatcctgcc tgcgtggact ggctgctaat ggagagctcc ctggggttgt   2640

cctggctctg gggagagaga cggagccttt agtacagcta tctgctggct ctaaaccttc   2700

tacgcctttg ggccgagcac tgaatgtctt gtactttaaa aaaatgtttc tgagacctct   2760

ttctacttta ctgtctccct agagatccta gaggatccct actgttttct gttttatgtg   2820

tttatacatt gtatgtaaca ataaagagaa aaaataaatc agctgtttaa gtgtgtggaa   2880

aaaaaaaaaa aaaaaa                                                    2896


<210> SEQ ID NO 129
<211> LENGTH: 2209
<212> TYPE: DNA
<213> ORGANISM: Homo sapiens

<400> SEQUENCE: 129

actgcgcgcg tcgtgcgtaa tgacgtcagc gccggcggag aatttcaaat tcgaacggct     60

ttggcgggcc gaggaaggac ctggtgtttt gatgaccgct gtcctgtcta gcagatactt    120

gcacggttta cagaaattcg gtccctgggt cgtgtcagga aactggaaaa aaggtcataa    180

gcatgaagcg cagttcagtt tccagcggtg gtgctggccg cctctccatg caggagttaa    240

gatcccagga tgtaaataaa caaggcctct ataccccctca aaccaaagag aaaccaacct    300

ttggaaagtt gagtataaac aaaccgacat ctgaaagaaa agtctcgcta tttggcaaaa    360

gaactagtgg acatggatcc cggaatagtc aacttggtat attttccagt tctgagaaaa    420

tcaaggaccc gagaccactt aatgacaaag cattcattca gcagtgtatt cgacaactct    480

gtgagtttct tacagaaaat ggttatgcac ataatgtgtc catgaaatct ctacaagctc    540

cctctgttaa agacttcctg aagatcttca catttcttta tggcttcctg tgcccctcat    600

acgaacttcc tgacacaaag tttgaagaag aggttccaag aatctttaaa gaccttgggt    660

atccttttgc actatccaaa agctccatgt acacagtggg ggctcctcat acatggcctc    720

acattgtggc agccttagtt tggctaatag actgcatcaa gatacatact gccatgaaag    780

aaagctcacc tttatttgat gatgggcagc cttggggaga agaaactgaa gatggaatta    840

tgcataataa gttgtttttg gactacacca taaaatgcta tgagagtttt atgagtggtg    900

ccgacagctt tgatgagatg aatgcagagc tgcagtcaaa actgaaggat ttatttaatg    960

tggatgcttt taagctggaa tcattagaag caaaaaacag agcattgaat gaacagattg   1020

caagattgga acaagaaaga gaaaaagaac cgaatcgtct agagtcgttg agaaaactga   1080

aggcttcctt acaaggagat gttcaaaagt atcaggcata catgagcaat ttggagtctc   1140

attcagccat tcttgaccag aaattaaatg gtctcaatga ggaaattgct agagtagaac   1200

tagaatgtga aacaataaaa caggagaaca ctcgactaca gaatatcatt gacaaccaga   1260

agtactcagt tgcagacatt gagcgaataa atcatgaaag aaatgaattg cagcagacta   1320

ttaataaatt aaccaaggac ctggaagctg aacaacagaa gttgtggaat gaggagttaa   1380
```

```
aatatgccag aggcaaagaa gcgattgaaa cacaattagc agagtatcac aaattggcta   1440

gaaaattaaa acttattcct aaaggtgctg agaattccaa aggttatgac tttgaaatta   1500

agtttaatcc cgaggctggt gccaactgcc ttgtcaaata cagggctcaa gtttatgtac   1560

ctcttaagga actcctgaat gaaactgaag aagaaattaa taaagcccta aataaaaaaa   1620

tgggtttgga ggatacttta gaacaattga atgcaatgat aacagaaagc aagagaagtg   1680

tgagaactct gaaagaagaa gttcaaaagc tggatgatct ttaccaacaa aaaattaagg   1740

aagcagagga agaggatgaa aaatgtgcca gtgagcttga gtccttggag aaacacaagc   1800

acctgctaga aagtactgtt aaccaggggc tcagtgaagc tatgaatgaa ttagatgctg   1860

ttcagcggga ataccaacta gttgtgcaaa ccacgactga agaaagacga aaagtgggaa   1920

ataacttgca acgtctgtta gagatggttg ctacacatgt tgggtctgta gagaaacatc   1980

ttgaggagca gattgctaaa gttgatagag aatatgaaga atgcatgtca gaagatctct   2040

cggaaaatat taaagagatt agagataagt atgagaagaa agctactcta attaagtctt   2100

ctgaagaatg aagataaaat gttgatcatg tatatatatc catagtgaat aaaattgtct   2160

cagtaaagtg taaaaaaaaa aaaaaaaaaa aaaaaaaaaa aaaaaaaaa              2209
```

```
<210> SEQ ID NO 130
<211> LENGTH: 1740
<212> TYPE: DNA
<213> ORGANISM: Homo sapiens

<400> SEQUENCE: 130

ctccctcctc tgcaccatga ctacctgcag ccgccagttc acctcctcca gctccatgaa     60

gggctcctgc ggcatcgggg gcggcatcgg gggcggctcc agccgcatct cctccgtcct    120

ggccggaggg tcctgccgcg cccccagcac ctacgggggc ggcctgtctg tctcatcctc    180

ccgcttctcc tctgggggag cctatgggtt gggggcggc tatggcggtg gcttcagcag    240

cagcagcagc agctttggta gtggctttgg gggaggatat ggtggtggcc ttggtgctgg    300

cttgggtggt ggctttggtg gtggctttgc tggtggtgat gggcttctgg tgggcagtga    360

gaaggtgacc atgcagaacc tcaacgaccg cctggcctcc tacctggaca aggtgcgtgc    420

tctggaggag gccaacgccg acctggaagt gaagatccgt gactggtacc agaggcagcg    480

gcctgctgag atcaaagact acagtcccta cttcaagacc attgaggacc tgaggaacaa    540

gattctcaca gccacagtgg acaatgccaa tgtccttctg cagattgaca atgcccgtct    600

ggccgcggat gacttccgca ccaagtatga gacagagttg aacctgcgca tgagtgtgga    660

agccgacatc aatggcctgc gcagggtgct ggacgaactg accctggcca gagctgacct    720

ggagatgcag attgagagcc tgaaggagga gctggcctac ctgaagaaga accacgagga    780

ggagatgaat gccctgagag gccaggtggg tggagatgtc aatgtggaga tggacgctgc    840

acctggcgtg gacctgagcc gcattctgaa cgagatgcgt gaccagtatg agaagatggc    900

agagaagaac cgcaaggatg ccgaggaatg gttcttcacc aagacagagg agctgaaccg    960

cgaggtggcc accaacagcg agctggtgca gagcggcaag agcgagatct cggagctccg   1020

gcgcaccatg cagaacctgg agattgagct gcagtcccag ctcagcatga aagcatccct   1080

ggagaacagc ctggaggaga ccaaaggtcg ctactgcatg cagctggccc agatccagga   1140

gatgattggc agcgtggagg agcagctggc ccagctccgc tgcgagatgg agcagcagaa   1200

ccaggagtac aagatcctgc tggacgtgaa gacgcggctg gagcaggaga tcgccaccta   1260
```

ccgccgcctg ctggagggcg aggacgccca cctctcctcc tcccagttct cctctggatc 1320
gcagtcatcc agagatgtga cctcctccag ccgccaaatc cgcaccaagg tcatggatgt 1380
gcacgatggc aaggtggtgt ccacccacga gcaggtcctt cgcaccaaga actgaggctg 1440
cccagccccg ctcaggccta ggaggccccc cgtgtggaca cagatcccac tggaagatcc 1500
cctctcctgc ccaagcactt cacagctgga ccctgcttca ccctcacccc ctcctggcaa 1560
tcaatacagc ttcattatct gagttgcata aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740

<210> SEQ ID NO 131
<211> LENGTH: 2895
<212> TYPE: DNA
<213> ORGANISM: Homo sapiens

<400> SEQUENCE: 131
ctcttttgca ggggccgttc ctcggggcat gacgctggct cctgcacaga tcctgctcct 60
ctgtggcctt cctgggctgc cctcccctcc tccgggactg ctctggactg acactgctca 120
ggttcggatt ccctcaaaga ctttgggaga caagacttgg tccccctttt acaaacaagg 180
gaacggaggc tctagaactg acttcctgaa aggcttggat ccaaagctcc ctcagttcag 240
cggccacgtc tatttccctc agacacaggg atccttgaac ctgtgggctg tatctccccg 300
cggacttgga agaatcccaa gagagtgggg ctcccacagg ctggagtgca atggtgtgat 360
ctcggctcac tgcaacctcc acctcccagg ttcaagctat tctcctgcct cagcctcctg 420
agtagctggg attacagatc ctggtggctg tggtcggtaa ttccagcttc gtgctggcta 480
caggtggatg atgcccacct ggctgccgat gacctctgca ccaagtgagg ctgggtctct 540
ggagctgccc caggggctgg acaagctgac cctggccggg gccaacctgg agatgcagat 600
tgagaacctc aaggaggacc tggtctacct gaagaagaac cacaagcagg aaatgaacgt 660
cctttgaggt caggtggatg aggatgtcag tgtgaagatg gacactgtgc ctggagtgaa 720
cctgagctgc atcctgaatg agatgcgtga ccaggacaag acattggtgg agaagagctg 780
caaggatgcc gagggctggt tcttcagcat ggtgggtggc cgtgcgtaag caggtgtgta 840
cacgtgtggg cacatgtgct gcatgctggt gcagctggag cactggcaga tccacaggct 900
gtcccagttg gaaggacttt tggaaaccag ttggaccagc ccctcatgtt ttagatgtaa 960
aacgtgaggc tcagagagga ctcaagctca cacagccctt cactgtggcc tgcaaaatag 1020
atccaggtct ctacaagtct ggtcttgggt ttccaccaca gctgtttaca ggatgtgcgt 1080
atttgaatac atatgtatac ccttggcaag cacaggctga gtatctccgg tatcctaggg 1140
acagcaacag gcgcaaaaga ataacaccca gtgcctgtct ttgaggtgct gcagttcagt 1200
aggaaaaaga aatgcaaatg accgcagagc aggctgaatt cctccaagtt ccaatgtggg 1260
tgcagaggct ctctgtgtgc agaaagaggg gctgaactgc gaggtggcca ccaacacaga 1320
ggccctgcag agtggctgga tagagatatg gagctctacg tctctgtgca gaacctgagc 1380
cgtcccagct cagcaagaaa gcatcgctgg agggcagcct ggtggagatg gaggtgtgtt 1440
acaggaccct gccggcccag ctgcaggggc ttaacagaag catggagcag cagctgtgcg 1500
agctctgctg cgacacggag caccaggacc acaagcacag gtccttctgg acgtgaagac 1560
gtggctggag caggagatcg ccacctaccg ccgcttgctg gaggttgagg acgcccagag 1620
gtgatactga cgatgcaggc tggagtctgg ctgaggagcc ttgaatgcca agttaaagcg 1680
tctggactag atcacgtagg caatggggag ccatggaggg atttggagca ggagagtgaa 1740
atgaacatca agagatttta gaacattcac tctggctgca gagggagaaa tggatcagag 1800
gggtcagggc ggggccagag agatgtgtca gggggctgga gcagggagtc tggccagaga 1860
agtcccgtgc ggtggtgggt agtggggcag gggaaggaag gtggtgcacg cagaagagag 1920
gttatagctc aaaacagcgg gactggatgc ctggatctcg ggtaagcat ggctcacagt 1980 caggactcag taagtgtcgg gagaacacat gaaggagcag gcattgatgg ccctgggttt 2040
ctggttctga tgactgtgtg agtggtgaag agcaaggtgg gtggtggttg ggtttgcagt 2100
tgggaagggt gatcaggcct tcagctgaga gtgtcccgga gtctccatgc ttagtcacac 2160
gttgcagctt tttgctcccc ggaaatggtg aagtccatct atagtctaac aacagtctct 2220
cctgctttaa ttgggtctat ttgttgggcc ctctgggtta tggaaaaacc acttgctcag 2280
cttctccttg taaattcctg gtgagtagcc acagagtgcc gccagaccta ctgctgtgct 2340
gtttcttttt cttcttcctg ctgtgctgaa cccctgccct ttcattcttg ggcctgcgct 2400
aatttctgtg cattcccaac tgtgattttt caccaattta ggggaacctc ctctgccagg 2460
gcctacttct ccccagcagt gcttgcaggt gcctgggctg gctggcatcc ctgggctgat 2520
gggtgcttct ctccctgcag gctggccact cagtactcct tgtccctggc ctcgcagccc 2580
acccgggaag ccacagtgac cagccaccag gtgtgccatc gtggaggaag tccaggttgg 2640
agaggtggtc ttcttctgtg agcaggtcca cttctccacc cactgagacc cctttctgtc 2700
tgcgacagcc ccacctcgag ggccacggca cagccatcag ctccagctcc cagcatgcta 2760
ctgccacgcc ccgagtgtcc gtctgggccc cggtgcatgg cctgttgtct ttctgtatct 2820
actttctgca gcccctcact gaggaggcct cctgggtttg tccagtgcct actattaaag 2880
ctttgctcca agttc 2895

<210> SEQ ID NO 132
<211> LENGTH: 2529
<212> TYPE: DNA
<213> ORGANISM: Homo sapiens

<400> SEQUENCE: 132
gcatcctttt tgggctgctc acagccccca gcctctatgg tgaagacata cttgctagca 60
gcgtcaccaa cttgctgcca agagatcagt gctgcaaggc aaggttattt ctaactgagc 120
agagcctgcc aggaagaaag cgtttgcacc ccacaccact gtgcaggtgt gaccggtgag 180
ctcacagctg ccccccaggc atgcccagcc cacttaatca ttcacagctc gacagctctc 240
tcgcccagcc cagttctgga agggataaaa agggggcatc accgttcctg ggtaacagag 300
ccaccttctg cgtcctgctg agctctgttc tctccagcac ctcccaaccc actagtgcct 360
ggttctcttg ctccaccagg aacaagccac catgtctcgc cagtcaagtg tgtccttccg 420
gagcgggggc agtcgtagct tcagcaccgc ctctgccatc accccgtctg tctcccgcac 480
cagcttcacc tccgtgtccc ggtccggggg tggcggtggt ggtggcttcg gcagggtcag 540
ccttgcgggt gcttgtggag tgggtggcta tggcagccgg agcctctaca acctgggggg 600
ctccaagagg atatccatca gcactagagg aggcagcttc aggaaccggt ttggtgctgg 660
tgctggaggc ggctatggct ttggaggtgg tgccggtagt ggatttggtt tcggcggtgg 720
agctggtggt ggctttgggc tcggtggcgg agctggcttt ggaggtggct tcggtggccc 780
tggctttcct gtctgccctc ctggaggtat ccaagaggtc actgtcaacc agagtctcct 840

-continued

```
gactcccctc aacctgcaaa tcgaccccag catccagagg gtgaggaccg aggagcgcga    900

gcagatcaag accctcaaca ataagtttgc ctccttcatc gacaaggtgc ggttcctgga    960

gcagcagaac aaggttctgg acaccaagtg gaccctgctg caggagcagg gcaccaagac   1020

tgtgaggcag aacctggagc cgttgttcga gcagtacatc aacaacctca ggaggcagct   1080

ggacagcatc gtgggggaac ggggccgcct ggactcagag ctgagaaaca tgcaggacct   1140

ggtggaagac ttcaagaaca agtatgagga tgaaatcaac aagcgtacca ctgctgagaa   1200

tgagtttgtg atgctgaaga aggatgtaga tgctgcctac atgaacaagg tggagctgga   1260

ggccaaggtt gatgcactga tggatgagat taacttcatg aagatgttct ttgatgcgga   1320

gctgtcccag atgcagacgc atgtctctga cacctcagtg gtcctctcca tggacaacaa   1380

ccgcaacctg gacctggata gcatcatcgc tgaggtcaag gcccagtatg aggagattgc   1440

caaccgcagc cggacagaag ccgagtcctg gtatcagacc aagtatgagg agctgcagca   1500

gacagctggc cggcatggcg atgacctccg caacaccaag catgagatca cagagatgaa   1560

ccggatgatc cagaggctga gagccgagat tgacaatgtc aagaaacagt gcgccaatct   1620

gcagaacgcc attgcggatg ccgagcagcg tggggagctg gccctcaagg atgccaggaa   1680

caagctggcc gagctggagg aggccctgca gaaggccaag caggacatgg cccggctgct   1740

gcgtgagtac caggagctca tgaacaccaa gctggccctg gacgtggaga tcgccactta   1800

ccgcaagctg ctggagggcg aggaatgcag actcagtgga gaaggagttg gaccagtcaa   1860

catctctgtt gtcacaagca gtgtttcctc tggatatggc agtggcagtg gctatggcgg   1920

tggcctcggt ggaggtcttg gcggcggcct cggtggaggt cttgccggag gtagcagtgg   1980

aagctactac tccagcagca gtgggggtgt cggcctaggt ggtgggctca gtgtgggggg   2040

ctctggcttc agtgcaagca gtggccgagg gctgggggtg ggctttggca gtggcggggg   2100

tagcagctcc agcgtcaaat ttgtctccac cacctcctcc tcccggaaga gcttcaagag   2160

ctaagaacct gctgcaagtc actgccttcc aagtgcagca acccagccca tggagattgc   2220

ctcttctagg cagttgctca agccatgttt tatccttttc tggagagtag tctagaccaa   2280

gccaattgca gaaccacatt ctttggttcc caggagagcc ccattcccag cccctggtct   2340

cccgtgccgc agttctatat tctgcttcaa atcagccttc aggtttccca cagcatggcc   2400

cctgctgaca cgagaaccca aagttttccc aaatctaaat catcaaaaca gaatccccac   2460

cccaatccca aattttgttt tggttctaac tacctccaga atgtgttcaa taaaatgctt   2520

ttataatat                                                           2529
```

<210> SEQ ID NO 133
<211> LENGTH: 6816
<212> TYPE: DNA
<213> ORGANISM: Homo sapiens

<400> SEQUENCE: 133

```
ggacggccga gcggcagggc gctcgcgcgc gcccactagt ggccggagga gaaggctccc     60

gcggaggccg cgctgcccgc cccctcccct ggggaggctc gcgttcccgc tgctcgcgcc    120

tgcgccgccc gccggcctca ggaacgcgcc ctcttcgccg gcgcgcgccc tcgcagtcac    180

cgccacccac cagctccggc accaacagca gcgccgctgc caccgcccac cttctgccgc    240

cgccaccaca gccaccttct cctcctccgc tgtcctctcc cgtcctcgcc tctgtcgact    300

atcaggtgaa ctttgaacca ggatggctga gccccgccag gagttcgaag tgatggaaga    360

tcacgctggg acgtacgggt tgggggacag gaaagatcag gggggctaca ccatgcacca    420
```

```
agaccaagag ggtgacacgg acgctggcct gaaagaatct cccctgcaga cccccactga    480
ggacggatct gaggaaccgg gctctgaaac ctctgatgct aagagcactc caacagcgga    540
agatgtgaca gcacccttag tggatgaggg agctcccggc aagcaggctg ccgcgcagcc    600
ccacacggag atcccagaag gaaccacagc tgaagaagca ggcattggag acacccccag    660
cctggaagac gaagctgctg gtcacgtgac ccaagagcct gaaagtggta aggtggtcca    720
ggaaggcttc ctccgagagc caggcccccc aggtctgagc caccagctca tgtccggcat    780
gcctggggct cccctcctgc ctgagggccc cagagaggcc acacgccaac cttcggggac    840
aggacctgag gacacagagg gcggccgcca cgcccctgag ctgctcaagc accagcttct    900
aggagacctg caccaggagg ggccgccgct gaagggggca gggggcaaag agaggccggg    960
gagcaaggag gaggtggatg aagaccgcga cgtcgatgag tcctcccccc aagactcccc   1020
tccctccaag gcctccccag cccaagatgg gcggcctccc cagacagccg ccagagaagc   1080
caccagcatc ccaggcttcc cagcggaggg tgccatcccc ctccctgtgg atttcctctc   1140
caaagtttcc acagagatcc cagcctcaga gcccgacggg cccagtgtag ggcgggccaa   1200
agggcaggat gccccccctgg agttcacgtt tcacgtggaa atcacaccca acgtgcagaa   1260
ggagcaggcg cactcggagg agcatttggg aagggctgca tttccagggg cccctggaga   1320
ggggccagag gcccggggcc cctctttggg agaggacaca aaagaggctg accttccaga   1380
gccctctgaa aagcagcctg ctgctgctcc gcgggggaag cccgtcagcc gggtccctca   1440
actcaaagct cgcatggtca gtaaaagcaa agacgggact ggaagcgatg acaaaaaagc   1500
caagacatcc acacgttcct ctgctaaaac cttgaaaaat aggccttgcc ttagccccaa   1560
acaccccact cctggtagct cagaccctct gatccaaccc tccagccctg ctgtgtgccc   1620
agagccacct tcctctccta aatacgtctc ttctgtcact tcccgaactg gcagttctgg   1680
agcaaaggag atgaaactca agggggctga tggtaaaacg aagatcgcca caccgcgggg   1740
agcagcccct ccaggccaga agggccaggc caacgccacc aggattccag caaaaacccc   1800
gcccgctcca aagacaccac ccagctctgc gactaagcaa gtccagagaa gaccaccccc   1860
tgcagggccc agatctgaga gaggtgaacc tccaaaatca ggggatcgca gcggctacag   1920
cagccccggc tccccaggca ctcccggcag ccgctcccgc accccgtccc ttccaacccc   1980
acccacccgg gagcccaaga aggtggcagt ggtccgtact ccacccaagt cgccgtcttc   2040
cgccaagagc cgcctgcaga cagcccccgt gcccatgcca gacctgaaga atgtcaagtc   2100
caagatcggc tccactgaga acctgaagca ccagccggga ggcgggaagg tgcagataat   2160
taataagaag ctggatctta gcaacgtcca gtccaagtgt ggctcaaagg ataatatcaa   2220
acacgtcccg ggaggcggca gtgtgcaaat agtctacaaa ccagttgacc tgagcaaggt   2280
gacctccaag tgtggctcat taggcaacat ccatcataaa ccaggaggtg gccaggtgga   2340
agtaaaatct gagaagcttg acttcaagga cagagtccag tcgaagattg ggtccctgga   2400
caatatcacc cacgtccctg gcggaggaaa taaaaagatt gaaacccaca agctgacctt   2460
ccgcgagaac gccaaagcca agacagacca cggggcggag atcgtgtaca agtcgccagt   2520
ggtgtctggg gacacgtctc cacggcatct cagcaatgtc tcctccaccg gcagcatcga   2580
catggtagac tcgccccagc tcgccacgct agctgacgag gtgtctgcct ccctggccaa   2640
gcagggtttg tgatcaggcc cctggggcgg tcaataattg tggagaggag agaatgagag   2700
agtgtggaaa aaaaaagaat aatgacccgg cccccgccct ctgcccccag ctgctcctcg   2760
```

-continued

```
cagttcggtt aattggttaa tcacttaacc tgcttttgtc actcggcttt ggctcgggac   2820

ttcaaaatca gtgatgggag taagagcaaa tttcatcttt ccaaattgat gggtgggcta   2880

gtaataaaat atttaaaaaa aaacattcaa aaacatggcc acatccaaca tttcctcagg   2940

caattccttt tgattctttt ttcttccccc tccatgtaga agagggagaa ggagaggctc   3000

tgaaagctgc ttctggggga tttcaaggga ctgggggtgc caaccacctc tggccctgtt   3060

gtgggggtgt cacagaggca gtggcagcaa caaaggattt gaaacttggt gtgttcgtgg   3120

agccacaggc agacgatgtc aaccttgtgt gagtgtgacg gggttgggg tggggcggga   3180

ggccacgggg gaggccgagg caggggctgg gcagaggga gaggaagcac aagaagtggg   3240

agtgggagag gaagccacgt gctggagagt agacatcccc ctccttgccg ctgggagagc   3300

caaggcctat gccacctgca gcgtctgagc ggccgcctgt ccttggtggc cgggggtggg   3360

ggcctgctgt gggtcagtgt gccaccctct gcagggcagc ctgtgggaga agggacagcg   3420

ggtaaaaaga gaaggcaagc tggcaggagg gtggcacttc gtggatgacc tccttagaaa   3480

agactgacct tgatgtcttg agagcgctgg cctcttcctc cctccctgca gggtaggggg   3540

cctgagttga ggggcttccc tctgctccac agaaaccctg ttttattgag ttctgaaggt   3600

tggaactgct gccatgattt tggccacttt gcagacctgg gactttaggg ctaaccagtt   3660

ctctttgtaa ggacttgtgc ctcttgggag acgtccaccc gtttccaagc ctgggccact   3720

ggcatctctg gagtgtgtgg gggtctggga ggcaggtccc gagccccctg tccttcccac   3780

ggccactgca gtcaccccgt ctgcgccgct gtgctgttgt ctgccgtgag agcccaatca   3840

ctgcctatac ccctcatcac acgtcacaat gtcccgaatt cccagcctca ccaccccttc   3900

tcagtaatga ccctggttgg ttgcaggagg tacctactcc atactgaggg tgaaattaag   3960

ggaaggcaaa gtccaggcac aagagtggga ccccagcctc tcactctcag ttccactcat   4020

ccaactggga ccctcaccac gaatctcatg atctgattcg gttccctgtc tcctcctccc   4080

gtcacagatg tgagccaggg cactgctcag ctgtgaccct aggtgtttct gccttgttga   4140

catggagaga gccctttccc ctgagaaggc ctggcccctt cctgtgctga gcccacagca   4200

gcaggctggg tgtcttggtt gtcagtggtg gcaccaggat ggaagggcaa ggcacccagg   4260

gcaggcccac agtcccgctg tcccccactt gcaccctagc ttgtagctgc caacctccca   4320

gacagcccag cccgctgctc agctccacat gcatagtatc agccctccac acccgacaaa   4380

ggggaacaca ccccccttgga aatggttctt ttcccccagt cccagctgga agccatgctg   4440

tctgttctgc tggagcagct gaacatatac atagatgttg ccctgccctc cccatctgca   4500

ccctgttgag ttgtagttgg atttgtctgt ttatgcttgg attcaccaga gtgactatga   4560

tagtgaaaag aaaaaaaaaa aaaaaaaagg acgcatgtat cttgaaatgc ttgtaaagag   4620

gtttctaacc caccctcacg aggtgtctct cacccccaca ctgggactcg tgtggcctgt   4680

gtggtgccac cctgctgggg cctcccaagt tttgaaaggc tttcctcagc acctgggacc   4740

caacagagac cagcttctag cagctaagga ggccgttcag ctgtgacgaa ggcctgaagc   4800

acaggattag gactgaagcg atgatgtccc cttccctact tccccttggg gctccctgtg   4860

tcagggcaca gactaggtct tgtggctggt ctggcttgcg gcgcgaggat ggttctctct   4920

ggtcatagcc cgaagtctca tggcagtccc aaaggaggct tacaactcct gcatcacaag   4980

aaaaaggaag ccactgccag ctggggggat ctgcagctcc cagaagctcc gtgagcctca   5040

gccacccctc agactgggtt cctctccaag ctcgccctct ggaggggcag cgcagcctcc   5100

caccaagggc cctgcgacca cagcagggat tgggatgaat tgcctgtcct ggatctgctc   5160
```

```
tagaggccca agctgcctgc ctgaggaagg atgacttgac aagtcaggag acactgttcc   5220
caaagccttg accagagcac ctcagcccgc tgaccttgca caaactccat ctgctgccat   5280
gagaaaaggg aagccgcctt tgcaaaacat tgctgcctaa agaaactcag cagcctcagg   5340
cccaattctg ccacttctgg tttgggtaca gttaaaggca accctgaggg acttggcagt   5400
agaaatccag ggcctcccct ggggctggca gcttcgtgtg cagctagagc tttacctgaa   5460
aggaagtctc tgggcccaga actctccacc aagagcctcc ctgccgttcg ctgagtccca   5520
gcaattctcc taagttgaag ggatctgaga aggagaagga aatgtggggt agatttggtg   5580
gtggttagag atatgccccc ctcattactg ccaacagttt cggctgcatt tcttcacgca   5640
cctcggttcc tcttcctgaa gttcttgtgc cctgctcttc agcaccatgg gccttcttat   5700
acggaaggct ctgggatctc cccctgtgg ggcaggctct tggggccagc ctaagatcat    5760
ggtttagggt gatcagtgct ggcagataaa ttgaaaaggc acgctggctt gtgatcttaa   5820
atgaggacaa tccccccagg gctgggcact cctcccctcc cctcacttct cccacctgca   5880
gagccagtgt ccttgggtgg gctagatagg atatactgta tgccggctcc ttcaagctgc   5940
tgactcactt tatcaatagt tccatttaaa ttgacttcag tggtgagact gtatcctgtt   6000
tgctattgct tgttgtgcta tggggggagg ggggaggaat gtgtaagata gttaacatgg   6060
gcaaagggag atcttggggt gcagcactta aactgcctcg taacccttt catgatttca    6120
accacatttg ctagagggag ggagcagcca cggagttaga ggcccttggg gtttctcttt   6180
tccactgaca ggctttccca ggcagctggc tagttcattc cctccccagc caggtgcagg   6240
cgtaggaata tggacatctg gttgctttgg cctgctgccc tctttcaggg gtcctaagcc   6300
cacaatcatg cctccctaag accttggcat ccttccctct aagccgttgg cacctctgtg   6360
ccacctctca cactggctcc agacacacag cctgtgcttt tggagctgag atcactcgct   6420
tcaccctcct catctttgtt ctccaagtaa agccacgagg tcggggcgag ggcagaggtg   6480
atcacctgcg tgtcccatct acagacctgc agcttcataa aacttctgat ttctcttcag   6540
ctttgaaaag ggttaccctg ggcactggcc tagagcctca cctcctaata gacttagccc   6600
catgagtttg ccatgttgag caggactatt tctggcactt gcaagtccca tgatttcttc   6660
ggtaattctg agggtggggg gagggacatg aaatcatctt agcttagctt tctgtctgtg   6720
aatgtctata tagtgtattg tgtgttttaa caaatgattt acactgactg ttgctgtaaa   6780
agtgaatttg gaaataaagt tattactctg attaaa                             6816
```

```
<210> SEQ ID NO 134
<211> LENGTH: 2372
<212> TYPE: DNA
<213> ORGANISM: Homo sapiens

<400> SEQUENCE: 134

gcaccgcgcg agcttggctg cttctggggc ctgtgtggcc ctgtgtgtcg gaaagatgga     60
gcaagaagcc gagcccgagg ggcggccgcg accccctctga ccgagatcct gctgctttcg   120
cagccaggag caccgtccct ccccggatta gtgcgtacga gcgcccagtg ccctggcccg    180
gagagtggaa tgatccccga ggcccagggc gtcgtgcttc cgcagtagtc agtccccgtg    240
aaggaaactg gggagtcttg agggaccccc gactccaagc gcgaaaaccc cggatggtga    300
ggagcaggca aatgtgcaat accaacatgt ctgtacctac tgatggtgct gtaaccacct    360
cacagattcc agcttcggaa caagagaccc tggttagacc aaagccattg cttttgaagt    420
```

-continued

```
tattaaagtc tgttggtgca caaaaagaca cttatactat gaaagaggtt cttttttatc    480
ttggccagta tattatgact aaacgattat atgatgagaa gcaacaacat attgtatatt    540
gttcaaatga tcttctagga gatttgtttg gcgtgccaag cttctctgtg aaagagcaca    600
ggaaaatata taccatgatc tacaggaact tggtagtagt caatcagcag gaatcatcgg    660
actcaggtac atctgtgagt gagaacaggt gtcaccttga aggtgggagt gatcaaaagg    720
accttgtaca agagcttcag gaagagaaac cttcatcttc acatttggtt tctagaccat    780
ctacctcatc tagaaggaga gcaattagtg agacagaaga aaattcagat gaattatctg    840
gtgaacgaca aagaaaacgc cacaaatctg atagtatttc cctttccttt gatgaaagcc    900
tggctctgtg tgtaataagg gagatatgtt gtgaaagaag cagtagcagt gaatctacag    960
ggacgccatc gaatccggat cttgatgctg gtgtaagtga acattcaggt gattggttgg   1020
atcaggattc agtttcagat cagtttagtg tagaatttga agttgaatct ctcgactcag   1080
aagattatag ccttagtgaa gaaggacaag aactctcaga tgaagatgat gaggtatatc   1140
aagttactgt gtatcaggca ggggagagtg atacagattc atttgaagaa gatcctgaaa   1200
tttccttagc tgactattgg aaatgcactt catgcaatga aatgaatccc ccccttccat   1260
cacattgcaa cagatgttgg gcccttcgtg agaattggct tcctgaagat aaagggaaag   1320
ataaagggga aatctctgag aaagccaaac tggaaaactc aacacaagct gaagagggct   1380
ttgatgttcc tgattgtaaa aaaactatag tgaatgattc cagagagtca tgtgttgagg   1440
aaaatgatga taaaattaca caagcttcac aatcacaaga aagtgaagac tattctcagc   1500
catcaacttc tagtagcatt atttatagca gccaagaaga tgtgaaagag tttgaaaggg   1560
aagaaaccca agacaaagaa gagagtgtgg aatctagttt gcccccttaat gccattgaac  1620
cttgtgtgat ttgtcaaggt cgacctaaaa atggttgcat tgtccatggc aaaacaggac   1680
atcttatggc ctgctttaca tgtgcaaaga agctaaagaa aaggaataag ccctgcccag   1740
tatgtagaca accaattcaa atgattgtgc taacttattt cccctagttg acctgtctat   1800
aagagaatta tatatttcta actatataac cctaggaatt tagacaacct gaaatttatt   1860
cacatatatc aaagtgagaa aatgcctcaa ttcacataga tttcttctct ttagtataat   1920
tgacctactt tggtagtgga atagtgaata cttactataa tttgacttga atatgtagct   1980
catcctttac accaactcct aattttaaat aatttctact ctgtcttaaa tgagaagtac   2040
ttggtttttt ttttcttaaa tatgtatatg acatttaaat gtaacttatt atttttttg    2100
agaccgagtc ttgctctgtt acccaggctg gagtgcagtg ggtgatcttg gctcactgca   2160
agctctgccc tccccgggtt cgcaccattc tcctgcctca gcctcccaat tagcttggcc   2220
tacagtcatc tgccaccaca cctggctaat tttttgtact tttagtagag acagggtttc   2280
accgtgttag ccaggatggt ctcgatctcc tgacctcgtg atccgcccac ctcggcctcc   2340
caaagtgctg ggattacagg catgagccac cg                                 2372
```

<210> SEQ ID NO 135
<211> LENGTH: 2486
<212> TYPE: DNA
<213> ORGANISM: Homo sapiens

<400> SEQUENCE: 135

```
gagatttgat tcccttggcg ggcggaagcg gccacaaccc ggcgatcgaa aagattctta     60
ggaacgccgt accagccgcg tctctcagga cagcaggccc ctgtccttct gtcgggcgcc    120
gctcagccgt gccctccgcc cctcaggttc tttttctaat tccaaataaa cttgcaagag    180
```

gactatgaaa gattatgatg aacttctcaa atattatgaa ttacatgaaa ctattgggac 240
aggtggcttt gcaaaggtca aacttgcctg ccatatcctt actggagaga tggtagctat 300
aaaaatcatg gataaaaaca cactagggag tgatttgccc cggatcaaaa cggagattga 360
ggccttgaag aacctgagac atcagcatat atgtcaactc taccatgtgc tagagacagc 420
caacaaaata ttcatggttc ttgagtactg ccctggagga gagctgtttg actatataat 480
ttcccaggat cgcctgtcag aagaggagac ccgggttgtc ttccgtcaga tagtatctgc 540
tgttgcttat gtgcacagcc agggctatgc tcacagggac ctcaagccag aaaatttgct 600
gtttgatgaa tatcataaat taaagctgat tgactttggt ctctgtgcaa aacccaaggg 660
taacaaggat taccatctac agacatgctg tgggagtctg gcttatgcag cacctgagtt 720
aatacaaggc aaatcatatc ttggatcaga ggcagatgtt tggagcatgg gcatactgtt 780
atatgttctt atgtgtggat ttctaccatt tgatgatgat aatgtaatgg ctttatacaa 840
gaagattatg agaggaaaat atgatgttcc caagtggctc tctcccagta gcattctgct 900
tcttcaacaa atgctgcagg tggacccaaa gaaacggatt tctatgaaaa atctattgaa 960
ccatccctgg atcatgcaag attacaacta tcctgttgag tggcaaagca agaatccttt 1020
tattcacctc gatgatgatt gcgtaacaga actttctgta catcacagaa acaacaggca 1080
aacaatggag gatttaattt cactgtggca gtatgatcac ctcacggcta cctatcttct 1140
gcttctagcc aagaaggctc ggggaaaacc agttcgttta aggctttctt ctttctcctg 1200
tggacaagcc agtgctaccc cattcacaga catcaagtca aataattgga gtctggaaga 1260
tgtgaccgca agtgataaaa attatgtggc gggattaata gactatgatt ggtgtgaaga 1320
tgatttatca acaggtgctg ctactccccg aacatcacag tttaccaagt actggacaga 1380
atcaaatggg gtggaatcta aatcattaac tccagcctta tgcagaacac ctgcaaataa 1440
attaaagaac aaagaaaatg tatatactcc taagtctgct gtaaagaatg aagagtactt 1500
tatgtttcct gagccaaaga ctccagttaa taagaaccag cataagagag aaatactcac 1560
tacgccaaat cgttacacta caccctcaaa agctagaaac cagtgcctga aagaaactcc 1620
aattaaaata ccagtaaatt caacaggaac agacaagtta atgacaggtg tcattagccc 1680
tgagaggcgg tgccgctcag tggaattgga tctcaaccaa gcacatatgg aggagactcc 1740
aaaaagaaag ggagccaaag tgtttgggag ccttgaaagg gggttggata aggttatcac 1800
tgtgctcacc aggagcaaaa ggaagggttc tgccagagac gggcccagaa gactaaagct 1860
tcactataac gtgactacaa ctagattagt gaatccagat caactgttga atgaaataat 1920
gtctattctt ccaaagaagc atgttgactt tgtacaaaag ggttatacac tgaagtgtca 1980
aacacagtca gattttggga aagtgacaat gcaatttgaa ttagaagtgt gccagcttca 2040
aaaacccgat gtggtgggta tcaggaggca gcggcttaag ggcgatgcct gggtttacaa 2100
aagattagtg gaagacatcc tatctagctg caaggtataa ttgatggatt cttccatcct 2160
gccggatgag tgtgggtgtg atacagccta cataaagact gttatgatcg ctttgatttt 2220
aaagttcatt ggaactacca acttgtttct aaagagctat cttaagacca atatctcttt 2280
gtttttaaac aaaagatatt attttgtgta tgaatctaaa tcaagcccat ctgtcattat 2340
gttactgtct tttttaatca tgtggttttg tatattaata attgttgact ttcttagatt 2400
cacttccata tgtgaatgta agctcttaac tatgtctctt tgtaatgtgt aatttctttc 2460
tgaaataaaa ccatttgtga atatag 2486

<210> SEQ ID NO 136
<211> LENGTH: 1140
<212> TYPE: DNA
<213> ORGANISM: Homo sapiens
<220> FEATURE:
<221> NAME/KEY: misc_feature
<222> LOCATION: (1140)..(1140)
<223> OTHER INFORMATION: n is a, c, g, t or u

<400> SEQUENCE: 136
gcagcggagg agcccagtcc acgatggccc ggtccctggt gtgccttggt gtcatcatct 60
tgctgtctgc cttctccgga cctggtgtca ggggtggtcc tatgcccaag ctggctgacc 120
ggaagctgtg tgcggaccag gagtgcagcc accctatctc catggctgtg gcccttcagg 180
actacatggc ccccgactgc cgattcctga ccattcaccg ggccaagtg gtgtatgtct 240 tctccaagct gaagggccgt gggcggctct tctggggagg cagcgttcag ggagattact 300
atggagatct ggctgctcgc ctgggctatt tccccagtag cattgtccga gaggaccaga 360
ccctgaaacc tggcaaagtc gatgtgaaga cagacaaatg ggatttctac tgccagtgag 420
ctcagcctac cgctggccct gccgtttccc ctccttgggt ttatgcaaat acaatcagcc 480
cagtgcaaaa aaaaaaaaaa aaaaaaaaaa cttcggagaa gagatagcaa caaaaggccg 540
cttgtgtgaa ggcgccaaaa gttttcgccc aagagacctt cggcctcccc cagggcgcgc 600
gcaaaggcgc cttgttttga caacctcttg gacaaccgga ggggctaccg cccggagacc 660
cctgtggtgg accccccggg caacccggtg tgacagggta ctcacccccca cggctttgtc 720 gggggtccca ccaaaggccc caaagaggct ctttcaaggc actattcctt gttgtagacc 780
ttgtgtgtgc cacaggcgcc aaagaaacct cggggggcta acaaacgcac gtgcttggca 840
gctccgagaa ggctctctcc cacccgaggg gtggacgcaa caggggggaat gggccatcat 900 attgttgccc ccggtgggca ccaactcttt ttcccccata gagaggcctt agcacactat 960
gtggggcacg ttattgccgc ctagagaaac cgagcgccag aaaatttcga aggggggggc 1020
gcttctcatc attttgcgca aaaccccctt gtgggagtat gccccgaact cctctggaac 1080
acacaagcga cacttgcgcg gggtctgcaa aaaacctcct gttgggaagc cggcttcacn 1140

<210> SEQ ID NO 137
<211> LENGTH: 12507
<212> TYPE: DNA
<213> ORGANISM: Homo sapiens

<400> SEQUENCE: 137
taccgggcgg aggtgagcgc ggcgccggct cctcctgcgg cggactttgg gtgcgacttg 60
acgagcggtg gttcgacaag tggccttgcg ggccggatcg tcccagtgga agagttgtaa 120
atttgcttct ggccttcccc tacggattat acctggcctt cccctacgga ttatactcaa 180
cttactgttt agaaaatgtg gcccacgaga cgcctggtta ctatcaaaag gagcggggtc 240
gacggtcccc actttcccct gagcctcagc acctgcttgt ttggaagggg tattgaatgt 300
gacatccgta tccagcttcc tgttgtgtca aaacaacatt gcaaaattga aatccatgag 360
caggaggcaa tattacataa tttcagttcc acaaatccaa cacaagtaaa tgggtctgtt 420
attgatgagc ctgtacggct aaaacatgga gatgtaataa ctattattga tcgttccttc 480
aggtatgaaa atgaaagtct tcagaatgga aggaagtcaa ctgaatttcc aagaaaaata 540
cgtgaacagg agccagcacg tcgtgtctca agatctagct tctcttctga ccctgatgag 600
aaagctcaag attccaaggc ctattcaaaa atcactgaag gaaaagtttc aggaaatcct 660
caggtacata tcaagaatgt caaagaagac agtaccgcag atgactcaaa agacagtgtt 720
gctcagggaa caactaatgt tcattcctca gaacatgctg gacgtaatgg cagaaatgca 780
gctgatccca tttctgggga ttttaaagaa atttccagcg ttaaattagt gagccgttat 840
ggagaattga agtctgttcc cactacacaa tgtcttgaca atagcaaaaa aaatgaatct 900
cccttttgga agctttatga gtcagtgaag aaagagttgg atgtaaaatc acaaaaagaa 960
aatgtcctac agtattgtag aaaatctgga ttacaaactg attacgcaac agagaaagaa 1020
agtgctgatg gtttacaggg ggagacccaa ctgttggtct cgcgtaagtc aagaccaaaa 1080
tctggtggga gcggccacgc tgtggcagag cctgcttcac ctgaacaaga gcttgaccag 1140
aacaagggga agggaagaga cgtggagtct gttcagactc ccagcaaggc tgtgggcgcc 1200
agctttcctc tctatgagcc ggctaaaatg aagacccctg tacaatattc acagcaacaa 1260
aattctccac aaaaacataa gaacaaagac ctgtatacta ctggtagaag agaatctgtg 1320
aatctgggta aaagtgaagg cttcaaggct ggtgataaaa ctcttactcc caggaagctt 1380
tcaactagaa atcgaacacc agctaaagtt gaagatgcag ctgactctgc cactaagcca 1440
gaaaatctct cttccaaaac cagaggaagt attcctacag atgtggaagt tctgcctacg 1500
gaaactgaaa ttcacaatga gccatttta actctgtggc tcactcaagt tgagaggaag 1560
atccaaaagg attccctcag caagcctgag aaattgggca ctacagctgg acagatgtgc 1620
tctgggttac ctggtcttag ttcagttgat atcaacaact ttggtgattc cattaatgag 1680
agtgagggaa tacctttgaa aagaaggcgt gtgtcctttg gtgggcacct aagacctgaa 1740
ctatttgatg aaaacttgcc tcctaatacg cctctcaaaa ggggagaagc cccaaccaaa 1800
agaaagtctc tggtaatgca cactccacct gtcctgaaga aaatcatcaa ggaacagcct 1860
caaccatcag gaaaacaaga gtcaggttca gaaatccatg tggaagtgaa ggcacaaagc 1920
ttggttataa gccctccagc tcctagtcct aggaaaactc cagttgccag tgatcaacgc 1980
cgtaggtcct gcaaaacagc ccctgcttcc agcagcaaat ctcagacaga ggttcctaag 2040
agaggaggga gaaagagtgg caacctgcct tcaaagagag tgtctatcag ccgaagtcaa 2100
catgatattt tacagatgat atgttccaaa agaagaagtg gtgcttcgga agcaaatctg 2160
attgttgcaa aatcatgggc agatgtagta aaacttggtg caaaacaaac acaaactaaa 2220
gtcataaaac atggtcctca aaggtcaatg aacaaaaggc aaagaagacc tgctactcca 2280
aagaagcctg tgggcgaagt tcacagtcaa tttagtacag gccacgcaaa ctctccttgt 2340
accataataa tagggaaagc tcatactgaa aaagtacatg tgcctgctcg accctacaga 2400
gtgctcaaca acttcatttc caaccaaaaa atggacttta aggaagatct ttcaggaata 2460
gctgaaatgt tcaagacccc agtgaaggag caaccgcagt tgacaagcac atgtcacatc 2520
gctatttcaa attcagagaa tttgcttgga aaacagtttc aaggaactga ttcaggagaa 2580
gaacctctgc tccccacctc agagagtttt ggaggaaatg tgttcttcag tgcacagaat 2640
gcagcaaaac agccatctga taaatgctct gcaagccctc ccttaagacg gcagtgtatt 2700
agagaaaatg gaaacgtagc aaaaacgccc aggaacacct acaaaatgac ttctctggag 2760
acaaaaactt cagatactga gacagagcct tcaaaaacag tatccactgc aaacaggtca 2820
ggaaggtcta cagagttcag gaatatacag aagctacctg tggaaagtaa gagtgaagaa 2880
acaaatacag aaattgttga gtgcatccta aaaagaggtc agaaggcaac actactacaa 2940
caaaggagag aaggagagat gaaggaaata gaaagacctt ttgagacata taaggaaaat 3000

-continued

```
attgaattaa aagaaaacga tgaaaagatg aaagcaatga agagatcaag aacttggggg   3060
cagaaatgtg caccaatgtc tgacctgaca gacctcaaga gcttgcctga tacagaactc   3120
atgaaagaca cggcacgtgg ccagaatctc ctccaaaccc aagatcatgc caaggcacca   3180
aagagtgaga aaggcaaaat cactaaaatg ccctgccagt cattacaacc agaaccaata   3240
aacaccccaa cacacacaaa acaacagttg aaggcatccc tggggaaagt aggtgtgaaa   3300
gaagagctcc tagcagtcgg caagttcaca cggacgtcag gggagaccac gcacacgcac   3360
agagagccag caggagatgg caagagcatc agaacgttta aggagtctcc aaagcagatc   3420
ctggacccag cagcccgtgt aactggaatg aagaagtggc caagaacgcc taaggaagag   3480
gcccagtcac tagaagacct ggctggcttc aaagagctct tccagacacc aggtccctct   3540
gaggaatcaa tgactgatga gaaaactacc aaaatagcct gcaaatctcc accaccagaa   3600
tcagtggaca ctccaacaag cacaaagcaa tggcctaaga gaagtctcag gaaagcagat   3660
gtagaggaag aattcttagc actcaggaaa ctaacaccat cagcagggaa agccatgctt   3720
acgcccaaac cagcaggagg tgatgagaaa gacattaaag catttatggg aactccagtg   3780
cagaaactgg acctggcagg aactttacct ggcagcaaaa gacagctaca gactcctaag   3840
gaaaaggccc aggctctaga agacctggct ggctttaaag agctcttcca gactcctggt   3900
cacaccgagg aattagtggc tgctggtaaa accactaaaa taccctgcga ctctccacag   3960
tcagacccag tggacacccc aacaagcaca aagcaacgac ccaagagaag tatcaggaaa   4020
gcagatgtag agggagaact cttagcgtgc aggaatctaa tgccatcagc aggcaaagcc   4080
atgcacacgc ctaaaccatc agtaggtgaa gagaaagaca tcatcatatt tgtgggaact   4140
ccagtgcaga aactggacct gacagagaac ttaaccggca gcaagagacg gccacaaact   4200
cctaaggaag aggcccaggc tctggaagac ctgactggct ttaaagagct cttccagacc   4260
cctggtcata ctgaagaagc agtggctgct ggcaaaacta ctaaaatgcc ctgcgaatct   4320
tctccaccag aatcagcaga caccccaaca agcacaagaa ggcagcccaa gacacctttg   4380
gagaaaaggg acgtacagaa ggagctctca gccctgaaga agctcacaca gacatcaggg   4440
gaaaccacac acacagataa agtaccagga ggtgaggata aaagcatcaa cgcgtttagg   4500
gaaactgcaa aacagaaact ggacccagca gcaagtgtaa ctggtagcaa gaggcaccca   4560
aaaactaagg aaaaggccca acccctagaa gacctggctg gcttgaaaga gctcttccag   4620
acaccagtat gcactgacaa gcccacgact cacgagaaaa ctaccaaaat agcctgcaga   4680
tcacaaccag acccagtgga cacaccaaca agctccaagc cacagtccaa gagaagtctc   4740
aggaaagtgg acgtagaaga agaattcttc gcactcagga aacgaacacc atcagcaggc   4800
aaagccatgc acacacccaa accagcagta agtggtgaga aaaacatcta cgcatttatg   4860
ggaactccag tgcagaaact ggacctgaca gagaacttaa ctggcagcaa gagacggcta   4920
caaactccta aggaaaaggc ccaggctcta gaagacctgg ctggctttaa agagctcttc   4980
cagacacgag gtcacactga ggaatcaatg actaacgata aaactgccaa agtagcctgc   5040
aaatcttcac aaccagaccc agacaaaaac ccagcaagct ccaagcgacg gctcaagaca   5100
tccctgggga aagtgggcgt gaaagaagag ctcctagcag ttggcaagct cacacagaca   5160
tcaggagaga ctacacacac acacacagag ccaacaggag atggtaagag catgaaagca   5220
tttatggagt ctccaaagca gatcttagac tcagcagcaa gtctaactgg cagcaagagg   5280
cagctgagaa ctcctaaggg aaagtctgaa gtccctgaag acctggccgg cttcatcgag   5340
ctcttccaga caccaagtca cactaaggaa tcaatgacta acgaaaaaac taccaaagta   5400
```

```
tcctacagag cttcacagcc agacctagtg gacaccccaa caagctccaa gccacagccc   5460
aagagaagtc tcaggaaagc agacactgaa gaagaatttt tagcatttag gaaacaaacg   5520
ccatcagcag gcaaagccat gcacacaccc aaaccagcag taggtgaaga gaaagacatc   5580
aacacgtttt tgggaactcc agtgcagaaa ctggaccagc caggaaattt acctggcagc   5640
aatagacggc tacaaactcg taaggaaaag gcccaggctc tagaagaact gactggcttc   5700
agagagcttt tccagacacc atgcactgat aaccccacga ctgatgagaa aactaccaaa   5760
aaaatactct gcaaatctcc gcaatcagac ccagcggaca ccccaacaaa cacaaagcaa   5820
cggcccaaga gaagcctcaa gaaagcagac gtagaggaag aatttttagc attcaggaaa   5880
ctaacaccat cagcaggcaa agccatgcac acgcctaaag cagcagtagg tgaagagaaa   5940
gacatcaaca catttgtggg gactccagtg gagaaactgg acctgctagg aaatttacct   6000
ggcagcaaga gacggccaca aactcctaaa gaaaaggcca aggctctaga agatctggct   6060
ggcttcaaag agctcttcca gacaccaggt cacactgagg aatcaatgac cgatgacaaa   6120
atcacagaag tatcctgcaa atctccacaa ccagacccag tcaaaacccc aacaagctcc   6180
aagcaacgac tcaagatatc cttggggaaa gtaggtgtga aagaagaggt cctaccagtc   6240
ggcaagctca cacagacgtc agggaagacc acacagacac acagagagac agcaggagat   6300
ggaaagagca tcaaagcgtt taaggaatct gcaaagcaga tgctggaccc agcaaactat   6360
ggaactggga tggagaggtg gccaagaaca cctaaggaag aggcccaatc actagaagac   6420
ctggccggct tcaaagagct cttccagaca ccagaccaca ctgaggaatc aacaactgat   6480
gacaaaacta ccaaaatagc ctgcaaatct ccaccaccag aatcaatgga cactccaaca   6540
agcacaagga ggcggcccaa aacacctttg ggaaaaggg atatagtgga agagctctca   6600
gccctgaagc agctcacaca gaccacacac acagacaaag taccaggaga tgaggataaa   6660
ggcatcaacg tgttcaggga aactgcaaaa cagaaactgg acccagcagc aagtgtaact   6720
ggtagcaaga ggcagccaag aactcctaag ggaaaagccc aaccccctaga agacttggct   6780
ggcttgaaag agctcttcca gacaccaata tgcactgaca agcccacgac tcatgagaaa   6840
actaccaaaa tagcctgcag atctccacaa ccagacccag tgggtacccc aacaatcttc   6900
aagccacagt ccaagagaag tctcaggaaa gcagacgtag aggaagaatc cttagcactc   6960
aggaaacgaa caccatcagt agggaaagct atggacacac ccaaaccagc aggaggtgat   7020
gagaaagaca tgaaagcatt tatgggaact ccagtgcaga aattggacct gccaggaaat   7080
ttacctggca gcaaaagatg gccacaaact cctaaggaaa aggcccaggc tctagaagac   7140
ctggctggct tcaaagagct cttccagaca ccaggcactg acaagcccac gactgatgag   7200
aaaactacca aaatagcctg caaatctcca caaccagacc cagtggacac cccagcaagc   7260
acaaagcaac ggcccaagag aaacctcagg aaagcagacg tagaggaaga atttttagca   7320
ctcaggaaac gaacaccatc agcaggcaaa gccatggaca caccaaaacc agcagtaagt   7380
gatgagaaaa atatcaacac atttgtggaa actccagtgc agaaactgga cctgctagga   7440
aatttacctg gcagcaagag acagccacag actcctaagg aaaaggctga ggctctagag   7500
gacctggttg gcttcaaaga actcttccag acaccaggtc acactgagga atcaatgact   7560
gatgacaaaa tcacagaagt atcctgtaaa tctccacagc cagagtcatt caaaacctca   7620
agaagctcca agcaaaggct caagataccc ctggtgaaag tggacatgaa agaagagccc   7680
ctagcagtca gcaagctcac acggacatca ggggagacta cgcaaacaca cacagagcca   7740
```

```
acaggagata gtaagagcat caaagcgttt aaggagtctc caaagcagat cctggaccca   7800
gcagcaagtg taactggtag caggaggcag ctgagaactc gtaaggaaaa ggcccgtgct   7860
ctagaagacc tggttgactt caaagagctc ttctcagcac caggtcacac tgaagagtca   7920
atgactattg acaaaaacac aaaaattccc tgcaaatctc ccccaccaga actaacagac   7980
actgccacga gcacaaagag atgccccaag acacgtccca ggaaagaagt aaaagaggag   8040
ctctcagcag ttgagaggct cacgcaaaca tcagggcaaa gcacacacac acacaaagaa   8100
ccagcaagcg gtgatgaggg catcaaagta ttgaagcaac gtgcaaagaa gaaaccaaac   8160
ccagtagaag aggaacccag caggagaagg ccaagagcac ctaaggaaaa ggcccaaccc   8220
ctggaagacc tggccggctt cacagagctc tctgaaacat caggtcacac tcaggaatca   8280
ctgactgctg gcaaagccac taaaataccc tgcgaatctc ccccactaga agtggtagac   8340
accacagcaa gcacaaagag gcatctcagg acacgtgtgc agaaggtaca agtaaaagaa   8400
gagccttcag cagtcaagtt cacacaaaca tcaggggaaa ccacggatgc agacaaagaa   8460
ccagcaggtg aagataaagg catcaaagca ttgaaggaat ctgcaaaaca gacaccggct   8520
ccagcagcaa gtgtaactgg cagcaggaga cggccaagag cacccaggga aagtgcccaa   8580
gccatagaag acctagctgg cttcaaagac ccagcagcag gtcacactga agaatcaatg   8640
actgatgaca aaaccactaa aataccctgc aaatcatcac cagaactaga agacaccgca   8700
acaagctcaa agagacggcc caggacacgt gcccagaaag tagaagtgaa ggaggagctg   8760
ttagcagttg gcaagctcac acaaacctca ggggagacca cgcacaccga caaagagccg   8820
gtaggtgagg gcaaaggcac gaaagcattt aagcaacctg caaagcggaa gctggacgca   8880
gaagatgtaa ttggcagcag gagacagcca agagcaccta aggaaaaggc ccaacccctg   8940
gaagatctgg ccagcttcca agagctctct caaacaccag gccacactga ggaactggca   9000
aatggtgctg ctgatagctt tacaagcgct ccaaagcaaa cacctgacag tggaaaacct   9060
ctaaaaatat ccagaagagt tcttcgggcc cctaaagtag aacccgtggg agacgtggta   9120
agcaccagag accctgtaaa atcacaaagc aaaagcaaca cttccctgcc cccactgccc   9180
ttcaagaggg gaggtggcaa agatggaagc gtcacgggaa ccaagaggct gcgctgcatg   9240
ccagcaccag aggaaattgt ggaggagctg ccagccagca agaagcagag ggttgctccc   9300
agggcaagag gcaaatcatc cgaacccgtg gtcatcatga agagaagttt gaggacttct   9360
gcaaaaagaa ttgaacctgc ggaagagctg aacagcaacg acatgaaaac caacaaagag   9420
gaacacaaat tacaagactc ggtccctgaa aataagggaa tatccctgcg ctccagacgc   9480
caaaataaga ctgaggcaga acagcaaata actgaggtct ttgtattagc agaaagaata   9540
gaaataaaca gaaatgaaaa gaagcccatg aagacctccc cagagatgga cattcagaat   9600
ccagatgatg gagcccggaa acccatacct agagacaaag tcactgagaa caaaaggtgc   9660
ttgaggtctg ctagacagaa tgagagctcc cagcctaagg tggcagagga gagcggaggg   9720
cagaagagtg cgaaggttct catgcagaat cagaaaggga aaggagaagc aggaaattca   9780
gactccatgt gcctgagatc aagaaagaca aaaagccagc ctgcagcaag cactttggag   9840
agcaaatctg tgcagagagt aacgcggagt gtcaagaggt gtgcagaaaa tccaaagaag   9900
gctgaggaca atgtgtgtgt caagaaaata agaaccagaa gtcataggga cagtgaagat   9960
atttgacaga aaaatcgaac tgggaaaaat ataataaagt tagttttgtg ataagttcta   10020
gtgcagtttt tgtcataaat tacaagtgaa ttctgtaagt aaggctgtca gtctgcttaa   10080
gggaagaaaa ctttggattt gctgggtctg aatcggcttc ataaactcca ctgggagcac   10140
```

```
tgctgggctc ctggactgag aatagttgaa caccgggggc tttgtgaagg agtctgggcc  10200
aaggtttgcc ctcagctttg cagaatgaag ccttgaggtc tgtcaccacc cacagccacc  10260
ctacagcagc cttaactgtg acacttgcca cactgtgtcg tcgtttgttt gcctatgtcc  10320
tccagggcac ggtggcagga acaactatcc tcgtctgtcc caacactgag caggcactcg  10380
gtaaacacga atgaatggat gagcgcacgg atgaatggag cttacaagat ctgtctttcc  10440
aatggccggg ggcatttggt ccccaaatta aggctattgg acatctgcac aggacagtcc  10500
tatttttgat gtcctttcct ttctgaaaat aaagttttgt gctttggaga atgactcgtg  10560
agcacatctt tagggaccaa gagtgacttt ctgtaaggag tgactcgtgg cttgccttgg  10620
tctcttggga atacttttct aactagggtt gctctcacct gagacattct ccacccgcgg  10680
aatctcaggg tcccaggctg tgggccatca cgacctcaaa ctggctccta atctccagct  10740
ttcctgtcat tgaaagcttc ggaagtttac tggctctgct cccgcctgtt ttctttctga  10800
ctctatctgg cagcccgatg ccacccagta caggaagtga caccagtact ctgtaaagca  10860
tcatcatcct tggagagact gagcactcag caccttcagc cacgatttca ggatcgcttc  10920
cttgtgagcc gctgcctccg aaatctcctt tgaagcccag acatctttct ccagcttcag  10980
acttgtagat ataactcgtt catcttcatt tactttccac tttgcccccct gtcctctctg  11040
tgttccccaa atcagagaat agcccgccat cccccaggtc acctgtctgg attcctcccc  11100
attcacccac cttgccaggt gcaggtgagg atggtgcacc agacagggta gctgtccccc  11160
aaaatgtgcc ctgtgcgggc agtgccctgt ctccacgttt gtttccccag tgtctggcgg  11220
ggagccaggt gacatcataa atacttgctg aatgaatgca gaaatcagcg gtactgactt  11280
gtactatatt ggctgccatg atagggttct cacagcgtca tccatgatcg taagggagaa  11340
tgacattctg cttgagggag ggaatagaaa ggggcaggga ggggacatct gagggcttca  11400
cagggctgca aagggtacag ggattgcacc agggcagaac aggggagggt gttcaaggaa  11460
gagtggctct tagcagaggc actttggaag gtgtgaggca taaatgcttc cttctacgta  11520
ggccaacctc aaaactttca gtaggaatgt tgctatgatc aagttgttct aacactttag  11580
acttagtagt aattatgaac ctcacataga aaaatttcat ccagccatat gcctgtggag  11640
tggaatattc tgtttagtag aaaaatcctt tagagttcag ctctaaccag aaatcttgct  11700
gaagtatgtc agcacctttt ctcaccctgg taagtacagt atttcaagag cacgctaagg  11760
gtggttttca ttttacaggg ctgttgatga tgggttaaaa atgttcattt aagggctacc  11820
cccgtgttta atagatgaac accacttcta cacaaccctc cttggtactg ggggagggag  11880
agatctgaca aatactgccc attcccctag gctgactgga tttgagaaca aatacccacc  11940
catttccacc atggtatggt aacttctctg agcttcagtt tccaagtgaa tttccatgta  12000
ataggacatt cccattaaat acaagctgtt tttactttt cgcctcccag ggcctgtggg  12060
atctggtccc ccagcctctc ttgggctttc ttacactaac tctgtaccta ccatctcctg  12120
cctcccttag gcaggcacct ccaaccacca cacactccct gctgttttcc ctgcctggaa  12180
ctttccctcc tgccccacca agatcatttc atccagtcct gagctcagct taagggaggc  12240
ttcttgcctg tgggttccct cacccccatg cctgtcctcc aggctggggc aggttcttag  12300
tttgcctgga attgttctgt acctctttgt agcacgtagt gttgtggaaa ctaagccact  12360
aattgagttt ctggctcccc tcctggggtt gtaagttttg ttcattcatg agggccgact  12420
gcatttcctg gttactctat cccagtgacc agccacagga gatgtccaat aaagtatgtg  12480
```

atgaaatggt cttaaaaaaa aaaaaaa 12507

<210> SEQ ID NO 138
<211> LENGTH: 3771
<212> TYPE: DNA
<213> ORGANISM: Homo sapiens

<400> SEQUENCE: 138
gcgccgggac gtggccagtt gcccgcctgc cccggagagc caggcgctaa ccagccgctc 60
tgcgccccgc gccctgcttg cccccattat ccagccttgc cccggcgccc tgacctgacg 120
ccctggcctg acgccctgct tcgtcgcctc ctttctctcc caggtgctgg accagggact 180
gagcgtcccc cggagagggt ccggtgtgac cccgacaaga agcagaaatg ggaagaaac 240 tggatctttc caagctcact gatgaagagg cccagcatgt cttggaagtt gttcaacgag 300
attttgacct ccgaaggaaa gaagaggaac ggctagaggc gttgaagggc aagattaaga 360
aggaaagctc caagagggag ctgctttccg acactgccca tctgaacgag acccactgcg 420
cccgctgcct gcagccctac cagctgcttg tgaatagcaa aaggcagtgc ctggaatgtg 480
gcctcttcac ctgcaaaagc tgtggccgcg tccacccgga ggagcagggc tggatctgtg 540
acccctgcca tctggccaga gtcgtgaaga tcggctcact ggagtggtac tatgagcatg 600
tgaaagcccg cttcaagagg ttcggaagtg ccaaggtcat ccggtccctc cacgggcggc 660
tgcagggtgg agctgggcct gaactgatat ctgaagagag aagtggagac agcgaccaga 720
cagatgagga tggagaacct ggctcagagg cccaggccca ggcccagccc tttggcagca 780
aaaaaaagcg cctcctctcc gtccacgact tcgacttcga gggagactca gatgactcca 840
ctcagcctca aggtcactcc ctgcacctgt cctcagtccc tgaggccagg gacagcccac 900
agtccctcac agatgagtcc tgctcagaga aggcagcccc tcacaaggct gagggcctgg 960
aggaggctga tactggggcc tctgggtgcc actcccatcc ggaagagcag ccgaccagca 1020
tctcaccttc cagacacggc gccctggctg agctctgccc gcctggaggc tcccacagga 1080
tggccctggg gactgctgct gcactcgggt cgaatgtcat caggaatgag cagctgcccc 1140
tgcagtactt ggccgatgtg gacacctctg atgaggaaag catccgggct cacgtgatgg 1200
cctcccacca ttccaagcgg agaggccggg cgtcttctga gagtcagatc tttgagctga 1260
ataagcatat ttcagctgtg gaatgcctgc tgacctacct ggagaacaca gttgtgcctc 1320
ccttggccaa gggtctaggt gctggagtgc gcacggaggc cgatgtagag gaggaggccc 1380
tgaggaggaa gctggaggag ctgaccagca acgtcagtga ccaggagacc tcgtccgagg 1440
aggaggaagc caaggacgaa aaggcagagc ccaacaggga caaatcagtt gggcctctcc 1500
cccaggcgga cccggaggtg ggcacggctg cccatcaaac caacagacag gaaaaaagcc 1560
cccaggaccc tggggacccc gtccagtaca acaggaccac agatgaggag ctgtcagagc 1620
tggaggacag agtggcagtg acggcctcag aagtccagca ggcagagagc gaggtttcag 1680
acattgaatc caggattgca gccctgaggg ccgcagggct cacggtgaag ccctcgggaa 1740
agccccggag gaagtcaaac ctcccgatat ttctccctcg agtggctggg aaacttggca 1800
agagaccaga ggacccaaat gcagaccctt caagtgaggc caaggcaatg gctgtgccct 1860
atcttctgag aagaaagttc agtaattccc tgaaaagtca aggtaaagat gatgattctt 1920
ttgatcggaa atcagtgtac cgaggctcgc tgacacagag aaaccccaac gcgaggaaag 1980
gaatggccag ccacaccttc gcgaaacctg tggtggccca ccagtcctaa cgggacagga 2040
cagagagaca gagcagccct gcactgtttt ccctccacca cagccatcct gtccctcatt 2100
ggctctgtgc tttccactat acacagtcac cgtcccaatg agaaacaaga aggagcaccc 2160
tccacatgga ctcccacctg caagtggaca gcgacattca gtcctgcact gctcacctgg 2220
gtttactgat gactcctggc tgccccacca tcctctctga tctgtgagaa acagctaagc 2280
tgctgtgact tccctttagg acaatgttgt gtaaatcttt gaaggacaca ccgaagacct 2340
ttatactgtg atcttttacc cctttcactc ttggctttct tatgttgctt tcatgaatgg 2400
aatggaaaaa agatgactca gttaaggcac cagccatatg tgtattcttg atggtctata 2460
tcggggtgtg agcagatgtt tgcgtatttc ttgtgggtgt gactggatat tagacatccg 2520
gacaagtgac tgaactaatg atctgctgaa taatgaagga ggaatagaca ccccagtccc 2580
caccctacgt gcacccgctc tgcaagttcc catgtgatct gtagaccagg ggaaattaca 2640
ctgcggtcaa gggcagagcc tgcacatgac agcaagtgag catttgatag atgctcagat 2700
gctagtgcag agagcctgct gggagacgaa gagacagcag gcagagctcc agatgggcaa 2760
ggaagaggct tggttctagc ctggctctgc ccctcactgc agtggatcca gtggggcaga 2820
ggacagaggg tcacaaccaa tgagggatgt ctgccaagga tgggggtgca gaggccacag 2880
gagtcagctt gccactcgcc cattggttac atagatgatc tctcagacag gctgggactc 2940
agagttattt cctagtatcg gtgtgcccca tccagtttta agtggagccc tccaagactc 3000
tccagagctg cctttgaaca tcctaacagt aatcacatct caccctccct gaggttcact 3060
ttagacagga cccaatggct gcactgcctt tgtcagaggg ggtgctgaga ggagtggctt 3120
cttttagaat caaacagtag agacaagagt caagccttgt gtcttcaagc attgaccaag 3180
ttaagtgttt ccttccctct ctcaataaga cacttccagg agctttccaa tctctcactt 3240
aaaactaagg tttgaatctc aaagtgttgc tgggaggctg atactcctgc aacttcagga 3300
gacctgtgag cacacattag cagctgtttc tctgactcct tgtggcatca gataaaaacg 3360
tgggagtttt tccatataat tcccagcctt acttataaat tctattcttt gaaaaaatta 3420
ttcaggctag gtaaggtggc tcatacctat aatcccagcc ctttgagagg ccaaggtggg 3480
agaattgctt gaggccagga gtttgagacc tcctgggcaa catagtgaga tcccatctct 3540
acaaaaaaca aaacaaaaaa attacccaag catgatggta tatgcctgta gtcgtaccta 3600
cttacttagg aggctgaggc aggaggatca cttgagccct ggaggttggg gctgcagtga 3660
gccatgatcg catcactata ctcgagcctg ggcaacagag tgagaccttg tctcttaaaa 3720
aaattaataa taaataaatg aaaataattc ttcagaaaaa aaaaaaaaaa a 3771

<210> SEQ ID NO 139
<211> LENGTH: 2240
<212> TYPE: DNA
<213> ORGANISM: Homo sapiens

<400> SEQUENCE: 139
aagcccagca gccccggggc ggatggctcc ggccgcctgg ctccgcagcg cggccgcgcg 60
cgccctcctg cccccgatgc tgctgctgct gctccagccg ccgccgctgc tggcccgggc 120
tctgccgccg gacgcccacc acctccatgc cgagaggagg gggccacagc cctggcatgc 180
agccctgccc agtagcccgg cacctgcccc tgccacgcag gaagcccccc ggcctgccag 240
cagcctcagg cctccccgct gtggcgtgcc cgacccatct gatgggctga gtgcccgcaa 300
ccgacagaag aggttcgtgc tttctggcgg gcgctgggag aagacggacc tcacctacag 360
gatccttcgg ttcccatggc agttggtgca ggagcaggtg cggcagacga tggcagaggc 420

-continued cctaaaggta tggagcgatg tgacgccact cacctttact gaggtgcacg agggccgtgc 480
tgacatcatg atcgacttcg ccaggtactg gcatggggac gacctgccgt ttgatgggcc 540
tgggggcatc ctggcccatg ccttcttccc caagactcac cgagaagggg atgtccactt 600
cgactatgat gagacctgga ctatcgggga tgaccagggc acagacctgc tgcaggtggc 660
agcccatgaa tttggccacg tgctggggct gcagcacaca acagcagcca aggccctgat 720
gtccgccttc tacacctttc gctacccact gagtctcagc ccagatgact gcaggggcgt 780
tcaacaccta tatggccagc cctggcccac tgtcacctcc aggaccccag ccctgggccc 840
ccaggctggg atagacacca atgagattgc accgctggag ccagacgccc cgccagatgc 900
ctgtgaggcc tcctttgacg cggtctccac catccgaggc gagctctttt tcttcaaagc 960
gggctttgtg tggcgcctcc gtgggggcca gctgcagccc ggctacccag cattggcctc 1020
tcgccactgg cagggactgc ccagccctgt ggacgctgcc ttcgaggatg cccagggcca 1080
catttggttc ttccaaggtg ctcagtactg ggtgtacgac ggtgaaaagc cagtcctggg 1140
ccccgcaccc ctcaccgagc tgggcctggt gaggttcccg gtccatgctg ccttggtctg 1200
gggtcccgag aagaacaaga tctacttctt ccgaggcagg gactactggc gtttccaccc 1260
cagcacccgg cgtgtagaca gtcccgtgcc ccgcagggcc actgactgga gaggggtgcc 1320
ctctgagatc gacgctgcct tccaggatgc tgatggctat gcctacttcc tgcgcggccg 1380
cctctactgg aagtttgacc ctgtgaaggt gaaggctctg gaaggcttcc cccgtctcgt 1440
gggtcctgac ttctttggct gtgccgagcc tgccaacact ttcctctgac catggcttgg 1500
atgccctcag gggtgctgac ccctgccagg ccacgaatat caggctagag acccatggcc 1560
atctttgtgg ctgtgggcac caggcatggg actgagccca tgtctcctca gggggatggg 1620
gtggggtaca accaccatga caactgccgg gagggccacg caggtcgtgg tcacctgcca 1680
gcgactgtct cagactgggc agggaggctt tggcatgact taagaggaag ggcagtcttg 1740
ggcccgctat gcaggtcctg gcaaacctgg ctgccctgtc tccatccctg tccctcaggg 1800
tagcaccatg gcaggactgg gggaactgga gtgtccttgc tgtatccctg ttgtgaggtt 1860
ccttccaggg gctggcactg aagcaagggt gctggggccc catggccttc agccctggct 1920
gagcaactgg gctgtagggc agggccactt cctgaggtca ggtcttggta ggtgcctgca 1980
tctgtctgcc ttctggctga caatcctgga aatctgttct ccagaatcca ggccaaaaag 2040
ttcacagtca aatggggagg ggtattcttc atgcaggaga ccccaggccc tggaggctgc 2100
aacatacctc aatcctgtcc caggccggat cctcctgaag ccctttcgc agcactgcta 2160 tcctccaaag ccattgtaaa tgtgtgtaca gtgtgtataa accttcttct tctttttttt 2220
tttttaaact gaggattgtc 2240

<210> SEQ ID NO 140
<211> LENGTH: 3167
<212> TYPE: DNA
<213> ORGANISM: Homo sapiens

<400> SEQUENCE: 140
tagcagcaca caagggttcg tgtttgtgga accaggtagc ttccttcaga gctgacattt 60
gcccacagcc agcctggccc agccccatac caccagccct ggcgctctgg ggcgtgaggt 120
gccttttctg cccccctgct ctagggcagg tggaaatcac ccatggtggg tctacatctg 180
atagaagcat cttatagttc tgcttctgga ccagaccatc ctgggttttt ctctgttctg 240
ctgaagggtt ccctccacgt gtccatcacc tcggtgaact cttgggagac ctgggaagat 300

-continued

```
gctggcctca cctctcgcct ctcctttccc tcattgtgct gccaccatcc ttctcacaca    360
ggctctccag ggagagctgg gcaggatggg atcttcctgg gttcccacct tgctccgtgc    420
cccctctcac tgttcctgaa gtgtggccac ggactgcctt gttttctgga aagtcccaag    480
tctggaccat gactgagcag cattctcggc tatctgccac ctgtctgggg ctcctggccc    540
ctcttagact cccctctccc ttctgtttcc cccgagcccc tgacttggac ctgcagggtg    600
gggagaggga tgggacgaga acctgtgctg gggccaaagg tcgcactggg ggaaggtgga    660
gccagggcag cagagtgcct ggcgtcggcc cctatcctgt cactagttcc cccgttctgg    720
cccctggcag gtttgtaacc ccagatcaga agtactccat ggacaacact ccccacacgc    780
caaccccgtt caagaacgcc ctggagaagt acggacccct gaagcccctg gtacgtggtg    840
tggtcactgc cgtggatctc tgcacagtgg gatcccttcg gttcatccaa ccatgttcag    900
tccacaggac ccttccctct gaggtctcat ttgattcttt ctcctgagaa gatgcagaga    960
tcctgataat ataaatgggg aagctgaggc tgctctttgt cacttcctcc gactgctcct   1020
gagcacctga gtttgcaagc acgcgccggc tggtgctaga gacatggtgg tatcccgtga   1080
cactcagcct caggatgggg gagactgatg tgaaatacaa ataacttaaa cactttcagg   1140
caaagataag cactgggcct agttcagaga agtggcaaat tgctactctg gcctgtctct   1200
gaccaactcc cagttctcta cagagcacgg gaaagcccct cggggacgtc tttcctgcag   1260
tgtgcaggct gcccttctcc cctgctcttc ccagttgatg ggatggttgt gttttctcta   1320
tgaaaaaagg agttggcacc ttgggctttc tgaaacacac aggtgtttta gaaatcagtg   1380
gagggtgaga gaaaggcatg gttgtggagg cactggactg tgaacaaggt ctgcagcggg   1440
tccccctgct gtctctctct actgcatgga gcctcctatg aagcccaagg tggctggggg   1500
ctgaggctcc cttgggcctg ccatggaact gattctgagt caagcagact ttccacggac   1560
catgctacat gagccgaggt gaggcactag ttagtgctcc tttcctgttg cagtggagat   1620
ttggctcctc tgtactaaaa tatctgcatg ctctccaaac aggtgtgagg gcaaatcaca   1680
tgaccttggc agctgtaatt aaagtttgtg ggggcttttc ggatgactta tgaggagtgg   1740
ctgtgattcg cacctttcac tcttagtagc actcgccctc ccctgttctc tgttgcctga   1800
agctggagag gtccttggaa ccccgaggcc tgagaaaggg aaatgggttt gagagccccc   1860
attagtgtgg aacaaagggt tgagtgagcc tgggctttga gctgtcgggg tcctaattca   1920
gcagctgtgt gactgtgtgc caggctgttg atctctgagc ttctgtttct acctgcttaa   1980
aatgacggtt actgcacagg gctgtgtgag ggttacagtg cgtctctggg ctgctcccag   2040
ccatggcagg cccctgggaa tcaaggtcat cagctgcttg tccaaggcag cagttagtgg   2100
ttgtgaatgg tgcgtgtgag atctgcatcc tggcgtcagg cctccttcct gccttaccca   2160
ggacagccca gttgcagctg ggttggtccc acagtcccac acacacacag cccgagtgtg   2220
gtgcctcacg tgggctgccc cgtgcctacc cacagccaca gaccccgcac ctggaggagg   2280
acttgaagga ggtgctgcgt tctgaggctg gcatcgaact catcatcgag gacgacatca   2340
ggcccgagaa gcagaagagg aagcctgggc tgcggcggag ccccatcaag aaagtccgga   2400
agtctctggc tcttgacatt gtggatgagg atgtgaagct gatgatgtcc acactgccca   2460
agtctctatc cttgccgaca actgcccctt caaactcttc cagcctcacc ctgtcaggta   2520
tcaaagaaga caacagcttg ctcaaccagg gcttcttgca ggccaagccc gagaaggcag   2580
cagtggccca gaagccccga agccacttca cgacacctgc ccctatgtcc agtgcctgga   2640
```

agacggtggc ctgcgggggg accagggacc agcttttcat gcaggagaaa gcccggcagc 2700
tcctgggccg cctgaagccc agccacacat ctcggaccct catcttgtcc tgaggtgttg 2760
agggtgtcac gagcccattc acatgtttac aggggttgtg ggggcagagg gggtctgtga 2820
atctgagagt cattcaggtg acctcctgca gggagccttc tgccaccagc ccctccccag 2880
actctcaggt ggaggcaaca gggccatgtg ctgccctgtt gccgagccca gctgtgggcg 2940
gctcctggtg ctaacaacaa agttccactt ccaggtctgc ctggttcccc ccccaaggcc 3000
acagggagct ccgtcagctt ctcccaagcc cacgtcaggc ctggcctcat ctcagaccct 3060
gcttaggatg ggggatgtgg ccaggggtgc tcctgtgctc accctctctt ggtgcatttt 3120
tttggaagaa taaaattgcc tctctctttg aaaaaaaaaa aaaaaaa 3167

<210> SEQ ID NO 141
<211> LENGTH: 2379
<212> TYPE: DNA
<213> ORGANISM: Homo sapiens

<400> SEQUENCE: 141
gacccccgag ctgtgctgct cgcggccgcc accgccgggc cccggccgtc cctggctccc 60
ctcctgcctc gagaagggca gggcttctca gaggcttggc gggaaaaaga acggagggag 120
ggatcgcgct gagtataaaa gccggttttc ggggctttat ctaactcgct gtagtaattc 180
cagcgagagg cagagggagc gagcgggcgg ccggctaggg tggaagagcc gggcgagcag 240
agctgcgctg cgggcgtcct gggaagggag atccggagcg aatagggggc ttcgcctctg 300
gcccagccct cccgctgatc ccccagccag cggtccgcaa cccttgccgc atccacgaaa 360
ctttgcccat agcagcgggc gggcactttg cactggaact tacaacaccc gagcaaggac 420
gcgactctcc cgacgcgggg aggctattct gcccatttgg ggacacttcc ccgccgctgc 480
caggacccgc ttctctgaaa ggctctcctt gcagctgctt agacgctgga ttttttttcgg 540 gtagtggaaa accagcagcc tcccgcgacg atgcccctca acgttagctt caccaacagg 600
aactatgacc tcgactacga ctcggtgcag ccgtatttct actgcgacga ggaggagaac 660
ttctaccagc agcagcagca gagcgagctg cagcccccgg cgcccagcga ggatatctgg 720
aagaaattcg agctgctgcc caccccgccc ctgtccccta gccgccgctc cgggctctgc 780
tcgccctcct acgttgcggt cacacccttc tcccttcggg gagacaacga cggcggtggc 840
gggagcttct ccacggccga ccagctggag atggtgaccg agctgctggg aggagacatg 900
gtgaaccaga gtttcatctg cgacccggac gacgagacct tcatcaaaaa catcatcatc 960
caggactgta tgtggagcgg cttctcggcc gccgccaagc tcgtctcaga gaagctggcc 1020
tcctaccagg ctgcgcgcaa agacagcggc agcccgaacc ccgcccgcgg ccacagcgtc 1080
tgctccacct ccagcttgta cctgcaggat ctgagcgccg ccgcctcaga gtgcatcgac 1140
ccctcggtgg tcttccccta ccctctcaac gacagcagct cgcccaagtc ctgcgcctcg 1200
caagactcca gcgccttctc tccgtcctcg gattctctgc tctcctcgac ggagtcctcc 1260
ccgcagggca gccccgagcc cctggtgctc catgaggaga caccgcccac caccagcagc 1320
gactctgagg aggaacaaga agatgaggaa gaaatcgatg ttgtttctgt ggaaaagagg 1380
caggctcctg gcaaaaggtc agagtctgga tcaccttctg ctggaggcca cagcaaacct 1440
cctcacagcc cactggtcct caagaggtgc cacgtctcca cacatcagca caactacgca 1500
gcgcctccct ccactcggaa ggactatcct gctgccaaga gggtcaagtt ggacagtgtc 1560
agagtcctga gacagatcag caacaaccga aaatgcacca gccccaggtc ctcggacacc 1620

-continued gaggagaatg tcaagaggcg aacacacaac gtcttggagc gccagaggag gaacgagcta 1680
aaacggagct tttttgccct gcgtgaccag atcccggagt tggaaaacaa tgaaaaggcc 1740
cccaaggtag ttatccttaa aaaagccaca gcatacatcc tgtccgtcca agcagaggag 1800
caaaagctca tttctgaaga ggacttgttg cggaaacgac gagaacagtt gaaacacaaa 1860
cttgaacagc tacggaactc ttgtgcgtaa ggaaaagtaa ggaaaacgat tccttctaac 1920
agaaatgtcc tgagcaatca cctatgaact tgtttcaaat gcatgatcaa atgcaacctc 1980
acaaccttgg ctgagtcttg agactgaaag atttagccat aatgtaaact gcctcaaatt 2040
ggactttggg cataaaagaa ctttttttatg cttaccatct ttttttttc tttaacagat 2100 ttgtatttaa gaattgtttt taaaaaattt taagatttac acaatgtttc tctgtaaata 2160
ttgccattaa atgtaaataa ctttaataaa acgtttatag cagttacaca gaatttcaat 2220
cctagtatat agtacctagt attataggta ctataaaccc taattttttt tatttaagta 2280
cattttgctt tttaaagttg atttttttct attgttttta gaaaaaataa aataactggc 2340
aaatatatca ttgagccaaa tcttaaaaaa aaaaaaaaa 2379

<210> SEQ ID NO 142
<211> LENGTH: 1799
<212> TYPE: DNA
<213> ORGANISM: Homo sapiens

<400> SEQUENCE: 142
gtgggaggat tgcattcagt ctagttcctg gttgccggct gaaataacct gctctccaaa 60
atgtccacaa aagtgactta agtcaggttc ccccaaacca gacaccaaga caagaatcca 120
tgtgtgtgtg actgaaggaa gtgctgggag agccccagct gcagcctgga tgtgaactgc 180
aactccaaag tgtgtccaga ctcaaggcaa gggcactagg ctttccagac ctcctactaa 240
gtcattgatc cagcactgcc ctgccaggac ataaatccct ggcacctctt gctctctgca 300
aaggagggca aagcagcttc aggagccctt gggagtcctc caaagagagt ctagggtaca 360
ggtccgaaag tagaagaaca cagaaggcag gccaggggca ctgtgagatg gtaaaagaga 420
tctgaaggga tccagaattc aagccaggaa gaagcagcaa tctgtcttct ggattaaaac 480
tgaagatcaa cctactttca acttactaag aaaggggatc atggacattg aagcatatct 540
tgaaagaatt ggctataaga agtctaggaa caaattggac ttggaaacat taactgatat 600
tcttcaacac cagatccgag ctgttccctt tgagaacctt aacatccatt gtggggatgc 660
catggactta ggcttagagg ccatttttga tcaagttgtg agaagaaatc ggggtggatg 720
gtgtctccag gtcaatcatc ttctgtactg ggctctgacc actattggtt ttgagaccac 780
gatgttggga gggtatgttt acagcactcc agccaaaaaa tacagcactg gcatgattca 840
ccttctcctg caggtgacca ttgatggcag gaactacatt gtcgatgctg ggtttggacg 900
ctcataccag atgtggcagc ctctggagtt aatttctggg aaggatcagc ctcaggtgcc 960
ttgtgtcttc cgtttgacgg aagagaatgg attctggtat ctagaccaaa tcagaaggga 1020
acagtacatt ccaaatgaag aatttcttca ttctgatctc ctagaagaca gcaaataccg 1080
aaaaatctac tcctttactc ttaagcctcg aacaattgaa gattttgagt ctatgaatac 1140
atacctgcag acatctccat catctgtgtt tactagtaaa tcattttgtt ccttgcagac 1200
cccagatggg gttcactgtt tggtgggctt caccctcacc cataggagat tcaattataa 1260
ggacaataca gatctaatag agttcaagac tctgagtgag gaagaaatag aaaaagtgct 1320

-continued

```
gaaaaatata tttaatattt ccttgcagag aaagcttgtg cccaaacatg gtgatagatt   1380

ttttactatt tagaataagg agtaaaacaa tcttgtctat ttgtcatcca gctcaccagt   1440

tatcaactga cgacctatca tgtatcttct gtacccttac cttattttga agaaaatcct   1500

agacatcaaa tcatttcacc tataaaaatg tcatcatata taattaaaca gctttttaaa   1560

gaaacataac cacaaacctt ttcaaataat aataataata ataataataa atgtctttta   1620

aagatggcct gtggttatct tggaaattgg tgatttatgc tagaaagctt ttaatgttgg   1680

tttattgttg aattcctaga aaagttttat gggtagatga gtaaataaaa tattgtaaaa   1740

aaacttattg tctataaagt atattaaaac attgttggct aatataaaaa aaaaaaaaa    1799
```

<210> SEQ ID NO 143
<211> LENGTH: 1644
<212> TYPE: DNA
<213> ORGANISM: Homo sapiens

<400> SEQUENCE: 143

```
gcgcgcgggt ttcgttgacc cgcggcgttc acgggaattg ttcgctttag tgccggcgcc     60

atggggtcgg agctgatcgg gcgcctagcc ccgcgcctgg gcctcgccga gcccgacatg    120

ctgaggaaag cagaggagta cttgcgcctg tcccgggtga agtgtgtcgg cctctccgca    180

cgcaccacgg agaccagcag tgcagtcatg tgcctggacc ttgcagcttc ctggatgaag    240

tgccccttgg acagggctta tttaattaaa ctttctggtt tgaacaagga gacatatcag    300

agctgtctta aatcttttga gtgtttactg ggcctgaatt caaatattgg aataagagac    360

ctagctgtac agtttagctg tatagaagca gtgaacatgg cttcaaagat actaaaaagc    420

tatgagtcca gtcttcccca gacacagcaa gtggatcttg acttatccag gccacttttc    480

acttctgctg cactgctttc agcatgcaag attctaaagc tgaaagtgga taaaaacaaa    540

atggtagcca catccggtgt aaaaaaagct atatttgatc gactgtgtaa acaactagag    600

aagattggac agcaggtcga cagagaacct ggagatgtag ctactccacc acggaagaga    660

aagaagatag tggttgaagc ccagcaaaag gaaatggaga aggtagagga gatgccacat    720

aaaccacaga aagatgaaga tctgacacag gattatgaag aatggaaaag aaaaattttg    780

gaaaatgctg ccagtgctca aaaggctaca gcagagtgat ttcagcttcc aaactggtat    840

acattccaaa ctgatagtac attgccatct ccaggaagac ttgacggctt tgggattttg    900

tttaaacttt tataataagg atcctaagac tgttgccttt aaatagcaaa gcagcctacc    960

tggaggctaa gtctgggcag tgggctggcc cctggtgtga gcattagacc agccacagtg   1020

cctgattggt atagccttat gtgctttcct acaaaatgga attggaggcc gggcgcagtg   1080

gctcacgcct gtaatcccag cactttggga ggccaaggtg ggtggatcac ctgaggtcag   1140

gagctcgaga ccagcctggc caacatggtg aaaccccatc tctactaaaa atacaaaaat   1200

tagccaggtg tgatggtgca tgcctgtaat cccagctcct cagtaggctg agacaggagc   1260

atcacttgaa cgtgggaggc agaggttgca gtgagccgag attgcaccac cgcactccag   1320

cctgggtgac agagcgagac ttatctcata aataaataga tagatactcc agcctgggtg   1380

acagagcgag acttatagat agatagatag atagatggat agatagatag atagatagat   1440

agatagataa acggaattgg agccattttg ctttaagtga atggcagtcc cttgtcttat   1500

tcagaatata aaattcagtc tgaatggcat cttacagatt ttacttcaat ttttgtgtac   1560

ggtatttttt atttgactaa atcaatatat tgtacagcct aagttaataa atgttattta   1620

tatatgcaaa aaaaaaaaaa aaaa                                           1644
```

<210> SEQ ID NO 144
<211> LENGTH: 13037
<212> TYPE: DNA
<213> ORGANISM: Homo sapiens

<400> SEQUENCE: 144
agtccacagc tgtcactaat cggggtaagc cttgttgtat ttgtgcgtgt gggtggcatt 60
ctcaatgaga actagcttca cttgtcattt gagtgaaatc tacaacccga ggcggctagt 120
gctcccgcac tactgggatc tgagatcttc ggagatgact gtcgcccgca gtacggagcc 180
agcagaagtc cgacccttcc tgggaatggg ctgtaccgag aggtccgact agccccaggg 240
ttttagtgag gggcagtgg aactcagcga gggactgaga gcttcacagc atgcacgagt 300
ttgatgccag agaaaaagtc gggagataaa ggagccgcgt gtcactaaat tgccgtcgca 360
gccgcagcca ctcaagtgcc ggacttgtga gtactctgcg tctccagtcc tcggacagaa 420
gttggagaac tctcttggag aactccccga gttaggagac gagatctcct aacaattact 480
actttttctt gcgctcccca cttgccgctc gctgggacaa acgacagcca cagttcccct 540
gacgacagga tggaggccaa gggcaggagc tgaccagcgc cgccctcccc cgcccccgac 600
ccaggaggtg gagatccctc cggtccagcc acattcaaca cccactttct cctccctctg 660
cccctatatt cccgaaaccc cctcctcctt cccttttccc tcctcctgga gacgggggag 720
gagaaaaggg gagtccagtc gtcatgactg agctgaaggc aaagggtccc cgggctcccc 780
acgtggcggg cggcccgccc tcccccgagg tcggatcccc actgctgtgt cgcccagccg 840
caggtccgtt cccggggagc cagacctcgg acaccttgcc tgaagtttcg gccataccta 900
tctccctgga cgggctactc ttccctcggc cctgccaggg acaggacccc tccgacgaaa 960
agacgcagga ccagcagtcg ctgtcggacg tggagggcgc atattccaga gctgaagcta 1020
caaggggtgc tggaggcagc agttctagtc ccccagaaaa ggacagcgga ctgctggaca 1080
gtgtcttgga cactctgttg gcgccctcag gtcccgggca gagccaaccc agccctcccg 1140
cctgcgaggt caccagctct tggtgcctgt ttggccccga acttcccgaa gatccaccgg 1200
ctgcccccgc cacccagcgg gtgttgtccc cgctcatgag ccggtccggg tgcaaggttg 1260
gagacagctc cgggacggca gctgcccata aagtgctgcc ccggggcctg tcaccagccc 1320
ggcagctgct gctcccggcc tctgagagcc ctcactggtc cggggcccca gtgaagccgt 1380
ctccgcaggc cgctgcggtg gaggttgagg aggaggatgg ctctgagtcc gaggagtctg 1440
cgggtccgct tctgaagggc aaacctcggg ctctgggtgg cgcggcggct ggaggaggag 1500
ccgcggctgt cccgccgggg gcggcagcag gaggcgtcgc cctggtcccc aaggaagatt 1560
cccgcttctc agcgcccagg gtcgccctgg tggagcagga cgcgccgatg gcgcccgggc 1620
gctccccgct ggccaccacg gtgatggatt tcatccacgt gcctatcctg cctctcaatc 1680
acgccttatt ggcagcccgc actcggcagc tgctggaaga cgaaagttac gacggcgggg 1740
ccggggctgc cagcgccttt gccccgccgc ggagttcacc ctgtgcctcg tccaccccgg 1800
tcgctgtagg cgacttcccc gactgcgcgt acccgcccga cgccgagccc aaggacgacg 1860
cgtaccctct ctatagcgac ttccagccgc ccgctctaaa gataaaggag gaggaggaag 1920
gcgcggaggc ctccgcgcgc tccccgcgtt cctaccttgt ggccggtgcc aaccccgcag 1980
ccttcccgga tttcccgttg ggccaccgc ccccgctgcc gccgcgagcg accccatcca 2040
gacccgggga agcggcggtg acggccgcac ccgccagtgc ctcagtctcg tctgcgtcct 2100

-continued

```
cctcggggtc gaccctggag tgcatcctgt acaaagcgga gggcgcgccg ccccagcagg   2160
gcccgttcgc gccgccgccc tgcaaggcgc cgggcgcgag cggctgcctg ctcccgcggg   2220
acggcctgcc ctccacctcc gcctctgccg ccgccgccgg ggcggccccc gcgctctacc   2280
ctgcactcgg cctcaacggg ctcccgcagc tcggctacca ggccgccgtg ctcaaggagg   2340
gcctgccgca ggtctacccg ccctatctca actacctgag gccggattca gaagccagcc   2400
agagcccaca atacagcttc gagtcattac ctcagaagat ttgtttaatc tgtggggatg   2460
aagcatcagg ctgtcattat ggtgtcctta cctgtgggag ctgtaaggtc ttctttaaga   2520
gggcaatgga agggcagcac aactacttat gtgctggaag aaatgactgc atcgttgata   2580
aaatccgcag aaaaaactgc ccagcatgtc gccttagaaa gtgctgtcag gctggcatgg   2640
tccttggagg tcgaaaattt aaaaagttca ataaagtcag agttgtgaga gcactggatg   2700
ctgttgctct cccacagcca gtgggcgttc caaatgaaag ccaagcccta agccagagat   2760
tcacttttc accaggtcaa gacatacagt tgattccacc actgatcaac ctgttaatga   2820
gcattgaacc agatgtgatc tatgcaggac atgacaacac aaaacctgac acctccagtt   2880
ctttgctgac aagtcttaat caactaggcg agaggcaact tctttcagta gtcaagtggt   2940
ctaaatcatt gccaggtttt cgaaacttac atattgatga ccagataact ctcattcagt   3000
attcttggat gagcttaatg gtgtttggtc taggatggag atcctacaaa cacgtcagtg   3060
ggcagatgct gtattttgca cctgatctaa tactaaatga acagcggatg aaagaatcat   3120
cattctattc attatgcctt accatgtggc agatcccaca ggagtttgtc aagcttcaag   3180
ttagccaaga agagttcctc tgtatgaaag tattgttact tcttaataca attcctttgg   3240
aagggctacg aagtcaaacc cagtttgagg agatgaggtc aagctacatt agagagctca   3300
tcaaggcaat tggtttgagg caaaaaggag ttgtgtcgag ctcacagcgt ttctatcaac   3360
ttacaaaact tcttgataac ttgcatgatc ttgtcaaaca acttcatctg tactgcttga   3420
atacatttat ccagtcccgg gcactgagtg ttgaatttcc agaaatgatg tctgaagtta   3480
ttgctgcaca attacccaag atattggcag ggatggtgaa acccttctc tttcataaaa   3540
agtgaatgtc atcttttct tttaaagaat taaattttgt ggtatgtctt tttgttttgg   3600
tcaggattat gaggtcttga gtttttataa tgttcttctg aaagccttac atttataaca   3660
tcatagtgtg taaatttaaa agaaaaattg tgaggttcta attattttct tttataaagt   3720
ataattagaa tgtttaactg ttttgtttac ccatattttc ttgaagaatt tacaagattg   3780
aaaaagtact aaaattgtta aagtaaacta tcttatccat attatttcat accatgtagg   3840
tgaggatttt taacttttgc atctaacaaa tcatcgactt aagagaaaaa atcttacatg   3900
taataacaca aagctattat atgttatttc taggtaactc cctttgtgtc aattatattt   3960
ccaaaaatga acctttaaaa tggtatgcaa aattttgtct atatatattt gtgtgaggag   4020
gaaattcata actttcctca gattttcaaa agtattttta atgcaaaaaa tgtagaaaga   4080
gtttaaaacc actaaaatag attgatgttc ttcaaactag gcaaaacaac tcatatgtta   4140
agaccatttt ccagattgga aacacaaatc tcttaggaag ttaataagta gattcatatc   4200
attatgcaaa tagtattgtg ggttttgtag gtttttaaaa taaccttttt tggggagaga   4260
attgtcctct aatgaggtat tgcgagtgga cataagaaat cagaagatta tggcctaact   4320
gtactcctta ccaactgtgg catgctgaaa gttagtcact cttactgatt ctcaattctc   4380
tcacctttga aagtagtaaa atatctttcc tgccaattgc tcctttgggt cagagcttat   4440
taacatcttt tcaaatcaaa ggaaagaaga aagggagagg aggaggaggg aggtatcaat   4500
```

tcacatacct ttctcctctt tatcctccac tatcatgaat tcatattatg tttcagccat 4560
gcaaatcttt ttaccatgaa atttcttcca gaattttccc cctttgacac aaattccatg 4620
catgtttcaa ccttcgagac tcagccaaat gtcatttctg taaaatcttc cctgagtctt 4680
ccaagcagta atttgccttc tcctagagtt tacctgccat tttgtgcaca tttgagttac 4740
agtagcatgt tattttacaa ttgtgactct cctgggagtc tgggagccat ataaagtggt 4800
caatagtgtt tgctgactga gagttgaatg acattttctc tctgtcttgg tattactgta 4860
gatttcgatc attctttggt tacatttctg catatttctg tacccatgac tttatcactt 4920
tcttctccca tgctttatct ccatcaatta tcttcattac ttttaaattt tccacctttg 4980
cttcctactt tgtgagatct ctccctttac tgactataac atagaagaat agaagtgtat 5040
tttatgtgtc ttaaggacaa tactttagat tccttgttct aagtttttaa actgaatgaa 5100
tggaatatta tttctctccc taagcaaaat tccacaaaac aattatttct tatgtttatg 5160
tagccttaaa ttgttttgta ctgtaaacct cagcataaaa actttcttca tttctaattt 5220
cattcaacaa atattgattg aatacctggt attagcacaa gaaaaatgtg ctaataagcc 5280
ttatgagaat ttggagctga agaaagacat ataactcagg aaagttacag tccagtagta 5340
ggtataaatt acagtgcctg ataaataggc attttaatat ttgtacactc aacgtatact 5400
aggtaggtgc aaaacattta catataattt tactgatacc catgcagcac aaaggtacta 5460
actttaaata ttaaataaca cctttatgtg tcagtaattc atttgcatta aatcttattg 5520
aaaaggcttt caatatattt tccccacaaa tgtcatccca agaaaaaagt atttttaaca 5580
tctcccaaat ataatagtta caggaaatct acctctgtga gagtgacacc tctcagaatg 5640
aactgtgtga cacaagaaaa tgaatgtagg tctatccaaa aaaaaacccca agaaacaaaa 5700
acaatattat tagcccttta tgcttaagtg atggactcag ggaacagttg atgttgtgat 5760
cattttatta tctgattctt gttactttga attaaaccaa tattttgatg atataaatca 5820
tttccaccag catatattta atttccataa taactttaaa attttctaat ttcactcaac 5880
tatgagggaa tagaatgtgg tggccacagg tttggctttt gttaaaatgt ttgatatctt 5940
cgatgttgat ctctgtctgc aatgtagatg tctaaacact aggatttaat atttaaggct 6000
aagctttaaa aataaagtac ctttttaaaa agaatatggc ttcaccaaat ggaaaatacc 6060
taatttctaa atctttttct ctacaaagtc ctatctacta atgtctccat tactatttag 6120
tcatcataac cattatcttc attttacatg tcgtgttctt tctggtagct ctaaaatgac 6180
actaaatcat aagaagacag gttacatatc aggaaatact tgaaggttac tgaaatagat 6240
tcttgagtta atgaaaatat tttctgtaaa aaggtttgaa aagccatttg agtctaaagc 6300
attatacctc cattatcagt agttatgtga caattgtgtg tgtgtttaat gtttaaagat 6360
gtggcacttt ttaataaggc aatgctatgc tattttttcc catttaacat taagataatt 6420
tattgctata cagatgatat ggaaatatga tgaacaatat ttttttgcc aaaactatgc 6480
cttgtaagta gccatggaat gtcaacctgt aacttaaatt atccacagat agtcatgtgt 6540
ttgatgatgg gcactgtgga gataactgac ataggactgt gcccccccttc tctgccactt 6600
actagctgga tgagattaag caagtcattt aactgctctg attaaacctg cctttcccaa 6660
gtgctttgta atgaatagaa atggaaacca aaaaaaacgt atacaggcct tcagaaatag 6720
taattgctac tattttgttt tcattaagcc atagttctgg ctataatttt atcaaactca 6780
ccagctatat tctacagtga aagcaggatt ctagaaagtc tcactgtttt atttatgtca 6840

-continued

```
ccatgtgcta tgatatattt ggttgaattc atttgaaatt agggctggaa gtattcaagt   6900
aatttcttct gctgaaaaaa tacagtgttt tgagtttagg gcctgtttta tcaaagttct   6960
aaagagccta tcactcttcc attgtagaca ttttaaaata atgacactga ttttaacatt   7020
tttaagtgtc tttttagaac agagagcctg actagaacac agcccctcca aaaacccatg   7080
ctcaaattat ttttactatg gcagcaattc cacaaaaggg aacaatgggt ttagaaatta   7140
caatgaagtc atcaacccaa aaaacatccc tatccctaag aaggttatga tataaaatgc   7200
ccacaagaaa tctatgtctg ctttaatctg tcttttattg ctttggaagg atggctatta   7260
catttttagt ttttgctgtg aatacctgag cagtttctct catccatact tatccttcac   7320
acatcagaag tcaggataga atatgaatca ttttaaaaac ttttacaact ccagagccat   7380
gtgcataaga agcattcaaa acttgccaaa acatacattt tttttcaaat ttaaagatac   7440
tctatttttg tattcaatag ctcaacaact gtggtcccca ctgataaagt gaagtggaca   7500
aggagacaag taatggcata agtttgtttt tcccaaagta tgcctgttca atagccattg   7560
gatgtgggaa atttctacat ctcttaaaat tttacagaaa atacatagcc agatagtcta   7620
gcaaaagttc accaagtcct aaattgctta tccttacttc actaagtcat gaaatcattt   7680
taatgaaaag aacatcacct aggttttgtg gtttcttttt ttcttattca tggctgagtg   7740
aaaacaacaa tctctgtttc tccctagcat ctgtggacta tttaatgtac cattattcca   7800
cactctatgg tccttactaa atacaaaatt gaacaaaaag cagtaaaaca actgactctt   7860
cacccatatt ataaaatata atccaagcca gattagtcaa catccataag atgaatccaa   7920
gctgaactgg gcctagatta ttgagttcag gttggatcac atccctattt attaataaac   7980
ttaggaaaga aggccttaca gaccatcagt tagctggagc taatagaacc tacacttcta   8040
aagttcggcc tagaatcaat gtggccttaa aagctgaaaa gaagcaggaa agaacagttt   8100
tcttcaataa tttgtccacc ctgtcactgg agaaaattta agaatttggg ggtgttggta   8160
gtaagttaaa cacagcagct gttcatggca gaaattattc aatacatacc ttctctgaat   8220
atcctataac caaagcaaag aaaaacacca aggggtttgt tctcctcctt ggagttgacc   8280
tcattccaag gcagagctca ggtcacaggc acaggggctg cgcccaagct tgtccgcagc   8340
cttatgcagc tgtggagtct ggaagactgt tgcaggactg ctggcctagt cccagaatgt   8400
cagcctcatt ttcgatttac tggctcttgt tgctgtatgt catgctgacc ttattgttaa   8460
acacaggttt gtttgctttt tttccactca tggagacatg ggagaggcat tatttttaag   8520
ctggttgaaa gctttaaccg ataaagcatt tttagagaaa tgtgaatcag gcagctaaga   8580
aagcatactc tgtccattac ggtaaagaaa atgcacagat tattaactct gcagtgtggc   8640
attagtgtcc tggtcaatat tcggatagat atgaataaaa tatttaaatg gtattgtaaa   8700
tagttttcag gacatatgct atagcttatt tttattatct tttgaaattg ctcttaatac   8760
atcaaatcct gatgtattca atttatcaga tataaattat tctaaatgaa gcccagttaa   8820
atgtttttgt cttgtcagtt atatgttaag tttctgatct ctttgtctat gacgtttact   8880
aatctgcatt tttactgtta tgaattattt tagacagcag tggtttcaag ctttttgcca   8940
ctaaaaatac cttttatttt ctcctccccc agaaaagtct ataccttgaa gtatctatcc   9000
accaaactgt acttctatta agaaatagtt attgtgtttt cttaatgttt tgttattcaa   9060
agacatatca atgaaagctg ctgagcagca tgaataacaa ttatatccac acagatttga   9120
tatattttgt gcagccttaa cttgatagta taaaatgtca ttgcttttta aataatagtt   9180
agtcaatgga cttctatcat agctttccta aactaggtta agatccagag ctttggggtc   9240
```

-continued

```
ataatatatt acatacaatt aagttatctt tttctaaggg ctttaaaatt catgagaata   9300
accaaaaaag gtatgtggag agttaataca aacataccat attcttgttg aaacagagat   9360
gtggctctgc ttgttctcca taaggtagaa atactttcca gaatttgcct aaactagtaa   9420
gccctgaatt tgctatgatt agggatagga agagattttc acatggcaga ctttagaatt   9480
cttcacttta gccagtaaag tatctccttt tgatcttagt attctgtgta ttttaacttt   9540
tctgagttgt gcatgtttat aagaaaaatc agcacaaagg gtttaagtta aagccttttt   9600
actgaaattt gaaagaaaca gaagaaaata tcaaagttct ttgtattttg agaggattaa   9660
atatgattta caaaagttac atggagggct ctctaaaaca ttaaattaat tattttttgt   9720
tgaaaagtct tactttaggc atcattttat tcctcagcaa ctagctgtga agcctttact   9780
gtgctgtatg ccagtcactc tgctagattg tggagattac cagtgttccc gtcttctccg   9840
agcttagagt tggatgggga ataaagacag gtaaacagat agctacaata ttgtactgtg   9900
aatgcttatg ctggaggaag tacagggaac tattggagca cctaagagga gcacctacct   9960
tgaatttagg ggttagcaga ggcatcctga aaaaagtcaa agctaagcca caatctataa  10020
gcagtttagg aattagcaga acgtgcgtgg tgaggagatg ccaaaggcaa gaagagaaga  10080
gtattccaaa caggagggat tccaaagaga gaagagtatc ccaaacaaca tttgcacaaa  10140
cctgatgggg agagagaatg tggggtgggg atggatgatg agactgaaga agaaagccag  10200
gtctagataa tcagtggcct tgtacaccat gttaaagagt gtagacttga ttctgttgta  10260
aacaggaaag cagcacaatt catatgaata ttttagaaga ctcccactgg aatatggaga  10320
ataaagttgg agatgactaa tcctggaagc agggagaaca tttttgagga agttgcacta  10380
ttttggtgaa aatgatgatc ataaacatga agaattgtag gtgatcatga cctcctctct  10440
aattttccag aagggttttg gaagatataa cataggaaca ttgacaggac tgacgaaagg  10500
agatgaaata caccatataa attgtcaaac acaaggccag atgtctaatt attttgctta  10560
tgtgttgaaa ttacaaattt ttcatcagga aaccaaaaac tacaaaactt agttttccca  10620
agtcccagaa ttctatctgt ccaaacaatc tgtaccactc cacctatatc cctacctttg  10680
catgtctgtc caacctcaaa gtccaggtct atacacacgg gtaagactag agcagttcaa  10740
gtttcagaaa atgagaaaga ggaactgagt tgtgctgaac ccatacaaaa taaacacatt  10800
ctttgtatag attcttggaa cctcgagagg aattcaccta actcataggt atttgatggt  10860
atgaatccat ggctgggctc ggcttttaaa aagccttatc tgggattcct tctatggaac  10920
caagttccat caaagcccat ttaaaagcct acattaaaaa caaaattctt gctgcattgt  10980
atacaaataa tgatgtcatg atcaaataat cagatgccat tatcaagtgg aattacaaaa  11040
tggtataccc actccaaaaa aaaaaaaaaa gctaaattct cagtagaaca ttgtgacttc  11100
atgagccctc cacagccttg gagctgagga gggagcactg gtgagcagta ggttgaagag  11160
aaaacttggc gcttaataat ctatccatgt tttttcatct aaaagagcct tctttttgga  11220
ttaccttatt caatttccat caaggaaatt gttagttcca ctaaccagac agcagctggg  11280
aaggcagaag cttactgtat gtacatggta gctgtgggaa ggaggtttct ttctccaggt  11340
cctcactggc catacaccag tcccttgtta gttatgcctg gtcatagacc cccgttgcta  11400
tcatctcata tttaagtctt tggcttgtga atttatctat tctttcagct tcagcactgc  11460
agagtgctgg gactttgcta acttccattt cttgctggct tagcacattc ctcataggcc  11520
cagctctttt ctcatctggc cctgctgtgg agtcaccttg ccccttcagg agagccatgg  11580
```

cttaccactg cctgctaagc ctccactcag ctgccaccac actaaatcca agcttctcta 11640
agatgttgca gactttacag gcaagcataa aaggcttgat cttcctggac ttccctttac 11700
ttgtctgaat ctcacctcct tcaactttca gtctcagaat gtaggcattt gtcctctttg 11760
ccctacatct tccttcttct gaatcatgaa agcctctcac ttcctcttgc tatgtgctgg 11820
aggcttctgt caggttttag aatgagttct catctagtcc tagtagcttt tgatgcttaa 11880
gtccaccttt taaggatacc tttgagattt agaccatgtt tttcgcttga gaaagcccta 11940
atctccagac ttgcctttct gtggatttca aagaccaact gaggaagtca aaagctgaat 12000
gttgactttc tttgaacatt tccgctataa caattccaat tctcctcaga gcaatatgcc 12060
tgcctccaac tgaccaggag aaaggtccag tgccaaagag aaaaacacaa agattaatta 12120
tttcagttga gcacatactt tcaaagtggt ttgggtattc atatgaggtt ttctgtcaag 12180
agggtgagac tcttcatcta tccatgtgtg cctgacagtt ctcctggcac tggctggtaa 12240
cagatgcaaa actgtaaaaa ttaagtgatc atgtatttta acgatatcat cacatactta 12300
ttttctatgt aatgttttaa atttccccta acatactttg actgttttgc acatggtaga 12360
tattcacatt tttttgtgtt gaagttgatg caatcttcaa agttatctac cccgttgctt 12420
attagtaaaa ctagtgttaa tacttggcaa gagatgcagg gaatctttct catgactcac 12480
gccctattta gttattaatg ctactaccct attttgagta agtagtaggt ccctaagtac 12540
attgtccaga gttatacttt taaagatatt tagccccata tacttcttga atctaaagtc 12600
atacaccttg ctcctcattt ctgagtggga aagacatttg agagtatgtt gacaattgtt 12660
ctgaaggttt ttgccaagaa ggtgaaactg tcctttcatc tgtgtatgcc tggggctggg 12720
tccctggcag tgatggggtg acaatgcaaa gctgtaaaaa ctaggtgcta gtgggcacct 12780
aatatcatca tcatatactt attttcaagc taatatgcaa aatcccatct ctgtttttaa 12840
actaagtgta gatttcagag aaaatatttt gtggttcaca taagaaaaca gtctactcag 12900
cttgacaagt gttttatgtt aaattggctg gtggtttgaa atgaatcatc ttcacataat 12960
gttttcttta aaaatattgt gaatttaact ctaattcttg ttattctgtg tgataataaa 13020
gaataaacta atttcta 13037

<210> SEQ ID NO 145
<211> LENGTH: 3180
<212> TYPE: DNA
<213> ORGANISM: Homo sapiens

<400> SEQUENCE: 145
attctatgct gcagcctaag catcattcct cttctcttct tagtggagat aaaattaccc 60
actgctctcc ttacatttac tttgtccata tttgctccta tgctctaggc tcgtgcacaa 120
caaacacagt gtgggccctt accctagaag ccaacttctc atgacctttc tctatctcca 180
gaatccatgc agtgggaatg aaggtaaaag aaggttttca tgggatccag ctgagagctc 240
tacggggaaa atggatctga ggagccatgt gctccatctc ttttatttta caggtagaga 300
ctaggggtat agagtgaggt gaattaccgc agtgacccac acattgttgg cagacctagg 360
attagaactc tgtcttcctg gttcccagct tggtgctttt gaaagcatac ttgctgcttt 420
cttaccggcc tggtgtctgc cactttggga cagagtgtgg acttgctcac ctgccccatt 480
tcttagggat tctcattctg tgtttgagca agaatattct tattctggaa agaaccacat 540
accacaggat tctgggtgag cataaggaag attgtcttgg ggatctgact tagctcacgt 600
atagtggcta tgatgaattc agtgtcttat tttttgcata tgtatatttt tagtctaata 660
ttgcctgggt gtctgagcaa gtctagatga atttaattgc tctcattttt cccctgcccc 720
tcttcctttg gtctctcttt taggaaatgt ttttctttca acattcgttt cattcattat 780
ttactcattc ggccaaccaa catttattga gtgccttccc tgtatcaggg acaggggctt 840
acaaagtaga atttgatccc acctctgccc tcagtagctc agtgtctaat ggaggtagtg 900
atgttcatta agcgtcgcca gatactgtgc taggtgctgt gcctgttctc tctcgcttgt 960
tcctcacaca cttgagaagg ccgaagctga ttcatagctt ggaaggcagg ggccttggat 1020
ttgaacccag gcctgaccaa tggcagaacc tatcagatgt gtggacagat gacattgcct 1080
ttctttcttt ggatatatca aaatcagcca gcaggcagga actcccattt tgagcaagca 1140
atgtgcagga atgatagggt atacagagag gaacaggaga tggcccctga cttccagcat 1200
gtgtctgatg gacatccagg ctgcaggcat catggtgctg tctagagaga tgagccaggt 1260
gcccagagcc catgggccaa tgctgccctt tcttgagcat gccaaacaaa gcggttggtg 1320
tgttagaggc acagtctcct ccactctaag taaaaatcag catgagtcct agcccacatt 1380
tccctagtga gtacaccaaa gatatctatg aactggcagt catcagtgac ttcctaaggt 1440
tccggaaatg catctcttac tcaggagtaa gcaatgatgt gcctgcggct ttacgagttc 1500
tcacagaatg actttctgga cccaaatgtt ttttctgctt caggactgtg aaggccttat 1560
tgttcgctct gccaccaagg tgaccgctga tgtcatcaac gcagctgaga aactccaggt 1620
ggtgggcagg gctggcacag gtgtggacaa tgtggatctg gaggccgcaa caaggaaggg 1680
catcttggtt atgaacaccc ccaatgggaa cagcctcagt gccgcagaac tcacttgtgg 1740
aatgatcatg tgcctggcca ggcagattcc ccaggcgacg gcttcgatga aggacggcaa 1800
atgggagcgg aagaagttca tgggaacaga gctgaatgga aagaccctgg gaattcttgg 1860
cctgggcagg attgggagag aggtagctac ccggatgcag tcctttggga tgaagactat 1920
agggtatgac cccatcattt ccccagaggt ctcggcctcc tttggtgttc agcagctgcc 1980
cctggaggag atctggcctc tctgtgattt catcactgtg cacactcctc tcctgccctc 2040
cacgacaggc ttgctgaatg acaacacctt tgcccagtgc aagaaggggg tgcgtgtggt 2100
gaactgtgcc cgtggaggga tcgtggacga aggcgccctg ctccgggccc tgcagtctgg 2160
ccagtgtgcc ggggctgcac tggacgtgtt tacggaagag ccgccacggg accgggcctt 2220
ggtggaccat gagaatgtca tcagctgtcc ccacctgggt gccagcacca aggaggctca 2280
gagccgctgt ggggaggaaa ttgctgttca gttcgtggac atggtgaagg ggaaatctct 2340
cacgggggtt gtgaatgccc aggcccttac cagtgccttc tctccacaca ccaagccttg 2400
gattggtctg gcagaagctc tggggacact gatgcgagcc tgggctgggt cccccaaagg 2460
gaccatccag gtgataacac agggaacatc cctgaagaat gctgggaact gcctaagccc 2520
cgcagtcatt gtcggcctcc tgaaagaggc ttccaagcag gcggatgtga acttggtgaa 2580
cgctaagctg ctggtgaaag aggctggcct caatgtcacc acctcccaca gccctgctgc 2640
accagggggg caaggcttcg gggaatgcct cctggccgtg gccctggcag gcgcccctta 2700
ccaggctgtg ggcttggtcc aaggcactac acctgtactg caggggctca atggagctgt 2760
cttcaggcca gaagtgcctc tccgcaggga cctgcccctg ctcctattcc ggactcagac 2820
ctctgaccct gcaatgctgc ctaccatgat tggcctcctg gcagaggcag gcgtgcggct 2880
gctgtcctac cagacttcac tggtgtcaga tggggagacc tggcacgtca tgggcatctc 2940
ctccttgctg cccagcctgg aagcgtggaa gcagcatgtg actgaagcct tccagttcca 3000

```
cttctaacct tggagctcac tggtccctgc ctctggggct tttctgaaga aacccaccca   3060

ctgtgatcaa tagggagaga aaatccacat tcttgggctg aacgcgagcc tctgacactg   3120

cttacactgc actctgaccc tgtagtacag caataaccgt ctaataaaga gcctaccccc   3180
```

<210> SEQ ID NO 146
<211> LENGTH: 1301
<212> TYPE: DNA
<213> ORGANISM: Homo sapiens
<220> FEATURE:
<221> NAME/KEY: misc_feature
<222> LOCATION: (1301)..(1301)
<223> OTHER INFORMATION: n is a, c, g, t or u

<400> SEQUENCE: 146

```
caaacaaaaa cagccaagct tttctgccaa aaagatgact gagaagactg ttaaagcaaa     60

aagctctgtt cctgcctcag atgatgccta tccagaaata gaaaaattct ttcccttcaa    120

tcctctagac tttgagagtt ttgacctgcc tgaagagcac cagattgcgc acctcccctt    180

gagtggagtg cctctcatga tccttgacga ggagagagag cttgaaaagc tgtttcagct    240

gggccccccct tcacctgtga agatgccctc tccaccatgg gaatccaatc tgttgcagtc    300

tccttcaagc attctgtcga ccctggatgt tgaattgcca cctgtttgct gtgacataga    360

tatttaaatt tcttagtgct tcagagtctg tgtgtatttg tattaataaa gcattcttta    420

acagaaaaaa aaaaaaaaaa aaaaaaaaaa aaaaaaaaaa aaaaaaaaaa aggggggga    480

gacacaaaaa gaattcccca agagggggcc acaagataat cagaggatat cacacaagat    540

ctctcggcgc accaacgacg gggccccaa ataagggaga gacccagaat cacaacagcc    600

aagacacggt ggacacgacg gaaacaaaca cacagcccag acacgggggc aaacacgcgc    660

gcacaccgcg gacaccatgg gacaaagcag acaccaccca caaaacaaca ccgcggaggg    720

ggaagaacaa caaaacaagt gcgcaaacag aacacaacca cagaaagaga aaaattaaaa    780

cggcccccaa gacggcgaca acacaacaaa acaaccacta cagagcgctc aacagccgag    840

taaaaacaca acaacggaca actaacacac aaaggaatga aacaaagcgg ggccacacac    900

cgacaccgga aatccggcga acaactcaca ccgagcgagg gtcccagaca acaaatacac    960

agacaacgaa accgagaaac aagaccagca agacgagcag gcaaaagaca aacaagacag   1020

aggagacgac gacgaacgca aaggacaaga ggacacaacg acgcgaggag cgagagcgag   1080

aggaagagac aacaaaaaga cacaaaagaa caacaagcaa gcagcgaaga acgacacaca   1140

accacacgag acagcaggag cagaggcgga gaaaacacaa cgagcaagcc aagaccaaga   1200

gaggagaaca aaataaaaaa atacgagagc aggcggacga gagcacgaga cgaacagaca   1260

aacgggaatc agaagcataa cgatccgcga cgcgaacaac n                       1301
```

<210> SEQ ID NO 147
<211> LENGTH: 3203
<212> TYPE: DNA
<213> ORGANISM: Homo sapiens

<400> SEQUENCE: 147

```
gtgcaccctg tcccagccgt cctgtcctgg ctgctcgctc tgcttcgctg cgcctccact     60

atgctctccc tccgtgtccc gctcgcgccc atcacggacc cgcagcagct gcagctctcg    120

ccgctgaagg ggctcagctt ggtcgacaag gagaacacgc cgccggccct gagcgggacc    180

cgcgtcctgg ccagcaagac cgcgaggagg atcttccagg agaaaacccc cgccgctttg    240

tcatcttccc catcgagtac catgatatct ggcagatgta taagaaggca gaggcttcct    300
```

-continued

```
tttggaccgc cgaggaggtg gacctctcca aggacattca gcactgggaa tccctgaaac    360
ccgaggagag atattttata tcccatgttc tggctttctt tgcagcaagc gatggcatag    420
taaatgaaaa cttggtggag cgatttagcc aagaagttca gattacagaa gcccgctgtt    480
tctatggctt ccaaattgcc atggaaaaca tacattctga aatgtatagt cttcttattg    540
acacttacat aaaagatccc aaagaaaggg aatttctctt caatgccatt gaaacgatgc    600
cttgtgtcaa gaagaaggca gactgggcct tgcgctggat tggggacaaa gaggctacct    660
atggtgaacg tgttgtagcc tttgctgcag tggaaggcat tttcttttcc ggttcttttg    720
cgtcgatatt ctggctcaag aaacgaggac tgatgcctgg cctcacattt tctaatgaac    780
ttattagcag agatgagggt ttacactgtg attttgcttg cctgatgttc aaacacctgg    840
tacacaaacc atcggaggag agagtaagag aaataattat caatgctgtt cggatagaac    900
aggagttcct cactgaggcc ttgcctgtga agctcattgg gatgaattgc actctaatga    960
agcaatacat tgagtttgtg gcagacagac ttatgctgga actgggtttt agcaaggttt   1020
tcagagtaga gaacccattt gactttatgg agaatatttc actggaagga aagactaact   1080
tctttgagaa gagagtaggc gagtatcaga ggatgggagt gatgtcaagt ccaacagaga   1140
attcttttac cttggatgct gacttctaaa tgaactgaag atgtgccctt acttggctga   1200
ttttttttt tccatctcat aagaaaaatc agctgaagtg ttaccaacta gccacaccat   1260
gaattgtccg taatgttcat taacagcatc tttaaaactg tgtagctacc tcacaaccag   1320
tcctgtctgt ttatagtgct ggtagtatca ccttttgcca gaaggcctgg ctggctgtga   1380
cttaccatag cagtgacaat ggcagtcttg gctttaaagt gaggggtgac cctttagtga   1440
gcttagcaca gcgggattaa acagtccttt aaccagcaca gccagttaaa agatgcagcc   1500
tcactgcttc aacgcagatt ttaatgttta cttaaatata aacctggcac tttacaaaca   1560
aataaacatt gtttgtactc acaaggcgat aatagcttga tttatttggt ttctacacca   1620
aatacattct cctgaccact aatgggagcc aattcacaat tcactaagtg actaaagtaa   1680
gttaaacttg tgtagactaa gcatgtaatt tttaagtttt attttaatga attaaaatat   1740
ttgttaacca actttaaagt cagtcctgtg tatacctaga tattagtcag ttggtgccag   1800
atagaagaca ggttgtgttt ttatcctgtg gcttgtgtag tgtcctggga ttctctgccc   1860
cctctgagta gagtgttgtg ggataaagga atctctcagg gcaaggagct tcttaagtta   1920
aatcactaga aatttagggg tgatctgggc cttcatatgt gtgagaagcc gtttcatttt   1980
atttctcact gtattttcct caacgtctgg ttgatgagaa aaaattcttg aagagttttc   2040
atatgtggga gctaaggtag tattgtaaaa tttcaagtca tccttaaaca aaatgatcca   2100
cctaagatct tgcccctgtt aagtggtgaa atcaactaga ggtggttcct acaagttgtt   2160
cattctagtt ttgtttggtg taagtaggtt gtgtgagtta attcatttat atttactatg   2220
tctgttaaat cagaaatttt ttattatcta tgttcttcta gattttacct gtagttcata   2280
cttcagtcac ccagtgtctt attctggcat tgtctaaatc tgagcattgt ctagggggat   2340
cttaaacttt agtaggaaac catgagctgt taatacagtt tccattcaaa tattaatttc   2400
agaatgaaac ataatttttt tttttttt ttgagatgga gtctcgctct gttgcccagg   2460
ctggagtgca gtggcgcgat tttggctcac tgtaacctcc atctcctggg ttcaagcaat   2520
tctcctgtct cagcctccct agtagctggg actgcaggta tgtgctacca cacctggcta   2580
atttttgtat ttttagtaga gatggagttt caccatattg gtcaggctgg tcttgaactc   2640
```

ctgacctcag gtgatccacc cacctcggcc tcccaaagtg ctgggattgc aggcgtgata 2700
aacaaatatt cttaataggg ctactttgaa ttaatctgcc tttatgtttg ggagaagaaa 2760
gctgagacat tgcatgaaag atgatgagag ataaatgttg atcttttggc cccatttgtt 2820
aattgtattc agtatttgaa cgtcgtcctg tttattgtta gttttcttca tcatttattg 2880
tatagacaat ttttaaatct ctgtaatatg atacattttc ctatctttta agttattgtt 2940
acctaaagtt aatccagatt atatggtcct tatatgtgta caacattaaa atgaaaggct 3000
ttgtcttgca ttgtgaggta caggcggaag ttggaatcag gttttaggat tctgtctctc 3060
attagctgaa taatgtgagg attaacttct gccagctcag accatttcct aatcagttga 3120
aagggaaaca agtatttcag tctcaaaatt gaataatgca caagtcttaa gtgattaaaa 3180
taaaactgtt cttatgtcag ttt 3203

<210> SEQ ID NO 148
<211> LENGTH: 4483
<212> TYPE: DNA
<213> ORGANISM: Homo sapiens

<400> SEQUENCE: 148
agcgggggca ctccagccct gcagcctccg gagtcagtgc cgcgcgcccg ccgccccgcg 60
ccttcctgct cgccgcacct ccgggagccg gggcgcaccc agcccgcagc gccgcctccc 120
cgcccgcgcc gcctccgacc gcaggccgag ggccgccact ggccgggggg accgggcagc 180
agcttgcggc cgcggagccg ggcaacgctg gggactgcgc cttttgtccc cggaggtccc 240
tggaagtttg cggcaggacg cgcgcgggga ggcggcggag gcagccccga cgtcgcggag 300
aacagggcgc agagccggca tggcatcgg gcgcagcgag gggggccgcc gcggggcagc 360
cctgggcgtg ctgctggcgc tgggcgcggc gcttctggcc gtgggctcgg ccagcgagta 420
cgactacgtg agcttccagt cggacatcgg cccgtaccag agcgggcgct tctacaccaa 480
gccacctcag tgcgtggaca tccccgcgga cctgcggctg tgccacaacg tgggctacaa 540
gaagatggtg ctgcccaacc tgctggagca cgagaccatg gcggaggtga agcagcaggc 600
cagcagctgg gtgcccctgc tcaacaagaa ctgccacgcc ggcacccagg tcttcctctg 660
ctcgctcttc gcgcccgtct gcctggaccg gcccatctac ccgtgtcgct ggctctgcga 720
ggccgtgcgc gactcgtgcg agccggtcat gcagttcttc ggcttctact ggcccgagat 780
gcttaagtgt gacaagttcc ccgaggggga cgtctgcatc gccatgacgc cgcccaatgc 840
caccgaagcc tccaagcccc aaggcacaac ggtgtgtcct ccctgtgaca acgagttgaa 900
atctgaggcc atcattgaac atctctgtgc cagcgagttt gcactgagga tgaaaataaa 960
agaagtgaaa aaagaaaatg gcgacaagaa gattgtcccc aagaagaaga agcccctgaa 1020
gttggggccc atcaagaaga aggacctgaa gaagcttgtg ctgtacctga agaatggggc 1080
tgactgtccc tgccaccagc tggacaacct cagccaccac ttcctcatca tgggccgcaa 1140
ggtgaagagc cagtacttgc tgacggccat ccacaagtgg gacaagaaaa acaaggagtt 1200
caaaaacttc atgaagaaaa tgaaaaacca tgagtgcccc acctttcagt ccgtgtttaa 1260
gtgattctcc cgggggcagg gtggggaggg agcctcgggt ggggtgggag cggggggac 1320
agtgccccgg gaacccggtg ggtcacacac acgcactgcg cctgtcagta gtggacattt 1380
aatccagtcg gcttgttctt gcagcattcc cgctcccttc cctccatagc cacgctccaa 1440
accccagggt agccatggcc gggtaaagca agggccattt agattaggaa ggtttttaag 1500
atccgcaatg tggagcagca gccactgcac aggaggaggt gacaaaccat ttccaacagc 1560

-continued

```
aacacagcca ctaaaacaca aaaaggggga ttgggcggaa agtgagagcc agcagcaaaa   1620
actacatttt gcaacttgtt ggtgtggatc tattggctga tctatgcctt tcaactagaa   1680
aattctaatg attggcaagt cacgttgttt tcaggtccag agtagtttct ttctgtctgc   1740
tttaaatgga aacagactca taccacactt acaattaagg tcaagcccag aaagtgataa   1800
gtgcagggag gaaaagtgca agtccattat gtaatagtga cagcaaaggg accaggggag   1860
aggcattgcc ttctctgccc acagtctttc cgtgtgattg tctttgaatc tgaatcagcc   1920
agtctcagat gccccaaagt ttcggttcct atgagcccgg ggcatgatct gatccccaag   1980
acatgtggag gggcagcctg tgcctgcctt tgtgtcagaa aaaggaaacc acagtgagcc   2040
tgagagagac ggcgattttc gggctgagaa ggcagtagtt ttcaaaacac atagttaaaa   2100
aagaaacaaa tgaaaaaaat tttagaacag tccagcaaat tgctagtcag ggtgaattgt   2160
gaaattgggt gaagagctta cgattctaat ctcatgtttt ttccttttca catttttaaa   2220
agaacaatga caaacaccca cttatttttc aaggttttaa aacagtctac attgagcatt   2280
tgaaaggtgt gctagaacaa ggtctcctga tccgtccgag gctgcttccc agaggagcag   2340
ctctccccag gcatttgcca agggaggcgg atttccctgg tagtgtagct gtgtggcttt   2400
ccttcctgaa gagtccgtgg ttgccctaga acctaacacc ccctagcaaa actcacagag   2460
ctttccgttt ttttctttcc tgtaaagaaa catttccttt gaacttgatt gcctatggat   2520
caaagaaatt cagaacagcc tgcctgtccc cccgcacttt ttacatatat ttgtttcatt   2580
tctgcagatg gaaagttgac atgggtgggg tgtccccatc cagcgagaga gtttaaaaag   2640
caaaacatct ctgcagtttt tcccaagtgc cctgagatac ttcccaaagc ccttatgttt   2700
aatcagcgat gtatataagc cagttcactt agacaacttt acccttcttg tccaatgtac   2760
aggaagtagt tctaaaaaaa atgcatatta atttcttccc ccaaagccgg attcttaatt   2820
ctctgcaaca ctttgaggac atttatgatt gtccctctgg gccaatgctt atacccagtg   2880
aggatgctgc agtgaggctg taaagtggcc ccctgcggcc ctagcctgac ccggaggaaa   2940
ggatggtaga ttctgttaac tcttgaagac tccagtatga aaatcagcat gcccgcctag   3000
ttacctaccg gagagttatc ctgataaatt aacctctcac agttagtgat cctgtccttt   3060
taacaccttt tttgtggggt tctctctgac ctttcatcgt aaagtgctgg ggaccttaag   3120
tgatttgcct gtaattttgg atgattaaaa aatgtgtata tatattagct aattagaaat   3180
attctacttc tctgttgtca aactgaaatt cagagcaagt tcctgagtgc gtggatctgg   3240
gtcttagttc tggttgattc actcaagagt tcagtgctca tacgtatctg ctcattttga   3300
caaagtgcct catgcaaccg ggccctctct ctgcggcaga gtccttagtg gaggggttta   3360
cctggaacat tagtagttac cacagaatac ggaagagcag gtgactgtgc tgtgcagctc   3420
tctaaatggg aattctcagg taggaagcaa cagcttcaga aagagctcaa aataaattgg   3480
aaatgtgaat cgcagctgtg ggttttacca ccgtctgtct cagagtccca ggaccttgag   3540
tgtcattagt tactttattg aaggttttag acccatagca gctttgtctc tgtcacatca   3600
gcaatttcag aaccaaaagg gaggctctct gtaggcacag agctgcacta tcacgagcct   3660
ttgtttttct ccacaaagta tctaacaaaa ccaatgtgca gactgattgg cctggtcatt   3720
ggtctccgag agaggaggtt tgcctgtgat ttcctaatta tcgctagggc caaggtggga   3780
tttgtaaagc tttacaataa tcattctgga tagagtcctg ggaggtcctt ggcagaactc   3840
agttaaatct ttgaagaata tttgtagtta tcttagaaga tagcatggga ggtgaggatt   3900
```

-continued

```
ccaaaaacat tttattttta aaatatcctg tgtaacactt ggctcttggt acctgtgggt   3960
tagcatcaag ttctccccag ggtagaattc aatcagagct ccagtttgca tttggatgtg   4020
taaattacag taatcccatt tcccaaacct aaaatctgtt tttctcatca gactctgagt   4080
aactggttgc tgtgtcataa cttcatagat gcaggaggct caggtgatct gtttgagcag   4140
agcaccctag gcagcctgca gggaataaca tactggccgt tctgacctgt tgccagcaga   4200
tacacaggac atggatgaaa ttcccgtttc ctctagtttc ttcctgtagt actcctcttt   4260
tagatcctaa gtctcttaca aaagctttga atactgtgaa aatgttttac attccatttc   4320
atttgtgttg tttttttaac tgcattttac cagatgtttt gatgttatcg cttatgttaa   4380
tagtaattcc cgtacgtgtt cattttattt tcatgctttt tcagccatgt atcaatattc   4440
acttgactaa aatcactcaa ttaatcaaaa aaaaaaaaaa aas                     4483
```

<210> SEQ ID NO 149
<211> LENGTH: 3637
<212> TYPE: DNA
<213> ORGANISM: Homo sapiens

<400> SEQUENCE: 149

```
agtcctgggc gaagggggcg gtggttcccc gcggcgctgc gcgcggcggt aattagtgat     60
tgtcttccag cttcgcgaag gctaggggcg cggctgccgg gtggctgcgc ggcgctgccc    120
ccggaccgag gggcagccaa cccaatgaaa ccaccgcgtg ttcgcgcctg gtagagattt    180
ctcgaagaca ccagtgggcc cgttccgagc cctctggacc gcccgtgtgg aaccaaacct    240
gcgcgcgtgg ccgggccgtg ggacaacgag gccgcggaga cgaaggcgca atggcgagga    300
agttatctgt aatcttgatc ctgacctttg ccctctctgt cacaaatccc cttcatgaac    360
taaaagcagc tgctttcccc cagaccactg agaaaattag tccgaattgg gaatctggca    420
ttaatgttga cttggcaatt tccacacggc aatatcatct acaacagctt ttctaccgct    480
atggagaaaa taattctttg tcagttgaag ggttcagaaa attacttcaa aatataggca    540
tagataagat taaaagaatc catatacacc atgaccacga ccatcactca gaccacgagc    600
atcactcaga ccatgagcgt cactcagacc atgagcatca ctcagaccac gagcatcact    660
ctgaccatga tcatcactct caccataatc atgctgcttc tggtaaaaat aagcgaaaag    720
ctctttgccc agaccatgac tcagatagtt caggtaaaga tcctagaaac agccagggga    780
aaggagctca ccgaccagaa catgccagtg gtagaaggaa tgtcaaggac agtgttagtg    840
ctagtgaagt gacctcaact gtgtacaaca ctgtctctga aggaactcac tttctagaga    900
caatagagac tccaagacct ggaaaactct tccccaaaga tgtaagcagc tccactccac    960
ccagtgtcac atcaaagagc cgggtgagcc ggctggctgg taggaaaaca aatgaatctg   1020
tgagtgagcc ccgaaaaggc tttatgtatt ccagaaacac aaatgaaaat cctcaggagt   1080
gtttcaatgc atcaaagcta ctgacatctc atggcatggg catccaggtt ccgctgaatg   1140
caacagagtt caactatctc tgtccagcca tcatcaacca aattgatgct agatcttgtc   1200
tgattcatac aagtgaaaag aaggctgaaa tccctccaaa gacctattca ttacaaatag   1260
cctgggttgg tggttttata gccatttcca tcatcagttt cctgtctctg ctgggggtta   1320
tcttagtgcc tctcatgaat cgggtgtttt tcaaatttct cctgagtttc cttgtggcac   1380
tggccgttgg gactttgagt ggtgatgctt ttttacacct tcttccacat tctcatgcaa   1440
gtcaccacca tagtcatagc catgaagaac cagcaatgga aatgaaaaga ggaccacttt   1500
tcagtcatct gtcttctcaa aacatagaag aaagtgccta ttttgattcc acgtggaagg   1560
```

-continued gtctaacagc tctaggaggc ctgtatttca tgtttcttgt tgaacatgtc ctcacattga 1620
tcaaacaatt taaagataag aagaaaaaga atcagaagaa acctgaaaat gatgatgatg 1680
tggagattaa gaagcagttg tccaagtatg aatctcaact ttcaacaaat gaggagaaag 1740
tagatacaga tgatcgaact gaaggctatt tacgagcaga ctcacaagag ccctccccact 1800 ttgattctca gcagcctgca gtcttggaag aagaagaggt catgatagct catgctcatc 1860
cacaggaagt ctacaatgaa tatgtaccca gagggtgcaa gaataaatgc cattcacatt 1920
tccacgatac actcggccag tcagacgatc tcattcacca ccatcatgac taccatcata 1980
ttctccatca tcaccaccac caaaaccacc atcctcacag tcacagccag cgctactctc 2040
gggaggagct gaaagatgcc ggcgtcgcca ctctggcctg gatggtgata atgggtgatg 2100
gcctgcacaa tttcagcgat ggcctagcaa ttggtgctgc ttttactgaa ggcttatcaa 2160
gtggtttaag tacttctgtt gctgtgttct gtcatgagtt gcctcatgaa ttaggtgact 2220
ttgctgttct actaaaggct ggcatgaccg ttaagcaggc tgtcctttat aatgcattgt 2280
cagccatgct ggcgtatctt ggaatggcaa caggaatttt cattggtcat tatgctgaaa 2340
atgtttctat gtggatattt gcacttactg ctggcttatt catgtatgtt gctctggttg 2400
atatggtacc tgaaatgctg cacaatgatg ctagtgacca tggatgtagc cgctgggggt 2460
atttcttttt acagaatgct gggatgcttt tgggttttgg aattatgtta cttatttcca 2520
tatttgaaca taaaatcgtg tttcgtataa atttctagtt aaggtttaaa tgctagagta 2580
gcttaaaaag ttgtcatagt ttcagtaggt catagggaga tgagtttgta tgctgtacta 2640
tgcagcgttt aaagttagtg ggttttgtga tttttgtatt gaatattgct gtctgttaca 2700
aagtcagtta aaggtacgtt ttaatattta agttattcta tcttggagat aaaatctgta 2760
tgtgcaattc accggtatta ccagtttatt atgtaaacaa gagatttggc atgacatgtt 2820
ctgtatgttt cagggaaaaa tgtctttaat gctttttcaa gaactaacac agttattcct 2880
atactggatt ttaggtctct gaagaactgc tggtgtttag gaataagaat gtgcatgaag 2940
cctaaaatac caagaaagct tatactgaat ttaagcaaag aaataaagga gaaaagagaa 3000
gaatctgaga attggggagg catagattct tataaaaatc acaaaatttg ttgtaaatta 3060
gaggggagaa atttagaatt aagtataaaa aggcagaatt agtatagagt acattcatta 3120
aacatttttg tcaggattat ttcccgtaaa aacgtagtga gcacttttca tatactaatt 3180
tagttgtaca tttaactttg tataatacag aaatctaaat atatttaatg aattcaagca 3240
atatatcact tgaccaagaa attggaattt caaaatgttc gtgcgggtat ataccagatg 3300
agtacagtga gtagttttat gtatcaccag actgggttat tgccaagtta tatatcacca 3360
aaagctgtat gactggatgt tctggttacc tggtttacaa aattatcaga gtagtaaaac 3420
tttgatatat atgaggatat taaaactaca ctaagtatca tttgattcga ttcagaaagt 3480
actttgatat ctctcagtgc ttcagtgcta tcattgtgag caattgtctt ttatatacgg 3540
tactgtagcc atactaggcc tgtctgtggc attctctaga tgtttctttt ttacacaata 3600
aattccttat atcagcttga aaaaaaaaaa aaaaaaa 3637

<210> SEQ ID NO 150
<211> LENGTH: 2208
<212> TYPE: DNA
<213> ORGANISM: Homo sapiens

<400> SEQUENCE: 150

```
aacgcacttg gcgcgcggcg cgggctgcag acggctgcga ggcgctgggc acaggtgtcc     60
tgatggcaaa tttcaagggc cacgcgcttc cagggagttt cttcctgatc attgggctgt    120
gttggtcagt gaagtacccg ctgaagtact ttagccacac gcggaagaac agcccactac    180
attactatca gcgtctcgag atcgtcgaag ccgcaattag gactttgttt tccgtcactg    240
ggatcctggc agagcagttt gttccggatg ggccccacct gcacctctac catgagaacc    300
actggataaa gttaatgaat tggcagcaca gcaccatgta cctattcttt gcagtctcag    360
gaattgttga catgctcacc tatctggtca gccacgttcc cttgggggtg gacagactgg    420
ttatggctgt ggcagtattc atggaaggtt tcctcttcta ctaccacgtc cacaaccggc    480
ctccgctgga ccagcacatc cactcactcc tgctgtatgc tctgttcgga gggtgtgtta    540
gtatctccct agaggtgatc ttccgggacc acattgtgct ggaacttttc cgaaccagtc    600
tcatcattct tcagggaacc tggttctggc agattgggtt tgtgctgttc ccaccttttg    660
gaacacccga atgggaccag aaggatgatg ccaacctcat gttcatcacc atgtgcttct    720
gctggcacta cctggctgcc ctcagcattg tggccgtcaa ctattctctt gtttactgcc    780
ttttgactcg gatgaagaga cacggaaggg gagaaatcat tggaattcag aagctgaatt    840
cagatgacac ttaccagacc gccctcttga gtggctcaga tgaggaatga gccgagatgc    900
ggagggcgca gatgtcccac tgcacagctg gaatgaatgg agttcatccc ctccacctga    960
atgcctgctg tggtctgatc ttaagggtct atatatttgc acctcctcat tcaacacagg   1020
gctggaggtt ctacaacagg aaatcaggcc tacagcatcc tgtgtatctt gcagttggga   1080
tttttaaaca tactataaag tctgtgttgg tatagtaccc ttcataagga aaaatgaagt   1140
aatgcctata agtagcaggc ctttgtgcct cagtgtcaag agaaatcaag agatgctaaa   1200
agctttacaa tggaagtggc ctcatggatg aatccggggt atgagcccag gagaacgtgc   1260
tgcttttggt aacttatccc tttttctctt aagaaagcag gtactttctt attagaaata   1320
tgttagaatg tgtaagcaaa cgacagtgcc tttagaatta caattctaac ttacatattt   1380
tttgaaagta aaataattca caagctttgg tattttaaaa ttattgttaa acatatcata   1440
actaatcata ccagggtact gcaataccac tgtttataag tgacaaaatt aggccaaagg   1500
tgattttttt ttaaatcagg aagctggtta ctggctctac tgagagttgg agccctgatg   1560
ttctgattct tcaaagtcac cctaaaagaa gatctgacag gaaagctgta taatgagata   1620
gaaaaacgtc aggtatggaa ggctttcagt tttaatatgg ctgaaagcaa aggataacga   1680
attcagaatt agtaatgtaa aatcttgata ccctaatctt gcttctggat ctgttctttt   1740
tttaaaaaaa cttccttcac cgcgcctata atcctagcac tttgggaggc cgaggcaggc   1800
agatcacggg gtcaggagat caagaccatc ctggctaaca tggtgaaacc ccgtctctac   1860
tgaaaataca aaaaattagc cgggtgtggt ggcgggcgcc tgtagttcca gctactcggg   1920
aggctgaggc aagagaatgg catgaacccg gtaggggagc ttgcagtgag cccagatcat   1980
gccactgtac tccagcctag gtgacagagc aagactctgt ctcaaaaaca agcaaacaga   2040
cttccttcaa caaatattta ttaaatatcc actttgcaac agcactgaaa tggctgtaag   2100
gactcctgag atatgtgtcc agcaaggagt ttacagtcaa acaggagaga catgcctgta   2160
```

gttacatcca gtgtgatggg tgctgagagg caagtacaaa ccacgatg 2208

<210> SEQ ID NO 151
<211> LENGTH: 1678
<212> TYPE: DNA
<213> ORGANISM: Homo sapiens
<220> FEATURE:
<221> NAME/KEY: misc_feature
<222> LOCATION: (523)..(523)
<223> OTHER INFORMATION: n is a, c, g, t or u
<220> FEATURE:
<221> NAME/KEY: misc_feature
<222> LOCATION: (569)..(569)
<223> OTHER INFORMATION: n is a, c, g, t or u
<220> FEATURE:
<221> NAME/KEY: misc_feature
<222> LOCATION: (961)..(961)
<223> OTHER INFORMATION: n is a, c, g, t or u
<220> FEATURE:
<221> NAME/KEY: misc_feature
<222> LOCATION: (1021)..(1021)
<223> OTHER INFORMATION: n is a, c, g, t or u
<220> FEATURE:
<221> NAME/KEY: misc_feature
<222> LOCATION: (1066)..(1066)
<223> OTHER INFORMATION: n is a, c, g, t or u
<220> FEATURE:
<221> NAME/KEY: misc_feature
<222> LOCATION: (1069)..(1069)
<223> OTHER INFORMATION: n is a, c, g, t or u
<220> FEATURE:
<221> NAME/KEY: misc_feature
<222> LOCATION: (1194)..(1194)
<223> OTHER INFORMATION: n is a, c, g, t or u
<220> FEATURE:
<221> NAME/KEY: misc_feature
<222> LOCATION: (1202)..(1202)
<223> OTHER INFORMATION: n is a, c, g, t or u
<220> FEATURE:
<221> NAME/KEY: misc_feature
<222> LOCATION: (1287)..(1287)
<223> OTHER INFORMATION: n is a, c, g, t or u
<220> FEATURE:
<221> NAME/KEY: misc_feature
<222> LOCATION: (1472)..(1472)
<223> OTHER INFORMATION: n is a, c, g, t or u

<400> SEQUENCE: 151
tcccgccgcg ccacttcgcc tgcctccgtc ccccgcccgc cgcgccatgc ctgtggccgg 60
ctcggagctg ccgcgccggc ccttgccccc cgccgcacag gagcgggacg ccgagccgcg 120
tccgccgcac ggggagctgc agtacctggg gcagatccaa cacatcctcc gctgcggcgt 180
caggaaggac gcccgcccgg gcaccggtac cctgccggta ttcggcatgc aggcgcgcta 240
cagcctgaga gatgaattcc ctctgctgac aaccaaacgt gtgttctgga acggtgcttc 300
ggaggagctg ctgtggctta tcaagggatc cacaaacgct atagacctgt cttccccggc 360
agcgaaaatc tcgggatgcc actggatccc gacactctct ggacaccctg ggattctcca 420
ccagagaaga acgcgacttg ggcccagttt gtggctctca gcggaggcct cctgtggcag 480
aatacataca tttccaatca gatcacttcc cggacacgga ccntgaccag cctgccaaaa 540
agtggatttc cccccacccc agaacccanc ccctgacgca cagaaaccaa cccattcgtt 600
gttgccgcct tgcgaacccc aaccagaatc tctccccccct ggccggcgcg cctgccgctg 660
ccaatgcccc tatggcggcc tcttggcccg caccttccaa ttggtcgccc tgcgcaacca 720
gcgagaaaac actggcccgc ccgtctcccc cccgctccgc ctaccccact taatgcgcct 780
ccgtggcatg acgcacgcgt ttggtgtccg ccgccgtctc atgtccgcgc ggtgtggacc 840 ccctttttctc tcgcggcaca tccccccctat tcccttgccc tttggggggc accccctcta 900
gacccgcgct tctcttctcg tccggtgggg gacattggtt tgcctgccgc ggcgggggcg 960
ntaaaaataa aaacagcctg ttagcccggc ccagtacccc cccccggccg gggccgcctt 1020
ncgtttgcat ttatacccca acccataaag ccgcgcccct ttagcnccnt aacttttgtg 1080
gtgtggcctc ccccctttttt cccggggagc agcaacggac atctgtacac taatgctggc 1140
cccgaccttt cccaaaaacc ccccgcccgt gtcccgtata aatttggtgc caancctgac 1200
gngttctccc ccgccctcgc cccgttggcc gcccgtttaa agcccccccg gtggttgcgc 1260
cgcccaacga gtccacctat agttaantcc accaacaccc ccaccttttc ctccccgccg 1320
catcttcccc acgtaccccc ttttgtcgcg agatggccac tccccccccc ctgtttgttt 1380
aaaacaacga gaatggtgct gccaacgctg gtcttttccc cccccggacc gcgaccgcca 1440
gggggaatac gtaccataag cccccgcgcc cnccttttttt ccccccctccc cgccaatcaa 1500 gatccgccgt ccattagacg tattattttt cccgcgatac acgaaaaaac agggccgccc 1560
atttataact aaattcccgt cgccgccgcg cggatatgtt tcccaaaata ccaccccccc 1620
ccccccattt tctttgcccc caactcctgc gcaccggtgt tcaccagcct cgcgccgc 1678

<210> SEQ ID NO 152
<211> LENGTH: 1611
<212> TYPE: DNA
<213> ORGANISM: Homo sapiens

<400> SEQUENCE: 152
ggacgcgtgg gtcgacccac gcgtccggac ccacgcgtcc ggtcgtgttc tccgagttcc 60
tgtctctctg ccaacgccgc ccggatggct tcccaaaacc gcgacccagc cgccactagc 120
gtcgccgccg cccgtaaagg agctgagccg agcgggggcg ccgcccgggg tccggtgggc 180
aaaaggctac agcaggagct gatgaccctc atggtgagtg attaagtgcc cagaacccca 240
gccttccatc caattttcag tagcctcctt ttttccgtca gctttttttgc tagacatagg 300 ggtaatgtaa tttgctccct cctgggaaag aagttcatac accccaccta caccatttct 360
tccagcagtc cctcctccca attccatccc cccacacgaa gttatctcga acacttccct 420
gaagtcatac aagaccctcc ctatccagtg tgtccctact tcctagcccc aaccaagctt 480
tacccacacc caactccccg cccttcttgg tatttctagc ctatgaattt ggttgcttta 540
ttttggatca gagtgatgag attaagggga ggctgggcgc ggtagctcac accttataat 600
cccaaagtgc tgggattaca ggcgtgagcc accgcgcccg gccagcaact aatattctaa 660
ttgaactaaa gcacaggatg ccaatttaca atccttagac caaagagtca ctgatgtctc 720
caccagataa gaggaaagca tcaggctagg catagtggct cacacctgta atctcagcac 780
tttgggaggc tgaggcaggc agatcacatg agcccaggag tttgagactg gcctgggcaa 840
catggtgaaa ccctgtctct aaaataaaaa ctaaactaaa aaaacttttt aaaaaggcag 900
tggggagcat cagaaccagc tcaacagttt gtctactgtc cggtcccaga gaaactcaag 960
attctagcaa gccccttgtg tggggcttgg gttgggacat gaggctgctg ctggagctta 1020
ctctgcaact gtttctccaa atgccaggta tatgaagacc tgaggtataa gctctcgcta 1080
gagttcccca gtggctaccc ttacaatgcg cccacagtga agttcctcac gccctgctat 1140
caccccaacg tggacaccca gggtaacata tgcctggaca tcctgaagga aaagtggtct 1200
gccctgtatg atgtcaggac cattctgctc tccatccaga gccttctagg agaacccaac 1260
attgatagtc ccttgaacac acatgctgcc gagctctgga aaaaccccac agcttttaag 1320

-continued

```
aagtacctgc aagaaaccta ctcaaagcag gtcaccagcc aggagccctg acccaggctg   1380

cccagcctgt ccttgtgtcg tctttttaat ttttccttag atggtctgtc ctttttgtga   1440

tttctgtata ggactcttta tcttgagctg tggtattttt gttttgtttt tgtcttttaa   1500

attaagcctc ggttgagccc ttgtatatta aataaatgca tttttgtcct tttttaaaaa   1560

aaaaataaaa aaaaaaaaaa aaaaaaaaaa aaaaaaaaaa aaaaaaaaaa a            1611
```

METHODS OF TREATING BREAST CANCER WITH TAXANE THERAPY

CROSS-REFERENCE TO RELATED APPLICATIONS

This application claims priority to, and the benefit of, U.S. Ser. No. 61/565,133, filed Nov. 30, 2011, and U.S. Ser. No. 61/635,048, filed Apr. 18, 2012. The contents of each of these applications are herein incorporated by reference in their entirety.

INCORPORATION-BY-REFERENCE OF SEQUENCE LISTING

The contents of the text file named "40448-513001US_ST25.txt", which was created on Sep. 10, 2013 and is 257 KB in size, are hereby incorporated by reference in their entireties.

FIELD OF THE INVENTION

This disclosure relates generally to the field of cancer biology, and specifically, to the fields of detection and identification of specific cancer cell phenotypes and correlation with appropriate therapies.

BACKGROUND OF THE INVENTION

Human breast cancers are classifiable into five molecular distinct intrinsic subtypes, Her2-enriched, Basal-like, Luminal A, Luminal B and normal-like (Perou et al. Nature, 406 (6797):747-52 (2000); Sorlie et al. PNAS, 98(19):10869-74 (2001)). Although differences in prognosis and molecular biology have been established, to date, there exists less evidence demonstrating a variation in chemosensitivity among the intrinsic subtypes.

Taxane therapy has proven to be effective against many types of tumors. However, side effects are associated with taxane therapy, including nausea and vomiting, loss of appetite, change in taste, thinned or brittle hair, pain in the joints of the arms or legs lasting two to three days, changes in the color of the nails, and tingling in the hands or toes. More serious side effects such include bruising or bleeding, pain/redness/swelling at the injection site, change in normal bowel habits for more than two days, fever, chills, cough, sore throat, difficulty swallowing, dizziness, shortness of breath, severe exhaustion, skin rash, facial flushing, female infertility by ovarian damage and chest pain. Based on these side-effects of taxane based therapy, there is a need in the art to determine types of cancer that respond best to taxane based therapy and which types of cancer would be better to treat with non-taxane based therapy.

SUMMARY OF THE INVENTION

The present invention provides methods of treating breast cancer in a subject in need thereof comprising: providing a sample from the subject; determining the expression of at least one gene from Table 1 in the sample; determining a proliferation signature based on the expression of said at least one gene in the sample; and administering a breast cancer treatment to the subject, wherein if the sample is classified as having a low proliferation signature, the subject is administered a breast cancer treatment comprising a taxane or taxane derivative and wherein if the sample is classified as not having a low proliferation signature, the subject is administered a breast cancer treatment not comprising a taxane or taxane derivative, thereby treating breast cancer in the subject.

The present invention also provides methods of screening for the likelihood of the effectiveness of a breast cancer treatment comprising a taxane or a taxane derivative in a subject in need thereof comprising: providing a sample from the subject; determining the expression of at least one gene from Table 1 in the sample; and determining a proliferation signature based on the expression of said at least one gene in the sample; wherein if the sample is classified as having a low proliferation signature, the breast cancer treatment comprising the taxane or taxane derivative is more likely to be effective in the subject.

The present invention also provides methods of treating breast cancer in a subject in need thereof comprising: providing a sample from the subject; determining the expression of at least one gene of Table 1 in said sample; determining the average gene expression of said at least one gene in said sample to obtain a proliferation signature; comparing the proliferation signature of the sample to a reference sample set; and administering a breast cancer treatment to the subject, wherein if the proliferation signature of the sample is within the lowest sub-range of the reference sample set, the proliferation signature of the sample is a low proliferation signature, and wherein if the sample is classified as having a low proliferation signature, the subject is subjected to a breast cancer treatment comprising a taxane or taxane derivative, administered weekly, and wherein if the sample is classified as not having a low proliferation signature, the subject is subjected to a breast cancer treatment not comprising a taxane or taxane derivative, administered weekly, thereby treating breast cancer in the subject.

The present invention also provides methods of screening for the likelihood of the effectiveness of a breast cancer treatment comprising a taxane or a taxane derivative, administered weekly, in a subject in need thereof comprising: providing a sample from the subject; determining the expression of at least one gene of Table 1 in said sample; determining the average gene expression of said at least one gene in said sample to obtain a proliferation signature; and comparing the proliferation signature of the sample to a reference sample set; wherein if the proliferation signature of the sample is within the lowest sub-range of the reference sample set, the proliferation signature of the sample is a low proliferation signature, and wherein if the sample is classified as having a low proliferation signature, the breast cancer treatment comprising the taxane or taxane derivative, administered weekly, is more likely to be effective in the subject.

The methods of the present invention can include determining the expression of at least one of, a combination of, or each of, the genes recited in Table 1. Preferably, the at least one gene is a proliferation gene. More preferably, the at least one gene is at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 genes listed in Table 1.

In some embodiments, the methods of the present invention can include determining the expression of at least one of, a combination of, or each of, the PAM50 intrinsic genes selected from ANLN, BIRC5, CCNB1, CCNE1, CDC20, CDC6, CDCA1, CENPF, CEP55, EXO1, KIF2C, KNTC2, MELK, MKI67, MYBL2, ORC6L, PTTG1, RRM2, TYMS, UBE2C and/or UBE2T. In some embodiments, the methods of the present invention can include determining the expression of at least one of, a combination of, or each of, the PAM50 intrinsic genes selected from ANLN, CCNB1, CCNE1, CDC20, CDC6, CDCA1, CENPF, CEP55, EXO1, KIF2C, KNTC2, MELK, MKI67, ORC6L, PTTG1, RRM2, TYMS, UBE2C and/or UBE2T. In some embodiments, the methods of the present invention can include determining the expression of at least one of, a combination of, or each of, the PAM50 intrinsic genes selected from BIRC5, CCNB1, CDC20, CDCA1/NUF2, CEP55, KNTC2/NDC80, MKI67, PTTG1, RRM2, TYMS and/or UBE2C. In some embodiments, the methods of the present invention can include determining the expression of at least one of, a combination of, or each of, the PAM50 intrinsic genes selected from ANLN, CCNB1, CDC20, CENPF, CEP55, KIF2C, MKI67, MYBL2, RRM2 and/or UBE2C. The expression of the at least one gene from Table 1 can be determined using the nanoreporter code system (nCounter® Analysis system).

The taxane or taxane derivative can be paclitaxel (Taxol®) or docetaxel (Taxotere®). Preferably, the taxane or taxane derivative is paclitaxel. The taxane or taxane derivative can be administered daily (once every 24 hours), weekly (once every 5-7 days), every two weeks (every 10-14 days) or monthly (once every 30 days). Preferably, the taxane or taxane derivative is administered weekly.

The breast cancer treatment comprising a taxane or taxane derivative can further comprises one or more members, or each of the members of the group consisting of anthracycline, cyclophosphamide and 5-fluorouracil. The anthracycline can be doxorubicin or epirubicin. The taxane or taxane derivative can be administered before, after, or simultaneously with, the administration of the anthracycline, cyclophosphamide and/or 5-fluorouracil. Preferably, the taxane or taxane derivative is administered before or after the administration of the anthracycline, cyclophosphamide and/or 5-fluorouracil.

The methods of the present invention can include determining at least one of, a combination of, or each of, the following: tumor size, tumor grade, nodal status, intrinsic subtype, estrogen receptor expression, progesterone receptor expression, HER2/ERBB2 expression and/or ROR score.

The sample can be a sampling of cells or tissues. The tissue can be obtained from a biopsy. The sample can be a sampling of bodily fluids. The bodily fluid can be blood, lymph, urine, saliva or nipple aspirate.

While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the disclosure encompassed by the appended claims.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
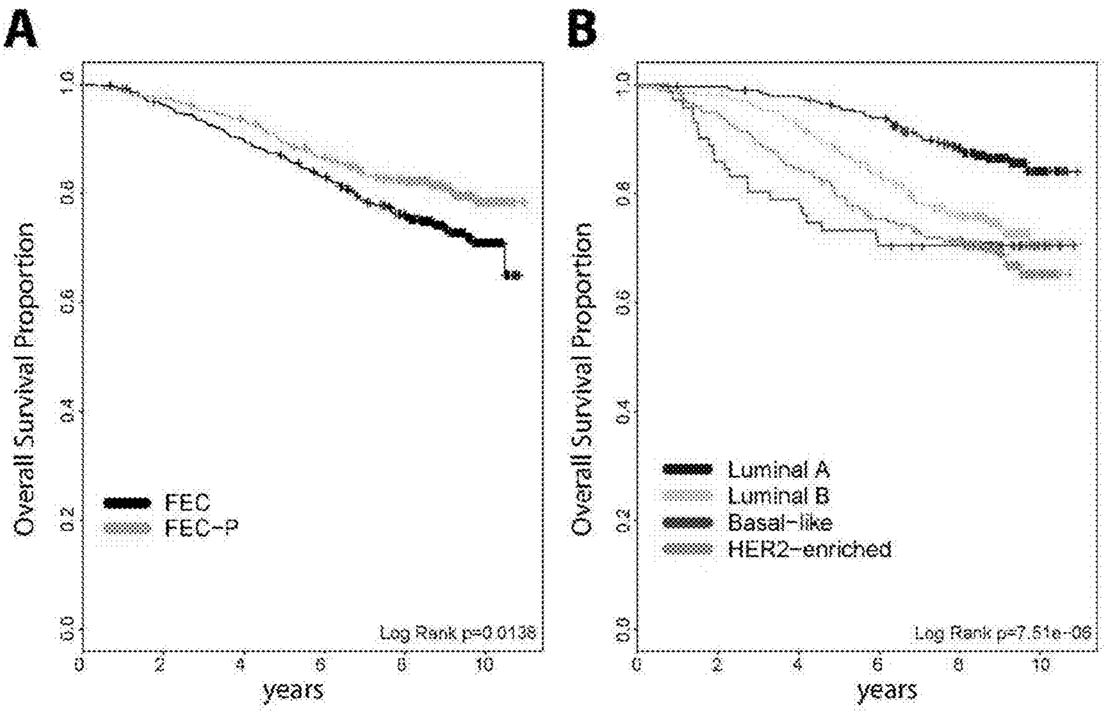
FIG. 1A is a line graph showing overall survival rates in the FEC and FEC-P treatment arms.
FIG. 1B is a line graph showing overall survival rates based on tumor subtypes.

The disclosure presents a method of determining whether a breast cancer treatment comprising a taxane or taxane derivative is optimal for administration to a patient suffering from breast cancer. Determining whether a breast cancer patient should receive a treatment including a taxane or taxane derivative includes determining the proliferation signature of the breast cancer using an intrinsic gene expression set. The disclosure also provides a method of treating breast cancer by determining whether a breast cancer patient should receive a treatment including a taxane or taxane derivative and then administering the optimal breast cancer treatment to the patient based on that determination.

Intrinsic genes, as described in Perou et al. (2000) Nature 406:747-752, are statistically selected to have low variation in expression between biological sample replicates from the same individual and high variation in expression across samples from different individuals. Thus, intrinsic genes are used as classifier genes for breast cancer classification. Although clinical information was not used to derive the breast cancer intrinsic subtypes, this classification has proved to have prognostic significance. Intrinsic gene screening can be used to classify breast cancers into various subtypes. The major intrinsic subtypes of breast cancer are referred to as Luminal A (LumA), Luminal B (LumB), HER2-enriched (Her-2-E), Basal-like, and Normal-like.

The PAM50 gene expression assay (Parker et al. J Clin Oncol., 27(8):1160-7 (2009) and International Publication No. WO 2009/158143, both incorporated herein, by reference, in their entireties) is able to identify intrinsic subtype from standard formalin fixed paraffin embedded tumor tissue. The methods utilize a supervised algorithm to classify subject samples according to breast cancer intrinsic subtype. This algorithm, referred to herein as the PAM50 classification model, is based on the gene expression profile of a defined subset of intrinsic genes that has been identified herein as superior for classifying breast cancer intrinsic subtypes. The subset of genes, along with primers specific for their detection, is provided in Table 1.

TABLE 1

PAM50 Intrinsic Gene List

| GENE | REPRESENTATIVE GENBANK ACCESSION NUMBER | FORWARD PRIMER | SEQ ID NO: | REVERSE PRIMER | SEQ ID NO: |
|---|---|---|---|---|---|
| ACTR3B | NM_020445\| NM_001040135 | AAAGATTCCTGGG ACCTGA | 1 | TGGGGCAGTTCTGTA TTACTTC | 51 |
| ANLN | NM_018685 | ACAGCCACTTTCA GAAGCAAG | 2 | CGATGGTTTTGTACA AGATTTCTC | 52 |
| BAG1 | NM_004323 | CTGGAAGAGTTGA ATAAAGAGC | 3 | GCAAATCCTTGGGCA GA | 53 |
| BCL2 | NM_000633 | TACCTGAACCGGC ACCTG | 4 | GCCGTACAGTTCCAC AAAGG | 54 |
| BIRC5 | NM_001012271 | GCACAAAGCCATT CTAAGTC | 5 | GACGCTTCCTATCAC TCTATTC | 55 |
| BLVRA | BX647539 | GCTGGCTGAGCAG AAAG | 6 | TTCCTCCATCAAGAG TTCAACA | 56 |
| CCNB1 | NM_031966 | CTTTCGCCTGAGCC TATTT | 7 | GGGCACATCCAGAT GTTT | 57 |
| CCNE1 | BC035498 | GGCCAAAATCGAC AGGAC | 8 | GGGTCTGCACAGACT GCAT | 58 |
| CDC20 | BG256659 | CTGTCTGAGTGCC GTGGAT | 9 | TCCTTGTAATGGGGA GACCA | 59 |
| CDC6 | NM_001254 | GTAAATCACCTTCT GAGCCT | 10 | ACTTGGGATATGTGA ATAAGACC | 60 |
| CDCA1 | NM_031423 | GGAGGCGGAAGAA ACCAG | 11 | GGGGAAAGACAAAG TTTCCA | 61 |
| CDH3 | BC041846 | GACAAGGAGAATC AAAAGATCAGC | 12 | ACTGTCTGGGTCCAT GGCTA | 62 |
| CENPF | NM_016343 | GTGGCAGCAGATC ACAA | 13 | GGATTTCGTGGTGGG TTC | 63 |
| CEP55 | AB091343 | CCTCACGAATTGCT GAACTT | 14 | CCACAGTCTGTGATA AACGG | 64 |
| CXXC5 | BC006428 | CATGAAATAGTGC ATAGTTTGCC | 15 | CCATCAACATTCTCT TTATGAACG | 65 |
| EGFR | NM_005228 | ACACAGAATCTAT ACCCACCAGAGT | 16 | ATCAACTCCCAAACG GTCAC | 66 |
| ERBB2 | NM_001005862 | GCTGGCTCTCACA CTGATAG | 17 | GCCCTTACACATCGG AGAAC | 67 |
| ESR1 | NM_001122742 | GCAGGGAGAGGAG TTTGT | 18 | GACTTCAGGGTGCTG GAC | 68 |
| EXO1 | NM_130398 | CCCATCCATGTGA GGAAGTATAA | 19 | TGTGAAGCCAGCAA TATGTATC | 69 |
| FGFR4 | AB209631 | CTTCTTGGACCTTG GCG | 20 | TATTGGGAGGCAGG AGGTTTA | 70 |
| FOXA1 | NM_004496 | GCTACTACGCAGA CACG | 21 | CTGAGTTCATGTTGC TGACC | 71 |
| FOXC1 | NM_001453 | GATGTTCGAGTCA CAGAGG | 22 | GACAGCTACTATTCC CGTT | 72 |
| GPR160 | AJ249248 | TTCGGCTGGAAGG AACC | 23 | TATGTGAGTAAGCTC GGAGAC | 73 |
| GRB7 | NM_005310 | CGTGGCAGATGTG AACGA | 24 | AGTGGGCATCCCGTA GA | 74 |

TABLE 1-continued

PAM50 Intrinsic Gene List

| GENE | REPRESENTATIVE GENBANK ACCESSION NUMBER | FORWARD PRIMER | SEQ ID NO: | REVERSE PRIMER | SEQ ID NO: |
|---|---|---|---|---|---|
| HSPC150 (UBE2T) | NM_014176 | GGAGATCCGTCAA CTCCAAA | 25 | AGTGGACATGCGAG TGGAG | 75 |
| KIF2C | NM_006845 | TGGGTCGTGTCAG GAAAC | 26 | CACCGCTGGAAACT GAAC | 76 |
| KNTC2 | NM_006101 | CGCAGTCATCCAG AGATGTG | 27 | CGTGCACATCCATGA CCTT | 77 |
| KRT14 | BC042437 | ACTCAGTACAAGA AAGAACCG | 28 | GAGGAGATGACCTT GCC | 78 |
| KRT17 | AK095281 | GTTGGACCAGTCA ACATCTCTG | 29 | GCCATAGCCACTGCC ACT | 79 |
| KRT5 | M21389 | TGTGGCTCATTAG GCAAC | 30 | CTTCGACTGGACTCT GT | 80 |
| MAPT | NM_001123066 | GACTCCAAGCGCG AAAAC | 31 | CAGACATGTTGGTAT TGCACATT | 81 |
| MDM2 | M92424 | CCAACAAAATATT CATGGTTCTTG | 32 | AGGCGATCCTGGGA AATTAT | 82 |
| MELK | NM_014791 | CCAGTAGCATTGT CCGAG | 33 | CCCATTTGTCTGTCT TCAC | 83 |
| MIA | BG765502 | GTCTCTGGTAATGC ACACT | 34 | CTGATGGTTGAGGCT GTT | 84 |
| MKI67 | NM_002417 | GTGGAATGCCTGC TGACC | 35 | CGCACTCCAGCACCT AGAC | 85 |
| MLPH | NM_024101 | AGGGGTGCCCTCT GAGAT | 36 | TCACAGGGTCAAACT TCCAGT | 86 |
| MMP11 | NM_005940 | CGAGATCGCCAAG ATGTT | 37 | GATGGTAGAGTTCCA GTGATT | 87 |
| MYBL2 | BX647151 | AGGCGAACACACA ACGTC | 38 | TCTGGTCACGCAGGG CAA | 88 |
| MYC | NM_002467 | AGCCTCGAACAAT TGAAGA | 39 | ACACAGATGATGGA GATGTC | 89 |
| NAT1 | BC013732 | ATCGACTGTGTAA ACAACTAGAGAAGA | 40 | AGTAGCTACATCTCC AGGTTCTCTG | 90 |
| ORC6L | NM_014321 | TTTAAGAGGGCAA TGGAAGG | 41 | CGGATTTTATCAACG ATGCAG | 91 |
| PGR | NM_000926 | TGCCGCAGAACTC ACTTG | 42 | CATTTGCCGTCCTTC ATCG | 92 |
| PHGDH | AK093306 | CCTCAGATGATGC CTATCCA | 43 | GCAGGTCAAAACTCT CAAAG | 93 |
| PTTG1 | BE904476 | CAGCAAGCGATGG CATAGT | 44 | AGCGGGCTTCTGTAA TCTGA | 94 |
| RRM2 | AK123010 | AATGCCACCGAAG CCTC | 45 | GCCTCAGATTTCAAC TCGT | 95 |
| SFRP1 | BC036503 | TCGAACTGAAGGC TATTTACGAG | 46 | CTGCTGAGAATCAA AGTGGGA | 96 |
| SLC39A6 | NM_012319 | GTCGAAGCCGCAA TTAGG | 47 | GGAACAAACTGCTCT GCCA | 97 |
| TMEM45B | AK098106 | CAAACGTGTGTTCT GGAAGG | 48 | ACAGCTCTTTAGCAT TTGTGGA | 98 |

TABLE 1-continued

PAM50 Intrinsic Gene List

| GENE | REPRESENTATIVE GENBANK ACCESSION NUMBER | FORWARD PRIMER | SEQ ID NO: | REVERSE PRIMER | SEQ ID NO: |
|---|---|---|---|---|---|
| TYMS | BQ056428 | TGCCCTGTATGATG TCAGGA | 49 | GGGACTATCAATGTT GGGTTCTC | 99 |
| UBE2C | BC032677 | GTGAGGGGTGTCA GCTCAGT | 50 | CACACAGTTCACTGC TCCACA | 100 |

Table 2 provides select sequences for the genes of Table 1.

TABLE 2

| GENBANK ACCESSION NUMBER | SEQUENCE | SEQ ID NO: |
|---|---|---|
| NM_020445 | CAGCGGCGCTGCGGCGGCTCGCGGGAGACGCTGCGCGCGGGGCTAGCGGGCGGCGGAGCGGACGGCGACG<br>GGGCGCTCTCGGGCTGCCGGCGGGGCCGAGCGCCGCGCGTCCCGAGCATGGCAGGCTCCCTGCCTCCCTG<br>CGTGGTGGACTGTGGCACCGGGTATACCAAGCTTGGCTACGCAGGCAACACTGAGCCCCAGTTCATTATT<br>CCTTCATGTATTGCCATCAGAGAGTCAGCAAAGGTAGTTGACCAAGCTCAAAGGAGAGTGTTGAGGGGAG<br>TTGATGACCTTGACTTTTTCATAGGAGATGAAGCCATCGATAAACCTACATATGCTACAAAGTGGCCGAT<br>ACGACATGGAATCATTGAAGACTGGGATCTTATGGAAAGGTTCATGGAGCAAGTGGTTTTTAAATATCTT<br>CGAGCTGAACCTGAGGACCATTATTTTTTAATGACAGAACCTCCACTCAATACACCAGAAAACAGAGAGT<br>ATCTTGCAGAAATTATGTTTGAATCATTTAACGTACCAGGACTCTACATTGCAGTTCAGGCAGTGCTGGC<br>CTTGGCGGCATCTTGGACATCTCGACAAGTGGGTGAACGTACGTTAACGGGGATAGTCATTGACAGCGGA<br>GATGGAGTCACCCATGTTATCCCAGTGGCAGAAGGTTATGTAATTGGAAGCTGCATCAAACACATCCCGA<br>TTGCAGGTAGAGATATTACGTATTTCATTCAACAGCTGCTAAGGGAGAGGGAGGTGGGAATCCCTCCTGA<br>GCAGTCACTGGAGACCGCAAAAGCCATTAAGGAGAAATACTGTTACATTTGCCCCGATATAGTCAAGGAA<br>TTTGCCAAGTATGATGTGGATCCCCGGAAGTGGATCAAACAGTACACGGGTATCAATGCGATCAACCAGA<br>AGAAGTTTGTTATAGACGTTGGTTACGAAAGATTCCTGGGACCTGAAATATTCTTTCACCCGGAGTTTGC<br>CAACCCAGACTTTATGGAGTCCATCTCAGATGTTGTTGATGAAGTAATACAGAACTGCCCCATCGATGTG<br>CGGCGCCCGCTGTATAAGAATGTCGTACTCTCAGGAGGCTCCACCATGTTCAGGGATTTCGGACGCCGAC<br>TGCAGAGGGATTTGAAGAGAGTGGTGGATGCTAGGCTGAGGCTCAGCGAGGAGCTCAGCGGCGGGAGGAT<br>CAAGCCGAAGCCTGTGGAGGTCCAGGTGGTCACGCATCACATGCAGCGCTACGCCGTGTGGTTCGGAGGC<br>TCCATGCTGGCCTCGACTCCCGAGTTCTTTCAGGTCTGCCACACCAAGAAGGACTATGAAGAGTACGGGC<br>CCAGCATCTGCCGCCACAACCCCGTCTTTGGAGTCATGTCCTAGTGTCTGCCTGAACGCGTCGTTCGATG<br>GTGTCACGTTGGGGAACAAGTGTCCTTCAGAACCCAGAGAAGGCCGCCGTTCTGTAAATAGCGACGTCGG<br>TGTTGCTGCCCAGCAGCGTGCTTGCATTGCCGGTGCATGAGGCGCGGCGCGGGCCCTTCAGTAAAAGCCA<br>TTTATCCGTGTGCCGACCGCTGTCTGCCAGCCTCCTCCTTCTCCCGCCCTCCTCACCCTCGCTCTCCCTC<br>CTCCTCCTCCTCCGAGCTGCTAGCTGACAAATACAATTCTGAAGGAATCCAAATGTGACTTTGAAAATTG<br>TTAGAGAAAACAACATTAGAAAATGGCGCAAAATCGTTAGGTCCCAGGAGAGAATGTGGGGGCGCAAACC<br>CTTTTCCTCCCAGCCTATTTTTGTAAATAAAATGTTTAAACTTGAAATACAAATCGATGTTTATATTTCC<br>TATCATTTTGTATTTTATGGTATTTGGTACAACTGGCTGATACTAAGCACGAATAGATATTGATGTTATG<br>GAGTGCTGTAATCCAAAGTTTTTAATTGTGAGGCATGTTCTGATATGTTTATAGGCAAACAAATAAAACA<br>GCAAACTTTTTTGCCACATGTTTGCTAGAAAATGATTATACTTTATTGGAGTGACATGAAGTTTGAACAC<br>TAAACAGTAATGTATGAGAATTACTACAGATACATGTATCTTTTAGTTTTTTTTGTTTGAACTTTCTGGA<br>GCTGTTTTATAGAAGATGATGGTTTGTTGTCGGTGAGTGTTGGATGAAATACTTCCTTGCACCATTGTAA<br>TAAAAGCTGTTAGAATATTTGTAAATATC | 101 |
| NM_001040135 | CAGCGGCGCTGCGGCGGCTCGCGGGAGACGCTGCGCGCGGGGCTAGCGGGCGGCGGAGCGGACGGCGACG<br>GGGCGCTCTCGGGCTGCCGGCGGGGCCGAGCGCCGCGCGTCCCGAGCATGGCAGGCTCCCTGCCTCCCTG<br>CGTGGTGGACTGTGGCACCGGGTATACCAAGCTTGGCTACGCAGGCAACACTGAGCCCCAGTTCATTATT<br>CCTTCATGTATTGCCATCAGAGAGTCAGCAAAGGTAGTTGACCAAGCTCAAAGGAGAGTGTTGAGGGGAG<br>TTGATGACCTTGACTTTTTCATAGGAGATGAAGCCATCGATAAACCTACATATGCTACAAAGTGGCCGAT<br>ACGACATGGAATCATTGAAGACTGGGATCTTATGGAAAGGTTCATGGAGCAAGTGGTTTTTAAATATCTT<br>CGAGCTGAACCTGAGGACCATTATTTTTTAATGACAGAACCTCCACTCAATACACCAGAAAACAGAGAGT<br>ATCTTGCAGAAATTATGTTTGAATCATTTAACGTACCAGGACTCTACATTGCAGTTCAGGCAGTGCTGGC<br>CTTGGCGGCATCTTGGACATCTCGACAAGTGGGTGAACGTACGTTAACGGGGATAGTCATTGACAGCGGA<br>GATGGAGTCACCCATGTTATCCCAGTGGCAGAAGGTTATGTAATTGGAAGCTGCATCAAACACATCCCGA<br>TTGCAGGTAGAGATATTACGTATTTCATTCAACAGCTGCTAAGGGAGAGGGAGGTGGGAATCCCTCCTGA<br>GCAGTCACTGGAGACCGCAAAAGCCATTAAGGAGAAATACTGTTACATTTGCCCCGATATAGTCAAGGAA<br>TTTGCCAAGTATGATGTGGATCCCCGGAAGTGGATCAAACAGTACACGGGTATCAATGCGATCAACCAGA<br>AGAAGTTTGTTATAGACGTTGGTTACGAAAGATTCCTGGGACCTGAAATATTCTTTCACCCGGAGTTTGC<br>CAACCCAGACTTTATGGAGTCCATCTCAGATGTTGTTGATGAAGTAATACAGAACTGCCCCATCGATGTG<br>CGGCGCCCGCTGTATAAGCCCGAGTTCTTTCAGGTCTGCCACACCAAGAAGGACTATGAAGAGTACGGGC<br>CCAGCATCTGCCGCCACAACCCCGTCTTTGGAGTCATGTCCTAGTGTCTGCCTGAACGCGTCGTTCGATG<br>GTGTCACGTTGGGGAACAAGTGTCCTTCAGAACCCAGAGAAGGCCGCCGTTCTGTAAATAGCGACGTCGG<br>TGTTGCTGCCCAGCAGCGTGCTTGCATTGCCGGTGCATGAGGCGCGGCGCGGGCCCTTCAGTAAAAGCCA<br>TTTATCCGTGTGCCGACCGCTGTCTGCCAGCCTCCTCCTTCTCCCGCCCTCCTCACCCTCGCTCTCCCTC<br>CTCCTCCTCCTCCGAGCTGCTAGCTGACAAATACAATTCTGAAGGAATCCAAATGTGACTTTGAAAATTG<br>TTAGAGAAAACAACATTAGAAAATGGCGCAAAATCGTTAGGTCCCAGGAGAGAATGTGGGGGCGCAAACC<br>CTTTTCCTCCCAGCCTATTTTTGTAAATAAAATGTTTAAACTTGAAATACAAATCGATGTTTATATTTCC<br>TATCATTTTGTATTTTATGGTATTTGGTACAACTGGCTGATACTAAGCACGAATAGATATTGATGTTATG | 102 |

TABLE 2-continued

| GENBANK ACCESSION NUMBER | SEQUENCE | SEQ ID NO: |
|---|---|---|
| | GAGTGCTGTAATCCAAAGTTTTTAATTGTGAGGCATGTTCTGATATGTTTATAGGCAAACAAATAAAACA<br>GCAAACTTTTTTGCCACATGTTTGCTAGAAAATGATTATACTTTATTGGAGTGACATGAAGTTTGAACAC<br>TAAACAGTAATGTATGAGAATTACTACAGATACATGTATCTTTTAGTTTTTTTTGTTTGAACTTTCTGGA<br>GCTGTTTTATAGAAGATGATGGTTTGTTGTCGGTGAGTGTTGGATGAAATACTTCCTTGCACCATTGTAA<br>TAAAAGCTGTTAGAATATTTGTAAATATC | |
| NM_018685 | CTCGGCGCTGAAATTCAAATTTGAACGGCTGCAGAGGCCGAGTCCGTCACTGGAAGCCGAGAGGAGAGGA<br>CAGCTGGTTGTGGGAGAGTTCCCCCGCCTCAGACTCCTGGTTTTTTCCAGGAGACACACTGAGCTGAGAC<br>TCACTTTTCTCTTCCTGAATTTGAACCACCGTTTCCATCGTCTCGTAGTCCGACGCCTGGGGCGATGGAT<br>CCGTTTACGGAGAAACTGCTGGAGCGAACCCGTGCCAGGCGAGAGAATCTTCAGAGAAAAATGGCTGAGA<br>GGCCCACAGCAGCTCCAAGGTCTATGACTCATGCTAAGCGAGCTAGACAGCCACTTTCAGAAGCAAGTAA<br>CCAGCAGCCCCTCTCTGGTGGTGAAGAGAAATCTTGTACAAAACCATCGCCATCAAAAAAACGCTGTTCT<br>GACAACACTGAAGTAGAAGTTTCTAACTTGGAAAATAAACAACCAGTTGAGTCGACATCTGCAAAATCTT<br>GTTCTCCAAGTCCTGTGTCTCCTCAGGTGCAGCCACAAGCAGCAGATACCATCAGTGATTCTGTTGCTGT<br>CCCGGCATCACTGCTGGGCATGAGGAGAGGGCTGAACTCAAGATTGGAAGCAACTGCAGCCTCCTCAGTT<br>AAAACACGTATGCAAAAACTTGCAGAGCAACGGCGCCGTTGGGATAATGATGATATGACAGATGACATTC<br>CTGAAAGCTCACTCTTCTCACCAATGCCATCAGAGGAAAAGGCTGCTTCCCCTCCCAGACCTCTGCTTTC<br>AAATGCCTCGGCAACTCCAGTTGGCAGAAGGGGCCGTCTGGCCAATCTTGCTGCAACTATTTGCTCCTGG<br>GAAGATGATGTAAATCACTCATTTGCAAAACAAAACAGTGTACAAGAACAGCCTGGTACCGCTTGTTTAT<br>CCAAATTTTCCTCTGCAAGTGGAGCATCTGCTAGGATCAATAGCAGCAGTGTTAAGCAGGAAGCTACATT<br>CTGTTCCCAAAGGGATGGCGATGCCTCTTTGAATAAAGCCCTATCCTCAAGTGCTGATGATGCGTCTTTG<br>GTTAATGCCTCAATTTCCAGCTCTGTGAAAGCTACTTCTCCAGTGAAATCTACTACATCTATCACTGATG<br>CTAAAAGTTGTGAGGGACAAAATCCTGAGCTACTTCCAAAAACTCCTATTAGTCCTCTGAAAACGGGGGT<br>ATCGAAACCAATTGTGAAGTCAACTTTATCCCAGACAGTTCCATCCAAGGGAGAATTAAGTAGAGAAATT<br>TGTCTGCAATCTCAATCTAAAGACAAATCTACGACACCAGGAGGAACAGGAATTAAGCCTTTCCTGGAAC<br>GCTTTGGAGAGCGTTGTCAAGAACATAGCAAAGAAAGTCCAGCTCGTAGCACACCCCACAGAACCCCCAT<br>TATTACTCCAAATACAAAGGCCATCCAAGAAAGATTATTCAAGCAAGACACATCTTCATCTACTACCCAT<br>TTAGCACAACAGCTCAAGCAGGAACGTCAAAAAGAACTAGCATGTCTTCGTGGCCGATTTGACAAGGGCA<br>ATATATGGAGTGCAGAAAAAGGCGGAAACTCAAAAAGCAAACAACTAGAAACCAAACAGGAAACTCACTG<br>TCAGAGCACTCCCCTCAAAAAACACCAAGGTGTTTCAAAAACTCAGTCACTTCCAGTAACAGAAAAGGTG<br>ACCGAAAACCAGATACCAGCCAAAAATTCTAGTACAGAACCTAAAGGTTTCACTGAATGCGAAATGACGA<br>AATCTAGCCCTTTGAAAATAACATTGTTTTTAGAAGAGGACAAATCCTTAAAAGTAACATCAGACCCAAA<br>GGTTGAGCAGAAAATTGAAGTGATACGTGAAATTGAGATGAGTGTGGATGATGATGATATCAATAGTTCG<br>AAAGTAATTAATGACCTCTTCAGTGATGTCCTAGAGGAAGGTGAACTAGATATGGAGAAGAGCCAAGAGG<br>AGATGGATCAAGCATTAGCAGAAAGCAGCGAAGAACAGGAAGATGCACTGAATATCTCCTCAATGTCTTT<br>ACTTGCACCATTGGCACAAACAGTTGGTGTGGTAAGTCCAGAGAGTTTAGTGTCCACACCTAGACTGGAA<br>TTGAAAGACACCAGCAGAAGTGATGAAAGTCCAAAACCAGGAAAATTCCAAAGAACTCGTGTCCCTCGAG<br>CTGAATCTGGTGATAGCCTTGGTTCTGAAGATCGTGATCTTCTTTACAGCATTGATGCATATAGATCTCA<br>AAGATTCAAAGAAACAGAACGTCCATCAATAAAGCAGGTGATTGTTCGGAAGGAAGATGTTACTTCAAAA<br>CTGGATGAAAAAAATAATGCCTTTCCTTGTCAAGTTAATATCAAACAGAAAATGCAGGAACTCAATAACG<br>AAATAAATATGCAACAGACAGTGATCTATCAAGCTAGCCAGGCTCTTAACTGCTGTGTTGATGAAGAACA<br>TGGAAAAGGGTCCCTAGAAGAAGCTGAAGCAGAAAGACTTCTTCTAATTGCAACTGGGAAGAGAACACTT<br>TTGATTGATGAATTGAATAAATTGAAGAACGAAGGACCTCAGAGGAAGAATAAGGCTAGTCCCCAAAGTG<br>AATTTATGCCATCCAAAGGATCAGTTACTTTGTCAGAAATCCGCTTGCCTCTAAAAGCAGATTTTGTCTG<br>CAGTACGGTTCAGAAACCAGATGCAGCAAATTACTATTACTTAATTATACTAAAAGCAGGAGCTGAAAAT<br>ATGGTAGCCACACCATTAGCAAGTACTTCAAACTCTCTTAACGGTGATGCTCTGACATTCACTACTACAT<br>TTACTCTGCAAGATGTATCCAATGACTTTGAAATAAATATTGAAGTTTACAGCTTGGTGCAAAAGAAAGA<br>TCCCTCAGGCCTTGATAAGAAGAAAAAAACATCCAAGTCCAAGGCTATTACTCCAAAGCGACTCCTCACA<br>TCTATAACCACAAAAAGCAACATTCATTCTTCAGTCATGGCCAGTCCAGGAGGTCTTAGTGCTGTGCGAA<br>CCAGCAACTTCGCCCTTGTTGGATCTTACACATTATCATTGTCTTCAGTAGGAAATACTAAGTTTGTTCT<br>GGACAAGGTCCCCTTTTTATCTTCTTTGGAAGGTCATATTTATTTAAAAATAAAATGTCAAGTGAATTCC<br>AGTGTTGAAGAAAGAGGTTTTCTAACCATATTTGAAGATGTTAGTGGTTTTGGTGCCTGGCATCGAAGAT<br>GGTGTGTTCTTTCTGGAAACTGTATATCTTATTGGACTTATCCAGATGATGAGAAACGCAAGAATCCCAT<br>AGGAAGGATAAATCTGGCTAATTGTACCAGTCGTCAGATAGAACCAGCCAACAGAGAATTTTGTGCAAGA<br>CGCAACACTTTTGAATTAATTACTGTCCGACCACAAAGAGAAGATGACCGAGAGACTCTTGTCAGCCAAT<br>GCAGGGACACACTCTGTGTTACCAAGAACTGGCTGTCTGCAGATACTAAAGAAGAGCGGGATCTCTGGAT<br>GCAAAAACTCAATCAAGTTCTTGTTGATATTCGCCTCTGGCAACCTGATGCTTGCTACAAACCTATTGGA<br>AAGCCTTAAACCGGGAAATTTCCATGCTATCTAGAGGTTTTTGATGTCATCTTAAGAAACACACTTAAGA<br>GCATCAGATTTACTGATTGCATTTTATGCTTTAAGTACGAAAGGGTTTGTGCCAATATTCACTACGTATT<br>ATGCAGTATTTATATCTTTTGTATGTAAAACTTTAACTGATTTCTGTCATTCATCAATGAGTAGAAGTAA<br>ATACATTATAGTTGATTTTGCTAAATCTTAATTTAAAAGCCTCATTTTCCTAGAAATCTAATTATTCAGT<br>TATTCATGACAATATTTTTTTAAAAGTAAGAAATTCTGAGTTGTCTTCTTGGAGCTGTAGGTCTTGAAGC<br>AGCAACGTCTTTCAGGGGTTGGAGACAGAAACCCATTCTCCAATCTCAGTAGTTTTTTCGAAAGGCTGTG<br>ATCATTTATTGATCGTGATATGACTTGTTACTAGGGTACTGAAAAAAATGTCTAAGGCCTTTACAGAAAC<br>ATTTTTAGTAATGAGGATGAGAACTTTTTCAAATAGCAAATATATATTGGCTTAAAGCATGAGGCTGTCT<br>TCAGAAAAGTGATGTGGACATAGGAGGCAATGTGTGAGACTTGGGGGTTCAATATTTTATATAGAAGAGT<br>TAATAAGCACATGGTTTACATTTACTCAGCTACTATATATGCAGTGTGGTGCACATTTTCACAGAATTCT<br>GGCTTCATTAAGATCATTATTTTTGCTGCGTAGCTTACAGACTTAGCATATTAGTTTTTTCTACTCCTAC<br>AAGTGTAAATTGAAAAATCTTTATATTAAAAAAGTAAACTGTTATGAAGCTGCTATGTACTAATAATACT<br>TTGCTTGCCAAAGTGTTTGGGTTTTGTTGTTGTTTGTTTGTTTGTTTGTTTTTGGTTCATGAACAACAGT<br>GTCTAGAAACCCATTTTGAAAGTGGAAAATTATTAAGTCACCTATCACCTTTAAACGCCTTTTTTTAAAA<br>TTATAAAATATTGTAAAGCAGGGTCTCAACTTTTAAATACACTTTGAACTTCTTCTCTGAATTATTAAAG<br>TTCTTTATGACCTCATTTATAAACACTAAATTCTGTCACCTCCTGTCATTTTATTTTTTATTCATTCAAA<br>TGTATTTTTTCTTGTGCATATTATAAAAATATATTTTATGAGCTCTTACTCAAATAAATACCTGTAAATG<br>TCTAAAGGAAAAAAAAAAAAAAAAAAA | 103 |

TABLE 2-continued

| GENBANK ACCESSION NUMBER | SEQUENCE | SEQ ID NO: |
|---|---|---|
| NM_004323 | AGGCCGGGGCGGGGCTGGGAAGTAGTCGGGCGGGGTTGTGAGACGCCGCGCTCAGCTTCCATCGCTGGGC<br>GGTCAACAAGTGCGGGCCTGGCTCAGCGCGGGGGGCGCGGAGACCGCGAGGCGACCGGGAGCGGCTGGG<br>TTCCCGGCTGCGCGCCCTTCGGCCAGGCCGGGAGCCGCGCCAGTCGGAGCCCCCGGCCCAGCGTGGTCCG<br>CCTCCCTCTCGGCGTCCACCTGCCCGGAGTACTGCCAGCGGGCATGACCGACCCACCAGGGGCGCCGCCG<br>CCGGCGCTCGCAGGCCGCGGATGAAGAAGAAAACCCGGCGCCGCTCGACCCGGAGCGAGGAGTTGACCCG<br>GAGCGAGGAGTTGACCCTGAGTGAGGAAGCGACCTGGAGTGAAGAGGCGACCCAGAGTGAGGAGGCGACC<br>CAGGGCGAAGAGATGAATCGGAGCCAGGAGGTGACCCGGGACGAGGAGTCGACCCGGAGCGAGGAGGTGA<br>CCAGGGAGGAAATGGCGGCAGCTGGGCTCACCGTGACTGTCACCCACAGCAATGAGAAGCACGACCTTCA<br>TGTTACCTCCCAGCAGGGCAGCAGTGAACCAGTTGTCCAAGACCTGGCCCAGGTTGTTGAAGAGGTCATA<br>GGGGTTCCACAGTCTTTTCAGAAACTCATATTTAAGGGAAAATCTCTGAAGGAAATGGAAACACCGTTGT<br>CAGCACTTGGAATACAAGATGGTTGCCGGGTCATGTTAATTGGGAAAAAGAACAGTCCACAGGAAGAGGT<br>TGAACTAAAGAAGTTGAAACATTTGGAGAAGTCTGTGGAGAAGATAGCTGACCAGCTGGAAGAGTTGAAT<br>AAAGAGCTTACTGGAATCCAGCAGGGTTTTCTGCCCAAGGATTTGCAAGCTGAAGCTCTCTGCAAACTTG<br>ATAGGAGAGTAAAAGCCACAATAGAGCAGTTTATGAAGATCTTGGAGGAGATTGACACACTGATCCTGCC<br>AGAAAATTTCAAAGACAGTAGATTGAAAAGGAAAGGCTTGGTAAAAAAGGTTCAGGCATTCCTAGCCGAG<br>TGTGACACAGTGGAGCAGAACATCTGCCAGGAGACTGAGCGGCTGCAGTCTACAAACTTTGCCCTGGCCG<br>AGTGAGGTGTAGCAGAAAAAGGCTGTGCTGCCCTGAAGAATGGCGCCACCAGCTCTGCCGTCTCTGGAGC<br>GGAATTTACCTGATTTCTTCAGGGCTGCTGGGGGCAACTGGCCATTTGCCAATTTTCCTACTCTCACACT<br>GGTTCTCAATGAAAAATAGTGTCTTTGTGATTTTGAGTAAAGCTCCTATCTGTTTTCTCCTTCTGTCTCT<br>GTGGTTGTACTGTCCAGCAATCCACCTTTTCTGGAGAGGGCCACCTCTGCCCAAATTTTCCCAGCTGTTT<br>GGACCTCTGGGTGCTTTCTTTGGGCTGGTGAGAGCTCTAATTTGCCTTGGGCCAGTTTCAGGTTTATAGG<br>CCCCCTCAGTCTTCAGATACATGAGGGCTTCTTTGCTCTTGTGATCGTGTAGTCCCATAGCTGTAAAACC<br>AGAATCACCAGGAGGTTGCACCTAGTCAGGAATATTGGGAATGGCCTAGAACAAGGTGTTTGGCACATAA<br>GTAGACCACTTATCCCTCATTGTGACCTAATTCCAGAGCATCTGGCTGGGTTGTTGGGTTCTAGACTTTG<br>TCCTCACCTCCCAGTGACCCTGACTAGCCACAGGCCATGAGATACCAGGGGGCCGTTCCTTGGATGGAGC<br>CTGTGGTTGATGCAAGGCTTCCTTGTCCCCAAGCAAGTCTTCAGAAGGTTAGAACCCAGTGTTGACTGAG<br>TCTGTGCTTGAAACCAGGCCAGAGCCATGGATTAGGAAGGGCAAAGAGAAGGCACCAGAATGAGTAAAGC<br>AGGCAGGTGGTGAAGCCAACCATAAACTTCTCAGGAGTGACATGTGCTTCCTTCAAAGGCATTTTTGTTA<br>ACCATATCCTTCTGAGTTCTATGTTTCCTTCACAGCTGTTCTATCCATTTTGTGGACTGTCCCCCACCCC<br>CACCCCATCATTGTTTTTAAAAAATTAAGGCCTGGCGCAGCAGCTCATGCCTATAATCCCAGCACTTTGG<br>GAGGCTGAGGCGGGCGGATCACTTGAGGCCAGGAGTTTGAGACCAGCCCAGGCAACATAGCAAAACCCCA<br>TTCTGCTTTAAAAAAAAAAAAAAAAAAAAATTAGCTTGGCGTAGTGGCATGTGCCTATAATCCCAGCTACT<br>GGGGAGGCTGAGGCACAAGAATCATTTGAACCTGGGAGGTAGAGGTTGCTGTGAGCCGAGATTACGCCCC<br>TGCACTCCAGCCTGGGTCACAGAGTGAGACTCCATCTCAGAAAAAAAAAAAAATTGAGTCAGGTGCAGTAG<br>CTCCTTCCTGTAGTCCCAGCTACTTGGGAGGCTGAGGCTAGAGGATCACTTGAGCCCAGGAGTTTGAGTC<br>TAGTCTGGGCAACATAGCAAGACCCCATCTCTAAAATTTAAGTAAGTAAAAGTAGATAAATAAAAAGAAA<br>AAAAAACTGTTTATGTGCTCATCATAAAGTAGAAGAGTGGTTTGCTTTTTTTTTTTTTTTTGGATTAATG<br>AGGAAATCATTCTGTGGCTCTAGTCATAATTTATGCTTAATAACATTGATAGTAGCCCTTTGCGCTATAA<br>CTCTACCTAAAGACTCACATCATTTGGCAGAGAGAGAGTCGTTGAAGTCCCAGGAATTCAGGACTGGGCA<br>GGTTAAGACCTCAGACAAGGTAGTAGAGGTAGACTTGTGGACAAGGCTCGGGTCCCAGCCCACCGCACCC<br>CAACTTTAATCAGAGTGGTTCACTATTGATCTATTTTTGTGTGATAGCTGTGTGGCGTGGGCCACAACAT<br>TTAATGAGAAGTTACTGTGCACCAAACTGCCGAACACCATTCTAAACTATTCATATATATTAGTCATTTA<br>ATTCTTACATAACTTGAGAGGTAGACAGATATCCTTATTTTAGAGATGAGGAAACCAAGAGAACTTAGGT<br>CATTAGCGCAAGGTTGTAGAGTAAGCGGCAAAGCCAAGACACAAAGCTGGGTGGTTTGGTTTCAGAGCCA<br>GTGCTTTTCCCCTCTACTGTACTGCCTCTCAACCAACACAGGGTTGCACAGGCCCATTCTCTGATTTTTT<br>TCCTCTTGTCCTCTGCCTCTCCCTCTAGCTCCCACTTCCTCTCTGCTCTAGTTCATTTTCTTTAGAGCAG<br>CCCGAGTGATCATGAAGTGCAAATCTTGCCATGTCAGTCCCCTGCTTAGAACCCTCCAATGGCTCACTTT<br>CTCTTTAGGCAAAAGTCTTTACCCCATGCCTTCTCCCATCTCATCTCAACCCCCTCATTTGTTGGCTGTC<br>TGCTGTCAGCCACTCTTCTTTCAGGTCCTCAGATGCACTGCACCCTCTCCTGCCTGGGGGTCTTTGCTCC<br>TGCTACTACCTCTGCTTGAACAGCTCCTCACCTTCCTTCCTCCAACCCTACCCTTGTATAGGTGACTTTT<br>GTTCATCCTTCAGAATTCAACTCACATGTCTCTTGCATGGAGAACCCTCACCTACTGTGTTGAGACCCTG<br>TCCAGCCCCCAGGTGGGATCCTCTCTCGACTTCCCATACATTTCTTTCACAGCATTTACATAGTCCATGA<br>TAGTTTACTTGTGGGATTATTTGGTTAATCTTTGCCTTTAACACCAGGGTTCCTTGGGTGAAGGAGCTTC<br>TTTATCTTGGTAACAGCATTATTTCAAGCATAACTTGTAATATAGTTATATTACATATATAACATATATA<br>TATATAACATAACATATATAACATATATAACAAGCATAACTTGTTATATAGTCTTGTATATAGTAAGACC<br>TCAATAAATATTTGGAGAACAAAAAAAAAAAAAAA | 104 |
| NM_000633 | TTTCTGTGAAGCAGAAGTCTGGGAATCGATCTGGAAATCCTCCTAATTTTTACTCCCTCTCCCCGCGACT<br>CCTGATTCATTGGGAAGTTTCAAATCAGCTATAACTGGAGAGTGCTGAAGATTGATGGGATCGTTGCCTT<br>ATGCATTTGTTTTGGTTTTACAAAAAGGAAACTTGACAGAGGATCATGCTGTACTTAAAAAATACAACAT<br>CACAGAGGAAGTAGACTGATATTAACAATACTTACTAATAATAACGTGCCTCATGAAATAAAGATCCGAA<br>AGGAATTGGAATAAAAATTTCCTGCATCTCATGCCAAGGGGGAAACACCAGAATCAAGTGTTCCGCGTGA<br>TTGAAGACACCCCCTCGTCCAAGAATGCAAAGCACATCCAATAAAATAGCTGGATTATAACTCCTCTTCT<br>TTCTCTGGGGGCCGTGGGGTGGGAGCTGGGGCGAGAGGTGCCGTTGGCCCCCGTTGCTTTTCCTCTGGGA<br>AGGATGGCGCACGCTGGGAGAACAGGGTACGATAACCGGGAGATAGTGATGAAGTACATCCATTATAAGC<br>TGTCGCAGAGGGGCTACGAGTGGGATGCGGGAGATGTGGGCGCCGCGCCCCCGGGGGCCGCCCCCGCACC<br>GGGCATCTTCTCCTCCCAGCCCGGGCACACGCCCCATCCAGCCGCATCCCGGGACCCGGTCGCCAGGACC<br>TCGCCGCTGCAGACCCCGGCTGCCCCCGGCGCCGCCGCGGGGCCTGCGCTCAGCCCGGTGCCACCTGTGG<br>TCCACCTGACCCTCCGCCAGGCCGGCGACGACTTCTCCCGCCGCTACCGCCGCGACTTCGCCGAGATGTC<br>CAGCCAGCTGCACCTGACGCCCTTCACCGCGCGGGGACGCTTTGCCACGGTGGTGGAGGAGCTCTTCAGG<br>GACGGGGTGAACTGGGGGAGGATTGTGGCCTTCTTTGAGTTCGGTGGGGTCATGTGTGTGGAGAGCGTCA<br>ACCGGGAGATGTCGCCCCTGGTGGACAACATCGCCCTGTGGATGACTGAGTACCTGAACCGGCACCTGCA<br>CACCTGGATCCAGGATAACGGAGGCTGGGATGCCTTTGTGGAACTGTACGGCCCCAGCATGCGGCCTCTG<br>TTTGATTTCTCCTGGCTGTCTCTGAAGACTCTGCTCAGTTTGGCCCTGGTGGGAGCTTGCATCACCCTGG<br>GTGCCTATCTGGGCCACAAGTGAAGTCAACATGCCTGCCCCAAACAAATATGCAAAAGGTTCACTAAAGC<br>AGTAGAAATAATATGCATTGTCAGTGATGTACCATGAAACAAAGCTGCAGGCTGTTTAAGAAAAAATAAC | 105 |

TABLE 2-continued

| GENBANK ACCESSION NUMBER | SEQUENCE | SEQ ID NO: |
|---|---|---|
| | ACACATATAAACATCACACACACAGACAGACACACACACACACAACAATTAACAGTCTTCAGGCAAAACG | |
| | TCGAATCAGCTATTTACTGCCAAAGGGAAATATCATTTATTTTTTACATTATTAAGAAAAAAAGATTTAT | |
| | TTATTTAAGACAGTCCCATCAAAACTCCTGTCTTTGGAAATCCGACCACTAATTGCCAAGCACCGCTTCG | |
| | TGTGGCTCCACCTGGATGTTCTGTGCCTGTAAACATAGATTCGCTTTCCATGTTGTTGGCCGGATCACCA | |
| | TCTGAAGAGCAGACGGATGGAAAAAGGACCTGATCATTGGGGAAGCTGGCTTTCTGGCTGCTGGAGGCTG | |
| | GGGAGAAGGTGTTCATTCACTTGCATTTCTTTGCCCTGGGGGCTGTGATATTAACAGAGGGAGGGTTCCT | |
| | GTGGGGGGAAGTCCATGCCTCCCTGGCCTGAAGAAGAGACTCTTTGCATATGACTCACATGATGCATACC | |
| | TGGTGGGAGGAAAAGAGTTGGGAACTTCAGATGGACCTAGTACCCACTGAGATTTCCACGCCGAAGGACA | |
| | GCGATGGGAAAAATGCCCTTAAATCATAGGAAAGTATTTTTTTAAGCTACCAATTGTGCCGAGAAAAGCA | |
| | TTTTAGCAATTTATACAATATCATCCAGTACCTTAAGCCCTGATTGTGTATATTCATATATTTTGGATAC | |
| | GCACCCCCCAACTCCCAATACTGGCTCTGTCTGAGTAAGAAACAGAATCCTCTGGAACTTGAGGAAGTGA | |
| | ACATTTCGGTGACTTCCGCATCAGGAAGGCTAGAGTTACCCAGAGCATCAGGCCGCCACAAGTGCCTGCT | |
| | TTTAGGAGACCGAAGTCCGCAGAACCTGCCTGTGTCCCAGCTTGGAGGCCTGGTCCTGGAACTGAGCCGG | |
| | GGCCCTCACTGGCCTCCTCCAGGGATGATCAACAGGGCAGTGTGGTCTCCGAATGTCTGGAAGCTGATGG | |
| | AGCTCAGAATTCCACTGTCAAGAAAGAGCAGTAGAGGGGTGTGGCTGGGCCTGTCACCCTGGGGCCCTCC | |
| | AGGTAGGCCCGTTTTCACGTGGAGCATGGGAGCCACGACCCTTCTTAAGACATGTATCACTGTAGAGGGA | |
| | AGGAACAGAGGCCCTGGGCCCTTCCTATCAGAAGGACATGGTGAAGGCTGGGAACGTGAGGAGAGGCAAT | |
| | GGCCACGGCCCATTTTGGCTGTAGCACATGGCACGTTGGCTGTGTGGCCTTGGCCCACCTGTGAGTTTAA | |
| | AGCAAGGCTTTAAATGACTTTGGAGAGGGTCACAAATCCTAAAAGAAGCATTGAAGTGAGGTGTCATGGA | |
| | TTAATTGACCCCTGTCTATGGAATTACATGTAAAACATTATCTTGTCACTGTAGTTTGGTTTTATTTGAA | |
| | AACCTGACAAAAAAAAAGTTCCAGGTGTGGAATATGGGGGTTATCTGTACATCCTGGGGCATTAAAAAAA | |
| | AAATCAATGGTGGGGAACTATAAAGAAGTAACAAAAGAAGTGACATCTTCAGCAAATAAACTAGGAAATT | |
| | TTTTTTTCTTCCAGTTTAGAATCAGCCTTGAAACATTGATGGAATAACTCTGTGGCATTATTGCATTATA | |
| | TACCATTTATCTGTATTAACTTTGGAATGTACTCTGTTCAATGTTTAATGCTGTGGTTGATATTTCGAAA | |
| | GCTGCTTTAAAAAAATACATGCATCTCAGCGTTTTTTTGTTTTTAATTGTATTTAGTTATGGCCTATACA | |
| | CTATTTGTGAGCAAAGGTGATCGTTTTCTGTTTGAGATTTTTATCTCTTGATTCTTCAAAAGCATTCTGA | |
| | GAAGGTGAGATAAGCCCTGAGTCTCAGCTACCTAAGAAAAACCTGGATGTCACTGGCCACTGAGGAGCTT | |
| | TGTTTCAACCAAGTCATGTGCATTTCCACGTCAACAGAATTGTTTATTGTGACAGTTATATCTGTTGTCC | |
| | CTTTGACCTTGTTTCTTGAAGGTTTCCTCGTCCCTGGGCAATTCCGCATTTAATTCATGGTATTCAGGAT | |
| | TACATGCATGTTTGGTTAAACCCATGAGATTCATTCAGTTAAAAATCCAGATGGCAAATGACCAGCAGAT | |
| | TCAAATCTATGGTGGTTTGACCTTTAGAGAGTTGCTTTACGTGGCCTGTTTCAACACAGACCCACCCAGA | |
| | GCCCTCCTGCCCTCCTTCCGCGGGGGCTTTCTCATGGCTGTCCTTCAGGGTCTTCCTGAAATGCAGTGGT | |
| | GCTTACGCTCCACCAAGAAAGCAGGAAACCTGTGGTATGAAGCCAGACCTCCCCGGCGGGCCTCAGGGAA | |
| | CAGAATGATCAGACCTTTGAATGATTCTAATTTTTAAGCAAAATATTATTTTATGAAAGGTTTACATTGT | |
| | CAAAGTGATGAATATGGAATATCCAATCCTGTGCTGCTATCCTGCCAAAATCATTTTAATGGAGTCAGTT | |
| | TGCAGTATGCTCCACGTGGTAAGATCCTCCAAGCTGCTTTAGAAGTAACAATGAAGAACGTGGACGTTTT | |
| | TAATATAAAGCCTGTTTTGTCTTTTGTTGTTGTTCAAACGGGATTCACAGAGTATTTGAAAAATGTATAT | |
| | ATATTAAGAGGTCACGGGGGCTAATTGCTGGCTGGCTGCCTTTTGCTGTGGGGTTTTGTTACCTGGTTTT | |
| | AATAACAGTAAATGTGCCCAGCCTCTTGGCCCCAGAACTGTACAGTATTGTGGCTGCACTTGCTCTAAGA | |
| | GTAGTTGATGTTGCATTTTCCTTATTGTTAAAAACATGTTAGAAGCAATGAATGTATATAAAAGCCTCAA | |
| | CTAGTCATTTTTTTCTCCTCTTCTTTTTTTTCATTATATCTAATTATTTTGCAGTTGGGCAACAGAGAAC | |
| | CATCCCTATTTTGTATTGAAGAGGGATTCACATCTGCATCTTAACTGCTCTTTATGAATGAAAAAACAGT | |
| | CCTCTGTATGTACTCCTCTTTACACTGGCCAGGGTCAGAGTTAAATAGAGTATATGCACTTTCCAAATTG | |
| | GGGACAAGGGCTCTAAAAAAAGCCCCAAAAGGAGAAGAACATCTGAGAACCTCCTCGGCCCTCCCAGTCC | |
| | CTCGCTGCACAAATACTCCGCAAGAGAGGCCAGAATGACAGCTGACAGGGTCTATGGCCATCGGGTCGTC | |
| | TCCGAAGATTTGGCAGGGGCAGAAAACTCTGGCAGGCTTAAGATTTGGAATAAAGTCACAGAATTAAGGA | |
| | AGCACCTCAATTTAGTTCAAACAAGACGCCAACATTCTCTCCACAGCTCACTTACCTCTCTGTGTTCAGA | |
| | TGTGGCCTTCCATTTATATGTGATCTTTGTTTTATTAGTAAATGCTTATCATCTAAAGATGTAGCTCTGG | |
| | CCCAGTGGGAAAAATTAGGAAGTGATTATAAATCGAGAGGAGTTATAATAATCAAGATTAAATGTAAATA | |
| | ATCAGGGCAATCCCAACACATGTCTAGCTTTCACCTCCAGGATCTATTGAGTGAACAGAATTGCAAATAG | |
| | TCTCTATTTGTAATTGAACTTATCCTAAAACAAATAGTTTATAAATGTGAACTTAAACTCTAATTAATTC | |
| | CAACTGTACTTTTAAGGCAGTGGCTGTTTTTAGACTTTCTTATCACTTATAGTTAGTAATGTACACCTAC | |
| | TCTATCAGAGAAAAACAGGAAAGGCTCGAAATACAAGCCATTCTAAGGAAATTAGGGAGTCAGTTGAAAT | |
| | TCTATTCTGATCTTATTCTGTGGTGTCTTTTGCAGCCCAGACAAATGTGGTTACACACTTTTTAAGAAAT | |
| | ACAATTCTACATTGTCAAGCTTATGAAGGTTCCAATCAGATCTTTATTGTTATTCAATTTGGATCTTTCA | |
| | GGGATTTTTTTTTAAATTATTATGGGACAAAGGACATTTGTTGGAGGGGTGGGAGGGAGGAAGAATTTT | |
| | TAAATGTAAAACATTCCCAAGTTTGGATCAGGGAGTTGGAAGTTTTCAGAATAACCAGAACTAAGGGTAT | |
| | GAAGGACCTGTATTGGGGTCGATGTGATGCCTCTGCGAAGAACCTTGTGTGACAAATGAGAAACATTTTG | |
| | AAGTTTGTGGTACGACCTTTAGATTCCAGAGACATCAGCATGGCTCAAAGTGCAGCTCCGTTTGGCAGTG | |
| | CAATGGTATAAATTTCAAGCTGGATATGTCTAATGGGTATTTAAACAATAAATGTGCAGTTTTAACTAAC | |
| | AGGATATTTAATGACAACCTTCTGGTTGGTAGGGACATCTGTTTCTAAATGTTTATTATGTACAATACAG | |
| | AAAAAAATTTTATAAAATTAAGCAATGTGAAACTGAATTGGAGAGTGATAATACAAGTCCTTTAGTCTTA | |
| | CCCAGTGAATCATTCTGTTCCATGTCTTTGGACAACCATGACCTTGGACAATCATGAAATATGCATCTCA | |
| | CTGGATGCAAAGAAAATCAGATGGAGCATGAATGGTACTGTACCGGTTCATCTGGACTGCCCCAGAAAAA | |
| | TAACTTCAAGCAAACATCCTATCAACAACAAGGTTGTTCTGCATACCAAGCTGAGCACAGAAGATGGGAA | |
| | CACTGGTGGAGGATGGAAAGGCTCGCTCAATCAAGAAAATTCTGAGACTATTAATAAATAAGACTGTAGT | |
| | GTAGATACTGAGTAAATCCATGCACCTAAACCTTTTGGAAAATCTGCCGTGGGCCCTCCAGATAGCTCAT | |
| | TTCATTAAGTTTTTCCCTCCAAGGTAGAATTTGCAAGAGTGACAGTGGATTGCATTTCTTTTGGGGAAGC | |
| | TTTCTTTTGGTGGTTTTGTTTATTATACCTTCTTAAGTTTTCAACCAAGGTTTGCTTTTGTTTTGAGTTA | |
| | CTGGGGTTATTTTTGTTTTAAATAAAAATAAGTGTACAATAAGTGTTTTTGTATTGAAAGCTTTTGTTAT | |
| | CAAGATTTTCATACTTTTACCTTCCATGGCTCTTTTTAAGATTGATACTTTTAAGAGGTGGCTGATATTC | |
| | TGCAACACTGTACACATAAAAAATACGGTAAGGATACTTTACATGGTTAAGGTAAAGTAAGTCTCCAGTT | |
| | GGCCACCATTAGCTATAATGGCACTTTGTTTGTGTTGTTGGAAAAAGTCACATTGCCATTAAACTTTCCT | |
| | TGTCTGTCTAGTTAATATTGTGAAGAAAAATAAAGTACAGTGTGAGATACTG | |

TABLE 2-continued

| GENBANK ACCESSION NUMBER | SEQUENCE | SEQ ID NO: |
|---|---|---|
| NM_001012271 | CCCAGAAGGCCGCGGGGGGTGGACCGCCTAAGAGGGCGTGCGCTCCCGACATGCCCCGCGGCGCGCCATT<br>AACCGCCAGATTTGAATCGCGGACCCGTTGGCAGAGGTGGCGGCGGCGGCATGGGTGCCCCGACGTTGC<br>CCCCTGCCTGGCAGCCCTTTCTCAAGGACCACCGCATCTCTACATTCAAGAACTGGCCCTTCTTGGAGGG<br>CTGCGCCTGCACCCCGGAGCGGATGGCCGAGGCTGGCTTCATCCACTGCCCCACTGAGAACGAGCCAGAC<br>TTGGCCCAGTGTTTCTTCTGCTTCAAGGAGCTGGAAGGCTGGGAGCCAGATGACGACCCCATTGGGCCGG<br>GCACGGTGGCTTACGCCTGTAATACCAGCACTTTGGGAGGCCGAGGCGGGCGGATCACGAGAGAGGAACA<br>TAAAAAGCATTCGTCCGGTTGCGCTTTCCTTTCTGTCAAGAAGCAGTTTGAAGAATTAACCCTTGGTGAA<br>TTTTTGAAACTGGACAGAGAAAGAGCCAAGAACAAAATTGCAAAGGAAACCAACAATAAGAAGAAAGAAT<br>TTGAGGAAACTGCGGAGAAAGTGCGCCGTGCCATCGAGCAGCTGGCTGCCATGGATTGAGGCCTCTGGCC<br>GGAGCTGCCTGGTCCCAGAGTGGCTGCACCACTTCCAGGGTTTATTCCCTGGTGCCACCAGCCTTCCTGT<br>GGGCCCCTTAGCAATGTCTTAGGAAAGGAGATCAACATTTTCAAATTAGATGTTTCAACTGTGCTCTTGT<br>TTTGTCTTGAAAGTGGCACCAGAGGTGCTTCTGCCTGTGCAGCGGGTGCTGCTGGTAACAGTGGCTGCTT<br>CTCTCTCTCTCTCTCTTTTTTGGGGGCTCATTTTTGCTGTTTTGATTCCCGGGCTTACCAGGTGAGAAGT<br>GAGGGAGGAAGAAGGCAGTGTCCCTTTTGCTAGAGCTGACAGCTTTGTTCGCGTGGGCAGAGCCTTCCAC<br>AGTGAATGTGTCTGGACCTCATGTTGTTGAGGCTGTCACAGTCCTGAGTGTGGACTTGGCAGGTGCCTGT<br>TGAATCTGAGCTGCAGGTTCCTTATCTGTCACACCTGTGCCTCCTCAGAGGACAGTTTTTTTGTTGTTGT<br>GTTTTTTTGTTTTTTTTTTTTTGGTAGATGCATGACTTGTGTGTGATGAGAGAATGGAGACAGAGTCCCT<br>GGCTCCTCTACTGTTTAACAACATGGCTTTCTTATTTTGTTTGAATTGTTAATTCACAGAATAGCACAAA<br>CTACAATTAAAACTAAGCACAAAGCCATTCTAAGTCATTGGGGAAACGGGGTGAACTTCAGGTGGATGAG<br>GAGACAGAATAGAGTGATAGGAAGCGTCTGGCAGATACTCCTTTTGCCACTGCTGTGTGATTAGACAGGC<br>CCAGTGAGCCGCGGGGCACATGCTGGCCGCTCCTCCCTCAGAAAAAGGCAGTGGCCTAAATCCTTTTTAA<br>ATGACTTGGCTCGATGCTGTGGGGGACTGGCTGGGCTGCTGCAGGCCGTGTGTCTGTCAGCCCAACCTTC<br>ACATCTGTCACGTTCTCCACACGGGGGAGAGACGCAGTCCGCCCAGGTCCCCGCTTTCTTTGGAGGCAGC<br>AGCTCCCGCAGGGCTGAAGTCTGGCGTAAGATGATGGATTTGATTCGCCCTCCTCCCTGTCATAGAGCTG<br>CAGGGTGGATTGTTACAGCTTCGCTGGAAACCTCTGGAGGTCATCTCGGCTGTTCCTGAGAAATAAAAAG<br>CCTGTCATTTCAAACACTGCTGTGGACCCTACTGGGTTTTTAAAATATTGTCAGTTTTTCATCGTCGTCC<br>CTAGCCTGCCAACAGCCATCTGCCCAGACAGCCGCAGTGAGGATGAGCGTCCTGGCAGAGACGCAGTTGT<br>CTCTGGGCGCTTGCCAGAGCCACGAACCCCAGACCTGTTTGTATCATCCGGGCTCCTTCCGGGCAGAAAC<br>AACTGAAAATGCACTTCAGACCCACTTATTTCTGCCACATCTGAGTCGGCCTGAGATAGACTTTTCCCTC<br>TAAACTGGGAGAATATCACAGTGGTTTTTGTTAGCAGAAAATGCACTCCAGCCTCTGTACTCATCTAAGC<br>TGCTTATTTTTGATATTTGTGTCAGTCTGTAAATGGATACTTCACTTTAATAACTGTTGCTTAGTAATTG<br>GCTTTGTAGAGAAGCTGGAAAAAAATGGTTTTGTCTTCAACTCCTTTGCATGCCAGGCGGTGATGTGGAT<br>CTCGGCTTCTGTGAGCCTGTGCTGTGGGCAGGGCTGAGCTGGAGCCGCCCCTCTCAGCCCGCCTGCCACG<br>GCCTTTCCTTAAAGGCCATCCTTAAAACCAGACCCTCATGGCTACCAGCACCTGAAAGCTTCCTCGACAT<br>CTGTTAATAAAGCCGTAGGCCCTTGTCTAAGTGCAACCGCCTAGACTTTCTTTCAGATACATGTCCACAT<br>GTCCATTTTTCAGGTTCTCTAAGTTGGAGTGGAGTCTGGGAAGGGTTGTGAATGAGGCTTCTGGGCTATG<br>GGTGAGGTTCCAATGGCAGGTTAGAGCCCCTCGGGCCAACTGCCATCCTGGAAAGTAGAGACAGCAGTGC<br>CCGCTGCCCAGAAGAGACCAGCAAGCCAAACTGGAGCCCCCATTGCAGGCTGTCGCCATGTGGAAAGAGT<br>AACTCACAATTGCCAATAAAGTCTCATGTGGTTTTATCTAAAAAAAAAAAAAAAAAAAAAAAAA | 106 |
| BX647539 | AATGAGGGTATTTATAAACTACTTAAATTATAAAAAGAATGAGACATCAGACTTACAGTTTTGGATACTA<br>ATTTTTTTCACTTAACGTTCATTATGTGATAGGAGTTTTCCATCCTATTATACCGCTGTGCGATCTGATC<br>TTGGGCACGTTAACCAACCTCTTGTTGCCTCGATTTTCTCACCTGTAAAAGTGGGGGTAATCATAATGCT<br>TACTTAGTAGGATAGCCCTGAAGAATAAGTGACTTAGCGAACATAAATAGCTTACAATAGGGTTTTCAGC<br>ATGGGAAGGATTCAGTAAATGTTAGCTGTCATCATCACCACCTACAAAGGAAGCAATACTGTGCTGAAAG<br>TTTTTCCATCATTAATGTAATTTCTATAGTACGATTCCCAAGAAGATATTAAAATTATGGAAATAAAGGT<br>ATTGGTATATTCCTAATTATTTCCTAAAAGATTGTATTGATAAATATGCTCATCCTTCCCTTAACGGGAT<br>GCATTCCAGAAAAACAAGTCAAATGTTAGACAAAGTATCAGAAGGGAAATTCTGTAGCCAGAGAGCTAAA<br>AATTACAATAGGGTCTCTAATTATACTTCAACTTTTTTAGGAATAATTCTCAGTGTGTTTTCCCACATTT<br>CATATGTAATTTTTTTTTTTTTTTTTTTTTGAGACAGAGCCTCGCCCTGTCACCAGGCTGGAGTACAGTG<br>GCGCGATCTCGGCTCACTGCAACTTCCACCTGCTGGGTTCAAGCAATTCTTCTGACCTCAGGTGATCCAC<br>CCGCCTCGGCCTCCCAAAGTGCTGGGATTATAACAGGCGTGGCATGAGTCACCGCGCCCGGCCGATCTTT<br>ACTTTTTTATTCTTTGTACCCCCTGCCTATCCAGTTAGCATGTGATTAAAGTCAAAGATTTGCCACTTTG<br>GGCCACATCTATTAATTTTCATCTTTGTTATAATTGTATTTAGTTTTTGATCTACACTGCTTATTACTCC<br>CAGTCATTTTTTATAGAACTGAAAATCTGGTAAAATACTCAAAATTGCACTGACTTCTATGTAGAGGCGA<br>CACTCCATCAGAACCGTGGGCTGACAGGGAATCCCACTGTGCAGGAGCTGCGCGCATTTTCATTTCTGAT<br>TCTCTTTGGCGTATCCAGGACTCTGATGACATGATCATATATTTATCAGTAGTAACAGGTTGGGCCATTT<br>GTTTTTTGTGGTAAATCATATATTTAAGATTTTAGAAATAAGTTGATAGCCATGTATTTTGGAATTTGAA<br>AAAGACATTGCATTACTCAGCTTCAAATTAAGCTTTAATCAAATAGTGAAACTTTCCATTAATGGACAGT<br>GTATACCTTTTTGTGTATTTAAAAAAAAAAACACTGAATATAGTGCCTTTGTGACAGGGGAGCTTGGTTC<br>CTGACAATGTCCTCTTGAGCCTTTTTTTTTTTTTTGAGATGGAGTCTCACTGTGTCACCCAGGCTGGAGT<br>GCAGTGGCGCCATCTTGGCTCACTGCAACCTCCGCCCCCTGGGTTCAAGTGATTCTCATTCCTCAGCTTC<br>CTAAGTAGCTGGGATTACAGGCACGCACCACCATGACCAGCTAATTTTTATACTTTTAGTAGAGACAGGG<br>TTTTGCCATGTTGGCTAGGTTGGTCTCGAACTCCTGACCTCAAGTAATCCACCCACCATGGCCTCCCCAA<br>AGTGCTGGGATTACAGGCGTGAGCCATTTCACCCGGCCTCTCTTCCGTCTTTGAGCTGTGAGGAAATAGC<br>TACATTACATGAGCTGCTAGATCTGCCTTATGGTCAGAAATGAAGGTTGAACTCTCAGGAACAGTGACAT<br>ATATACACACTGATATTTCCAAAGTACAATGCCCCAAATTGATCCACAAAGGAATTAAGGTCATTTGCAA<br>CAAAATCACAGAATAGTAACAAATAAATAGAAGATAAATATGGCCAGGGATGCTGCAAACTGATATACTG<br>CCAAGTTTATCAGTTGGGAATCCCAACAGTGAAAAGCATAAAAATGAAAGGAATTTTAAGGAGACTTTTT<br>ATAGAAGAGTGGGAAGGATTGGAGGAGCCAACAAGTGATGGTGAGGCACACAGGGAAGAGCTTCAGTGGG<br>CACCATCCCCTCTCTGGTTTGAAGGGGTAGGGAGGGGACCAGAGCTGGGAGGAGGGGGCTGGAATACTGC<br>TGGAGGAGCCACTCCCTTCCAGACCTGCTGTGGCCATCACAGAATGCAGCCACTGCCAGAGCAGCAGCCC<br>GAGGAACCAGGCAGGGGGAGCACAAGTACCCTAGCCTCTCTCTTTCTGTTTCTTGCCTGCCGATCTCCTC<br>CACTGGCTAAACCCAGCTGGATGCTAAGAGTACAGTCAGCCTGCCTGCTGAGGAGGGACCACCAGGGACC<br>ACCATCAGCAAGGGATCCAATGTCTTTCTGCCTCTGCAGAATGAAGGTTGGGGCGCGGGGGGCGCTCTAC<br>TTCTTAGGATATTGTGGGAATAAAAGGAAATAGGCAAAAAATGTTTTTGAAAAACAAAGCACATACTGC | 107 |

TABLE 2-continued

| GENBANK ACCESSION NUMBER | SEQUENCE | SEQ ID NO: |
|---|---|---|
| | GCACCCGTGGGCCACTACTGCTTTTGACCCCTGGCTCTGTTTCATGAAGTAATGTCGTGTCATTCTCTTT<br>TTAGGTGCTACAGGATTTCTTTAGGTTTGTTTTCTGTCCACCATATTTCAACTCATGTGTGCTGTTTGTT<br>GTGCTAAAACAAATATTTGCTGATGCCTGAGTGAATAGTTGAATATTTTATATAAGTCAAATTTATACGT<br>AATGATTTTTCTTGTAACTTAGCCGTTTCTCTTTTACAAACTCAGAAAACCTCAGACTTTGAAAAGGCCT<br>TGAAGTTCCTCACCTGAAATCTGAGAACTTGGAGCGCCTTAAAAAATCTAAAGGAAAACAAAACAGTGAA<br>AGAACATGATATAGTCAGTGTAGAGAATAAAATTATTTATGTAATTAATATTGAGGATGCAGATAACACA<br>TTGTGAAATCTTGCTTGTAAAAAATCTCGATCTGCTGAAGAAAGATGTTCTCTCTAGAGATCTTTGAAAG<br>CATAATTATTGAGCTTTTAAAATGTTAGAAACAAAAGTTAGACCCACACATATTCTGGCGTGTGGAAGAT<br>TTGCATTCCTTCCCCTGCCCGCCCCGCCCCCACACTTGTGAGTTGTGCCTGTGTACGCAGTTCCTGTAGC<br>ACTCGGCTGGGCAGAAATCATCTTTCAGCACTAAGGGAACATAGTTATGATCTGGACCTTCTGGGAGTGG<br>TCAGTGCCCAAGAACAGGTATGGGACTCCAGAAAGTTCTGCTCTCAACCCTATTTTGAAATAGAGTTACA<br>CATTGTTCTACAATTATTTGAGTTAATAAGCAGCTCTTTTCAAACGTGATTATGCCCTTCCAAGTTTAAA<br>TACACTAGACTTTAGTGAAAGTAATTGACCTCATCTCATTTCTCTCCTGTTATATTAAGATCACTTTCAG<br>TAAAAGGTAGAAGCTTTTGAAGTGGTGAGGAGGAGGTAGAGGAGGGACATAGAGCAGATAGGGGCTGGAA<br>AGTGGGGTGAGGAAGAGAGTGGCTTCTCTTTGGCAGAGTACCAAGGAAAAGCCCTATCTGTACAGAACCT<br>TTGTGCCTGGGAACTTGATGGCTGCAACCTGAGCCTCAACCTAGTTTGCTTGCGGAGCCAGAAGAGAAGC<br>TAAAAACCTTCAGTTAACCAAGCCAGACACCAAGAAAGTTAAACCGAAAGAGAACCCCCCACCCCCCGCA<br>AAAAAAAGAAGTAAAGTGGGTTAAAGTGATATCATGTTAGCACAGAAAGAGAACATAAGGGTCATCTAAG<br>TTCATCTGCCCCCTCTTCTATTTCAAGGTGCAGAAACTAAGGCACAAGGGACCCCGTGTCCTGCTCTTGA<br>TCACATAGCTAGTGGGTGCCAAGCCAGGTCTAGAACTCTGTTCTCTGGGGTCACAGGCTGGCTCTTCATC<br>CCTCTAGAGAGATAGCTCATCTGTGTGCACCTGAGCCCGTTGTGTTTCGGAGTCAAAGCAAATAAAGGCT<br>CAAACTCCAAGACTGTTTTGCAGACCGGCTGCAGTAGATATGGGGGGAGGAGAAACCTGCTTTAAATTGC<br>TTCAAGCAAGTTGTTTCTGCAAAGGTGTTGACTTTTTTCTTTCAACTTTCTAGTGAGTCACTGCAGCCTG<br>AGCTGTTATTTGTCATTATGCAATAATTCAGGAACTAACTCAAGATTCTTCTTTTTAAATTATTTGTTTA<br>TTTAGAGACAGAGTCTTGCTCTGTTGCCCAGGCTGGAGTGCAGTGGTGTGATCTCGGCTCACTGCAGCCT<br>CTGCCTCCTGGGTTCAAGCAATTCTCATGTCTCAGCCTCCCGAATAGCTGGTATTGCAGGCTCGTGCCAC<br>CACCCCCTGCTAATTTTTGTAATTTTAGTGGAGACACGGTTTCGCCATGTTGGCCGGGCTCGTCTTGAGC<br>TCCTGGCCTCAGGTGATCCGCCCGCCTCGGCCTCCCAAAGTGCTGGGATTGCAGCCGTGAGCCTCCACAC<br>CCGGCCTATTTATTTATTTTTAAATTGGCTGCTCTTAGAAAGGCATACCATGTTTCTGGATGGGAAGGCT<br>TATTAATTCACCCTAATTTAATGTATAAATTTGATGCAATCATAGTCACAGTCCCAGTGGAATTTTTTAA<br>CTTGGTAAGATGTTCTAAAATTAATGAGAGAACTTGAATTACCAGGTATTGAAACACTGTAAAGCCACAA<br>TCATGTAAACAGTATGTTATAACCATGGGAATAGAGGTCTGTGATACAGCAGAAAAAAGTGAAAAAAAGA<br>ATAACTGTATTCATAAAAATTTAAATGTGGAGTCACTGGGGGAAAGGATTAAATATTCGATAATGTAGAA<br>ACAACTCAACTATTTGGAGAAATGTAAATTTAGAGCCTTATCTCATGCCATATACCAAAATACTATTTAG<br>ATTTGATTAAAAAATAAAAAAAAAAAAAAAAAA | |
| NM_031966 | CGAACGCCTTCGCGCGATCGCCCTGGAAACGCATTCTCTGCGACCGGCAGCCGCCAATGGGAAGGGAGTG<br>AGTGCCACGAACAGGCCAATAAGGAGGGAGCAGTGCGGGGTTTAAATCTGAGGCTAGGCTGGCTCTTCTC<br>GGCGTGCTGCGGCGGAACGGCTGTTGGTTTCTGCTGGGTGTAGGTCCTTGGCTGGTCGGGCCTCCGGTGT<br>TCTGCTTCTCCCCGCTGAGCTGCTGCCTGGTGAAGAGGAAGCCATGGCGCTCCGAGTCACCAGGAACTCG<br>AAAATTAATGCTGAAAATAAGGCGAAGATCAACATGGCAGGCGCAAAGCGCGTTCCTACGGCCCCTGCTG<br>CAACCTCCAAGCCCGGACTGAGGCCAAGAACAGCTCTTGGGGACATTGGTAACAAAGTCAGTGAACAACT<br>GCAGGCCAAAATGCCTATGAAGAAGGAAGCAAAACCTTCAGCTACTGGAAAAGTCATTGATAAAAAACTA<br>CCAAAACCTCTTGAAAAGGTACCTATGCTGGTGCCAGTGCCAGTGTCTGAGCCAGTGCCAGAGCCAGAAC<br>CTGAGCCAGAACCTGAGCCTGTTAAAGAAGAAAAACTTTCGCCTGAGCCTATTTTGGTTGATACTGCCTC<br>TCCAAGCCCAATGGAAACATCTGGATGTGCCCCTGCAGAAGAAGACCTGTGTCAGGCTTTCTCTGATGTA<br>ATTCTTGCAGTAAATGATGTGGATGCAGAAGATGGAGCTGATCCAAACCTTTGTAGTGAATATGTGAAAG<br>ATATTTATGCTTATCTGAGACAACTTGAGGAAGAGCAAGCAGTCAGACCAAAATACCTACTGGGTCGGGA<br>AGTCACTGGAAACATGAGAGCCATCCTAATTGACTGGCTAGTACAGGTTCAAATGAAATTCAGGTTGTTG<br>CAGGAGACCATGTACATGACTGTCTCCATTATTGATCGGTTCATGCAGAATAATTGTGTGCCCAAGAAGA<br>TGCTGCAGCTGGTTGGTGTCACTGCCATGTTTATTGCAAGCAAATATGAAGAAATGTACCCTCCAGAAAT<br>TGGTGACTTTGCTTTTGTGACTGACAACACTTATACTAAGCACCAAATCAGACAGATGGAAATGAAGATT<br>CTAAGAGCTTTAAACTTTGGTCTGGGTCGGCCTCTACCTTTGCACTTCCTTCGGAGAGCATCTAAGATTG<br>GAGAGGTTGATGTCGAGCAACATACTTTGGCCAAATACCTGATGGAACTAACTATGTTGGACTATGACAT<br>GGTGCACTTTCCTCCTTCTCAAATTGCAGCAGGAGCTTTTTGCTTAGCACTGAAAATTCTGGATAATGGT<br>GAATGGACACCAACTCTACAACATTACCTGTCATATACTGAAGAATCTCTTCTTCCAGTTATGCAGCACC<br>TGGCTAAGAATGTAGTCATGGTAAATCAAGGACTTACAAAGCACATGACTGTCAAGAACAAGTATGCCAC<br>ATCGAAGCATGCTAAGATCAGCACTCTACCACAGCTGAATTCTGCACTAGTTCAAGATTTAGCCAAGGCT<br>GTGGCAAAGGTGTAACTTGTAAACTTGAGTTGGAGTACTATATTTACAAATAAAATTGGCACCATGTGCC<br>ATCTGTACATATTACTGTTGCATTTACTTTTAATAAAGCTTGTGGCCCCTTTTACTTTTTTATAGCTTAA<br>CTAATTTGAATGTGGTTACTTCCTACTGTAGGGTAGCGGAAAAGTTGTCTTAAAAGGTATGGTGGGGATA<br>TTTTTAAAAACTCCTTTTGGTTTACCTGGGGATCCAATTGATGTATATGTTTATATACTGGGTTCTTGTT<br>TTATATACCTGGCTTTTACTTTATTAATATGAGTTACTGAAGGTGATGGAGGTATTTGAAAATTTTACTT<br>CCATAGGACATACTGCATGTAAGCCAAGTCATGGAGAATCTGCTGCATAGCTCTATTTTAAAGTAAAAGT<br>CTACCACCGAATCCCTAGTCCCCCTGTTTTCTGTTTCTTCTTGTGATTGCTGCCATAATTCTAAGTTATT<br>TACTTTTACCACTATTTAAGTTATCAACTTTAGCTAGTATCTTCAAACTTTCACTTTGAAAAATGAGAAT<br>TTTATATTCTAAGCCAGTTTTCATTTTGGTTTTGTGTTTTGGTTAATAAAACAATACTCAAATACAAAAA<br>AAAAAAA | 108 |
| BC035498 | GCGGCCGCCAGCGCGGTGTAGGGGGCAGGCGCGGATCCCGCCACCGCCGCGCGCTCGGCCCGCCGACTCC<br>CGGCGCCGCCGCCGCCACTGCCGTCGCCGCCGCCGCCTGCCGGGACTGGAGCGCGCCGTCCGCCGCGGAC<br>AAGACCCTGGCCTCAGGCCGGAGCAGCCCCATCATGCCGAGGGAGCGCAGGGAGCGGGATGCGAAGGAGC<br>GGGACACCATGAAGGAGGACGGCGGCGCGGAGTTCTCGGCTCGCTCCAGGAAGAGGAAGGCAAACGTGAC<br>CGTTTTTTTGCAGGATCCAGATGAAGAAATGGCCAAAATCGACAGGACGGCGAGGGACCAGTGTGGGAGC<br>CAGCCTTGGGACAATAATGCAGTCTGTGCAGACCCCTGCTCCCTGATCCCCACACCTGACAAAGAAGATG<br>ATGACCGGGTTTACCCAAACTCAACGTGCAAGCCTCGGATTATTGCACCATCCAGAGGCTCCCCGCTGCC | 110 |

TABLE 2-continued

| GENBANK ACCESSION NUMBER | SEQUENCE | SEQ ID NO: |
|---|---|---|
| | TGTACTGAGCTGGGCAAATAGAGAGGAAGTCTGGAAAATCATGTTAAACAAGGAAAAGACATACTTAAGG<br>GATCAGCACTTTCTTGAGCAACACCCTCTTCTGCAGCCAAAAATGCGAGCAATTCTTCTGGATTGGTTAA<br>TGGAGGTGTGTGAAGTCTATAAACTTCACAGGGAGACCTTTTACTTGGCACAAGATTTCTTTGACCGGTA<br>TATGGCGACACAAGAAAATGTTGTAAAAACTCTTTTACAGCTTATTGGGATTTCATCTTTATTTATTGCA<br>GCCAAACTTGAGGAAATCTATCCTCCAAAGTTGCACCAGTTTGCGTATGTGACAGATGGAGCTTGTTCAG<br>GAGATGAAATTCTCACCATGGAATTAATGATTATGAAGGCCCTTAAGTGGCGTTTAAGTCCCCTGACTAT<br>TGTGTCCTGGCTGAATGTATACATGCAGGTTGCATATCTAAATGACTTACATGAAGTGCTACTGCCGCAG<br>TATCCCCAGCAAATCTTTATACAGATTGCAGAGCTGTTGGATCTCTGTGTCCTGGATGTTGACTGCCTTG<br>AATTTCCTTATGGTATACTTGCTGCTTCGGCCTTGTATCATTTCTCGTCATCTGAATTGATGCAAAAGGT<br>TTCAGGGTATCAGTGGTGCGACATAGAGAACTGTGTCAAGTGGATGGTTCCATTTGCCATGGTTATAAGG<br>GAGACGGGGAGCTCAAAACTGAAGCACTTCAGGGGCGTCGCTGATGAAGATGCACACAACATACAGACCC<br>ACAGAGACAGCTTGGATTTGCTGGACAAAGCCCGAGCAAAGAAAGCCATGTTGTCTGAACAAAATAGGGC<br>TTCTCCTCTCCCCAGTGGGCTCCTCACCCCGCCACAGAGCGGTAAGAAGCAGAGCAGCGGGCCGGAAATG<br>GCGTGACCACCCCATCCTTCTCCACCAAAGACAGTTGCGCGCCTGCTCCACGTTCTCTTCTGTCTGTTGC<br>AGCGGAGGCGTGCGTTTGCTTTTACAGATATCTGAATGGAAGAGTGTTTCTTCCACAACAGAAGTATTTC<br>TGTGGATGGCATCAAACAGGGCAAAGTGTTTTTATTGAATGCTTATAGGTTTTTTTTAAATAAGTGGGT<br>CAAGTACACCAGCCACCTCCAGACACCAGTGCGTGCTCCCGATGCTGCTATGGAAGGTGCTACTTGACCT<br>AAGGGACTCCCACAACAACAAAAGCTTGAAGCTGTGGAGGGCCACGGTGGCGTGGCTCTCCTCGCAGGTG<br>TTCTGGGCTCCGTTGTACCAAGTGGAGCAGGTGGTTGCGGGCAAGCGTTGTGCAGAGCCCATAGCCAGCT<br>GGGCAGGGGGCTGCCCTCTCCACATTATCAGTTGACAGTGTACAATGCCTTTGATGAACTGTTTTGTAAG<br>TGCTGCTATATCTATCCATTTTTTAATAAAGATAATACTGTTTTTGAAAAAAAAAAAAAAAAAAAAAAAA<br>AAAAAAAAAAAAAAAAAAAAAAAAAAAAAAAAAAAAAAAAAAAAAAAAAAA | |
| BG256659 | GAGGGCACGGGCTCCGTAGGCACCAACTGCAAGGACCCCTCCCCCTGCGGGCGCTCCCATGGCACAGTTC<br>GCGTTCGAGAGTGACCTGCACTCGCTGCTTCAGCTGGATGCACCCATCCCCAATGCACCCCCTGCGCGCT<br>GGCAGCGCAAAGCCAAGGAAGCCGCAGGCCCGGCCCCCTCACCCATGCGGGCCGCCAACCGATCCCACAG<br>CGCCGGCAGGACTCCGGGCCGAACTCCTGGCAAATCCAGTTCCAAGGTTCAGACCACTCCTAGCAAACCT<br>GGCGGTGACCGCTATATCCCCCATCGCAGTGCTGCCCAGATGGAGGTGGCCAGCTTCCTCCTGAGCAAGG<br>AGAACCAGCCTGAAAACAGCCAGACGCCCACCAAGAAGGAACATCAGAAAGCCTGGGCTTTGAACCTGAA<br>CGGTTTTGATGTAGAGGAAGCCAAGATCCTTCGGCTCAGTGGAAAAACCACAAAAATGCGCCAGAGGGTT<br>ATCACGAACAGACTGAAAGTACTCTACAGCCAAAAGGCCACTCCTGGCTCCAGCCGGAAGACCTGCCGTT<br>TACATTCCTTCCCTGCCAAGACCGTATCCTGGATGCGCCTGAAATCGAATGACTATTAACTGAACCTGTG<br>GGACTGGCAGTCCGGGGAATGTCCGGGCCGGGCCACGGCCACGAGGTGTTCCGTGTGGAGTGCAAGCTGG<br>GACACACCGTGCCGCTTGTGCACAGGGCCACGCGGGGAAATAATCCCGGGGCGCGCAAAGCGGCACTGGC<br>GAGAGCCGCACGGGCCGGTGCTGGGGGTGGTACAACAGGCCAAAACAACACACAAGGCCAACAAGACATA<br>CGCGCGCTGACACCACGGTGCAAAGCGCTCAGACGAGTAGTAACCGGCACTGTGGTTGCTGCCTCCCCAC<br>CTCTCCCGCTCTCAGCGTAAGATAAAAGAAAGAAGAGCAAAAAGCAAAGAAAGAAGACGAGACGAGACAC<br>ACAGGAACGAACAGTAAAGCAAGCTAAAGCAAACGCAAGACCAGACAACAGAAATAGAAAGAACCAACAG<br>AGAGGAGACAGAACAGGACGCCAGCAACATAGCAACAAACGAACAGAAGAGAGCACTAAACAAAAGCAGC<br>AGCAAGACGAGACAGGAGAGAAGGAGGAAGGAGGGCCGAGCGAGCAGGGAGCGCGAGCAGCGAGGCGAAG<br>CAGCAGACAAGGGCAGGCGAAGGGCAACGAGAGGAGGCACCACACAAAAAGGAGAGGGGACAGGAGAAGC<br>AGCGAGAGAAGCGGAGGAGCAACAAGAGGAAGAAAAGGAGAGGGAGAGGAGGGAGAGAGCGGAAGGAGGA<br>AGAAACAGCACGAGGCGACGAAGGGGGGAGACGCGGGGGCAGGAAAAGACACAGGAAGGCAGCGCGGAGG<br>AGGAGAAGGGGAAGCAGGAAGGAGACGGAAGGAGAAGAGGGAGAGGACAGCGCAAGAGAGCGCGCGCGGC<br>GACAGCGAGGGACGGAGCGAGAGAGAGGAAACGGAAAGCGAGAGGGAAGAGGAGAGGCAACGCAGCGAAC<br>CAACCGAAAACAGCAGAAAGAGAGGAGAAGGACGCGCAAAGAGGCAAGCGCAAGACGACAGGAAACGAAG<br>CGAGAGACGAGAAGCCGGTGACGAGCAGGAGAAAGGGAAGGCAGGAGACAGGACAGGCGGAAGAGAGACA<br>CGCGAGACGCAAAGAGTGAGCAGAACGAAGCGAAGAGCAACGCACGAGAGAAACGAC | 111 |
| NM_001254 | GAGCGCGGCTGGAGTTTGCTGCTGCCGCTGTGCAGTTTGTTCAGGGGCTTGTGGTGGTGAGTCCGAGAGG<br>CTGCGTGTGAGAGACGTGAGAAGGATCCTGCACTGAGGAGGTGGAAAGAAGAGGATTGCTCGAGGAGGCC<br>TGGGGTCTGTGAGGCAGCGGAGCTGGGTGAAGGCTGCGGGTTCCGGCGAGGCCTGAGCTGTGCTGTCGTC<br>ATGCCTCAAACCCGATCCCAGGCACAGGCTACAATCAGTTTTCCAAAAAGGAAGCTGTCTCGGGCATTGA<br>ACAAAGCTAAAAACTCCAGTGATGCCAAACTAGAACCAACAAATGTCCAAACCGTAACCTGTTCTCCTCG<br>TGTAAAAGCCCTGCCTCTCAGCCCCAGGAAACGTCTGGGCGATGACAACCTATGCAACACTCCCCATTTA<br>CCTCCTTGTTCTCCACCAAAGCAAGGCAAGAAAGAGAATGGTCCCCCTCACTCACATACACTTAAGGGAC<br>GAAGATTGGTATTTGACAATCAGCTGACAATTAAGTCTCCTAGCAAAAGAGAACTAGCCAAAGTTCACCA<br>AAACAAAATACTTTCTTCAGTTAGAAAAAGTCAAGAGATCACAACAAATTCTGAGCAGAGATGTCCACTG<br>AAGAAAGAATCTGCATGTGTGAGACTATTCAAGCAAGAAGGCACTTGCTACCAGCAAGCAAAGCTGGTCC<br>TGAACACAGCTGTCCCAGATCGGCTGCCTGCCAGGGAAAGGGAGATGGATGTCATCAGGAATTTCTTGAG<br>GGAACACATCTGTGGGAAAAAAGCTGGAAGCCTTTACCTTTCTGGTGCTCCTGGAACTGGAAAAACTGCC<br>TGCTTAAGCCGGATTCTGCAAGACCTCAAGAAGGAACTGAAAGGCTTTAAAACTATCATGCTGAATTGCA<br>TGTCCTTGAGGACTGCCCAGGCTGTATTCCCAGCTATTGCTCAGGAGATTTGTCAGGAAGAGGTATCCAG<br>GCCAGCTGGGAAGGACATGATGAGGAAATTGGAAAAACATATGACTGCAGAGAAGGGCCCCATGATTGTG<br>TTGGTATTGGACGAGATGGATCAACTGGACAGCAAAGGCCAGGATGTATTGTACACGCTATTTGAATGGC<br>CATGGCTAAGCAATTCTCACTTGGTGCTGATTGGTATTGCTAATACCCTGGATCTCACAGATAGAATTCT<br>ACCTAGGCTTCAAGCTAGAGAAAAATGTAAGCCACAGCTGTTGAACTTCCCACCTTATACCAGAAATCAG<br>ATAGTCACTATTTTGCAAGATCGACTTAATCAGGTATCTAGAGATCAGGTTCTGGACAATGCTGCAGTTC<br>AATTCTGTGCCCGCAAAGTCTCTGCTGTTTCAGGAGATGTTCGCAAAGCACTGGATGTTTGCAGGAGAGC<br>TATTGAAATTGTAGAGTCAGATGTCAAAAGCCAGACTATTCTCAAACCACTGTCTGAATGTAAATCACCT<br>TCTGAGCCTCTGATTCCCAAGAGGGTTGGTCTTATTCACATATCCCAAGTCATCTCAGAAGTTGATGGTA<br>ACAGGATGACCTTGAGCCAAGAAGGAGCACAAGATTCCTTCCCTCTTCAGCAGAAGATCTTGGTTTGCTC<br>TTTGATGCTCTTGATCAGGCAGTTGAAAATCAAAGAGGTCACTCTGGGGAAGTTATATGAAGCCTACAGT<br>AAAGTCTGTCGCAAACAGCAGGTGGCGGCTGTGGACCAGTCAGAGTGTTTGTCACTTTCAGGGCTCTTGG<br>AAGCCAGGGGCATTTTAGGATTAAAGAGAAACAAGGAAACCCGTTTGACAAAGGTGTTTTTCAAGATTGA<br>AGAGAAAGAAATAGAACATGCTCTGAAAGATAAAGCTTTAATTGGAAATATCTTAGCTACTGGATTGCCT | 112 |

TABLE 2-continued

| GENBANK ACCESSION NUMBER | SEQUENCE | SEQ ID NO: |
|---|---|---|
| | TAAATTCTTCTCTTACACCCCACCCGAAAGTATTCAGCTGGCATTTAGAGAGCTACAGTCTTCATTTTAG | |
| | TGCTTTACACATTCGGGCCTGAAAACAAATATGACCTTTTTACTTGAAGCCAATGAATTTTAATCTATA | |
| | GATTCTTTAATATTAGCACAGAATAATATCTTTGGGTCTTACTATTTTTACCCATAAAAGTGACCAGGTA | |
| | GACCCTTTTTAATTACATTCACTACTTCTACCACTTGTGTATCTCTAGCCAATGTGCTTGCAAGTGTACA | |
| | GATCTGTGTAGAGGAATGTGTGTATATTTACCTCTTCGTTTGCTCAAACATGAGTGGGTATTTTTTTGTT | |
| | TGTTTTTTTTGTTGTTGTTGTTTTTGAGGCGCGTCTCACCCTGTTGCCCAGGCTGGAGTGCAATGGCGCG | |
| | TTCTCTGCTCACTACAGCACCCGCTTCCCAGGTTGAAGTGATTCTCTTGCCTCAGCCTCCCGAGTAGCTG | |
| | GGATTACAGGTGCCCACCACCGCGCCCAGCTAATTTTTTAATTTTTAGTAGAGACAGGGTTTTACCATGT | |
| | TGGCCAGGCTGGTCTTGAACTCCTGACCCTCAAGTGATCTGCCCACCTTGGCCTCCCTAAGTGCTGGGAT | |
| | TATAGGCGTGAGCCACCATGCTCAGCCATTAAGGTATTTTGTTAAGAACTTTAAGTTTAGGGTAAGAAGA | |
| | ATGAAAATGATCCAGAAAAAATGCAAGCAAGTCCACATGGAGATTTGGAGGACACTGGTTAAAGAATTTAT | |
| | TTCTTTGTATAGTATACTATGTTCATGGTGCAGATACTACAACATTGTGGCATTTTAGACTCGTTGAGTT | |
| | TCTTGGGCACTCCCAAGGGCGTTGGGGTCATAAGGAGACTATAACTCTACAGATTGTGAATATATTTATT | |
| | TTCAAGTTGCATTCTTTGTCTTTTTAAGCAATCAGATTTCAAGAGAGCTCAAGCTTTCAGAAGTCAATGT | |
| | GAAAATTCCTTCCTAGGCTGTCCCACAGTCTTTGCTGCCCTTAGATGAAGCCACTTGTTTCAAGATGACT | |
| | ACTTTGGGGTTGGGTTTTCATCTAAACACATTTTTCCAGTCTTATTAGATAAATTAGTCCATATGGTTGG | |
| | TTAATCAAGAGCCTTCTGGGTTTGGTTTGGTGGCATTAAATGG | |
| NM_031423 | GCGGAATGGGGCGGGACTTCCAGTAGGAGGCGGCAAGTTTGAAAAGTGATGACGGTTGACGTTTGCTGAT | 113 |
| | TTTTGACTTTGCTTGTAGCTGCTCCCCGAACTCGCCGTCTTCCTGTCGGCGGCCGGCACTGTAGATTAAC | |
| | AGGAAACTTCCAAGATGGAAACTTTGTCTTTCCCCAGATATAATGTAGCTGAGATTGTGATTCATATTCG | |
| | CAATAAGATCTTAACAGGAGCTGATGGTAAAAACCTCACCAAGAATGATCTTTATCCAAATCCAAAGCCT | |
| | GAAGTCTTGCACATGATCTACATGAGAGCCTTACAAATAGTATATGGAATTCGACTGGAACATTTTTACA | |
| | TGATGCCAGTGAACTCTGAAGTCATGTATCCACATTTAATGGAAGGCTTCTTACCATTCAGCAATTTAGT | |
| | TACTCATCTGGACTCATTTTTGCCTATCTGCCGGGTGAATGACTTTGAGACTGCTGATATTCTATGTCCA | |
| | AAAGCAAAACGGACAAGTCGGTTTTTAAGTGGCATTATCAACTTTATTCACTTCAGAGAAGCATGCCGTG | |
| | AAACGTATATGGAATTTCTTTGGCAATATAAATCCTCTGCGGACAAAATGCAACAGTTAAACGCCGCACA | |
| | CCAGGAGGCATTAATGAAACTGGAGAGACTTGATTCTGTTCCAGTTGAAGAGCAAGAAGAGTTCAAGCAG | |
| | CTTTCAGATGGAATTCAGGAGCTACAACAATCACTAAATCAGGATTTTCATCAAAAAACGATAGTGCTGC | |
| | AAGAGGGAAATTCCCAAAAGAAGTCAAATATTTCAGAGAAAACCAAGCGTTTGAATGAACTAAAATTGTC | |
| | GGTGGTTTCTTTGAAAGAAATACAAGAGAGTTTGAAAACAAAAATTGTGGATTCTCCAGAGAAGTTAAAG | |
| | AATTATAAAGAAAAAATGAAAGATACGGTCCAGAAGCTTAAAAATGCCAGACAAGAAGTGGTGGAGAAAT | |
| | ATGAAATCTATGGAGACTCAGTTGACTGCCTGCCTTCATGTCAGTTGGAAGTGCAGTTATATCAAAAGAA | |
| | AATACAGGACCTTTCAGATAATAGGGAAAAATTAGCCAGTATCTTAAAGGAGAGCCTGAACTTGGAGGAC | |
| | CAAATTGAGAGTGATGAGTCAGAACTGAAGAAATTGAAGACTGAAGAAAATTCGTTCAAAAGACTGATGA | |
| | TTGTGAAGAAGGAAAAACTTGCCACAGCACAATTCAAAATAAATAAGAAGCATGAAGATGTTAAGCAATA | |
| | CAAACGCACAGTAATTGAGGATTGCAATAAAGTTCAAGAAAAAAGAGGTGCTGTCTATGAACGAGTAACC | |
| | ACAATTAATCAAGAAATCCAAAAAATTAAACTTGGAATTCAACAACTAAAAGATGCTGCTGAAAGGGAGA | |
| | AACTGAAGTCCCAGGAAATATTTCTAAACTTGAAAACTGCTTTGGAGAAATACCACGACGGTATTGAAAA | |
| | GGCAGCAGAGGACTCCTATGCTAAGATAGATGAGAAGACAGCTGAACTGAAGAGGAAGATGTTCAAAATG | |
| | TCAACCTGATTAACAAAATTACATGTCTTTTTGTAAATGGCTTGCCATCTTTTAATTTTCTATTTAGAAA | |
| | GAAAAGTTGAAGCGAATGGAAGTATCAGAAGTACCAAATAATGTTGGCTTCATCAGTTTTTATACACTCT | |
| | CATAAGTAGTTAATAAGATGAATTTAATGTAGGCTTTTATTAATTTATAATTAAAATAACTTGTGCAGCT | |
| | ATTCATGTCTCTACTCTGCCCCTTGTTGTAAATAGTTTGAGTAAAACAAAACTAGTTACCTTTGAAATAT | |
| | ATATATTTTTTTCTGTTACTATC | |
| BC041846 | GGCTAGCGCGGGAGGTGGAGAAAGAGGCTTGGGCGGCCCCGCTGTAGCCGCGTGTGGGAGGACGCACGGG | 114 |
| | CCTGCTTCAAAGCTTTGGGATAACAGCGCCTCCGGGGGATAATGAATGCGGAGCCTCCGTTTTCAGTCGA | |
| | CTTCAGATGTGTCTCCACTTTTTTCCGCTGTAGCCGCAAGGCAAGGAAACATTTCTCTTCCCGTACTGAG | |
| | GAGGCTGAGGAGTGCACTGGGTGTTCTTTTCTCCTCTAACCCAGAACTGCGAGACAGAGGCTGAGTCCCT | |
| | GTAAAGAACAGCTCCAGAAAAGCCAGGAGAGCGCAGGAGGGCATCCGGGAGGCCAGGAGGGGTTCGCTGG | |
| | GGCCTCAACCGCACCCACATCGGTCCCACCTGCGAGGGGGCGGACCTCGTGGCGCTGGACCAATCAGCA | |
| | CCCACCTGCGCTCACCTGGCCTCCTCCCGCTGGCTCCCGGGGGCTGCGGTGCTCAAAGGGGCAAGAGCTG | |
| | AGCGGAACACCGGCCCGCCGTCGCGGCAGCTGCTTCACCCCTCTCTCTGCAGCCATGGGGCTCCCTCGTG | |
| | GACCTCTCGCGTCTCTCCTCCTTCTCCAGGTTTGCTGGCTGCAGTGCGCGGCCTCCGAGCCGTGCCGGGC | |
| | GGTCTTCAGGGAGGCTGAAGTGACCTTGGAGGCGGGAGGCGCGGAGCAGGAGCCCGGCCAGGCGCTGGGG | |
| | AAAGTATTCATGGGCTGCCCTGGGCAAGAGCCAGCTCTGTTTAGCACTGATAATGATGACTTCACTGTGC | |
| | GGAATGGCGAGACAGTCCAGGAAAGAAGGTCACTGAAGGAAAGGAATCCATTGAAGATCTTCCCATCCAA | |
| | ACGTATCTTACGAAGACACAAGAGAGATTGGGTGGTTGCTCCAATATCTGTCCCTGAAAATGGCAAGGGT | |
| | CCCTTCCCCCAGAGACTGAATCAGCTCAAGTCTAATAAAGATAGAGACACCAAGATTTTCTACAGCATCA | |
| | CGGGGCCGGGGGCAGACAGCCCCCCTGAGGGTGTCTTCGCTGTAGAGAAGGAGACAGGCTGGTTGTTGTT | |
| | GAATAAGCCACTGGACCGGGAGGAGATTGCCAAGTATGAGCTCTTTGGCCACGCTGTGTCAGAGAATGGT | |
| | GCCTCAGTGGAGGACCCCATGAACATCTCCATCATAGTGACCGACCAGAATGACCACAAGCCCAAGTTTA | |
| | CCCAGGACACCTTCCGAGGGAGTGTCTTAGAGGGAGTCCTACCAGGTACTTCTGTGATGCAGATGACAGC | |
| | CACAGATGAGGATGATGCCATCTACACCTACAATGGGGTGGTTGCTTACTCCATCCATAGCCAAGAACCA | |
| | AAGGACCCACACGACCTCATGTTCACAATTCACCGGAGCACAGGCACCATCAGCGTCATCTCCAGTGGCC | |
| | TGGACCGGGAAAAAGTCCCTGAGTACACACTGACCATCCAGGCCACAGACATGGATGGGGACGGCTCCAC | |
| | CACCACGGCAGTGGCAGTAGTGGAGATCCTTGATGCCAATGACAATGCTCCCATGTTTGACCCCCAGAAG | |
| | TACGAGGCCCATGTGCCTGAGAATGCAGTGGGCCATGAGGTGCAGAGGCTGACGGTCACTGATCTGGACG | |
| | CCCCCAACTCACCAGCGTGGCGTGCCACCTACCTTATCATGGGCGGTGACGACGGGGACCATTTTACCAT | |
| | CACCACCCACCCTGAGAGCAACCAGGGCATCCTGACAACCAGGAAGGGTTTGGATTTTGAGGCCAAAAAC | |
| | CAGCACACCCTGTACGTTGAAGTGACCAACGAGGCCCCTTTTGTGCTGAAGCTCCCAACCTCCACAGCCA | |
| | CCATAGTGGTCCACGTGGAGGATGTGAATGAGGCACCTGTGTTTGTCCCACCCTCCAAAGTCGTTGAGGT | |
| | CCAGGAGGGCATCCCCACTGGGGAGCCTGTGTGTGTCTACACTGCAGAAGACCCTGACAAGGAGAATCAA | |
| | AAGATCAGCTACCGCATCCTGAGAGACCCAGCAGGGTGGCTAGCCATGGACCCAGACAGTGGGCAGGTCA | |
| | CAGCTGTGGGCACCCTCGACCGTGAGGATGAGCAGTTTGTGAGGAACAACATCTATGAAGTCATGGTCTT | |

TABLE 2-continued

| GENBANK ACCESSION NUMBER | SEQUENCE | SEQ ID NO: |
|---|---|---|
| | GGCCATGGACAATGGAAGCCCTCCCACCACTGGCACGGGAACCCTTCTGCTAACACTGATTGATGTCAAC<br>GACCATGGCCCAGTCCCTGAGCCCCGTCAGATCACCATCTGCAACCAAAGCCCTGTGCGCCAGGTGCTGA<br>ACATCACGGACAAGGACCTGTCTCCCCACACCTCCCCTTTCCAGGCCCAGCTCACAGATGACTCAGACAT<br>CTACTGGACGGCAGAGGTCAACGAGGAAGGTGACACAGTGGTCTTGTCCCTGAAGAAGTTCCTGAAGCAG<br>GATACATATGACGTGCACCTTTCTCTGTCTGACCATGGCAACAAAGAGCAGCTGACGGTGATCAGGGCCA<br>CTGTGTGCGACTGCCATGGCCATGTCGAAACCTGCCCTGGACCCTGGAAAGGAGGTTTCATCCTCCCTGT<br>GCTGGGGGCTGTCCTGGCTCTGCTGTTCCTCCTGCTGGTGCTGCTTTTGTTGGTGAGAAAGAAGCGGAAG<br>ATCAAGGAGCCCCTCCTACTCCCAGAAGATGACACCCGTGACAACGTCTTCTACTATGGCGAAGAGGGGG<br>GTGGCGAAGAGGACCAGGACTATGACATCACCCAGCTCCACCGAGGTCTGGAGGCCAGGCCGGAGGTGGT<br>TCTCCGCAATGACGTGGCACCAACCATCATCCCGACACCCATGTACCGTCCTAGGCCAGCCAACCCAGAT<br>GAAATCGGCAACTTTATAATTGAGAACCTGAAGGCGGCTAACACAGACCCCACAGCCCCGCCCTACGACA<br>CCCTCTTGGTGTTCGACTATGAGGGCAGCGGCTCCGACGCCGCGTCCCTGAGCTCCCTCACCTCCTCCGC<br>CTCCGACCAAGACCAAGATTACGATTATCTGAACGAGTGGGGCAGCCGCTTCAAGAAGCTGGCAGACATG<br>TACGGTGGCGGGGAGGACGACTAGGCGGCCTGCCTGCAGGGCTGGGGACCAAACGTCAGGCCACAGAGCA<br>TCTCCAAGGGGTCTCAGTTCCCCCTTCAGCTGAGGACTTCGGAGCTTGTCAGGAAGTGGCCGTAGCAACT<br>TGGCGGAGACAGGCTATGAGTCTGACGTTAGAGTGGTTGCTTCCTTAGCCTTTCAGGATGGAGGAATGTG<br>GGCAGTTTGACTTCAGCACTGAAAACCTCTCCACCTGGGCCAGGGTTGCCTCAGAGGCCAAGTTTCCAGA<br>AGCCTCTTACCTGCCGTAAAATGCTCAACCCTGTGTCCTGGGCCTGGGCCTGCTGTGACTGACCTACAGT<br>GGACTTTCTCTCTGGAATGGAACCTTCTTAGGCCTCCTGGTGCAACTTAATTTTTTTTTTTAATGCTATC<br>TTCAAAACGTTAGAGAAAGTTCTTCAAAAGTGCAGCCCAGAGCTGCTGGGCCCACTGGCCGTCCTGCATT<br>TCTGGTTTCCAGACCCCAATGCCTCCCATTCGGATGGATCTCTGCGTTTTTATACTGAGTGTGCCTAGGT<br>TGCCCCTTATTTTTTATTTTCCCTGTTGCGTTGCTATAGATGAAGGGTGAGGACAATCGTGTATATGTAC<br>TAGAACTTTTTTATTAAAGAAACTTTTCCCAAAAAAAAAAAAAAAA | |
| NM_016343 | GAGACCAGAAGCGGGCGAATTGGGCACCGGTGGCGGCTGCGGGCAGTTTGAATTAGACTCTGGGCTCCAG<br>CCCGCCGAAGCCGCGCCAGAACTGTACTCTCCGAGAGGTCGTTTTCCCGTCCCCGAGAGCAAGTTTATTT<br>ACAAATGTTGGAGTAATAAAGAAGGCAGAACAAAATGAGCTGGGCTTTGGAAGAATGGAAAGAAGGGCTG<br>CCTACAAGAGCTCTTCAGAAAATTCAAGAGCTTGAAGGACAGCTTGACAAACTGAAGAAGGAAAAGCAGC<br>AAAGGCAGTTTCAGCTTGACAGTCTCGAGGCTGCGCTGCAGAAGCAAAAACAGAAGGTTGAAAATGAAAA<br>AACCGAGGGTACAAACCTGAAAAGGGAGAATCAAAGATTGATGGAAATATGTGAAAGTCTGGAGAAAACT<br>AAGCAGAAGATTTCTCATGAACTTCAAGTCAAGGAGTCACAAGTGAATTTCCAGGAAGGACAACTGAATT<br>CAGGCAAAAAACAAATAGAAAAACTGGAACAGGAACTTAAAAGGTGTAAATCTGAGCTTGAAAGAAGCCA<br>ACAAGCTGCGCAGTCTGCAGATGTCTCTCTGAATCCATGCAATACACCACAAAAAATTTTTACAACTCCA<br>CTAACACCAAGTCAATATTATAGTGGTTCCAAGTATGAAGATCTAAAAGAAAAATATAATAAAGAGGTTG<br>AAGAACGAAAAAGATTAGAGGCAGAGGTTAAAGCCTTGCAGGCTAAAAAAGCAAGCCAGACTCTTCCACA<br>AGCCACCATGAATCACCGCGACATTGCCCGGCATCAGGCTTCATCATCTGTGTTCTCATGGCAGCAAGAG<br>AAGACCCCAAGTCATCTTTCATCTAATTCTCAAAGAACTCCAATTAGGAGAGATTTCTCTGCATCTTACT<br>TTTCTGGGGAACAAGAGGTGACTCCAAGTCGATCAACTTTGCAAATAGGGAAAAGAGATGCTAATAGCAG<br>TTTCTTTGACAATTCTAGCAGTCCTCATCTTTTGGATCAATTAAAAGCGCAGAATCAAGAGCTAAGAAAC<br>AAGATTAATGAGTTGGAACTACGCCTGCAAGGACATGAAAAAGAAATGAAAGGCCAAGTGAATAAGTTTC<br>AAGAACTCCAACTCCAACTGGAGAAAGCAAAAGTGGAATTAATTGAAAAAGAGAAAGTTTTGAACAAATG<br>TAGGGATGAACTAGTGAGAACAACAGCACAATACGACCAGGCGTCAACCAAGTATACTGCATTGGAACAA<br>AAACTGAAAAAATTGACGGAAGATTTGAGTTGTCAGCGACAAAATGCAGAAAGTGCCAGATGTTCTCTGG<br>AACAGAAAATTAAGGAAAAAGAAAAGGAGTTTCAAGAGGAGCTCTCCCGTCAACAGCGTTCTTTCCAAAC<br>ACTGGACCAGGAGTGCATCCAGATGAAGGCCAGACTCACCCAGGAGTTACAGCAAGCCAAGAATATGCAC<br>AACGTCCTGCAGGCTGAACTGGATAAACTCACATCAGTAAAGCAACAGCTAGAAAACAATTTGGAAGAGT<br>TTAAGCAAAAGTTGTGCAGAGCTGAACAGGCGTTCCAGGCGAGTCAGATCAAGGAGAATGAGCTGAGGAG<br>AAGCATGGAGGAAATGAAGAAGGAAAACAACCTCCTTAAGAGTCACTCTGAGCAAAAGGCCAGAGAAGTC<br>TGCCACCTGGAGGCAGAACTCAAGAACATCAAACAGTGTTTAAATCAGAGCCAGAATTTTGCAGAAGAAA<br>TGAAAGCGAAGAATACCTCTCAGGAAACCATGTTAAGAGATCTTCAAGAAAAAATAAATCAGCAAGAAAA<br>CTCCTTGACTTTAGAAAAACTGAAGCTTGCTGTGGCTGATCTGGAAAAGCAGCGAGATTGTTCTCAAGAC<br>CTTTTGAAGAAAAGAGAACATCACATTGAACAACTTAATGATAAGTTAAGCAAGACAGAGAAAGAGTCCA<br>AAGCCTTGCTGAGTGCTTTAGAGTTAAAAAAGAAAGAATATGAAGAATTGAAAGAAGAGAAAACTCTGTT<br>TTCTTGTTGGAAAAGTGAAAACGAAAAACTTTTAACTCAGATGGAATCAGAAAAGGAAAACTTGCAGAGT<br>AAAATTAATCACTTGGAAACTTGTCTGAAGACACAGCAAATAAAAAGTCATGAATACAACGAGAGAGTAA<br>GAACGCTGGAGATGGACAGAGAAAACCTAAGTGTCGAGATCAGAAACCTTCACAACGTGTTAGACAGTAA<br>GTCAGTGGAGGTAGAGACCCAGAAACTAGCTTATATGGAGCTACAGCAGAAAGCTGAGTTCTCAGATCAG<br>AAACATCAGAAGGAAATAGAAAATATGTGTTTGAAGACTTCTCAGCTTACTGGGCAAGTTGAAGATCTAG<br>AACACAAGCTTCAGTTACTGTCAAATGAAATAATGGACAAAGACCGGTGTTACCAAGACTTGCATGCCGA<br>ATATGAGAGCCTCAGGGATCTGCTAAAATCCAAAGATGCTTCTCTGGTGACAAATGAAGATCATCAGAGA<br>AGTCTTTTGGCTTTTGATCAGCAGCCTGCCATGCATCATTCCTTTGCAAATATAATTGGAGAACAAGGAA<br>GCATGCCTTCAGAGAGGAGTGAATGTCGTTTAGAAGCAGACCAAAGTCCGAAAAATTCTGCCATCCTACA<br>AAATAGAGTTGATTCACTTGAATTTTCATTAGAGTCTCAAAAACAGATGAACTCAGACCTGCAAAAGCAG<br>TGTGAAGAGTTGGTGCAAATCAAAGGAGAAATAGAAGAAAATCTCATGAAAGCAGAACAGATGCATCAAA<br>GTTTTGTGGCTGAAACAAGTCAGCGCATTAGTAAGTTACAGGAAGACACTTCTGCTCACCAGAATGTTGT<br>TGCTGAAACCTTAAGTGCCCTTGAGAACAAGGAAAAAGAGCTGCAACTTTTAAATGATAAGGTAGAAACT<br>GAGCAGGCAGAGATTCAAGAATTAAAAAAGAGCAACCATCTACTTGAAGACTCTCTAAAGGAGCTACAAC<br>TTTTATCCGAAACCCTAAGCTTGGAGAAGAAAGAAATGAGTTCCATCATTTCTCTAAATAAAAGGGAAAT<br>TGAAGAGCTGACCCAAGAGAATGGGACTCTTAAGGAAATTAATGCATCCTTAAATCAAGAGAAGATGAAC<br>TTAATCCAGAAAAGTGAGAGTTTTGCAAACTATATAGATGAAAGGGAGAAAAGCATTTCAGAGTTATCTG<br>ATCAGTACAAGCAAGAAAAACTTATTTTACTACAAAGATGTGAAGAAACCGGAAATGCATATGAGGATCT<br>TAGTCAAAAATACAAAGCAGCACAGGAAAAGAATTCTAAATTAGAATGCTTGCTAAATGAATGCACTAGT<br>CTTTGTGAAAATAGGAAAAATGAGTTGGAACAGCTAAAGGAAGCATTTGCAAAGGAACACCAAGAATTCT<br>TAACAAAATTAGCATTTGCTGAAGAAAGAAATCAGAATCTGATGCTAGAGTTGGAGACAGTGCAGCAAGC<br>TCTGAGATCTGAGATGACAGATAACCAAAACAATTCTAAGAGCGAGGCTGGTGGTTTAAAGCAAGAAATC<br>ATGACTTTAAAGGAAGAACAAAACAAAATGCAAAAGGAAGTTAATGACTTATTACAAGAGAATGAACAGC | 115 |

TABLE 2-continued

| GENBANK ACCESSION NUMBER | SEQUENCE | SEQ ID NO: |
|---|---|---|
| | TGATGAAGGTAATGAAGACTAAACATGAATGTCAAAATCTAGAATCAGAACCAATTAGGAACTCTGTGAA | |
| | AGAAAGAGAGAGTGAGAGAAATCAATGTAATTTTAAACCTCAGATGGATCTTGAAGTTAAAGAAATTTCT | |
| | CTAGATAGTTATAATGCGCAGTTGGTGCAATTAGAAGCTATGCTAAGAAATAAGGAATTAAAACTTCAGG | |
| | AAAGTGAGAAGGAGAAGGAGTGCCTGCAGCATGAATTACAGACAATTAGAGGAGATCTTGAAACCAGCAA | |
| | TTTGCAAGACATGCAGTCACAAGAAATTAGTGGCCTTAAAGACTGTGAAATAGATGCGGAAGAAAAGTAT | |
| | ATTTCAGGGCCTCATGAGTTGTCAACAAGTCAAAACGACAATGCACACCTTCAGTGCTCTCTGCAAACAA | |
| | CAATGAACAAGCTGAATGAGCTAGAGAAAATATGTGAAATACTGCAGGCTGAAAAGTATGAACTCGTAAC | |
| | TGAGCTGAATGATTCAAGGTCAGAATGTATCACAGCAACTAGGAAAATGGCAGAAGAGGTAGGGAAACTA | |
| | CTAAATGAAGTTAAAATATTAAATGATGACAGTGGTCTTCTCCATGGTGAGTTAGTGGAAGACATACCAG | |
| | GAGGTGAATTTGGTGAACAACCAAATGAACAGCACCCTGTGTCTTTGGCTCCATTGGACGAGAGTAATTC | |
| | CTACGAGCACTTGACATTGTCAGACAAAGAAGTTCAAATGCACTTTGCCGAATTGCAAGAGAAATTCTTA | |
| | TCTTTACAAAGTGAACACAAAATTTTACATGATCAGCACTGTCAGATGAGCTCTAAAATGTCAGAGCTGC | |
| | AGACCTATGTTGACTCATTAAAGGCCGAAAATTTGGTCTTGTCAACGAATCTGAGAAACTTTCAAGGTGA | |
| | CTTGGTGAAGGAGATGCAGCTGGGCTTGGAGGAGGGGCTCGTTCCATCCCTGTCATCCTCTTGTGTGCCT | |
| | GACAGCTCTAGTCTTAGCAGTTTGGGAGACTCCTCCTTTTACAGAGCTCTTTTAGAACAGACAGGAGATA | |
| | TGTCTCTTTTGAGTAATTTAGAAGGGGCTGTTTCAGCAAACCAGTGCAGTGTAGATGAAGTATTTTGCAG | |
| | CAGTCTGCAGGAGGAGAATCTGACCAGGAAAGAAACCCCTTCGGCCCCAGCGAAGGGTGTTGAAGAGCTT | |
| | GAGTCCCTCTGTGAGGTGTACCGGCAGTCCCTCGAGAAGCTAGAAGAGAAAATGGAAAGTCAAGGGATTA | |
| | TGAAAAATAAGGAAATTCAAGAGCTCGAGCAGTTATTAAGTTCTGAAAGGCAAGAGCTTGACTGCCTTAG | |
| | GAAGCAGTATTTGTCAGAAAATGAACAGTGGCAACAGAAGCTGACAAGCGTGACTCTGGAGATGGAGTCC | |
| | AAGTTGGCGGCAGAAAAGAAACAGACGGAACAACTGTCACTTGAGCTGGAAGTAGCACGACTCCAGCTAC | |
| | AAGGTCTGGACTTAAGTTCTCGGTCTTTGCTTGGCATCGACACAGAAGATGCTATTCAAGGCCGAAATGA | |
| | GAGCTGTGACATATCAAAAGAACATACTTCAGAAACTACAGAAAGAACACCAAAGCATGATGTTCATCAG | |
| | ATTTGTGATAAAGATGCTCAGCAGGACCTCAATCTAGACATTGAGAAAATAACTGAGACTGGTGCAGTGA | |
| | AACCCACAGGAGAGTGCTCTGGGGAACAGTCCCCAGATACCAATTATGAGCCTCCAGGGGAAGATAAAAC | |
| | CCAGGGCTCTTCAGAATGCATTTCTGAATTGTCATTTTCTGGTCCTAATGCTTTGGTACCTATGGATTTC | |
| | CTGGGGAATCAGGAAGATATCCATAATCTTCAACTGCGGGTAAAAGAGACATCAAATGAGAATTTGAGAT | |
| | TACTTCATGTGATAGAGGACCGTGACAGAAAAGTTGAAAGTTTGCTAAATGAAATGAAAGAATTAGACTC | |
| | AAAACTCCATTTACAGGAGGTACAACTAATGACCAAAATTGAAGCATGCATAGAATTGGAAAAAATAGTT | |
| | GGGGAACTTAAGAAAGAAAACTCAGATTTAAGTGAAAAATTGGAATATTTTTCTTGTGATCACCAGGAGT | |
| | TACTCCAGAGAGTAGAAACTTCTGAAGGCCTCAATTCTGATTTAGAAATGCATGCAGATAAATCATCACG | |
| | TGAAGATATTGGAGATAATGTGGCCAAGGTGAATGACAGCTGGAAGGAGAGATTTCTTGATGTGGAAAAT | |
| | GAGCTGAGTAGGATCAGATCGGAGAAAGCTAGCATTGAGCATGAAGCCCTCTACCTGGAGGCTGACTTAG | |
| | AGGTAGTTCAAACAGAGAAGCTATGTTTAGAAAAAGACAATGAAAATAAGCAGAAGGTTATTGTCTGCCT | |
| | TGAAGAAGAACTCTCAGTGGTCACAAGTGAGAGAAACCAGCTTCGTGGAGAATTAGATACTATGTCAAAA | |
| | AAAACCACGGCACTGGATCAGTTGTCTGAAAAAATGAAGGAGAAAACACAAGAGCTTGAGTCTCATCAAA | |
| | GTGAGTGTCTCCATTGCATTCAGGTGGCAGAGGCAGAGGTGAAGGAAAAGACGGAACTCCTTCAGACTTT | |
| | GTCCTCTGATGTGAGTGAGCTGTTAAAAGACAAAACTCATCTCCAGGAAAAGCTGCAGAGTTTGGAAAAG | |
| | GACTCACAGGCACTGTCTTTGACAAAATGTGAGCTGGAAAACCAAATTGCACAACTGAATAAAGAGAAAG | |
| | AATTGCTTGTCAAGGAATCTGAAAGCCTGCAGGCCAGACTGAGTGAATCAGATTATGAAAAGCTGAATGT | |
| | CTCCAAGGCCTTGGAGGCCGCACTGGTGGAGAAAGGTGAGTTCGCATTGAGGCTGAGCTCAACACAGGAG | |
| | GAAGTGCATCAGCTGAGAAGAGGCATCGAGAAACTGAGAGTTCGCATTGAGGCCGATGAAAAGAAGCAGC | |
| | TGCACATCGCAGAGAAACTGAAAGAACGCGAGCGGGAGAATGATTCACTTAAGGATAAAGTTGAGAACCT | |
| | TGAAAGGGAATTGCAGATGTCAGAAGAAAACCAGGAGCTAGTGATTCTTGATGCCGAGAATTCCAAAGCA | |
| | GAAGTAGAGACTCTAAAAACACAAATAGAAGAGATGGCCAGAAGCCTGAAAGTTTTTGAATTAGACCTTG | |
| | TCACGTTAAGGTCTGAAAAAGAAAATCTGACAAAACAAATACAAGAAAAACAAGGTCAGTTGTCAGAACT | |
| | AGACAAGTTACTCTCTTCATTTAAAAGTCTGTTAGAAGAAAAGGAGCAAGCAGAGATACAGATCAAAGAA | |
| | GAATCTAAAACTGCAGTGGAGATGCTTCAGAATCAGTTAAAGGAGCTAAATGAGGCAGTAGCAGCCTTGT | |
| | GTGGTGACCAAGAAATTATGAAGGCCACAGAACAGAGTCTAGACCCACCAATAGAGGAAGAGCATCAGCT | |
| | GAGAAATAGCATTGAAAAGCTGAGAGCCCGCCTAGAAGCTGATGAAAAGAAGCAGCTCTGTGTCTTACAA | |
| | CAACTGAAGGAAAGTGAGCATCATGCAGATTTACTTAAGGGTAGAGTGGAGAACCTTGAAAGAGAGCTAG | |
| | AGATAGCCAGGACAAACCAAGAGCATGCAGCTCTTGAGGCAGAGAATTCCAAAGGAGAGGTAGAGACCCT | |
| | AAAAGCAAAAATAGAAGGGATGACCCAAAGTCTGAGAGGTCTGGAATTAGATGTTGTTACTATAAGGTCA | |
| | GAAAAAGAAAATCTGACAAATGAATTACAAAAAGAGCAAGAGCGAATATCTGAATTAGAAATAATAAATT | |
| | CATCATTTGAAAATATTTTGCAAGAAAAAGAGCAAGAGAAAGTACAGATGAAAGAAAAATCAAGCACTGC | |
| | CATGGAGATGCTTCAAACACAATTAAAAGAGCTCAATGAGAGAGTGGCAGCCCTGCATAATGACCAAGAA | |
| | GCCTGTAAGGCCAAAGAGCAGAATCTTAGTAGTCAAGTAGAGTGTCTTGAACTTGAGAAGGCTCAGTTGC | |
| | TACAAGGCCTTGATGAGGCCAAAAATAATTATATTGTTTTGCAATCTTCAGTGAATGGCCTCATTCAAGA | |
| | AGTAGAAGATGGCAAGCAGAAACTGGAGAAGAAGGATGAAGAAATCAGTAGACTGAAAAATCAAATTCAA | |
| | GACCAAGAGCAGCTTGTCTCTAAACTGTCCCAGGTGGAAGGAGAGCACCAACTTTGGAAGGAGCAAAACT | |
| | TAGAACTGAGAAATCTGACAGTGGAATTGGAGCAGAAGATCCAAGTGCTACAATCCAAAAATGCCTCTTT | |
| | GCAGGACACATTAGAAGTGCTGCAGAGTTCTTACAAGAATCTAGAGAATGAGCTTGAATTGACAAAAATG | |
| | GACAAAATGTCCTTTGTTGAAAAAGTAAACAAAATGACTGCAAAGGAAACTGAGCTGCAGAGGGAAATGC | |
| | ATGAGATGGCACAGAAAACAGCAGAGCTGCAAGAAGAACTCAGTGGAGAGAAAAATAGGCTAGCTGGAGA | |
| | GTTGCAGTTACTGTTGGAAGAAATAAAGAGCAGCAAAGATCAATTGAAGGAGCTCACACTAGAAAATAGT | |
| | GAATTGAAGAAGAGCCTAGATTGCATGCACAAAGACCAGGTGGAAAAGGAAGGGAAAGTGAGAGAGGAAA | |
| | TAGCTGAATATCAGCTACGGCTTCATGAAGCTGAAAAGAAACACCAGGCTTTGCTTTTGGACACAAACAA | |
| | ACAGTATGAAGTAGAAATCCAGACATACCGAGAGAAATTGACTTCTAAAGAAGAATGTCTCAGTTCACAG | |
| | AAGCTGGAGATAGACCTTTTAAAGTCTAGTAAAGAAGAGCTCAATAATTCATTGAAAGCTACTACTCAGA | |
| | TTTTGGAAGAATTGAAGAAAACCAAGATGGACAATCTAAAATATGTAAATCAGTTGAAGAAGGAAAATGA | |
| | ACGTGCCCAGGGGAAAATGAAGTTGTTGATCAAATCCTGTAAACAGCTGGAAGAGGAAAAGGAGATACTG | |
| | CAGAAAGAACTCTCTCAACTTCAAGCTGCACAGGAGAAGCAGAAAACAGGTACTGTTATGGATACCAAGG | |
| | TCGATGAATTAACAACTGAGATCAAAGAACTGAAAGAAACTCTTGAAGAAAAAACCAAGGAGGCAGATGA | |
| | ATACTTGGATAAGTACTGTTCCTTGCTTATAAGCCATGAAAAGTTAGAGAAAGCTAAAGAGATGTTAGAG | |
| | ACACAAGTGGCCCATCTGTGTTCACAGCAATCTAAACAAGATTCCCGAGGGTCTCCTTTGCTAGGTCCAG | |
| | TTGTTCCAGGACCATCTCCAATCCCTTCTGTTACTGAAAAGAGGTTATCATCTGGCCAAAATAAAGCTTC | |

TABLE 2-continued

| GENBANK ACCESSION NUMBER | SEQUENCE | SEQ ID NO: |
|---|---|---|
| | AGGCAAGAGGCAAAGATCCAGTGGAATATGGGAGAATGGTAGAGGACCAACACCTGCTACCCCAGAGAGC<br>TTTTCTAAAAAAAGCAAGAAAGCAGTCATGAGTGGTATTCACCCTGCAGAAGACACGGAAGGTACTGAGT<br>TTGAGCCAGAGGGACTTCCAGAAGTTGTAAAGAAAGGGTTTGCTGACATCCCGACAGGAAAGACTAGCCC<br>ATATATCCTGCGAAGAACAACCATGGCAACTCGGACCAGCCCCCGCCTGGCTGCACAGAAGTTAGCGCTA<br>TCCCCACTGAGTCTCGGCAAAGAAAATCTTGCAGAGTCCTCCAAACCAACAGCTGGTGGCAGCAGATCAC<br>AAAAGGTCAAAGTTGCTCAGCGGAGCCCAGTAGATTCAGGCACCATCCTCCGAGAACCCACCACGAAATC<br>CGTCCCAGTCAATAATCTTCCTGAGAGAAGTCCGACTGACAGCCCCAGAGAGGGCCTGAGGGTCAAGCGA<br>GGCCGACTTGTCCCCAGCCCCAAAGCTGGACTGGAGTCCAACGGCAGTGAGAACTGTAAGGTCCAGTGAA<br>GGCACTTTGTGTGTCAGTACCCCTGGGAGGTGCCAGTCATTGAATAGATAAGGCTGTGCCTACAGGACTT<br>CTCTTTAGTCAGGGCATGCTTTATTAGTGAGGAGAAAACAATTCCTTAGAAGTCTTAAATATATTGTACT<br>CTTTAGATCTCCCATGTGTAGGTATTGAAAAAGTTTGGAAGCACTGATCACCTGTTAGCATTGCCATTCC<br>TCTACTGCAATGTAAATAGTATAAAGCTATGTATATAAAGCTTTTTGGTAATATGTTACAATTAAAATGA<br>CAAGCACTATATCACAATCTCTGTTTGTATGTGGGTTTTACACTAAAAAAATGCAAAACACATTTTATTC<br>TTCTAATTAACAGCTCCTAGGAAAATGTAGACTTTTGCTTTATGATATTCTATCTGTAGTATGAGGCATG<br>GAATAGTTTTGTATCGGGAATTTCTCAGAGCTGAGTAAAATGAAGGAAAAGCATGTTATGTGTTTTTAAG<br>GAAAATGTGCACACATATACATGTAGGAGTGTTTATCTTTCTCTTACAATCTGTTTTAGACATCTTTGCT<br>TATGAAACCTGTACATATGTGTGTGTGGGTATGTGTTTATTTCCAGTGAGGGCTGCAGGCTTCCTAGAGG<br>TGTGCTATACCATGCGTCTGTCGTTGTGCTTTTTTCTGTTTTTAGACCAATTTTTTACAGTTCTTTGGTA<br>AGCATTGTCGTATCTGGTGATGGATTAACATATAGCCTTTGTTTTCTAATAAAATAGTCGCCTTCGTTTT<br>CTGTAAAAAAAAAAAAAAAAAAAAA | |
| AB091343 | GGCACGAGGGGCCGACGCGAGCGCCGCGCTTCGCTTCAGCTGCTAGCTGGCCCAAGGGAGGCGACCGCGG<br>AGGGTGGCGAGGGGCGGCCAGGACCCGCAGCCCCGGGGCCGGGCCGGTCCGGACCGCCAGGGAGGGCAGG<br>TCAGTGGGCAGATCGCGTCCGCGGGATTCAATCTCTGCCCGCTCTGATAACAGTCCTTTTCCCTGGCGCT<br>CACTTCGTGCCTGGCACCCGGCTGGGCGCCTCAAGACCGTTGTCTCTTCGATCGCTTCTTTGGACTTGGC<br>GACCATTTCAGAGATGTCTTCCAGAAGTACCAAAGATTTAATTAAAAGTAAGTGGGGATCGAAGCCTAGT<br>AACTCCAAATCCGAAACTACATTAGAAAAATTAAAGGGAGAAATTGCACACTTAAAGACATCAGTGGATG<br>AAATCACAAGTGGGAAAGGAAAGCTGACTGATAAAGAGAGACACAGACTTTTGGAGAAAATTCGAGTCCT<br>TGAGGCTGAGAAGGAGAAGAATGCTTATCAACTCACAGAGAAGGACAAAGAAATACAGCGACTGAGAGAC<br>CAACTGAAGGCCAGATATAGTACTACCGCATTGCTTGAACAGCTGGAAGAGACAACGAGAGAAGGAGAAA<br>GGAGGGAGCAGGTGTTGAAAGCCTTATCTGAAGAGAAAGACGTATTGAAACAACAGTTGTCTGCTGCAAC<br>CTCACGAATTGCTGAACTTGAAAGCAAAACCAATACACTCCGTTTATCACAGACTGTGGCTCCAAACTGC<br>TTCAACTCATCAATAAATAATATTCATGAAATGGAAATACAGCTGAAAGATGCTCTGGAGAAAAATCAGC<br>AGTGGCTCGTGTATGATCAGCAGCGGGAAGTCTATGTAAAAGGACTTTTAGCAAAGATCTTTGAGTTGGA<br>AAAGAAAACGGAAACAGCTGCTCATTCACTCCCACAGCAGACAAAAAAGCCTGAATCAGAAGGTTATCTT<br>CAAGAAGAGAAGCAGAAATGTTACAACGATCTCTTGGCAAGTGCAAAAAAAGATCTTGAGGTTGAACGAC<br>AAACCATAACTCAGCTGAGTTTTGAACTGAGTGAATTTCGAAGAAAATATGAAGAAACCCAAAAAGAAGT<br>TCACAATTTAAATCAGCTGTTGTATTCACAAAGAAGGGCAGATGTGCAACATCTGGAAGATGATAGGCAT<br>AAAACAGAGAAGATACAAAAACTCAGGGAAGAGAATGATATTGCTAGGGGAAAACTTGAAGAAGAGAAGA<br>AGAGATCCGAAGAGCTCTTATCTCAGGTCCAGTTTCTTTACACATCTCTGCTAAAGCAGCAAGAAGAACA<br>AACAAGGGTAGCTCTGTTGGAACAACAGATGCAGGCATGTACTTTAGACTTTGAAAATGAAAAACTCGAC<br>CGTCAACATGTGCAGCATCAATTGCATGTAATTCTTAAGGAGCTCCGAAAAGCAAGAAATCAAATAACAC<br>AGTTGGAATCCTTGAAACAGCTTCATGAGTTTGCCATCACAGAGCCATTAGTCACTTTCCAAGGAGAGAC<br>TGAAAACAGAGAAAAAGTTGCCGCCTCACCAAAAAGTCCCACTGCTGCACTCAATGAAAGCCTGGTGGAA<br>TGTCCCAAGTGCAATATACAGTATCCAGCCACTGAGCATCGCGATCTGCTTGTCCATGTGGAATACTGTT<br>CAAAGTAGCAAAATAAGTATTTGTTTTGATATTAAAAGATTCAATACTGTATTTTCTGTTAGCTTGTGGG<br>CATTTTGAATTATATATTTCACATTTTGCATAAAACTGCCTATCTACCTTTGACACTCCAGCATGCTAGT<br>GAATCATGTATCTTTTAGGCTGCTGTGCATTTCTCTTGGCAGTGATACCTCCCTGACATGGTTCATCATC<br>AGGCTGCAATGACAGAATGTGGTGAGCAGCGTCTACTGAGACTACTAACATTTTGCACTGTCAAAATACT<br>TGGTGAGGAAAAGATAGCTCAGGTTATTGCTAATGGGTTAATGCACCAGCAAGCAAAATATTTTATGTTT<br>TGGGGGTTTGAAAAATCAAAGATAATTAACCAAGGATCTTAACTGTGTTCGCATTTTTTATCCAAGCACT<br>TAGAAAACCTACAATCCTAATTTTGATGTCCATTGTTAAGAGGTGGTGATAGATACTATTTTTTTTTTCA<br>TATTGTATAGCGGTTATTAGAAAAGTTGGGGATTTTCTTGATCTTTATTGCTGCTTACCATTGAAACTTA<br>ACCCAGCTGTGTTCCCCAACTCTGTTCTGCGCACGAAACAGTATCTGTTTGAGGCATAATCTTAAGTGGC<br>CACACACAATGTTTTCTCTTATGTTATCTGGCAGTAACTGTAACTTGAATTACATTAGCACATTCTGCTT<br>AGCTAAAATTGTTAAAATAAACTTTAATAAACCCATGTAGCCCTCTCATTTGATTGACAGTATTTTAGTT<br>ATTTTTGGCATTCTTAAAGCTGGGCAATGTAATGATCAGATCTTTGTTTGTCTGAACAGGTATTTTTATA<br>CATGCTTTTTGTAAACCAAAAACTTTTAAATTTCTTCAGGTTTTCTAACATGCTTACCACTGGGCTACTG<br>TAAATGAGAAAAGAATAAAATTATTTAATGTTTTAAAAAAAAAAAAAAA | 116 |
| BC006428 | GGCGGCTGAGCCTGAGCGGGGATGTAGAGGCGGCGGCAGCAGAGGCGGCACTGGCGGCAAGAGCAGACGC<br>CCGAGCCGAGCGAGAAGAGCGGCAGAGCCTTATCCCCTGAAGCCGGGCCCCGCGTCCCAGCCCTGCCCAG<br>CCCGCGCCCAGCCATGCGCGCCGCCTGCTGAGTCCGGGCGCCGCACGCTGAGCCCTCCGCCCGCGAGCCG<br>CGCTCAGCTCGGGGGTGATTAGTTGCTTTTTGTTGTTTTTTAATTTGGGCCGCGGGGAGGGGGAGGAGGG<br>GCAGGTGCTGCAGGCTCCCCCCCCTCCCCGCCTCGGGCCAGCCGCGGCGGCGCGACTCGGGCTCCGGACC<br>CGGGCACTGCTGGCGGCTGGAGCGGAGCGCACCGCGGCGGTGGTGCCCAGAGCGGAGCGCAGCTCCCTGC<br>CCCGCCCCTCCCCCTCGGCCTCGCGGCGACGGCGGCGGTGGCGGCTTGGACGACTCGGAGAGCCGAGTGA<br>AGACATTTCCACCTGGACACCTGACCATGTGCCTGCCCTGAGCAGCGAGGCCCACCAGGCATCTCTGTTG<br>TGGGCAGCAGGGCCAGGTCCTGGTCTGTGGACCCTCGGCAGTTGGCAGGCTCCCTCTGCAGTGGGGTCTG<br>GGCCTCGGCCCCACCATGTCGAGCCTCGGCGGTGGCTCCCAGGATGCCGGCGGCAGTAGCAGCAGCAGCA<br>CCAATGGCAGCGGTGGCAGTGGCAGCAGTGGCCCAAAGGCAGGAGCAGCAGACAAGAGTGCAGTGGTGGC<br>TGCCGCCGCACCAGCCTCAGTGGCAGATGACACACCACCCCCCGAGCGTCGGAACAAGAGCGGTATCATC<br>AGTGAGCCCCTCAACAAGAGCCTGCGCCGCTCCCGCCCGCTCTCCCACTACTCTTCTTTTGGCAGCAGTG<br>GTGGTAGTGGCGGTGGCAGCATGATGGGCGGAGAGTCTGCTGACAAGGCCACTGCGGCTGCAGCCGCTGC<br>CTCCCTGTTGGCCAATGGGCATGACCTGGCGGCGGCCATGGCGGTGGACAAAAGCAACCCTACCTCAAAG<br>CACAAAAGTGGTGCTGTGGCCAGCCTGCTGAGCAAGGCAGAGCGGGCCACGGAGCTGGCAGCCGAGGGAC | 117 |

TABLE 2-continued

| GENBANK ACCESSION NUMBER | SEQUENCE | SEQ ID NO: |
|---|---|---|
| | AGCTGACGCTGCAGCAGTTTGCGCAGTCCACAGAGATGCTGAAGCGCGTGGTGCAGGAGCATCTCCCGCT | |
| | GATGAGCGAGGCGGGTGCTGGCCTGCCTGACATGGAGGCTGTGGCAGGTGCCGAAGCCCTCAATGGCCAG | |
| | TCCGACTTCCCCTACCTGGGCGCTTTCCCCATCAACCCAGGCCTCTTCATTATGACCCCGGCAGGTGTGT | |
| | TCCTGGCCGAGAGCGCGCTGCACATGGCGGGCCTGGCTGAGTACCCCATGCAGGGAGAGCTGGCCTCTGC | |
| | CATCAGCTCCGGCAAGAAGAAGCGGAAACGCTGCGGCATGTGCGCGCCCTGCCGGCGGCGCATCAACTGC | |
| | GAGCAGTGCAGCAGTTGTAGGAATCGAAAGACTGGCCATCAGATTTGCAAATTCAGAAAATGTGAGGAAC | |
| | TCAAAAAGAAGCCTTCCGCTGCTCTGGAGAAGGTGATGCTTCCGACGGGAGCCGCCTTCCGGTGGTTTCA | |
| | GTGACGGCGGCGGAACCCAAAGCTGCCCTCTCCGTGCAATGTCACTGCTCGTGTGGTCTCCAGCAAGGGA | |
| | TTCGGGCGAAGACAAACGGATGCACCCGTCTTTAGAACCAAAAATATTCTCTCACAGATTTCATTCCTGT | |
| | TTTTATATATATATTTTTTGTTGTCGTTTTAACATCTCCACGTCCCTAGCATAAAAAGAAAAAGAAAAAA | |
| | ATTTAAACTGCTTTTTCGGAAGAACAACAACAAAAAAGAGGTAAAGACGAATCTATAAAGTACCGAGACT | |
| | TCCTGGGCAAAGAATGGACAATCAGTTTCCTTCCTGTGTCGATGTCGATGTTGTCTGTGCAGGAGATGCA | |
| | GTTTTTGTGTAGAGAATGTAAATTTTCTGTAACCTTTTGAAATCTAGTTACTAATAAGCACTACTGTAAT | |
| | TTAGCACAGTTTAACTCCACCCTCATTTAAACTTCCTTTGATTCTTTCCGACCATGAAATAGTGCATAGT | |
| | TTGCCTGGAGAATCCACTCACGTTCATAAAGAGAATGTTGATGGCGCCGTGTAGAAGCCGCTCTGTATCC | |
| | ATCCACGCGTGCAGAGCTGCCAGCAGGGAGCTCACAGAAGGGGAGGGAGCACCAGGCCAGCTGAGCTGCA | |
| | CCCACAGTCCCGAGACTGGGATCCCCCACCCCAACAGTGATTTTGGAAAAAAAAATGAAAGTTCTGTTCG | |
| | TTTATCCATTGCGATCTGGGGAGCCCCATCTCGATATTTCCAATCCTGGCTACTTTTCTTAGAGAAAATA | |
| | AGTCCTTTTTTTCTGGCCTTGCTAATGGCAACAGAAGAAAGGGCTTCTTTGCGTGGTCCCCTGCTGGTGG | |
| | GGGTGGGTCCCCAGGGGGCCCCCTGCGGCCTGGGCCCCCCTGCCCACGGCCAGCTTCCTGCTGATGAACA | |
| | TGCTGTTTGTATTGTTTTAGGAAACCAGGCTGTTTTGTGAATAAAACGAATGCATGTTTGTGTCACGAAA | |
| | AAAAAAAAAAAAAAAAAAAAAAAAAAAAAAAAAAAAAAAAAA | |
| NM_005228 | CCCCGGCGCAGCGCGGCCGCAGCAGCCTCCGCCCCCCGCACGGTGTGAGCGCCCGACGCGGCCGAGGCGG | 118 |
| | CCGGAGTCCCGAGCTAGCCCCGGCGGCCGCCGCCGCCCAGACCGGACGACAGGCCACCTCGTCGGCGTCC | |
| | GCCCGAGTCCCCGCCTCGCCGCCAACGCCACAACCACCGCGCACGGCCCCCTGACTCCGTCCAGTATTGA | |
| | TCGGGAGAGCCGGAGCGAGCTCTTCGGGGAGCAGCGATGCGACCCTCCGGGACGGCCGGGGCAGCGCTCC | |
| | TGGCGCTGCTGGCTGCGCTCTGCCCGGCGAGTCGGGCTCTGGAGGAAAAGAAAGTTTGCCAAGGCACGAG | |
| | TAACAAGCTCACGCAGTTGGGCACTTTTGAAGATCATTTTCTCAGCCTCCAGAGGATGTTCAATAACTGT | |
| | GAGGTGGTCCTTGGGAATTTGGAAATTACCTATGTGCAGAGGAATTATGATCTTTCCTTCTTAAAGACCA | |
| | TCCAGGAGGTGGCTGGTTATGTCCTCATTGCCCTCAACACAGTGGAGCGAATTCCTTTGGAAAACCTGCA | |
| | GATCATCAGAGGAAATATGTACTACGAAAATTCCTATGCCTTAGCAGTCTTATCTAACTATGATGCAAAT | |
| | AAAACCGGACTGAAGGAGCTGCCCATGAGAAATTTACAGGAAATCCTGCATGGCGCCGTGCGGTTCAGCA | |
| | ACAACCCTGCCCTGTGCAACGTGGAGAGCATCCAGTGGCGGGACATAGTCAGCAGTGACTTTCTCAGCAA | |
| | CATGTCGATGGACTTCCAGAACCACCTGGGCAGCTGCCAAAAGTGTGATCCAAGCTGTCCCAATGGGAGC | |
| | TGCTGGGGTGCAGGAGAGGAGAACTGCCAGAAACTGACCAAAATCATCTGTGCCCAGCAGTGCTCCGGGC | |
| | GCTGCCGTGGCAAGTCCCCCAGTGACTGCTGCCACAACCAGTGTGCTGCAGGCTGCACAGGCCCCCGGGA | |
| | GAGCGACTGCCTGGTCTGCCGCAAATTCCGAGACGAAGCCACGTGCAAGGACACCTGCCCCCCACTCATG | |
| | CTCTACAACCCCACCACGTACCAGATGGATGTGAACCCCGAGGGCAAATACAGCTTTGGTGCCACCTGCG | |
| | TGAAGAAGTGTCCCCGTAATTATGTGGTGACAGATCACGGCTCGTGCGTCCGAGCCTGTGGGGCCGACAG | |
| | CTATGAGATGGAGGAAGACGGCGTCCGCAAGTGTAAGAAGTGCGAAGGGCCTTGCCGCAAAGTGTGTAAC | |
| | GGAATAGGTATTGGTGAATTTAAAGACTCACTCTCCATAAATGCTACGAATATTAAACACTTCAAAAACT | |
| | GCACCTCCATCAGTGGCGATCTCCACATCCTGCCGGTGGCATTTAGGGGTGACTCCTTCACACATACTCC | |
| | TCCTCTGGATCCACAGGAACTGGATATTCTGAAAACCGTAAAGGAAATCACAGGGTTTTTGCTGATTCAG | |
| | GCTTGGCCTGAAAACAGGACGGACCTCCATGCCTTTGAGAACCTAGAAATCATACGCGGCAGGACCAAGC | |
| | AACATGGTCAGTTTTCTCTTGCAGTCGTCAGCCTGAACATAACATCCTTGGGATTACGCTCCCTCAAGGA | |
| | GATAAGTGATGGAGATGTGATAATTTCAGGAAACAAAAATTTGTGCTATGCAAATACAATAAACTGGAAA | |
| | AAACTGTTTGGGACCTCCGGTCAGAAAACCAAAATTATAAGCAACAGAGGTGAAAACAGCTGCAAGGCCA | |
| | CAGGCCAGGTCTGCCATGCCTTGTGCTCCCCCGAGGGCTGCTGGGGCCCGGAGCCCAGGGACTGCGTCTC | |
| | TTGCCGGAATGTCAGCCGAGGCAGGGAATGCGTGGACAAGTGCAACCTTCTGGAGGGTGAGCCAAGGGAG | |
| | TTTGTGGAGAACTCTGAGTGCATACAGTGCCACCCAGAGTGCCTGCCTCAGGCCATGAACATCACCTGCA | |
| | CAGGACGGGGACCAGACAACTGTATCCAGTGTGCCCACTACATTGACGGCCCCCACTGCGTCAAGACCTG | |
| | CCCGGCAGGAGTCATGGGAGAAAACAACACCCTGGTCTGGAAGTACGCAGACGCCGGCCATGTGTGCCAC | |
| | CTGTGCCATCCAAACTGCACCTACGGATGCACTGGGCCAGGTCTTGAAGGCTGTCCAACGAATGGGCCTA | |
| | AGATCCCGTCCATCGCCACTGGGATGGTGGGGGCCCTCCTCTTGCTGCTGGTGGTGGCCCTGGGGATCGG | |
| | CCTCTTCATGCGAAGGCGCCACATCGTTCGGAAGCGCACGCTGCGGAGGCTGCTGCAGGAGAGGGAGCTT | |
| | GTGGAGCCTCTTACACCCAGTGGAGAAGCTCCCAACCAAGCTCTCTTGAGGATCTTGAAGGAAACTGAAT | |
| | TCAAAAAGATCAAAGTGCTGGGCTCCGGTGCGTTCGGCACGGTGTATAAGGGACTCTGGATCCCAGAAGG | |
| | TGAGAAAGTTAAAATTCCCGTCGCTATCAAGGAATTAAGAGAAGCAACATCTCCGAAAGCCAACAAGGAA | |
| | ATCCTCGATGAAGCCTACGTGATGGCCAGCGTGGACAACCCCCACGTGTGCCGCCTGCTGGGCATCTGCC | |
| | TCACCTCCACCGTGCAGCTCATCACGCAGCTCATGCCCTTCGGCTGCCTCCTGGACTATGTCCGGGAACA | |
| | CAAAGACAATATTGGCTCCCAGTACCTGCTCAACTGGTGTGTGCAGATCGCAAAGGGCATGAACTACTTG | |
| | GAGGACCGTCGCTTGGTGCACCGCGACCTGGCAGCCAGGAACGTACTGGTGAAAACACCGCAGCATGTCA | |
| | AGATCACAGATTTTGGGCTGGCCAAACTGCTGGGTGCGGAAGAGAAAGAATACCATGCAGAAGGAGGCAA | |
| | AGTGCCTATCAAGTGGATGGCATTGGAATCAATTTTACACAGAATCTATACCCACCAGAGTGATGTCTGG | |
| | AGCTACGGGGTGACCGTTTGGGAGTTGATGACCTTTGGATCCAAGCCATATGACGGAATCCCTGCCAGCG | |
| | AGATCTCCTCCATCCTGGAGAAAGGAGAACGCCTCCCTCAGCCACCCATATGTACCATCGATGTCTACAT | |
| | GATCATGGTCAAGTGCTGGATGATAGACGCAGATAGTCGCCCAAAGTTCCGTGAGTTGATCATCGAATTC | |
| | TCCAAAATGGCCCGAGACCCCCAGCGCTACCTTGTCATTCAGGGGGATGAAAGAATGCATTTGCCAAGTC | |
| | CTACAGACTCCAACTTCTACCGTGCCCTGATGGATGAAGAAGACATGGACGACGTGGTGGATGCCGACGA | |
| | GTACCTCATCCCACAGCAGGGCTTCTTCAGCAGCCCCTCCACGTCACGGACTCCCCTCCTGAGCTCTCTG | |
| | AGTGCAACCAGCAACAATTCCACCGTGGCTTGCATTGATAGAAATGGGCTGCAAAGCTGTCCCATCAAGG | |
| | AAGACAGCTTCTTGCAGCGATACAGCTCAGACCCCACAGGCGCCTTGACTGAGGACAGCATAGACGACAC | |
| | CTTCCTCCCAGTGCCTGAATACATAAACCAGTCCGTTCCCAAAAGGCCCGCTGGCTCTGTGCAGAATCCT | |
| | GTCTATCACAATCAGCCTCTGAACCCCGCGCCCAGCAGAGACCCACACTACCAGGACCCCCACAGCACTG | |
| | CAGTGGGCAACCCCGAGTATCTCAACACTGTCCAGCCCACCTGTGTCAACAGCACATTCGACAGCCCTGC | |

TABLE 2-continued

| GENBANK ACCESSION NUMBER | SEQUENCE | SEQ ID NO: |
|---|---|---|
| | CCACTGGGCCCAGAAAGGCAGCCACCAAATTAGCCTGGACAACCCTGACTACCAGCAGGACTTCTTTCCC<br>AAGGAAGCCAAGCCAAATGGCATCTTTAAGGGCTCCACAGCTGAAAATGCAGAATACCTAAGGGTCGCGC<br>CACAAAGCAGTGAATTTATTGGAGCATGACCACGGAGGATAGTATGAGCCCTAAAAATCCAGACTCTTTC<br>GATACCCAGGACCAAGCCACAGCAGGTCCTCCATCCCAACAGCCATGCCCGCATTAGCTCTTAGACCCAC<br>AGACTGGTTTTGCAACGTTTACACCGACTAGCCAGGAAGTACTTCCACCTCGGGCACATTTTGGGAAGTT<br>GCATTCCTTTGTCTTCAAACTGTGAAGCATTTACAGAAACGCATCCAGCAAGAATATTGTCCCTTTGAGC<br>AGAAATTTATCTTTCAAAGAGGTATATTTGAAAAAAAAAAAAAGTATATGTGAGGATTTTTATTGATTGG<br>GGATCTTGGAGTTTTTCATTGTCGCTATTGATTTTTACTTCAATGGGCTCTTCCAACAAGGAAGAAGCTT<br>GCTGGTAGCACTTGCTACCCTGAGTTCATCCAGGCCCAACTGTGAGCAAGGAGCACAAGCCACAAGTCTT<br>CCAGAGGATGCTTGATTCCAGTGGTTCTGCTTCAAGGCTTCCACTGCAAAACACTAAAGATCCAAGAAGG<br>CCTTCATGGCCCCAGCAGGCCGGATCGGTACTGTATCAAGTCATGGCAGGTACAGTAGGATAAGCCACTC<br>TGTCCCTTCCTGGGCAAAGAAGAAACGGAGGGGATGGAATTCTTCCTTAGACTTACTTTTGTAAAAATGT<br>CCCCACGGTACTTACTCCCCACTGATGGACCAGTGGTTTCCAGTCATGAGCGTTAGACTGACTTGTTTGT<br>CTTCCATTCCATTGTTTTGAAACTCAGTATGCTGCCCCTGTCTTGCTGTCATGAAATCAGCAAGAGAGGA<br>TGACACATCAAATAATAACTCGGATTCCAGCCCACATTGGATTCATCAGCATTTGGACCAATAGCCCACA<br>GCTGAGAATGTGGAATACCTAAGGATAGCACCGCTTTTGTTCTCGCAAAAACGTATCTCCTAATTTGAGG<br>CTCAGATGAAATGCATCAGGTCCTTTGGGGCATAGATCAGAAGACTACAAAAATGAAGCTGCTCTGAAAT<br>CTCCTTTAGCCATCACCCCAACCCCCCAAAATTAGTTTGTGTTACTTATGGAAGATAGTTTTCTCCTTTT<br>ACTTCACTTCAAAAGCTTTTTACTCAAAGAGTATATGTTCCCTCCAGGTCAGCTGCCCCCAAACCCCCTC<br>CTTACGCTTTGTCACACAAAAAGTGTCTCTGCCTTGAGTCATCTATTCAAGCACTTACAGCTCTGGCCAC<br>AACAGGGCATTTTACAGGTGCGAATGACAGTAGCATTATGAGTAGTGTGGAATTCAGGTAGTAAATATGA<br>AACTAGGGTTTGAAATTGATAATGCTTTCACAACATTTGCAGATGTTTTAGAAGGAAAAAAGTTCCTTCC<br>TAAAATAATTTCTCTACAATTGGAAGATTGGAAGATTCAGCTAGTTAGGAGCCCACCTTTTTTCCTAATC<br>TGTGTGTGCCCTGTAACCTGACTGGTTAACAGCAGTCCTTTGTAAACAGTGTTTTAAACTCTCCTAGTCA<br>ATATCCACCCCATCCAATTTATCAAGGAAGAAATGGTTCAGAAAATATTTTCAGCCTACAGTTATGTTCA<br>GTCACACACACATACAAAATGTTCCTTTTGCTTTTAAAGTAATTTTTGACTCCCAGATCAGTCAGAGCCC<br>CTACAGCATTGTTAAGAAAGTATTTGATTTTTGTCTCAATGAAAATAAAACTATATTCATTTCCACTCTA<br>AAAAAAAAAAAAAAAA | |
| NM_001005862 | GTTCCCGGATTTTTGTGGGCGCCTGCCCCGCCCCTCGTCCCCCTGCTGTGTCCATATATCGAGGCGATAG<br>GGTTAAGGGAAGGCGGACGCCTGATGGGTTAATGAGCAAACTGAAGTGTTTTCCATGATCTTTTTTGAGT<br>CGCAATTGAAGTACCACCTCCCGAGGGTGATTGCTTCCCCATGCGGGGTAGAACCTTTGCTGTCCTGTTC<br>ACCACTCTACCTCCAGCACAGAATTTGGCTTATGCCTACTCAATGTGAAGATGATGAGGATGAAAACCTT<br>TGTGATGATCCACTTCCACTTAATGAATGGTGGCAAAGCAAAGCTATATTCAAGACCACATGCAAAGCTA<br>CTCCCTGAGCAAAGAGTCACAGATAAAACGGGGGCACCAGTAGAATGGCCAGGACAAACGCAGTGCAGCA<br>CAGAGACTCAGACCCTGGCAGCCATGCCTGCGCAGGCAGTGATGAGAGTGACATGTACTGTTGTGGACAT<br>GCACAAAAGTGAGTGTGCACCGGCACAGACATGAAGCTGCGGCTCCCTGCCAGTCCCGAGACCCACCTGG<br>ACATGCTCCGCCACCTCTACCAGGGCTGCCAGGTGGTGCAGGGAAACCTGGAACTCACCTACCTGCCCAC<br>CAATGCCAGCCTGTCCTTCCTGCAGGATATCCAGGAGGTGCAGGGCTACGTGCTCATCGCTCACAACCAA<br>GTGAGGCAGGTCCCACTGCAGAGGCTGCGGATTGTGCGAGGCACCCAGCTCTTTGAGGACAACTATGCCC<br>TGGCCGTGCTAGACAATGGAGACCCGCTGAACAATACCACCCCTGTCACAGGGGCCTCCCCAGGAGGCCT<br>GCGGGAGCTGCAGCTTCGAAGCCTCACAGAGATCTTGAAAGGAGGGGTCTTGATCCAGCGGAACCCCCAG<br>CTCTGCTACCAGGACACGATTTTGTGGAAGGACATCTTCCACAAGAACAACCAGCTGGCTCTCACACTGA<br>TAGACACCAACCGCTCTCGGGCCTGCCACCCCTGTTCTCCGATGTGTAAGGGCTCCCGCTGCTGGGGAGA<br>GAGTTCTGAGGATTGTCAGAGCCTGACGCGCACTGTCTGTGCCGGTGGCTGTGCCCGCTGCAAGGGGCCA<br>CTGCCCACTGACTGCTGCCATGAGCAGTGTGCTGCCGGCTGCACGGGCCCCAAGCACTCTGACTGCCTGG<br>CCTGCCTCCACTTCAACCACAGTGGCATCTGTGAGCTGCACTGCCCAGCCCTGGTCACCTACAACACAGA<br>CACGTTTGAGTCCATGCCCAATCCCGAGGGCCGGTATACATTCGGCGCCAGCTGTGTGACTGCCTGTCCC<br>TACAACTACCTTTCTACGGACGTGGGATCCTGCACCCTCGTCTGCCCCCTGCACAACCAAGAGGTGACAG<br>CAGAGGATGGAACACAGCGGTGTGAGAAGTGCAGCAAGCCCTGTGCCCGAGTGTGCTATGGTCTGGGCAT<br>GGAGCACTTGCGAGAGGTGAGGGCAGTTACCAGTGCCAATATCCAGGAGTTTGCTGGCTGCAAGAAGATC<br>TTTGGGAGCCTGGCATTTCTGCCGGAGAGCTTTGATGGGGACCCAGCCTCCAACACTGCCCCGCTCCAGC<br>CAGAGCAGCTCCAAGTGTTTGAGACTCTGGAAGAGATCACAGGTTACCTATACATCTCAGCATGGCCGGA<br>CAGCCTGCCTGACCTCAGCGTCTTCCAGAACCTGCAAGTAATCCGGGGACGAATTCTGCACAATGGCGCC<br>TACTCGCTGACCCTGCAAGGGCTGGGCATCAGCTGGCTGGGGCTGCGCTCACTGAGGGAACTGGGCAGTG<br>GACTGGCCCTCATCCACCATAACACCCACCTCTGCTTCGTGCACACGGTGCCCTGGGACCAGCTCTTTCG<br>GAACCCGCACCAAGCTCTGCTCCACACTGCCAACCGGCCAGAGGACGAGTGTGTGGGCGAGGGCCTGGCC<br>TGCCACCAGCTGTGCGCCCGAGGGCACTGCTGGGGTCCAGGGCCCACCCAGTGTGTCAACTGCAGCCAGT<br>TCCTTCGGGGCCAGGAGTGCGTGGAGGAATGCCGAGTACTGCAGGGGCTCCCCAGGGAGTATGTGAATGC<br>CAGGCACTGTTTGCCGTGCCACCCTGAGTGTCAGCCCCAGAATGGCTCAGTGACCTGTTTTGGACCGGAG<br>GCTGACCAGTGTGTGGCCTGTGCCCACTATAAGGACCCTCCCTTCTGCGTGGCCCGCTGCCCCAGCGGTG<br>TGAAACCTGACCTCTCCTACATGCCCATCTGGAAGTTTCCAGATGAGGAGGGCGCATGCCAGCCTTGCCC<br>CATCAACTGCACCCACTCCTGTGTGGACCTGGATGACAAGGGCTGCCCCGCCGAGCAGAGAGCCAGCCCT<br>CTGACGTCCATCATCTCTGCGGTGGTTGGCATTCTGCTGGTCGTGGTCTTGGGGGTGGTCTTTGGGATCC<br>TCATCAAGCGACGGCAGCAGAAGATCCGGAAGTACACGATGCGGAGACTGCTGCAGGAAACGGAGCTGGT<br>GGAGCCGCTGACACCTAGCGGAGCGATGCCCAACCAGGCGCAGATGCGGATCCTGAAAGAGACGGAGCTG<br>AGGAAGGTGAAGGTGCTTGGATCTGGCGCTTTTGGCACAGTCTACAAGGGCATCTGGATCCCTGATGGGG<br>AGAATGTGAAAATTCCAGTGGCCATCAAAGTGTTGAGGGAAAACACATCCCCCAAAGCCAACAAAGAAAT<br>CTTAGACGAAGCATACGTGATGGCTGGTGTGGGCTCCCCATATGTCTCCCGCCTTCTGGGCATCTGCCTG<br>ACATCCACGGTGCAGCTGGTGACACAGCTTATGCCCTATGGCTGCCTCTTAGACCATGTCCGGGAAAACC<br>GCGGACGCCTGGGCTCCCAGGACCTGCTGAACTGGTGTATGCAGATTGCCAAGGGGATGAGCTACCTGGA<br>GGATGTGCGGCTCGTACACAGGGACTTGGCCGCTCGGAACGTGCTGGTCAAGAGTCCCAACCATGTCAAA<br>ATTACAGACTTCGGGCTGGCTCGGCTGCTGGACATTGACGAGACAGAGTACCATGCAGATGGGGGCAAGG<br>TGCCCATCAAGTGGATGGCGCTGGAGTCCATTCTCCGCCGGCGGTTCACCCACCAGAGTGATGTGTGGAG<br>TTATGGTGTGACTGTGTGGGAGCTGATGACTTTTGGGGCCAAACCTTACGATGGGATCCCAGCCCGGGAG<br>ATCCCTGACCTGCTGGAAAAGGGGGAGCGGCTGCCCCAGCCCCCCATCTGCACCATTGATGTCTACATGA | 119 |

TABLE 2-continued

| GENBANK ACCESSION NUMBER | SEQUENCE | SEQ ID NO: |
|---|---|---|
| | TCATGGTCAAATGTTGGATGATTGACTCTGAATGTCGGCCAAGATTCCGGGAGTTGGTGTCTGAATTCTC | |
| | CCGCATGGCCAGGGACCCCCAGCGCTTTGTGGTCATCCAGAATGAGGACTTGGGCCCAGCCAGTCCCTTG | |
| | GACAGCACCTTCTACCGCTCACTGCTGGAGGACGATGACATGGGGGACCTGGTGGATGCTGAGGAGTATC | |
| | TGGTACCCCAGCAGGGCTTCTTCTGTCCAGACCCTGCCCCGGGCGCTGGGGGCATGGTCCACCACAGGCA | |
| | CCGCAGCTCATCTACCAGGAGTGGCGGTGGGGACCTGACACTAGGGCTGGAGCCCTCTGAAGAGGAGGCC | |
| | CCCAGGTCTCCACTGGCACCCTCCGAAGGGGCTGGCTCCGATGTATTTGATGGTGACCTGGGAATGGGGG | |
| | CAGCCAAGGGGCTGCAAAGCCTCCCCACACATGACCCCAGCCCTCTACAGCGGTACAGTGAGGACCCCAC | |
| | AGTACCCCTGCCCTCTGAGACTGATGGCTACGTTGCCCCCCTGACCTGCAGCCCCCAGCCTGAATATGTG | |
| | AACCAGCCAGATGTTCGGCCCCAGCCCCCTTCGCCCCGAGAGGGCCCTCTGCCTGCTGCCCGACCTGCTG | |
| | GTGCCACTCTGGAAAGGCCCAAGACTCTCTCCCCAGGGAAGAATGGGGTCGTCAAAGACGTTTTTGCCTT | |
| | TGGGGGTGCCGTGGAGAACCCCGAGTACTTGACACCCCAGGGAGGAGCTGCCCCTCAGCCCCACCCTCCT | |
| | CCTGCCTTCAGCCCAGCCTTCGACAACCTCTATTACTGGGACCAGGACCCACCAGAGCGGGGGGCTCCAC | |
| | CCAGCACCTTCAAAGGGACACCTACGGCAGAGAACCCAGAGTACCTGGGTCTGGACGTGCCAGTGTGAAC | |
| | CAGAAGGCCAAGTCCGCAGAAGCCCTGATGTGTCCTCAGGGAGCAGGGAAGGCCTGACTTCTGCTGGCAT | |
| | CAAGAGGTGGGAGGGCCCTCCGACCACTTCCAGGGGAACCTGCCATGCCAGGAACCTGTCCTAAGGAACC | |
| | TTCCTTCCTGCTTGAGTTCCCAGATGGCTGGAAGGGGTCCAGCCTCGTTGGAAGAGGAACAGCACTGGGG | |
| | AGTCTTTGTGGATTCTGAGGCCCTGCCCAATGAGACTCTAGGGTCCAGTGGATGCCACAGCCCAGCTTGG | |
| | CCCTTTCCTTCCAGATCCTGGGTACTGAAAGCCTTAGGGAAGCTGGCCTGAGAGGGGAAGCGGCCCTAAG | |
| | GGAGTGTCTAAGAACAAAAGCGACCCATTCAGAGACTGTCCCTGAAACCTAGTACTGCCCCCCATGAGGA | |
| | AGGAACAGCAATGGTGTCAGTATCCAGGCTTTGTACAGAGTGCTTTTCTGTTTAGTTTTTACTTTTTTTG | |
| | TTTTGTTTTTTTAAAGATGAAATAAAGACCCAGGGGGAGAATGGGTGTTGTATGGGGAGGCAAGTGTGGG | |
| | GGGTCCTTCTCCACACCCACTTTGTCCATTTGCAAATATATTTTGGAAAACAGCTA | |
| NM_001122742 | ATGGTCATAACAGCCTCCTGTCTACCGACTCAGAACGGATTTTACCAAAACTGAAAATGCAGGCTCCATG | 120 |
| | CTCAGAAGCTCTTTAACAGGCTCGAAAGGTCCATGCTCCTTTCTCCTGCCCATTCTATAGCATAAGAAGA | |
| | CAGTCTCTGAGTGATAATCTTCTCTTCAAGAAGAAGAAAACTAGGAAGGAGTAAGCACAAAGATCTCTTC | |
| | ACATTCTCCGGGACTGCGGTACCAAATATCAGCACAGCACTTCTTGAAAAAGGATGTAGATTTTAATCTG | |
| | AACTTTGAACCATCACTGAGGTGGCCCGCCGGTTTCTGAGCCTTCTGCCCTGCGGGGACACGGTCTGCAC | |
| | CCTGCCCGCGGCCACGGACCATGACCATGACCCTCCACACCAAAGCATCTGGGATGGCCCTACTGCATCA | |
| | GATCCAAGGGAACGAGCTGGAGCCCCTGAACCGTCCGCAGCTCAAGATCCCCCTGGAGCGGCCCCTGGGC | |
| | GAGGTGTACCTGGACAGCAGCAAGCCCGCCGTGTACAACTACCCCGAGGGCGCCGCCTACGAGTTCAACG | |
| | CCGCGGCCGCCGCCAACGCGCAGGTCTACGGTCAGACCGGCCTCCCCTACGGCCCCGGGTCTGAGGCTGC | |
| | GGCGTTCGGCTCCAACGGCCTGGGGGGTTTCCCCCCACTCAACAGCGTGTCTCCGAGCCCGCTGATGCTA | |
| | CTGCACCCGCCGCCGCAGCTGTCGCCTTTCCTGCAGCCCCACGGCCAGCAGGTGCCCTACTACCTGGAGA | |
| | ACGAGCCCAGCGGCTACACGGTGCGCGAGGCCGGCCCGCCGGCATTCTACAGGCCAAATTCAGATAATCG | |
| | ACGCCAGGGTGGCAGAGAAAGATTGGCCAGTACCAATGACAAGGGAAGTATGGCTATGGAATCTGCCAAG | |
| | GAGACTCGCTACTGTGCAGTGTGCAATGACTATGCTTCAGGCTACCATTATGGAGTCTGGTCCTGTGAGG | |
| | GCTGCAAGGCCTTCTTCAAGAGAAGTATTCAAGGACATAACGACTATATGTGTCCAGCCACCAACCAGTG | |
| | CACCATTGATAAAAACAGGAGGAAGAGCTGCCAGGCCTGCCGGCTCCGCAAATGCTACGAAGTGGGAATG | |
| | ATGAAAGGTGGGATACGAAAAGACCGAAGAGGAGGGAGAATGTTGAAACACAAGCGCCAGAGAGATGATG | |
| | GGGAGGGCAGGGGTGAAGTGGGGTCTGCTGGAGACATGAGAGCTGCCAACCTTTGGCCAAGCCCGCTCAT | |
| | GATCAAACGCTCTAAGAAGAACAGCCTGGCCTTGTCCCTGACGGCCGACCAGATGGTCAGTGCCTTGTTG | |
| | GATGCTGAGCCCCCCATACTCTATTCCGAGTATGATCCTACCAGACCCTTCAGTGAAGCTTCGATGATGG | |
| | GCTTACTGACCAACCTGGCAGACAGGGAGCTGGTTCACATGATCAACTGGGCGAAGAGGGTGCCAGGCTT | |
| | TGTGGATTTGACCCTCCATGATCAGGTCCACCTTCTAGAATGTGCCTGGCTAGAGATCCTGATGATTGGT | |
| | CTCGTCTGGCGCTCCATGGAGCACCCAGGGAAGCTACTGTTTGCTCCTAACTTGCTCTTGGACAGGAACC | |
| | AGGGAAAATGTGTAGAGGGCATGGTGGAGATCTTCGACATGCTGCTGGCTACATCATCTCGGTTCCGCAT | |
| | GATGAATCTGCAGGGAGAGGAGTTTGTGTGCCTCAAATCTATTATTTTGCTTAATTCTGGAGTGTACACA | |
| | TTTCTGTCCAGCACCCTGAAGTCTCTGGAAGAGAAGGACCATATCCACCGAGTCCTGGACAAGATCACAG | |
| | ACACTTTGATCCACCTGATGGCCAAGGCAGGCCTGACCCTGCAGCAGCAGCACCAGCGGCTGGCCCAGCT | |
| | CCTCCTCATCCTCTCCCACATCAGGCACATGAGTAACAAAGGCATGGAGCATCTGTACAGCATGAAGTGC | |
| | AAGAACGTGGTGCCCCTCTATGACCTGCTGCTGGAGATGCTGGACGCCCACCGCCTACATGCGCCCACTA | |
| | GCCGTGGAGGGGCATCCGTGGAGGAGACGGACCAAAGCCACTTGGCCACTGCGGGCTCTACTTCATCGCA | |
| | TTCCTTGCAAAAGTATTACATCACGGGGGAGGCAGAGGGTTTCCCTGCCACGGTCTGAGAGCTCCCTGGC | |
| | TCCCACACGGTTCAGATAATCCCTGCTGCATTTTACCCTCATCATGCACCACTTTAGCCAAATTCTGTCT | |
| | CCTGCATACACTCCGGCATGCATCCAACACCAATGGCTTTCTAGATGAGTGGCCATTCATTTGCTTGCTC | |
| | AGTTCTTAGTGGCACATCTTCTGTCTTCTGTTGGGAACAGCCAAAGGGATTCCAAGGCTAAATCTTTGTA | |
| | ACAGCTCTCTTTCCCCCTTGCTATGTTACTAAGCGTGAGGATTCCCGTAGCTCTTCACAGCTGAACTCAG | |
| | TCTATGGGTTGGGGCTCAGATAACTCTGTGCATTTAAGCTACTTGTAGAGACCCAGGCCTGGAGAGTAGA | |
| | CATTTTGCCTCTGATAAGCACTTTTTAAATGGCTCTAAGAATAAGCCACAGCAAAGAATTTAAAGTGGCT | |
| | CCTTTAATTGGTGACTTGGAGAAAGCTAGGTCAAGGGTTTATTATAGCACCCTCTTGTATTCCTATGGCA | |
| | ATGCATCCTTTTATGAAAGTGGTACACCTTAAAGCTTTTATATGACTGTAGCAGAGTATCTGGTGATTGT | |
| | CAATTCATTCCCCCTATAGGAATACAAGGGGCACACAGGGAAGGCAGATCCCCTAGTTGGCAAGACTATT | |
| | TTAACTTGATACACTGCAGATTCAGATGTGCTGAAAGCTCTGCCTCTGGCTTTCCGGTCATGGGTTCCAG | |
| | TTAATTCATGCCTCCCATGGACCTATGGAGAGCAGCAAGTTGATCTTAGTTAAGTCTCCCTATATGAGGG | |
| | ATAAGTTCCTGATTTTTGTTTTTATTTTTGTGTTACAAAAGAAAGCCCTCCCTCCCTGAACTTGCAGTAA | |
| | GGTCAGCTTCAGGACCTGTTCCAGTGGGCACTGTACTTGGATCTTCCCGGCGTGTGTGTGCCTTACACAG | |
| | GGGTGAACTGTTCACTGTGGTGATGCATGATGAGGGTAAATGGTAGTTGAAAGGAGCAGGGGCCCTGGTG | |
| | TTGCATTTAGCCCTGGGGCATGGAGCTGAACAGTACTTGTGCAGGATTGTTGTGGCTACTAGAGAACAAG | |
| | AGGGAAAGTAGGGCAGAAACTGGATACAGTTCTGAGGCACAGCCAGACTTGCTCAGGGTGGCCCTGCCAC | |
| | AGGCTGCAGCTACCTAGGAACATTCCTTGCAGACCCCGCATTGCCCTTTGGGGGTGCCCTGGGATCCCTG | |
| | GGGTAGTCCAGCTCTTCTTCATTTCCCAGCGTGGCCCTGGTTGGAAGAAGCAGCTGTCACAGCTGCTGTA | |
| | GACAGCTGTGTTCCTACAATTGGCCCAGCACCCTGGGGCACGGGAGAAGGGTGGGGACCGTTGCTGTCAC | |
| | TACTCAGGCTGACTGGGGCCTGGTCAGATTACGTATGCCCTTGGTGGTTTAGAGATAATCCAAAATCAGG | |
| | GTTTGGTTTGGGGAAGAAAATCCTCCCCCTTCCTCCCCCGCCCCGTTCCCTACCGCCTCCACTCCTGCCA | |
| | GCTCATTTCCTTCAATTTCCTTTGACCTATAGGCTAAAAAAGAAAGGCTCATTCCAGCCACAGGGCAGCC | |

TABLE 2-continued

| GENBANK ACCESSION NUMBER | SEQUENCE | SEQ ID NO: |
|---|---|---|
| | TTCCCTGGGCCTTTGCTTCTCTAGCACAATTATGGGTTACTTCCTTTTTCTTAACAAAAAAGAATGTTTG<br>ATTTCCTCTGGGTGACCTTATTGTCTGTAATTGAAACCCTATTGAGAGGTGATGTCTGTGTTAGCCAATG<br>ACCCAGGTGAGCTGCTCGGGCTTCTCTTGGTATGTCTTGTTTGGAAAAGTGGATTTCATTCATTTCTGAT<br>TGTCCAGTTAAGTGATCACCAAAGGACTGAGAATCTGGGAGGGCAAAAAAAAAAAAAAAGTTTTTATGTG<br>CACTTAAATTTGGGGACAATTTTATGTATCTGTGTTAAGGATATGTTTAAGAACATAATTCTTTTGTTGC<br>TGTTTGTTTAAGAAGCACCTTAGTTTGTTTAAGAAGCACCTTATATAGTATAATATATATTTTTTTGAAA<br>TTACATTGCTTGTTTATCAGACAATTGAATGTAGTAATTCTGTTCTGGATTTAATTTGACTGGGTTAACA<br>TGCAAAAACCAAGGAAAAATATTTAGTTTTTTTTTTTTTTTTTGTATACTTTTCAAGCTACCTTGTCATG<br>TATACAGTCATTTATGCCTAAAGCCTGGTGATTATTCATTTAAATGAAGATCACATTTCATATCAACTTT<br>TGTATCCACAGTAGACAAAATAGCACTAATCCAGATGCCTATTGTTGGATACTGAATGACAGACAATCTT<br>ATGTAGCAAAGATTATGCCTGAAAAGGAAAATTATTCAGGGCAGCTAATTTTGCTTTTACCAAAATATCA<br>GTAGTAATATTTTTGGACAGTAGCTAATGGGTCAGTGGGTTCTTTTTAATGTTTATACTTAGATTTTCTT<br>TTAAAAAAATTAAAATAAAACAAAAAAAAATTTCTAGGACTAGACGATGTAATACCAGCTAAAGCCAAAC<br>AATTATACAGTGGAAGGTTTTACATTATTCATCCAATGTGTTTCTATTCATGTTAAGATACTACTACATT<br>TGAAGTGGGCAGAGAACATCAGATGATTGAAATGTTCGCCCAGGGGTCTCCAGCAACTTTGGAAATCTCT<br>TTGTATTTTTACTTGAAGTGCCACTAATGGACAGCAGATATTTTCTGGCTGATGTTGGTATTGGGTGTAG<br>GAACATGATTTAAAAAAAAACTCTTGCCTCTGCTTTCCCCCACTCTGAGGCAAGTTAAAATGTAAAAGAT<br>GTGATTTATCTGGGGGGCTCAGGTATGGTGGGGAAGTGGATTCAGGAATCTGGGGAATGGCAAATATATT<br>AAGAAGAGTATTGAAAGTATTTGGAGGAAAATGGTTAATTCTGGGTGTGCACCAGGGTTCAGTAGAGTCC<br>ACTTCTGCCCTGGAGACCACAAATCAACTAGCTCCATTTACAGCCATTTCTAAAATGGCAGCTTCAGTTC<br>TAGAGAAGAAAGAACAACATCAGCAGTAAAGTCCATGGAATAGCTAGTGGTCTGTGTTTCTTTTCGCCAT<br>TGCCTAGCTTGCCGTAATGATTCTATAATGCCATCATGCAGCAATTATGAGAGGCTAGGTCATCCAAAGA<br>GAAGACCCTATCAATGTAGGTTGCAAAATCTAACCCCTAAGGAAGTGCAGTCTTTGATTTGATTTCCCTA<br>GTAACCTTGCAGATATGTTTAACCAAGCCATAGCCCATGCCTTTTGAGGGCTGAACAAATAAGGGACTTA<br>CTGATAATTTACTTTTGATCACATTAAGGTGTTCTCACCTTGAAATCTTATACACTGAAATGGCCATTGA<br>TTTAGGCCACTGGCTTAGAGTACTCCTTCCCCTGCATGACACTGATTACAAATACTTTCCTATTCATACT<br>TTCCAATTATGAGATGGACTGTGGGTACTGGGAGTGATCACTAACACCATAGTAATGTCTAATATTCACA<br>GGCAGATCTGCTTGGGGAAGCTAGTTATGTGAAAGGCAAATAGAGTCATACAGTAGCTCAAAAGGCAACC<br>ATAATTCTCTTTGGTGCAGGTCTTGGGAGCGTGATCTAGATTACACTGCACCATTCCCAAGTTAATCCCC<br>TGAAAACTTACTCTCAACTGGAGCAAATGAACTTTGGTCCCAAATATCCATCTTTTCAGTAGCGTTAATT<br>ATGCTCTGTTTCCAACTGCATTTCCTTTCCAATTGAATTAAAGTGTGGCCTCGTTTTTAGTCATTTAAAA<br>TTGTTTTCTAAGTAATTGCTGCCTCTATTATGGCACTTCAATTTTGCACTGTCTTTTGAGATTCAAGAAA<br>AATTTCTATTCTTTTTTTTGCATCCAATTGTGCCTGAACTTTTAAAATATGTAAATGCTGCCATGTTCCA<br>AACCCATCGTCAGTGTGTGTGTTTAGAGCTGTGCACCCTAGAAACAACATATTGTCCCATGAGCAGGTGC<br>CTGAGACACAGACCCCTTTGCATTCACAGAGAGGTCATTGGTTATAGAGACTTGAATTAATAAGTGACAT<br>TATGCCAGTTTCTGTTCTCTCACAGGTGATAAACAATGCTTTTTGTGCACTACATACTCTTCAGTGTAGA<br>GCTCTTGTTTTATGGGAAAAGGCTCAAATGCCAAATTGTGTTTGATGGATTAATATGCCCTTTTGCCGAT<br>GCATACTATTACTGATGTGACTCGGTTTTGTCGCAGCTTTGCTTTGTTTAATGAAACACACTTGTAAACC<br>TCTTTTGCACTTTGAAAAAGAATCCAGCGGGATGCTCGAGCACCTGTAAACAATTTTCTCAACCTATTTG<br>ATGTTCAAATAAAGAATTAAACTAAA | |
| NM_130398 | AAATTGAAAGGTCAGCCTTTCGCGCGCTGTGTAGGCAAGTTACCCGTGTTCTGCGTTGCCGGCCGTGGGT<br>GCTCTGGCCACAGTGAGTTAGGGGCGTCGGAGCGGGTTTCTCCAACCGCAATCGGCTCCGCTCAAGGGGA<br>GGAGGAGAGTCCCTTCTCGGAAGGCCTAAGGAAACGTGTCGTCTGGAATGGGCTTGGGGGCCACGCCTGC<br>ACATCTCCGCGAGACAGAGGGATAAAGTGAAGATGGTGCTGTTATTGTTACCTCGAGTGCCACATGCGAC<br>CTCTGAGATATGTACACAGTCATTCTTACTATCGCACTCAGCCATTCTTACTACGCTAAAGAAGAAATAA<br>TTATTCGAGGATATTTGCCTGGCCCAGAAGAAACTTATGTAAATTTCATGAACTATTATATCCGTTTTCC<br>TCGGAGTGAGAGAAAACTCTTTTTAGATATCATCTGAGAGAACTAGTGAATCCCAGTCACTGAGTGGAGT<br>TGAGAGTCTAAGAACCTCTGAAATTTGAGAACTGCTGGACCAGAGCCTTTAGAGCTCTGATAAGGTGTCA<br>ACAGGGTAGTTAATTTGGCACCATGGGGATACAGGGATTGCTACAATTTATCAAAGAAGCTTCAGAACCC<br>ATCCATGTGAGGAAGTATAAAGGGCAGGTAGTAGCTGTGGATACATATTGCTGGCTTCACAAAGGAGCTA<br>TTGCTTGTGCTGAAAAACTAGCCAAAGGTGAACCTACTGATAGGTATGTAGGATTTTGTATGAAATTTGT<br>AAATATGTTACTATCTCATGGGATCAAGCCTATTCTCGTATTTGATGGATGTACTTTACCTTCTAAAAAG<br>GAAGTAGAGAGATCTAGAAGAGAAAGACGACAAGCCAATCTTCTTAAGGGAAAGCAACTTCTTCGTGAGG<br>GGAAAGTCTCGGAAGCTCGAGAGTGTTTCACCCGGTCTATCAATATCACACATGCCATGGCCCACAAAGT<br>AATTAAAGCTGCCCGGTCTCAGGGGGTAGATTGCCTCGTGGCTCCCTATGAAGCTGATGCGCAGTTGGCC<br>TATCTTAACAAAGCGGGAATTGTGCAAGCCATAATTACAGAGGACTCGGATCTCCTAGCTTTTGGCTGTA<br>AAAAGGTAATTTTAAAGATGGACCAGTTTGGAAATGGACTTGAAATTGATCAAGCTCGGCTAGGAATGTG<br>CAGACAGCTTGGGGATGTATTCACGGAAGAGAAGTTTCGTTACATGTGTATTCTTTCAGGTTGTGACTAC<br>CTGTCATCACTGCGTGGGATTGGATTAGCAAAGGCATGCAAAGTCCTAAGACTAGCCAATAATCCAGATA<br>TAGTAAAGGTTATCAAGAAAATTGGACATTATCTCAAGATGAATATCACGGTACCAGAGGATTACATCAA<br>CGGGTTTATTCGGGCCAACAATACCTTCCTCTATCAGCTAGTTTTTGATCCCATCAAAAGGAAACTTATT<br>CCTCTGAACGCCTATGAAGATGATGTTGATCCTGAAACACTAAGCTACGCTGGGCAATATGTTGATGATT<br>CCATAGCTCTTCAAATAGCACTTGGAAATAAAGATATAAATACTTTTGAACAGATCGATGACTACAATCC<br>AGACACTGCTATGCCTGCCCATTCAAGAAGTCATAGTTGGGATGACAAAACATGTCAAAAGTCAGCTAAT<br>GTTAGCAGCATTTGGCATAGGAATTACTCTCCCAGACCAGAGTCGGGTACTGTTTCAGATGCCCCACAAT<br>TGAAGGAAAATCCAAGTACTGTGGGAGTGGAACGAGTGATTAGTACTAAAGGGTTAAATCTCCCAAGGAA<br>ATCATCCATTGTGAAAAGACCAAGAAGTGCAGAGCTGTCAGAAGATGACCTGTTGAGTCAGTATTCTCTT<br>TCATTTACGAAGAAGACCAAGAAAAATAGCTCTGAAGGCAATAAATCATTGAGCTTTTCTGAAGTGTTTG<br>TGCCTGACCTGGTAAATGGACCTACTAACAAAAAGAGTGTAAGCACTCCACCTAGGACGAGAAATAAATT<br>TGCAACATTTTTACAAAGGAAAAATGAAGAAAGTGGTGCAGTTGTGGTTCCAGGGACCAGAAGCAGGTTT<br>TTTTGCAGTTCAGATTCTACTGACTGTGTATCAAACAAAGTGAGCATCCAGCCTCTGGATGAAACTGCTG<br>TCACAGATAAAGAGAACAATCTGCATGAATCAGAGTATGGAGACCAAGAAGGCAAGAGACTGGTTGACAC<br>AGATGTAGCACGTAATTCAAGTGATGACATTCCGAATAATCATATTCCAGGTGATCATATTCCAGACAAG<br>GCAACAGTGTTTACAGATGAAGAGTCCTACTCTTTTGAGAGCAGCAAATTTACAAGGACCATTTCACCAC<br>CCACTTTGGGAACACTAAGAAGTTGTTTTAGTTGGTCTGGAGGTCTTGGAGATTTTTCAAGAACGCCGAG | 121 |

TABLE 2-continued

| GENBANK ACCESSION NUMBER | SEQUENCE | SEQ ID NO: |
|---|---|---|
| | CCCCTCTCCAAGCACAGCATTGCAGCAGTTCCGAAGAAAGAGCGATTCCCCCACCTCTTTGCCTGAGAAT<br>AATATGTCTGATGTGTCGCAGTTAAAGAGCGAGGAGTCCAGTGACGATGAGTCTCATCCCTTACGAGAAG<br>AGGCATGTTCTTCACAGTCCCAGGAAAGTGGAGAATTCTCACTGCAGAGTTCAAATGCATCAAAGCTTTC<br>TCAGTGCTCTAGTAAGGACTCTGATTCAGAGGAATCTGATTGCAATATTAAGTTACTTGACAGTCAAAGT<br>GACCAGACCTCCAAGCTACGTTTATCTCATTTCTCAAAAAAAGACACACCTCTAAGGAACAAGGTTCCTG<br>GGCTATATAAGTCCAGTTCTGCAGACTCTCTTTCTACAACCAAGATCAAACCTCTAGGACCTGCCAGAGC<br>CAGTGGGCTGAGCAAGAAGCCGGCAAGCATCCAGAAGAGAAAGCATCATAATGCCGAGAACAAGCCGGGG<br>TTACAGATCAAACTCAATGAGCTCTGGAAAAACTTTGGATTTAAAAAAGATTCTGAAAAGCTTCCTCCTT<br>GTAAGAAACCCCTGTCCCCAGTCAGAGATAACATCCAACTAACTCCAGAAGCGGAAGAGGATATATTTAA<br>CAAACCTGAATGTGGCCGTGTTCAAAGAGCAATATTCCAGTAAATGCAGACTGCTGCAAAGCTTTTGCCT<br>GCAAGAGAATCTGATCAATTTGAAGTCCCTGTTTGGGAATGAGGCACTTATCAGCATGAAGAATTTTTTC<br>TCATTCTGTGCCATTTTAAAAATAGAATACATTTTGTATATTAACTTTATAATTGGGTTGTGGTTTTTTT<br>GCTCAGCTTTTTATATTTTTATAAGAAGCTAAATAGAAGAATAATTGTATCTCTGACAGGTTTTTGGAGG<br>TTTTAGTGTTAATTGGGAAAATCCTCTGGAGTTTATAAAAGTCTACTCTAAATATTTCTGTAATGTTGTC<br>AAGTAGAAAGATAGTAAATGGAGAAACTACAAAAAAAAAAAAAAAAAA | |
| AB209631 | CCATGACCTGCCTTGAGAAGGGGCAGGGGAAGCCAGATGGACTGGAAGTGGAGTGGCAGTGACCAAGGAG<br>GAGGAGGTGTGATAGGCTTCCCACGCAGGGTAGATCCAGAGACACCAGTGCCACCCATAGGCCCCTAGGA<br>CTGCAGTGGTCACCCGATTCCTTTGTCCCAGCTGAGACTCAGTTCTGAGTGTTCTATTTTGGGGAACAGA<br>GGCGTCCTTGGTAGCATTTGGAAGAGGATAGCCAGCTGGGGTGTGTGTACATCACAGCCTGACAGTAACA<br>GCATCCGAACCAGAGGTGACTGGCTAAGGGCAGACCCAGGGCAACAGGTTAACCGTTCTAGGGCCGGGCA<br>CAGGGAGGAGAACATTCCAACACTCTGTGTGCCCAGTGCCGACGCACGTTCTCTCTTTTATCCTCAAAAC<br>AGTCCTATGAGGATATAAGCCAGAGAGAGACAGAGACAAGGAATTACAAGTTGGTGAGAGTCAGGATTTG<br>AACTTGGCTCTGGCAGATGGAAAATTAGGGTCTGTATTCTTTACAAAACCGTGTGTGCCTCAGATGGAGT<br>TGGTGCATAACAAGCAGAGGTATCCAGGGTCGCGGTCCTGCTTGCCACGGAAGGGGCCGCCTTGTCAGTT<br>GTGACCACCCAGCCCTGGAAATGTCAGTAATGCTGTAAGGAGTGGGGATCGGATCAGATGCCATCCAGAT<br>GCTGAAGTTTGACCTTGTGTCATTTTTCACTTTCTTTTTTGGCTCTTCTGCAATCAATTCATTTATTTAG<br>CAAAAAAGAAATTATGTGTGCCGAGAGCATGCAGAAGATATGTCTCCGTTCTCTGCTTCCCTCCAAAAAA<br>GAATCCCAAAACTGCTTTCTGTGAACGTGTGCCAGGGTCCCAGCAGGACTCAGGGAGAGCAGGAAGCCCA<br>GCCCAGACCCCTTGCACAACCTACCGTGGGGAGGCCTTAGGCTCTGGCTACTACAGAGCTGGTTCCAGTC<br>TGCACTGCCACAGCCTGGCCAGGGACTTGGACACATCTGCTGGCCACTTCCTGTCTCAGTTTCCTTATCT<br>GCAAAATAAGGGAAAAGCCCCCACAAAGGTGCACGTGTAGCAGGAGCTCTTTTCCCTCCCTATTTTAGGA<br>AGGCAGTTGGTGGGAAGTCCAGCTTGGGTCCCTGAGAGCTGTGAGAAGGAGATGCGGCTGCTGCTGGCCC<br>TGTTGGGGGTCCTGCTGAGTGTGCCTGGGCCTCCAGTCTTGTCCCTGGAGGCCTCTGAGGAAGTGGAGCT<br>TGGTATGGCTTCTGAGGTGGGAGAGGGTGGCAGGGGTGGGAAGAGTGGGCACCAGGAGGGGGCTGCTGGG<br>CTGAGCAAAGCTGGAAAGGATCCTTGCCCAGGCCCTGAGAAGGTGGCGGCAGGGCAGGGCTCAACCACTG<br>AGACTCAGTCAGTGCCTGGCTTCCAGCAAGCATTCATCTATCACTGTGTCTGCGAGAGAGGACTGGCCTT<br>GCAGGGCGCAGGGCCCTAAGCTGGGCTGCAGAGCTGGTGGTGAGCTCCTTGCCTGGGTGTGTGTGCGTGT<br>GTGTGTGTGTTCTGTGCACTGGGTGTGTGACCTAGGAGGTCCAGGCAGCATGTGTGGTATAAGCATTATG<br>AGGGTGATATGCCCCGGTGCAGCATGACCCTGTATGTGGCACCAACAGCATGTGCCTTGTGTGTGTGTGT<br>GTCCGTATGTGTGTGTGTGTATGCGTGTGTGTGTGTGTGTGTGTGTGTCTTGGCCACTGTCATGTGCACT<br>AAATGCTGTGTGTGTGACATGCCCCAAGAGTGTGGCATTTGCCCTGGGTGTGGCATCCGCAGCATGTGGC<br>TGTGTGGGTGTCAAGGAGTGGTGGCTCCTTCAGCATGCGTTGCGAAGTGCTTGTGCCCTGCATGTGCGGT<br>GTGTTCTCTGTACACAGGAGGCTGCCTCAGATGGGGCTGCGGGGTCTGCTGACCTCTGCCCTCTGCCCAC<br>AGAGCCCTGCCTGGCTCCCAGCCTGGAGCAGCAAGAGCAGGAGCTGACAGTAGCCCTTGGGCAGCCTGTG<br>CGGCTGTGCTGTGGGCGGGCTGAGCGTGGTGGCCACTGGTACAAGGAGGGCAGTCGCCTGGCACCTGCTG<br>GCCGTGTACGGGGCTGGAGGGGCCGCCTAGAGATTGCCAGCTTCCTACCTGAGGATGCTGGCCGCTACCT<br>CTGCCTGGCACGAGGCTCCATGATCGTCCTGCAGAATCTCACCTTGATTACAGGTGACTCCTTGACCTCC<br>AGCAACGATGATGAGGACCCCAAGTCCCATAGGGACCTCTCGAATAGGCACAGTTACCCCCAGCAAGGTC<br>AGTAGGTCTCCAAGGACTTGTGTCCCCGCTGCTGCTCATCTGATCACTGAGAAGAGGAGGCCTGTGTGGG<br>AACACACGGTCATTCTAGGGGCCTTCCCCTGCCCTCCAGCACCCTACTGGACACACCCCCAGCGCATGGA<br>GAAGAAACTGCATGCAGTACCTGCGGGGAACACCGTCAAGTTCCGCTGTCCAGCTGCAGGCAACCCCACG<br>CCCACCATCCGCTGGCTTAAGGATGGACAGGCCTTTCATGGGGAGAACCGCATTGGAGGCATTCGGCTGC<br>GCCATCAGCACTGGAGTCTCGTGATGGAGAGCGTGGTGCCCTCGGACCGCGGCACATACACCTGCCTGGT<br>AGAGAACGCTGTGGGCAGCATCCGTTATAACTACCTGCTAGATGTGCTGGAGCGGTCCCCGCACCGGCCC<br>ATCCTGCAGGCCGGGCTCCCGGCCAACACCACAGCCGTGGTGGGCAGCGACGTGGAGCTGCTGTGCAAGG<br>TGTACAGCGATGCCCAGCCCCACATCCAGTGGCTGAAGCACATCGTCATCAACGGCAGCAGCTTCGGAGC<br>CGACGGTTTCCCCTATGTGCAAGTCCTAAAGACTGCAGACATCAATAGCTCAGAGGTGGAGGTCCTGTAC<br>CTGCGGAACGTGTCAGCCGAGGACGCAGGCGAGTACACCTGCCTCGCAGGCAATTCCATCGGCCTCTCCT<br>ACCAGTCTGCCTGGCTCACGGTGCTGCCAGGTGAGCACCTGAAGGGCCAGGAGATGCTGCGAGATGCCCC<br>TCTGGGCCAGCAGTGGGGGCTGTGGCCTGTTGGGTGGTCAGTCTCTGTTGGCCTGTGGGGTCTGGCCTGG<br>GGGGCAGTGTGTGGATTTGTGGGTTTGAGCTGTATGACAGCCCCTCTGTGCCTCTCCACACGTGGCCGTC<br>CATGTGACCGTCTGCTGAGGTGTGGGTGCCTGGGACTGGGCATAACTACAGCTTCCTCCGTGTGTGTCCC<br>CACATATGTTGGGAGCTGGGAGGGACTGAGTTAGGGTGCACGGGGCGGCCAGTCTCACCACTGACCAGTT<br>TGTCTGTCTGTGTGTGTCCATGTGCGAGGGCAGAGGAGGACCCCACATGGACCGCAGCAGCGCCCGAGGC<br>CAGGTATACGGACATCATCCTGTACGCGTCGGGCTCCCTGGCCTTGGCTGTGCTCCTGCTGCTGGCCAGG<br>CTGTATCGAGGGCAGGCGCTCCACGGCCGGCACCCCCGCCCGCCCGCCACTGTGCAGAAGCTCTCCCGCT<br>TCCCTCTGGCCCGACAGTTCTCCCTGGAGTCAGGCTCTTCCGGCAAGTCAAGCTCATCCCTGGTACGAGG<br>CGTGCGTCTCTCCTCCAGCGGCCCCGCCTTGCTCGCCGGCCTCGTGAGTCTAGATCTACCTCTCGACCCA<br>CTATGGGAGTTCCCCCGGGACAGGCTGGTGCTTGGGAAGCCCCTAGGCGAGGGCTGCTTTGGCCAGGTAG<br>TACGTGCAGAGGCCTTTGGCATGGACCCTGCCCGGCCTGACCAAGCCAGCACTGTGGCCGTCAAGATGCT<br>CAAAGACAACGCCTCTGACAAGGACCTGGCCGACCTGGTCTCGGAGATGGAGGTGATGAAGCTGATCGGC<br>CGACACAAGAACATCATCAACCTGCTTGGTGTCTGCACCCAGGAAGGGCCCCTGTACGTGATCGTGGAGT<br>GCGCCGCCAAGGGAAACCTGCGGGAGTTCCTGCGGGCCCGGCGCCCCCCAGGCCCCGACCTCAGCCCCGA<br>CGGTCCTCGGAGCAGTGAGGGGCCGCTCTCCTTCCCAGTCCTGGTCTCCTGCGCCTACCAGGTGGCCCGA<br>GGCATGCAGTATCTGGAGTCCCGGAAGTGTATCCACCGGGACCTGGCTGCCCGCAATGTGCTGGTGACTG | 122 |

TABLE 2-continued

| GENBANK ACCESSION NUMBER | SEQUENCE | SEQ ID NO: |
|---|---|---|
| | AGGACAATGTGATGAAGATTGCTGACTTTGGGCTGGCCCGCGGCGTCCACCACATTGACTACTATAAGAA<br>AACCAGCAACGGCCGCCTGCCTGTGAAGTGGATGGCGCCCGAGGCCTTGTTTGACCGGGTGTACACACAC<br>CAGAGTGACGTGTGGTCTTTTGGGATCCTGCTATGGGAGATCTTCACCCTCGGGGGCTCCCCGTATCCTG<br>GCATCCCGGTGGAGGAGCTGTTCTCGCTGCTGCGGGAGGGACATCGGATGGACCGACCCCCACACTGCCC<br>CCCAGAGCTGTACGGGCTGATGCGTGAGTGCTGGCACGCAGCGCCCTCCCAGAGGCCTACCTTCAAGCAG<br>CTGGTGGAGGCGCTGGACAAGGTCCTGCTGGCCGTCTCTGAGGAGTACCTCGACCTCCGCCTGACCTTCG<br>GACCCTATTCCCCCTCTGGTGGGGACGCCAGCAGCACCTGCTCCTCCAGCGATTCTGTCTTCAGCCACGA<br>CCCCCTGCCATTGGGATCCAGCTCCTTCCCCTTCGGGTCTGGGGTGCAGACATGAGCAAGGCTCAAGGCT<br>GTGCAGGCACATAGGCTGGTGGCCTTGGGCCTTGGGGCTCAGCCACAGCCTGACACAGTGCTCGACCTTG<br>ATAGCATGGGGCCCCTGGCCCAGAGTTGCTGTGCCGTGTCCAAGGGCCGTGCCCTTGCCCTTGGAGCTGC<br>CGTGCCTGTGTCCTGATGGCCCAAATGTCAGGGTTCTGCTCGGCTTCTTGGACCTTGGCGCTTAGTCCCC<br>ATCCCGGGTTTGGCTGAGCCTGGCTGGAGAGCTGCTATGCTAAACCTCCTGCCTCCCAATACCAGCAGGA<br>GGTTCTGGGCCTCTGAACCCCCTTTCCCCACACCTCCCCCTGCTGCTGCCCCAGCGTCTTGACGGGA<br>GCATTGGCCCCTGAGCCCAGAGAAGCTGGAAGCCTGCCGAAAACAGGAGCAAATGGCGTTTTATAAATTA<br>TTTTTTTGAAAT | |
| NM_004496 | TAAGATCCACATCAGCTCAACTGCACTTGCCTCGCAGAGGCAGCCCGCTCACTTCCCGCGGAGGCGCTCC<br>CCGGCGCCGCGCTCCGCGGCAGCCGCCTGCCCCCGGCGCTGCCCCCGCCCGCCGCGCCGCCGCCGCCGCC<br>GCGCACGCCGCGCCCCGCAGCTCTGGGCTTCCTCTTCGCCCGGGTGGCGTTGGGCCCGCGCGGGCGCTCG<br>GGTGACTGCAGCTGCTCAGCTCCCCTCCCCCGCCCCGCGCCGCGCGGCCGCCCGTCGCTTCGCACAGGGC<br>TGGATGGTTGTATTGGGCAGGGTGGCTCCAGGATGTTAGGAACTGTGAAGATGGAAGGGCATGAAACCAG<br>CGACTGGAACAGCTACTACGCAGACACGCAGGAGGCCTACTCCTCCGTCCCGGTCAGCAACATGAACTCA<br>GGCCTGGGCTCCATGAACTCCATGAACACCTACATGACCATGAACACCATGACTACGAGCGGCAACATGA<br>CCCCGGCGTCCTTCAACATGTCCTATGCCAACCCGGGCCTAGGGGCCGGCCTGAGTCCCGGCGCAGTAGC<br>CGGCATGCCGGGGGGCTCGGCGGGCGCCATGAACAGCATGACTGCGGCCGGCGTGACGGCCATGGGTACG<br>GCGCTGAGCCCGAGCGGCATGGGCGCCATGGGTGCGCAGCAGGCGGCCTCCATGAATGGCCTGGGCCCCT<br>ACGCGGCCGCCATGAACCCGTGCATGAGCCCCATGGCGTACGCGCCGTCCAACCTGGGCCGCAGCCGCGC<br>GGGCGGCGGCGGCGACGCCAAGACGTTCAAGCGCAGCTACCCGCACGCCAAGCCGCCCTACTCGTACATC<br>TCGCTCATCACCATGGCCATCCAGCAGGCGCCCAGCAAGATGCTCACGCTGAGCGAGATCTACCAGTGGA<br>TCATGGACCTCTTCCCCTATTACCGGCAGAACCAGCAGCGCTGGCAGAACTCCATCCGCCACTCGCTGTC<br>CTTCAATGACTGCTTCGTCAAGGTGGCACGCTCCCCGGACAAGCCGGGCAAGGGCTCCTACTGGACGCTG<br>CACCCGGACTCCGGCAACATGTTCGAGAACGGCTGCTACTTGCGCCGCCAGAAGCGCTTCAAGTGCGAGA<br>AGCAGCCGGGGGCCGGCGGCGGGGGCGGGAGCGGAAGCGGGGGCAGCGGCGCCAAGGGCGGCCCTGAGAG<br>CCGCAAGGACCCCTCTGGCGCCTCTAACCCCAGCGCCGACTCGCCCCTCCATCGGGGTGTGCACGGGAAG<br>ACCGGCCAGCTAGAGGGCGCGCCGGCCCCCGGGCCCGCCGCCAGCCCCCAGACTCTGGACCACAGTGGGG<br>CGACGGCGACAGGGGGCGCCTCGGAGTTGAAGACTCCAGCCTCCTCAACTGCGCCCCCCATAAGCTCCGG<br>GCCCGGGGCGCTGGCCTCTGTGCCCGCCTCTCACCCGGCACACGGCTTGGCACCCCACGAGTCCCAGCTG<br>CACCTGAAAGGGGACCCCCACTACTCCTTCAACCACCCGTTCTCCATCAACAACCTCATGTCCTCCTCGG<br>AGCAGCAGCATAAGCTGGACTTCAAGGCATACGAACAGGCACTGCAATACTCGCCTTACGGCTCTACGTT<br>GCCCGCCAGCCTGCCTCTAGGCAGCGCCTCGGTGACCACCAGGAGCCCCATCGAGCCCTCAGCCCTGGAG<br>CCGGCGTACTACCAAGGTGTGTATTCCAGACCCGTCCTAAACACTTCCTAGCTCCCGGGACTGGGGGGTT<br>TGTCTGGCATAGCCATGCTGGTAGCAAGAGAGAAAAAATCAACAGCAAACAAAACCACACAAACCAAACC<br>GTCAACAGCATAATAAAATCCCAACAACTATTTTTATTTCATTTTTCATGCACAACCTTTCCCCCAGTGC<br>AAAAGACTGTTACTTTATTATTGTATTCAAAATTCATTGTGTATATTACTACAAAGACAACCCCAAACCA<br>ATTTTTTTCCTGCGAAGTTTAATGATCCACAAGTGTATATATGAAATTCTCCTCCTTCCTTGCCCCCCTC<br>TCTTTCTTCCCTCTTTCCCCTCCAGACATTCTAGTTTGTGGAGGGTTATTTAAAAAAACAAAAAAGGAAG<br>ATGGTCAAGTTTGTAAAATATTTGTTTGTGCTTTTTCCCCCTCCTTACCTGACCCCCTACGAGTTTACAG<br>GTCTGTGGCAATACTCTTAACCATAAGAATTGAAATGGTGAAGAAACAAGTATACACTAGAGGCTCTTAA<br>AAGTATTGAAAGACAATACTGCTGTTATATAGCAAGACATAAACAGATTATAAACATCAGAGCCATTTGC<br>TTCTCAGTTTACATTTCTGATACATGCAGATAGCAGATGTCTTTAAATGAAATACATGTATATTGTGTAT<br>GGACTTAATTATGCACATGCTCAGATGTGTAGACATCCTCCGTATATTTACATAACATATAGAGGTAATA<br>GATAGGTGATATACATGATACATTCTCAAGAGTTGCTTGACCGAAAGTTACAAGGACCCCAACCCCTTTG<br>TCCTCTCTACCCACAGATGGCCCTGGGAATCAATTCCTCAGGAATTGCCCTCAAGAACTCTGCTTCTTGC<br>TTTGCAGAGTGCCATGGTCATGTCATTCTGAGGTCACATAACACATAAAATTAGTTTCTATGAGTGTATA<br>CCATTTAAAGAATTTTTTTTTCAGTAAAAGGGAATATTACAATGTTGGAGGAGAGATAAGTTATAGGGAG<br>CTGGATTTCAAAACGTGGTCCAAGATTCAAAAATCCTATTGATAGTGGCCATTTTAATCATTGCCATCGT<br>GTGCTTGTTTCATCCAGTGTTATGCACTTTCCACAGTTGGACATGGTGTTAGTATAGCCAGACGGGTTTC<br>ATTATTATTTCTCTTTGCTTTCTCAATGTTAATTTATTGCATGGTTTATTCTTTTTCTTTACAGCTGAAA<br>TTGCTTTAAATGATGGTTAAAATTACAAATTAAATTGTTAATTTTTATCAATGTGATTGTAATTAAAAAT<br>ATTTTGATTTAAATAACAAAAATAATACCAGATTTTAAGCCGTGGAAAATGTTCTTGATCATTTGCAGTT<br>AAGGACTTTAAATAAATCAAATGTTAACAAAAAAAAAAAAAAAA | 123 |
| NM_001453 | ATGCAGGCGCGCTACTCCGTGTCCAGCCCCAACTCCCTGGGAGTGGTGCCCTACCTCGGCGGCGAGCAGA<br>GCTACTACCGCGCGGCGGCCGCGGCGGCCGGGGGCGGCTACACCGCCATGCCGGCCCCCATGAGCGTGTA<br>CTCGCACCCTGCGCACGCCGAGCAGTACCCGGGCGGCATGGCCCGCGCCTACGGGCCCTACACGCCGCAG<br>CCGCAGCCCAAGGACATGGTGAAGCCGCCCTATAGCTACATCGCGCTCATCACCATGGCCATCCAGAACG<br>CCCCGGACAAGAAGATCACCCTGAACGGCATCTACCAGTTCATCATGGACCGCTTCCCCTTCTACCGGGA<br>CAACAAGCAGGGCTGGCAGAACAGCATCCGCCACAACCTCTCGCTCAACGAGTGCTTCGTCAAGGTGCCG<br>CGCGACGACAAGAAGCCGGGCAAGGGCAGCTACTGGACGCTGGACCCGGACTCCTACAACATGTTCGAGA<br>ACGGCAGCTTCCTGCGGCGGCGGCGGCGCTTCAAGAAGAAGGACGCGGTGAAGGACAAGGAGGAGAAGGA<br>CAGGCTGCACCTCAAGGAGCCGCCCCCGCCCGGCCGCCAGCCCCCGCCCGCGCCGCCGGAGCAGGCCGAC<br>GGCAACGCGCCCGGTCCGCAGCCGCCGCCCGTGCGCATCCAGGACATCAAGACCGAGAACGGTACGTGCC<br>CCTCGCCGCCCCAGCCCCTGTCCCCGGCCGCCGCCCTGGGCAGCGGCAGCGCCGCCGCGGTGCCCAAGAT<br>CGAGAGCCCCGACAGCAGCAGCAGCAGCCTGTCCAGCGGGAGCAGCCCCCCGGGCAGCCTGCCGTCGGCG<br>CGGCCGCTCAGCCTGGACGGTGCGGATTCCGCGCCGCCGCCGCCCGCGCCCTCCGCCCCGCCGCCGCACC<br>ATAGCCAGGGCTTCAGCGTGGACAACATCATGACGTCGCTGCGGGGGTCGCCGCAGAGCGCGGCCGCGGA | 124 |

TABLE 2-continued

| GENBANK ACCESSION NUMBER | SEQUENCE | SEQ ID NO: |
|---|---|---|
| | GCTCAGCTCCGGCCTTCTGGCCTCGGCGGCCGCGTCCTCGCGCGCGGGGATCGCACCCCCGCTGGCGCTC<br>GGCGCCTACTCGCCCGGCCAGAGCTCCCTCTACAGCTCCCCCTGCAGCCAGACCTCCAGCGCGGGCAGCT<br>CGGGCGGCGGCGGCGGCGGCGGCGCGGGGGCCGCGGGGGGCGCGGGCGGCGCCGGGACCTACCACTGCAACCT<br>GCAAGCCATGAGCCTGTACGCGGCCGGCGAGCGCGGGGGCCACTTGCAGGGCGCGCCCGGGGGCGCGGGC<br>GGCTCGGCCGTGGACGACCCCCTGCCCGACTACTCTCTGCCTCCGGTCACCAGCAGCAGCTCGTCGTCCC<br>TGAGTCACGGCGGCGGCGGCGGCGGCGGCGGGGGAGGCCAGGAGGCCGGCCACCACCCTGCGGCCCACCA<br>AGGCCGCCTCACCTCGTGGTACCTGAACCAGGCGGGCGGAGACCTGGGCCACTTGGCGAGCGCGGCGGCG<br>GCGGCGGCGGCCGCAGGCTACCCGGGCCAGCAGCAGAACTTCCACTCGGTGCGGGAGATGTTCGAGTCAC<br>AGAGGATCGGCTTGAACAACTCTCCAGTGAACGGGAATAGTAGCTGTCAAATGGCCTTCCCTTCCAGCCA<br>GTCTCTGTACCGCACGTCCGGAGCTTTCGTCTACGACTGTAGCAAGTTTTGACACACCCTCAAAGCCGAA<br>CTAAATCGAACCCCAAAGCAGGAAAAGCTAAAGGAACCCATCAAGGCAAAATCGAAACTAAAAAAAAAA<br>ATCCAATTAAAAAAAACCCCTGAGAATATTCACCACACCAGCGAACAGAATATCCCTCCAAAAATTCAGC<br>TCACCAGCACCAGCACGAAGAAAACTCTATTTTCTTAACCGATTAATTCAGAGCCACCTCCACTTTGCCT<br>TGTCTAAATAAACAAACCCGTAAACTGTTTTATACAGAGACAGCAAAATCTTGGTTTATTAAAGGACAGT<br>GTTACTCCAGATAACACGTAAGTTTCTTCTTGCTTTTCAGAGACCTGCTTTCCCCTCCTCCCGTCTCCCC<br>TCTCTTGCCTTCTTCCTTGCCTCTCACCTGTAAGATATTATTTTATCCTATGTTGAAGGGAGGGGGAAAG<br>TCCCCGTTTATGAAAGTCGCTTTCTTTTTATTCATGGACTTGTTTTAAAATGTAAATTGCAACATAGTAA<br>TTTATTTTTAATTTGTAGTTGGATGTCGTGGACCAAACGCCAGAAAGTGTTCCCAAAACCTGACGTTAAA<br>TTGCCTGAAACTTTAAATTGTGCTTTTTTTCTCATTATAAAAAGGGAAACTGTATTAATCTTATTCTATC<br>CTCTTTTCTTTCTTTTTGTTGAACATATTCATTGTTTGTTTATTAATAAATTACCATTCAGTTTGAATGA<br>GACCTATATGTCTGGATACTTTAATAGAGCTTTAATTATTACGAAAAAAGATTTCAGAGATAAAACACTA<br>GAAGTTACCTATTCTCCACCTAAATCTCTGAAAAATGGAGAAACCCCTCTGACTAGTCCATGTCAAATTTT<br>ACTAAAAGTCTTTTTGTTTAGATTTATTTTCCTGCAGCATCTTCTGCAAAATGTACTATATAGTCAGCTT<br>GCTTTGAGGCTAGTAAAAAGATATTTTTCTAAACAGATTGGAGTTGGCATATAAACAAATACGTTTTCTC<br>ACTAATGACAGTCCATGATTCGGAAATTTTAAGCCCATGAATCAGCCGCGGTCTTACCACGGTGATGCCT<br>GTGTGCCGAGAGATGGGACTGTGCGGCCAGATATGCACAGATAAATATTTGGCTTGTGTATTCCATATAA<br>AATTGCAGTGCATATTATACATCCCTGTGAGCCAGATGCTGAATAGATATTTTCCTATTATTTCAGTCCT<br>TTATAAAAGGAAAAATAAACCAGTTTTTAAATGTATGTATATAATTCTCCCCATTTACAATCCTTCATG<br>TATTACATAGAAGGATTGCTTTTTTAAAAATATACTGCGGGTTGGAAAGGGATATTTAATCTTTGAGAAA<br>CTATTTTAGAAAATATGTTTGTAGAACAATTATTTTTGAAAAAGATTTAAAGCAATAACAAGAAGGAAGG<br>CGAGAGGAGCAGAACATTTTGGTCTAGGGTGGTTTCTTTTTAAACCATTTTTTCTTGTTAATTTACAGTT<br>AAACCTAGGGGACAATCCGGATTGGCCCTCCCCCTTTTGTAAATAACCCAGGAAATGTAATAAATTCATT<br>ATCTTAGGGTGATCTGCCCTGCCAATCAGACTTTGGGGAGATGGCGATTTGATTACAGACGTTCGGGGGG<br>GTGGGGGGCTTGCAGTTTGTTTTGGAGATAATACAGTTTCCTGCTATCTGCCGCTCCTATCTAGAGGCAA<br>CACTTAAGCAGTAATTGCTGTTGCTTGTTGTCAAAATTTGATCATTGTTAAAGGATTGCTGCAAATAAAT<br>ACACTTTAATTTCAGTCAAAAA | |
| AJ249248 | GTGGCCTCGAGGTGGTGGCAGGGCCGCCCCCTGCAGTCCGGAGACGAACGCACGGACCGGGCCTCCGGAG<br>GCAGGTTCGGCTGGAAGGAACCGCTCTCGCTTCGTCCTACACTTGCGCAAATGTCTCCGAGCTTACTCAC<br>ATAGCATATTGGTATATCAAAATGAAATGCAAGGAACCAAAAATAACATAATTGAAGGCAGTAAAAGTGA<br>AATTAAATAGGAAGATCATCAGTCAAGGAAGACCCACTGGAGAGGACAGAAAATGAAGCAGTGTTTTATC<br>ATGTGTATTTCAGCAGGTCTTCTTGAAATTTAACTAAAAATATGACTGCTCTCTCTTCAGAGAACTGCTC<br>TTTTCAGTACCAGTTACGTCAAACAAACCAGCCCCTAGACGTTAACTATCTGCTATTCTTGATCATACTT<br>GGGAAAATATTATTAAATATCCTTACACTAGGAATGAGAAGAAAAAACACCTGTCAAAATTTTATGGAAT<br>ATTTTTGCATTTCACTAGCATTCGTTGATCTTTTACTTTTGGTAAACATTTCCATTATATTGTATTTCAG<br>GGATTTTGTACTTTTAAGCATTAGGTTCACTAAATACCACATCTGCCTATTTACTCAAATTATTTCCTTT<br>ACTTATGGCTTTTTGCATTATCCAGTTTTCCTGACAGCTTGTATAGATTATTGCCTGAATTTCTCTAAAA<br>CAACCAAGCTTTCATTTAAGTGTCAAAAATTATTTTATTTCTTTACAGTAATTTTAATTTGGATTTCAGT<br>CCTTGCTTATGTTTTGGGAGACCCAGCCATCTACCAAAGCCTGAAGGCACAGAATGCTTATTCTCGTCAC<br>TGTCCTTTCTATGTCAGCATTCAGAGTTACTGGCTGTCATTTTTCATGGTGATGATTTTATTTGTAGCTT<br>TCATAACCTGTTGGGAAGAAGTTACTACTTTGGTACAGGCTATCAGGATAACTTCCTATATGAATGAAAC<br>TATCTTATATTTTCCTTTTTCATCCCACTCCAGTTATACTGTGAGATCTAAAAAAATATTCTTATCCAAG<br>CTCATTGTCTGTTTTCTCAGTACCTGGTTACCATTTGTACTACTTCAGGTAATCATTGTTTTACTTAAAG<br>TTCAGATTCCAGCATATATTGAGATGAATATTCCCTGGTTATACTTTGTCAATAGTTTTCTCATTGCTAC<br>AGTGTATTGGTTTAATTGTCACAAGCTTAATTTAAAAGACATTGGATTACCTTTGGATCCATTTGTCAAC<br>TGGAAGTGCTGCTTCATTCCACTTACAATTCCTAATCTTGAGCAAATTGAAAAGCCTATATCAATAATGA<br>TTTGTTAATATTATTAATTAAAAGTTACAGCTGTCATAAGATCATAATTTTATGAACAGAAAGAACTCAG<br>GACATATTAAAAAATAAACTGAACTAAAACAACTTTTGCCCCCTGACTGATAGCATTTCAGAATGTGTCT<br>TTTGAAGGGCTATACCAGTTATTAAATAGTGTTTTATTTTAAAAACAAAATAATTCCAAGAAGTTTTTAT<br>AGTTATTCAGGGACACTATATTACAAATATTACTTTGTTATTAACACAAAAAGTGATAAGAGTTAACATT<br>TGGCTATACTGATGTTTGTGTTACTCAAAAAAACTACTGGATGCAAACTGTTATGTAAATCTGAGATTTC<br>ACTGACAACTTTAAGATATCAACCTAAACATTTTTATTAAATGTTCAAATGTAAGCAAGAAAAAAAAAA | 125 |
| NM_005310 | ACCCGCCCCCATCTGCCCAAGATAATTTTAGTTTCCTTGGGCCTGGAATCTGGACACACAGGGCTCCCCC<br>CCGCCTCTGACTTCTCTGTCCGAAGTCGGGACACCCTCCTACCACCTGTAGAGAAGCGGGAGTGGATCTG<br>AAATAAAATCCAGGAATCTGGGGGTTCCTAGACGGAGCCAGACTTCGGAACGGGTGTCCTGCTACTCCTG<br>CTGGGGCTCCTCCAGGACAAGGGCACACAACTGGTTCCGTTAAGCCCCTCTCTCGCTCAGACGCCATGGA<br>GCTGGATCTGTCTCCACCTCATCTTAGCAGCTCTCCGGAAGACCTTTGCCCAGCCCCTGGGACCCCTCCT<br>GGGACTCCCCGGCCCCCTGATACCCCTCTGCCTGAGGAGGTAAAGAGGTCCCAGCCTCTCCTCATCCCAA<br>CCACCGGCAGGAAACTTCGAGAGGAGGAGAGGCGTGCCACCTCCCTCCCCTCTATCCCCAACCCCTTCCC<br>TGAGCTCTGCAGTCCTCCCTCACAGAGCCCAATTCTCGGGGGCCCCTCCAGTGCAAGGGGGCTGCTCCCC<br>CGCGATGCCAGCCGCCCCCATGTAGTAAAGGTGTACAGTGAGGATGGGGCCTGCAGGTCTGTGGAGGTGG<br>CAGCAGGTGCCACAGCTCGCCACGTGTGTGAAATGCTGGTGCAGCGAGCTCACGCCTTGAGCGACGAGAC<br>CTGGGGGCTGGTGGAGTGCCACCCCCACCTAGCACTGGAGCGGGGTTTGGAGGACCACGAGTCCGTGGTG<br>GAAGTGCAGGCTGCCTGGCCCGTGGGCGGAGATAGCCGCTTCGTCTTCCGGAAAAACTTCGCCAAGTACG<br>AACTGTTCAAGAGCTCCCCACACTCCCTGTTCCCAGAAAAAATGGTCTCCAGCTGTCTCGATGCACACAC | 126 |

TABLE 2-continued

| GENBANK ACCESSION NUMBER | SEQUENCE | SEQ ID NO: |
| --- | --- | --- |
| | TGGTATATCCCATGAAGACCTCATCCAGAACTTCCTGAATGCTGGCAGCTTTCCTGAGATCCAGGGCTTT<br>CTGCAGCTGCGGGGTTCAGGACGGAAGCTTTGGAAACGCTTTTTCTGCTTCTTGCGCCGATCTGGCCTCT<br>ATTACTCCACCAAGGGCACCTCTAAGGATCCGAGGCACCTGCAGTACGTGGCAGATGTGAACGAGTCCAA<br>CGTGTACGTGGTGACGCAGGGCCGCAAGCTCTACGGGATGCCCACTGACTTCGGTTTCTGTGTCAAGCCC<br>AACAAGCTTCGAAATGGCCACAAGGGGCTTCGGATCTTCTGCAGTGAAGATGAGCAGAGCCGCACCTGCT<br>GGCTGGCTGCCTTCCGCCTCTTCAAGTACGGGGTGCAGCTGTACAAGAATTACCAGCAGGCACAGTCTCG<br>CCATCTGCATCCATCTTGTTTGGGCTCCCCACCCTTGAGAAGTGCCTCAGATAATACCCTGGTGGCCATG<br>GACTTCTCTGGCCATGCTGGGCGTGTCATTGAGAACCCCCGGGAGGCTCTGAGTGTGGCCCTGGAGGAGG<br>CCCAGGCCTGGAGGAAGAAGACAAACCACCGCCTCAGCCTGCCCATGCCAGCCTCCGGCACGAGCCTCAG<br>TGCAGCCATCCACCGCACCCAACTCTGGTTCCACGGGCGCATTTCCCGTGAGGAGAGCCAGCGGCTTATT<br>GGACAGCAGGGCTTGGTAGACGGCCTGTTCCTGGTCCGGGAGAGTCAGCGGAACCCCCAGGGCTTTGTCC<br>TCTCTTTGTGCCACCTGCAGAAAGTGAAGCATTATCTCATCCTGCCGAGCGAGGAGGAGGGCCGCCTGTA<br>CTTCAGCATGGATGATGGCCAGACCCGCTTCACTGACCTGCTGCAGCTCGTGGAGTTCCACCAGCTGAAC<br>CGCGGCATCCTGCCGTGCTTGCTGCGCCATTGCTGCACGCGGGTGGCCCTCTGACCAGGCCGTGGACTGG<br>CTCATGCCTCAGCCCGCCTTCAGGCTGCCCGCCGCCCCTCCACCCATCCAGTGGACTCTGGGGCGCGGCC<br>ACAGGGGACGGGATGAGGAGCGGGAGGGTTCCGCCACTCCAGTTTTCTCCTCTGCTTCTTTGCCTCCCTC<br>AGATAGAAAACAGCCCCCACTCCAGTCCACTCCTGACCCCTCTCCTCAAGGGAAGGCCTTGGGTGGCCCC<br>CTCTCCTTCTCCTAGCTCTGGAGGTGCTGCTCTAGGGCAGGGAATTATGGGAGAAGTGGGGGCAGCCCAG<br>GCGGTTTCACGCCCCACACTTTGTACAGACCGAGAGGCCAGTTGATCTGCTCTGTTTTATACTAGTGACA<br>ATAAAGATTATTTTTTGATACAAAAAAAAAAAAAAAAAAAAAAA | |
| NM_014176 | AGTCAGAGGTCGCGCAGGCGCTGGTACCCCGTTGGTCCGCGCGTTGCTGCGTTGTGAGGGGTGTCAGCTC<br>AGTGCATCCCAGGCAGCTCTTAGTGTGGAGCAGTGAACTGTGTGTGGTTCCTTCTACTTGGGGATCATGC<br>AGAGAGCTTCACGTCTGAAGAGAGAGCTGCACATGTTAGCCACAGAGCCACCCCCAGGCATCACATGTTG<br>GCAAGATAAAGACCAAATGGATGACCTGCGAGCTCAAATATTAGGTGGAGCCAACACACCTTATGAGAAA<br>GGTGTTTTTAAGCTAGAAGTTATCATTCCTGAGAGGTACCCATTTGAACCTCCTCAGATCCGATTTCTCA<br>CTCCAATTTATCATCCAAACATTGATTCTGCTGGAAGGATTTGTCTGGATGTTCTCAAATTGCCACCAAA<br>AGGTGCTTGGAGACCATCCCTCAACATCGCAACTGTGTTGACCTCTATTCAGCTGCTCATGTCAGAACCC<br>AACCCTGATGACCCGCTCATGGCTGACATATCCTCAGAATTTAAATATAATAAGCCAGCCTTCCTCAAGA<br>ATGCCAGACAGTGGACAGAGAAGCATGCAAGACAGAAACAAAAGGCTGATGAGGAAGAGATGCTTGATAA<br>TCTACCAGAGGCTGGTGACTCCAGAGTACACAACTCAACACAGAAAAGGAAGGCCAGTCAGCTAGTAGGC<br>ATAGAAAAGAAATTTCATCCTGATGTTTAGGGGACTTGTCCTGGTTCATCTTAGTTAATGTGTTCTTTGC<br>CAAGGTGATCTAAGTTGCCTACCTTGAATTTTTTTTAAATATATTTGATGACATAATTTTTGTGTAGTT<br>TATTTATCTTGTACATATGTATTTTGAAATCTTTTAAACCTGAAAAATAAATAGTCATTTAATGTTGAAA<br>AAAAAAAAAAAAAAAAAAAAAAAA | 127 |
| NM_006845 | ACGCTTGCGCGCGGGATTTAAACTGCGGCGGTTTACGCGGCGTTAAGACTTCGTAGGGTTAGCGAAATTG<br>AGGTTTCTTGGTATTGCGCGTTTCTCTTCCTTGCTGACTCTCCGAATGGCCATGGACTCGTCGCTTCAGG<br>CCCGCCTGTTTCCCGGTCTCGCTATCAAGATCCAACGCAGTAATGGTTTAATTCACAGTGCCAATGTAAG<br>GACTGTGAACTTGGAGAAATCCTGTGTTTCAGTGGAATGGGCAGAAGGAGGTGCCACAAAGGGCAAAGAG<br>ATTGATTTTGATGATGTGGCTGCAATAAACCCAGAACTCTTACAGCTTCTTCCCTTACATCCGAAGGACA<br>ATCTGCCCTTGCAGGAAAATGTAACAATCCAGAAACAAAAACGGAGATCCGTCAACTCCAAAATTCCTGC<br>TCCAAAAGAAAGTCTTCGAAGCCGCTCCACTCGCATGTCCACTGTCTCAGAGCTTCGCATCACGGCTCAG<br>GAGAATGACATGGAGGTGGAGCTGCCTGCAGCTGCAAACTCCCGCAAGCAGTTTTCAGTTCCTCCTGCCC<br>CCACTAGGCCTTCCTGCCCTGCAGTGGCTGAAATACCATTGAGGATGGTCAGCGAGGAGATGGAAGAGCA<br>AGTCCATTCCATCCGAGGCAGCTCTTCTGCAAACCCTGTGAACTCAGTTCGGAGGAAATCATGTCTTGTG<br>AAGGAAGTGGAAAAAATGAAGAACAAGCGAGAAGAGAAGAAGGCCCAGAACTCTGAAATGAGAATGAAGA<br>GAGCTCAGGAGTATGACAGTAGTTTTCCAAACTGGGAATTTGCCCGAATGATTAAAGAATTTCGGGCTAC<br>TTTGGAATGTCATCCACTTACTATGACTGATCCTATCGAAGAGCACAGAATATGTGTCTGTGTTAGGAAA<br>CGCCCACTGAATAAGCAAGAATTGGCCAAGAAAGAAATTGATGTGATTTCCATTCCTAGCAAGTGTCTCC<br>TCTTGGTACATGAACCCAAGTTGAAAGTGGACTTAACAAAGTATCTGGAGAACCAAGCATTCTGCTTTGA<br>CTTTGCATTTGATGAAACAGCTTCGAATGAAGTTGTCTACAGGTTCACAGCAAGGCCACTGGTACAGACA<br>ATCTTTGAAGGTGGAAAAGCAACTTGTTTTGCATATGGCCAGACAGGAAGTGGCAAGACACATACTATGG<br>GCGGAGACCTCTCTGGGAAAGCCCAGAATGCATCCAAAGGGATCTATGCCATGGCCTCCCGGGACGTCTT<br>CCTCCTGAAGAATCAACCCTGCTACCGGAAGTTGGGCCTGGAAGTCTATGTGACATTCTTCGAGATCTAC<br>AATGGGAAGCTGTTTGACCTGCTCAACAAGAAGGCCAAGCTGCGCGTGCTGGAGGACGGCAAGCAACAGG<br>TGCAAGTGGTGGGGCTGCAGGAGCATCTGGTTAACTCTGCTGATGATGTCATCAAGATGATCGACATGGG<br>CAGCGCCTGCAGAACCTCTGGGCAGACATTTGCCAACTCCAATTCCTCCCGCTCCCACGCGTGCTTCCAA<br>ATTATTCTTCGAGCTAAAGGGAGAATGCATGGCAAGTTCTCTTTGGTAGATCTGGCAGGGAATGAGCGAG<br>GCGCGGACACTTCCAGTGCTGACCGGCAGACCCGCATGGAGGGCGCAGAAATCAACAAGAGTCTCTTAGC<br>CCTGAAGGAGTGCATCAGGGCCCTGGGACAGAACAAGGCTCACACCCCGTTCCGTGAGAGCAAGCTGACA<br>CAGGTGCTGAGGGACTCCTTCATTGGGGAGAACTCTAGGACTTGCATGATTGCCACGATCTCACCAGGCA<br>TAAGCTCCTGTGAATATACTTTAAACACCCTGAGATATGCAGACAGGGTCAAGGAGCTGAGCCCCCACAG<br>TGGGCCCAGTGGAGAGCAGTTGATTCAAATGGAAACAGAAGAGATGGAAGCCTGCTCTAACGGGGCGCTG<br>ATTCCAGGCAATTTATCCAAGGAAGAGGAGGAACTGTCTTCCCAGATGTCCAGCTTTAACGAAGCCATGA<br>CTCAGATCAGGGAGCTGGAGGAGAAGGCTATGGAAGAGCTCAAGGAGATCATACAGCAAGGACCAGACTG<br>GCTTGAGCTCTCTGAGATGACCGAGCAGCCAGACTATGACCTGGAGACCTTTGTGAACAAAGCGGAATCT<br>GCTCTGGCCCAGCAAGCCAAGCATTTCTCAGCCCTGCGAGATGTCATCAAGGCCTTGCGCCTGGCCATGC<br>AGCTGGAAGAGCAGGCTAGCAGACAAATAAGCAGCAAGAAACGGCCCCAGTGACGACTGCAAATAAAAAT<br>CTGTTTGGTTTGACACCCAGCCTCTTCCCTGGCCCTCCCCAGAGAACTTTGGGTACCTGGTGGGTCTAGG<br>CAGGGTCTGAGCTGGGACAGGTTCTGGTAAATGCCAAGTATGGGGGCATCTGGGCCCAGGGCAGCTGGGG<br>AGGGGGTCAGAGTGACATGGGACACTCCTTTTCTGTTCCTCAGTTGTCGCCCTCACGAGAGGAAGGAGCT<br>CTTAGTTACCCTTTTGTGTTGCCCTTCTTTCCATCAAGGGGAATGTTCTCAGCATAGAGCTTTCTCCGCA<br>GCATCCTGCCTGCGTGGACTGGCTGCTAATGGAGAGCTCCCTGGGGTTGTCCTGGCTCTGGGGAGAGAGA | 128 |

TABLE 2-continued

| GENBANK ACCESSION NUMBER | SEQUENCE | SEQ ID NO: |
|---|---|---|
| | CGGAGCCTTTAGTACAGCTATCTGCTGGCTCTAAACCTTCTACGCCTTTGGGCCGAGCACTGAATGTCTT<br>GTACTTTAAAAAAATGTTTCTGAGACCTCTTTCTACTTTACTGTCTCCCTAGAGATCCTAGAGGATCCCT<br>ACTGTTTTCTGTTTTATGTGTTTATACATTGTATGTAACAATAAAGAGAAAAAATAAATCAGCTGTTTAA<br>GTGTGTGGAAAAAAAAAAAAAAAAAA | |
| NM_006101 | ACTGCGCGCGTCGTGCGTAATGACGTCAGCGCCGGCGGAGAATTTCAAATTCGAACGGCTTTGGCGGGCC<br>GAGGAAGGACCTGGTGTTTTGATGACCGCTGTCCTGTCTAGCAGATACTTGCACGGTTTACAGAAATTCG<br>GTCCCTGGGTCGTGTCAGGAAACTGGAAAAAAGGTCATAAGCATGAAGCGCAGTTCAGTTTCCAGCGGTG<br>GTGCTGGCCGCCTCTCCATGCAGGAGTTAAGATCCCAGGATGTAAATAAACAAGGCCTCTATACCCCTCA<br>AACCAAAGAGAAACCAACCTTTGGAAAGTTGAGTATAAACAAACCGACATCTGAAAGAAAAGTCTCGCTA<br>TTTGGCAAAAGAACTAGTGGACATGGATCCCGGAATAGTCAACTTGGTATATTTTCCAGTTCTGAGAAAA<br>TCAAGGACCCGAGACCACTTAATGACAAAGCATTCATTCAGCAGTGTATTCGACAACTCTGTGAGTTTCT<br>TACAGAAAATGGTTATGCACATAATGTGTCCATGAAATCTCTACAAGCTCCCTCTGTTAAAGACTTCCTG<br>AAGATCTTCACATTTCTTTATGGCTTCCTGTGCCCCTCATACGAACTTCCTGACACAAAGTTTGAAGAAG<br>AGGTTCCAAGAATCTTTAAAGACCTTGGGTATCCTTTTGCACTATCCAAAAGCTCCATGTACACAGTGGG<br>GGCTCCTCATACATGGCCTCACATTGTGGCAGCCTTAGTTTGGCTAATAGACTGCATCAAGATACATACT<br>GCCATGAAAGAAAGCTCACCTTTATTTGATGATGGGCAGCCTTGGGGAGAAGAAACTGAAGATGGAATTA<br>TGCATAATAAGTTGTTTTTGGACTACACCATAAAATGCTATGAGAGTTTTATGAGTGGTGCCGACAGCTT<br>TGATGAGATGAATGCAGAGCTGCAGTCAAAACTGAAGGATTTATTTAATGTGGATGCTTTTAAGCTGGAA<br>TCATTAGAAGCAAAAAACAGAGCATTGAATGAACAGATTGCAAGATTGGAACAAGAAAGAGAAAAAGAAC<br>CGAATCGTCTAGAGTCGTTGAGAAAACTGAAGGCTTCCTTACAAGGAGATGTTCAAAAGTATCAGGCATA<br>CATGAGCAATTTGGAGTCTCATTCAGCCATTCTTGACCAGAAATTAAATGGTCTCAATGAGGAAATTGCT<br>AGAGTAGAACTAGAATGTGAAACAATAAAACAGGAGAACACTCGACTACAGAATATCATTGACAACCAGA<br>AGTACTCAGTTGCAGACATTGAGCGAATAAATCATGAAAGAAATGAATTGCAGCAGACTATTAATAAATT<br>AACCAAGGACCTGGAAGCTGAACAACAGAAGTTGTGGAATGAGGAGTTAAAATATGCCAGAGGCAAAGAA<br>GCGATTGAAACACAATTAGCAGAGTATCACAAATTGGCTAGAAAATTAAAACTTATTCCTAAAGGTGCTG<br>AGAATTCCAAAGGTTATGACTTTGAAATTAAGTTTAATCCCGAGGCTGGTGCCAACTGCCTTGTCAAATA<br>CAGGGCTCAAGTTTATGTACCTCTTAAGGAACTCCTGAATGAAACTGAAGAAGAAATTAATAAAGCCCTA<br>AATAAAAAAATGGGTTTGGAGGATACTTTAGAACAATTGAATGCAATGATAACAGAAAGCAAGAGAAGTG<br>TGAGAACTCTGAAAGAAGAAGTTCAAAAGCTGGATGATCTTTACCAACAAAAAATTAAGGAAGCAGAGGA<br>AGAGGATGAAAAATGTGCCAGTGAGCTTGAGTCCTTGGAGAAACACAAGCACCTGCTAGAAAGTACTGTT<br>AACCAGGGGCTCAGTGAAGCTATGAATGAATTAGATGCTGTTCAGCGGGAATACCAACTAGTTGTGCAAA<br>CCACGACTGAAGAAAGACGAAAAGTGGGAAATAACTTGCAACGTCTGTTAGAGATGGTTGCTACACATGT<br>TGGGTCTGTAGAGAAACATCTTGAGGAGCAGATTGCTAAAGTTGATAGAGAATATGAAGAATGCATGTCA<br>GAAGATCTCTCGGAAAATATTAAAGAGATTAGAGATAAGTATGAGAAGAAAGCTACTCTAATTAAGTCTT<br>CTGAAGAATGAAGATAAAATGTTGATCATGTATATATATCCATAGTGAATAAAATTGTCTCAGTAAAGTG<br>TAAAAAAAAAAAAAAAAAAAAAAAAAAAAAAAAAAAAAA | 129 |
| BC042437 | CTCCCTCCTCTGCACCATGACTACCTGCAGCCGCCAGTTCACCTCCTCCAGCTCCATGAAGGGCTCCTGC<br>GGCATCGGGGGCGGCATCGGGGGCGGCTCCAGCCGCATCTCCTCCGTCCTGGCCGGAGGGTCCTGCCGCG<br>CCCCCAGCACCTACGGGGGCGGCCTGTCTGTCTCATCCTCCCGCTTCTCCTCTGGGGGAGCCTATGGGTT<br>GGGGGGCGGCTATGGCGGTGGCTTCAGCAGCAGCAGCAGCAGCTTTGGTAGTGGCTTTGGGGGAGGATAT<br>GGTGGTGGCCTTGGTGCTGGCTTGGGTGGTGGCTTTGGTGGTGGCTTTGCTGGTGGTGATGGGCTTCTGG<br>TGGGCAGTGAGAAGGTGACCATGCAGAACCTCAACGACCGCCTGGCCTCCTACCTGGACAAGGTGCGTGC<br>TCTGGAGGAGGCCAACGCCGACCTGGAAGTGAAGATCCGTGACTGGTACCAGAGGCAGCGGCCTGCTGAG<br>ATCAAAGACTACAGTCCCTACTTCAAGACCATTGAGGACCTGAGGAACAAGATTCTCACAGCCACAGTGG<br>ACAATGCCAATGTCCTTCTGCAGATTGACAATGCCCGTCTGGCCGCGGATGACTTCCGCACCAAGTATGA<br>GACAGAGTTGAACCTGCGCATGAGTGTGGAAGCCGACATCAATGGCCTGCGCAGGGTGCTGGACGAACTG<br>ACCCTGGCCAGAGCTGACCTGGAGATGCAGATTGAGAGCCTGAAGGAGGAGCTGGCCTACCTGAAGAAGA<br>ACCACGAGGAGGAGATGAATGCCCTGAGAGGCCAGGTGGGTGGAGATGTCAATGTGGAGATGGACGCTGC<br>ACCTGGCGTGGACCTGAGCCGCATTCTGAACGAGATGCGTGACCAGTATGAGAAGATGGCAGAGAAGAAC<br>CGCAAGGATGCCGAGGAATGGTTCTTCACCAAGACAGAGGAGCTGAACCGCGAGGTGGCCACCAACAGCG<br>AGCTGGTGCAGAGCGGCAAGAGCGAGATCTCGGAGCTCCGGCGCACCATGCAGAACCTGGAGATTGAGCT<br>GCAGTCCCAGCTCAGCATGAAAGCATCCCTGGAGAACAGCCTGGAGGAGACCAAAGGTCGCTACTGCATG<br>CAGCTGGCCCAGATCCAGGAGATGATTGGCAGCGTGGAGGAGCAGCTGGCCCAGCTCCGCTGCGAGATGG<br>AGCAGCAGAACCAGGAGTACAAGATCCTGCTGGACGTGAAGACGCGGCTGGAGCAGGAGATCGCCACCTA<br>CCGCCGCCTGCTGGAGGGCGAGGACGCCCACCTCTCCTCCTCCCAGTTCTCCTCTGGATCGCAGTCATCC<br>AGAGATGTGACCTCCTCCAGCCGCCAAATCCGCACCAAGGTCATGGATGTGCACGATGGCAAGGTGGTGT<br>CCACCCACGAGCAGGTCCTTCGCACCAAGAACTGAGGCTGCCCAGCCCCGCTCAGGCCTAGGAGGCCCCC<br>CGTGTGGACACAGATCCCACTGGAAGATCCCCTCTCCTGCCCAAGCACTTCACAGCTGGACCCTGCTTCA<br>CCCTCACCCCCTCCTGGCAATCAATACAGCTTCATTATCTGAGTTGCATAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAA | 130 |
| AK095281 | CTCTTTTGCAGGGGCCGTTCCTCGGGGCATGACGCTGGCTCCTGCACAGATCCTGCTCCTCTGTGGCCTT<br>CCTGGGCTGCCCTCCCCTCCTCCGGGACTGCTCTGGACTGACACTGCTCAGGTTCGGATTCCCTCAAAGA<br>CTTTGGGAGACAAGACTTGGTCCCCCTTTTACAAACAAGGGAACGGAGGCTCTAGAACTGACTTCCTGAA<br>AGGCTTGGATCCAAAGCTCCCTCAGTTCAGCGGCCACGTCTATTTCCCTCAGACACAGGGATCCTTGAAC<br>CTGTGGGCTGTATCTCCCCGCGGACTTGGAAGAATCCCAAGAGAGTGGGGCTCCCACAGGCTGGAGTGCA<br>ATGGTGTGATCTCGGCTCACTGCAACCTCCACCTCCCAGGTTCAAGCTATTCTCCTGCCTCAGCCTCCTG<br>AGTAGCTGGGATTACAGATCCTGGTGGCTGTGGTCGGTAATTCCAGCTTCGTGCTGGCTACAGGTGGATG<br>ATGCCCACCTGGCTGCCGATGACCTCTGCACCAAGTGAGGCTGGGTCTCTGGAGCTGCCCCAGGGGCTGG<br>ACAAGCTGACCCTGGCCGGGGCCAACCTGGAGATGCAGATTGAGAACCTCAAGGAGGACCTGGTCTACCT<br>GAAGAAGAACCACAAGCAGGAAATGAACGTCCTTTGAGGTCAGGTGGATGAGGATGTCAGTGTGAAGATG<br>GACACTGTGCCTGGAGTGAACCTGAGCTGCATCCTGAATGAGATGCGTGACCAGGACAAGACATTGGTGG<br>AGAAGAGCTGCAAGGATGCCGAGGGCTGGTTCTTCAGCATGGTGGGTGGCCGTGCGTAAGCAGGTGTGTA | 131 |

TABLE 2-continued

| GENBANK ACCESSION NUMBER | SEQUENCE | SEQ ID NO: |
|---|---|---|
| | CACGTGTGGGCACATGTGCTGCATGCTGGTGCAGCTGGAGCACTGGCAGATCCACAGGCTGTCCCAGTTG GAAGGACTTTTGGAAACCAGTTGGACCAGCCCCTCATGTTTTAGATGTAAAACGTGAGGCTCAGAGAGGA CTCAAGCTCACACAGCCCTTCACTGTGGCCTGCAAAATAGATCCAGGTCTCTACAAGTCTGGTCTTGGGT TTCCACCACAGCTGTTTACAGGATGTGCGTATTTGAATACATATGTATACCCTTGGCAAGCACAGGCTGA GTATCTCCGGTATCCTAGGGACAGCAACAGGCGCAAAAGAATAACACCCAGTGCCTGTCTTTGAGGTGCT GCAGTTCAGTAGGAAAAAGAAATGCAAATGACCGCAGAGCAGGCTGAATTCCTCCAAGTTCCAATGTGGG TGCAGAGGCTCTCTGTGTGCAGAAAGAGGGGCTGAACTGCGAGGTGGCCACCAACACAGAGGCCCTGCAG AGTGGCTGGATAGAGATATGGAGCTCTACGTCTCTGTGCAGAACCTGAGCCGTCCCAGCTCAGCAAGAAA GCATCGCTGGAGGGCAGCCTGGTGGAGATGGAGGTGTGTTACAGGACCCTGCCGGCCCAGCTGCAGGGGC TTAACAGAAGCATGGAGCAGCAGCTGTGCGAGCTCTGCTGCGACACGGAGCACCAGGACCACAAGCACAG GTCCTTCTGGACGTGAAGACGTGGCTGGAGCAGGAGATCGCCACCTACCGCCGCTTGCTGGAGGTTGAGG ACGCCCAGAGGTGATACTGACGATGCAGGCTGGAGTCTGGCTGAGGAGCCTTGAATGCCAAGTTAAAGCG TCTGGACTAGATCACGTAGGCAATGGGGAGCCATGGAGGGATTTGGAGCAGGAGAGTGAAATGAACATCA AGAGATTTTAGAACATTCACTCTGGCTGCAGAGGGAGAAATGGATCAGAGGGGTCAGGGCGGGGCCAGAG AGATGTGTCAGGGGGCTGGAGCAGGGAGTCTGGCCAGAGAAGTCCCGTGCGGTGGTGGGTAGTGGGGCAG GGGAAGGAAGGTGGTGCACGCAGAAGAGAGGTTATAGCTCAAAACAGCGGGACTGGATGCCTGGATCTCG GGGTAAGCATGGCTCACAGTCAGGACTCAGTAAGTGTCGGGAGAACACATGAAGGAGCAGGCATTGATGG CCCTGGGTTTCTGGTTCTGATGACTGTGTGAGTGGTGAAGAGCAAGGTGGGTGGTGGTTGGGTTTGCAGT TGGGAAGGGTGATCAGGCCTTCAGCTGAGAGTGTCCCGGAGTCTCCATGCTTAGTCACACGTTGCAGCTT TTTGCTCCCCGGAAATGGTGAAGTCCATCTATAGTCTAACAACAGTCTCTCCTGCTTTAATTGGGTCTAT TTGTTGGGCCCTCTGGGTTATGGAAAAACCACTTGCTCAGCTTCTCCTTGTAAATTCCTGGTGAGTAGCC ACAGAGTGCCGCCAGACCTACTGCTGTGCTGTTTCTTTTTCTTCTTCCTGCTGTGCTGAACCCCTGCCCT TTCATTCTTGGGCCTGCGCTAATTTCTGTGCATTCCCAACTGTGATTTTTCACCAATTTAGGGGAACCTC CTCTGCCAGGGCCTACTTCTCCCCAGCAGTGCTTGCAGGTGCCTGGGCTGGCTGGCATCCCTGGGCTGAT GGGTGCTTCTCTCCCTGCAGGCTGGCCACTCAGTACTCCTTGTCCCTGGCCTCGCAGCCCACCCGGGAAG CCACAGTGACCAGCCACCAGGTGTGCCATCGTGGAGGAAGTCCAGGTTGGAGAGGTGGTCTTCTTCTGTG AGCAGGTCCACTTCTCCACCCACTGAGACCCCTTTCTGTCTGCGACAGCCCCACCTCGAGGGCCACGGCA CAGCCATCAGCTCCAGCTCCCAGCATGCTACTGCCACGCCCCGAGTGTCCGTCTGGGCCCCGGTGCATGG CCTGTTGTCTTTCTGTATCTACTTTCTGCAGCCCCTCACTGAGGAGGCCTCCTGGGTTTGTCCAGTGCCT ACTATTAAAGCTTTGCTCCAAGTTC | |
| M21389 | GCATCCTTTTTGGGCTGCTCACAGCCCCCAGCCTCTATGGTGAAGACATACTTGCTAGCAGCGTCACCAA CTTGCTGCCAAGAGATCAGTGCTGCAAGGCAAGGTTATTTCTAACTGAGCAGAGCCTGCCAGGAAGAAAG CGTTTGCACCCCACACCACTGTGCAGGTGTGACCGGTGAGCTCACAGCTGCCCCCCAGGCATGCCCAGCC CACTTAATCATTCACAGCTCGACAGCTCTCTCGCCCAGCCCAGTTCTGGAAGGGATAAAAAGGGGGCATC ACCGTTCCTGGGTAACAGAGCCACCTTCTGCGTCCTGCTGAGCTCTGTTCTCTCCAGCACCTCCCAACCC ACTAGTGCCTGGTTCTCTTGCTCCACCAGGAACAAGCCACCATGTCTCGCCAGTCAAGTGTGTCCTTCCG GAGCGGGGGCAGTCGTAGCTTCAGCACCGCCTCTGCCATCACCCCGTCTGTCTCCCGCACCAGCTTCACC TCCGTGTCCCGGTCCGGGGGTGGCGGTGGTGGTGGCTTCGGCAGGGTCAGCCTTGCGGGTGCTTGTGGAG TGGGTGGCTATGGCAGCCGGAGCCTCTACAACCTGGGGGGCTCCAAGAGGATATCCATCAGCACTAGAGG AGGCAGCTTCAGGAACCGGTTTGGTGCTGGTGCTGGAGGCGGCTATGGCTTTGGAGGTGGTGCCGGTAGT GGATTTGGTTTCGGCGGTGGAGCTGGTGGTGGCTTTGGGCTCGGTGGCGGAGCTGGCTTTGGAGGTGGCT TCGGTGGCCCTGGCTTTCCTGTCTGCCCTCCTGGAGGTATCCAAGAGGTCACTGTCAACCAGAGTCTCCT GACTCCCCTCAACCTGCAAATCGACCCCAGCATCCAGAGGGTGAGGACCGAGGAGCGCGAGCAGATCAAG ACCCTCAACAATAAGTTTGCCTCCTTCATCGACAAGGTGCGGTTCCTGGAGCAGCAGAACAAGGTTCTGG ACACCAAGTGGACCCTGCTGCAGGAGCAGGGCACCAAGACTGTGAGGCAGAACCTGGAGCCGTTGTTCGA GCAGTACATCAACAACCTCAGGAGGCAGCTGGACAGCATCGTGGGGGAACGGGGCCGCCTGGACTCAGAG CTGAGAAACATGCAGGACCTGGTGGAAGACTTCAAGAACAAGTATGAGGATGAAATCAACAAGCGTACCA CTGCTGAGAATGAGTTTGTGATGCTGAAGAAGGATGTAGATGCTGCCTACATGAACAAGGTGGAGCTGGA GGCCAAGGTTGATGCACTGATGGATGAGATTAACTTCATGAAGATGTTCTTTGATGCGGAGCTGTCCCAG ATGCAGACGCATGTCTCTGACACCTCAGTGGTCCTCTCCATGGACAACAACCGCAACCTGGACCTGGATA GCATCATCGCTGAGGTCAAGGCCCAGTATGAGGAGATTGCCAACCGCAGCCGGACAGAAGCCGAGTCCTG GTATCAGACCAAGTATGAGGAGCTGCAGCAGACAGCTGGCCGGCATGGCGATGACCTCCGCAACACCAAG CATGAGATCACAGAGATGAACCGGATGATCCAGAGGCTGAGAGCCGAGATTGACAATGTCAAGAAACAGT GCGCCAATCTGCAGAACGCCATTGCGGATGCCGAGCAGCGTGGGGAGCTGGCCCTCAAGGATGCCAGGAA CAAGCTGGCCGAGCTGGAGGAGGCCCTGCAGAAGGCCAAGCAGGACATGGCCCGGCTGCTGCGTGAGTAC CAGGAGCTCATGAACACCAAGCTGGCCCTGGACGTGGAGATCGCCACTTACCGCAAGCTGCTGGAGGGCG AGGAATGCAGACTCAGTGGAGAAGGAGTTGGACCAGTCAACATCTCTGTTGTCACAAGCAGTGTTTCCTC TGGATATGGCAGTGGCAGTGGCTATGGCGGTGGCCTCGGTGGAGGTCTTGGCGGCGGCCTCGGTGGAGGT CTTGCCGGAGGTAGCAGTGGAAGCTACTACTCCAGCAGCAGTGGGGGTGTCGGCCTAGGTGGTGGGCTCA GTGTGGGGGGCTCTGGCTTCAGTGCAAGCAGTGGCCGAGGGCTGGGGGTGGGCTTTGGCAGTGGCGGGGG TAGCAGCTCCAGCGTCAAATTTGTCTCCACCACCTCCTCCTCCCGGAAGAGCTTCAAGAGCTAAGAACCT GCTGCAAGTCACTGCCTTCCAAGTGCAGCAACCCAGCCCATGGAGATTGCCTCTTCTAGGCAGTTGCTCA AGCCATGTTTTATCCTTTTCTGGAGAGTAGTCTAGACCAAGCCAATTGCAGAACCACATTCTTTGGTTCC CAGGAGAGCCCCATTCCCAGCCCCTGGTCTCCCGTGCCGCAGTTCTATATTCTGCTTCAAATCAGCCTTC AGGTTTCCCACAGCATGGCCCCTGCTGACACGAGAACCCAAAGTTTTCCCAAATCTAAATCATCAAAACA GAATCCCCACCCCAATCCCAAATTTTGTTTTGGTTCTAACTACCTCCAGAATGTGTTCAATAAAATGCTT TTATAATAT | 132 |
| NM_001123066 | GGACGGCCGAGCGGCAGGGCGCTCGCGCGCGCCCACTAGTGGCCGGAGGAGAAGGCTCCCGCGGAGGCCG CGCTGCCCGCCCCCTCCCCTGGGGAGGCTCGCGTTCCCGCTGCTCGCGCCTGCGCCGCCCGCCGGCCTCA GGAACGCGCCCTCTTCGCCGGCGCGCGCCCTCGCAGTCACCGCCACCCACCAGCTCCGGCACCAACAGCA GCGCCGCTGCCACCGCCCACCTTCTGCCGCCGCCACCACAGCCACCTTCTCCTCCTCCGCTGTCCTCTCC CGTCCTCGCCTCTGTCGACTATCAGGTGAACTTTGAACCAGGATGGCTGAGCCCCGCCAGGAGTTCGAAG TGATGGAAGATCACGCTGGGACGTACGGGTTGGGGGACAGGAAAGATCAGGGGGGCTACACCATGCACCA AGACCAAGAGGGTGACACGGACGCTGGCCTGAAAGAATCTCCCCTGCAGACCCCCACTGAGGACGGATCT | 133 |

TABLE 2-continued

| GENBANK ACCESSION NUMBER | SEQUENCE | SEQ ID NO: |
|---|---|---|
| | GAGGAACCGGGCTCTGAAACCTCTGATGCTAAGAGCACTCCAACAGCGGAAGATGTGACAGCACCCTTAG | |
| | TGGATGAGGGAGCTCCCGGCAAGCAGGCTGCCGCGCAGCCCCACACGGAGATCCCAGAAGGAACCACAGC | |
| | TGAAGAAGCAGGCATTGGAGACACCCCCAGCCTGGAAGACGAAGCTGCTGGTCACGTGACCCAAGAGCCT | |
| | GAAAGTGGTAAGGTGGTCCAGGAAGGCTTCCTCCGAGAGCCAGGCCCCCCAGGTCTGAGCCACCAGCTCA | |
| | TGTCCGGCATGCCTGGGGCTCCCCTCCTGCCTGAGGGCCCCAGAGAGGCCACACGCCAACCTTCGGGGAC | |
| | AGGACCTGAGGACACAGAGGGCGGCCGCCACGCCCCTGAGCTGCTCAAGCACCAGCTTCTAGGAGACCTG | |
| | CACCAGGAGGGGCCGCCGCTGAAGGGGGCAGGGGGCAAAGAGAGGCCGGGGAGCAAGGAGGAGGTGGATG | |
| | AAGACCGCGACGTCGATGAGTCCTCCCCCCAAGACTCCCCTCCCTCCAAGGCCTCCCCAGCCCAAGATGG | |
| | GCGGCCTCCCCAGACAGCCGCCAGAGAAGCCACCAGCATCCCAGGCTTCCCAGCGGAGGGTGCCATCCCC | |
| | CTCCCTGTGGATTTCCTCTCCAAAGTTTCCACAGAGATCCCAGCCTCAGAGCCCGACGGGCCCAGTGTAG | |
| | GGCGGGCCAAAGGGCAGGATGCCCCCCTGGAGTTCACGTTTCACGTGGAAATCACACCCAACGTGCAGAA | |
| | GGAGCAGGCGCACTCGGAGGAGCATTTGGGAAGGGCTGCATTTCCAGGGGCCCCTGGAGAGGGGCCAGAG | |
| | GCCCGGGGCCCCTCTTTGGGAGAGGACACAAAAGAGGCTGACCTTCCAGAGCCCTCTGAAAAGCAGCCTG | |
| | CTGCTGCTCCGCGGGGGAAGCCCGTCAGCCGGGTCCCTCAACTCAAAGCTCGCATGGTCAGTAAAAGCAA | |
| | AGACGGGACTGGAAGCGATGACAAAAAAGCCAAGACATCCACACGTTCCTCTGCTAAAACCTTGAAAAAT | |
| | AGGCCTTGCCTTAGCCCCAAACACCCCACTCCTGGTAGCTCAGACCCTCTGATCCAACCCTCCAGCCCTG | |
| | CTGTGTGCCCAGAGCCACCTTCCTCTCCTAAATACGTCTCTTCTGTCACTTCCCGAACTGGCAGTTCTGG | |
| | AGCAAAGGAGATGAAACTCAAGGGGGCTGATGGTAAAACGAAGATCGCCACACCGCGGGGAGCAGCCCCT | |
| | CCAGGCCAGAAGGGCCAGGCCAACGCCACCAGGATTCCAGCAAAAACCCCGCCCGCTCCAAAGACACCAC | |
| | CCAGCTCTGCGACTAAGCAAGTCCAGAGAAGACCACCCCCTGCAGGGCCCAGATCTGAGAGAGGTGAACC | |
| | TCCAAAATCAGGGGATCGCAGCGGCTACAGCAGCCCCGGCTCCCCAGGCACTCCCGGCAGCCGCTCCCGC | |
| | ACCCCGTCCCTTCCAACCCCACCCACCCGGGAGCCCAAGAAGGTGGCAGTGGTCCGTACTCCACCCAAGT | |
| | CGCCGTCTTCCGCCAAGAGCCGCCTGCAGACAGCCCCCGTGCCCATGCCAGACCTGAAGAATGTCAAGTC | |
| | CAAGATCGGCTCCACTGAGAACCTGAAGCACCAGCCGGGAGGCGGGAAGGTGCAGATAATTAATAAGAAG | |
| | CTGGATCTTAGCAACGTCCAGTCCAAGTGTGGCTCAAAGGATAATATCAAACACGTCCCGGGAGGCGGCA | |
| | GTGTGCAAATAGTCTACAAACCAGTTGACCTGAGCAAGGTGACCTCCAAGTGTGGCTCATTAGGCAACAT | |
| | CCATCATAAACCAGGAGGTGGCCAGGTGGAAGTAAAATCTGAGAAGCTTGACTTCAAGGACAGAGTCCAG | |
| | TCGAAGATTGGGTCCCTGGACAATATCACCCACGTCCCTGGCGGAGGAAATAAAAAGATTGAAACCCACA | |
| | AGCTGACCTTCCGCGAGAACGCCAAAGCCAAGACAGACCACGGGGCGGAGATCGTGTACAAGTCGCCAGT | |
| | GGTGTCTGGGGACACGTCTCCACGGCATCTCAGCAATGTCTCCTCCACCGGCAGCATCGACATGGTAGAC | |
| | TCGCCCCAGCTCGCCACGCTAGCTGACGAGGTGTCTGCCTCCCTGGCCAAGCAGGGTTTGTGATCAGGCC | |
| | CCTGGGGCGGTCAATAATTGTGGAGAGGAGAGAATGAGAGAGTGTGGAAAAAAAAAGAATAATGACCCGG | |
| | CCCCCGCCCTCTGCCCCCAGCTGCTCCTCGCAGTTCGGTTAATTGGTTAATCACTTAACCTGCTTTTGTC | |
| | ACTCGGCTTTGGCTCGGGACTTCAAAATCAGTGATGGGAGTAAGAGCAAATTTCATCTTTCCAAATTGAT | |
| | GGGTGGGCTAGTAATAAAATATTTAAAAAAAAACATTCAAAAACATGGCCACATCCAACATTTCCTCAGG | |
| | CAATTCCTTTTGATTCTTTTTTCTTCCCCCTCCATGTAGAAGAGGGAGAAGGAGAGGCTCTGAAAGCTGC | |
| | TTCTGGGGGATTTCAAGGGACTGGGGGTGCCAACCACCTCTGGCCCTGTTGTGGGGGTGTCACAGAGGCA | |
| | GTGGCAGCAACAAAGGATTTGAAACTTGGTGTGTTCGTGGAGCCACAGGCAGACGATGTCAACCTTGTGT | |
| | GAGTGTGACGGGGGTTGGGGTGGGGCGGGAGGCCACGGGGGAGGCCGAGGCAGGGGCTGGGCAGAGGGGA | |
| | GAGGAAGCACAAGAAGTGGGAGTGGGAGAGGAAGCCACGTGCTGGAGAGTAGACATCCCCCTCCTTGCCG | |
| | CTGGGAGAGCCAAGGCCTATGCCACCTGCAGCGTCTGAGCGGCCGCCTGTCCTTGGTGGCCGGGGGTGGG | |
| | GGCCTGCTGTGGGTCAGTGTGCCACCCTCTGCAGGGCAGCCTGTGGGAGAAGGGACAGCGGGTAAAAAGA | |
| | GAAGGCAAGCTGGCAGGAGGGTGGCACTTCGTGGATGACCTCCTTAGAAAAGACTGACCTTGATGTCTTG | |
| | AGAGCGCTGGCCTCTTCCTCCCTCCCTGCAGGGTAGGGGGCCTGAGTTGAGGGGCTTCCCTCTGCTCCAC | |
| | AGAAACCCTGTTTTATTGAGTTCTGAAGGTTGGAACTGCTGCCATGATTTTGGCCACTTTGCAGACCTGG | |
| | GACTTTAGGGCTAACCAGTTCTCTTTGTAAGGACTTGTGCCTCTTGGGAGACGTCCACCCGTTTCCAAGC | |
| | CTGGGCCACTGGCATCTCTGGAGTGTGTGGGGGTCTGGGAGGCAGGTCCCGAGCCCCCTGTCCTTCCCAC | |
| | GGCCACTGCAGTCACCCCGTCTGCGCCGCTGTGCTGTTGTCTGCCGTGAGAGCCCAATCACTGCCTATAC | |
| | CCCTCATCACACGTCACAATGTCCCGAATTCCCAGCCTCACCACCCCTTCTCAGTAATGACCCTGGTTGG | |
| | TTGCAGGAGGTACCTACTCCATACTGAGGGTGAAATTAAGGGAAGGCAAAGTCCAGGCACAAGAGTGGGA | |
| | CCCCAGCCTCTCACTCTCAGTTCCACTCATCCAACTGGGACCCTCACCACGAATCTCATGATCTGATTCG | |
| | GTTCCCTGTCTCCTCCTCCCGTCACAGATGTGAGCCAGGGCACTGCTCAGCTGTGACCCTAGGTGTTTCT | |
| | GCCTTGTTGACATGGAGAGAGCCCTTTCCCCTGAGAAGGCCTGGCCCCTTCCTGTGCTGAGCCCACAGCA | |
| | GCAGGCTGGGTGTCTTGGTTGTCAGTGGTGGCACCAGGATGGAAGGGCAAGGCACCCAGGGCAGGCCCAC | |
| | AGTCCCGCTGTCCCCCACTTGCACCCTAGCTTGTAGCTGCCAACCTCCCAGACAGCCCAGCCCGCTGCTC | |
| | AGCTCCACATGCATAGTATCAGCCCTCCACACCCGACAAAGGGGAACACACCCCCTTGGAAATGGTTCTT | |
| | TTCCCCCAGTCCCAGCTGGAAGCCATGCTGTCTGTTCTGCTGGAGCAGCTGAACATATACATAGATGTTG | |
| | CCCTGCCCTCCCCATCTGCACCCTGTTGAGTTGTAGTTGGATTTGTCTGTTTATGCTTGGATTCACCAGA | |
| | GTGACTATGATAGTGAAAAGAAAAAAAAAAAAAAAAAAAGGACGCATGTATCTTGAAATGCTTGTAAAGAG | |
| | GTTTCTAACCCACCCTCACGAGGTGTCTCTCACCCCCACACTGGGACTCGTGTGGCCTGTGTGGTGCCAC | |
| | CCTGCTGGGGCCTCCCAAGTTTTGAAAGGCTTTCCTCAGCACCTGGGACCCAACAGAGACCAGCTTCTAG | |
| | CAGCTAAGGAGGCCGTTCAGCTGTGACGAAGGCCTGAAGCACAGGATTAGGACTGAAGCGATGATGTCCC | |
| | CTTCCCTACTTCCCCTTGGGGCTCCCTGTGTCAGGGCACAGACTAGGTCTTGTGGCTGGTCTGGCTTGCG | |
| | GCGCGAGGATGGTTCTCTCTGGTCATAGCCCGAAGTCTCATGGCAGTCCCAAAGGAGGCTTACAACTCCT | |
| | GCATCACAAGAAAAAGGAAGCCACTGCCAGCTGGGGGGATCTGCAGCTCCCAGAAGCTCCGTGAGCCTCA | |
| | GCCACCCCTCAGACTGGGTTCCTCTCCAAGCTCGCCCTCTGGAGGGGCAGCGCAGCCTCCCACCAAGGGC | |
| | CCTGCGACCACAGCAGGGATTGGGATGAATTGCCTGTCCTGGATCTGCTCTAGAGGCCCAAGCTGCCTGC | |
| | CTGAGGAAGGATGACTTGACAAGTCAGGAGACACTGTTCCCAAAGCCTTGACCAGAGCACCTCAGCCCGC | |
| | TGACCTTGCACAAACTCCATCTGCTGCCATGAGAAAAGGGAAGCCGCCTTTGCAAAACATTGCTGCCTAA | |
| | AGAAACTCAGCAGCCTCAGGCCCAATTCTGCCACTTCTGGTTTGGGTACAGTTAAAGGCAACCCTGAGGG | |
| | ACTTGGCAGTAGAAATCCAGGGCCTCCCCTGGGGCTGGCAGCTTCGTGTGCAGCTAGAGCTTTACCTGAA | |
| | AGGAAGTCTCTGGGCCCAGAACTCTCCACCAAGAGCCTCCCTGCCGTTCGCTGAGTCCCAGCAATTCTCC | |
| | TAAGTTGAAGGGATCTGAGAAGGAGAAGGAAATGTGGGGTAGATTTGGTGGTGGTTAGAGATATGCCCCC | |
| | CTCATTACTGCCAACAGTTTCGGCTGCATTTCTTCACGCACCTCGGTTCCTCTTCCTGAAGTTCTTGTGC | |
| | CCTGCTCTTCAGCACCATGGGCCTTCTTATACGGAAGGCTCTGGGATCTCCCCCTTGTGGGGCAGGCTCT | |
| | TGGGGCCAGCCTAAGATCATGGTTTAGGGTGATCAGTGCTGGCAGATAAATTGAAAAGGCACGCTGGCTT | |

TABLE 2-continued

| GENBANK ACCESSION NUMBER | SEQUENCE | SEQ ID NO: |
| --- | --- | --- |
| | GTGATCTTAAATGAGGACAATCCCCCCAGGGCTGGGCACTCCTCCCCTCCCCTCACTTCTCCCACCTGCA GAGCCAGTGTCCTTGGGTGGGCTAGATAGGATATACTGTATGCCGGCTCCTTCAAGCTGCTGACTCACTT TATCAATAGTTCCATTTAAATTGACTTCAGTGGTGAGACTGTATCCTGTTTGCTATTGCTTGTTGTGCTA TGGGGGGAGGGGGGAGGAATGTGTAAGATAGTTAACATGGGCAAAGGGAGATCTTGGGGTGCAGCACTTA AACTGCCTCGTAACCCTTTTCATGATTTCAACCACATTTGCTAGAGGGAGGGAGCAGCCACGGAGTTAGA GGCCCTTGGGGTTTCTCTTTTCCACTGACAGGCTTTCCCAGGCAGCTGGCTAGTTCATTCCCTCCCCAGC CAGGTGCAGGCGTAGGAATATGGACATCTGGTTGCTTTGGCCTGCTGCCCTCTTTCAGGGGTCCTAAGCC CACAATCATGCCTCCCTAAGACCTTGGCATCCTTCCCTCTAAGCCGTTGGCACCTCTGTGCCACCTCTCA CACTGGCTCCAGACACACAGCCTGTGCTTTTGGAGCTGAGATCACTCGCTTCACCCTCCTCATCTTTGTT CTCCAAGTAAAGCCACGAGGTCGGGGCGAGGGCAGAGGTGATCACCTGCGTGTCCCATCTACAGACCTGC AGCTTCATAAAACTTCTGATTTCTCTTCAGCTTTGAAAAGGGTTACCCTGGGCACTGGCCTAGAGCCTCA CCTCCTAATAGACTTAGCCCCATGAGTTTGCCATGTTGAGCAGGACTATTTCTGGCACTTGCAAGTCCCA TGATTTCTTCGGTAATTCTGAGGGTGGGGGGAGGGACATGAAATCATCTTAGCTTAGCTTTCTGTCTGTG AATGTCTATATAGTGTATTGTGTGTTTTAACAAATGATTTACACTGACTGTTGCTGTAAAAGTGAATTTG GAAATAAAGTTATTACTCTGATTAAA | |
| M92424 | GCACCGCGCGAGCTTGGCTGCTTCTGGGGCCTGTGTGGCCCTGTGTGTCGGAAAGATGGAGCAAGAAGCC GAGCCCGAGGGGCGGCCGCGACCCCTCTGACCGAGATCCTGCTGCTTTCGCAGCCAGGAGCACCGTCCCT CCCCGGATTAGTGCGTACGAGCGCCCAGTGCCCTGGCCCGGAGAGTGGAATGATCCCCGAGGCCCAGGGC GTCGTGCTTCCGCAGTAGTCAGTCCCCGTGAAGGAAACTGGGGAGTCTTGAGGGACCCCCGACTCCAAGC GCGAAAACCCCGGATGGTGAGGAGCAGGCAAATGTGCAATACCAACATGTCTGTACCTACTGATGGTGCT GTAACCACCTCACAGATTCCAGCTTCGGAACAAGAGACCCTGGTTAGACCAAAGCCATTGCTTTTGAAGT TATTAAAGTCTGTTGGTGCACAAAAAGACACTTATACTATGAAAGAGGTTCTTTTTTATCTTGGCCAGTA TATTATGACTAAACGATTATATGATGAGAAGCAACAACATATTGTATATTGTTCAAATGATCTTCTAGGA GATTTGTTTGGCGTGCCAAGCTTCTCTGTGAAAGAGCACAGGAAAATATATACCATGATCTACAGGAACT TGGTAGTAGTCAATCAGCAGGAATCATCGGACTCAGGTACATCTGTGAGTGAGAACAGGTGTCACCTTGA AGGTGGGAGTGATCAAAAGGACCTTGTACAAGAGCTTCAGGAAGAGAAACCTTCATCTTCACATTTGGTT TCTAGACCATCTACCTCATCTAGAAGGAGAGCAATTAGTGAGACAGAAGAAAATTCAGATGAATTATCTG GTGAACGACAAAGAAAACGCCACAAATCTGATAGTATTTCCCTTTCCTTTGATGAAAGCCTGGCTCTGTG TGTAATAAGGGAGATATGTTGTGAAAGAAGCAGTAGCAGTGAATCTACAGGGACGCCATCGAATCCGGAT CTTGATGCTGGTGTAAGTGAACATTCAGGTGATTGGTTGGATCAGGATTCAGTTTCAGATCAGTTTAGTG TAGAATTTGAAGTTGAATCTCTCGACTCAGAAGATTATAGCCTTAGTGAAGAAGGACAAGAACTCTCAGA TGAAGATGATGAGGTATATCAAGTTACTGTGTATCAGGCAGGGGAGAGTGATACAGATTCATTTGAAGAA GATCCTGAAATTTCCTTAGCTGACTATTGGAAATGCACTTCATGCAATGAAATGAATCCCCCCCTTCCAT CACATTGCAACAGATGTTGGGCCCTTCGTGAGAATTGGCTTCCTGAAGATAAAGGGAAAGATAAAGGGGA AATCTCTGAGAAAGCCAAACTGGAAAACTCAACACAAGCTGAAGAGGGCTTTGATGTTCCTGATTGTAAA AAAACTATAGTGAATGATTCCAGAGAGTCATGTGTTGAGGAAAATGATGATAAAATTACACAAGCTTCAC AATCACAAGAAAGTGAAGACTATTCTCAGCCATCAACTTCTAGTAGCATTATTTATAGCAGCCAAGAAGA TGTGAAAGAGTTTGAAAGGGAAGAAACCCAAGACAAAGAAGAGAGTGTGGAATCTAGTTTGCCCCTTAAT GCCATTGAACCTTGTGTGATTTGTCAAGGTCGACCTAAAAATGGTTGCATTGTCCATGGCAAAACAGGAC ATCTTATGGCCTGCTTTACATGTGCAAAGAAGCTAAAGAAAAGGAATAAGCCCTGCCCAGTATGTAGACA ACCAATTCAAATGATTGTGCTAACTTATTTCCCCTAGTTGACCTGTCTATAAGAGAATTATATATTTCTA ACTATATAACCCTAGGAATTTAGACAACCTGAAATTTATTCACATATATCAAAGTGAGAAAATGCCTCAA TTCACATAGATTTCTTCTCTTTAGTATAATTGACCTACTTTGGTAGTGGAATAGTGAATACTTACTATAA TTTGACTTGAATATGTAGCTCATCCTTTACACCAACTCCTAATTTTAAATAATTTCTACTCTGTCTTAAA TGAGAAGTACTTGGTTTTTTTTTTCTTAAATATGTATATGACATTTAAATGTAACTTATTATTTTTTTTG AGACCGAGTCTTGCTCTGTTACCCAGGCTGGAGTGCAGTGGGTGATCTTGGCTCACTGCAAGCTCTGCCC TCCCCGGGTTCGCACCATTCTCCTGCCTCAGCCTCCCAATTAGCTTGGCCTACAGTCATCTGCCACCACA CCTGGCTAATTTTTTGTACTTTTAGTAGAGACAGGGTTTCACCGTGTTAGCCAGGATGGTCTCGATCTCC TGACCTCGTGATCCGCCCACCTCGGCCTCCCAAAGTGCTGGGATTACAGGCATGAGCCACCG | 134 |
| NM_014791 | GAGATTTGATTCCCTTGGCGGGCGGAAGCGGCCACAACCCGGCGATCGAAAAGATTCTTAGGAACGCCGT ACCAGCCGCGTCTCTCAGGACAGCAGGCCCCTGTCCTTCTGTCGGGCGCCGCTCAGCCGTGCCCTCCGCC CCTCAGGTTCTTTTTCTAATTCCAAATAAACTTGCAAGAGGACTATGAAAGATTATGATGAACTTCTCAA ATATTATGAATTACATGAAACTATTGGGACAGGTGGCTTTGCAAAGGTCAAACTTGCCTGCCATATCCTT ACTGGAGAGATGGTAGCTATAAAAATCATGGATAAAAACACACTAGGGAGTGATTTGCCCCGGATCAAAA CGGAGATTGAGGCCTTGAAGAACCTGAGACATCAGCATATATGTCAACTCTACCATGTGCTAGAGACAGC CAACAAAATATTCATGGTTCTTGAGTACTGCCCTGGAGGAGAGCTGTTTGACTATATAATTTCCCAGGAT CGCCTGTCAGAAGAGGAGACCCGGGTTGTCTTCCGTCAGATAGTATCTGCTGTTGCTTATGTGCACAGCC AGGGCTATGCTCACAGGGACCTCAAGCCAGAAAATTTGCTGTTTGATGAATATCATAAATTAAAGCTGAT TGACTTTGGTCTCTGTGCAAAACCCAAGGGTAACAAGGATTACCATCTACAGACATGCTGTGGGAGTCTG GCTTATGCAGCACCTGAGTTAATACAAGGCAAATCATATCTTGGATCAGAGGCAGATGTTTGGAGCATGG GCATACTGTTATATGTTCTTATGTGTGGATTTCTACCATTTGATGATGATAATGTAATGGCTTTATACAA GAAGATTATGAGAGGAAAATATGATGTTCCCAAGTGGCTCTCTCCCAGTAGCATTCTGCTTCTTCAACAA ATGCTGCAGGTGGACCCAAAGAAACGGATTTCTATGAAAAATCTATTGAACCATCCCTGGATCATGCAAG ATTACAACTATCCTGTTGAGTGGCAAAGCAAGAATCCTTTTATTCACCTCGATGATGATTGCGTAACAGA ACTTTCTGTACATCACAGAAACAACAGGCAAACAATGGAGGATTTAATTTCACTGTGGCAGTATGATCAC CTCACGGCTACCTATCTTCTGCTTCTAGCCAAGAAGGCTCGGGGAAAACCAGTTCGTTTAAGGCTTTCTT CTTTCTCCTGTGGACAAGCCAGTGCTACCCCATTCACAGACATCAAGTCAAATAATTGGAGTCTGGAAGA TGTGACCGCAAGTGATAAAAATTATGTGGCGGGATTAATAGACTATGATTGGTGTGAAGATGATTTATCA ACAGGTGCTGCTACTCCCCGAACATCACAGTTTACCAAGTACTGGACAGAATCAAATGGGGTGGAATCTA AATCATTAACTCCAGCCTTATGCAGAACACCTGCAAATAAATTAAAGAACAAAGAAAATGTATATACTCC TAAGTCTGCTGTAAAGAATGAAGAGTACTTTATGTTTCCTGAGCCAAAGACTCCAGTTAATAAGAACCAG CATAAGAGAGAAATACTCACTACGCCAAATCGTTACACTACACCCTCAAAAGCTAGAAACCAGTGCCTGA AAGAAACTCCAATTAAAATACCAGTAAATTCAACAGGAACAGACAAGTTAATGACAGGTGTCATTAGCCC TGAGAGGCGGTGCCGCTCAGTGGAATTGGATCTCAACCAAGCACATATGGAGGAGACTCCAAAAAGAAAG | 135 |

TABLE 2-continued

| GENBANK ACCESSION NUMBER | SEQUENCE | SEQ ID NO: |
|---|---|---|
| | GGAGCCAAAGTGTTTGGGAGCCTTGAAAGGGGGTTGGATAAGGTTATCACTGTGCTCACCAGGAGCAAAA<br>GGAAGGGTTCTGCCAGAGACGGGCCCAGAAGACTAAAGCTTCACTATAACGTGACTACAACTAGATTAGT<br>GAATCCAGATCAACTGTTGAATGAAATAATGTCTATTCTTCCAAAGAAGCATGTTGACTTTGTACAAAAG<br>GGTTATACACTGAAGTGTCAAACACAGTCAGATTTTGGGAAAGTGACAATGCAATTTGAATTAGAAGTGT<br>GCCAGCTTCAAAAACCCGATGTGGTGGGTATCAGGAGGCAGCGGCTTAAGGGCGATGCCTGGGTTTACAA<br>AAGATTAGTGGAAGACATCCTATCTAGCTGCAAGGTATAATTGATGGATTCTTCCATCCTGCCGGATGAG<br>TGTGGGTGTGATACAGCCTACATAAAGACTGTTATGATCGCTTTGATTTTAAAGTTCATTGGAACTACCA<br>ACTTGTTTCTAAAGAGCTATCTTAAGACCAATATCTCTTTGTTTTTAAACAAAAGATATTATTTTGTGTA<br>TGAATCTAAATCAAGCCCATCTGTCATTATGTTACTGTCTTTTTTAATCATGTGGTTTTGTATATTAATA<br>ATTGTTGACTTTCTTAGATTCACTTCCATATGTGAATGTAAGCTCTTAACTATGTCTCTTTGTAATGTGT<br>AATTTCTTTCTGAAATAAAACCATTTGTGAATATAG | |
| BG765502 | GCAGCGGAGGAGCCCAGTCCACGATGGCCCGGTCCCTGGTGTGCCTTGGTGTCATCATCTTGCTGTCTGC<br>CTTCTCCGGACCTGGTGTCAGGGGTGGTCCTATGCCCAAGCTGGCTGACCGGAAGCTGTGTGCGGACCAG<br>GAGTGCAGCCACCCTATCTCCATGGCTGTGGCCCTTCAGGACTACATGGCCCCCGACTGCCGATTCCTGA<br>CCATTCACCGGGGCCAAGTGGTGTATGTCTTCTCCAAGCTGAAGGGCCGTGGGCGGCTCTTCTGGGGAGG<br>CAGCGTTCAGGGAGATTACTATGGAGATCTGGCTGCTCGCCTGGGCTATTTCCCCAGTAGCATTGTCCGA<br>GAGGACCAGACCCTGAAACCTGGCAAAGTCGATGTGAAGACAGACAAATGGGATTTCTACTGCCAGTGAG<br>CTCAGCCTACCGCTGGCCCTGCCGTTTCCCCTCCTTGGGTTTATGCAAATACAATCAGCCCAGTGCAAAA<br>AAAAAAAAAAAAAAAAAAAACTTCGGAGAAGAGATAGCAACAAAAGGCCGCTTGTGTGAAGGCGCCAAAA<br>GTTTTCGCCCAAGAGACCTTCGGCCTCCCCCAGGGCGCGCGCAAAGGCGCCTTGTTTTGACAACCTCTTG<br>GACAACCGGAGGGGCTACCGCCCGGAGACCCCTGTGGTGGACCCCCCGGGCAACCCGGTGTGACAGGGTA<br>CTCACCCCCACGGCTTTGTCGGGGGTCCCACCAAAGGCCCCAAAGAGGCTCTTTCAAGGCACTATTCCTT<br>GTTGTAGACCTTGTGTGTGCCACAGGCGCCAAAGAAACCTCGGGGGGCTAACAAACGCACGTGCTTGGCA<br>GCTCCGAGAAGGCTCTCTCCCACCCGAGGGGTGGACGCAACAGGGGGAATGGCCATCATATTGTTGCCC<br>CCGGTGGGCACCAACTCTTTTTCCCCCATAGAGAGGCCTTAGCACACTATGTGGGGCACGTTATTGCCGC<br>CTAGAGAAACCGAGCGCCAGAAAATTTCGAAGGGGGGGGCGCTTCTCATCATTTTGCGCAAAACCCCCTT<br>GTGGGAGTATGCCCCGAACTCCTCTGGAACACACAAGCGACACTTGCGCGGGGTCTGCAAAAAACCTCCT<br>GTTGGGAAGCCGGCTTCACN | 136 |
| NM_002417 | TACCGGGCGGAGGTGAGCGCGGCGCCGGCTCCTCCTGCGGCGGACTTTGGGTGCGACTTGACGAGCGGTG<br>GTTCGACAAGTGGCCTTGCGGGCCGGATCGTCCCAGTGGAAGAGTTGTAAATTTGCTTCTGGCCTTCCCC<br>TACGGATTATACCTGGCCTTCCCCTACGGATTATACTCAACTTACTGTTTAGAAAATGTGGCCCACGAGA<br>CGCCTGGTTACTATCAAAAGGAGCGGGGTCGACGGTCCCCACTTTCCCCTGAGCCTCAGCACCTGCTTGT<br>TTGGAAGGGGTATTGAATGTGACATCCGTATCCAGCTTCCTGTTGTGTCAAAACAACATTGCAAAATTGA<br>AATCCATGAGCAGGAGGCAATATTACATAATTTCAGTTCCACAAATCCAACACAAGTAAATGGGTCTGTT<br>ATTGATGAGCCTGTACGGCTAAAACATGGAGATGTAATAACTATTATTGATCGTTCCTTCAGGTATGAAA<br>ATGAAAGTCTTCAGAATGGAAGGAAGTCAACTGAATTTCCAAGAAAAATACGTGAACAGGAGCCAGCACG<br>TCGTGTCTCAAGATCTAGCTTCTCTTCTGACCCTGATGAGAAAGCTCAAGATTCCAAGGCCTATTCAAAA<br>ATCACTGAAGGAAAAGTTTCAGGAAATCCTCAGGTACATATCAAGAATGTCAAAGAAGACAGTACCGCAG<br>ATGACTCAAAAGACAGTGTTGCTCAGGGAACAACTAATGTTCATTCCTCAGAACATGCTGGACGTAATGG<br>CAGAAATGCAGCTGATCCCATTTCTGGGGATTTTAAAGAAATTTCCAGCGTTAAATTAGTGAGCCGTTAT<br>GGAGAATTGAAGTCTGTTCCCACTACACAATGTCTTGACAATAGCAAAAAAAATGAATCTCCCTTTTGGA<br>AGCTTTATGAGTCAGTGAAGAAAGAGTTGGATGTAAAATCACAAAAAGAAAATGTCCTACAGTATTGTAG<br>AAAATCTGGATTACAAACTGATTACGCAACAGAGAAAGAAAGTGCTGATGGTTTACAGGGGGAGACCCAA<br>CTGTTGGTCTCGCGTAAGTCAAGACCAAAATCTGGTGGGAGCGGCCACGCTGTGGCAGAGCCTGCTTCAC<br>CTGAACAAGAGCTTGACCAGAACAAGGGGAAGGGAAGAGACGTGGAGTCTGTTCAGACTCCCAGCAAGGC<br>TGTGGGCGCCAGCTTTCCTCTCTATGAGCCGGCTAAAATGAAGACCCCTGTACAATATTCACAGCAACAA<br>AATTCTCCACAAAAACATAAGAACAAAGACCTGTATACTACTGGTAGAAGAGAATCTGTGAATCTGGGTA<br>AAAGTGAAGGCTTCAAGGCTGGTGATAAAACTCTTACTCCCAGGAAGCTTTCAACTAGAAATCGAACACC<br>AGCTAAAGTTGAAGATGCAGCTGACTCTGCCACTAAGCCAGAAAATCTCTCTTCCAAAACCAGAGGAAGT<br>ATTCCTACAGATGTGGAAGTTCTGCCTACGGAAACTGAAATTCACAATGAGCCATTTTTAACTCTGTGGC<br>TCACTCAAGTTGAGAGGAAGATCCAAAAGGATTCCCTCAGCAAGCCTGAGAAATTGGGCACTACAGCTGG<br>ACAGATGTGCTCTGGGTTACCTGGTCTTAGTTCAGTTGATATCAACAACTTTGGTGATTCCATTAATGAG<br>AGTGAGGGAATACCTTTGAAAAGAAGGCGTGTGTCCTTTGGTGGGCACCTAAGACCTGAACTATTTGATG<br>AAAACTTGCCTCCTAATACGCCTCTCAAAAGGGGAGAAGCCCCAACCAAAAGAAAGTCTCTGGTAATGCA<br>CACTCCACCTGTCCTGAAGAAAATCATCAAGGAACAGCCTCAACCATCAGGAAAACAAGAGTCAGGTTCA<br>GAAATCCATGTGGAAGTGAAGGCACAAAGCTTGGTTATAAGCCCTCCAGCTCCTAGTCCTAGGAAAACTC<br>CAGTTGCCAGTGATCAACGCCGTAGGTCCTGCAAAACAGCCCCTGCTTCCAGCAGCAAATCTCAGACAGA<br>GGTTCCTAAGAGAGGAGGGAGAAAGAGTGGCAACCTGCCTTCAAAGAGAGTGTCTATCAGCCGAAGTCAA<br>CATGATATTTTACAGATGATATGTTCCAAAAGAAGAAGTGGTGCTTCGGAAGCAAATCTGATTGTTGCAA<br>AATCATGGGCAGATGTAGTAAAACTTGGTGCAAAACAAACACAAACTAAAGTCATAAAACATGGTCCTCA<br>AAGGTCAATGAACAAAAGGCAAAGAAGACCTGCTACTCCAAAGAAGCCTGTGGGCGAAGTTCACAGTCAA<br>TTTAGTACAGGCCACGCAAACTCTCCTTGTACCATAATAATAGGGAAAGCTCATACTGAAAAAGTACATG<br>TGCCTGCTCGACCCTACAGAGTGCTCAACAACTTCATTTCCAACCAAAAAATGGACTTTAAGGAAGATCT<br>TTCAGGAATAGCTGAAATGTTCAAGACCCCAGTGAAGGAGCAACCGCAGTTGACAAGCACATGTCACATC<br>GCTATTTCAAATTCAGAGAATTTGCTTGGAAAACAGTTTCAAGGAACTGATTCAGGAGAAGAACCTCTGC<br>TCCCCACCTCAGAGAGTTTTGGAGGAAATGTGTTCTTCAGTGCACAGAATGCAGCAAAACAGCCATCTGA<br>TAAATGCTCTGCAAGCCCTCCCTTAAGACGGCAGTGTATTAGAGAAAATGGAAACGTAGCAAAAACGCCC<br>AGGAACACCTACAAAATGACTTCTCTGGAGACAAAAACTTCAGATACTGAGACAGAGCCTTCAAAAACAG<br>TATCCACTGCAAACAGGTCAGGAAGGTCTACAGAGTTCAGGAATATACAGAAGCTACCTGTGGAAAGTAA<br>GAGTGAAGAAACAAATACAGAAATTGTTGAGTGCATCCTAAAAAGAGGTCAGAAGGCAACACTACTACAA<br>CAAAGGAGAGAAGGAGAGATGAAGGAAATAGAAAGACCTTTTGAGACATATAAGGAAAATATTGAATTAA<br>AAGAAAACGATGAAAAGATGAAAGCAATGAAGAGATCAAGAACTTGGGGGCAGAAATGTGCACCAATGTC<br>TGACCTGACAGACCTCAAGAGCTTGCCTGATACAGAACTCATGAAAGACACGGCACGTGGCCAGAATCTC<br>CTCCAAACCCAAGATCATGCCAAGGCACCAAAGAGTGAGAAAGGCAAAATCACTAAAATGCCCTGCCAGT | 137 |

TABLE 2-continued

| GENBANK ACCESSION NUMBER | SEQUENCE | SEQ ID NO: |
|---|---|---|
| | CATTACAACCAGAACCAATAAACACCCCAACACACACAAAACAACAGTTGAAGGCATCCCTGGGGAAAGT | |
| | AGGTGTGAAAGAAGAGCTCCTAGCAGTCGGCAAGTTCACACGGACGTCAGGGGAGACCACGCACACGCAC | |
| | AGAGAGCCAGCAGGAGATGGCAAGAGCATCAGAACGTTTAAGGAGTCTCCAAAGCAGATCCTGGACCCAG | |
| | CAGCCCGTGTAACTGGAATGAAGAAGTGGCCAAGAACGCCTAAGGAAGAGGCCCAGTCACTAGAAGACCT | |
| | GGCTGGCTTCAAAGAGCTCTTCCAGACACCAGGTCCCTCTGAGGAATCAATGACTGATGAGAAAACTACC | |
| | AAAATAGCCTGCAAATCTCCACCACCAGAATCAGTGGACACTCCAACAAGCACAAAGCAATGGCCTAAGA | |
| | GAAGTCTCAGGAAAGCAGATGTAGAGGAAGAATTCTTAGCACTCAGGAAACTAACACCATCAGCAGGGAA | |
| | AGCCATGCTTACGCCCAAACCAGCAGGAGGTGATGAGAAAGACATTAAAGCATTTATGGGAACTCCAGTG | |
| | CAGAAACTGGACCTGGCAGGAACTTTACCTGGCAGCAAAAGACAGCTACAGACTCCTAAGGAAAAGGCCC | |
| | AGGCTCTAGAAGACCTGGCTGGCTTTAAAGAGCTCTTCCAGACTCCTGGTCACACCGAGGAATTAGTGGC | |
| | TGCTGGTAAAACCACTAAAATACCCTGCGACTCTCCACAGTCAGACCCAGTGGACACCCCAACAAGCACA | |
| | AAGCAACGACCCAAGAGAAGTATCAGGAAAGCAGATGTAGAGGGAGAACTCTTAGCGTGCAGGAATCTAA | |
| | TGCCATCAGCAGGCAAAGCCATGCACACGCCTAAACCATCAGTAGGTGAAGAGAAAGACATCATCATATT | |
| | TGTGGGAACTCCAGTGCAGAAACTGGACCTGACAGAGAACTTAACCGGCAGCAAGAGACGGCCACAAACT | |
| | CCTAAGGAAGAGGCCCAGGCTCTGGAAGACCTGACTGGCTTTAAAGAGCTCTTCCAGACCCCTGGTCATA | |
| | CTGAAGAAGCAGTGGCTGCTGGCAAAACTACTAAAATGCCCTGCGAATCTTCTCCACCAGAATCAGCAGA | |
| | CACCCCAACAAGCACAAGAAGGCAGCCCAAGACACCTTTGGAGAAAAGGGACGTACAGAAGGAGCTCTCA | |
| | GCCCTGAAGAAGCTCACACAGACATCAGGGGAAACCACACACACAGATAAAGTACCAGGAGGTGAGGATA | |
| | AAAGCATCAACGCGTTTAGGGAAACTGCAAAACAGAAACTGGACCCAGCAGCAAGTGTAACTGGTAGCAA | |
| | GAGGCACCCAAAAACTAAGGAAAAGGCCCAACCCCTAGAAGACCTGGCTGGCTTGAAAGAGCTCTTCCAG | |
| | ACACCAGTATGCACTGACAAGCCCACGACTCACGAGAAAACTACCAAAATAGCCTGCAGATCACAACCAG | |
| | ACCCAGTGGACACACCAACAAGCTCCAAGCCACAGTCCAAGAGAAGTCTCAGGAAAGTGGACGTAGAAGA | |
| | AGAATTCTTCGCACTCAGGAAACGAACACCATCAGCAGGCAAAGCCATGCACACACCCAAACCAGCAGTA | |
| | AGTGGTGAGAAAAACATCTACGCATTTATGGGAACTCCAGTGCAGAAACTGGACCTGACAGAGAACTTAA | |
| | CTGGCAGCAAGAGACGGCTACAAACTCCTAAGGAAAAGGCCCAGGCTCTAGAAGACCTGGCTGGCTTTAA | |
| | AGAGCTCTTCCAGACACGAGGTCACACTGAGGAATCAATGACTAACGATAAAACTGCCAAAGTAGCCTGC | |
| | AAATCTTCACAACCAGACCCAGACAAAAACCCAGCAAGCTCCAAGCGACGGCTCAAGACATCCCTGGGGA | |
| | AAGTGGGCGTGAAAGAAGAGCTCCTAGCAGTTGGCAAGCTCACACAGACATCAGGAGAGACTACACACAC | |
| | ACACACAGAGCCAACAGGAGATGGTAAGAGCATGAAAGCATTTATGGAGTCTCCAAAGCAGATCTTAGAC | |
| | TCAGCAGCAAGTCTAACTGGCAGCAAGAGGCAGCTGAGAACTCCTAAGGGAAAGTCTGAAGTCCCTGAAG | |
| | ACCTGGCCGGCTTCATCGAGCTCTTCCAGACACCAAGTCACACTAAGGAATCAATGACTAACGAAAAAAC | |
| | TACCAAAGTATCCTACAGAGCTTCACAGCCAGACCTAGTGGACACCCCAACAAGCTCCAAGCCACAGCCC | |
| | AAGAGAAGTCTCAGGAAAGCAGACACTGAAGAAGAATTTTTAGCATTTAGGAAACAAACGCCATCAGCAG | |
| | GCAAAGCCATGCACACACCCAAACCAGCAGTAGGTGAAGAGAAAGACATCAACACGTTTTTGGGAACTCC | |
| | AGTGCAGAAACTGGACCAGCCAGGAAATTTACCTGGCAGCAATAGACGGCTACAAACTCGTAAGGAAAAG | |
| | GCCCAGGCTCTAGAAGAACTGACTGGCTTCAGAGAGCTTTTCCAGACACCATGCACTGATAACCCCACGA | |
| | CTGATGAGAAAACTACCAAAAAAATACTCTGCAAATCTCCGCAATCAGACCCAGCGGACACCCCAACAAA | |
| | CACAAAGCAACGGCCCAAGAGAAGCCTCAAGAAAGCAGACGTAGAGGAAGAATTTTTAGCATTCAGGAAA | |
| | CTAACACCATCAGCAGGCAAAGCCATGCACACGCCTAAAGCAGCAGTAGGTGAAGAGAAAGACATCAACA | |
| | CATTTGTGGGGACTCCAGTGGAGAAACTGGACCTGCTAGGAAATTTACCTGGCAGCAAGAGACGGCCACA | |
| | AACTCCTAAAGAAAAGGCCAAGGCTCTAGAAGATCTGGCTGGCTTCAAAGAGCTCTTCCAGACACCAGGT | |
| | CACACTGAGGAATCAATGACCGATGACAAAATCACAGAAGTATCCTGCAAATCTCCACAACCAGACCCAG | |
| | TCAAAACCCCAACAAGCTCCAAGCAACGACTCAAGATATCCTTGGGGAAAGTAGGTGTGAAAGAAGAGGT | |
| | CCTACCAGTCGGCAAGCTCACACAGACGTCAGGGAAGACCACACAGACACACAGAGAGACAGCAGGAGAT | |
| | GGAAAGAGCATCAAAGCGTTTAAGGAATCTGCAAAGCAGATGCTGGACCCAGCAAACTATGGAACTGGGA | |
| | TGGAGAGGTGGCCAAGAACACCTAAGGAAGAGGCCCAATCACTAGAAGACCTGGCCGGCTTCAAAGAGCT | |
| | CTTCCAGACACCAGACCACACTGAGGAATCAACAACTGATGACAAAACTACCAAAATAGCCTGCAAATCT | |
| | CCACCACCAGAATCAATGGACACTCCAACAAGCACAAGGAGGCGGCCCAAAACACCTTTGGGGAAAAGGG | |
| | ATATAGTGGAAGAGCTCTCAGCCCTGAAGCAGCTCACACAGACCACACACACAGACAAAGTACCAGGAGA | |
| | TGAGGATAAAGGCATCAACGTGTTCAGGGAAACTGCAAAACAGAAACTGGACCCAGCAGCAAGTGTAACT | |
| | GGTAGCAAGAGGCAGCCAAGAACTCCTAAGGGAAAAGCCCAACCCCTAGAAGACTTGGCTGGCTTGAAAG | |
| | AGCTCTTCCAGACACCAATATGCACTGACAAGCCCACGACTCATGAGAAAACTACCAAAATAGCCTGCAG | |
| | ATCTCCACAACCAGACCCAGTGGGTACCCCAACAATCTTCAAGCCACAGTCCAAGAGAAGTCTCAGGAAA | |
| | GCAGACGTAGAGGAAGAATCCTTAGCACTCAGGAAACGAACACCATCAGTAGGGAAAGCTATGGACACAC | |
| | CCAAACCAGCAGGAGGTGATGAGAAAGACATGAAAGCATTTATGGGAACTCCAGTGCAGAAATTGGACCT | |
| | GCCAGGAAATTTACCTGGCAGCAAAAGATGGCCACAAACTCCTAAGGAAAAGGCCCAGGCTCTAGAAGAC | |
| | CTGGCTGGCTTCAAAGAGCTCTTCCAGACACCAGGCACTGACAAGCCCACGACTGATGAGAAAACTACCA | |
| | AAATAGCCTGCAAATCTCCACAACCAGACCCAGTGGACACCCCAGCAAGCACAAAGCAACGGCCCAAGAG | |
| | AAACCTCAGGAAAGCAGACGTAGAGGAAGAATTTTTAGCACTCAGGAAACGAACACCATCAGCAGGCAAA | |
| | GCCATGGACACACCAAAACCAGCAGTAAGTGATGAGAAAAATATCAACACATTTGTGGAAACTCCAGTGC | |
| | AGAAACTGGACCTGCTAGGAAATTTACCTGGCAGCAAGAGACAGCCACAGACTCCTAAGGAAAAGGCTGA | |
| | GGCTCTAGAGGACCTGGTTGGCTTCAAAGAACTCTTCCAGACACCAGGTCACACTGAGGAATCAATGACT | |
| | GATGACAAAATCACAGAAGTATCCTGTAAATCTCCACAGCCAGAGTCATTCAAAACCTCAAGAAGCTCCA | |
| | AGCAAAGGCTCAAGATACCCCTGGTGAAAGTGGACATGAAAGAAGAGCCCCTAGCAGTCAGCAAGCTCAC | |
| | ACGGACATCAGGGGAGACTACGCAAACACACACAGAGCCAACAGGAGATAGTAAGAGCATCAAAGCGTTT | |
| | AAGGAGTCTCCAAAGCAGATCCTGGACCCAGCAGCAAGTGTAACTGGTAGCAGGAGGCAGCTGAGAACTC | |
| | GTAAGGAAAAGGCCCGTGCTCTAGAAGACCTGGTTGACTTCAAAGAGCTCTTCTCAGCACCAGGTCACAC | |
| | TGAAGAGTCAATGACTATTGACAAAAACACAAAAATTCCCTGCAAATCTCCCCCACCAGAACTAACAGAC | |
| | ACTGCCACGAGCACAAAGAGATGCCCCAAGACACGTCCCAGGAAAGAAGTAAAAGAGGAGCTCTCAGCAG | |
| | TTGAGAGGCTCACGCAAACATCAGGGCAAAGCACACACACACACAAAGAACCAGCAAGCGGTGATGAGGG | |
| | CATCAAAGTATTGAAGCAACGTGCAAAGAAGAAACCAAACCCAGTAGAAGAGGAACCCAGCAGGAGAAGG | |
| | CCAAGAGCACCTAAGGAAAAGGCCCAACCCCTGGAAGACCTGGCCGGCTTCACAGAGCTCTCTGAAACAT | |
| | CAGGTCACACTCAGGAATCACTGACTGCTGGCAAAGCCACTAAAATACCCTGCGAATCTCCCCCACTAGA | |
| | AGTGGTAGACACCACAGCAAGCACAAAGAGGCATCTCAGGACACGTGTGCAGAAGGTACAAGTAAAAGAA | |
| | GAGCCTTCAGCAGTCAAGTTCACACAAACATCAGGGGAAACCACGGATGCAGACAAAGAACCAGCAGGTG | |
| | AAGATAAAGGCATCAAAGCATTGAAGGAATCTGCAAAACAGACACCGGCTCCAGCAGCAAGTGTAACTGG | |

TABLE 2-continued

| GENBANK ACCESSION NUMBER | SEQUENCE | SEQ ID NO: |
|---|---|---|
| | CAGCAGGAGACGGCCAAGAGCACCCAGGGAAAGTGCCCAAGCCATAGAAGACCTAGCTGGCTTCAAAGAC | |
| | CCAGCAGCAGGTCACACTGAAGAATCAATGACTGATGACAAAACCACTAAAATACCCTGCAAATCATCAC | |
| | CAGAACTAGAAGACACCGCAACAAGCTCAAAGAGACGGCCCAGGACACGTGCCCAGAAAGTAGAAGTGAA | |
| | GGAGGAGCTGTTAGCAGTTGGCAAGCTCACACAAACCTCAGGGGAGACCACGCACACCGACAAAGAGCCG | |
| | GTAGGTGAGGGCAAAGGCACGAAAGCATTTAAGCAACCTGCAAAGCGGAAGCTGGACGCAGAAGATGTAA | |
| | TTGGCAGCAGGAGACAGCCAAGAGCACCTAAGGAAAAGGCCCAACCCCTGGAAGATCTGGCCAGCTTCCA | |
| | AGAGCTCTCTCAAACACCAGGCCACACTGAGGAACTGGCAAATGGTGCTGCTGATAGCTTTACAAGCGCT | |
| | CCAAAGCAAACACCTGACAGTGGAAAACCTCTAAAAATATCCAGAAGAGTTCTTCGGGCCCCTAAAGTAG | |
| | AACCCGTGGGAGACGTGGTAAGCACCAGAGACCCTGTAAAATCACAAAGCAAAAGCAACACTTCCCTGCC | |
| | CCCACTGCCCTTCAAGAGGGGAGGTGGCAAAGATGGAAGCGTCACGGGAACCAAGAGGCTGCGCTGCATG | |
| | CCAGCACCAGAGGAAATTGTGGAGGAGCTGCCAGCCAGCAAGAAGCAGAGGGTTGCTCCCAGGGCAAGAG | |
| | GCAAATCATCCGAACCCGTGGTCATCATGAAGAGAAGTTTGAGGACTTCTGCAAAAAGAATTGAACCTGC | |
| | GGAAGAGCTGAACAGCAACGACATGAAAACCAACAAAGAGGAACACAAATTACAAGACTCGGTCCCTGAA | |
| | AATAAGGGAATATCCCTGCGCTCCAGACGCCAAAATAAGACTGAGGCAGAACAGCAAATAACTGAGGTCT | |
| | TTGTATTAGCAGAAAGAATAGAAATAAACAGAAATGAAAAGAAGCCCATGAAGACCTCCCCAGAGATGGA | |
| | CATTCAGAATCCAGATGATGGAGCCCGGAAACCCATACCTAGAGACAAAGTCACTGAGAACAAAAGGTGC | |
| | TTGAGGTCTGCTAGACAGAATGAGAGCTCCCAGCCTAAGGTGGCAGAGGAGAGCGGAGGGCAGAAGAGTG | |
| | CGAAGGTTCTCATGCAGAATCAGAAAGGGAAAGGAGAAGCAGGAAATTCAGACTCCATGTGCCTGAGATC | |
| | AAGAAAGACAAAAAGCCAGCCTGCAGCAAGCACTTTGGAGAGCAAATCTGTGCAGAGAGTAACGCGGAGT | |
| | GTCAAGAGGTGTGCAGAAAATCCAAAGAAGGCTGAGGACAATGTGTGTGTCAAGAAAATAAGAACCAGAA | |
| | GTCATAGGGACAGTGAAGATATTTGACAGAAAAATCGAACTGGGAAAAATATAATAAAGTTAGTTTTGTG | |
| | ATAAGTTCTAGTGCAGTTTTTGTCATAAATTACAAGTGAATTCTGTAAGTAAGGCTGTCAGTCTGCTTAA | |
| | GGGAAGAAAACTTTGGATTTGCTGGGTCTGAATCGGCTTCATAAACTCCACTGGGAGCACTGCTGGGCTC | |
| | CTGGACTGAGAATAGTTGAACACCGGGGGCTTTGTGAAGGAGTCTGGGCCAAGGTTTGCCCTCAGCTTTG | |
| | CAGAATGAAGCCTTGAGGTCTGTCACCACCCACAGCCACCCTACAGCAGCCTTAACTGTGACACTTGCCA | |
| | CACTGTGTCGTCGTTTGTTTGCCTATGTCCTCCAGGGCACGGTGGCAGGAACAACTATCCTCGTCTGTCC | |
| | CAACACTGAGCAGGCACTCGGTAAACACGAATGAATGGATGAGCGCACGGATGAATGGAGCTTACAAGAT | |
| | CTGTCTTTCCAATGGCCGGGGGCATTTGGTCCCCAAATTAAGGCTATTGGACATCTGCACAGGACAGTCC | |
| | TATTTTTGATGTCCTTTCCTTTCTGAAAATAAAGTTTTGTGCTTTGGAGAATGACTCGTGAGCACATCTT | |
| | TAGGGACCAAGAGTGACTTTCTGTAAGGAGTGACTCGTGGCTTGCCTTGGTCTCTTGGGAATACTTTTCT | |
| | AACTAGGGTTGCTCTCACCTGAGACATTCTCCACCCGCGGAATCTCAGGGTCCCAGGCTGTGGGCCATCA | |
| | CGACCTCAAACTGGCTCCTAATCTCCAGCTTTCCTGTCATTGAAAGCTTCGGAAGTTTACTGGCTCTGCT | |
| | CCCGCCTGTTTTCTTTCTGACTCTATCTGGCAGCCCGATGCCACCCAGTACAGGAAGTGACACCAGTACT | |
| | CTGTAAAGCATCATCATCCTTGGAGAGACTGAGCACTCAGCACCTTCAGCCACGATTTCAGGATCGCTTC | |
| | CTTGTGAGCCGCTGCCTCCGAAATCTCCTTTGAAGCCCAGACATCTTTCTCCAGCTTCAGACTTGTAGAT | |
| | ATAACTCGTTCATCTTCATTTACTTTCCACTTTGCCCCCTGTCCTCTCTGTGTTCCCCAAATCAGAGAAT | |
| | AGCCCGCCATCCCCCAGGTCACCTGTCTGGATTCCTCCCCATTCACCCACCTTGCCAGGTGCAGGTGAGG | |
| | ATGGTGCACCAGACAGGGTAGCTGTCCCCCAAAATGTGCCCTGTGCGGGCAGTGCCCTGTCTCCACGTTT | |
| | GTTTCCCCAGTGTCTGGCGGGGAGCCAGGTGACATCATAAATACTTGCTGAATGAATGCAGAAATCAGCG | |
| | GTACTGACTTGTACTATATTGGCTGCCATGATAGGGTTCTCACAGCGTCATCCATGATCGTAAGGGAGAA | |
| | TGACATTCTGCTTGAGGGAGGGAATAGAAAGGGGCAGGGAGGGGACATCTGAGGGCTTCACAGGGCTGCA | |
| | AAGGGTACAGGGATTGCACCAGGGCAGAACAGGGGAGGGTGTTCAAGGAAGAGTGGCTCTTAGCAGAGGC | |
| | ACTTTGGAAGGTGTGAGGCATAAATGCTTCCTTCTACGTAGGCCAACCTCAAAACTTTCAGTAGGAATGT | |
| | TGCTATGATCAAGTTGTTCTAACACTTTAGACTTAGTAGTAATTATGAACCTCACATAGAAAAATTTCAT | |
| | CCAGCCATATGCCTGTGGAGTGGAATATTCTGTTTAGTAGAAAAATCCTTTAGAGTTCAGCTCTAACCAG | |
| | AAATCTTGCTGAAGTATGTCAGCACCTTTTCTCACCCTGGTAAGTACAGTATTTCAAGAGCACGCTAAGG | |
| | GTGGTTTTCATTTTACAGGGCTGTTGATGATGGGTTAAAAATGTTCATTTAAGGGCTACCCCCGTGTTTA | |
| | ATAGATGAACACCACTTCTACACAACCCTCCTTGGTACTGGGGGAGGGAGAGATCTGACAAATACTGCCC | |
| | ATTCCCCTAGGCTGACTGGATTTGAGAACAAATACCCACCCATTTCCACCATGGTATGGTAACTTCTCTG | |
| | AGCTTCAGTTTCCAAGTGAATTTCCATGTAATAGGACATTCCCATTAAATACAAGCTGTTTTTACTTTTT | |
| | CGCCTCCCAGGGCCTGTGGGATCTGGTCCCCCAGCCTCTCTTGGGCTTTCTTACACTAACTCTGTACCTA | |
| | CCATCTCCTGCCTCCCTTAGGCAGGCACCTCCAACCACCACACACTCCCTGCTGTTTTCCCTGCCTGGAA | |
| | CTTTCCCTCCTGCCCCACCAAGATCATTTCATCCAGTCCTGAGCTCAGCTTAAGGGAGGCTTCTTGCCTG | |
| | TGGGTTCCCTCACCCCCATGCCTGTCCTCCAGGCTGGGGCAGGTTCTTAGTTTGCCTGGAATTGTTCTGT | |
| | ACCTCTTTGTAGCACGTAGTGTTGTGGAAACTAAGCCACTAATTGAGTTTCTGGCTCCCCTCCTGGGGTT | |
| | GTAAGTTTTGTTCATTCATGAGGGCCGACTGCATTTCCTGGTTACTCTATCCCAGTGACCAGCCACAGGA | |
| | GATGTCCAATAAAGTATGTGATGAAATGGTCTTAAAAAAAAAAAAAA | |
| NM_024101 | GCGCCGGGACGTGGCCAGTTGCCCGCCTGCCCCGGAGAGCCAGGCGCTAACCAGCCGCTCTGCGCCCCGC | 138 |
| | GCCCTGCTTGCCCCCATTATCCAGCCTTGCCCCGGCGCCCTGACCTGACGCCCTGGCCTGACGCCCTGCT | |
| | TCGTCGCCTCCTTTCTCTCCCAGGTGCTGGACCAGGGACTGAGCGTCCCCCGGAGAGGGTCCGGTGTGAC | |
| | CCCGACAAGAAGCAGAAATGGGGAAGAAACTGGATCTTTCCAAGCTCACTGATGAAGAGGCCCAGCATGT | |
| | CTTGGAAGTTGTTCAACGAGATTTTGACCTCCGAAGGAAAGAAGAGGAACGGCTAGAGGCGTTGAAGGGC | |
| | AAGATTAAGAAGGAAAGCTCCAAGAGGGAGCTGCTTTCCGACACTGCCCATCTGAACGAGACCCACTGCG | |
| | CCCGCTGCCTGCAGCCCTACCAGCTGCTTGTGAATAGCAAAAGGCAGTGCCTGGAATGTGGCCTCTTCAC | |
| | CTGCAAAAGCTGTGGCCGCGTCCACCCGGAGGAGCAGGGCTGGATCTGTGACCCCTGCCATCTGGCCAGA | |
| | GTCGTGAAGATCGGCTCACTGGAGTGGTACTATGAGCATGTGAAAGCCCGCTTCAAGAGGTTCGGAAGTG | |
| | CCAAGGTCATCCGGTCCCTCCACGGGCGGCTGCAGGGTGGAGCTGGGCCTGAACTGATATCTGAAGAGAG | |
| | AAGTGGAGACAGCGACCAGACAGATGAGGATGGAGAACCTGGCTCAGAGGCCCAGGCCCAGGCCCAGCCC | |
| | TTTGGCAGCAAAAAAAAGCGCCTCCTCTCCGTCCACGACTTCGACTTCGAGGGAGACTCAGATGACTCCA | |
| | CTCAGCCTCAAGGTCACTCCCTGCACCTGTCCTCAGTCCCTGAGGCCAGGGACAGCCCACAGTCCCTCAC | |
| | AGATGAGTCCTGCTCAGAGAAGGCAGCCCCTCACAAGGCTGAGGGCCTGGAGGAGGCTGATACTGGGGCC | |
| | TCTGGGTGCCACTCCCATCCGGAAGAGCAGCCGACCAGCATCTCACCTTCCAGACACGGCGCCCTGGCTG | |
| | AGCTCTGCCCGCCTGGAGGCTCCCACAGGATGGCCCTGGGGACTGCTGCTGCACTCGGGTCGAATGTCAT | |
| | CAGGAATGAGCAGCTGCCCCTGCAGTACTTGGCCGATGTGGACACCTCTGATGAGGAAAGCATCCGGGCT | |
| | CACGTGATGGCCTCCCACCATTCCAAGCGGAGAGGCCGGGCGTCTTCTGAGAGTCAGATCTTTGAGCTGA | |

TABLE 2-continued

| GENBANK ACCESSION NUMBER | SEQUENCE | SEQ ID NO: |
|---|---|---|
| | ATAAGCATATTTCAGCTGTGGAATGCCTGCTGACCTACCTGGAGAACACAGTTGTGCCTCCCTTGGCCAA GGGTCTAGGTGCTGGAGTGCGCACGGAGGCCGATGTAGAGGAGGAGGCCCTGAGGAGGAAGCTGGAGGAG CTGACCAGCAACGTCAGTGACCAGGAGACCTCGTCCGAGGAGGAGGAAGCCAAGGACGAAAAGGCAGAGC CCAACAGGGACAAATCAGTTGGGCCTCTCCCCCAGGCGGACCCGGAGGTGGGCACGGCTGCCCATCAAAC CAACAGACAGGAAAAAAGCCCCCAGGACCCTGGGGACCCCGTCCAGTACAACAGGACCACAGATGAGGAG CTGTCAGAGCTGGAGGACAGAGTGGCAGTGACGGCCTCAGAAGTCCAGCAGGCAGAGAGCGAGGTTTCAG ACATTGAATCCAGGATTGCAGCCCTGAGGGCCGCAGGGCTCACGGTGAAGCCCTCGGGAAAGCCCCGGAG GAAGTCAAACCTCCCGATATTTCTCCCTCGAGTGGCTGGGAAACTTGGCAAGAGACCAGAGGACCCCAAAT GCAGACCCCTTCAAGTGAGGCCAAGGCAATGGCTGTGCCCTATCTTCTGAGAAGAAAGTTCAGTAATTCCC TGAAAAGTCAAGGTAAAGATGATGATTCTTTTGATCGGAAATCAGTGTACCGAGGCTCGCTGACACAGAG AAACCCCAACGCGAGGAAAGGAATGGCCAGCCACACCTTCGCGAAACCTGTGGTGGCCCACCAGTCCTAA CGGGACAGGACAGAGAGACAGAGCAGCCCTGCACTGTTTTCCCTCCACCACAGCCATCCTGTCCCTCATT GGCTCTGTGCTTTCCACTATACACAGTCACCGTCCCAATGAGAAACAAGAAGGAGCACCCTCCACATGGA CTCCCACCTGCAAGTGGACAGCGACATTCAGTCCTGCACTGCTCACCTGGGTTTACTGATGACTCCTGGC TGCCCCACCATCCTCTCTGATCTGTGAGAAACAGCTAAGCTGCTGTGACTTCCCTTTAGGACAATGTTGT GTAAATCTTTGAAGGACACACCGAAGACCTTTATACTGTGATCTTTTACCCCTTTCACTCTTGGCTTTCT TATGTTGCTTTCATGAATGGAATGGAAAAAAGATGACTCAGTTAAGGCACCAGCCATATGTGTATTCTTG ATGGTCTATATCGGGGTGTGAGCAGATGTTTGCGTATTTCTTGTGGGTGTGACTGGATATTAGACATCCG GACAAGTGACTGAACTAATGATCTGCTGAATAATGAAGGAGGAATAGACACCCCAGTCCCCACCCTACGT GCACCCGCTCTGCAAGTTCCCATGTGATCTGTAGACCAGGGGAAATTACACTGCGGTCAAGGGCAGAGCC TGCACATGACAGCAAGTGAGCATTTGATAGATGCTCAGATGCTAGTGCAGAGAGCCTGCTGGGAGACGAA GAGACAGCAGGCAGAGCTCCAGATGGGCAAGGAAGAGGCTTGGTTCTAGCCTGGCTCTGCCCCTCACTGC AGTGGATCCAGTGGGGCAGAGGACAGAGGGTCACAACCAATGAGGGATGTCTGCCAAGGATGGGGGTGCA GAGGCCACAGGAGTCAGCTTGCCACTCGCCCATTGGTTACATAGATGATCTCTCAGACAGGCTGGGACTC AGAGTTATTTCCTAGTATCGGTGTGCCCCATCCAGTTTTAAGTGGAGCCCTCCAAGACTCTCCAGAGCTG CCTTTGAACATCCTAACAGTAATCACATCTCACCCTCCCTGAGGTTCACTTTAGACAGGACCCAATGGCT GCACTGCCTTTGTCAGAGGGGGTGCTGAGAGGAGTGGCTTCTTTTAGAATCAAACAGTAGAGACAAGAGT CAAGCCTTGTGTCTTCAAGCATTGACCAAGTTAAGTGTTTCCTTCCCTCTCTCAATAAGACACTTCCAGG AGCTTTCCAATCTCTCACTTAAAACTAAGGTTTGAATCTCAAAGTGTTGCTGGGAGGCTGATACTCCTGC AACTTCAGGAGACCTGTGAGCACACATTAGCAGCTGTTTCTCTGACTCCTTGTGGCATCAGATAAAAACG TGGGAGTTTTTCCATATAATTCCCAGCCTTACTTATAAATTCTATTCTTTGAAAAAATTATTCAGGCTAG GTAAGGTGGCTCATACCTATAATCCCAGCCCTTTGAGAGGCCAAGGTGGGAGAATTGCTTGAGGCCAGGA GTTTGAGACCTCCTGGGCAACATAGTGAGATCCCATCTCTACAAAAAACAAAACAAAAAAATTACCCAAG CATGATGGTATATGCCTGTAGTCGTACCTACTTACTTAGGAGGCTGAGGCAGGAGGATCACTTGAGCCCT GGAGGTTGGGGCTGCAGTGAGCCATGATCGCATCACTATACTCGAGCCTGGGCAACAGAGTGAGACCTTG TCTCTTAAAAAAATTAATAATAAATAAATGAAAATAATTCTTCAGAAAAAAAAAAAAAAAA | |
| NM_005940 | AAGCCCAGCAGCCCCGGGGCGGATGGCTCCGGCCGCCTGGCTCCGCAGCGCGGCCGCGCGCGCCCTCCTG CCCCCGATGCTGCTGCTGCTGCTCCAGCCGCCGCCGCTGCTGGCCCGGGCTCTGCCGCCGGACGCCCACC ACCTCCATGCCGAGAGGAGGGGGCCACAGCCCTGGCATGCAGCCCTGCCCAGTAGCCCGGCACCTGCCCC TGCCACGCAGGAAGCCCCCCGGCCTGCCAGCAGCCTCAGGCCTCCCCGCTGTGGCGTGCCCGACCCATCT GATGGGCTGAGTGCCCGCAACCGACAGAAGAGGTTCGTGCTTTCTGGCGGGCGCTGGGAGAAGACGGACC TCACCTACAGGATCCTTCGGTTCCCATGGCAGTTGGTGCAGGAGCAGGTGCGGCAGACGATGGCAGAGGC CCTAAAGGTATGGAGCGATGTGACGCCACTCACCTTTACTGAGGTGCACGAGGGCCGTGCTGACATCATG ATCGACTTCGCCAGGTACTGGCATGGGGACGACCTGCCGTTTGATGGGCCTGGGGGCATCCTGGCCCATG CCTTCTTCCCCAAGACTCACCGAGAAGGGGATGTCCACTTCGACTATGATGAGACCTGGACTATCGGGGA TGACCAGGGCACAGACCTGCTGCAGGTGGCAGCCCATGAATTTGGCCACGTGCTGGGGCTGCAGCACACA ACAGCAGCCAAGGCCCTGATGTCCGCCTTCTACACCTTTCGCTACCCACTGAGTCTCAGCCCAGATGACT GCAGGGGCGTTCAACACCTATATGGCCAGCCCTGGCCCACTGTCACCTCCAGGACCCCAGCCCTGGGCCC CCAGGCTGGGATAGACACCAATGAGATTGCACCGCTGGAGCCAGACGCCCCGCCAGATGCCTGTGAGGCC TCCTTTGACGCGGTCTCCACCATCCGAGGCGAGCTCTTTTTCTTCAAAGCGGGCTTTGTGTGGCGCCTCC GTGGGGGCCAGCTGCAGCCCGGCTACCCAGCATTGGCCTCTCGCCACTGGCAGGGACTGCCCAGCCCTGT GGACGCTGCCTTCGAGGATGCCCAGGGCCACATTTGGTTCTTCCAAGGTGCTCAGTACTGGGTGTACGAC GGTGAAAAGCCAGTCCTGGGCCCCGCACCCCTCACCGAGCTGGGCCTGGTGAGGTTCCCGGTCCATGCTG CCTTGGTCTGGGGTCCCGAGAAGAACAAGATCTACTTCTTCCGAGGCAGGGACTACTGGCGTTTCCACCC CAGCACCCGGCGTGTAGACAGTCCCGTGCCCCGCAGGGCCACTGACTGGAGAGGGGTGCCCTCTGAGATC GACGCTGCCTTCCAGGATGCTGATGGCTATGCCTACTTCCTGCGCGGCCGCCTCTACTGGAAGTTTGACC CTGTGAAGGTGAAGGCTCTGGAAGGCTTCCCCCGTCTCGTGGGTCCTGACTTCTTTGGCTGTGCCGAGCC TGCCAACACTTTCCTCTGACCATGGCTTGGATGCCCTCAGGGGTGCTGACCCCTGCCAGGCCACGAATAT CAGGCTAGAGACCCATGGCCATCTTTGTGGCTGTGGGCACCAGGCATGGGACTGAGCCCATGTCTCCTCA GGGGGATGGGGTGGGGTACAACCACCATGACAACTGCCGGGAGGGCCACGCAGGTCGTGGTCACCTGCCA GCGACTGTCTCAGACTGGGCAGGGAGGCTTTGGCATGACTTAAGAGGAAGGGCAGTCTTGGGCCCGCTAT GCAGGTCCTGGCAAACCTGGCTGCCCTGTCTCCATCCCTGTCCCTCAGGGTAGCACCATGGCAGGACTGG GGGAACTGGAGTGTCCTTGCTGTATCCCTGTTGTGAGGTTCCTTCCAGGGGCTGGCACTGAAGCAAGGGT GCTGGGGCCCCATGGCCTTCAGCCCTGGCTGAGCAACTGGGCTGTAGGGCAGGGCCACTTCCTGAGGTCA GGTCTTGGTAGGTGCCTGCATCTGTCTGCCTTCTGGCTGACAATCCTGGAAATCTGTTCTCCAGAATCCA GGCCAAAAAGTTCACAGTCAAATGGGGAGGGGTATTCTTCATGCAGGAGACCCCAGGCCCTGGAGGCTGC AACATACCTCAATCCTGTCCCAGGCCGGATCCTCCTGAAGCCCTTTTCGCAGCACTGCTATCCTCCAAAG CCATTGTAAATGTGTGTACAGTGTGTATAAACCTTCTTCTTCTTTTTTTTTTTTTAAACTGAGGATTGTC | 139 |
| BX647151 | TAGCAGCACACAAGGGTTCGTGTTTGTGGAACCAGGTAGCTTCCTTCAGAGCTGACATTTGCCCACAGCC AGCCTGGCCCAGCCCCATACCACCAGCCCTGGCGCTCTGGGGCGTGAGGTGCCTTTTCTGCCCCCCTGCT CTAGGGCAGGTGGAAATCACCCATGGTGGGTCTACATCTGATAGAAGCATCTTATAGTTCTGCTTCTGGA CCAGACCATCCTGGGTTTTTCTCTGTTCTGCTGAAGGGTTCCCTCCACGTGTCCATCACCTCGGTGAACT CTTGGGAGACCTGGGAAGATGCTGGCCTCACCTCTCGCCTCTCCTTTCCCTCATTGTGCTGCCACCATCC TTCTCACACAGGCTCTCCAGGGAGAGCTGGGCAGGATGGGATCTTCCTGGGTTCCCACCTTGCTCCGTGC | 140 |

TABLE 2-continued

| GENBANK ACCESSION NUMBER | SEQUENCE | SEQ ID NO: |
|---|---|---|
| | CCCCTCTCACTGTTCCTGAAGTGTGGCCACGGACTGCCTTGTTTTCTGGAAAGTCCCAAGTCTGGACCAT<br>GACTGAGCAGCATTCTCGGCTATCTGCCACCTGTCTGGGGCTCCTGGCCCCTCTTAGACTCCCCTCTCCC<br>TTCTGTTTCCCCCGAGCCCCTGACTTGGACCTGCAGGGTGGGGAGAGGGATGGGACGAGAACCTGTGCTG<br>GGGCCAAAGGTCGCACTGGGGGAAGGTGGAGCCAGGGCAGCAGAGTGCCTGGCGTCGGCCCCTATCCTGT<br>CACTAGTTCCCCCGTTCTGGCCCCTGGCAGGTTTGTAACCCCAGATCAGAAGTACTCCATGGACAACACT<br>CCCCACACGCCAACCCCGTTCAAGAACGCCCTGGAGAAGTACGGACCCCTGAAGCCCCTGGTACGTGGTG<br>TGGTCACTGCCGTGGATCTCTGCACAGTGGGATCCCTTCGGTTCATCCAACCATGTTCAGTCCACAGGAC<br>CCTTCCCTCTGAGGTCTCATTTGATTCTTTCTCCTGAGAAGATGCAGAGATCCTGATAATATAAATGGGG<br>AAGCTGAGGCTGCTCTTTGTCACTTCCTCCGACTGCTCCTGAGCACCTGAGTTTGCAAGCACGCGCCGGC<br>TGGTGCTAGAGACATGGTGGTATCCCGTGACACTCAGCCTCAGGATGGGGGAGACTGATGTGAAATACAA<br>ATAACTTAAACACTTTCAGGCAAAGATAAGCACTGGGCCTAGTTCAGAGAAGTGGCAAATTGCTACTCTG<br>GCCTGTCTCTGACCAACTCCCAGTTCTCTACAGAGCACGGGAAAGCCCCTCGGGGACGTCTTTCCTGCAG<br>TGTGCAGGCTGCCCTTCTCCCCTGCTCTTCCCAGTTGATGGGATGGTTGTGTTTTCTCTATGAAAAAAGG<br>AGTTGGCACCTTGGGCTTTCTGAAACACACAGGTGTTTTAGAAATCAGTGGAGGGTGAGAGAAAGGCATG<br>GTTGTGGAGGCACTGGACTGTGAACAAGGTCTGCAGCGGGTCCCCCTGCTGTCTCTCTCTACTGCATGGA<br>GCCTCCTATGAAGCCCAAGGTGGCTGGGGGCTGAGGCTCCCTTGGGCCTGCCATGGAACTGATTCTGAGT<br>CAAGCAGACTTTCCACGGACCATGCTACATGAGCCGAGGTGAGGCACTAGTTAGTGCTCCTTTCCTGTTG<br>CAGTGGAGATTTGGCTCCTCTGTACTAAAATATCTGCATGCTCTCCAAACAGGTGTGAGGGCAAATCACA<br>TGACCTTGGCAGCTGTAATTAAAGTTTGTGGGGGCTTTTCGGATGACTTATGAGGAGTGGCTGTGATTCG<br>CACCTTTCACTCTTAGTAGCACTCGCCCTCCCCTGTTCTCTGTTGCCTGAAGCTGGAGAGGTCCTTGGAA<br>CCCCGAGGCCTGAGAAAGGGAAATGGGTTTGAGAGCCCCCATTAGTGTGGAACAAAGGGTTGAGTGAGCC<br>TGGGCTTTGAGCTGTCGGGGTCCTAATTCAGCAGCTGTGTGACTGTGTGCCAGGCTGTTGATCTCTGAGC<br>TTCTGTTTCTACCTGCTTAAAATGACGGTTACTGCACAGGGCTGTGTGAGGGTTACAGTGCGTCTCTGGG<br>CTGCTCCCAGCCATGGCAGGCCCCTGGGAATCAAGGTCATCAGCTGCTTGTCCAAGGCAGCAGTTAGTGG<br>TTGTGAATGGTGCGTGTGAGATCTGCATCCTGGCGTCAGGCCTCCTTCCTGCCTTACCCAGGACAGCCCA<br>GTTGCAGCTGGGTTGGTCCCACAGTCCCACACACACACAGCCCGAGTGTGGTGCCTCACGTGGGCTGCCC<br>CGTGCCTACCCACAGCCACAGACCCCGCACCTGGAGGAGGACTTGAAGGAGGTGCTGCGTTCTGAGGCTG<br>GCATCGAACTCATCATCGAGGACGACATCAGGCCCGAGAAGCAGAAGAGGAAGCCTGGGCTGCGGCGGAG<br>CCCCATCAAGAAAGTCCGGAAGTCTCTGGCTCTTGACATTGTGGATGAGGATGTGAAGCTGATGATGTCC<br>ACACTGCCCAAGTCTCTATCCTTGCCGACAACTGCCCCTTCAAACTCTTCCAGCCTCACCCTGTCAGGTA<br>TCAAAGAAGACAACAGCTTGCTCAACCAGGGCTTCTTGCAGGCCAAGCCCGAGAAGGCAGCAGTGGCCCA<br>GAAGCCCCGAAGCCACTTCACGACACCTGCCCCTATGTCCAGTGCCTGGAAGACGGTGGCCTGCGGGGGG<br>ACCAGGGACCAGCTTTTCATGCAGGAGAAAGCCCGGCAGCTCCTGGGCCGCCTGAAGCCCAGCCACACAT<br>CTCGGACCCTCATCTTGTCCTGAGGTGTTGAGGGTGTCACGAGCCCATTCACATGTTTACAGGGGTTGTG<br>GGGGCAGAGGGGGTCTGTGAATCTGAGAGTCATTCAGGTGACCTCCTGCAGGGAGCCTTCTGCCACCAGC<br>CCCTCCCCAGACTCTCAGGTGGAGGCAACAGGGCCATGTGCTGCCCTGTTGCCGAGCCCAGCTGTGGGCG<br>GCTCCTGGTGCTAACAACAAAGTTCCACTTCCAGGTCTGCCTGGTTCCCCCCCAAGGCCACAGGGAGCT<br>CCGTCAGCTTCTCCCAAGCCCACGTCAGGCCTGGCCTCATCTCAGACCCTGCTTAGGATGGGGGATGTGG<br>CCAGGGGTGCTCCTGTGCTCACCCTCTCTTGGTGCATTTTTTTGGAAGAATAAAATTGCCTCTCTCTTTG<br>AAAAAAAAAAAAAAAAA | |
| NM_002467 | GACCCCCGAGCTGTGCTGCTCGCGGCCGCCACCGCCGGGCCCCGGCCGTCCCTGGCTCCCCTCCTGCCTC<br>GAGAAGGGCAGGGCTTCTCAGAGGCTTGGCGGGAAAAAGAACGGAGGGAGGGATCGCGCTGAGTATAAAA<br>GCCGGTTTTCGGGGCTTTATCTAACTCGCTGTAGTAATTCCAGCGAGAGGCAGAGGGAGCGAGCGGGCGG<br>CCGGCTAGGGTGGAAGAGCCGGGCGAGCAGAGCTGCGCTGCGGGCGTCCTGGGAAGGGAGATCCGGAGCG<br>AATAGGGGGCTTCGCCTCTGGCCCAGCCCTCCCGCTGATCCCCCAGCCAGCGGTCCGCAACCCTTGCCGC<br>ATCCACGAAACTTTGCCCATAGCAGCGGGCGGGCACTTTGCACTGGAACTTACAACACCCGAGCAAGGAC<br>GCGACTCTCCCGACGCGGGGAGGCTATTCTGCCCATTTGGGGACACTTCCCCGCCGCTGCCAGGACCCGC<br>TTCTCTGAAAGGCTCTCCTTGCAGCTGCTTAGACGCTGGATTTTTTTCGGGTAGTGGAAAACCAGCAGCC<br>TCCCGCGACGATGCCCCTCAACGTTAGCTTCACCAACAGGAACTATGACCTCGACTACGACTCGGTGCAG<br>CCGTATTTCTACTGCGACGAGGAGGAGAACTTCTACCAGCAGCAGCAGCAGAGCGAGCTGCAGCCCCCGG<br>CGCCCAGCGAGGATATCTGGAAGAAATTCGAGCTGCTGCCCACCCCGCCCCTGTCCCCTAGCCGCCGCTC<br>CGGGCTCTGCTCGCCCTCCTACGTTGCGGTCACACCCTTCTCCCTTCGGGGAGACAACGACGGCGGTGGC<br>GGGAGCTTCTCCACGGCCGACCAGCTGGAGATGGTGACCGAGCTGCTGGGAGGAGACATGGTGAACCAGA<br>GTTTCATCTGCGACCCGGACGACGAGACCTTCATCAAAAACATCATCATCCAGGACTGTATGTGGAGCGG<br>CTTCTCGGCCGCCGCCAAGCTCGTCTCAGAGAAGCTGGCCTCCTACCAGGCTGCGCGCAAAGACAGCGGC<br>AGCCCGAACCCCGCCCGCGGCCACAGCGTCTGCTCCACCTCCAGCTTGTACCTGCAGGATCTGAGCGCCG<br>CCGCCTCAGAGTGCATCGACCCCTCGGTGGTCTTCCCCTACCCTCTCAACGACAGCAGCTCGCCCAAGTC<br>CTGCGCCTCGCAAGACTCCAGCGCCTTCTCTCCGTCCTCGGATTCTCTGCTCTCCTCGACGGAGTCCTCC<br>CCGCAGGGCAGCCCCGAGCCCCTGGTGCTCCATGAGGAGACACCGCCCACCACCAGCAGCGACTCTGAGG<br>AGGAACAAGAAGATGAGGAAGAAATCGATGTTGTTTCTGTGGAAAAGAGGCAGGCTCCTGGCAAAAGGTC<br>AGAGTCTGGATCACCTTCTGCTGGAGGCCACAGCAAACCTCCTCACAGCCCACTGGTCCTCAAGAGGTGC<br>CACGTCTCCACACATCAGCACAACTACGCAGCGCCTCCCTCCACTCGGAAGGACTATCCTGCTGCCAAGA<br>GGGTCAAGTTGGACAGTGTCAGAGTCCTGAGACAGATCAGCAACAACCGAAAATGCACCAGCCCCAGGTC<br>CTCGGACACCGAGGAGAATGTCAAGAGGCGAACACACAACGTCTTGGAGCGCCAGAGGAGGAACGAGCTA<br>AAACGGAGCTTTTTTGCCCTGCGTGACCAGATCCCGGAGTTGGAAAACAATGAAAAGGCCCCCAAGGTAG<br>TTATCCTTAAAAAAGCCACAGCATACATCCTGTCCGTCCAAGCAGAGGAGCAAAAGCTCATTTCTGAAGA<br>GGACTTGTTGCGGAAACGACGAGAACAGTTGAAACACAAACTTGAACAGCTACGGAACTCTTGTGCGTAA<br>GGAAAAGTAAGGAAAACGATTCCTTCTAACAGAAATGTCCTGAGCAATCACCTATGAACTTGTTTCAAAT<br>GCATGATCAAATGCAACCTCACAACCTTGGCTGAGTCTTGAGACTGAAAGATTTAGCCATAATGTAAACT<br>GCCTCAAATTGGACTTTGGGCATAAAAGAACTTTTTTATGCTTACCATCTTTTTTTTTTCTTTAACAGAT<br>TTGTATTTAAGAATTGTTTTTAAAAAATTTTAAGATTTACACAATGTTTCTCTGTAAATATTGCCATTAA<br>ATGTAAATAACTTTAATAAAACGTTTATAGCAGTTACACAGAATTTCAATCCTAGTATATAGTACCTAGT<br>ATTATAGGTACTATAAACCCTAATTTTTTTTATTTAAGTACATTTTGCTTTTTAAAGTTGATTTTTTTCT<br>ATTGTTTTTAGAAAAAATAAAATAACTGGCAAATATATCATTGAGCCAAATCTTAAAAAAAAAAAAAAA | 141 |

TABLE 2-continued

| GENBANK ACCESSION NUMBER | SEQUENCE | SEQ ID NO: |
|---|---|---|
| BC013732 | GTGGGAGGATTGCATTCAGTCTAGTTCCTGGTTGCCGGCTGAAATAACCTGCTCTCCAAAATGTCCACAA<br>AAGTGACTTAAGTCAGGTTCCCCCAAACCAGACACCAAGACAAGAATCCATGTGTGTGTGACTGAAGGAA<br>GTGCTGGGAGAGCCCCAGCTGCAGCCTGGATGTGAACTGCAACTCCAAAGTGTGTCCAGACTCAAGGCAA<br>GGGCACTAGGCTTTCCAGACCTCCTACTAAGTCATTGATCCAGCACTGCCCTGCCAGGACATAAATCCCT<br>GGCACCTCTTGCTCTCTGCAAAGGAGGGCAAAGCAGCTTCAGGAGCCCTTGGGAGTCCTCCAAAGAGAGT<br>CTAGGGTACAGGTCCGAAAGTAGAAGAACACAGAAGGCAGGCCAGGGGCACTGTGAGATGGTAAAAGAGA<br>TCTGAAGGGATCCAGAATTCAAGCCAGGAAGAAGCAGCAATCTGTCTTCTGGATTAAAACTGAAGATCAA<br>CCTACTTTCAACTTACTAAGAAAGGGGATCATGGACATTGAAGCATATCTTGAAAGAATTGGCTATAAGA<br>AGTCTAGGAACAAATTGGACTTGGAAACATTAACTGATATTCTTCAACACCAGATCCGAGCTGTTCCCTT<br>TGAGAACCTTAACATCCATTGTGGGGATGCCATGGACTTAGGCTTAGAGGCCATTTTTGATCAAGTTGTG<br>AGAAGAAATCGGGGTGGATGGTGTCTCCAGGTCAATCATCTTCTGTACTGGGCTCTGACCACTATTGGTT<br>TTGAGACCACGATGTTGGGAGGGTATGTTTACAGCACTCCAGCCAAAAAATACAGCACTGGCATGATTCA<br>CCTTCTCCTGCAGGTGACCATTGATGGCAGGAACTACATTGTCGATGCTGGGTTTGGACGCTCATACCAG<br>ATGTGGCAGCCTCTGGAGTTAATTTCTGGGAAGGATCAGCCTCAGGTGCCTTGTGTCTTCCGTTTGACGG<br>AAGAGAATGGATTCTGGTATCTAGACCAAATCAGAAGGGAACAGTACATTCCAAATGAAGAATTTCTTCA<br>TTCTGATCTCCTAGAAGACAGCAAATACCGAAAAATCTACTCCTTTACTCTTAAGCCTCGAACAATTGAA<br>GATTTTGAGTCTATGAATACATACCTGCAGACATCTCCATCATCTGTGTTTACTAGTAAATCATTTTGTT<br>CCTTGCAGACCCCAGATGGGGTTCACTGTTTGGTGGGCTTCACCCTCACCCATAGGAGATTCAATTATAA<br>GGACAATACAGATCTAATAGAGTTCAAGACTCTGAGTGAGGAAGAAATAGAAAAAGTGCTGAAAAATATA<br>TTTAATATTTCCTTGCAGAGAAAGCTTGTGCCCAAACATGGTGATAGATTTTTTACTATTTAGAATAAGG<br>AGTAAAACAATCTTGTCTATTTGTCATCCAGCTCACCAGTTATCAACTGACGACCTATCATGTATCTTCT<br>GTACCCTTACCTTATTTTGAAGAAAATCCTAGACATCAAATCATTTCACCTATAAAAATGTCATCATATA<br>TAATTAAACAGCTTTTTAAAGAAACATAACCACAAACCTTTTCAAATAATAATAATAATAATAATAATAA<br>ATGTCTTTTAAAGATGGCCTGTGGTTATCTTGGAAATTGGTGATTTATGCTAGAAAGCTTTTAATGTTGG<br>TTTATTGTTGAATTCCTAGAAAAGTTTTATGGGTAGATGAGTAAATAAAATATTGTAAAAAAACTTATTG<br>TCTATAAAGTATATTAAAACATTGTTGGCTAATATAAAAAAAAAAAAAA | 142 |
| NM_014321 | GCGCGCGGGTTTCGTTGACCCGCGGCGTTCACGGGAATTGTTCGCTTTAGTGCCGGCGCCATGGGGTCGG<br>AGCTGATCGGGCGCCTAGCCCCGCGCCTGGGCCTCGCCGAGCCCGACATGCTGAGGAAAGCAGAGGAGTA<br>CTTGCGCCTGTCCCGGGTGAAGTGTGTCGGCCTCTCCGCACGCACCACGGAGACCAGCAGTGCAGTCATG<br>TGCCTGGACCTTGCAGCTTCCTGGATGAAGTGCCCCTTGGACAGGGCTTATTTAATTAAACTTTCTGGTT<br>TGAACAAGGAGACATATCAGAGCTGTCTTAAATCTTTTGAGTGTTTACTGGGCCTGAATTCAAATATTGG<br>AATAAGAGACCTAGCTGTACAGTTTAGCTGTATAGAAGCAGTGAACATGGCTTCAAAGATACTAAAAAGC<br>TATGAGTCCAGTCTTCCCCAGACACAGCAAGTGGATCTTGACTTATCCAGGCCACTTTTCACTTCTGCTG<br>CACTGCTTTCAGCATGCAAGATTCTAAAGCTGAAAGTGGATAAAAACAAAATGGTAGCCACATCCGGTGT<br>AAAAAAAGCTATATTTGATCGACTGTGTAAACAACTAGAGAAGATTGGACAGCAGGTCGACAGAGAACCT<br>GGAGATGTAGCTACTCCACCACGGAAGAGAAAGAAGATAGTGGTTGAAGCCCCAGCAAAGGAAATGGAGA<br>AGGTAGAGGAGATGCCACATAAACCACAGAAAGATGAAGATCTGACACAGGATTATGAAGAATGGAAAAG<br>AAAAATTTTGGAAAATGCTGCCAGTGCTCAAAAGGCTACAGCAGAGTGATTTCAGCTTCCAAACTGGTAT<br>ACATTCCAAACTGATAGTACATTGCCATCTCCAGGAAGACTTGACGGCTTTGGGATTTTGTTTAAACTTT<br>TATAATAAGGATCCTAAGACTGTTGCCTTTAAATAGCAAAGCAGCCTACCTGGAGGCTAAGTCTGGGCAG<br>TGGGCTGGCCCCTGGTGTGAGCATTAGACCAGCCACAGTGCCTGATTGGTATAGCCTTATGTGCTTTCCT<br>ACAAAATGGAATTGGAGGCCGGGCGCAGTGGCTCACGCCTGTAATCCCAGCACTTTGGGAGGCCAAGGTG<br>GGTGGATCACCTGAGGTCAGGAGCTCGAGACCAGCCTGGCCAACATGGTGAAACCCCATCTCTACTAAAA<br>ATACAAAAATTAGCCAGGTGTGATGGTGCATGCCTGTAATCCCAGCTCCTCAGTAGGCTGAGACAGGAGC<br>ATCACTTGAACGTGGGAGGCAGAGGTTGCAGTGAGCCGAGATTGCACCACCGCACTCCAGCCTGGGTGAC<br>AGAGCGAGACTTATCTCATAAATAAATAGATAGATACTCCAGCCTGGGTGACAGAGCGAGACTTATAGAT<br>AGATAGATAGATAGATGGATAGATAGATAGATAGATAGATAGATAGATAAACGGAATTGGAGCCATTTTG<br>CTTTAAGTGAATGGCAGTCCCTTGTCTTATTCAGAATATAAAATTCAGTCTGAATGGCATCTTACAGATT<br>TTACTTCAATTTTTGTGTACGGTATTTTTTATTTGACTAAATCAATATATTGTACAGCCTAAGTTAATAA<br>ATGTTATTTATATATGCAAAAAAAAAAAAAAAAA | 143 |
| NM_000926 | AGTCCACAGCTGTCACTAATCGGGGTAAGCCTTGTTGTATTTGTGCGTGTGGGTGGCATTCTCAATGAGA<br>ACTAGCTTCACTTGTCATTTGAGTGAAATCTACAACCCGAGGCGGCTAGTGCTCCCGCACTACTGGGATC<br>TGAGATCTTCGGAGATGACTGTCGCCCGCAGTACGGAGCCAGCAGAAGTCCGACCCTTCCTGGGAATGGG<br>CTGTACCGAGAGGTCCGACTAGCCCCAGGGTTTTAGTGAGGGGGCAGTGGAACTCAGCGAGGGACTGAGA<br>GCTTCACAGCATGCACGAGTTTGATGCCAGAGAAAAAGTCGGGAGATAAAGGAGCCGCGTGTCACTAAAT<br>TGCCGTCGCAGCCGCAGCCACTCAAGTGCCGGACTTGTGAGTACTCTGCGTCTCCAGTCCTCGGACAGAA<br>GTTGGAGAACTCTCTTGGAGAACTCCCCGAGTTAGGAGACGAGATCTCCTAACAATTACTACTTTTTCTT<br>GCGCTCCCCACTTGCCGCTCGCTGGGACAAACGACAGCCACAGTTCCCCTGACGACAGGATGGAGGCCAA<br>GGGCAGGAGCTGACCAGCGCCGCCCTCCCCCGCCCCCGACCCAGGAGGTGGAGATCCCTCCGGTCCAGCC<br>ACATTCAACACCCACTTTCTCCTCCCTCTGCCCCTATATTCCCGAAACCCCCTCCTCCTTCCCTTTTCCC<br>TCCTCCTGGAGACGGGGGAGGAGAAAAGGGGAGTCCAGTCGTCATGACTGAGCTGAAGGCAAAGGGTCCC<br>CGGGCTCCCCACGTGGCGGGCGGCCCGCCCTCCCCCGAGGTCGGATCCCCACTGCTGTGTCGCCCAGCCG<br>CAGGTCCGTTCCCGGGGAGCCAGACCTCGGACACCTTGCCTGAAGTTTCGGCCATACCTATCTCCCTGGA<br>CGGGCTACTCTTCCCTCGGCCCTGCCAGGGACAGGACCCCTCCGACGAAAAGACGCAGGACCAGCAGTCG<br>CTGTCGGACGTGGAGGGCGCATATTCCAGAGCTGAAGCTACAAGGGGTGCTGGAGGCAGCAGTTCTAGTC<br>CCCCAGAAAAGGACAGCGGACTGCTGGACAGTGTCTTGGACACTCTGTTGGCGCCCTCAGGTCCCGGGCA<br>GAGCCAACCCAGCCCTCCCGCCTGCGAGGTCACCAGCTCTTGGTGCCTGTTTGGCCCCGAACTTCCCGAA<br>GATCCACCGGCTGCCCCCGCCACCCAGCGGGTGTTGTCCCCGCTCATGAGCCGGTCCGGGTGCAAGGTTG<br>GAGACAGCTCCGGGACGGCAGCTGCCCATAAAGTGCTGCCCCGGGGCCTGTCACCAGCCCGGCAGCTGCT<br>GCTCCCGGCCTCTGAGAGCCCTCACTGGTCCGGGGCCCCAGTGAAGCCGTCTCCGCAGGCCGCTGCGGTG<br>GAGGTTGAGGAGGAGGATGGCTCTGAGTCCGAGGAGTCTGCGGGTCCGCTTCTGAAGGGCAAACCTCGGG<br>CTCTGGGTGGCGCGGCGGCTGGAGGAGGAGCCGCGGCTGTCCCGCCGGGGGCGGCAGCAGGAGGCGTCGC<br>CCTGGTCCCCAAGGAAGATTCCCGCTTCTCAGCGCCCAGGGTCGCCCTGGTGGAGCAGGACGCGCCGATG<br>GCGCCCGGGCGCTCCCCGCTGGCCACCACGGTGATGGATTTCATCCACGTGCCTATCCTGCCTCTCAATC | 144 |

TABLE 2-continued

| GENBANK ACCESSION NUMBER | SEQUENCE | SEQ ID NO: |
|---|---|---|
| | ACGCCTTATTGGCAGCCCGCACTCGGCAGCTGCTGGAAGACGAAAGTTACGACGGCGGGGCCGGGGCTGC | |
| | CAGCGCCTTTGCCCCGCCGCGGAGTTCACCCTGTGCCTCGTCCACCCCGGTCGCTGTAGGCGACTTCCCC | |
| | GACTGCGCGTACCCGCCCGACGCCGAGCCCAAGGACGACGCGTACCCTCTCTATAGCGACTTCCAGCCGC | |
| | CCGCTCTAAAGATAAAGGAGGAGGAGGAAGGCGCGGAGGCCTCCGCGCGCTCCCCGCGTTCCTACCTTGT | |
| | GGCCGGTGCCAACCCCGCAGCCTTCCCGGATTTCCCGTTGGGGCCACCGCCCCCGCTGCCGCCGCGAGCG | |
| | ACCCCATCCAGACCCGGGGAAGCGGCGGTGACGGCCGCACCCGCCAGTGCCTCAGTCTCGTCTGCGTCCT | |
| | CCTCGGGGTCGACCCTGGAGTGCATCCTGTACAAAGCGGAGGGCGCGCCGCCCCAGCAGGGCCCGTTCGC | |
| | GCCGCCGCCCTGCAAGGCGCCGGGCGCGAGCGGCTGCCTGCTCCCGCGGGACGGCCTGCCCTCCACCTCC | |
| | GCCTCTGCCGCCGCCGCCGGGGCGGCCCCCGCGCTCTACCCTGCACTCGGCCTCAACGGGCTCCCGCAGC | |
| | TCGGCTACCAGGCCGCCGTGCTCAAGGAGGGCCTGCCGCAGGTCTACCCGCCCTATCTCAACTACCTGAG | |
| | GCCGGATTCAGAAGCCAGCCAGAGCCCACAATACAGCTTCGAGTCATTACCTCAGAAGATTTGTTTAATC | |
| | TGTGGGGATGAAGCATCAGGCTGTCATTATGGTGTCCTTACCTGTGGGAGCTGTAAGGTCTTCTTTAAGA | |
| | GGGCAATGGAAGGGCAGCACAACTACTTATGTGCTGGAAGAAATGACTGCATCGTTGATAAAATCCGCAG | |
| | AAAAAACTGCCCAGCATGTCGCCTTAGAAAGTGCTGTCAGGCTGGCATGGTCCTTGGAGGTCGAAAATTT | |
| | AAAAAGTTCAATAAAGTCAGAGTTGTGAGAGCACTGGATGCTGTTGCTCTCCCACAGCCAGTGGGCGTTC | |
| | CAAATGAAAGCCAAGCCCTAAGCCAGAGATTCACTTTTTCACCAGGTCAAGACATACAGTTGATTCCACC | |
| | ACTGATCAACCTGTTAATGAGCATTGAACCAGATGTGATCTATGCAGGACATGACAACACAAAACCTGAC | |
| | ACCTCCAGTTCTTTGCTGACAAGTCTTAATCAACTAGGCGAGAGGCAACTTCTTTCAGTAGTCAAGTGGT | |
| | CTAAATCATTGCCAGGTTTTCGAAACTTACATATTGATGACCAGATAACTCTCATTCAGTATTCTTGGAT | |
| | GAGCTTAATGGTGTTTGGTCTAGGATGGAGATCCTACAAACACGTCAGTGGGCAGATGCTGTATTTTGCA | |
| | CCTGATCTAATACTAAATGAACAGCGGATGAAAGAATCATCATTCTATTCATTATGCCTTACCATGTGGC | |
| | AGATCCCACAGGAGTTTGTCAAGCTTCAAGTTAGCCAAGAAGAGTTCCTCTGTATGAAAGTATTGTTACT | |
| | TCTTAATACAATTCCTTTGGAAGGGCTACGAAGTCAAACCCAGTTTGAGGAGATGAGGTCAAGCTACATT | |
| | AGAGAGCTCATCAAGGCAATTGGTTTGAGGCAAAAAGGAGTTGTGTCGAGCTCACAGCGTTTCTATCAAC | |
| | TTACAAAACTTCTTGATAACTTGCATGATCTTGTCAAACAACTTCATCTGTACTGCTTGAATACATTTAT | |
| | CCAGTCCCGGGCACTGAGTGTTGAATTTCCAGAAATGATGTCTGAAGTTATTGCTGCACAATTACCCAAG | |
| | ATATTGGCAGGGATGGTGAAACCCCTTCTCTTTCATAAAAAGTGAATGTCATCTTTTTCTTTTAAAGAAT | |
| | TAAATTTTGTGGTATGTCTTTTTGTTTTGGTCAGGATTATGAGGTCTTGAGTTTTTATAATGTTCTTCTG | |
| | AAAGCCTTACATTTATAACATCATAGTGTGTAAATTTAAAAGAAAAATTGTGAGGTTCTAATTATTTTCT | |
| | TTTATAAAGTATAATTAGAATGTTTAACTGTTTTGTTTACCCATATTTTCTTGAAGAATTTACAAGATTG | |
| | AAAAAGTACTAAAATTGTTAAAGTAAACTATCTTATCCATATTATTTCATACCATGTAGGTGAGGATTTT | |
| | TAACTTTTGCATCTAACAAATCATCGACTTAAGAGAAAAAATCTTACATGTAATAACACAAAGCTATTAT | |
| | ATGTTATTTCTAGGTAACTCCCTTTGTGTCAATTATATTTCCAAAAATGAACCTTTAAAATGGTATGCAA | |
| | AATTTTGTCTATATATATTTGTGTGAGGAGGAAATTCATAACTTTCCTCAGATTTTCAAAAGTATTTTTA | |
| | ATGCAAAAAATGTAGAAAGAGTTTAAAACCACTAAAATAGATTGATGTTCTTCAAACTAGGCAAAACAAC | |
| | TCATATGTTAAGACCATTTTCCAGATTGGAAACACAAATCTCTTAGGAAGTTAATAAGTAGATTCATATC | |
| | ATTATGCAAATAGTATTGTGGGTTTTGTAGGTTTTAAAATAACCTTTTTTGGGGAGAGAATTGTCCTCT | |
| | AATGAGGTATTGCGAGTGGACATAAGAAATCAGAAGATTATGGCCTAACTGTACTCCTTACCAACTGTGG | |
| | CATGCTGAAAGTTAGTCACTCTTACTGATTCTCAATTCTCTCACCTTTGAAAGTAGTAAAATATCTTTCC | |
| | TGCCAATTGCTCCTTTGGGTCAGAGCTTATTAACATCTTTTCAAATCAAAGGAAAGAAGAAAGGGAGAGG | |
| | AGGAGGAGGGAGGTATCAATTCACATACCTTTCTCCTCTTTATCCTCCACTATCATGAATTCATATTATG | |
| | TTTCAGCCATGCAAATCTTTTTACCATGAAATTTCTTCCAGAATTTTCCCCCTTTGACACAAATTCCATG | |
| | CATGTTTCAACCTTCGAGACTCAGCCAAATGTCATTTCTGTAAAATCTTCCCTGAGTCTTCCAAGCAGTA | |
| | ATTTGCCTTCTCCTAGAGTTTACCTGCCATTTTGTGCACATTTGAGTTACAGTAGCATGTTATTTTACAA | |
| | TTGTGACTCTCCTGGGAGTCTGGGAGCCATATAAAGTGGTCAATAGTGTTTGCTGACTGAGAGTTGAATG | |
| | ACATTTTCTCTCTGTCTTGGTATTACTGTAGATTTCGATCATTCTTTGGTTACATTTCTGCATATTTCTG | |
| | TACCCATGACTTTATCACTTTCTTCTCCCATGCTTTATCTCCATCAATTATCTTCATTACTTTTAAATTT | |
| | TCCACCTTTGCTTCCTACTTTGTGAGATCTCTCCCTTTACTGACTATAACATAGAAGAATAGAAGTGTAT | |
| | TTTATGTGTCTTAAGGACAATACTTTAGATTCCTTGTTCTAAGTTTTTAAACTGAATGAATGGAATATTA | |
| | TTTCTCTCCCTAAGCAAAATTCCACAAAACAATTATTTCTTATGTTTATGTAGCCTTAAATTGTTTTGTA | |
| | CTGTAAACCTCAGCATAAAAACTTTCTTCATTTCTAATTTCATTCAACAAATATTGATTGAATACCTGGT | |
| | ATTAGCACAAGAAAAATGTGCTAATAAGCCTTATGAGAATTTGGAGCTGAAGAAAGACATATAACTCAGG | |
| | AAAGTTACAGTCCAGTAGTAGGTATAAATTACAGTGCCTGATAAATAGGCATTTTAATATTTGTACACTC | |
| | AACGTATACTAGGTAGGTGCAAAACATTTACATATAATTTTACTGATACCCATGCAGCACAAAGGTACTA | |
| | ACTTTAAATATTAAATAACACCTTTATGTGTCAGTAATTCATTTGCATTAAATCTTATTGAAAAGGCTTT | |
| | CAATATATTTTCCCCACAAATGTCATCCCAAGAAAAAAGTATTTTTAACATCTCCCAAATATAATAGTTA | |
| | CAGGAAATCTACCTCTGTGAGAGTGACACCTCTCAGAATGAACTGTGTGACACAAGAAAATGAATGTAGG | |
| | TCTATCCAAAAAAAACCCCAAGAAACAAAAACAATATTATTAGCCCTTTATGCTTAAGTGATGGACTCAG | |
| | GGAACAGTTGATGTTGTGATCATTTTATTATCTGATTCTTGTTACTTTGAATTAAACCAATATTTTGATG | |
| | ATATAAATCATTTCCACCAGCATATATTTAATTTCCATAATAACTTTAAAATTTTCTAATTTCACTCAAC | |
| | TATGAGGGAATAGAATGTGGTGGCCACAGGTTTGGCTTTTGTTAAAATGTTTGATATCTTCGATGTTGAT | |
| | CTCTGTCTGCAATGTAGATGTCTAAACACTAGGATTTAATATTTAAGGCTAAGCTTTAAAAATAAAGTAC | |
| | CTTTTTAAAAAGAATATGGCTTCACCAAATGGAAAATACCTAATTTCTAAATCTTTTTCTCTACAAAGTC | |
| | CTATCTACTAATGTCTCCATTACTATTTAGTCATCATAACCATTATCTTCATTTTACATGTCGTGTTCTT | |
| | TCTGGTAGCTCTAAAATGACACTAAATCATAAGAAGACAGGTTACATATCAGGAAATACTTGAAGGTTAC | |
| | TGAAATAGATTCTTGAGTTAATGAAAATATTTTCTGTAAAAAGGTTTGAAAAGCCATTTGAGTCTAAAGC | |
| | ATTATACCTCCATTATCAGTAGTTATGTGACAATTGTGTGTGTGTTTAATGTTTAAAGATGTGGCACTTT | |
| | TTAATAAGGCAATGCTATGCTATTTTTTCCCATTTAACATTAAGATAATTTATTGCTATACAGATGATAT | |
| | GGAAATATGATGAACAATATTTTTTTTGCCAAAACTATGCCTTGTAAGTAGCCATGGAATGTCAACCTGT | |
| | AACTTAAATTATCCACAGATAGTCATGTGTTTGATGATGGGCACTGTGGAGATAACTGACATAGGACTGT | |
| | GCCCCCCTTCTCTGCCACTTACTAGCTGGATGAGATTAAGCAAGTCATTTAACTGCTCTGATTAAACCTG | |
| | CCTTTCCCAAGTGCTTTGTAATGAATAGAAATGGAAACCAAAAAAAACGTATACAGGCCTTCAGAAATAG | |
| | TAATTGCTACTATTTTGTTTTCATTAAGCCATAGTTCTGGCTATAATTTTATCAAACTCACCAGCTATAT | |
| | TCTACAGTGAAAGCAGGATTCTAGAAAGTCTCACTGTTTTATTTATGTCACCATGTGCTATGATATATTT | |
| | GGTTGAATTCATTTGAAATTAGGGCTGGAAGTATTCAAGTAATTTCTTCTGCTGAAAAAATACAGTGTTT | |
| | TGAGTTTAGGGCCTGTTTTATCAAAGTTCTAAAGAGCCTATCACTCTTCCATTGTAGACATTTTAAAATA | |

TABLE 2-continued

| GENBANK ACCESSION NUMBER | SEQUENCE | SEQ ID NO: |
|---|---|---|
| | ATGACACTGATTTTAACATTTTTAAGTGTCTTTTTAGAACAGAGAGCCTGACTAGAACACAGCCCCTCCA | |
| | AAAACCCATGCTCAAATTATTTTTACTATGGCAGCAATTCCACAAAAGGGAACAATGGGTTTAGAAATTA | |
| | CAATGAAGTCATCAACCCAAAAAACATCCCTATCCCTAAGAAGGTTATGATATAAAATGCCCACAAGAAA | |
| | TCTATGTCTGCTTTAATCTGTCTTTTATTGCTTTGGAAGGATGGCTATTACATTTTTAGTTTTTGCTGTG | |
| | AATACCTGAGCAGTTTCTCTCATCCATACTTATCCTTCACACATCAGAAGTCAGGATAGAATATGAATCA | |
| | TTTTAAAAACTTTTACAACTCCAGAGCCATGTGCATAAGAAGCATTCAAAACTTGCCAAAACATACATTT | |
| | TTTTTCAAATTTAAAGATACTCTATTTTTGTATTCAATAGCTCAACAACTGTGGTCCCCACTGATAAAGT | |
| | GAAGTGGACAAGGAGACAAGTAATGGCATAAGTTTGTTTTTCCCAAAGTATGCCTGTTCAATAGCCATTG | |
| | GATGTGGGAAATTTCTACATCTCTTAAAATTTTACAGAAAATACATAGCCAGATAGTCTAGCAAAAGTTC | |
| | ACCAAGTCCTAAATTGCTTATCCTTACTTCACTAAGTCATGAAATCATTTTAATGAAAAGAACATCACCT | |
| | AGGTTTTGTGGTTTCTTTTTTTCTTATTCATGGCTGAGTGAAAACAACAATCTCTGTTTCTCCCTAGCAT | |
| | CTGTGGACTATTTAATGTACCATTATTCCACACTCTATGGTCCTTACTAAATACAAAATTGAACAAAAAG | |
| | CAGTAAAACAACTGACTCTTCACCCATATTATAAAATATAATCCAAGCCAGATTAGTCAACATCCATAAG | |
| | ATGAATCCAAGCTGAACTGGGCCTAGATTATTGAGTTCAGGTTGGATCACATCCCTATTTATTAATAAAC | |
| | TTAGGAAAGAAGGCCTTACAGACCATCAGTTAGCTGGAGCTAATAGAACCTACACTTCTAAAGTTCGGCC | |
| | TAGAATCAATGTGGCCTTAAAAGCTGAAAAGAAGCAGGAAAGAACAGTTTTCTTCAATAATTTGTCCACC | |
| | CTGTCACTGGAGAAAATTTAAGAATTTGGGGGTGTTGGTAGTAAGTTAAACACAGCAGCTGTTCATGGCA | |
| | GAAATTATTCAATACATACCTTCTCTGAATATCCTATAACCAAAGCAAAGAAAAACACCAAGGGGTTTGT | |
| | TCTCCTCCTTGGAGTTGACCTCATTCCAAGGCAGAGCTCAGGTCACAGGCACAGGGGCTGCGCCCAAGCT | |
| | TGTCCGCAGCCTTATGCAGCTGTGGAGTCTGGAAGACTGTTGCAGGACTGCTGGCCTAGTCCCAGAATGT | |
| | CAGCCTCATTTTCGATTTACTGGCTCTTGTTGCTGTATGTCATGCTGACCTTATTGTTAAACACAGGTTT | |
| | GTTTGCTTTTTTTCCACTCATGGAGACATGGGAGAGGCATTATTTTTAAGCTGGTTGAAAGCTTTAACCG | |
| | ATAAAGCATTTTTAGAGAAATGTGAATCAGGCAGCTAAGAAAGCATACTCTGTCCATTACGGTAAAGAAA | |
| | ATGCACAGATTATTAACTCTGCAGTGTGGCATTAGTGTCCTGGTCAATATTCGGATAGATATGAATAAAA | |
| | TATTTAAATGGTATTGTAAATAGTTTTCAGGACATATGCTATAGCTTATTTTTATTATCTTTTGAAATTG | |
| | CTCTTAATACATCAAATCCTGATGTATTCAATTTATCAGATATAAATTATTCTAAATGAAGCCCAGTTAA | |
| | ATGTTTTTGTCTTGTCAGTTATATGTTAAGTTTCTGATCTCTTTGTCTATGACGTTTACTAATCTGCATT | |
| | TTTACTGTTATGAATTATTTTAGACAGCAGTGGTTTCAAGCTTTTTGCCACTAAAAATACCTTTTATTTT | |
| | CTCCTCCCCCAGAAAAGTCTATACCTTGAAGTATCTATCCACCAAACTGTACTTCTATTAAGAAATAGTT | |
| | ATTGTGTTTTCTTAATGTTTTGTTATTCAAAGACATATCAATGAAAGCTGCTGAGCAGCATGAATAACAA | |
| | TTATATCCACACAGATTTGATATATTTTGTGCAGCCTTAACTTGATAGTATAAAATGTCATTGCTTTTTA | |
| | AATAATAGTTAGTCAATGGACTTCTATCATAGCTTTCCTAAACTAGGTTAAGATCCAGAGCTTTGGGGTC | |
| | ATAATATATTACATACAATTAAGTTATCTTTTTCTAAGGGCTTTAAAATTCATGAGAATAACCAAAAAAG | |
| | GTATGTGGAGAGTTAATACAAACATACCATATTCTTGTTGAAACAGAGATGTGGCTCTGCTTGTTCTCCA | |
| | TAAGGTAGAAATACTTTCCAGAATTTGCCTAAACTAGTAAGCCCTGAATTTGCTATGATTAGGGATAGGA | |
| | AGAGATTTTCACATGGCAGACTTTAGAATTCTTCACTTTAGCCAGTAAAGTATCTCCTTTTGATCTTAGT | |
| | ATTCTGTGTATTTTAACTTTTCTGAGTTGTGCATGTTTATAAGAAAAATCAGCACAAAGGGTTTAAGTTA | |
| | AAGCCTTTTTACTGAAATTTGAAAGAAACAGAAGAAAATATCAAAGTTCTTTGTATTTTGAGAGGATTAA | |
| | ATATGATTTACAAAAGTTACATGGAGGGCTCTCTAAAACATTAAATTAATTATTTTTTGTTGAAAAGTCT | |
| | TACTTTAGGCATCATTTTATTCCTCAGCAACTAGCTGTGAAGCCTTTACTGTGCTGTATGCCAGTCACTC | |
| | TGCTAGATTGTGGAGATTACCAGTGTTCCCGTCTTCTCCGAGCTTAGAGTTGGATGGGGAATAAAGACAG | |
| | GTAAACAGATAGCTACAATATTGTACTGTGAATGCTTATGCTGGAGGAAGTACAGGGAACTATTGGAGCA | |
| | CCTAAGAGGAGCACCTACCTTGAATTTAGGGGTTAGCAGAGGCATCCTGAAAAAAGTCAAAGCTAAGCCA | |
| | CAATCTATAAGCAGTTTAGGAATTAGCAGAACGTGCGTGGTGAGGAGATGCCAAAGGCAAGAAGAGAAGA | |
| | GTATTCCAAACAGGAGGGATTCCAAAGAGAGAAGAGTATCCCAAACAACATTTGCACAAACCTGATGGGG | |
| | AGAGAGAATGTGGGGTGGGGATGGATGATGAGACTGAAGAAGAAAGCCAGGTCTAGATAATCAGTGGCCT | |
| | TGTACACCATGTTAAAGAGTGTAGACTTGATTCTGTTGTAAACAGGAAAGCAGCACAATTCATATGAATA | |
| | TTTTAGAAGACTCCCACTGGAATATGGAGAATAAAGTTGGAGATGACTAATCCTGGAAGCAGGGAGAACA | |
| | TTTTTGAGGAAGTTGCACTATTTTGGTGAAAATGATGATCATAAACATGAAGAATTGTAGGTGATCATGA | |
| | CCTCCTCTCTAATTTTCCAGAAGGGTTTTGGAAGATATAACATAGGAACATTGACAGGACTGACGAAAGG | |
| | AGATGAAATACACCATATAAATTGTCAAACACAAGGCCAGATGTCTAATTATTTTGCTTATGTGTTGAAA | |
| | TTACAAATTTTTCATCAGGAAACCAAAAACTACAAAACTTAGTTTTCCCAAGTCCCAGAATTCTATCTGT | |
| | CCAAACAATCTGTACCACTCCACCTATATCCCTACCTTTGCATGTCTGTCCAACCTCAAAGTCCAGGTCT | |
| | ATACACACGGGTAAGACTAGAGCAGTTCAAGTTTCAGAAAATGAGAAAGAGGAACTGAGTTGTGCTGAAC | |
| | CCATACAAAATAAACACATTCTTTGTATAGATTCTTGGAACCTCGAGAGGAATTCACCTAACTCATAGGT | |
| | ATTTGATGGTATGAATCCATGGCTGGGCTCGGCTTTTAAAAAGCCTTATCTGGGATTCCTTCTATGGAAC | |
| | CAAGTTCCATCAAAGCCCATTTAAAAGCCTACATTAAAAACAAAATTCTTGCTGCATTGTATACAAATAA | |
| | TGATGTCATGATCAAATAATCAGATGCCATTATCAAGTGGAATTACAAAATGGTATACCCACTCCAAAAA | |
| | AAAAAAAAAAGCTAAATTCTCAGTAGAACATTGTGACTTCATGAGCCCTCCACAGCCTTGGAGCTGAGGA | |
| | GGGAGCACTGGTGAGCAGTAGGTTGAAGAGAAAACTTGGCGCTTAATAATCTATCCATGTTTTTTCATCT | |
| | AAAAGAGCCTTCTTTTTGGATTACCTTATTCAATTTCCATCAAGGAAATTGTTAGTTCCACTAACCAGAC | |
| | AGCAGCTGGGAAGGCAGAAGCTTACTGTATGTACATGGTAGCTGTGGGAAGGAGGTTTCTTTCTCCAGGT | |
| | CCTCACTGGCCATACACCAGTCCCTTGTTAGTTATGCCTGGTCATAGACCCCCGTTGCTATCATCTCATA | |
| | TTTAAGTCTTTGGCTTGTGAATTTATCTATTCTTTCAGCTTCAGCACTGCAGAGTGCTGGGACTTTGCTA | |
| | ACTTCCATTTCTTGCTGGCTTAGCACATTCCTCATAGGCCCAGCTCTTTTCTCATCTGGCCCTGCTGTGG | |
| | AGTCACCTTGCCCCTTCAGGAGAGCCATGGCTTACCACTGCCTGCTAAGCCTCCACTCAGCTGCCACCAC | |
| | ACTAAATCCAAGCTTCTCTAAGATGTTGCAGACTTTACAGGCAAGCATAAAAGGCTTGATCTTCCTGGAC | |
| | TTCCCTTTACTTGTCTGAATCTCACCTCCTTCAACTTTCAGTCTCAGAATGTAGGCATTTGTCCTCTTTG | |
| | CCCTACATCTTCCTTCTTCTGAATCATGAAAGCCTCTCACTTCCTCTTGCTATGTGCTGGAGGCTTCTGT | |
| | CAGGTTTTAGAATGAGTTCTCATCTAGTCCTAGTAGCTTTTGATGCTTAAGTCCACCTTTTAAGGATACC | |
| | TTTGAGATTTAGACCATGTTTTTCGCTTGAGAAAGCCCTAATCTCCAGACTTGCCTTTCTGTGGATTTCA | |
| | AAGACCAACTGAGGAAGTCAAAAGCTGAATGTTGACTTTCTTTGAACATTTCCGCTATAACAATTCCAAT | |
| | TCTCCTCAGAGCAATATGCCTGCCTCCAACTGACCAGGAGAAAGGTCCAGTGCCAAAGAGAAAAACACAA | |
| | AGATTAATTATTTCAGTTGAGCACATACTTTCAAAGTGGTTTGGGTATTCATATGAGGTTTTCTGTCAAG | |
| | AGGGTGAGACTCTTCATCTATCCATGTGTGCCTGACAGTTCTCCTGGCACTGGCTGGTAACAGATGCAAA | |
| | ACTGTAAAAATTAAGTGATCATGTATTTTAACGATATCATCACATACTTATTTTCTATGTAATGTTTTAA | |

TABLE 2-continued

| GENBANK ACCESSION NUMBER | SEQUENCE | SEQ ID NO: |
|---|---|---|
| | ATTTCCCCTAACATACTTTGACTGTTTTGCACATGGTAGATATTCACATTTTTTTGTGTTGAAGTTGATG<br>CAATCTTCAAAGTTATCTACCCCGTTGCTTATTAGTAAAACTAGTGTTAATACTTGGCAAGAGATGCAGG<br>GAATCTTTCTCATGACTCACGCCCTATTTAGTTATTAATGCTACTACCCTATTTTGAGTAAGTAGTAGGT<br>CCCTAAGTACATTGTCCAGAGTTATACTTTTAAAGATATTTAGCCCCATATACTTCTTGAATCTAAAGTC<br>ATACACCTTGCTCCTCATTTCTGAGTGGGAAAGACATTTGAGAGTATGTTGACAATTGTTCTGAAGGTTT<br>TTGCCAAGAAGGTGAAACTGTCCTTTCATCTGTGTATGCCTGGGGCTGGGTCCCTGGCAGTGATGGGGTG<br>ACAATGCAAAGCTGTAAAAACTAGGTGCTAGTGGGCACCTAATATCATCATCATATACTTATTTTCAAGC<br>TAATATGCAAAATCCCATCTCTGTTTTTAAACTAAGTGTAGATTTCAGAGAAAATATTTTGTGGTTCACA<br>TAAGAAAACAGTCTACTCAGCTTGACAAGTGTTTTATGTTAAATTGGCTGGTGGTTTGAAATGAATCATC<br>TTCACATAATGTTTTCTTTAAAAATATTGTGAATTTAACTCTAATTCTTGTTATTCTGTGTGATAATAAA<br>GAATAAACTAATTTCTA | |
| AK093306 | ATTCTATGCTGCAGCCTAAGCATCATTCCTCTTCTCTTCTTAGTGGAGATAAAATTACCCACTGCTCTCC<br>TTACATTTACTTTGTCCATATTTGCTCCTATGCTCTAGGCTCGTGCACAACAAACACAGTGTGGGCCCTT<br>ACCCTAGAAGCCAACTTCTCATGACCTTTCTCTATCTCCAGAATCCATGCAGTGGGAATGAAGGTAAAAG<br>AAGGTTTTCATGGGATCCAGCTGAGAGCTCTACGGGGAAAATGGATCTGAGGAGCCATGTGCTCCATCTC<br>TTTTATTTTACAGGTAGAGACTAGGGGTATAGAGTGAGGTGAATTACCGCAGTGACCCACACATTGTTGG<br>CAGACCTAGGATTAGAACTCTGTCTTCCTGGTTCCCAGCTTGGTGCTTTTGAAAGCATACTTGCTGCTTT<br>CTTACCGGCCTGGTGTCTGCCACTTTGGGACAGAGTGTGGACTTGCTCACCTGCCCCATTTCTTAGGGAT<br>TCTCATTCTGTGTTTGAGCAAGAATATTCTTATTCTGGAAAGAACCACATACCACAGGATTCTGGGTGAG<br>CATAAGGAAGATTGTCTTGGGGATCTGACTTAGCTCACGTATAGTGGCTATGATGAATTCAGTGTCTTAT<br>TTTTTGCATATGTATATTTTTAGTCTAATATTGCCTGGGTGTCTGAGCAAGTCTAGATGAATTTAATTGC<br>TCTCATTTTTCCCCTGCCCCTCTTCCTTTGGTCTCTCTTTTAGGAAATGTTTTTCTTTCAACATTCGTTT<br>CATTCATTATTTACTCATTCGGCCAACCAACATTTATTGAGTGCCTTCCCTGTATCAGGGACAGGGGCTT<br>ACAAAGTAGAATTTGATCCCACCTCTGCCCTCAGTAGCTCAGTGTCTAATGGAGGTAGTGATGTTCATTA<br>AGCGTCGCCAGATACTGTGCTAGGTGCTGTGCCTGTTCTCTCTCGCTTGTTCCTCACACACTTGAGAAGG<br>CCGAAGCTGATTCATAGCTTGGAAGGCAGGGGCCTTGGATTTGAACCCAGGCCTGACCAATGGCAGAACC<br>TATCAGATGTGTGGACAGATGACATTGCCTTTCTTTCTTTGGATATATCAAAATCAGCCAGCAGGCAGGA<br>ACTCCCATTTTGAGCAAGCAATGTGCAGGAATGATAGGGTATACAGAGAGGAACAGGAGATGGCCCCTGA<br>CTTCCAGCATGTGTCTGATGGACATCCAGGCTGCAGGCATCATGGTGCTGTCTAGAGAGATGAGCCAGGT<br>GCCCAGAGCCCATGGGCCAATGCTGCCCTTTCTTGAGCATGCCAAACAAAGCGGTTGGTGTGTTAGAGGC<br>ACAGTCTCCTCCACTCTAAGTAAAAATCAGCATGAGTCCTAGCCCACATTTCCCTAGTGAGTACACCAAA<br>GATATCTATGAACTGGCAGTCATCAGTGACTTCCTAAGGTTCCGGAAATGCATCTCTTACTCAGGAGTAA<br>GCAATGATGTGCCTGCGGCTTTACGAGTTCTCACAGAATGACTTTCTGGACCCAAATGTTTTTTCTGCTT<br>CAGGACTGTGAAGGCCTTATTGTTCGCTCTGCCACCAAGGTGACCGCTGATGTCATCAACGCAGCTGAGA<br>AACTCCAGGTGGTGGGCAGGGCTGGCACAGGTGTGGACAATGTGGATCTGGAGGCCGCAACAAGGAAGGG<br>CATCTTGGTTATGAACACCCCCAATGGGAACAGCCTCAGTGCCGCAGAACTCACTTGTGGAATGATCATG<br>TGCCTGGCCAGGCAGATTCCCCAGGCGACGGCTTCGATGAAGGACGGCAAATGGGAGCGGAAGAAGTTCA<br>TGGGAACAGAGCTGAATGGAAAGACCCTGGGAATTCTTGGCCTGGGCAGGATTGGGAGAGAGGTAGCTAC<br>CCGGATGCAGTCCTTTGGGATGAAGACTATAGGGTATGACCCCATCATTTCCCCAGAGGTCTCGGCCTCC<br>TTTGGTGTTCAGCAGCTGCCCCTGGAGGAGATCTGGCCTCTCTGTGATTTCATCACTGTGCACACTCCTC<br>TCCTGCCCTCCACGACAGGCTTGCTGAATGACAACACCTTTGCCCAGTGCAAGAAGGGGGTGCGTGTGGT<br>GAACTGTGCCCGTGGAGGGATCGTGGACGAAGGCGCCCTGCTCCGGGCCCTGCAGTCTGGCCAGTGTGCC<br>GGGGCTGCACTGGACGTGTTTACGGAAGAGCCGCCACGGGACCGGGCCTTGGTGGACCATGAGAATGTCA<br>TCAGCTGTCCCCACCTGGGTGCCAGCACCAAGGAGGCTCAGAGCCGCTGTGGGGAGGAAATTGCTGTTCA<br>GTTCGTGGACATGGTGAAGGGGAAATCTCTCACGGGGGTTGTGAATGCCCAGGCCCTTACCAGTGCCTTC<br>TCTCCACACACCAAGCCTTGGATTGGTCTGGCAGAAGCTCTGGGGACACTGATGCGAGCCTGGGCTGGGT<br>CCCCCAAAGGGACCATCCAGGTGATAACACAGGGAACATCCCTGAAGAATGCTGGGAACTGCCTAAGCCC<br>CGCAGTCATTGTCGGCCTCCTGAAAGAGGCTTCCAAGCAGGCGGATGTGAACTTGGTGAACGCTAAGCTG<br>CTGGTGAAAGAGGCTGGCCTCAATGTCACCACCTCCCACAGCCCTGCTGCACCAGGGGGGCAAGGCTTCG<br>GGGAATGCCTCCTGGCCGTGGCCCTGGCAGGCGCCCCTTACCAGGCTGTGGGCTTGGTCCAAGGCACTAC<br>ACCTGTACTGCAGGGGCTCAATGGAGCTGTCTTCAGGCCAGAAGTGCCTCTCCGCAGGGACCTGCCCCTG<br>CTCCTATTCCGGACTCAGACCTCTGACCCTGCAATGCTGCCTACCATGATTGGCCTCCTGGCAGAGGCAG<br>GCGTGCGGCTGCTGTCCTACCAGACTTCACTGGTGTCAGATGGGGAGACCTGGCACGTCATGGGCATCTC<br>CTCCTTGCTGCCCAGCCTGGAAGCGTGGAAGCAGCATGTGACTGAAGCCTTCCAGTTCCACTTCTAACCT<br>TGGAGCTCACTGGTCCCTGCCTCTGGGGCTTTTCTGAAGAAACCCACCCACTGTGATCAATAGGGAGAGA<br>AAATCCACATTCTTGGGCTGAACGCGAGCCTCTGACACTGCTTACACTGCACTCTGACCCTGTAGTACAG<br>CAATAACCGTCTAATAAAGAGCCTACCCCC | 145 |
| BE904476 | CAAACAAAAACAGCCAAGCTTTTCTGCCAAAAAGATGACTGAGAAGACTGTTAAAGCAAAAAGCTCTGTT<br>CCTGCCTCAGATGATGCCTATCCAGAAATAGAAAAATTCTTTCCCTTCAATCCTCTAGACTTTGAGAGTT<br>TTGACCTGCCTGAAGAGCACCAGATTGCGCACCTCCCCTTGAGTGGAGTGCCTCTCATGATCCTTGACGA<br>GGAGAGAGAGCTTGAAAAGCTGTTTCAGCTGGGCCCCCCTTCACCTGTGAAGATGCCCTCTCCACCATGG<br>GAATCCAATCTGTTGCAGTCTCCTTCAAGCATTCTGTCGACCCTGGATGTTGAATTGCCACCTGTTTGCT<br>GTGACATAGATATTTAAATTTCTTAGTGCTTCAGAGTCTGTGTGTATTTGTATTAATAAAGCATTCTTTA<br>ACAGAAAAAAAAAAAAAAAAAAAAAAAAAAAAAAAAAAAAAAAAAAAAAAGGGGGGGAGACACAAAAA<br>GAATTCCCCAAGAGGGGGCCACAAGATAATCAGAGGATATCACACAAGATCTCTCGGCGCACCAACGACG<br>GGGGCCCCAAATAAGGGAGAGACCCAGAATCACAACAGCCAAGACACGGTGGACACGACGGAAACAAACA<br>CACAGCCCAGACACGGGGGCAAACACGCGCGCACACCGCGGACACCATGGGACAAAGCAGACACCACCCA<br>CAAAACAACACCGCGGAGGGGGAAGAACAACAAAACAAGTGCGCAAACAGAACACAACCACAGAAAGAGA<br>AAAATTAAAACGGCCCCCAAGACGGCGACAACACAACAAAACAACCACTACAGAGCGCTCAACAGCCGAG<br>TAAAAACACAACAACGGACAACTAACACACAAAGGAATGAAACAAAGCGGGGCCACACACCGACACCGGA<br>AATCCGGCGAACAACTCACACCGAGCGAGGGTCCCAGACAACAAATACACAGACAACGAAACCGAGAAAC<br>AAGACCAGCAAGACGAGCAGGCAAAAGACAAACAAGACAGAGGAGACGACGACGAACGCAAAGGACAAGA | 146 |

TABLE 2-continued

| GENBANK ACCESSION NUMBER | SEQUENCE | SEQ ID NO: |
|---|---|---|
| | GGACACAACGACGCGAGGAGCGAGAGCGAGAGGAAGAGACAACAAAAAGACACAAAAGAACAACAAGCAA<br>GCAGCGAAGAACGACACACAACCACACGAGACAGCAGGAGCAGAGGCGGAGAAAACACAACGAGCAAGCC<br>AAGACCAAGAGAGGAGAACAAAATAAAAAAATACGAGAGCAGGCGGACGAGAGCACGAGACGAACAGACA<br>AACGGGAATCAGAAGCATAACGATCCGCGACGCGAACAACN | |
| AK123010 | GTGCACCCTGTCCCAGCCGTCCTGTCCTGGCTGCTCGCTCTGCTTCGCTGCGCCTCCACTATGCTCTCCC<br>TCCGTGTCCCGCTCGCGCCCATCACGGACCCGCAGCAGCTGCAGCTCTCGCCGCTGAAGGGGCTCAGCTT<br>GGTCGACAAGGAGAACACGCCGCCGGCCCTGAGCGGGACCCGCGTCCTGGCCAGCAAGACCGCGAGGAGG<br>ATCTTCCAGGAGAAAACCCCCGCCGCTTTGTCATCTTCCCCATCGAGTACCATGATATCTGGCAGATGTA<br>TAAGAAGGCAGAGGCTTCCTTTTGGACCGCCGAGGAGGTGGACCTCTCCAAGGACATTCAGCACTGGGAA<br>TCCCTGAAACCCGAGGAGAGATATTTTATATCCCATGTTCTGGCTTTCTTTGCAGCAAGCGATGGCATAG<br>TAAATGAAAACTTGGTGGAGCGATTTAGCCAAGAAGTTCAGATTACAGAAGCCCGCTGTTTCTATGGCTT<br>CCAAATTGCCATGGAAAACATACATTCTGAAATGTATAGTCTTCTTATTGACACTTACATAAAAGATCCC<br>AAAGAAAGGGAATTTCTCTTCAATGCCATTGAAACGATGCCTTGTGTCAAGAAGAAGGCAGACTGGGCCT<br>TGCGCTGGATTGGGGACAAAGAGGCTACCTATGGTGAACGTGTTGTAGCCTTTGCTGCAGTGGAAGGCAT<br>TTTCTTTTCCGGTTCTTTTGCGTCGATATTCTGGCTCAAGAAACGAGGACTGATGCCTGGCCTCACATTT<br>TCTAATGAACTTATTAGCAGAGATGAGGGTTTACACTGTGATTTTGCTTGCCTGATGTTCAAACACCTGG<br>TACACAAACCATCGGAGGAGAGAGTAAGAGAAATAATTATCAATGCTGTTCGGATAGAACAGGAGTTCCT<br>CACTGAGGCCTTGCCTGTGAAGCTCATTGGGATGAATTGCACTCTAATGAAGCAATACATTGAGTTTGTG<br>GCAGACAGACTTATGCTGGAACTGGGTTTTAGCAAGGTTTTCAGAGTAGAGAACCCATTTGACTTTATGG<br>AGAATATTTCACTGGAAGGAAAGACTAACTTCTTTGAGAAGAGAGTAGGCGAGTATCAGAGGATGGGAGT<br>GATGTCAAGTCCAACAGAGAATTCTTTTACCTTGGATGCTGACTTCTAAATGAACTGAAGATGTGCCCTT<br>ACTTGGCTGATTTTTTTTTTTCCATCTCATAAGAAAAATCAGCTGAAGTGTTACCAACTAGCCACACCAT<br>GAATTGTCCGTAATGTTCATTAACAGCATCTTTAAAACTGTGTAGCTACCTCACAACCAGTCCTGTCTGT<br>TTATAGTGCTGGTAGTATCACCTTTTGCCAGAAGGCCTGGCTGGCTGTGACTTACCATAGCAGTGACAAT<br>GGCAGTCTTGGCTTTAAAGTGAGGGGTGACCCTTTAGTGAGCTTAGCACAGCGGGATTAAACAGTCCTTT<br>AACCAGCACAGCCAGTTAAAAGATGCAGCCTCACTGCTTCAACGCAGATTTTAATGTTTACTTAAATATA<br>AACCTGGCACTTTACAAACAAATAAACATTGTTTGTACTCACAAGGCGATAATAGCTTGATTTATTTGGT<br>TTCTACACCAAATACATTCTCCTGACCACTAATGGGAGCCAATTCACAATTCACTAAGTGACTAAAGTAA<br>GTTAAACTTGTGTAGACTAAGCATGTAATTTTTAAGTTTTATTTTAATGAATTAAAATATTTGTTAACCA<br>ACTTTAAAGTCAGTCCTGTGTATACCTAGATATTAGTCAGTTGGTGCCAGATAGAAGACAGGTTGTGTTT<br>TTATCCTGTGGCTTGTGTAGTGTCCTGGGATTCTCTGCCCCCTCTGAGTAGAGTGTTGTGGGATAAAGGA<br>ATCTCTCAGGGCAAGGAGCTTCTTAAGTTAAATCACTAGAAATTTAGGGGTGATCTGGGCCTTCATATGT<br>GTGAGAAGCCGTTTCATTTTATTTCTCACTGTATTTTCCTCAACGTCTGGTTGATGAGAAAAAATTCTTG<br>AAGAGTTTTCATATGTGGGAGCTAAGGTAGTATTGTAAAATTTCAAGTCATCCTTAAACAAAATGATCCA<br>CCTAAGATCTTGCCCCTGTTAAGTGGTGAAATCAACTAGAGGTGGTTCCTACAAGTTGTTCATTCTAGTT<br>TTGTTTGGTGTAAGTAGGTTGTGTGAGTTAATTCATTTATATTTACTATGTCTGTTAAATCAGAAATTTT<br>TTATTATCTATGTTCTTCTAGATTTTACCTGTAGTTCATACTTCAGTCACCCAGTGTCTTATTCTGGCAT<br>TGTCTAAATCTGAGCATTGTCTAGGGGGATCTTAAACTTTAGTAGGAAACCATGAGCTGTTAATACAGTT<br>TCCATTCAAATATTAATTTCAGAATGAAACATAATTTTTTTTTTTTTTTTTTGAGATGGAGTCTCGCTCT<br>GTTGCCCAGGCTGGAGTGCAGTGGCGCGATTTTGGCTCACTGTAACCTCCATCTCCTGGGTTCAAGCAAT<br>TCTCCTGTCTCAGCCTCCCTAGTAGCTGGGACTGCAGGTATGTGCTACCACACCTGGCTAATTTTTGTAT<br>TTTTAGTAGAGATGGAGTTTCACCATATTGGTCAGGCTGGTCTTGAACTCCTGACCTCAGGTGATCCACC<br>CACCTCGGCCTCCCAAAGTGCTGGGATTGCAGGCGTGATAAACAAATATTCTTAATAGGGCTACTTTGAA<br>TTAATCTGCCTTTATGTTTGGGAGAAGAAAGCTGAGACATTGCATGAAAGATGATGAGAGATAAATGTTG<br>ATCTTTTGGCCCCATTTGTTAATTGTATTCAGTATTTGAACGTCGTCCTGTTTATTGTTAGTTTTCTTCA<br>TCATTTATTGTATAGACAATTTTTAAATCTCTGTAATATGATACATTTTCCTATCTTTTAAGTTATTGTT<br>ACCTAAAGTTAATCCAGATTATATGGTCCTTATATGTGTACAACATTAAAATGAAAGGCTTTGTCTTGCA<br>TTGTGAGGTACAGGCGGAAGTTGGAATCAGGTTTTAGGATTCTGTCTCTCATTAGCTGAATAATGTGAGG<br>ATTAACTTCTGCCAGCTCAGACCATTTCCTAATCAGTTGAAAGGGAAACAAGTATTTCAGTCTCAAAATT<br>GAATAATGCACAAGTCTTAAGTGATTAAAATAAAACTGTTCTTATGTCAGTTT | 147 |
| BC036503 | AGCGGGGGCACTCCAGCCCTGCAGCCTCCGGAGTCAGTGCCGCGCGCCCGCCGCCCCGCGCCTTCCTGCT<br>CGCCGCACCTCCGGGAGCCGGGGCGCACCCAGCCCGCAGCGCCGCCTCCCCGCCCGCGCCGCCTCCGACC<br>GCAGGCCGAGGGCCGCCACTGGCCGGGGGGACCGGGCAGCAGCTTGCGGCCGCGGAGCCGGGCAACGCTG<br>GGGACTGCGCCTTTTGTCCCCGGAGGTCCCTGGAAGTTTGCGGCAGGACGCGCGCGGGGAGGCGGCGGAG<br>GCAGCCCCGACGTCGCGGAGAACAGGGCGCAGAGCCGGCATGGGCATCGGGCGCAGCGAGGGGGGCCGCC<br>GCGGGGCAGCCCTGGGCGTGCTGCTGGCGCTGGGCGCGGCGCTTCTGGCCGTGGGCTCGGCCAGCGAGTA<br>CGACTACGTGAGCTTCCAGTCGGACATCGGCCCGTACCAGAGCGGGCGCTTCTACACCAAGCCACCTCAG<br>TGCGTGGACATCCCCGCGGACCTGCGGCTGTGCCACAACGTGGGCTACAAGAAGATGGTGCTGCCCAACC<br>TGCTGGAGCACGAGACCATGGCGGAGGTGAAGCAGCAGGCCAGCAGCTGGGTGCCCCTGCTCAACAAGAA<br>CTGCCACGCCGGCACCCAGGTCTTCCTCTGCTCGCTCTTCGCGCCCGTCTGCCTGGACCGGCCCATCTAC<br>CCGTGTCGCTGGCTCTGCGAGGCCGTGCGCGACTCGTGCGAGCCGGTCATGCAGTTCTTCGGCTTCTACT<br>GGCCCGAGATGCTTAAGTGTGACAAGTTCCCCGAGGGGGACGTCTGCATCGCCATGACGCCGCCCAATGC<br>CACCGAAGCCTCCAAGCCCCAAGGCACAACGGTGTGTCCTCCCTGTGACAACGAGTTGAAATCTGAGGCC<br>ATCATTGAACATCTCTGTGCCAGCGAGTTTGCACTGAGGATGAAAATAAAAGAAGTGAAAAAAGAAAATG<br>GCGACAAGAAGATTGTCCCCAAGAAGAAGAAGCCCCTGAAGTTGGGGCCCATCAAGAAGAAGGACCTGAA<br>GAAGCTTGTGCTGTACCTGAAGAATGGGGCTGACTGTCCCTGCCACCAGCTGGACAACCTCAGCCACCAC<br>TTCCTCATCATGGGCCGCAAGGTGAAGAGCCAGTACTTGCTGACGGCCATCCACAAGTGGGACAAGAAAA<br>ACAAGGAGTTCAAAAACTTCATGAAGAAAATGAAAAACCATGAGTGCCCCACCTTTCAGTCCGTGTTTAA<br>GTGATTCTCCCGGGGGCAGGGTGGGGAGGGAGCCTCGGGTGGGGTGGGAGCGGGGGGGACAGTGCCCCGG<br>GAACCCGGTGGGTCACACACACGCACTGCGCCTGTCAGTAGTGGACATTTAATCCAGTCGGCTTGTTCTT<br>GCAGCATTCCCGCTCCCTTCCCTCCATAGCCACGCTCCAAACCCCAGGGTAGCCATGGCCGGGTAAAGCA<br>AGGGCCATTTAGATTAGGAAGGTTTTTAAGATCCGCAATGTGGAGCAGCAGCCACTGCACAGGAGGAGGT<br>GACAAACCATTTCCAACAGCAACACAGCCACTAAAACACAAAAAGGGGGATTGGGCGGAAAGTGAGAGCC<br>AGCAGCAAAAACTACATTTTGCAACTTGTTGGTGTGGATCTATTGGCTGATCTATGCCTTTCAACTAGAA | 148 |

TABLE 2-continued

| GENBANK ACCESSION NUMBER | SEQUENCE | SEQ ID NO: |
|---|---|---|
| | AATTCTAATGATTGGCAAGTCACGTTGTTTTCAGGTCCAGAGTAGTTTCTTTCTGTCTGCTTTAAATGGA | |
| | AACAGACTCATACCACACTTACAATTAAGGTCAAGCCCAGAAAGTGATAAGTGCAGGGAGGAAAAGTGCA | |
| | AGTCCATTATGTAATAGTGACAGCAAAGGGACCAGGGGAGAGGCATTGCCTTCTCTGCCCACAGTCTTTC | |
| | CGTGTGATTGTCTTTGAATCTGAATCAGCCAGTCTCAGATGCCCCAAAGTTTCGGTTCCTATGAGCCCGG | |
| | GGCATGATCTGATCCCCAAGACATGTGGAGGGGCAGCCTGTGCCTGCCTTTGTGTCAGAAAAAGGAAACC | |
| | ACAGTGAGCCTGAGAGAGACGGCGATTTTCGGGCTGAGAAGGCAGTAGTTTTCAAAACACATAGTTAAAA | |
| | AAGAAACAAATGAAAAAAATTTTAGAACAGTCCAGCAAATTGCTAGTCAGGGTGAATTGTGAAATTGGGT | |
| | GAAGAGCTTACGATTCTAATCTCATGTTTTTTCCTTTTCACATTTTTAAAAGAACAATGACAAACACCCA | |
| | CTTATTTTTCAAGGTTTTAAAACAGTCTACATTGAGCATTTGAAAGGTGTGCTAGAACAAGGTCTCCTGA | |
| | TCCGTCCGAGGCTGCTTCCCAGAGGAGCAGCTCTCCCCAGGCATTTGCCAAGGGAGGCGGATTTCCCTGG | |
| | TAGTGTAGCTGTGTGGCTTTCCTTCCTGAAGAGTCCGTGGTTGCCCTAGAACCTAACACCCCCTAGCAAA | |
| | ACTCACAGAGCTTTCCGTTTTTTTCTTTCCTGTAAAGAAACATTTCCTTTGAACTTGATTGCCTATGGAT | |
| | CAAAGAAATTCAGAACAGCCTGCCTGTCCCCCCGCACTTTTTACATATATTTGTTTCATTTCTGCAGATG | |
| | GAAAGTTGACATGGGTGGGGTGTCCCCATCCAGCGAGAGAGTTTAAAAAGCAAAACATCTCTGCAGTTTT | |
| | TCCCAAGTGCCCTGAGATACTTCCCAAAGCCCTTATGTTTAATCAGCGATGTATATAAGCCAGTTCACTT | |
| | AGACAACTTTACCCTTCTTGTCCAATGTACAGGAAGTAGTTCTAAAAAAAATGCATATTAATTTCTTCCC | |
| | CCAAAGCCGGATTCTTAATTCTCTGCAACACTTTGAGGACATTTATGATTGTCCCTCTGGGCCAATGCTT | |
| | ATACCCAGTGAGGATGCTGCAGTGAGGCTGTAAAGTGGCCCCCTGCGGCCCTAGCCTGACCCGGAGGAAA | |
| | GGATGGTAGATTCTGTTAACTCTTGAAGACTCCAGTATGAAAATCAGCATGCCCGCCTAGTTACCTACCG | |
| | GAGAGTTATCCTGATAAATTAACCTCTCACAGTTAGTGATCCTGTCCTTTTAACACCTTTTTTGTGGGGT | |
| | TCTCTCTGACCTTTCATCGTAAAGTGCTGGGGACCTTAAGTGATTTGCCTGTAATTTTGGATGATTAAAA | |
| | AATGTGTATATATATTAGCTAATTAGAAATATTCTACTTCTCTGTTGTCAAACTGAAATTCAGAGCAAGT | |
| | TCCTGAGTGCGTGGATCTGGGTCTTAGTTCTGGTTGATTCACTCAAGAGTTCAGTGCTCATACGTATCTG | |
| | CTCATTTTGACAAAGTGCCTCATGCAACCGGGCCCTCTCTCTGCGGCAGAGTCCTTAGTGGAGGGGTTTA | |
| | CCTGGAACATTAGTAGTTACCACAGAATACGGAAGAGCAGGTGACTGTGCTGTGCAGCTCTCTAAATGGG | |
| | AATTCTCAGGTAGGAAGCAACAGCTTCAGAAAGAGCTCAAAATAAATTGGAAATGTGAATCGCAGCTGTG | |
| | GGTTTTACCACCGTCTGTCTCAGAGTCCCAGGACCTTGAGTGTCATTAGTTACTTTATTGAAGGTTTTAG | |
| | ACCCATAGCAGCTTTGTCTCTGTCACATCAGCAATTTCAGAACCAAAAGGGAGGCTCTCTGTAGGCACAG | |
| | AGCTGCACTATCACGAGCCTTTGTTTTTCTCCACAAAGTATCTAACAAAACCAATGTGCAGACTGATTGG | |
| | CCTGGTCATTGGTCTCCGAGAGAGGAGGTTTGCCTGTGATTTCCTAATTATCGCTAGGGCCAAGGTGGGA | |
| | TTTGTAAAGCTTTACAATAATCATTCTGGATAGAGTCCTGGGAGGTCCTTGGCAGAACTCAGTTAAATCT | |
| | TTGAAGAATATTTGTAGTTATCTTAGAAGATAGCATGGGAGGTGAGGATTCCAAAAACATTTTATTTTTA | |
| | AAATATCCTGTGTAACACTTGGCTCTTGGTACCTGTGGGTTAGCATCAAGTTCTCCCCAGGGTAGAATTC | |
| | AATCAGAGCTCCAGTTTGCATTTGGATGTGTAAATTACAGTAATCCCATTTCCCAAACCTAAAATCTGTT | |
| | TTTCTCATCAGACTCTGAGTAACTGGTTGCTGTGTCATAACTTCATAGATGCAGGAGGCTCAGGTGATCT | |
| | GTTTGAGCAGAGCACCCTAGGCAGCCTGCAGGGAATAACATACTGGCCGTTCTGACCTGTTGCCAGCAGA | |
| | TACACAGGACATGGATGAAATTCCCGTTTCCTCTAGTTTCTTCCTGTAGTACTCCTCTTTTAGATCCTAA | |
| | GTCTCTTACAAAAGCTTTGAATACTGTGAAAATGTTTTACATTCCATTTCATTTGTGTTGTTTTTTTAAC | |
| | TGCATTTTACCAGATGTTTTGATGTTATCGCTTATGTTAATAGTAATTCCCGTACGTGTTCATTTTATTT | |
| | TCATGCTTTTTCAGCCATGTATCAATATTCACTTGACTAAAATCACTCAATTAATCAAAAAAAAAAAAAA | |
| | AA | |
| NM_012319 | AGTCCTGGGCGAAGGGGGCGGTGGTTCCCCGCGGCGCTGCGCGCGGCGGTAATTAGTGATTGTCTTCCAG | 149 |
| | CTTCGCGAAGGCTAGGGGCGCGGCTGCCGGGTGGCTGCGCGGCGCTGCCCCCGGACCGAGGGGCAGCCAA | |
| | CCCAATGAAACCACCGCGTGTTCGCGCCTGGTAGAGATTTCTCGAAGACACCAGTGGGCCCGTTCCGAGC | |
| | CCTCTGGACCGCCCGTGTGGAACCAAACCTGCGCGCGTGGCCGGGCCGTGGGACAACGAGGCCGCGGAGA | |
| | CGAAGGCGCAATGGCGAGGAAGTTATCTGTAATCTTGATCCTGACCTTTGCCCTCTCTGTCACAAATCCC | |
| | CTTCATGAACTAAAAGCAGCTGCTTTCCCCCAGACCACTGAGAAAATTAGTCCGAATTGGGAATCTGGCA | |
| | TTAATGTTGACTTGGCAATTTCCACACGGCAATATCATCTACAACAGCTTTTCTACCGCTATGGAGAAAA | |
| | TAATTCTTTGTCAGTTGAAGGGTTCAGAAAATTACTTCAAAATATAGGCATAGATAAGATTAAAAGAATC | |
| | CATATACACCATGACCACGACCATCACTCAGACCACGAGCATCACTCAGACCATGAGCGTCACTCAGACC | |
| | ATGAGCATCACTCAGACCACGAGCATCACTCTGACCATGATCATCACTCTCACCATAATCATGCTGCTTC | |
| | TGGTAAAAATAAGCGAAAAGCTCTTTGCCCAGACCATGACTCAGATAGTTCAGGTAAAGATCCTAGAAAC | |
| | AGCCAGGGGAAAGGAGCTCACCGACCAGAACATGCCAGTGGTAGAAGGAATGTCAAGGACAGTGTTAGTG | |
| | CTAGTGAAGTGACCTCAACTGTGTACAACACTGTCTCTGAAGGAACTCACTTTCTAGAGACAATAGAGAC | |
| | TCCAAGACCTGGAAAACTCTTCCCCAAAGATGTAAGCAGCTCCACTCCACCCAGTGTCACATCAAAGAGC | |
| | CGGGTGAGCCGGCTGGCTGGTAGGAAAACAAATGAATCTGTGAGTGAGCCCCGAAAAGGCTTTATGTATT | |
| | CCAGAAACACAAATGAAAATCCTCAGGAGTGTTTCAATGCATCAAAGCTACTGACATCTCATGGCATGGG | |
| | CATCCAGGTTCCGCTGAATGCAACAGAGTTCAACTATCTCTGTCCAGCCATCATCAACCAAATTGATGCT | |
| | AGATCTTGTCTGATTCATACAAGTGAAAAGAAGGCTGAAATCCCTCCAAAGACCTATTCATTACAAATAG | |
| | CCTGGGTTGGTGGTTTTATAGCCATTTCCATCATCAGTTTCCTGTCTCTGCTGGGGGTTATCTTAGTGCC | |
| | TCTCATGAATCGGGTGTTTTTCAAATTTCTCCTGAGTTTCCTTGTGGCACTGGCCGTTGGGACTTTGAGT | |
| | GGTGATGCTTTTTTACACCTTCTTCCACATTCTCATGCAAGTCACCACCATAGTCATAGCCATGAAGAAC | |
| | CAGCAATGGAAATGAAAAGAGGACCACTTTTCAGTCATCTGTCTTCTCAAAACATAGAAGAAAGTGCCTA | |
| | TTTTGATTCCACGTGGAAGGGTCTAACAGCTCTAGGAGGCCTGTATTTCATGTTTCTTGTTGAACATGTC | |
| | CTCACATTGATCAAACAATTTAAAGATAAGAAGAAAAAGAATCAGAAGAAACCTGAAAATGATGATGATG | |
| | TGGAGATTAAGAAGCAGTTGTCCAAGTATGAATCTCAACTTTCAACAAATGAGGAGAAAGTAGATACAGA | |
| | TGATCGAACTGAAGGCTATTTACGAGCAGACTCACAAGAGCCCTCCCACTTTGATTCTCAGCAGCCTGCA | |
| | GTCTTGGAAGAAGAAGAGGTCATGATAGCTCATGCTCATCCACAGGAAGTCTACAATGAATATGTACCCA | |
| | GAGGGTGCAAGAATAAATGCCATTCACATTTCCACGATACACTCGGCCAGTCAGACGATCTCATTCACCA | |
| | CCATCATGACTACCATCATATTCTCCATCATCACCACCACCAAAACCACCATCCTCACAGTCACAGCCAG | |
| | CGCTACTCTCGGGAGGAGCTGAAAGATGCCGGCGTCGCCACTCTGGCCTGGATGGTGATAATGGGTGATG | |
| | GCCTGCACAATTTCAGCGATGGCCTAGCAATTGGTGCTGCTTTTACTGAAGGCTTATCAAGTGGTTTAAG | |
| | TACTTCTGTTGCTGTGTTCTGTCATGAGTTGCCTCATGAATTAGGTGACTTTGCTGTTCTACTAAAGGCT | |
| | GGCATGACCGTTAAGCAGGCTGTCCTTTATAATGCATTGTCAGCCATGCTGGCGTATCTTGGAATGGCAA | |
| | CAGGAATTTTCATTGGTCATTATGCTGAAAATGTTTCTATGTGGATATTTGCACTTACTGCTGGCTTATT | |

TABLE 2-continued

| GENBANK ACCESSION NUMBER | SEQUENCE | SEQ ID NO: |
|---|---|---|
| | CATGTATGTTGCTCTGGTTGATATGGTACCTGAAATGCTGCACAATGATGCTAGTGACCATGGATGTAGC<br>CGCTGGGGGTATTTCTTTTTACAGAATGCTGGGATGCTTTTGGGTTTTGGAATTATGTTACTTATTTCCA<br>TATTTGAACATAAAATCGTGTTTCGTATAAATTTCTAGTTAAGGTTTAAATGCTAGAGTAGCTTAAAAAG<br>TTGTCATAGTTTCAGTAGGTCATAGGGAGATGAGTTTGTATGCTGTACTATGCAGCGTTTAAAGTTAGTG<br>GGTTTTGTGATTTTTGTATTGAATATTGCTGTCTGTTACAAAGTCAGTTAAAGGTACGTTTTAATATTTA<br>AGTTATTCTATCTTGGAGATAAAATCTGTATGTGCAATTCACCGGTATTACCAGTTTATTATGTAAACAA<br>GAGATTTGGCATGACATGTTCTGTATGTTTCAGGGAAAAATGTCTTTAATGCTTTTTCAAGAACTAACAC<br>AGTTATTCCTATACTGGATTTTAGGTCTCTGAAGAACTGCTGGTGTTTAGGAATAAGAATGTGCATGAAG<br>CCTAAAATACCAAGAAAGCTTATACTGAATTTAAGCAAAGAAATAAAGGAGAAAAGAGAAGAATCTGAGA<br>ATTGGGGAGGCATAGATTCTTATAAAAATCACAAAATTTGTTGTAAATTAGAGGGGAGAAATTTAGAATT<br>AAGTATAAAAAGGCAGAATTAGTATAGAGTACATTCATTAAACATTTTTGTCAGGATTATTTCCCGTAAA<br>AACGTAGTGAGCACTTTTCATATACTAATTTAGTTGTACATTTAACTTTGTATAATACAGAAATCTAAAT<br>ATATTTAATGAATTCAAGCAATATATCACTTGACCAAGAAATTGGAATTTCAAAATGTTCGTGCGGGTAT<br>ATACCAGATGAGTACAGTGAGTAGTTTTATGTATCACCAGACTGGGTTATTGCCAAGTTATATATCACCA<br>AAAGCTGTATGACTGGATGTTCTGGTTACCTGGTTTACAAAATTATCAGAGTAGTAAAACTTTGATATAT<br>ATGAGGATATTAAAACTACACTAAGTATCATTTGATTCGATTCAGAAAGTACTTTGATATCTCTCAGTGC<br>TTCAGTGCTATCATTGTGAGCAATTGTCTTTTATATACGGTACTGTAGCCATACTAGGCCTGTCTGTGGC<br>ATTCTCTAGATGTTTCTTTTTTACACAATAAATTCCTTATATCAGCTTGAAAAAAAAAAAAAAAAAA | |
| AK098106 | AACGCACTTGGCGCGCGGCGCGGGCTGCAGACGGCTGCGAGGCGCTGGGCACAGGTGTCCTGATGGCAAA<br>TTTCAAGGGCCACGCGCTTCCAGGGAGTTTCTTCCTGATCATTGGGCTGTGTTGGTCAGTGAAGTACCCG<br>CTGAAGTACTTTAGCCACACGCGGAAGAACAGCCCACTACATTACTATCAGCGTCTCGAGATCGTCGAAG<br>CCGCAATTAGGACTTTGTTTTCCGTCACTGGGATCCTGGCAGAGCAGTTTGTTCCGGATGGCCCCACCT<br>GCACCTCTACCATGAGAACCACTGGATAAAGTTAATGAATTGGCAGCACAGCACCATGTACCTATTCTTT<br>GCAGTCTCAGGAATTGTTGACATGCTCACCTATCTGGTCAGCCACGTTCCCTTGGGGGTGGACAGACTGG<br>TTATGGCTGTGGCAGTATTCATGGAAGGTTTCCTCTTCTACTACCACGTCCACAACCGGCCTCCGCTGGA<br>CCAGCACATCCACTCACTCCTGCTGTATGCTCTGTTCGGAGGGTGTGTTAGTATCTCCCTAGAGGTGATC<br>TTCCGGGACCACATTGTGCTGGAACTTTTCCGAACCAGTCTCATCATTCTTCAGGGAACCTGGTTCTGGC<br>AGATTGGGTTTGTGCTGTTCCCACCTTTTGGAACACCCGAATGGGACCAGAAGGATGATGCCAACCTCAT<br>GTTCATCACCATGTGCTTCTGCTGGCACTACCTGGCTGCCCTCAGCATTGTGGCCGTCAACTATTCTCTT<br>GTTTACTGCCTTTTGACTCGGATGAAGAGACACGGAAGGGGAGAAATCATTGGAATTCAGAAGCTGAATT<br>CAGATGACACTTACCAGACCGCCCTCTTGAGTGGCTCAGATGAGGAATGAGCCGAGATGCGGAGGGCGCA<br>GATGTCCCACTGCACAGCTGGAATGAATGGAGTTCATCCCCTCCACCTGAATGCCTGCTGTGGTCTGATC<br>TTAAGGGTCTATATATTTGCACCTCCTCATTCAACACAGGGCTGGAGGTTCTACAACAGGAAATCAGGCC<br>TACAGCATCCTGTGTATCTTGCAGTTGGGATTTTTAAACATACTATAAAGTCTGTGTTGGTATAGTACCC<br>TTCATAAGGAAAAATGAAGTAATGCCTATAAGTAGCAGGCCTTTGTGCCTCAGTGTCAAGAGAAATCAAG<br>AGATGCTAAAAGCTTTACAATGGAAGTGGCCTCATGGATGAATCCGGGGTATGAGCCCAGGAGAACGTGC<br>TGCTTTTGGTAACTTATCCCTTTTTCTCTTAAGAAAGCAGGTACTTTCTTATTAGAAATATGTTAGAATG<br>TGTAAGCAAACGACAGTGCCTTTAGAATTACAATTCTAACTTACATATTTTTTGAAAGTAAAATAATTCA<br>CAAGCTTTGGTATTTTAAAATTATTGTTAAACATATCATAACTAATCATACCAGGGTACTGCAATACCAC<br>TGTTTATAAGTGACAAAATTAGGCCAAAGGTGATTTTTTTTTAAATCAGGAAGCTGGTTACTGGCTCTAC<br>TGAGAGTTGGAGCCCTGATGTTCTGATTCTTCAAAGTCACCCTAAAAGAAGATCTGACAGGAAAGCTGTA<br>TAATGAGATAGAAAAACGTCAGGTATGGAAGGCTTTCAGTTTTAATATGGCTGAAAGCAAAGGATAACGA<br>ATTCAGAATTAGTAATGTAAAATCTTGATACCCTAATCTTGCTTCTGGATCTGTTCTTTTTTTAAAAAAA<br>CTTCCTTCACCGCGCCTATAATCCTAGCACTTTGGGAGGCCGAGGCAGGCAGATCACGGGGTCAGGAGAT<br>CAAGACCATCCTGGCTAACATGGTGAAACCCCGTCTCTACTGAAAATACAAAAAATTAGCCGGGTGTGGT<br>GGCGGGCGCCTGTAGTTCCAGCTACTCGGGAGGCTGAGGCAAGAGAATGGCATGAACCCGGTAGGGGAGC<br>TTGCAGTGAGCCCAGATCATGCCACTGTACTCCAGCCTAGGTGACAGAGCAAGACTCTGTCTCAAAAACA<br>AGCAAACAGACTTCCTTCAACAAATATTTATTAAATATCCACTTTGCAACAGCACTGAAATGGCTGTAAG<br>GACTCCTGAGATATGTGTCCAGCAAGGAGTTTACAGTCAAACAGGAGAGACATGCCTGTAGTTACATCCA<br>GTGTGATGGGTGCTGAGAGGCAAGTACAAACCACGATG | 150 |
| BQ056428 | TCCCGCCGCGCCACTTCGCCTGCCTCCGTCCCCCGCCCGCCGCGCCATGCCTGTGGCCGGCTCGGAGCTG<br>CCGCGCCGGCCCTTGCCCCCCGCCGCACAGGAGCGGGACGCCGAGCCGCGTCCGCCGCACGGGGAGCTGC<br>AGTACCTGGGGCAGATCCAACACATCCTCCGCTGCGGCGTCAGGAAGGACGCCCGCCCGGGCACCGGTAC<br>CCTGCCGGTATTCGGCATGCAGGCGCGCTACAGCCTGAGAGATGAATTCCCTCTGCTGACAACCAAACGT<br>GTGTTCTGGAACGGTGCTTCGGAGGAGCTGCTGTGGCTTATCAAGGGATCCACAAACGCTATAGACCTGT<br>CTTCCCCGGCAGCGAAAATCTCGGGATGCCACTGGATCCCGACACTCTCTGGACACCCTGGGATTCTCCA<br>CCAGAGAAGAACGCGACTTGGGCCCAGTTTGTGGCTCTCAGCGGAGGCCTCCTGTGGCAGAATACATACA<br>TTTCCAATCAGATCACTTCCCGGACACGGACCNTGACCAGCCTGCCAAAAAGTGGATTTCCCCCCACCCC<br>AGAACCCANCCCCTGACGCACAGAAACCAACCCATTCGTTGTTGCCGCCTTGCGAACCCCAACCAGAATC<br>TCTCCCCCCTGGCCGGCGCGCCTGCCGCTGCCAATGCCCCTATGGCGGCCTCTTGGCCCGCACCTTCCAA<br>TTGGTCGCCCTGCGCAACCAGCGAGAAAACACTGGCCCGCCCGTCTCCCCCCCGCTCCGCCTACCCCACT<br>TAATGCGCCTCCGTGGCATGACGCACGCGTTTGGTGTCCGCCGCCGTCTCATGTCCGCGCGGTGTGGACC<br>CCCTTTTCTCTCGCGGCACATCCCCCCTATTCCCTTGCCCTTTGGGGGGCACCCCCTCTAGACCCGCGCT<br>TCTCTTCTCGTCCGGTGGGGGACATTGGTTTGCCTGCCGCGGCGGGGGCGNTAAAAATAAAAACAGCCTG<br>TTAGCCCGGCCCAGTACCCCCCCCCGGCCGGGGCCGCCTTNCGTTTGCATTTATACCCCAACCCATAAAG<br>CCGCGCCCCTTTAGCNCCNTAACTTTTGTGGTGTGGCCTCCCCCCTTTTTCCCGGGGAGCAGCAACGGAC<br>ATCTGTACACTAATGCTGGCCCCGACCTTTCCCAAAAACCCCCCGCCCGTGTCCCGTATAAATTTGGTGC<br>CAANCCTGACGNGTTCTCCCCCGCCCTCGCCCCGTTGGCCGCCCGTTTAAAGCCCCCCCGGTGGTTGCGC<br>CGCCCAACGAGTCCACCTATAGTTAANTCCACCAACACCCCCACCTTTTCCTCCCCGCCGCATCTTCCCC<br>ACGTACCCCCTTTTGTCGCGAGATGGCCACTCCCCCCCCCCTGTTTGTTTAAAACAACGAGAATGGTGCT<br>GCCAACGCTGGTCTTTTCCCCCCCCGGACCGCGACCGCCAGGGGGAATACGTACCATAAGCCCCCGCGCC<br>CNCCTTTTTTCCCCCCTCCCCGCCAATCAAGATCCGCCGTCCATTAGACGTATTATTTTTCCCGCGATAC<br>ACGAAAAAACAGGGCCGCCCATTTATAACTAAATTCCCGTCGCCGCCGCGCGGATATGTTTCCCAAAATA<br>CCACCCCCCCCCCCCCATTTTCTTTGCCCCCAACTCCTGCGCACCGGTGTTCACCAGCCTCGCGCCGC | 151 |

TABLE 2-continued

| GENBANK ACCESSION NUMBER | SEQUENCE | SEQ ID NO: |
|---|---|---|
| BC032677 | GGACGCGTGGGTCGACCCACGCGTCCGGACCCACGCGTCCGGTCGTGTTCTCCGAGTTCCTGTCTCTCTG<br>CCAACGCCGCCCGGATGGCTTCCCAAAACCGCGACCCAGCCGCCACTAGCGTCGCCGCCGCCCGTAAAGG<br>AGCTGAGCCGAGCGGGGGCGCCGCCCGGGGTCCGGTGGGCAAAAGGCTACAGCAGGAGCTGATGACCCTC<br>ATGGTGAGTGATTAAGTGCCCAGAACCCCAGCCTTCCATCCAATTTTCAGTAGCCTCCTTTTTTCCGTCA<br>GCTTTTTTGCTAGACATAGGGGTAATGTAATTTGCTCCCTCCTGGGAAAGAAGTTCATACACCCCACCTA<br>CACCATTTCTTCCAGCAGTCCCTCCTCCCAATTCCATCCCCCCACACGAAGTTATCTCGAACACTTCCCT<br>GAAGTCATACAAGACCCTCCCTATCCAGTGTGTCCCTACTTCCTAGCCCCAACCAAGCTTTACCCACACC<br>CAACTCCCCGCCCTTCTTGGTATTTCTAGCCTATGAATTTGGTTGCTTTATTTTGGATCAGAGTGATGAG<br>ATTAAGGGGAGGCTGGGCGCGGTAGCTCACACCTTATAATCCCAAAGTGCTGGGATTACAGGCGTGAGCC<br>ACCGCGCCCGGCCAGCAACTAATATTCTAATTGAACTAAAGCACAGGATGCCAATTTACAATCCTTAGAC<br>CAAAGAGTCACTGATGTCTCCACCAGATAAGAGGAAAGCATCAGGCTAGGCATAGTGGCTCACACCTGTA<br>ATCTCAGCACTTTGGGAGGCTGAGGCAGGCAGATCACATGAGCCCAGGAGTTTGAGACTGGCCTGGGCAA<br>CATGGTGAAACCCTGTCTCTAAAATAAAAACTAAACTAAAAAAACTTTTTAAAAAGGCAGTGGGGAGCAT<br>CAGAACCAGCTCAACAGTTTGTCTACTGTCCGGTCCCAGAGAAACTCAAGATTCTAGCAAGCCCCTTGTG<br>TGGGGCTTGGGTTGGGACATGAGGCTGCTGCTGGAGCTTACTCTGCAACTGTTTCTCCAAATGCCAGGTA<br>TATGAAGACCTGAGGTATAAGCTCTCGCTAGAGTTCCCCAGTGGCTACCCTTACAATGCGCCCACAGTGA<br>AGTTCCTCACGCCCTGCTATCACCCCAACGTGGACACCCAGGGTAACATATGCCTGGACATCCTGAAGGA<br>AAAGTGGTCTGCCCTGTATGATGTCAGGACCATTCTGCTCTCCATCCAGAGCCTTCTAGGAGAACCCAAC<br>ATTGATAGTCCCTTGAACACACATGCTGCCGAGCTCTGGAAAAACCCCACAGCTTTTAAGAAGTACCTGC<br>AAGAAACCTACTCAAAGCAGGTCACCAGCCAGGAGCCCTGACCCAGGCTGCCCAGCCTGTCCTTGTGTCG<br>TCTTTTTAATTTTTCCTTAGATGGTCTGTCCTTTTTGTGATTTCTGTATAGGACTCTTTATCTTGAGCTG<br>TGGTATTTTTGTTTTGTTTTTGTCTTTTAAATTAAGCCTCGGTTGAGCCCTTGTATATTAAATAAATGCA<br>TTTTTGTCCTTTTTTAAAAAAAAAATAAAAAAAAAAAAAAAAAAAAAAAAAAAAAAAAAAAAAAAAAAAA<br>A | 152 |

The subset of the genes that maybe assayed for expression include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49 or all 50 of the genes listed in Table 2.

The gene set contains many genes that are known markers for proliferation. The methods of the present invention provide for the determination of subsets of genes that provide a proliferation signature. The methods of the present invention can include determining the expression of at least one proliferation gene. Preferably, the at least one proliferation gene is least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 genes listed in Table 1 or Table 2.

The methods of the present invention can include determining the expression of at least one of, a combination of, or each of, a 21-gene subset of the PAM50 intrinsic genes selected from ANLN, BIRC5, CCNB1, CCNE1, CDC20, CDC6, CDCA1, CENPF, CEP55, EXO1, KIF2C, KNTC2, MELK, MKI67, MYBL2, ORC6L, PTTG1, RRM2, TYMS, UBE2C and/or UBE2T. The methods of the present invention can include determining the expression of at least one of, a combination of, or each of, a 19-gene subset of the PAM50 intrinsic genes selected from ANLN, CCNB1, CCNE1, CDC20, CDC6, CDCA1, CENPF, CEP55, EXO1, KIF2C, KNTC2, MELK, MKI67, ORC6L, PTTG1, RRM2, TYMS, UBE2C and/or UBE2T. The methods of the present invention can include determining the expression of at least one of, a combination of, or each of, a 18-gene subset of the PAM50 intrinsic genes selected from ANLN, CCNE1, CDC20, CDC6, CDCA1, CENPF, CEP55, EXO1, KIF2C, KNTC2, MELK, MKI67, ORC6L, PTTG1, RRM2, TYMS, UBE2C and/or UBE2T. The methods of the present invention can include determining the expression of at least one of, a combination of, or each of, a 11-gene subset of the PAM50 intrinsic genes selected from BIRC5, CCNB1, CDC20, CDCA1/NUF2, CEP55, KNTC2/NDC80, MKI67, PTTG1, RRM2, TYMS and/or UBE2C. The methods of the present invention can include determining the expression of at least one of, a combination of, or each of, a 10-gene subset of the PAM50 intrinsic genes selected from ANLN, CCNB1, CDC20, CENPF, CEP55, KIF2C, MKI67, MYBL2, RRM2 and/or UBE2C.

Methods of determining a proliferation signature from a biological sample are as described in Nielsen et al. Clin. Cancer Res., 16(21):5222-5232 (2009) and supplemental online material and in Bastien et al. BMC Medical Genomics, 5:44 (2012) (published online) and supplemental online material (these documents are incorporated herein, by reference, in their entireties).

The present invention provides methods for determining a proliferation signature (also referred to as proliferation score or p-score, these terms are utilized interchangeably herein) of a breast cancer sample from a subject. The expression of one or more of the genes listed in Table 1 may be determined using methods known in the art and described herein, and normalized to control housekeeping genes (i.e., MRPL19, PSMC4, SF3A1, PUM1, ACTB, GAPD, GUSB, RPLPO, and TFRC). Preferably, the one or more genes from Table 1 are a subset of genes known for proliferation (e.g., cell cycle regulated genes see Bastien et al., BMC Medical Genomics 5:44-, 2012), as described herein. Optionally, the gene expression can be also normalized to a control sample by determining the ratio of each gene between the sample and a control sample. While any control sample known in the art may be utilized, one exemplary control sample comprises in vitro transcribed RNA sequences of each gene at a known concentration. The mean of all the log ratios or normalized values of each proliferation gene can be calculated to determine the average proliferation gene expression of the sample. The proliferation signature can be determined by scaling the calculated average gene expression to a range of, for example 1-10 (e.g., FIG. 4), wherein the scaling is determined by a reference sample set. The lowest value of the proliferation signature corresponds to the lowest proliferation signature in the reference sample set, and the highest value of the proliferation signature corresponds to the highest proliferation signature, and the proliferation signature of a sample can be determined through linear interpolation between the highest and lowest values of the reference sample set.

The reference sample set is a population of breast cancer samples wherein the proliferation signature of each sample has been determined as described supra. The reference sample set must be of sufficient size such that the set can be used to assess various clinical variables, for example response to treatment regimen, estrogen receptor status, and tumor size and the like, with statistical significance. In some embodiments, the reference sample set comprises primary breast cancer tissue from subjects diagnosed with breast cancer and "normal" breast tissue samples from reduction mammoplasties or non-cancerous breast tissue. These samples can be classified to particular breast cancer intrinsic subtypes, for example Luminal A, Luminal B, Basal-like and Her2 using the PAM50 classification model described herein. For example, the reference sample set contains at least 100 samples, at least 200 samples, at least 300 samples, at least 400 samples, at least 500 samples, at least 600 samples, at least 700 samples, at least 800 samples, at least 900 samples, or at least 1000 samples. Preferably, the reference sample set contains at least 500 samples.

The proliferation signatures of each reference sample in the reference sample set can be arranged from lowest to highest, for example 1 to 10. Once arranged by proliferation signature, the reference sample set can then be divided into sub-ranges, wherein each sub-range is a non-overlapping fraction of the reference set. The proliferation signature of the sample can be compared to reference sample set. These sub-ranges are used to determine the cutoff threshold limits for a low proliferation signature. For example, the sub-range can be 50%, 33%, 30%, 25%, 20%, 15%, 10%, or 5% of the proliferation signatures of the arranged reference sample set. Irrespective of the number of sub-ranges, the proliferation signature of the sample is deemed to be a low proliferation signature if it is present within the lowest sub-range of the reference sample set. For example, if the reference sample set is divided into three sub-ranges, the classification of a low proliferation signature is assigned if the proliferation signature of the sample is present within the lowest 33% of proliferation scores of the arranged reference sample set.

Definitions

For the purposes of the present disclosure, "breast cancer" includes, for example, those conditions classified by biopsy or histology as malignant pathology. The clinical delineation of breast cancer diagnoses is well known in the medical arts. One of skill in the art will appreciate that breast cancer refers to any malignancy of the breast tissue, including, for example, carcinomas and sarcomas. Particular embodiments of breast cancer include ductal carcinoma in situ (DCIS), lobular carcinoma in situ (LCIS), or mucinous carcinoma. Breast cancer also refers to infiltrating ductal (IDC) or infiltrating lobular carcinoma (ILC). In most embodiments of the disclosure, the subject of interest is a human patient suspected of or actually diagnosed with breast cancer.

For the purposes of the present disclosure, "taxane or taxane derivatives" are diterpenes, a class of drugs used in cancer chemotherapy produced by the plants of the genus Taxus (yews). These drugs are used to treat a wide variety of cancers including breast cancer. However, this class of drugs is extremely toxic and produces significant deleterious side effects. Taxanes and taxane derivatives include paclitaxel (Taxol®) or docetaxel (Taxotere®).

For the purposes of the present disclosure, "a breast cancer treatment comprising taxane or a taxane derivative" is a breast cancer treatment that includes a taxane or a taxane derivative. These treatments can also include other cancer agents. These other agents can include anthracycline, cyclophosphamide or 5-fluorouracil, or a combination thereof.

For the purposes of the present disclosure, "a breast cancer treatment not comprising taxane or a taxane derivative" is a breast cancer treatment that does not include any taxane or a taxane derivative. These treatments contain other anti-cancer agents. These other agents can include anthracycline, cyclophosphamide or 5-fluorouracil, or a combination thereof.

Preferably taxanes and taxane derivatives are administered intravenously, but can be administered by any method known in the art. Taxanes or taxane derivatives can be administered at dosages from about 75 $mg/m^2$ to about 300 $mg/m^2$, preferably from about 75 $mg/m^2$ to about 175 $mg/m^2$, and most preferably about 100 $mg/m^2$. It is preferred that dosages be administered over a time period of about 1 to about 24 hours or weekly (5-7 days). Dosages can be repeated from 1 to about 4 weeks or more, preferably from about 2 to about 3 weeks. Preferably, the dosage schedule is eight 1-week courses of paclitaxel administered via a 60-minute intravenous infusion.

Preferably anthracyclines are administered intravenously, but can be administered by any method known in the art. Anthracyclines can be administered at dosages from 10 $mg/^{m2}$ to 300 $mg/^{m2}$ per week. Anthracyclines can be administered at 20-200 $mg/^{m2}$, 30-100 $mg/^{m2}$, or 35-75 $mg/^{m2}$ per week. Preferably, the anthracycline is administered at about 60 mg/m2 per week. Anthracyclines include daunorubicin, doxorubicin, epirubicin, idarubicin, valrubicin and mitoxantrone.

Preferably 5-fluorouracil is administered intravenously, but can be administered by any method known in the art. 5-fluorouracil can be administered at dosages from 25 $mg/m^2$ to 1000 $mg/m^2$ per week. 5-fluorouracil can be administered at 50-900 $mg/m^2$, 100-800 $mg/m^2$, 300-700 $mg/m^2$ or 450-650 $mg/m^2$ per week. Preferably, 5-fluorouracil is administered at about 500 $mg/m^2$ per week.

Preferably cyclophosphamide is administered orally, but can be administered by any method known in the art. Cyclophosphamide can be administered at dosages from 10 $mg/m^2$ to 300 $mg/m^2$ per day. Cyclophosphamide can be administered at 20-200 $mg/m^2$, 30-100 $mg/m^2$, or 40-80 $mg/m^2$ per day. Preferably, cyclophosphamide is administered at about 75 $mg/m^2$ per day.

Methods, schedules and dosages for administering taxanes or taxane derivatives, anthracyclines, 5-fluorouracil and/or cyclophosphamide are described in Martin et al., J Natl Cancer Inst. 100(11):805-14, 2008, which is incorporated herein, by reference, in its entirety.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Clinical Variables

As described herein, a number of clinical and prognostic breast cancer factors are known in the art and are used to predict treatment outcome and the likelihood of disease recurrence. Such factors include, for example, lymph node involvement, tumor size, histologic grade, estrogen and progesterone hormone receptor status, HER-2 levels, and tumor ploidy. In one embodiment, risk of relapse (ROR) score is provided for a subject diagnosed with or suspected of having breast cancer. This score uses the PAM50 classification model in combination with clinical factors of lymph node status (N) and tumor size (T). Assessment of clinical variables is based on the American Joint Committee on Cancer (AJCC) standardized system for breast cancer staging. In this system, primary tumor size is categorized on a scale of 0-4 (TO: no evidence of primary tumor; T1: <2 cm; T2: >2 cm-<5 cm; T3: >5 cm; T4: tumor of any size with direct spread to chest wall or skin). Lymph node status is classified as N0-N3 (NO: regional lymph nodes are free of metastasis; N1: metastasis to movable, same-side axillary lymph node(s); N2: metastasis to same-side lymph node(s) fixed to one another or to other structures; N3: metastasis to same-side lymph nodes beneath the breastbone). Methods of identifying breast cancer patients and staging the disease are well known and may include manual examination, biopsy, review of patient's and/or family history, and imaging techniques, such as mammography, magnetic resonance imaging (MRI), and positron emission tomography (PET).

Sample Source

In one embodiment of the present disclosure, breast cancer subtype is assessed through the evaluation of expression patterns, or profiles, of the intrinsic genes listed in Table 1 in one or more subject samples. For the purpose of discussion, the term subject, or subject sample, refers to an individual regardless of health and/or disease status. A subject can be a subject, a study participant, a control subject, a screening subject, or any other class of individual from whom a sample is obtained and assessed in the context of the disclosure. Accordingly, a subject can be diagnosed with breast cancer, can present with one or more symptoms of breast cancer, or a predisposing factor, such as a family (genetic) or medical history (medical) factor, for breast cancer, can be undergoing treatment or therapy for breast cancer, or the like. Alternatively, a subject can be healthy with respect to any of the aforementioned factors or criteria. It will be appreciated that the term "healthy" as used herein, is relative to breast cancer status, as the term "healthy" cannot be defined to correspond to any absolute evaluation or status. Thus, an individual defined as healthy with reference to any specified disease or disease criterion, can in fact be diagnosed with any other one or more diseases, or exhibit any other one or more disease criterion, including one or more cancers other than breast cancer. However, the healthy controls are preferably free of any cancer.

In particular embodiments, the methods for predicting breast cancer intrinsic subtypes include collecting a biological sample comprising a cancer cell or tissue, such as a breast tissue sample or a primary breast tumor tissue sample. By "biological sample" is intended any sampling of cells, tissues, or bodily fluids in which expression of an intrinsic gene can be detected. Examples of such biological samples include, but are not limited to, biopsies and smears. Bodily fluids useful in the present disclosure include blood, lymph, urine, saliva, nipple aspirates, gynecological fluids, or any other bodily secretion or derivative thereof. Blood can include whole blood, plasma, serum, or any derivative of blood. In some embodiments, the biological sample includes breast cells, particularly breast tissue from a biopsy, such as a breast tumor tissue sample. Biological samples may be obtained from a subject by a variety of techniques including, for example, by scraping or swabbing an area, by using a needle to aspirate cells or bodily fluids, or by removing a tissue sample (i.e., biopsy). Methods for collecting various biological samples are well known in the art. In some embodiments, a breast tissue sample is obtained by, for example, fine needle aspiration biopsy, core needle biopsy, or excisional biopsy. Fixative and staining solutions may be applied to the cells or tissues for preserving the specimen and for facilitating examination. Biological samples, particularly breast tissue samples, may be transferred to a glass slide for viewing under magnification. In one embodiment, the biological sample is a formalin-fixed, paraffin-embedded breast tissue sample, particularly a primary breast tumor sample. In various embodiments, the tissue sample is obtained from a pathologist-guided tissue core sample.

Expression Profiling

In various embodiments, the present disclosure provides methods for classifying, prognosticating, or monitoring breast cancer in subjects. In this embodiment, data obtained from analysis of intrinsic gene expression is evaluated using one or more pattern recognition algorithms. Such analysis methods may be used to form a predictive model, which can be used to classify test data. For example, one convenient and particularly effective method of classification employs multivariate statistical analysis modeling, first to form a model (a "predictive mathematical model") using data ("modeling data") from samples of known subtype (e.g., from subjects known to have a particular breast cancer intrinsic subtype: LumA, LumB, Basal-like, HER2-enriched, or normal-like), and second to classify an unknown sample (e.g., "test sample") according to subtype. Pattern recognition methods have been used widely to characterize many different types of problems ranging, for example, over linguistics, fingerprinting, chemistry and psychology. In the context of the methods described herein, pattern recognition is the use of multivariate statistics, both parametric and non-parametric, to analyze data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. However, this type of approach may not be suitable for developing a clinical assay that can be used to classify samples derived from subjects independent of the initial sample population used to train the prediction algorithm.

The other approach is termed "supervised" whereby a training set of samples with known class or outcome is used to produce a mathematical model which is then evaluated with independent validation data sets. Here, a "training set" of intrinsic gene expression data is used to construct a statistical model that predicts correctly the "subtype" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each subtype in terms of its intrinsic gene expression profile. It is also possible to obtain confidence limits on any predictions, for example, a level of probability to be placed on the goodness of fit. The robustness of the predictive models can also be checked using cross-validation, by leaving out selected samples from the analysis.

The PAM50 classification model described herein is based on the gene expression profile for a plurality of subject samples using the intrinsic genes listed in Table 1. The plurality of samples includes a sufficient number of samples derived from subjects belonging to each subtype class. By "sufficient samples" or "representative number" in this context is intended a quantity of samples derived from each subtype that is sufficient for building a classification model that can reliably distinguish each subtype from all others in the group. A supervised prediction algorithm is developed based on the profiles of objectively-selected prototype samples for "training" the algorithm. The samples are selected and subtyped using an expanded intrinsic gene set according to the methods disclosed in International Patent Publication WO 2007/061876, which is herein incorporated by reference in its entirety. Alternatively, the samples can be subtyped according to any known assay for classifying breast cancer subtypes. After stratifying the training samples according to subtype, a centroid-based prediction algorithm is used to construct centroids based on the expression profile of the intrinsic gene set described in Table 1.

In one embodiment, the prediction algorithm is the nearest centroid methodology related to that described in Narashiman and Chu (2002) PNAS 99:6567-6572, which is herein incorporated by reference in its entirety. In the present disclosure, the method computes a standardized centroid for each subtype. This centroid is the average gene expression for each gene in each subtype (or "class") divided by the within-class standard deviation for that gene. Nearest centroid classification takes the gene expression profile of a new sample, and compares it to each of these class centroids. Subtype prediction is done by calculating the Spearman's rank correlation of each test case to the five centroids, and assigning a sample to a subtype based on the nearest centroid.

Detection of Intrinsic Gene Expression

Any methods available in the art for detecting expression of the intrinsic genes listed in Table 1 are encompassed herein. By "detecting expression" is intended determining the quantity or presence of an RNA transcript or its expression product of an intrinsic gene. Methods for detecting expression of the intrinsic genes of the disclosure, that is, gene expression profiling, include methods based on hybridization analysis of polynucleotides, methods based on sequencing of polynucleotides, immunohistochemistry methods, and proteomics-based methods. The methods generally detect expression products (e.g., mRNA) of the intrinsic genes listed in Table 1. In preferred embodiments, PCR-based methods, such as reverse transcription PCR (RT-PCR) (Weis et al., TIG 8:263-64, 1992), and array-based methods such as microarray (Schena et al., Science 270:467-70, 1995) are used. By "microarray" is intended an ordered arrangement of hybridizable array elements, such as, for example, polynucleotide probes, on a substrate. The term "probe" refers to any molecule that is capable of selectively binding to a specifically intended target biomolecule, for example, a nucleotide transcript or a protein encoded by or corresponding to an intrinsic gene. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Many expression detection methods use isolated RNA. The starting material is typically total RNA isolated from a biological sample, such as a tumor or tumor cell line, and corresponding normal tissue or cell line, respectively. If the source of RNA is a primary tumor, RNA (e.g., mRNA) can be extracted, for example, from frozen or archived paraffin-embedded and fixed (e.g., formalin-fixed) tissue samples (e.g., pathologist-guided tissue core samples).

General methods for RNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker, Lab Invest. 56:A67, (1987); and De Andres et al. Biotechniques 18:42-44, (1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns Other commercially available RNA isolation kits include MASTERPURE™ Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155). Isolated RNA can be used in hybridization or amplification assays that include, but are not limited to, PCR analyses and probe arrays. One method for the detection of RNA levels involves contacting the isolated RNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 60, 100, 250, or 500 nucleotides in length and sufficient to specifically hybridize under stringent conditions to an intrinsic gene of the present disclosure, or any derivative DNA or RNA. Hybridization of an mRNA with the probe indicates that the intrinsic gene in question is being expressed. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probes are immobilized on a solid surface and the mRNA is contacted with the probes, for example, in an Agilent gene chip array. A skilled artisan can readily adapt known mRNA detection methods for use in detecting the level of expression of the intrinsic genes of the present disclosure.

An alternative method for determining the level of intrinsic gene expression product in a sample involves the process of nucleic acid amplification, for example, by RT-PCR (U.S. Pat. No. 4,683,202), ligase chain reaction (Barany, PNAS USA 88: 189-93, (1991)), self-sustained sequence replication (Guatelli et al., Proc. Natl. Acad. Sci. USA 87: 1874-78, (1990)), transcriptional amplification system (Kwoh et al., Proc. Natl. Acad. ScL USA 86: 1173-77, (1989)), Q-Beta Replicase (Lizardi et al., Bio/Technology 6:1197, (1988)), rolling circle replication (U.S. Pat. No. 5,854,033), or any other nucleic acid amplification method, followed by the detection of the amplified molecules using techniques well known to those of skill in the art. These detection schemes are especially useful for the detection of nucleic acid molecules if such molecules are present in very low numbers.

In particular aspects of the disclosure, intrinsic gene expression is assessed by quantitative RT-PCR. Numerous different PCR or QPCR protocols are known in the art and exemplified herein below and can be directly applied or adapted for use using the presently-described compositions for the detection and/or quantification of the intrinsic genes listed in Table 1. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR. However, preferred are cyclers with real time fluorescence measurement capabilities, for example, SMARTCYCLER® (Cepheid, Sunnyvale, Calif.), ABI PRISM 7700® (Applied Biosystems, Foster City, Calif.), ROTOR-GENE™ (Corbett Research, Sydney, Australia), LIGHTCYCLER® (Roche Diagnostics Corp, Indianapolis, Ind.), ICYCLER® (Biorad Laboratories, Hercules, Calif.) and MX4000® (Stratagene, La Jolla, Calif.).

In another embodiment of the disclosure, microarrays are used for expression profiling. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316. High-density oligonucleotide arrays are particularly useful for determining the gene expression profile for a large number of RNAs in a sample.

In a preferred embodiment, the nCounter® Analysis system is used to detect intrinsic gene expression. The basis of the nCounter® Analysis system is the unique code assigned to each nucleic acid target to be assayed (International Patent Application No. PCT/US2008/059959 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system.

Specific reporter and capture probes are synthesized for each target. Briefly, sequence-specific DNA oligonucleotide probes are attached to code-specific reporter molecules. Capture probes are made by ligating a second sequence-specific DNA oligonucleotide for each target to a universal oligonucleotide containing biotin. Reporter and capture probes are all pooled into a single hybridization mixture, the "probe library".

The relative abundance of each target is measured in a single multiplexed hybridization reaction. The sample is combined with the probe library, and hybridization occurs in solution. After hybridization, the tripartite hybridized complexes are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies).

Purified reactions are deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technlogies). The expression level of a target is measured by imaging each sample and counting the number of times the code for that target is detected. For each sample, typically 600 fields-of-view (FOV) are imaged (1376×1024 pixels) representing approximately 10 $mm^2$ of the binding surface. Typical imaging density is 100-1200 counted reporters per field of view depending on the degree of multiplexing, the amount of sample input, and overall target abundance. Data is output in simple spreadsheet format listing the number of counts per target, per sample.

This system can be used along with nanoreporters. Additional disclosure regarding nanoreporters can be found in International Publication No. WO 07/076,129 and WO 07/076,132, the contents of which are incorporated herein in their entireties. Further, the term nucleic acid probes and nanoreporters can include the rationally designed (e.g. synthetic sequences) described in International Publication No. WO 2010/019826, incorporated herein by reference in its entirety.

Data Processing

It is often useful to pre-process gene expression data, for example, by addressing missing data, translation, scaling, normalization, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may be replaced or "filled" with, for example, the mean value of a column ("mean fill"); a random value ("random fill"); or a value based on a principal component analysis ("principal component fill").

"Translation" of the descriptor coordinate axes can be useful. Examples of such translation include normalization and mean centering. "Normalization" may be used to remove sample-to-sample variation. For microarray data, the process of normalization aims to remove systematic errors by balancing the fluorescence intensities of the two labeling dyes. The dye bias can come from various sources including differences in dye labeling efficiencies, heat and light sensitivities, as well as scanner settings for scanning two channels. Some commonly used methods for calculating normalization factor include: (i) global normalization that uses all genes on the array; (ii) housekeeping genes normalization that uses constantly expressed housekeeping/invariant genes; and (iii)

internal controls normalization that uses known amount of exogenous control genes added during hybridization (Quackenbush Nat. Genet. 32 (Suppl.), 496-501 (2002)). In one embodiment, the intrinsic genes disclosed herein can be normalized to control housekeeping genes. For example, the housekeeping genes described in U.S. Patent Publication 2008/0032293, which is herein incorporated by reference in its entirety, can be used for normalization. Exemplary housekeeping genes include MRPL19, PSMC4, SF3A1, PUM1, ACTB, GAPD, GUSB, RPLPO, and TFRC. It will be understood by one of skill in the art that the methods disclosed herein are not bound by normalization to any particular housekeeping genes, and that any suitable housekeeping gene(s) known in the art can be used.

Many normalization approaches are possible, and they can often be applied at any of several points in the analysis. In one embodiment, microarray data is normalized using the LOWESS method, which is a global locally weighted scatter plot smoothing normalization function. In another embodiment, qPCR data is normalized to the geometric mean of set of multiple housekeeping genes.

“Mean centering” may also be used to simplify interpretation. Usually, for each descriptor, the average value of that descriptor for all samples is subtracted. In this way, the mean of a descriptor coincides with the origin, and all descriptors are “centered” at zero. In “unit variance scaling,” data can be scaled to equal variance. Usually, the value of each descriptor is scaled by 1/StDev, where StDev is the standard deviation for that descriptor for all samples. “Pareto scaling” is, in some sense, intermediate between mean centering and unit variance scaling. In pareto scaling, the value of each descriptor is scaled by Usqrt(StDev), where StDev is the standard deviation for that descriptor for all samples. In this way, each descriptor has a variance numerically equal to its initial standard deviation. The pareto scaling may be performed, for example, on raw data or mean centered data.

“Logarithmic scaling” may be used to assist interpretation when data have a positive skew and/or when data spans a large range, e.g., several orders of magnitude. Usually, for each descriptor, the value is replaced by the logarithm of that value. In “equal range scaling,” each descriptor is divided by the range of that descriptor for all samples. In this way, all descriptors have the same range, that is, 1. However, this method is sensitive to presence of outlier points. In “autoscaling,” each data vector is mean centered and unit variance scaled. This technique is a very useful because each descriptor is then weighted equally, and large and small values are treated with equal emphasis. This can be important for genes expressed at very low, but still detectable, levels.

In one embodiment, data is collected for one or more test samples and classified using the PAM50 classification model described herein. When comparing data from multiple analyses (e.g., comparing expression profiles for one or more test samples to the centroids constructed from samples collected and analyzed in an independent study), it will be necessary to normalize data across these data sets. In one embodiment, Distance Weighted Discrimination (DWD) is used to combine these data sets together (Benito et al. (2004) Bioinformatics 20(1): 105-114, incorporated by reference herein in its entirety). DWD is a multivariate analysis tool that is able to identify systematic biases present in separate data sets and then make a global adjustment to compensate for these biases; in essence, each separate data set is a multi-dimensional cloud of data points, and DWD takes two points clouds and shifts one such that it more optimally overlaps the other.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

Calculation of Risk of Relapse

Provided herein are methods for predicting breast cancer outcome within the context of the intrinsic subtype and optionally other clinical variables. Outcome may refer to overall or disease-specific survival, event-free survival, or outcome in response to a particular treatment or therapy. In particular, the methods may be used to predict the likelihood of long-term, disease-free survival. “Predicting the likelihood of survival of a breast cancer patient” is intended to assess the risk that a patient will die as a result of the underlying breast cancer. “Long-term, disease-free survival” is intended to mean that the patient does not die from or suffer a recurrence of the underlying breast cancer within a period of at least five years, or at least ten or more years, following initial diagnosis or treatment.

In one embodiment, outcome is predicted based on classification of a subject according to subtype. This classification is based on expression profiling using the list of intrinsic genes listed in Table 1. In addition to providing a subtype assignment, the PAM50 bioinformatics model provides a measurement of the similarity of a test sample to all four subtypes which is translated into a Risk of Relapse (ROR) score that can be used in any patient population regardless of disease status and treatment options. The intrinsic subtypes and ROR also have value in the prediction of pathological complete response in women treated with, for example, neoadjuvant taxane and anthracycline chemotherapy (Rouzier et al., J Clin Oncol 23:8331-9 (2005), incorporated herein by reference in its entirety). Thus, in various embodiments of the present disclosure, a risk of relapse (ROR) model is used to predict outcome. Using these risk models, subjects can be stratified into low, medium, and high risk of relapse groups. Calculation of ROR can provide prognostic information to guide treatment decisions and/or monitor response to therapy.

In some embodiments described herein, the prognostic performance of the PAM50-defined intrinsic subtypes and/or other clinical parameters is assessed utilizing a Cox Proportional Hazards Model Analysis, which is a regression method for survival data that provides an estimate of the hazard ratio and its confidence interval. The Cox model is a well-recognized statistical technique for exploring the relationship between the survival of a patient and particular variables. This statistical method permits estimation of the hazard (i.e., risk) of individuals given their prognostic variables (e.g., intrinsic gene expression profile with or without additional clinical factors, as described herein). The “hazard ratio” is the risk of death at any given time point for patients displaying particular prognostic variables. See generally Spruance et al., Antimicrob. Agents & Chemo. 48:2787-92 (2004).

The PAM50 classification model described herein can be trained for risk of relapse using subtype distances (or correlations) alone, or using subtype distances with clinical variables as discussed supra. In one embodiment, the risk score for a test sample is calculated using intrinsic subtype distances alone using the following equation:

ROR=0.05*Basal+0.11*Her2+−0.25*LumA+ 0.07*LumB+−0.11*Normal, where the variables "Basal," "Her2," "LumA," "LumB," and "Normal" are the distances to the centroid for each respective classifier when the expression profile from a test sample is compared to centroids constructed using the gene expression data deposited with the Gene Expression Omnibus (GEO).

Risk score can also be calculated using a combination of breast cancer subtype and the clinical variables tumor size (T) and lymph nodes status (N) using the following equation: ROR (full)=0.05*Basal+0.1*Her2+−0.19*LumA+ 0.05*LumB+−0.09*Normal+0.16*T+0.08*N, again when comparing test expression profiles to centroids constructed using the gene expression data deposited with GEO as accession number GSE2845.

In yet another embodiment, risk score for a test sample is calculated using intrinsic subtype distances alone using the following equation:

ROR-S=0.05*Basal+0.12*Her2+−0.34*LumA+ 0.0.23*LumB, where the variables "Basal," "Her2," "LumA," and "LumB" are as described supra and the test expression profiles are compared to centroids constructed using the gene expression data deposited with GEO as accession number GSE2845. In yet another embodiment, risk score can also be calculated using a combination of breast cancer subtype and the clinical variable tumor size (T) using the following equation (where the variables are as described supra): ROR-C=0.05*Basal+0.1 1*Her2+−0.23*LumA+0.09*LumB+ 0.17*T.

In yet another embodiment, risk score for a test sample is calculated using intrinsic subtype distances in combination with the proliferation signature ("Prolif") using the following equation:

ROR-P=−0.001*Basal+0.7*Her2+−0.95*LumA+ 0.49*LumB+0.34*Prolif, where the variables "Basal," "Her2," "LumA," "LumB" and "Prolif" are as described supra and the test expression profiles are compared to centroids constructed using the gene expression data deposited with GEO as accession number GSE2845. In yet another embodiment, risk score can also be calculated using a combination of breast cancer subtype, proliferation signature and the clinical variable tumor size (T) using the following equation (where the variables are as described supra): ROR-PT=−0.001*Basal+0.73*Her2+−0.9*LumA+0.05*LumB+ 0.13*T+0.33*Prolif.

Detection of Subtypes

Immunohistochemistry for estrogen (ER), progesterone (PgR), HER2, and Ki67 was performed concurrently on serial sections with the standard streptavidin-biotin complex method with 3,3'-diaminobenzidine as the chromogen. Staining for ER, PgR, and HER2 interpretation can be performed as described previously (Cheang et al., Clin Cancer Res. 2008; 14(5):1368-1376.), however any method known in the art may be used.

For example, a Ki67 antibody (clone SP6; ThermoScientific, Fremont, Calif.) can be applied at a 1:200 dilution for 32 minutes, by following the Ventana Benchmark automated immunostainer (Ventana, Tucson Ariz.) standard Cell Conditioner 1 (CC1, a proprietary buffer) protocol at 98° C. for 30 minutes. An ER antibody (clone SP1; ThermoFisher Scientific, Fremont Calif.) can be used at 1:250 dilution with 10-minute incubation, after an 8-minute microwave antigen retrieval in 10 mM sodium citrate (pH 6.0). Ready-to-use PR antibody (clone 1E2; Ventana) can be used by following the CC1 protocol as above. HER2 staining can be done with a SP3 antibody (ThermoFisher Scientific) at a 1:100 dilution after antigen retrieval in 0.05 M Tris buffer (pH 10.0) with heating to 95° C. in a steamer for 30 minutes. For HER2 fluorescent in situ hybridization (FISH) assay, slides can be hybridized with probes to LSI (locus-specific identifier) HER2/neu and to centromere 17 by use of the PathVysion HER-2 DNA Probe kit (Abbott Molecular, Abbott Park, Ill.) according to manufacturer's instructions, with modifications to pretreatment and hybridization as previously described (Brown L A, Irving J, Parker R, et al. Amplification of EMSY, a novel oncogene on 11q13, in high grade ovarian surface epithelial carcinomas. Gynecol Oncol. 2006; 100(2):264-270). Slides can then be counterstained with 4',6-diamidino-2-phenylindole, stained material was visualized on a Zeiss Axioplan epifluorescent microscope, and signals were analyzed with a Metafer image acquisition system (Metasystems, Altlussheim, Germany) Biomarker expression from immunohistochemistry assays can then be scored by two pathologists, who were blinded to the clinicopathological characteristics and outcome and who used previously established and published criteria for biomarker expression levels that had been developed on other breast cancer cohorts.

Tumors were considered positive for ER or PR if immunostaining was observed in more than 1% of tumor nuclei, as described previously. Tumors were considered positive for HER2 if immunostaining was scored as 3+ according to HercepTest criteria, with an amplification ratio for fluorescent in situ hybridization of 2.0 or more being the cut point that was used to segregate immunohistochemistry equivocal tumors (scored as 2+) (Yaziji, et al., JAMA, 291(16):1972-1977 (2004)). Ki67 was visually scored for percentage of tumor cell nuclei with positive immunostaining above the background level by two pathologists.

Other methods can also be used to detect subtypes. These techniques include ELISA, Western blots, Northern blots, or FACS analysis.

Kits

The present disclosure also describes kits useful for classifying breast cancer intrinsic subtypes and/or providing prognostic information to identify breast cancers that are more responsive to anthracyclines. These kits comprise a set of capture probes and/or primers specific for the intrinsic genes listed in Table 1. The kit may further comprise a computer readable medium.

In one embodiment of the present disclosure, the capture probes are immobilized on an array. By "array" is intended a solid support or a substrate with peptide or nucleic acid probes attached to the support or substrate. Arrays typically comprise a plurality of different capture probes that are coupled to a surface of a substrate in different, known locations. The arrays of the disclosure comprise a substrate having a plurality of capture probes that can specifically bind an intrinsic gene expression product. The number of capture probes on the substrate varies with the purpose for which the array is intended. The arrays may be low-density arrays or high-density arrays and may contain 4 or more, 8 or more, 12 or more, 16 or more, 32 or more addresses, but will minimally comprise capture probes for the 50 intrinsic genes listed in Table 1.

Techniques for the synthesis of these arrays using mechanical synthesis methods are described in, e.g., U.S. Pat. No. 5,384,261, incorporated herein by reference in its entirety for all purposes. The array may be fabricated on a surface of virtually any shape or even a multiplicity of surfaces. Arrays may be probes (e.g., nucleic-acid binding probes) on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation on the device. See, for example, U.S. Pat. Nos. 5,856,174 and 5,922,591 herein incorporated by reference.

In another embodiment, the kit comprises a set of oligonucleotide primers sufficient for the detection and/or quantitation of each of the intrinsic genes listed in Table 1. The oligonucleotide primers may be provided in a lyophilized or reconstituted form, or may be provided as a set of nucleotide sequences. In one embodiment, the primers are provided in a microplate format, where each primer set occupies a well (or multiple wells, as in the case of replicates) in the microplate. The microplate may further comprise primers sufficient for the detection of one or more housekeeping genes as discussed infra. The kit may further comprise reagents and instructions sufficient for the amplification of expression products from the genes listed in Table 1.

In order to facilitate ready access, e.g., for comparison, review, recovery, and/or modification, the molecular signatures/expression profiles are typically recorded in a database. Most typically, the database is a relational database accessible by a computational device, although other formats, e.g., manually accessible indexed files of expression profiles as photographs, analogue or digital imaging readouts, spreadsheets, etc. can be used. Regardless of whether the expression patterns initially recorded are analog or digital in nature, the expression patterns, expression profiles (collective expression patterns), and molecular signatures (correlated expression patterns) are stored digitally and accessed via a database. Typically, the database is compiled and maintained at a central facility, with access being available locally and/or remotely.

EXAMPLES

Example 1

Proliferation Signature Predicts Response to Weekly Adjuvant Paclitaxel in Breast Cancer Patients, Samples and Clinical Data The GEICAM/9906 trial was a prospective adjuvant multicenter randomized phase III study (n=1,246 subjects) comparing six cycles of Fluorouracil, Epirubicin, and Cyclophosphamide Alone (FEC, control arm) versus four cycles of FEC followed by eight weekly cycles of paclitaxel at 100 mg/m2 (FEC-P, experimental arm) in node-positive breast cancers. The primary endpoint of the GEICAM/9906 clinical trial was disease-free survival. Secondary endpoints were: (a) overall survival; (b) prognostic and predictive value of molecular/genomic markers and (c) safety. The study was performed in accordance with the Declaration of Helsinki, approved by the ethics committees at all participating institutions and the Spanish Health Authority, and it was registered at www.clinicaltrials.gov (identifier code: NCT00129922). All patients provided written informed consent for therapy randomization and molecular analyses. Details of the study design and patients' characteristics have been previously reported (Martin et al., J Natl Cancer Inst 100: 805-814, 2008; Martin et al., Breast Cancer Res Treat 123:149-157, 2010). Formalin-fixed, paraffin-embedded tumor blocks were available on 825 patients. H&E sections from each FFPE tissue block were reviewed by a pathologist at GEICAM's central laboratory. At least two tumor cores were extracted from areas containing representative invasive breast carcinoma using a 1 mm core punch. A detailed protocol of RNA extraction from FFPE tissue, and the RT-qPCR PAM50 assay have been previously described (Parker et al., J Clin Oncol 27:1160-1167, 2009).

PAM50 Subtype Classification

Samples were gene expression profiled using the previously described RT-qPCR assay and analyzed using the clinical algorithm for subtype prediction (Parker et al., J Clin Oncol 27:1160-1167, 2009; Amp Laboratories: PAM50 Breast Cancer Intrinsic Classifier Information. at the World Wide Web (www) aruplab.com/Lab-Tests/General-Oncology/PAM50/index.jsp). Samples were assigned into the following intrinsic subtype categories: Luminal A, Luminal B, HER2-enriched, Basal-like and Normal-like. Samples classified as Normal-like were excluded from further analyses due to the potential for misclassification resulting from normal breast tissue or stroma contamination within the tumor specimen (Elloumi et al., BMC Med Genomics 4:54, 2011). In addition to the subtype classification, a PAM50proliferation score was calculated using the previously described 11-gene signature (BIRC5, CCNB1, CDC20, CDCA1, CEP55, KNTC2, MKI67, PTTG1, RRM2, TYMS, UBE2C) (Nielsen et al., Clin Cancer Res 16(21):5222-32, 2010). The significance of proliferation was evaluated using a classification into quartiles, and using the proliferation scores as a continuous variable.

Immunohistochemical (IHC) Ki-67 Quantification

Ki-67 status was assessed in a central laboratory on paraffin sections by an immunohistochemical method using Clone MIB 1 antibody (DakoCytomation, Glostrup, Denmark). Ki67 score was defined as the percentage of total number of tumor cells with nuclear staining.

Statistical Analysis

This analysis has a prospective-retrospective design (retrospective analysis of a randomized prospective trial) with pre-specified study objectives and pre-specified laboratory assays in a predefined population. The primary pre-specified objectives of the study were to determine whether the PAM50 subtypes, and/or the PAM50 proliferation score, were associated with OS and/or predictive of paclitaxel benefit. The Kaplan-Meier method was used to estimate overall survival (OS), and the log-rank test was used to compare OS between groups. Univariate and multivariate Cox proportional hazard models were used to examine the association of each variable with survival, and interaction between treatment and PAM50 subtype and proliferation. The results are presented in accordance with reporting recommendations for tumor marker prognostic studies (REMARK) criteria (McShane et al., J Clin Oncol 23:9067-9072, 2005).

Patient Demographics

Figure 5:
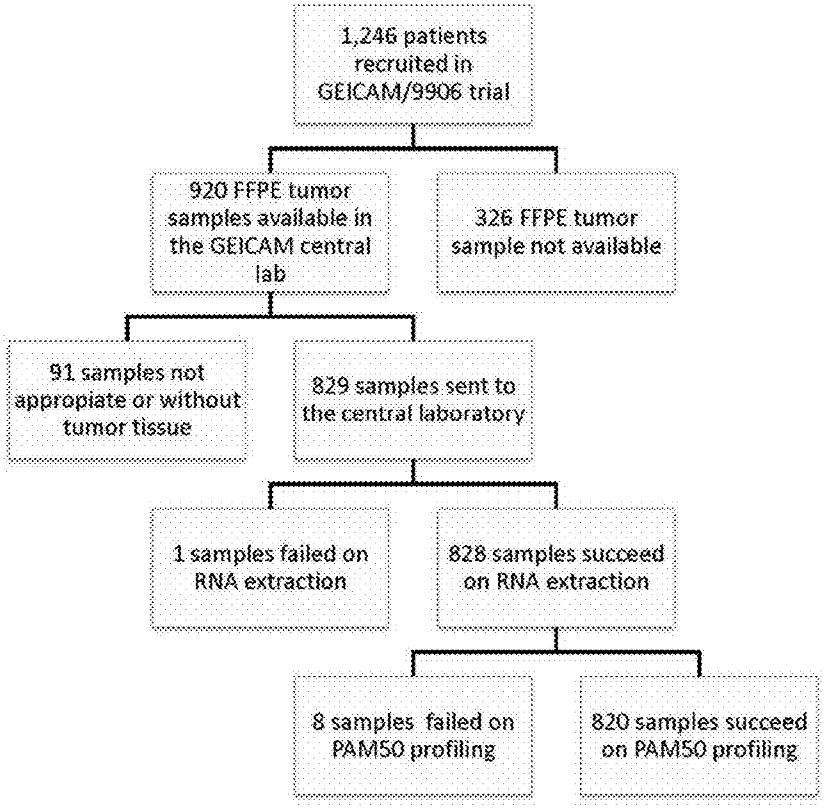
FIG. 5 is a schematic of the GEICAM/9906 trial sample set.

Tumor blocks were available for 825 patients, and PAM50 genomic profiling was successful in 820 samples (99.4%) of patients whose signed informed consent was obtained (FIG. 5), which represents 66% of the original 1,246 sample set of the GEICAM/9906 trial (Martin et al., J Natl Cancer Inst 100: 805-814, 2008). The demographic and prognostic features, as well as the 10-year OS of patients included in this sub-study were similar to those of the overall study population. The distribution of the patient's clinical-pathological characteristics included in this study is shown in Table 3.

TABLE 3

| Patient Clinical-Pathological Characteristics. | | | |
|---|---|---|---|
| Variables | Arm FEC N = 417 (%) | Arm FEC-P N = 403 (%) | Total Sample N = 820 (%) |
| Age (y) | | | |
| <50 | 197 (47.2) | 197 (48.9) | 394 (48.0) |
| >=50 | 220 (52.8) | 206 (51.1) | 426 (52.0) |
| Menopausal Status | | | |
| Pre | 223 (53.5) | 220 (54.6) | 443 (54.0) |
| Post | 194 (46.5) | 183 (45.4) | 377 (46.0) |
| Nodal status | | | |
| 1-3 | 257 (64.0) | 250 (62.0) | 507 (61.8) |
| >4 | 160 (38.4) | 153 (38.0) | 313 (38.2) |
| Histological grade | | | |
| G1 | 54 (12.9) | 54 (13.4) | 108 (13.2) |
| G2 | 175 (42.0) | 162 (40.2) | 337 (41.1) |
| G3 | 160 (38.4) | 156 (38.7) | 316 (38.5) |
| GX | 28 (6.7) | 31 (7.7) | 59 (7.2) |
| Primary Tumor Size | | | |
| T1 | 158 (37.9) | 184 (45.7) | 342 (41.7) |
| T2 | 236 (56.6) | 196 (48.6) | 432 (52.7) |
| T3 | 23 (5.5) | 23 (5.7) | 46 (5.6) |
| Estrogen receptor | | | |
| Negative | 95 (22.8) | 77 (19.1) | 172 (21.0) |
| Positive | 321 (77.0) | 324 (80.4) | 645 (78.7) |
| Progesterone receptor | | | |
| Negative | 143 (34.3) | 103 (25.6) | 246 (30.0) |
| Positive | 272 (65.2) | 298 (73.9) | 570 (70.0) |
| Her2 status | | | |
| Negative | 369 (88.5) | 329 (81.6) | 698 (85.1) |
| Positive | 45 (10.8) | 71 (17.6) | 116 (14.1) |
| Ki-67-IHC | | | |
| Low (<=13%) | 278 (66.7) | 279 (62.9) | 557 (67.9) |
| High (>13%) | 132 (31.7) | 111 (27.5) | 243 (29.6) |
| Subtype_Prediction | | | |
| Luminal A | 129 (30.9) | 149 (37.0) | 278 (33.9) |
| Luminal B | 146 (35.0) | 118 (29.3) | 264 (32.1) |
| Her2-enriched | 85 (20.4) | 91 (22.6) | 176 (21.4) |
| Basal-like | 45 (10.8) | 26 (6.4) | 71 (8.7) |
| Normal-like | 12 (2.9) | 19 (4.7) | 31 (3.9) |
| 11-GeneProliferation | | | |
| Low (lowest quartile, <=3.9) | 98 (23.5) | 110 (27.3) | 208 (25.4) |
| High (>3.9) | 319 (76.5) | 293 (72.7) | 612 (74.6) |
| 11-GeneProliferation | | | |
| Low (lowest tertile, <=4.4) | 128 (30.7) | 153 (38.0) | 281 (34.3) |
| High (>4.4) | 289 (69.3) | 250 (62.0) | 539 (65.7) |

Overall Survival Outcomes

Figure 2:
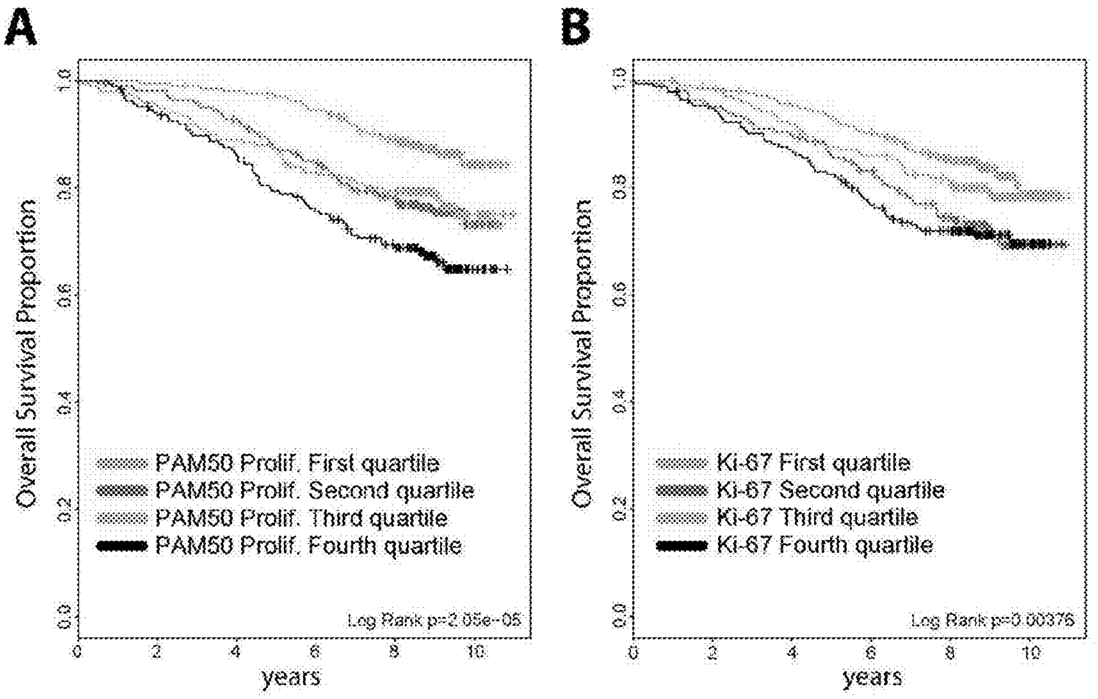
FIG. 2A is a line graph showing overall survival rates based on proliferation scores.
FIG. 2B is a line graph showing overall survival rates based on Ki-67.

With a median follow up of 8.7 years, OS of the FEC-P arm was significantly superior compared to the FEC arm (hazard ratio [HR] for O δ 0.693, 95% confidence interval [CI] 0.693-0.927, p=0.013) with 10-year OS rates in the FEC and FEC-P arms of 70.90% and 78.44%, respectively (FIG. 1A). Univariate analysis revealed the following variables significantly associated with OS: menopausal status, nodal status, histopathological grade, tumor size, estrogen receptor (ER) status, progesterone receptor (PR) status, Ki67, PAM50 subtypes and proliferation score. As expected, the PAM50 Luminal A tumors showed the best outcome (84.04% OS at 10 years), followed by Luminal B (70.75%), Basal-like (70.42%) and HER2-enriched (65.19%) (FIG. 1B). Compared to Luminal A tumors, Luminal B, HER2-enriched and Basal-like tumors showed a HR for OS of 1.99 (1.35-2.97), 2.60 (1.52-4.40) and 2.62 (1.74-3.95), respectively. Interestingly, although the proliferation score and Ki-67 were found significantly associated with OS (FIG. 2), the separation of the curves by quartile distribution was found to be greater using the proliferation score compared to Ki-67 by IHC.

Among the variables evaluated, tumor size, nodal status and proliferation signature were found to be independent predictors of OS in multivariate analysis with treatment arm showing a tendency for significance (p=0.067). (Table 4). Of note, Ki-67 by IHC and histological grade were superseded by the information provided by the proliferation signature.

TABLE 4

| Prediction Variables | | | |
|---|---|---|---|
| Variables | p-value | HR | CI 95% |
| Treatment Arm (FEC-P as reference) FEC | 0.067 | 1.323 | 0.981-1.784 |
| Age (<50 as reference) >=50 | 0.551 | 0.839 | 0.471-1.495 |
| Menopausal status (pre as reference) Postmenopausal | 0.129 | 1.562 | 0.878-2.778 |
| Primary tumor size (T1 as reference) | 0.003 | | |
| T2 | 0.009 | 1.572 | 1.120-2.206 |
| T3 | 0.002 | 2.464 | 1.412-4.302 |
| Nodal status (1-3 as reference) 4+ | <0.0001 | 1.816 | 1.347-2.449 |
| ER (positive as reference) Negative | 0.634 | 1.105 | 0.732-1.670 |
| PR (positive as reference) Negative | 0.183 | 1.302 | 0.883-1.919 |
| Her2 (positive as reference) Negative | 0.798 | 0.949 | 0.636-1.417 |
| 11-GeneProliferation (low, first quartile, as reference) High | 0.013 | 1.765 | 1.130-2.758 |
| Subtype PAM50 (luminal A as reference) Rest | 0.138 | 1.361 | 0.906-2.044 |

Effect of Paclitaxel in the PAM50 Subtypes and Proliferation Score

Figure 3:
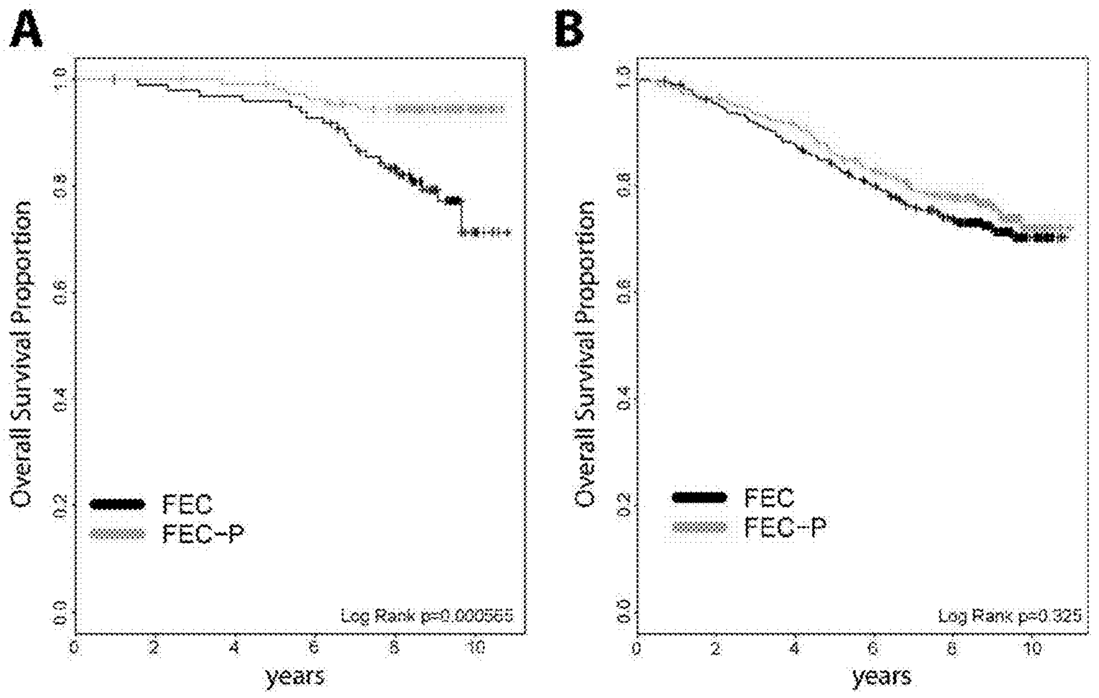
FIG. 3A is a line graph showing overall survival rates in the FEC and FEC-P treatment arms in patients whose tumors had a low proliferation score.
FIG. 3B is a line graph showing overall survival rates in the FEC and FEC-P treatment arms in other proliferation score groups.

Kaplan-Meier plots for OS comparing treatment with FEC-P vs. FEC were evaluated in each group category defined by the PAM50 assay. The individual PAM50 subtypes were not found predictive of paclitaxel efficacy. On the other hand, a benefit from paclitaxel was observed in patients whose tumors had a low proliferation score (HR=0.23 within the lowest quartile, CI 0.09-0.57, p<0.001), showing an improvement of the 10-year OS from 71.24% to 94.42% (FIG. 3A). The PAM50 subtype distribution within the low quartile group (n=181) of the proliferation score was as follows: Luminal A 76.24%, Luminal B 6.63%, HER2-enriched 17.13% and Basal-like 0%. No benefit of paclitaxel was observed within the other proliferation score groups when evaluated individually, or when combined into one group (FIG. 3B), where the univariate HR for OS was 0.85 (CI 0.62-1.16). Similar data was obtained when the proliferation score was evaluated using tertiles.

Relationship of the Proliferation Score and Paclitaxel Treatment Benefit

To test the statistical validity of the relationship between the magnitude of paclitaxel benefit and the proliferation score, a formal test of statistical interaction between proliferation score and paclitaxel treatment was performed. In a multivariate analysis of Cox models containing paclitaxel treatment and proliferation score, the tests for interaction were found to be statistically significant (p=0.006 as a continuous variable; p=0.019 as group categories using quartile expression). In addition, a multivariate model for the interaction between Proliferation Score and paclitaxel treatment that was adjusted for all clinical-pathological variables showed continued significance of the interaction between proliferation score and paclitaxel treatment (Table 5).

TABLE 5

Interaction of Paclitaxel Treatment with the proliferation signature in a Multivariate Cox Proportional Hazard Model

| Variables | p-value | HR | CI 95% |
|---|---|---|---|
| Treatment Arm (FEC-P as reference) FEC | 0.008 | 3.457 | 1.374-8.696 |
| Age (<50 as reference) >=50 | 0.545 | 0.833 | 0.461-1.506 |
| Menopausal status (pre as reference) Postmenopausal | 0.107 | 1.630 | 0.901-2.951 |
| Primary tumor size (T1 as reference) | 0.004 | | |
| T2 | 0.018 | 1.515 | 1.074-2.136 |
| T3 | 0.002 | 2.586 | 1.435-4.659 |
| Histological grade (G1 as reference) | 0.125 | | |
| G2 | 0.069 | 1.875 | 0.951-3.694 |
| G3 | 0.057 | 1.977 | 0.980-3.989 |
| GX | 0.852 | 1.092 | 0.436-2.735 |
| Nodal status (1-3 as reference) 4+ | 0.001 | 1.648 | 1.217-2.230 |
| ER (positive as reference) Negative | 0.980 | 1.006 | 0.630-1.608 |
| PR (positive as reference) Negative | 0.143 | 1.347 | 0.904-2.007 |
| Her2 (positive as reference) Negative | 0.726 | 1.080 | 0.703-1.659 |
| Ki-67 (continuous) | 0.710 | 1.002 | 0.991-1.013 |
| 11-GeneProliferation (low as reference) High | 0.008 | 3.234 | 1.354-7.723 |
| 11-GeneProliferation*arm | 0.031 | 0.342 | 0.129-0.908 |
| Subtype PAM50 (luminal A as reference) | 0.621 | | |
| Luminal B | 0.431 | 1.199 | 0.763-1.886 |
| Her2-enriched | 0.128 | 1.478 | 0.894-2.445 |
| Basal-like | 0.633 | 1.194 | 0.576-2.475 |
| Normal-like | 0.584 | 1.348 | 0.463-3.928 |

Figure 4:
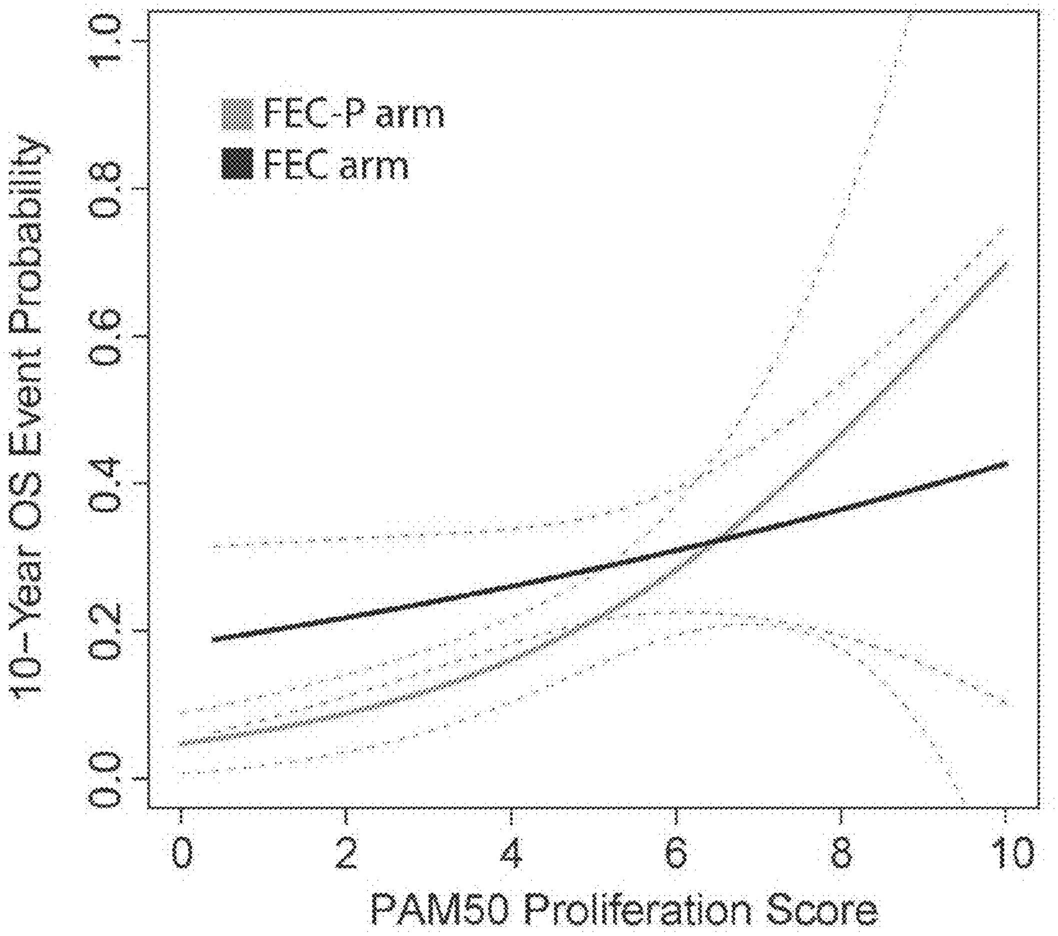
FIG. 4 is a line graph showing 10 year overall survival as a linear function of the proliferation score for both the FEC and FEC-P treatment arms.

To explore the degree of benefit from paclitaxel treatment in relationship to the Proliferation score as a continuous function, the likelihood of OS was fit as a linear function of the Proliferation score for both arms. As expected, the magnitude of paclitaxel benefit appeared to increase continuously as the Proliferation score decreased (FIG. 4 and Table 6).

TABLE 6

Hazard Ratios of FEC-T v. FEC within Low Risk Groups

| | | | DFS Univariate | | OS Univariate | |
|---|---|---|---|---|---|---|
| Variable | Criteria | #Pts | HR | p-value | HR | p-value |
| ARM FEC-T v. FEC | Low (cutoff 20%) | 163/817 | 0.431 | 0.016 | 0.188 | 0.0028 |
| ARM FEC-T v. FEC | Low (cutoff 25%) | 204/817 | 0.531 | 0.037 | 0.24 | 0.0021 |
| ARM FEC-T v. FEC | Low (cutoff 33%) | 272/817 | 0.61 | 0.044 | 0.427 | 0.01 |
| ARM FEC-T v. FEC | Low (cutoff 50%) | 408/817 | 0.695 | 0.048 | 0.584 | 0.02 |

Paclitaxel Benefit and Clinical-Pathological Variables

In order to identify other predictors of response to weekly paclitaxel, the interaction of paclitaxel treatment with clinical-pathological variables (age, menopausal status, histological grade, tumor size, ER [IHC] status, PR [IHC] status, Ki-67 ([IHC] and HER2 status [IHC/CISH]) was also evaluated. No significant interactions between these variables and treatment were found.

Discussion

In the era of personalized medicine, new tools that may be able to provide clinically useful prognostic and predictive information for breast cancer patients are needed. Two genomic assays (OncotypeDX and Mammaprint) provide prognostic information in early breast cancer (Van de Vijver et al., N Engl J Med 347:1999-2009, 2002; Buyse et al., J Natl Cancer Inst 98: 1183-92, 2006; Paik et al., N Engl J Med 351:2817-26, 2004), and OncotypeDX provides predictive information of benefit from adjuvant chemotherapy (cyclophosphamide-methotrexate-fluorouracil (CMF) or cyclophosphamide-doxorubicin(Adriamycin®)-fluorouracil (CAF)) in ER-positive disease (Paik et al., J Clin Oncol 24:3726-34, 2006; Albain et al., Lancet Oncol 11: 55-65, 2010). However, the ability of these and other assays, to predict treatment benefit to modern taxane regimens, and/or the benefit to specific drugs, is unclear.

It has been previously reported that the benefit of adding weekly adjuvant paclitaxel to anthracycline-based chemotherapy is small (De Laurentiis et al., J Clin Oncol 26:44-53, 2008; Nowak et al., Lancet Oncol 5: 372-80, 2004; Tang, Cancer Investigation 27:489-495, 2009; Bria et al., Cancer 106: 2337-2344, 2006). Thus, identification of which patients might benefit the most from this drug and schedule seems justified. Traditional clinical-pathological parameters (i.e. age, tumor size, number of positive nodes, ER status, PR status, and HER2 status) and the PAM50 intrinsic subtypes were not found to be predictive of adjuvant paclitaxel efficacy.

A measure of proliferation is an important component of tests used for prognosis, especially in early stage ER-positive breast cancer. Proliferation is also incorporated into histological grading, either by counting mitotic figures (i.e. modified Nottingham-Bloom-Richardson score) or by developing a mitotic index using a cell cycle regulated biomarker such as Ki-67 (Simpson et al., J Clin Oncol. 18(10):2059-69, 2000; Meyer et al., Mod Pathol. 2005 August; 18(8):1067-78. Erratum in: Mod Pathol 18(12):1649, 2005; Dowsett et al., J Natl Cancer Inst 99(2):167-70, 2007). In this study, it was found that the proliferation score signature, which is the average expression value of 11 proliferation-related genes, was predictive for benefit of weekly paclitaxel in the adjuvant setting. Although no pre-specified cutoffs of this signature were tested in the GEICAM/9906 trial here, the HR for OS in the low quartile group was noteworthy (HR=0.232, p=0.002). In addition, the test of interaction between paclitaxel treatment and Proliferation score was statistically significant, even when all other clinical-pathological variables were considered. Interestingly, the proliferation-related biomarker, Ki-67 by IHC, did not predict paclitaxel benefit despite being evaluated at a central pathology laboratory, while the 11-gene proliferation score was significant.

What is claimed is:

1. A method of treating breast cancer in a subject in need thereof comprising:

(a) providing a sample from the subject;

(b) determining expression in the sample of a combination of at least five genes selected from the group consisting of ANLN, BIRC5, CCNB1, CCNE1, CDC20, CDC6, CDCA1, CENPF, CEP55, EXO1, KIF2C, KNTC2, MELK, MKI67, MYBL2, ORC6L, PTTG1, RRM2, TYMS, UBE2C, and UBE2T, wherein the at least five genes comprise CDC20, CEP55, MKI67, RRM2 and UBE2C;

(c) determining a proliferation signature based on the expression of each of the at least five genes in the sample; and (d) administering a breast cancer treatment to the subject, wherein if the sample is classified as having a low proliferation signature, the subject is subjected to a breast cancer treatment comprising a taxane or taxane derivative, administered weekly, and wherein if the sample is classified as not having a low proliferation signature, the subject is subjected to a breast cancer treatment not comprising a taxane or taxane derivative, administered weekly, thereby treating breast cancer in the subject.

2. The method of claim 1, further comprising determining the expression of at least one gene selected from ANLN, BIRC5, CCNB1, CCNE1, CDC6, CDCA1, CENPF, EXO1, KIF2C, KNTC2, MELK, MYBL2, ORC6L, PTTG1, TYMS, and UBE2T.

3. The method of claim 1, comprising determining the expression of each of the genes selected from ANLN, BIRC5, CCNB1, CCNE1, CDC20, CDC6, CDCA1, CENPF, CEP55, EXO1, KIF2C, KNTC2, MELK, MKI67, MYBL2, ORC6L, PTTG1, RRM2, TYMS, UBE2C and UBE2T.

4. The method of claim 1, comprising determining the expression of each of the genes selected from ANLN, CCNE1, CDC20, CDC6, CDCA1, CENPF, CEP55, EXO1, KIF2C, KNTC2, MELK, MKI67, ORC6L, PTTG1, RRM2, TYMS, UBE2C and UBE2T.

5. The method of claim 1, comprising determining the expression of each of the genes selected from BIRC5, CCNB1, CDC20, CDCA1/NUF2, CEP55, KNTC2/NDC80, MKI67, PTTG1, RRM2, TYMS and UBE2C.

6. The method of claim 1, comprising determining the expression of each of the genes selected from ANLN, CCNB1, CDC20, CENPF, CEP55, KIF2C, MKI67, MYBL2, RRM2and UBE2C.

7. The method of claim 1, wherein the taxane or taxane derivative is paclitaxel.

8. The method of claim 1, wherein the breast cancer treatment comprising a taxane or taxane derivative further comprises one or more members of the group consisting of anthracycline, cyclophosphamide and 5-fluorouracil.

9. The method of claim 8, wherein the anthracycline is selected from the group consisting of doxorubicin and epirubicin.

10. The method of claim 8, wherein taxane or taxane derivative is administered before or after with the administration of the anthracycline, cyclophosphamide or 5-fluorouracil.

11. The method of claim 1, wherein the breast cancer treatment comprising a taxane or taxane derivative further comprises each of the members of the group consisting of anthracycline, cyclophosphamide and 5-fluorouracil.

12. The method of claim 11, wherein the anthracycline is selected from the group consisting of doxorubicin and epirubicin.

13. The method of claim 11, wherein taxane or taxane derivative is administered before, after or simultaneously with, the administration of the anthracycline, cyclophosphamide and 5-fluorouracil.

14. The method of claim 1, further comprising determining at least one of the following: tumor size, tumor grade, nodal status, intrinsic subtype, estrogen receptor expression, progesterone receptor expression, and HER2/ERBB2 expression.

15. The method of claim 1, further comprising determining each of the following: tumor size, tumor grade, nodal status, intrinsic subtype, estrogen receptor expression, progesterone receptor expression, and HER2/ERBB2 expression.

16. The method of claim 1, wherein the sample is a sampling of cells or tissues.

17. The method of claim 1, wherein the tissue is obtained from a biopsy.

18. The method of claim 1, wherein the sample is a sampling of a bodily fluid.

19. The method of 18, wherein the bodily fluid is selected from the group consisting of blood, lymph, urine, saliva and nipple aspirate.

20. The method of claim 1, wherein the expression of the at least one gene is determined using a nanoreporter code system.

* * * * *

UNITED STATES PATENT AND TRADEMARK OFFICE

CERTIFICATE OF CORRECTION

PATENT NO. : 9,181,588 B2
APPLICATION NO. : 13/690891
DATED : November 10, 2015
INVENTOR(S) : Charles M. Perou et al.

It is certified that error appears in the above-identified patent and that said Letters Patent is hereby corrected as shown below:

In The Specification

At column 1, line 12, please insert, between the section of CROSS-REFERENCE TO RELATED APPLICATIONS and the section of INCORPORATION-BY-REFERENCE OF SEQUENCE LISTING, a new section on federal government support as set forth below:

--GOVERNMENT SUPPORT

This invention was made with Government support under Grant No. P50 CA582230, R01 CA095614, and U01 CA114722 awarded by the National Institutes of Health. The Government has certain rights in the invention.--

Signed and Sealed this
Twelfth Day of April, 2016

Michelle K. Lee
*Director of the United States Patent and Trademark Office*